US011186645B2

(12) United States Patent
Rosenthal et al.

(10) Patent No.: US 11,186,645 B2
(45) Date of Patent: Nov. 30, 2021

(54) ISOLATED NUCLEIC ACIDS ENCODING ANTI-SORTILIN ANTIBODIES

(71) Applicant: Alector LLC, South San Francisco, CA (US)

(72) Inventors: Arnon Rosenthal, Woodside, CA (US); Tina Schwabe, San Francisco, CA (US); Michael Kurnellas, San Francisco, CA (US); Robert Pejchal, Lebanon, NH (US); Anthony B. Cooper, Lebanon, NH (US)

(73) Assignee: Alector LLC, South San Francisco, CA (US)

( * ) Notice: Subject to any disclaimer, the term of this patent is extended or adjusted under 35 U.S.C. 154(b) by 16 days.

(21) Appl. No.: 16/741,658

(22) Filed: Jan. 13, 2020

(65) Prior Publication Data
US 2020/0223928 A1    Jul. 16, 2020

Related U.S. Application Data

(60) Division of application No. 16/134,830, filed on Sep. 18, 2018, which is a division of application No. 15/285,359, filed on Oct. 4, 2016, now Pat. No. 10,087,255, which is a continuation-in-part of application No. PCT/US2016/026519, filed on Apr. 7, 2016.

(60) Provisional application No. 62/144,270, filed on Apr. 7, 2015.

(51) Int. Cl.
*C07K 16/28* (2006.01)
*A61K 31/7088* (2006.01)

(52) U.S. Cl.
CPC ...... *C07K 16/2863* (2013.01); *A61K 31/7088* (2013.01); *C07K 16/286* (2013.01); *C07K 2317/14* (2013.01); *C07K 2317/21* (2013.01); *C07K 2317/31* (2013.01); *C07K 2317/34* (2013.01); *C07K 2317/55* (2013.01); *C07K 2317/56* (2013.01); *C07K 2317/76* (2013.01); *C07K 2317/92* (2013.01); *C07K 2319/30* (2013.01); *C07K 2319/32* (2013.01)

(58) Field of Classification Search
CPC .......................... C07K 16/286; C07K 16/2863
See application file for complete search history.

(56) References Cited

U.S. PATENT DOCUMENTS

| | | |
|---|---|---|
| RE30,985 E | 6/1982 | Cartaya |
| 4,560,655 A | 12/1985 | Baker |
| 4,657,760 A | 4/1987 | Kung et al. |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 5,122,469 A | 6/1992 | Mather et al. |
| 5,206,344 A | 4/1993 | Katre et al. |
| 5,225,212 A | 7/1993 | Martin et al. |
| 5,229,275 A | 7/1993 | Goroff et al. |
| 5,530,101 A | 6/1996 | Queen et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,573,905 A | 11/1996 | Lerner et al. |
| 5,585,089 A | 12/1996 | Queen et al. |
| 5,587,458 A | 12/1996 | King et al. |
| 5,591,669 A | 1/1997 | Krimpenfort et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,237 A | 7/1997 | Carter et al. |
| 5,661,016 A | 8/1997 | Lonberg et al. |
| 5,693,761 A | 12/1997 | Queen et al. |
| 5,693,762 A | 12/1997 | Queen et al. |
| 5,731,168 A | 3/1998 | Carter et al. |
| 5,739,277 A | 4/1998 | Presta et al. |
| 5,750,373 A | 5/1998 | Garrard et al. |
| 5,766,886 A | 6/1998 | Studnicka et al. |
| 5,770,429 A | 6/1998 | Lonberg et al. |
| 5,789,199 A | 8/1998 | Joly et al. |
| 5,821,337 A | 10/1998 | Carter et al. |
| 5,840,523 A | 11/1998 | Simmons et al. |
| 5,869,046 A | 2/1999 | Presta et al. |

(Continued)

FOREIGN PATENT DOCUMENTS

| | | |
|---|---|---|
| EP | 0308936 B1 | 7/1994 |
| EP | 0404097 B1 | 9/1996 |

(Continued)

OTHER PUBLICATIONS

Alegre et al. (1994). "A Non-Activating "Humanized" Anti-CD3 Monoclonal Antibody Retains Immunosuppressive Properties In Vivo," Transplantation 57(11):1537-1543.
Almagro et al. (2008). "Humanization of Antibodies," Frontiers in Bio-Science 13:1619-1633.
Al-Shawi et al. (2007). "ProNGF, Sortilin, and Age-Related Neurodegeneration," Annals of the New York Academy of Sciences, pp. 208-215.
Al-Shawi et al. (2008). "Neurotoxic and Neurotrophic Roles of proNGF and the Receptor Sortilin in the Adult and Ageing Nervous System," European Journal of Neuroscience 27:2103-2114.

(Continued)

*Primary Examiner* — Gyan Chandra
(74) *Attorney, Agent, or Firm* — Morrison & Foerster LLP

(57) ABSTRACT

The present disclosure is generally directed to compositions that include antibodies, e.g., monoclonal, chimeric, humanized antibodies, antibody fragments, etc., that specifically bind on or more epitopes within a Sortilin protein, e.g., human Sortilin or a mammalian Sortilin, and use of such compositions in preventing, reducing risk, or treating an individual in need thereof.

48 Claims, 63 Drawing Sheets
(18 of 63 Drawing Sheet(s) Filed in Color)

Specification includes a Sequence Listing.

(56) References Cited

U.S. PATENT DOCUMENTS

| | | |
|---|---|---|
| 5,869,619 A | 2/1999 | Studnicka |
| 5,959,177 A | 9/1999 | Hein et al. |
| 6,040,498 A | 3/2000 | Stomp et al. |
| 6,075,181 A | 6/2000 | Kucherlapati et al. |
| 6,150,584 A | 11/2000 | Kucherlapati et al. |
| 6,248,516 B1 | 6/2001 | Winter et al. |
| 6,417,429 B1 | 7/2002 | Hein et al. |
| 6,420,548 B1 | 7/2002 | Vézina et al. |
| 6,982,321 B2 | 1/2006 | Winter |
| 7,041,870 B2 | 5/2006 | Tomizuka et al. |
| 7,087,409 B2 | 8/2006 | Barbas, III et al. |
| 7,125,978 B1 | 10/2006 | Vézina et al. |
| 7,189,826 B2 | 3/2007 | Rodman |
| 7,527,791 B2 | 5/2009 | Adams et al. |
| 8,008,009 B2 | 8/2011 | Choquet-Kastylevsky et al. |
| 8,066,997 B2 | 11/2011 | Nykjaer et al. |
| 8,460,657 B2 | 6/2013 | Nykjaer et al. |
| 8,614,299 B2 | 12/2013 | Baurin et al. |
| 8,703,125 B2 | 4/2014 | Pedersen et al. |
| 8,748,384 B2 | 6/2014 | Andersen et al. |
| 8,795,627 B2 | 8/2014 | Starr et al. |
| 8,815,808 B2 | 8/2014 | Nykjaer et al. |
| 8,877,714 B2 | 11/2014 | Starr et al. |
| 8,986,690 B2 | 3/2015 | Nykjaer et al. |
| 9,061,045 B2 | 6/2015 | Choquet-Kastylevsky et al. |
| 9,062,126 B2 | 6/2015 | Zankel et al. |
| 9,084,745 B2 | 7/2015 | Nykjaer et al. |
| 9,234,036 B2 | 1/2016 | Anderson et al. |
| 9,605,073 B2 | 3/2017 | Nykjaer et al. |
| 9,670,263 B2 | 6/2017 | Pedersen et al. |
| 9,822,366 B2 | 11/2017 | Aikawa et al. |
| 10,087,255 B2 | 10/2018 | Rosenthal et al. |
| 10,308,718 B2 | 6/2019 | Rosenthal et al. |
| 10,428,150 B2 | 10/2019 | Rosenthal et al. |
| 10,478,421 B1 | 11/2019 | Sparks et al. |
| 10,849,896 B2 | 12/2020 | Patel et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2006/0025576 A1 | 2/2006 | Miller et al. |
| 2007/0061900 A1 | 3/2007 | Murphy et al. |
| 2007/0148167 A1 | 6/2007 | Strohl |
| 2007/0292936 A1 | 12/2007 | Barthelemy et al. |
| 2008/0069820 A1 | 3/2008 | Fuh et al. |
| 2009/0002360 A1 | 1/2009 | Chen et al. |
| 2009/0055944 A1 | 2/2009 | Korman et al. |
| 2009/0068200 A1 | 3/2009 | Choquet-Kastylevsky et al. |
| 2009/0181855 A1 | 7/2009 | Vasquez et al. |
| 2010/0028333 A1 | 2/2010 | Getty et al. |
| 2010/0056386 A1 | 3/2010 | Vasquez et al. |
| 2010/0092481 A1 | 4/2010 | Lanzavecchia et al. |
| 2010/0280227 A1 | 11/2010 | Ambrose et al. |
| 2012/0039865 A1 | 2/2012 | Strittmatter et al. |
| 2012/0315244 A1 | 12/2012 | Yuan et al. |
| 2013/0115222 A1 | 5/2013 | Hempstead et al. |
| 2013/0171173 A1 | 7/2013 | Choquet-Kastylevsky et al. |
| 2013/0336988 A1 | 12/2013 | Hempstead et al. |
| 2014/0004108 A1 | 1/2014 | Yuan et al. |
| 2015/0299304 A1 | 10/2015 | Nykjaer et al. |
| 2016/0024172 A1 | 1/2016 | Zankel et al. |
| 2016/0060346 A1 | 3/2016 | Andersen et al. |
| 2016/0194631 A1 | 7/2016 | Yuan et al. |
| 2016/0349276 A1 | 12/2016 | Jepsen et al. |
| 2017/0049855 A1 | 2/2017 | Liu et al. |
| 2017/0096486 A1 | 4/2017 | Landberg |
| 2017/0158766 A1 | 6/2017 | Nykjaer et al. |
| 2017/0240611 A1 | 8/2017 | Pedersen et al. |
| 2017/0246263 A1 | 8/2017 | Concino et al. |
| 2017/0267761 A1 | 9/2017 | Biilmann Ronn et al. |
| 2017/0318057 A1 | 11/2017 | Nykjaer et al. |
| 2018/0265586 A1 | 9/2018 | Rosenthal et al. |
| 2019/0023788 A1 | 1/2019 | Ronn et al. |
| 2019/0062433 A1 | 2/2019 | Rosenthal et al. |
| 2019/0085084 A1 | 3/2019 | Rosenthal et al. |
| 2019/0127475 A1 | 5/2019 | Rosenthal et al. |
| 2020/0024348 A1 | 1/2020 | Schwabe et al. |
| 2020/0330553 A1 | 10/2020 | Ito et al. |
| 2020/0392229 A1 | 12/2020 | Paul et al. |

FOREIGN PATENT DOCUMENTS

| | | |
|---|---|---|
| EP | 0546073 B1 | 9/1997 |
| JP | 2014-519517 A | 8/2014 |
| WO | WO-1987/00195 A1 | 1/1987 |
| WO | WO-1987/04462 A1 | 7/1987 |
| WO | WO-1990/03430 A1 | 4/1990 |
| WO | WO-1991/00360 A1 | 1/1991 |
| WO | WO-1991/10741 A1 | 7/1991 |
| WO | WO-1992/20373 A1 | 11/1992 |
| WO | WO-1993/01161 A1 | 1/1993 |
| WO | WO-1993/08829 A1 | 5/1993 |
| WO | WO-1993/11161 A1 | 6/1993 |
| WO | WO-1993/16185 A2 | 8/1993 |
| WO | WO-1994/04690 A1 | 3/1994 |
| WO | WO-1996/27011 A1 | 9/1996 |
| WO | WO-1996/33735 A1 | 10/1996 |
| WO | WO-1996/34096 A1 | 10/1996 |
| WO | WO-1997/11971 A1 | 4/1997 |
| WO | WO-1997/17852 A1 | 5/1997 |
| WO | WO-1998/24893 A2 | 6/1998 |
| WO | WO-1999/58572 A1 | 11/1999 |
| WO | WO-2004/042072 A2 | 5/2004 |
| WO | WO-2004/056385 A2 | 7/2004 |
| WO | WO-2005/044293 A2 | 5/2005 |
| WO | WO-2006/138343 A2 | 12/2006 |
| WO | WO-2007/035716 A2 | 3/2007 |
| WO | WO-2007/088305 A1 | 8/2007 |
| WO | WO-2007/106585 A2 | 9/2007 |
| WO | WO-2008/036682 A2 | 3/2008 |
| WO | WO-2008/052016 A2 | 5/2008 |
| WO | WO-2008/074329 A2 | 6/2008 |
| WO | WO-2008/076262 A2 | 6/2008 |
| WO | WO-2008/079246 A2 | 7/2008 |
| WO | WO-2008/086452 A2 | 7/2008 |
| WO | WO-2009/036379 A2 | 3/2009 |
| WO | WO-2009/089004 A1 | 7/2009 |
| WO | WO-2009/132656 A2 | 11/2009 |
| WO | WO-2009/140972 A2 | 11/2009 |
| WO | WO-2009/155932 A2 | 12/2009 |
| WO | WO-2010/022175 A1 | 2/2010 |
| WO | WO-2010/028333 A2 | 3/2010 |
| WO | WO-2010/069331 A2 | 6/2010 |
| WO | WO-2010/105256 A1 | 9/2010 |
| WO | WO-2011/041582 A2 | 4/2011 |
| WO | WO-2011/159762 A1 | 12/2011 |
| WO | WO-2012/009568 A2 | 1/2012 |
| WO | WO-2012/068332 A2 | 5/2012 |
| WO | WO-2012/171057 A1 | 12/2012 |
| WO | WO-2014/071131 A1 | 5/2014 |
| WO | WO-2014/179363 A1 | 11/2014 |
| WO | WO-2015/006504 A1 | 1/2015 |
| WO | WO-2015/119989 A1 | 8/2015 |
| WO | WO-2015/121166 A1 | 8/2015 |
| WO | WO-2015/144860 A1 | 10/2015 |
| WO | WO-2016/025523 A1 | 2/2016 |
| WO | WO-2016/164608 A1 | 10/2016 |
| WO | WO-2016/164637 A1 | 10/2016 |
| WO | WO-2017/009327 A1 | 1/2017 |
| WO | WO-2017/024137 A1 | 2/2017 |
| WO | WO-2019246071 A1 | 12/2019 |
| WO | WO-2020037434 A1 | 2/2020 |
| WO | WO-2020051624 A1 | 3/2020 |

(56) References Cited

FOREIGN PATENT DOCUMENTS

| WO | WO-2020120749 A1 | 6/2020 |
|---|---|---|
| WO | WO-2020191212 A1 | 9/2020 |

OTHER PUBLICATIONS

Andersen et al. (2010). "Identification of a Linear Epitope in Sortilin that Partakes in Pro-Neurotrophin Binding," J. Biol. Chem. 285(16):12210-12222.

Angal et al. (1993). "A Single Amino Acid Substitution Abolishes the Heterogeneity of Chimeric Mouse/Human (IgG4) Antibody," Molecular Immunology 30(1):105-108.

Armour et al. (2003). "Differential Binding To Human Fcγriia and Fcγriib Receptors by Human IgG Wildtype and Mutant Antibodies," Molecular Immunology 40:585-593.

Arnett et al. (2007). "proNGF, sortilin, and p75NTR: Potential Mediators of Injury-Induced Apoptosis in the Mouse Dorsal Root Ganglion," Brain Research1183:32-42.

Asquith et al. (2009). "Animal Models of Rheumatoid Arthritis," Eur. J. Immunol. 39:2040-2044.

Baker et al. (2006). "Mutations in Progranulin Cause Tau-Negative Frontotemporal Dementia Linked to Chromosome 17," Nature 442:916-919.

Barbas et al. (1994). "In Vitro Evolution of a Neutralizing Human Antibody to Human Immunodeficiency Virus Type 1 to Enhance Affinity and Broaden Strain Cross-Reactivity," Proc Nat. Acad. Sci. USA 9:3809-3813.

Barnes et al. (1980). "Methods for Growth of Cultured Cells in Serum-Free Medium," Analytical Biochemistry. 102:255-270.

Bath et al. (2006). "Variant BDNF (Val66Met) impact on Brain Structure and Function," Cognitive, Affective, & Behavioral Neuroscience 6(1):79-85.

Beattie et al. (2002). "ProNGF Induces p75-Mediated Death of Oligodendrocytes following Spinal Cord Injury," Neuron 36(3):375-386.

Boerner et al. (1991). "Production of Antigen-Specific Human Monoclonal Antibodies From In Vitro-Primed Human Splenocytes," Journal of Immunology 147(1):86-95.

Bolt et al. (1993). "The Generation of a Humanized, Non-Mitogenic Cd3 Monoclonal Antibody Which Retains In Vitro Immunosuppressive Properties," European Journal Immunol. 23:403-411.

Brennan et al. (1985). "Preparation of Bispecific Antibodies by Chemical Recombination of Monoclonal Immunoglobulin G1 Fragments," Science 229:81-83.

Bruggemann et al. (1993). "Designer Mice: The Production of Human Antibody Repertoires in Transgenic Animals," Year Immunol. 7:33-40.

Cantoni et al. (2015). "Trem2 Regulates Microglial Cell Activation in Response to Demyelination In Vivo," Acta Neuropathol, 129(3):429-447.

Cao et al. (2011). "Macrophage Polarization in the Maculae of Age-Related Macular Degeneration: A Pilot Study," Pathology International 61:528-535.

Capel et al. (1994). "Heterogeneity of Human IgG Fc Receptors," Immunomethods 4:25-34.

Carecchio et al. (2011). "Cerebrospinal Fluid Biomarkers in Progranulin Mutations Carriers," Journal of Alzheimer's Disease 27:781-790.

Carlo et al. (2013). "The Pro-neurotrophin Receptor Sortilin is a Major neuronal APOE Receptor for Catabolism of Amyloid-β peptide in the Brain," J. Neurosc, 33(1):358-370.

Carrasquillo et al. (2010). "Genome-Wide Screen Identifies rs646776 near Sortilin as a Regulator of Progranulin Levels in Human Plasma," The American Journal of Human Genetics 87:890-897.

Carter et al. (1992). "High Level *Escherichia coli* Expression and Production of a Bivalent Humanized Antibody Fragment," Bio/technology10:163-167.

Carter et al. (1992). "Humanization of an Anti-p185HER2 Antibody for Human Cancer Therapy," Proc. Natl. Acad. Sci. USA 89:4285-4289.

Chang et al. (2002). "Retinal Degeneration Mutants in the Mouse," Vision Research 42:517-525.

Chao et al. (2006). "Isolating and Engineering Human Antibodies Using Yeast Surface Display," Nature Protocols 1(2):755-768.

Chen et al. (2005). "Sortilin Controls Intracellular Sorting of Brain-Derived Neurotrophic Factor to the Regulated Secretory Pathway," The Journal of Neuroscience 25(26):6156-6166.

Chesselet. (2008). "In Vivo Alpha-Synuclein Overexpression in Rodents: A Useful Model Of Parkinson's Disease?," Exp Neurol 209(1):22-27.

Chothia et al. (1987). "Canonical Structures for the Hypervariable Regions of Immunoglobulins," J. Mol. Biol, 196:901-917.

Chu et al. (2008). "Inhibition of B Cell Receptor-Mediated Activation of Primary Human B Cells by Coengagement of CD19 and FcγRIIb With Fc-Engineered Antibodies," Mol. Immunol. 45(15):3926-3933.

Clackson et al. (1991). "Making Antibody Fragments Using Phage Display Libraries," Nature 352(15):624-628.

Counts et al. (2004). "Reduction of Cortical TrkA but not p75NTR Protein in Early-Stage Alzheimer's Disease," Ann. Neurol. 56:520-531.

Counts et al. (2005). "The Role of Nerve Growth Factor Receptors in Cholinergic BasalForebrain Degeneration in Prodromal Alzheimer Disease," J. Neuropathol. Exp. Neurol, 64(4):263-272.

Cruts et al. (2008). "Loss of Progranulin Function in Frontotemporal Lobar Degeneration," Trends Genetics 24(4):186-194.

Cunningham et al. (1989). "High-Resolution Epitope Mapping of Hgh-Receptor Interactions by Alanine-Scanning Mutagenesis," Science 244:1081-1085.

Daeron (1997). "FC Receptor Biology," Annu. Rev. Immunol. 15:203-234.

Dall' Acqua et al. (2006). "Properties of Human IgG1s Engineered for Enhanced Binding to the Neonatal Fc Receptor (FcRn)," The Journal of Biological Chemistry 281(33):23514-23524.

Daneman et al. (2010). "The Mouse Blood-Brain Barrier Transcriptome: A New Resource for Understanding the Development and Function of Brain Endothelial Cells," PLoS One 5(10):1-16.

Davidson et al. (2014). "A High-Throughput Shotgun Mutagenesis Approach to Mapping B-Cell Antibody Epitopes," Immunology 143(1):13-20.

Davis et al. (2007). "Abatacept Binds to the Fc Receptor Cd64 but Does not Mediate Complement-Dependent Cytotoxicity or Antibody-Dependent Cellular Cytotoxicity," The Journal of Rheumatology 34(11):2204-2210.

De Haas et al. (1995). "Fcγ Receptors of Phagocytes," J. Lab. Clin. Med. 126(4):330-341.

De Muynck, L. et al. (2013). "The Neurotrophic Properties of Progranulin Depend on the Granulin E Domain but do not Require Sortilin Binding," Neurobiol Aging. 34(11):2541-2547.

Demetriades et al. (2013). "AAV-Mediated Neurotrophin-4 Is Neuroprotective in Murine Model of Microbead-Induced Glaucoma with Neurotrophin Expression in the Visual Pathway," Investigative Ophthalmology & Visual Science, vol. 54, 3 pages.

Ducry et al. (2010). "Antibody-Drug Conjugates: Linking Cytotoxic Payloads to Monoclonal Antibodies," Bioconjug. Chem. 21(1):5-13.

Duman et al. (1997). "A Molecular and Cellular Theory of Depression," Arch Gen Psychiatry 54(7):597-606.

Egan et al. (2003). "The BDNF val66met Polymorphism Affects Activity-Dependent Secretion of Bdnf and Human Memory and Hippocampal Function," Cell 112:257-269.

Egashira et al. (2013). "The Growth Factor Progranulin Attenuates Neuronal Injury Induced by Cerebral Ischemia-Reperfusion Through the Suppression of Neutrophil Recruitment," Journal of Neuroinflammation 10(105):1-13.

El-Danaf et al. (2015). "Characteristic Patterns of Dendritic Remodeling in Early-Stage Glaucoma: Evidence from Genetically Identified Retinal Ganglion Cell Types," The Journal of Neuroscience 35(6):2329-2343.

Estep et al. (2013). "High Throughput Solution-Based Measurement of Antibody-Antigen Affinity and Epitope Binning," mAbs. 5(2):270-278.

(56) References Cited

OTHER PUBLICATIONS

Fahnestock et al. (2001). "The Precursor Pro-Nerve Growth Factor is the Predominant Form of Nerve Growth Factor in Brain and is Increased in Alzheimer's Disease," Molecular and Cellular Neuroscience 18:210-220.

Fan. (2008). "Differential effects of Pro-BDNF on Sensory Neurons after Sciatic Nerve Transection in Neonatal Rats," European Journal of Neuroscience 27:2380-2390.

Feldhaus et al. (2004)."Yeast Display of Antibody Fragments: A Discovery and Characterization Platform," Journal of Immunological Methods 290:69-80.

Fellouse et al. (2004). "Synthetic Antibodies from a Four-Amino-Acid Code: A Dominant Role for Tyrosine in Antigen Recognition," PNAS 101(34):12467-12472.

Finan. (2011). "BACE1 Retrograde Trafficking is Uniquely Regulated by the Cytoplasmic Domain of Sortilin," The Journal of Biological Chemistry 286(14):12602-12616.

Fishwild. (1996). "High-Avidity Human IggK Monoclonal Antibodies from a Novel Strain of Minilocus Transgenic Mice," Nature Biotechnology 14:845-851.

Fournier et al. (2011). "Identification of a Receptor Mediating Nogo-66 Inhibition of Axonal Regeneration," Nature 409(6818):341-346.

Frank. (2002). "The SPOT-Synthesis Technique Synthetic Peptide Arrays on Membrane Supports—Principles and Applications," Journal of Immunological Methods 267:13-26.

Gabathuler. (2010). "Approaches to Transport Therapeutic Drugs across the Blood-Brain Barrier to Treat Brain Diseases", Neurobiology of Disease 37:48-57.

Galimberti et al. (2010). "GRN Variability Contributes to Sporadic Frontotemporal Lobar Degeneration," Journal of Alzheimer's Disease 19(1):171-177.

Gargini et al. (2007). "Retinal Organization in the Retinal Degeneration 10 (Rd10) Mutant Mouse: A Morphological and Erg Study," The Journal of Comparative Neurology 500(2): 222-238.

Gerngross (2004). "Advances in the Production of Human Therapeutic Proteins in Yeasts and Filamentous Fungi," Nature Biotechnology 22(11):1409-1414.

Graham et al. (1977). "Characteristics of a Human Cell Line Transformed by DNA from Human Adenovirus Type 5," Journal of General Virology 36(1):59-74.

Griffiths et al. (1993). "Human Anti-self Antibodies with High Specificity from Phage Display Libraries," The EMBO Journal 12(2):725-734.

Grossniklaus et al. (2010). "Animal Models of Choroidal and Retinal Neovascularization," Progress in Retinal and Eye Research 29(6):500-519.

Gruber et al. (1994). "Efficient Tumor Cell Lysis Mediated by a Bispecific Single Chain Antibody Expressed in *Escherichia coli*," The Journal of Immunology 152(11):5368-5374.

Guo et al. (2012). "Prevention of LPS-lnduced Acute Lung Injury in Mice by Progranulin," Mediators of Inflammation 2012(540794):1-10.

Gupta et al. (2003). "Activated Microglia in Human Retinitis Pigmentosa, Late-Onset Retinal Degeneration, and Age-Related Macular Degeneration," Experimental Eye Research 76:463-471.

Gustafsen et al. (2014). "The Hypercholesterolemia-Risk Gene SORT1 Facilitates PCSK9 Secretion," Cell Metabolism 19:310-318.

Gustafsen. (2013). "Sortilin and SorLA Display Distinct Roles in Processing and Trafficking of Amyloid Precursor Protein," The Journal of Neuroscience 33(1):64-71.

Ham et al. (1979). "Media and Growth Requirements," Methods in Enzymology LVII:44-93.

Hamers-Casterman et al. (1993). "Naturally Occurring Antibodies Devoid of Light Chains." Nature 363:446-448.

Harrington et al. (Apr. 20, 2004). "Secreted proNGF is a Pathophysiological Death-Inducing Ligand after Adult CNS Injury," PNAS 101(16):6226-6230.

Harris. (1995). "Production of Humanized Monoclonal Antibodies for in Vivo Iimaging and Therapy," Therapeutic Monoclonals, Biochemical Society Transactions 23:1035-1038.

Hawkins et al. (1992). "Selection of Phage Antibodies by Binding Affinity: Mimicking Affinity Maturation," Journal of Molecular Biology 226:889-896.

Hezareh et al. (2001). "Effector Function Activities of a Panel of Mutants of a Broadly Neutralizing Antibody against Human Immunodeficiency Virus Type 1," Journal of Virology vol. 75(24):12161-12168.

Holliger et al. (1993). ""Diabodies": Small Bivalent and Bispecific Antibody Fragments," Proceedings of the National Academy of Sciences 90:6444-6448.

Hongo et al. (1995). "Development and Characterization of Murine Monoclonal Antibodies to the Latency-Associated Peptide of Transforming Growth Factor β1," Hybridoma 14(3):253-260.

Hoogenboom et al. (1992). "By-Passing Immunisation. Human Antibodies from Synthetic Repertoires of Germline Hh Gene Segments Rearranged in Vitro," Journal of Molecular Biology 227:381-388.

Hu et al. (2005). "Nogo-A Interacts with the Nogo-66 Receptor through Multiple Sites to Create an Isoform-Selective Subnanomolar Agonist," The Journal of Neuroscience 25(22):5298-5304.

Hu et al. (2010). "Sortilin-Mediated Endocytosis Determines Levels of the Frontotemporal Dementia Protein, Progranulin," Neuron 68:654-667.

Hudson et al. (2003). "Engineered Antibodies," Nat. Med. 9(1):129-134.

Hurle et al. (1994)."Protein Engineering Techniques for Antibody Humanization," Current Opinion in Biotechnology 5:428-433.

Hutchins et al. (1995). "Improved Biodistribution, Tumor Targeting, and Reduced Immunogenicity in Mice with a Gamma 4 Variant of Campath-IH," Proc. Natl. Acad. Sci. 92:11980-11984.

Hutton et al. (1998). "Association of Missense and 5'-Splice-Site Mutations in Tau with the Inherited Dementia FTDP-17," Nature 393:702-705.

Jackson et al. (1995). "In Vitro Antibody Maturation. Improvement of a High Affinity, Neutralizing Antibody against IL-1 Beta," The Journal of Immunology 157(7):3310-3319.

Jakobovits et al. (1993) "Germ-line Transmission and Expression of a Human-derived Yeast Artificial Chromosome," Nature 362:255-258.

Jakobovits et al. (1993). "Analysis of Homozygous Mutant Chimeric Mice: Deletion of the Immunoglobulin Heavy-chain Joining Region Blocks B-Cell Development and Antibody Production," Proceedings of the National Academy of Sciences 90:2551-2555.

Jansen et al. (2007). "Roles for the Pro-Neurotrophin Receptor Sortilin in Neuronal Development, Aging and Brain Injury," Nature Neuroscience 10(11):1449-1457.

Jefferis et al. (2009). "Human Immunoglobulin Allotypes: Possible Implications for Immunogenicity," MAbs 1(4):332-338.

Johnson et al. (1993). "Human antibody engineering: Current Opinion in Structural Biology," Current Opinion in Structural Biology 3(4):564-571.

Johnson et al. (2011). "Apolipoprotein E4 Exaggerates Diabetic Dyslipidemia and Atherosclerosis in Mice Lacking the LDL Receptor," Diabetes 60(9):2285-2294.

Jones et al. (1986). "Replacing the Complementarity-Determining Regions in a Human Antibody with Those from a Mouse," Nature 321:522-525.

Kanda et al. (2006). "Comparison of Cell Lines for Stable Production of Fucose-Negative Antibodies With Enhanced ADCC," Biotechnol. Bioeng. 94(4):680-688.

Kjolby et al. (2010). "Sort1, Encoded by the Cardiovascular Risk Locus 1p13.3, Is a Regulator of Hepatic Lipoprotein Export," Cell Metabolism 12:213-223.

Klinger et al. (2011). "SorLA Regulates the Activity of Lipoprotein Lipase by Intracellular Trafficking," Journal of Cell Science 124(7):1095-1105.

Kohler et al. (1975). "Continuous Cultures of Fused Cells Secreting Antibody of Predefined Specificity," Nature 256:495-497.

(56) References Cited

OTHER PUBLICATIONS

Kostelny et al. (1992). "Formation of a Bispecific Antibody by the Use of Leucine Zippers," The Journal of Immunology 148(5):1547-1553.
Kozbor et al. (1984). "A Human Hybrid Myeloma for Production of Human Monoclonal Antibodies," The Journal of Immunology 133(6):3001-3005.
Kuipers et al. (2006). "Brain-Derived Neurotrophic Factor Mechanisms and Function in Adult Synaptic Plasticity: New Insights and Implications for Therapy," Current Opinion in Drug Discovery & Development 9(5):580-586.
Kyte et al. (1982). "A Simple Method for Displaying the Hydropathic Character of a Protein," J. Mol. Biol. 157(1):105-132.
Laird et al. (2010). "Progranulin is Neurotrophic in Vivo and Protects against a Mutant TDP-43 Induced Axonopathy," PLOS ONE 5(10):1-7.
Langer. (1990). "New Methods of Drug Delivery," Science 249(4976):1527-1533.
Lauren et al. (2009). "Cellular Prion Protein Mediates Impairment of Synaptic Plasticity by Amyloid-β Oligomers," Nature 457:1128-1132.
Lavail et al. (2011). "Retinal Degeneration Rat Model Resource Availability of P23H and S334ter Mutant Rhodopsin Transgenic Rats and RCS Inbred and RCS Congenic Strains of Rats," UCSF School of Medicine, 12 pages.
Lazar et al. (2006). "Engineered Antibody Fc variants with Enhanced Effector Function," PNAS 103(11):4005-4010.
Lee et al. (2004). "Bivalent Antibody Phage Display Mimics Natural Immunoglobulin," Journal of Immunological Methods 284:119-132.
Lee et al. (2004). "High-affinity Human Antibodies from Phage-displayed Synthetic Fab Libraries with a Single Framework Scaffold," Journal of Molecular Biology 340:1073-1093.
Lee et al. (2014). "Targeted Manipulation of the Sortilin-Progranulin Axis Rescues Progranulin Haploinsufficiency," Human Molecular Genetics 23(6):1467-1478.
Li et al. (2006). "Optimization of Humanized IgGs in Glycoengineered Pichia Pastoris," Nature Biotechnology 24(2):210-215.
Li et al. (2006). "Human Antibodies for Immunotherapy Development Generated via a Human B Cell Hybridoma Technology," PNAS 103(10):3557-3562.
Lightle et al. (2010). "Mutations Within a Human IgG2 Antibody Form Distinct and Homogeneous Disulfide Isomers but do not Affect Fc Gamma Receptor or C1q Binding," Protein Sci. 19(4):753-762.
Lipovsek et al. (2004). "In-vitro protein evolution by ribosome display and mRNA display," Journal of Immunological Methods 290:51-67.
Lonberg et al. (1995). "Human Antibodies from Transgenic Mice," International Reviews of Immunology. 13:65-93.
Lonberg et al. (1994). "Antigen-Specific Human Antibodies from Mice Comprising Four Distinct Genetic Modifications," Nature 368:856-859.
Lonberg. (2008). "Fully Human Antibodies From Transgenic Mouse and Phage Display Platforms," Curr. Opin. Immunol. 20(4):450-459.
Lütje et al. (2014). "Anti-CEA Antibody Fragments Labeled with [18F]AIF for PET Imaging of CEA-Expressing Tumors," Bioconjugate Chemistry, 25:335-341.
Lynaugh et al. (2013). "Rapid Fc Glycosylation Analysis of Fc Fusions with IdeS and Liquid Chromatography Mass Spectrometry," mAbs, 5:641-645.
Maguire-Zeiss. (2008). "α-Synuclein: A Therapeutic Target for Parkinson's Disease?," Pharmacological Research 58(5-6): 271-280.
Marks et al. (1991). "By-Passing Immunization: Human Antibodies From V-Gene Libraries Displayed on Phage," Journal of Molecular Biology 222(3): 581-597.
Marks et al. (1992)."By-Passing Immunization: Building High Affinity Human Antibodies by Chain Shuffling," Bio/Technology 10:779-782.
Martens et al. (2012). "Progranulin Deficiency Promotes Neuroinflammation and Neuron Loss Following Toxin-Induced Injury," The Journal of Clinical Investigation 122(11):3955-3959.
Mather et al. (1982). "Culture of Testicular Cells in Hormone-Supplemented Serum-Free Medium," Annals of the New York Academy of Sciences, Testicular Cell Culture 383:44-68.
Mather. (1980). "Establishment and Characterization of Two Distinct Mouse Testicular Epithelial Cell Lines," Biology of Reproduction 23:243-252.
McCafferty et al. (1990). "Phage Antibodies: Filamentous Phage Displaying Antibody Variable Domains," Nature 348:552-554.
McEarchern et al. (2007). "Engineered Anti-CD70 Antibody with Multiple Effector Functions Exhibits in Vitro and in Vivo Antitumor Activities," Blood 109(3):1185-1192.
Michalski et al. (2003). "Pro-Brain-Derived Neurotrophic Factor is Decreased in Parietal Cortex in Alzheimer's Disease," Molecular Brain Research 111:148-154.
Milstein et al. (1983). "Hybrid Hybridomas and their use in Immunohistochemistry," Nature 305:537-540.
Minami et al. (2014). "Progranulin Protects against Amyloid β Deposition and Toxicity in Alzheimer's disease Mouse Models," Nature Medicine 20(10):1157-1164.
Mizoguchi. (2012). "Animal models of inflammatory bowel disease," Progress in Molecular Biology and Translational Science 105:263-320.
Morimoto et al. (1992). "Single-Step Purification of F(ab')2 Fragments of Mouse Monoclonal Antibodies (Immunoglobulins G1) by Hydrophobic Interaction High Performance Liquid Chromatography Using TSKgel Phenyl-5PW," Journal of Biochemical and Biophysical Methods 24:107-117.
Morrison et al. (1984). "Chimeric Human Antibody Molecules: Mouse Antigen-binding Domains with Human Constant Region Domains," Proc. Nat'l Acad. Sci 81:6851-6855.
Morrison. (1994). "Success in Specification," Nature 368:812-813.
Munson et al. (1980). "Ligand: A Versatile Computerized Approach for Characterization of Ligand-binding Systems," Analytical Biochemistry 107:220-239.
Nakamura et al. (2007)."Intracellular Sortilin Expression Pattern Regulates proNGF-Induced Naturally Occurring Cell Death during Development," Cell Death and Differentiation 14:1552-1554.
Neary et al. (1998). "Frontotemporal Lobar Degeneration: A Consensus on Clinical Diagnostic Criteria," Neurology 51:1546-1554.
Neuberger. (1996). "Generating high-avidity human Mabs in mice," Nature Biotechnology 14:826.
Neumann et al. (2007). "TDP-43 Proteinopathy in Frontotemporal Lobar Degeneration and Amyotrophic Lateral Sclerosis," Arch Neurol. 64(10):1388-1394.
Nguyen et al. (2013). "Progranulin: at the Interface of Neurodegenerative and Metabolic Diseases," Trends in Endocrinology and Metabolism 24(12):597-606.
Nilsson et al. (2007)."Apolipoprotein A-V Interaction with Members of the Low Density Lipoprotein Receptor Gene Family," Biochemistry 46(12):3896-3904.
Nilsson et al. (2008). "Endocytosis of Apolipoprotein A-V by Members of the Low Density Lipoprotein Receptor and the Vps10p Domain Receptor Families," The Journal of Biological Chemistry 283(38):25920-25927.
Nykjaer et al. (2005). "p75NTR—Live or Let Die," Current Opinion in Neurobiology 15:49-57.
Nykjaer et al. (2012). "Sortilin: A Receptor to Regulate Neuronal Viability and Function," Trends in Neurosciences 35(4):261-270.
Nykjaer et al. (2004). "Sortilin is Essential for proNGF Induced Neuronal Cell Death," Nature 427:843-848.
Oganesyan et al. (2008). "Structural characterization of a Human Fc Fragment Engineered for Lack of Effector Functions," Acta Crystallography 64:700-704.
Okazaki et al. (2004). "Fucose Depletion From Human IgG1 Oligosaccharide Enhances Binding Enthalpy and Association Rate Between IgG1 and FcγRIIIa," J. Mol. Biol. 336(5):1239-1249.

(56) References Cited

OTHER PUBLICATIONS

Pang et al. (2004). "Cleavage of proBDNF by tPA/ Plasmin Is Essential for Long-Term Hippocampal Plasticity," Science 306:487-491.
Pedraza et al. (2005). "Pro-NGF Isolated from the Human Brain Affected by Alzheimer's Disease Induces Neuronal Apoptosis Mediated by p75NTR," American Journal of Pathology 166(2):533-543.
Peng et al. (2005). "Precursor form of Brain-Derived Neurolrophic Factor and Mature Brain-Derived Neurotrophic Factor are Decreased in the Pre-Clinical Stages of Alzheimer's Disease," Journal of Neurochemistry 93:1412-1421.
Peng et al. (2010). "TREM2- and DAP12-Dependent Activation of PI3K Requires DAP10 and Is Inhibited by SHIP1," Science Signaling 3(122): 1-15.
Pennesi et al. (2012). "Animal Models of Age Related Macular Degeneration," Molecular Aspects of Medicine 33(4):1-40.
Peters et al. (2012). "Engineering an Improved IgG4 Molecule with Reduced Disulfide Bond Heterogeneity and Increased Fab Domain Thermal Stability," The Journal of Biological Chemistry 287(29):24525-24533.
Plückthun. (1992). "Mono- and Bivalent Antibody Fragments Produced in *Escherichia coli*: Engineering, Folding and Antigen Binding," Immunological Reviews130:151-188.
Presta et al. (1993). "Humanization of an Antibody Directed Against IgE," The Journal of Immunology 151(5):2623-2632.
Presta. (1992). "Antibody Engineering," Current Opinion in Structural Biology 2:593-596.
Provenzano. (2008). "p75NTR and Sortilin Increase After Facial Nerve Injury," Laryngoscope 118:87-93.
Quistgaard et al. (2009). "Ligands Bind to Sortilin in the Tunnel of a Ten-Bladed β-Propeller Domain," Nature Structural & Molecular Biology 16(1):96-98.
Quistgaard et al. (2014). "Revisiting the Structure of the Vps10 Domain of Human Sortilin and its Interaction With Neurotensin," Protein Sci. 23(9):1291-1300.
Ratnavalli et al. (2002). "The Prevalence of Frontotemporal Dementia," Neurology 58(1 of 2):1615-1621.
Ravetch et al. (1991). "Fc Receptors," Annual Review Immunology 9:457-492.
Reddy et al. (2000). "Elimination of Fc Receptor-Dependent Effector Functions of a Modified IgG4 Monoclonal Antibody to Human CD4," The Journal of Immunology 164:1925-1933.
Reineke et al. (2002). "Identification of Distinct Antibody Epitopes and Mimotopes from a Peptide Array of 5520 Randomly Generated Sequences," J. Immunol. Methods 267(1):37-51.
Riechmann et al. (1988). "Reshaping Human Antibodies for Therapy," Nature 332:323-327.
Ripka et al. (1986). "Two Chinese Hamster Ovary Glycosylation Mutants Affected in the Conversion of GDP-Mannose to GDP-Fucose," Arch Biochem. Biophys. 249(2):533-545.
Rizo et al. (1992). "Conslained Peptides: Models of Bioactive Peptides and Protein Substructures," Annu. Rev. Biochem. 61:387-418.
Roberts et al. (1997). "RNA-Peptide Fusions for the In Vitro Selection of Peptides and Proteins," Proc. Natl. Acad. Sci. USA 94:12297-12302.
Rosok et al. (1996). "Combinatorial Library Strategy for the Rapid Humanization of Anticarcinoma BR96 Fab," The Journal of Biological Chemistry 271(37):22611-22618.
Sazinsky et al. (2008). "Aglycosylated Immunoglobulin G1 Variants Productively Engage Activating Fc Receptors," PNAS 105(51):20167-20172.
Schaffitzel et al. (1999). "Ribosome Display: An In Vitro Method for Selection and Evolution of Antibodies from Libraries," Journal of Immunological Methods 231:119-135.
Scharn et al. (2000). "Spatially Addressed Synthesis of Amino- and Amino-Oxy-Substituted 1,3,5-Triazine Arrays on Polymeric Membranes," Journal of Combinatorial Chemistry 2(4):361-369.

Schier et al. (1996). "Identification of Functional and Structural Amino-Acid Residues by Parsimonious Mutagenesis," Gene 169:147-155.
Schymick et al. (2007). "Progranulin Mutations and Amyotrophic Lateral Sclerosis or Amyotrophic Lateral Sclerosis—Frontotemporal Dementia Phenotypes," Journal of Neurology, Neurosurgery and Psychiatry 78:754-756.
Seelaar et al. (2011). "Clinical, Genetic and Pathological Heterogeneity of Frontotemporal Dementia: A Review," J Neurol Neurosurg Psychiatry 82:476-486.
Seidah et al. (1996). "Cellular Processing of the Nerve Growth Factor Precursor by the Mammalian Pro-Protein Convertases," Biochem. J. 314:951-960.
Seno et al. (2009). "Efficient Colonic Mucosal Wound Repair Requires Trem2 Signaling," PNAS 106(1):256-261.
Shalaby et al. (1992). "Development of Humanized Bispecific Antibodies Reactive with Cytotoxic Lymphocytes and Tumor Cells Overexpressing the HER2 Protooncogene," The Journal of Experimental Medicine 175:217-225.
Sheriff et al. (1996). "Redefining the Minimal Antigen-binding Fragment," Nature Structural & Molecular Biology 3(9):733-736.
Shirayama et al. (2002). "Brain-Derived Neurotrophic Factor Produces Antidepressant Effects in Behavioral Models of Depression," The Journal of Neuroscience 22(8):3251-3261.
Sidhu et al. (2004). "Phage-displayed Antibody Libraries of Synthetic Heavy Chain Complementarity Determining Regions," Journal of Molecular Biology 338(2):299-310.
Sieber et al. (2013). "Attenuated Inflammatory Response in Triggering Receptor Expressed on Myeloid Cells 2 (TREM2) Knock-Out Mice Following Stroke," PLoS One 8(1):e52982.
Siegel et al. (2004). "High Efficiency Recovery and Epitope-Specific Sorting of an scFv Yeast Display Library," Journal of Immunological Methods 286:141-153.
Sims et al. (1993). "A Humanized CD18 Antibody Can Block Function Without Cell Destruction," The Journal of Immunology 151(4):2296-2308.
Skeldal et al. (2012)."Mapping of the Interaction Site between Sortilin and the p75 Neurotrophin Receptor Reveals a Regulatory Role for the Sortilin Intracellular Domain in p75 Neurotrophin Receptor Shedding and Apoptosis," The Journal of Biological Chemistry 287(52):43798-43809.
Skerra. (1993). "Bacterial Expression of Immunoglobulin Fragments," Current Opinion in Immunology 5:256-262.
Strohl. (2009). "Optimization of Fc-mediated Effector Functions of Monoclonal Antibodies," Current Opinion in Biotechnology 20:685-691.
Suresh et al. (1986). "Bispecific Monoclonal Antibodies from Hybrid Hybridomas," Methods in Enzymology 121:210-228.
Tanaka et al. (2013)."Increased Lysosomal Biogenesis in Activated Microglia and Exacerbated Neuronal Damage After Traumatic Brain Injury in Progranulin-Deficient Mice," Neuroscience 250:8-19.
Tanaka et al. (2013). "Exacerbated Inflammatory Responses Related to Activated Microglia After Traumatic Brain Injury in Progranulin-Deficient Mice," Neuroscience 231:49-60.
Tang et al. (2011). "The Growth Factor Progranulin Binds to TNF Receptors and is Therapeutic against Inflammatory Arthritis in Mice," Science 332:478-484.
Tao et al. (2012). "Neuroprotective Effects of Progranulin in Ischemic Mice," Brain Research 1436:130-136.
Tavaré et al. (2014). "Engineered Antibody Fragments for Immuno-PET Imaging of Endogenous CD8+ T Cells in Vivo," PNAS 111(3):1108-1113.
Teng et al. (2005). "ProBDNF Induces Neuronal Apoptosis via Activation of a Receptor Complex of p75 NTR and Sortilin," The Journal of Neuroscience 25(22):5455-5463.
Traunecker et al. (1991). "Bispecific Single Chain Molecules (Janusins) Target Cytotoxic Lymphocytes on HIV Infected Cells," The EMBO Journal 10(12):3655-3659.
Tutt et al. (1991). "Trispecific F(ab')3 Derivatives that Use Cooperative Signaling Via the TCR/CD3 Complex and CD2 to Activate and Redirect Resting Cytotoxic T Cells1," The Journal of Immunology 147(1):60-69.

(56) References Cited

OTHER PUBLICATIONS

Urlaub et al. (1980). "Isolation of Chinese Hamster Cell Mutants Deficient in Dihydrofolate Reductase Activity," Proc. Natl. Acad. Sci. 77(7):4216-4220.
Vaegter et al. (2011). "Sortilin Associates with Trk Receptors to Enhance Anterograde Transport and Neurotrophin Signaling," Nature Neuroscience 14(1):54-61.
Vafa et al. (2014). "An Engineered Fc Variant of an Igg Eliminates All Immune Effector Functions Via Structural Perturbations," Methods 65:114-126.
Van Dijk et al. (2001)."Human Antibodies as Next Generation Therapeutics," Current Opinion in Chemical Biology 5:368-374.
Van Kampen et al. (2014). "Progranulin Gene Delivery Protects Dopaminergic Neurons in a Mouse Model of Parkinson's Disease," Plos One 9(5):1-10.
Vaswani et al. (1998). "Humanized Antibodies as Potential Therapeutic Drugs," Annals of Allergy, Asthma & Immunology 81:105-115.
Verhoeyen et al. (1988). "Reshaping Human Antibodies: Grafting an Antilysozyme Activity," Science 239:1534-1536.
Vollmers et al. (2005). "Death by Stress: Natural IgM-Induced Apoptosis," Methods Find. Exp. Clin. Pharmacol. 27(3):185-191.
Vollmers et al. (2005). "The "Early Birds": Natural IgM Antibodies and Immune Surveillance," Histol. Histopathol. 20(3):927-937.
Volosin et al. (2006). "Interaction of Survival and Death Signaling in Basal Forebrain Neurons: Roles of Neurotrophins and Proneurotrophins," The Journal of Neuroscience 26(29):7756-7766.
Volosin et al. (2008). "Induction of Proneurotrophins and Activation of P75ntr-Mediated Apoptosis Via Neurotrophin Receptor-Interacting Factor in Hippocampal Neurons After Seizures," The Journal of Neuroscience 28(39):1-25.
Wang et al. (2015). "TREM2 Lipid Sensing Sustains the Microglial Response in an Alzheimer's Disease Model," Cell 160(6):1061-1071.
Waterhouse et al. (1993). "Combinatorial Infection and In Vivo Recombination: A Strategy for Making Large Phage Antibody Repertoires," Nucleic Acids Research 21(9):2265-2266.
Wei et al. (2007). "Enhanced Protein Expressions of Sortilin and p75NTR in Retina of Rat Following Elevated Intraocular Pressure-Induced Retinal Ischemia," Neuroscience Letters 429(2-3):169-174.
White et al. (2015). "Conformation of the Human Immunoglobulin G2 Hinge Imparts Superagonistic Properties to Immunoslimulatory Anticancer Antibodies," Cancer Cell 27(1):138-148.
Wiehr et al. (2014). "Pharmacokinetics and PETImaging Properties of Two Recombinant Anti-PSMAAntibody Fragments in Comparison to their Parental Antibody," The Prostate 24:743-755.
Wilkinson et al. (2013). "Monovalent IgG4 Molecules: Immunoglobulin Fc Mutations that Result in a Monomeric Structure," mAbs 5(3):406-417.
Willnow et al. (2011). "Sortilins: New Players in Lipoprotein Metabolism," Current Opinion in Lipidology 22(2):79-85.
Willnow et al. (2008). "VPS10P-Domain Receptors-Regulators of Neuronal Viability and Function," Nature Reviews Neuroscience 9:899-909.
Wilson et al. (2011). "An Fcγ Receptor-Dependent Mechanism Drives Antibody-Mediated Target-Receptor Signaling in Cancer Cells," Cancer Cell 19(1):101-113.
Winter et al. (1994). "Making Antibodies by Phage Display Technology," Annu. Rev. Immunol. 12:433-455.
Xu et al. (2013). "Addressing Polyspecificity of Antibodies Selected from an in Vitro Yeast presentation system: a FACS-based, high-throughput selection and analytical tool," Protein Engineering, Design & Selection 26(10):663-670.
Xu et al. (2000). "In Vitro Characterization of Five Humanized OKT3 Effector Function Variant Antibodies," Cell Immunol. 200(1):16-26.
Xu et al. (2000). "Diversity in the CDR3 Region of VH Is Sufficient for Most Antibody Specificities," Immunity 13:37-45.
Yamane-Ohnuki et al. (2004). "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotechnol. Bioeng. 87(5):614-622.
Yano et al. (2009)."Proneurotrophin-3 Is a Neuronal Apoptotic Ligand: Evidence for Retrograde-Directed Cell Killing," The Journal of Neuroscience 29(47):14790-14802.
Yelton et al. (1995). "Affinity matualion of the BR96 anti-carcinoma antibody by codon-based mutagenesis," The Journal of Immunology 155:1994-2004.
Yin et al. (2009). "Exaggerated Inflammation, Impaired Host Defense, and Neuropathology in Progranulin-Deficient Mice," J. Exp. Med. 207(1):117-128.
Yune et al. (2007). "Minocycline Alleviates Death of Oligodendrocytes by Inhibiting Pro-Nerve Growth Factor Production in Microglia after Spinal Cord Injury," The Journal of Neuroscience 27(29):7751-7761.
Zapata et al. (1995). "Engineering Linear F(ab')2 Fragments for Efficient Production in *Escherichia coli* and Enhanced Antiproliferative Activity," Protien Engineering Designs and Selections 8(10):1057-1062.
Zhao et al. (2015). "Progranulin Knockout Accelerates Intervertebral Disc Degeneration in Aging Mice," Scientific Reports 5(Article No. 9102), 9 pages.
Zheng et al. (2011)."C-Terminus of Progranulin Interacts with the Beta-Propeller Region of Sortilin to Regulate Progranulin Trafficking," PLoS One 6(6), 7 pages.
European Search Report dated Aug. 13, 2018 for EP Application No. 16777311.8 filed on Oct. 20, 2017, 10 pages.
International Search Report and Written Opinion received for PCT Patent Application No. PCT/US2016/026519 dated Sep. 14, 2016, 18 pages.
Invitation to pay additional fee received for PCT Patent Application No. PCT/US2016/026519 dated Jul. 8, 2016, 3 pages.
International Preliminary Report on Patentability received for PCT Patent Application No. PCT/US2016/026519 dated Oct. 19, 2017, 13 pages.
Singaporean Search Report and Written Opinion dated Dec. 5, 2018 for SG Application No. 11201708220R, filed Apr. 7, 2016, 12 pages.
Altmann et al., (2016). "Progranulin overexpression in sensory neurons attenuates neuropathic pain in mice: Role of autophagy," Neurobiology of Disease, 96:294-311.
Armour et al. (1999). "Recombinant Human IgG Molecules Lacking FcGamma Receptor I Binding and Monocyte Triggering Activities," Eur. J. Immunol. 29:2613-2624.
Armour et al. (Jun. 25-28, 2000). "Mutant IgG Lacking FcγRIII Binding and ADCC Activities,"The Haematology Journal, poster Session 1, Presented at the 5th Annual Meeting of the European Haematology Association, Birmingham, UK, 1(Suppl.1):27, 2 pages.
Arrant et al., (2018). "Progranulin Gene Therapy Improves Lysosomal Dysfunction and Microglial Pathology Associated with Frontotemporal Dementia and Neuronal Ceroid Lipofuscinosis," Journal of Neuroscience, 38:2341-2358.
Baca et al., (1997). "Antibody Humanization Using Monovalent Phage Display," The Journal of Biological Chemistry, 272(16):10678-10684.
BD Transduction Laboratories, (2008). "Purified Mouse Anti-Neurotensin Receptor 3 Product Information—Technical Data Sheet," available online at <http://www.bdbiosciences.com/ds/pm/tds/612100.pdf>, 2 pages.
Birch et al., (2007). "Age-related macular degeneration: a target for nanotechnology derived medicines," International Journal of Nanomedicine, 2:65-77.
Chamow et al., (1996). "Immunoadhesins: principles and applications," Trends Biotechnol., 14:52-60.
Gorno et al., (2011). "Classification of primary progressive aphasia and its variants," Neurology, 76(11):1006-1014.
Kanazawa et al., (2015). "Multiple therapeutic effects of progranulin on experimental acute ischaemic stroke," Brain, 138:1932-1948.
Lagier-Tourenne et al., (2009). "Rethinking ALS: the FUS about TDP-43," Cell, 136:1001-4.
Meeter et al., (2016). "Progranulin Levels in Plasma and Cerebrospinal Fluid in Granulin Mutation Carriers," Dement Geriatr Cogn Disord Extra, 6:330-340.

(56) References Cited

OTHER PUBLICATIONS

Menzel et al., (2016). "Progranulin Protects Against Exaggerated Axonal Injury and Astrogliosis Following Traumatic Brain Injury," GLIA, 65:278-292.
Nguyen et al., (2013). Trends in Endocrinology and Metabolism, 24, 597-606.
NovusBio, (2020). "Datasheet: Sortilin Antibody (1B3) H00006272-M01," Online catalogue NovusBio, May 6, 2020, available online at <https://www.novusbio.com/products/sortilin-antibody-1b3_h00006272-m01>, 4 pages.
Schofield et al., (2010). "Low serum progranulin predicts the presence of mutations: a prospective study," J Alzheimers Dis, 22(3):981-4.
Sela-Chung et al., (2013). "The Structural Basis of Antibody-Antigen Recognition," Front Immunol., 4:302, 13 pages.
Shields et al., (2001). "High Resolution Mapping of the Binding Site on Human IgG1 for FcγRI, FcγRII, FcγRIII, and FcRn and Design of IgG1 Variants with Improved Binding to the FcγR," The Journal of Biological Chemistry, 276(9):6591-6604.
Sleegers et al., (2008). "Progranulin genetic variability contributes to amyotrophic lateral sclerosis," Neurology, 71:253-9.
Smith et al., (2012). "Strikingly different clinicopathological phenotypes determined by progranulin-mutation dosage," Am J Hum Genet, 90:1102-7.
Tauffenberger et al., (2013). "Reduction of polyglutamine toxicity by TDP-43, FUS and progranulin in Huntington's disease models," Hum Mol Genet, 22:782-94.
Vercellino et al., (2016). "Progranulin genetic polymorphisms influence progression of disability and relapse recovery in multiple sclerosis," 22(8):1007-1012.
Wang et al., (2019). "Progranulin deficiency exacerbates spinal cord injury by promoting neuroinflammation and cell apoptosis in mice," Journal of Neuroinflammation, 16:238, 12 pages.
Yu et al., (2010). "The spectrum of mutations in progranulin: a collaborative study screening 545 cases of neurodegeneration," Arch Neurol, 67(2):161-170, 18 pages.
Yu et al., (2016). "Progranulin deficiency leads to severe inflammation, lung injury and cell death in a mouse model of endotoxic shock," J. Cell Mol. Med., 20(3):506-517.
International Preliminary Report on Patentability received for PCT Patent Application No. PCT/US2019/041614 dated Jan. 19, 2021, 7 pages.
International Search Report and Written Opinion received for PCT Patent Application No. PCT/US2019/041614 dated Sep. 25, 2019, 13 pages.

| Mutation | Binding Reactivity (%WT) | | | | |
|---|---|---|---|---|---|
| | S15-6 Fab | S2-2 Fab High Stringency | S22-9 Fab High Stringency | S60 Fab | S82-8 Fab High Stringency |
| R88A | 115.2 (31) | 14 (12) | 87.1 (9) | 106.8 (11) | 85.1 (3) |
| F105A | 57.2 (3) | 83.5 (43) | 81.1 (11) | 4.5 (1) | 68 (13) |
| L108A | 129.1 (108) | 145.4 (25) | 123.5 (21) | 1.3 (1) | 144.1 (22) |
| R109A | 66.3 (20) | 86.9 (9) | 79 (11) | 0.1 (0) | 82.8 (14) |
| G110A | 143.5 (97) | 175.3 (60) | 116.7 (5) | 3.4 (2) | 143 (10) |
| D403A | 10.1 (1) | 66.8 (28) | 101.4 (13) | 34.2 (3) | 57.2 (21) |
| D449A | 1.0 (0) | 82.6 (20) | 82.1 (4) | 69.4 (2) | 104.9 (20) |
| T451A | 10.1 (1) | 98.7 (104) | 88.7 (3) | 159.4 (53) | 100.6 (27) |
| H461A | 12.2 (1) | 77.7 (30) | 76.3 (2) | 51.1 (21) | 67.0 (39) |
| G495A | 7.1 (1) | 104.8 (12) | 76.8 (15) | 62.1 (13) | 125.4 (21) |
| Y513A | 98.8 (19) | 83.8 (14) | 77.6 (7) | 43.2 (60) | 26.6 (5) |
| S530A | 100.4 (6) | 61.4 (7) | 10.8 (4) | 86.9 (28) | 53.5 (101) |
| I537A | 86.2 (27) | 69.3 (8) | 74.2 (12) | 12.6 (1) | 86.7 (14) |
| D552A | 51.7 (5) | 2.7 (2) | 72.9 (4) | 22.7 (9) | 39.2 (5) |
| F569A | 148.4 (38) | 96.7 (59) | 175.2 (14) | 12.7 (12) | 98.1 (3) |
| E590A | 69.4 (11) | 104.6 (33) | 97.3 (6) | 5.0 (4) | 98.2 (14) |
| F592A | 195.8 (31) | 134.9 (12) | 106.2 (38) | 0.9 (1) | 114.5 (77) |
| L593A | 121.9 (15) | 113.7 (3) | 110.6 (48) | 2.2 (4) | 49.5 (6) |
| S595A | 133.0 (22) | 118.4 (31) | 115.7 (20) | 2.7 (1) | 92.2 (34) |
| W597A | 140.0 (17) | 115.9 (56) | 91.7 (10) | 4.5 (1) | 82.2 (8) |
| I619A | 120.7 (59) | 124.7 (16) | 157.6 (26) | 134.6 (7) | 20.1 (4) |
| L621A | 138.1 (65) | 60.3 (29) | 21.6 (37) | 124.8 (21) | 43.1 (12) |
| E628A | 120.6 (8) | 59.7 (21) | 88.2 (34) | 112.2 (20) | 20.5 (17) |
| D632A | 129.2 (38) | 21.9 (2) | 17.9 (1) | 119.5 (33) | 6.6 (0) |
| L636A | 102.2 (14) | 74.4 (1) | 62 (9) | 95.4 (23) | 26.8 (11) |
| Q641A | 97.6 (5) | 61.9 (3) | 80 (42) | 77.8 (0) | 18.1 (10) |
| R646A | 88.8 (2) | 47.2 (2) | 79.4 (38) | 60.4 (4) | 22.7 (12) |
| Y679A | 75.1 (31) | 33.5 (11) | 60.4 (31) | 50.6 (11) | 10.7 (5) |

FIG. 16D

| day | 0 (4h) | 2 | 5 | 8 | 12 |
|---|---|---|---|---|---|
| S20 huIgG | *** | **** | **** | **** | * |
| S20 msIgG | **** | **** | **** | **** | n.s. |

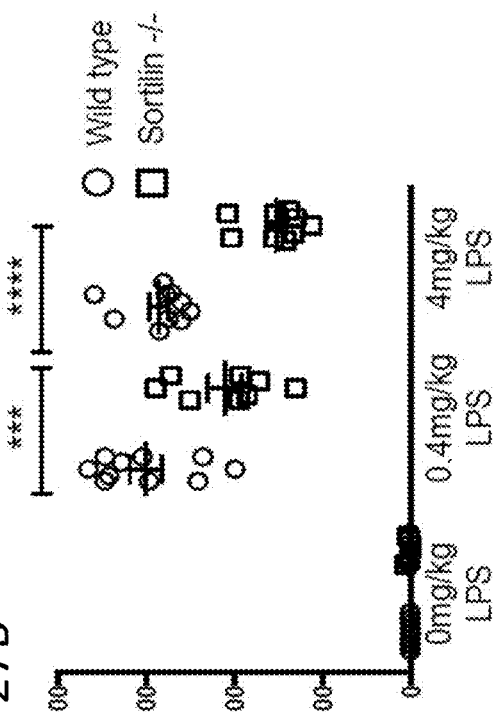
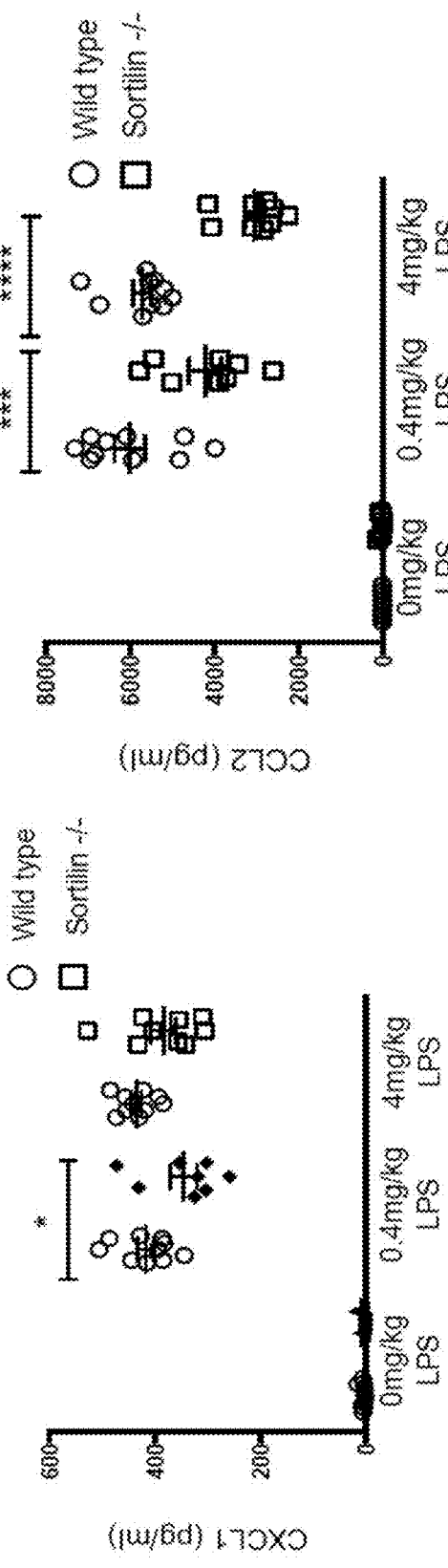
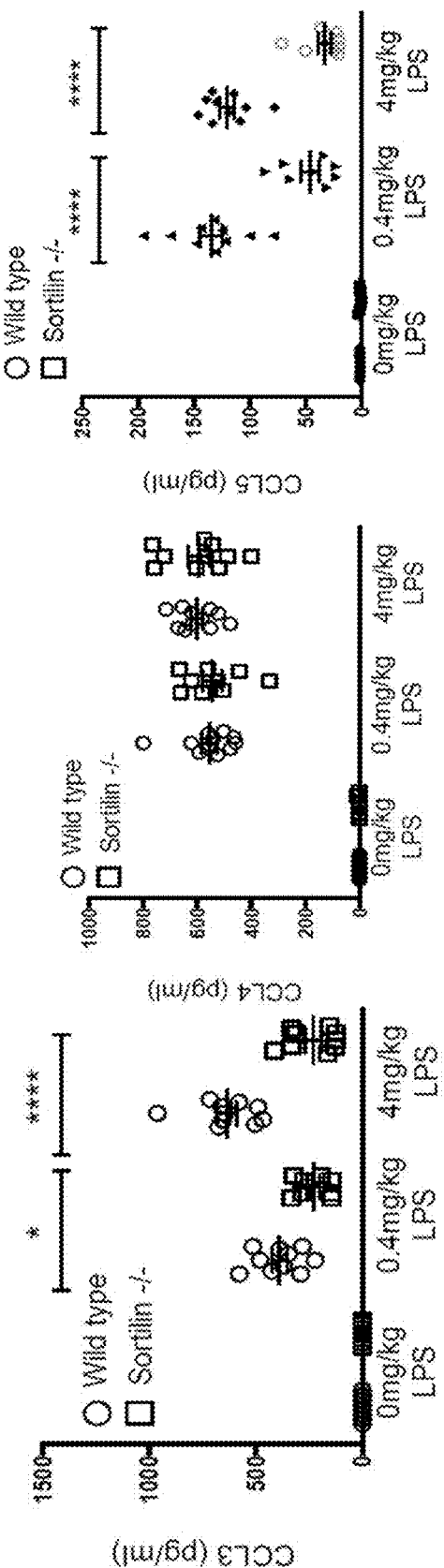
FIG. 27A, FIG. 27B, FIG. 27C, FIG. 27D, FIG. 27E

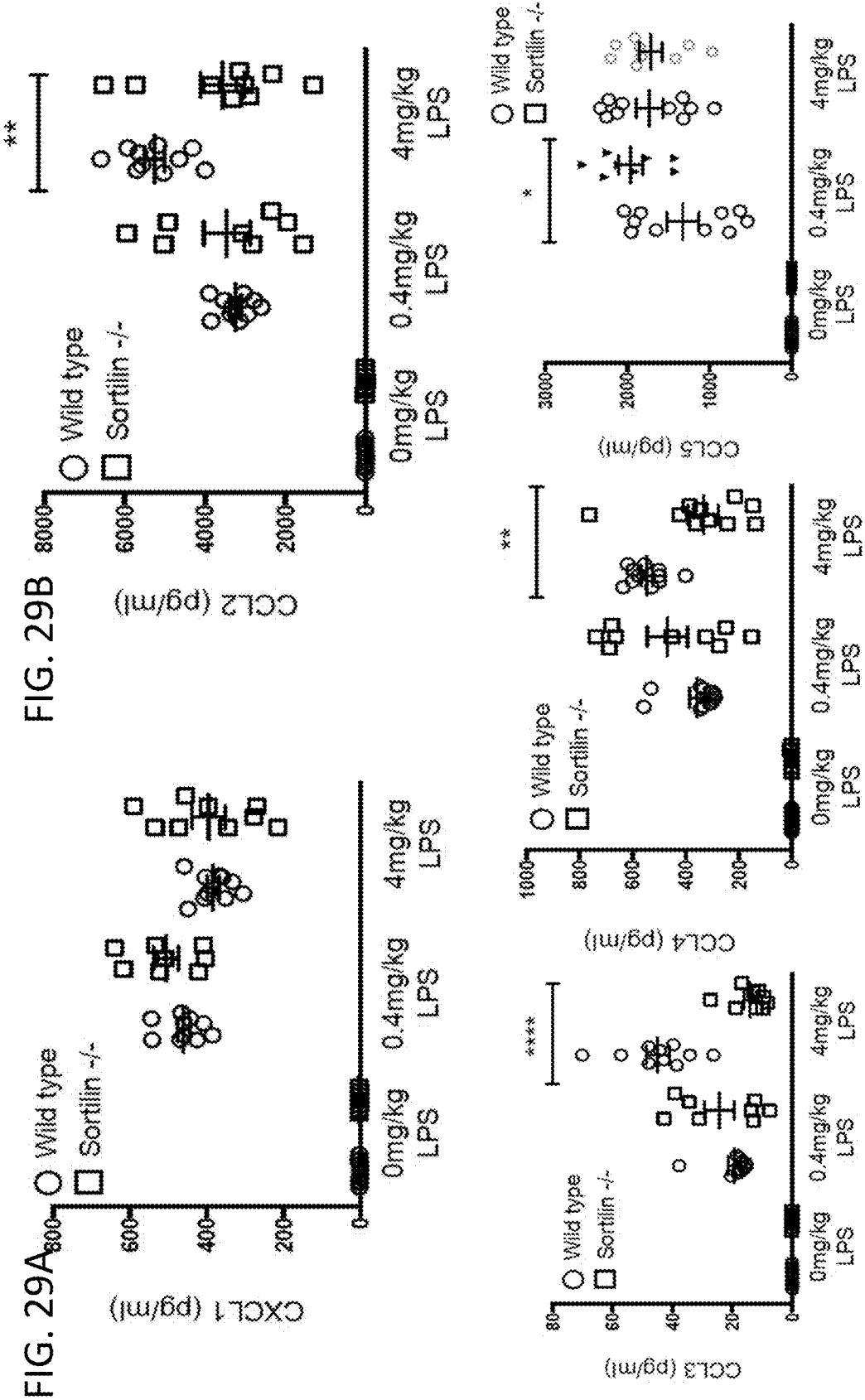

ISOLATED NUCLEIC ACIDS ENCODING ANTI-SORTILIN ANTIBODIES

CROSS-REFERENCE TO RELATED APPLICATIONS

This application is a Divisional of U.S. application Ser. No. 16/134,830, filed Sep. 18, 2018, which is a Divisional of U.S. application Ser. No. 15/285,359, filed Oct. 4, 2016, now U.S. Pat. No. 10,087,255, issued Oct. 2, 2018, which is a Continuation-In-Part of International Application No. PCT/US2016/026519, filed Apr. 7, 2016, which claims the benefit of U.S. Provisional Application No. 62/144,270, filed Apr. 7, 2015, each of which is hereby incorporated by reference in its entirety.

STATEMENT REGARDING FEDERALLY SPONSORED RESEARCH OR DEVELOPMENT

This invention was made with government support under Award Number R44AG050363 awarded by the National Institutes of Health. The government has certain rights in the invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735022000214SEQLIST.TXT, date recorded: Sep. 11, 2019, size: 345 KB).

FIELD OF THE INVENTION

This present disclosure relates to anti-Sortilin antibodies and therapeutic uses of such antibodies.

BACKGROUND OF THE INVENTION

Sortilin is a Type I transmembrane protein that acts both as a receptor of several ligands, and in the sorting of select cargo from the trans-Golgi network (TGN) to late endosomes and lysosomes for degradation. Sortilin harbors a large eytracellular domain that is part of the VPS10 family, homologous to yeast VPS10P, and contains of a 10-blade beta-propeller structure and a cysteine-rich 10CC module (Nykjaer, A et al., (2012) Trends Neurosci 35: 261-270 and Zheng, Y et al., (2011) PLoS One 6: e21023). A small fraction of Sortilin may be shed by activity of ADAM10 or gamma-Secretase (5%) (Nykjaer, A et al., (2012) Trends Neurosci 35: 261-270; and Willnow, T E et al., (2011) Curr Opin Lipidol 22: 79-85).

Sortilin binds the secreted protein Progranulin (PGRN) and targets it for lysosomal degradation, thus negatively regulating extracellular levels of PGRN (Hu, F er al. (2010) Neuron 68, 654-667. In line with this, deficiency of Sortilin significantly increases plasma PGRN levels both in mouse models in vivo and human cells in vitro (Carrasquillo, M. M et al., (2010) Am J Hum Genet 87, 890-897; Lee, W. C et al., (2014) 23, 1467-1478). Moreover, a polymorphism in Sortilin was shown to be strongly associated with PGRN serum levies in humans (Carrasquillo M M c al., 2010). Am J Hum Genet. 10; 87(6):890-7).

Progranulin (PGRN) is a secreted, growth factor-like, tropic, and anti-inflammatory protein, which also plays a role as an adipokine involved in diet-induced obesity and insulin resistance (Nguyen D A et al., (2013). Trends in Endocrinology and Metabolism, 24, 597-606). Progranulin deficiency accounts for roughly 25% of all heritable forms of frontotemporal dementia (FTD), an early-onset neurodegenerative disease. Patients with heterozygous loss-of-function mutations in PGRN have ~50% reduced extracellular levels of the protein and they will invariably develop FTD, making PGRN a causal gene for the disease (Baker, M et al., (2006) Nature 442, 916-919; Carecchio M et al., (2011) J Alzheimers Dis 27, 781-790; Cruts, M et al., (2008) Trends Genet 24, 186-194; Galimberti, D et al., (2010) J Alzheimers Dis 19, 171-177). In addition, PGRN mutant alleles have been identified in Alzheimer's disease patients (Seelaar, H et al., (2011). Journal of neurology, neurosurgery, and psychiatry 82, 476-486). Importantly, PGRN acts protective in several disease models with increased PGRN levels accelerating behavioral recovery from ischemia (Tao, J et al., (2012) Brain Res 1436, 130-136; Egashira, Y. et al., (2013). J Neuroinflammation 10, 105), suppressing locomotor deficits in a Parkinson's disease model (Van Kampen, J. M et al. (2014). PLoS One 9, e97032), attenuating pathology in a model of amyotriphic lateral scleoris (Laird, A. S et al., (2010). PLoS One 5, e13368.) and arforitis (Tang, W et al., (2011). Science 332, 478-484) and preventing memory deficits in an Alzheimer's disease model (Minami, S. S et al., 2014). Nat Med 20, 1157-1164).

Sortilin also binds directly to pro-neurotroplains, such as pro-nerve growth factor (pro-NGF), pro-BDNF, pro-neurotrophin-3, etc., which harbor a pro-domain and are typically pro-apoptotic. Such pro-neurotrophin precursors are released during stress, and Sortilin is involved in regulating their release as well as binding on the receiving cell and stimulation of apoptosis conhinetion with p75NTR (Willnow, T E et al., (2008) Nat Rev Neurosci 9: 899-909; Nykjaer, A e al., Trends Neurosci. 35: 261-270; and Nykjaer, A et al., (2004) Nature 427: 843-848; Hiroko Yano et al., (2009) J Neurosci.; 29: 14790-14802. Teng H. K., et al., J. Neurosci. 25:5455-5463(2005)). Sortilin also binds to p75NTR directly (Skeldal S et al., (2012) J Biol Chem.; 287:437981. Sortilin also binds to neurotensin M a region that partially overlaps with Progranulin binding, (Quistgaard, E M et al., (2009) Nat Struct Mol Biol 16: 96-98; and Zheng, Y et al., PLoS One. 6: e21023). Sortilin also interacts with the Trk receptors NTRK1, NTRK2, and NTRK3; and can regulate their anterograde axonal transport and signaling (Vaegter, C B et al., (2011) Nat. Neurosci. 14:54-61). Sortilin also interacts with and regulates the processing and trafficking of amyloid precursor protein and the resulting production of pathological beta amyloid peptides (Gustafsen C et al., (2013). J Neurosci. 2; 33(1):64-71.

Sortilin has also been shown to bind to apolipoproteins and lipoprotein lipase, and thus deficiency leads to reduced. VLDL release from liver and reduced cholesterol (Willnow, T E et al., (2011) Curr Opin Lipidol 22: 79-85 Kjolby, M et al., (2010) Cell Metab 12: 213-223; Nilsson S K et al., (2007) Biochemistry 46: 3896-3904; Nilsson, S K et al., (2008) J Biol Chem 283: 25920-25927; and Klinger, S C et al., (2011) J Cell Sci 124: 1095-1105). Recently, Sortilin has also been implicated in binding to APP directly (Gustafsen, C et al., (2013) J. Neurosc. 33:64-71) and also to the APP processing enzyme BACE1 (Gustafsen, C et al., (2013) J. Neurosc. 33:64-71 and Finan, G M et al., J Biol Chem 286: 12602-12616). Sortilin also binds to apolipoprotein F (APOE), to the A beta peptide (Carlo, A S et al., (2013) J, Neurose, 33: 358-370), and to PCSK9 (Gustafson et al, (2014) Cell Metab, 19: 310-318). Sortilin has also been shown to bind to and regulate extracellular levels of PCSK9, which directs low-density lipoprotein receptor for degradation in lysosomes, resulting in increased levels of LDL cholesterol (Gustafsen C et al., (2014). Cell Metab. 2014 Feb. 4; 19(2):310-8).

When present at intracellular vesicles such as endosomes, the amino-terminal extracellular domain of Sortilin is directed towards the lumen, where cargo of the vesicle is present. The carboxy-terminal intracellular/cytoplasmic domain of Sortilin however, binds to a series of adaptor proteins, which regulate its trafficking from the surface and within intracellular compartments. These include AP2 (a claforin adaptor to modulate endocytosis from the cell surface) and the Retromer Complex/API, which modulate movement from early endosomes to Golgi for recycling, and interaction with GGA (Golgi-localizing, gamma-ear containing, ADP-ribosylation factor binding) family proteins for movement from Golgi directly to early endosomes, usually for subsequent degradation through lysosomes. Thus, Sortilin can bind to ligands at its luminal domain, while engaging the cytoplasmic adaptors that determine its destination to determine intracellular fates, such as degradation for Progranulin and other factors.

Through its various interactions with proteins, such as Progranulin, Sortilin and its multiple ligands have been shown to be involved in various diseases, disorders, and conditions, such as frontotemporal dementia, amyotriphic lateral sclerosis, amyotriphic lateral sclerosis-frontotemporal dementia phenotypes, Alzheimer's disease, Parkinson's disease, depression, neuropsyciatric disorders, vascular dementia, seizures, retinal dystrophy, age related macular degeneration, glaucoma, traumatic brain injury, aging, seizures, wound healing, stroke, arforitis, and atherosclerotic vascular diseases.

Accordingly, there is a need for therapeutic antibodies that specifically bind Sortilin proteins and block the binding of Sortilin to its ligands, such as Progranulin, or otherwise modulate the effective concentration of the ligands, in order to treat one or more diseases, disorders, and conditions associated with Sortilin activity.

All references cited herein, including patent applications and publications, are hereby incorporated by reference in their entirety.

SUMMARY OF THE INVENTION

The present disclosure is generally directed to anti-Sortilin antibodies and methods of using such antibodies. The methods provided herein find use in preventing, reducing risk, or treating an individual having frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotriphic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arforitis, multiple sclerosis, metabolic disorder, obesity, insulin resistance, type 2 diabetes, tissue or vascular damage, an injury, intervertebral disc degeneration, or one or more undesirable symptoms of normal aging.

Certain aspects of the present disclosure are based, at least in part, on the identification of anti-Sortilin antibodies that are capable of blocking the interaction between Sortilin and Progranulin (see, e.g., Example 4), anti-Sortilin antibodies that are capable of increasing extracellular levels of Progranulin secreted by cells in culture and from cells in the brains of mouse models of Alzheimer's disease see, e.g., Example 5), anti-Sortilin antibodies that are capable of decreasing cellular levels of Sortilin in human primary monocytes (see, e.g., Example 25), and anti-Sortilin antibodies that are capable of increasing cellular levels of Progranulin in vivo (see, e.g. Example 26). Surprisingly, one class of antibodies was shown to be capable of increasing extracellular levels of Progranulin without being able to block the interaction between Sortilin and Progranulin (e.g., antibodies S-2, S-15, and S-22) while a second class of antibodies was shown to be capable of both blocking the interaction between Sortilin and Progranulin and increasing extracellular levels of Progranulin (e.g., antibodies S-8, S-49, and S-60). Moreover, anti-Sortilin antibodies capable of increasing extracellular levels of Progranulin (e.g., antibodies S-2, S-8, S-15, S-22, S-49, and S-60) were surprisingly shown to also reduce cellular levels of Sortilin, such as cell surface levels of Sortilin (see, e.g., Example 5). Furthermore, cellular levels of Sortilin were shown to be strongly and inversely correlated with increases in cellular levels of Progranulin (see, e.g., FIG. 10B-10E and FIGS. 23B and 23C). Anti-Sortilin antibodies capable of increasing extracellular levels of Progranulin are also capable of blocking pro-NGF binding to Sortilin (see, e.g., Example 6). Other aspects of the present disclosure are based, at least in part, on the identification of anti-Sortilin antibodies that block the interaction between Sortilin and Progranulin and are capable of increasing extracellular levels of Progranulin without reducing cellular levels of Sortilin (e.g., antibody S-30 and Example 30). Other aspects of the present disclosure are based, at least in part, on the identification of anti-Sortilin antibodies that block the interaction between Sortilin and Progranulin without increasing extracellular levels of Progranulin or reducing cellular levels of Sortilin (e.g., antibodies S-5 and S-64 and Example 5).

Accordingly, certain aspects of the present disclosure relate to an isolated (e.g., monoclonal) anti-Sortilin antibody, wherein the anti-Sortilin antibody has a property selected from the group consisting of: increasing extracellular levels of Progranulin, increasing cellular levels of Progranulin, decreasing cellular levels of Sortilin, inhibiting interaction between Sortilin and Progranulin, and any combination thereof.

In certain embodiments that may be combined with any of the preceding embodiments, the antibody decreases cell surface levels of Sortilin, decreases intracellular levels of Sortilin, decreases total levels of Sortilin, or any combination thereof. In certain embodiments that may be combined with any of the preceding embodiments, the anti-Sortilin antibody induces Sortilin degradation, Sortilin cleavage, Sortilin internalization, Sortilin down regulation, or any combination thereof. In certain embodiments that may be combined with any of the preceding embodiments, the anti-Sortilin antibody decreases cellular levels of Sortilin and does not inhibit the interaction between Sortilin and Progranulin. In certain embodiments that may be combined with any of the preceding embodiments, the anti-Sortilin antibody decreases cellular levels of Sortilin and inhibits the interaction between Sortilin and Progranulin. In certain embodiments that may be combined with any of the preceding embodiments, the anti-Sortilin antibody decreases cellular levels of Sortilin and increases cellular levels of Progranulin. In certain embodiments that may be combined with any of the preceding embodiments, the anti-Sortilin antibody increases cellular levels of Progranulin and does not inhibit the interaction between Sortilin and Progranulin. In certain embodiments that may be combined with any of the preceding embodiments, the anti-Sortilin antibody inhibits the interaction between Sortilin and Progranulin and increases cellular levels of Progranulin. In certain embodiments that may be combined with any of the preceding embodiments, the anti-Sortilin antibody increases levels of Progranulin in vivo. In certain embodiments that may be combined with any of the preceding embodiments, the anti-Sortilin antibody increases levels of Progranulin in vivo without decreasing cellular levels of Sortilin. In certain embodiments that may be combined with any of the preceding embodiments, the anti-Sortilin antibody increases levels of Progranulin in brain. In certain embodiments that may be combined with any of the preceding embodiments, the anti-Sortilin antibody increases cellular levels of Progranulin in blood. In certain embodiments that may be combined with any of the preceding embodiments, the anti-Sortilin antibody increases cellular levels of Progranulin in one or more peripheral organs. In certain embodiments that may be combined with any of the preceding embodiments, the anti-Sortilin antibody increases levels of Progranulin in brain, blood, one or more peripheral organs, or any combination thereof. In certain embodiments that may be combined with any of the preceding embodiments, the anti-Sortilin antibody decreases cellular levels of Sortilin in vivo. In certain embodiments that may be combined with any of the preceding embodiments, the anti-Sortilin antibody decreases cellular levels of Sortilin in brain. In certain embodiments that may be combined with any of the preceding embodiments, the anti-Sortilin antibody decreases cellular levels of Sortilin in one or more peripheral organs. In certain embodiments that may be combined with any of the preceding embodiments, the anti-Sortilin antibody decreases cellular levels of Sortilin in brain, one or more peripheral organs, or any combination thereof. In certain embodiments that may be combined with any of the preceding embodiments, the anti-Sortilin antibody inhibits the interaction between Sortilin and Progranulin and does not decrease cellular levels of Sortilin. In certain embodiments that may be combined with any of the preceding embodiments, the anti-Sortilin antibody increases cellular levels of Progranulin and does not decrease cellular levels of Sortilin. In certain embodiments that may be combined with any of the preceding embodiments, the anti-Sortilin antibody increases extracellular levels of Progranulin and does not inhibit the interaction between Sortilin and Progranulin. In certain embodiments that may be combined with any of the preceding embodiments, the anti-Sortilin antibody increases extracellular levels of Progranulin and inhibits the interaction between Sortilin and Progranulin. In certain embodiments that may be combined with any of the preceding embodiments, the anti-Sortilin antibody decreases cellular levels of Sortilin, increases extracellular levels of Progranulin, and does not inhibit the interaction between Sortilin and Progranulin. In certain embodiments that may be combined with any of the preceding embodiments, the anti-Sortilin antibody decreases cellular levels of Sortilin, increases extracellular levels of Progranulin, and inhibits the interaction between Sortilin and Progranulin. In certain embodiments that may be combined with any of the preceding embodiments, the anti-Sortilin antibody decreases cellular levels of Sortilin, increases cellular levels of Progranulin, and does not inhibit the interaction between Sortilin and Progranulin. In certain embodiments that may be combined with any of the preceding embodiments, the anti-Sortilin antibody decreases cellular levels of Sortilin, increases cellular levels of Progranulin, and inhibits the interaction between Sortilin and Progranulin. In certain embodiments that may be combined with any of the preceding embodiments, the anti-Sortilin antibody decreases cellular levels of Sortilin, increases extracellular levels of Progranulin, increases cellular levels of Progranulin, and does not inhibit the interaction between Sortilin and Progranulin. In certain embodiments that may be combined with any of the preceding embodiments, the anti-Sortilin antibody decreases cellular levels of Sot Olin, increases extracellular levels of Progranulin, inhibits the interaction between Sortilin and Progranulin, and does not increase cellular levels of Progranulin. In certain embodiments that may be combined with any of the preceding embodiments, the anti-Sortilin antibody decreases cellular levels of Sortilin, increases cellular levels of Progranulin, inhibits the interaction between Sortilin and Progranulin, and does not increase extracellular levels of Progranulin. In certain embodiments that may be combined with any of the preceding embodiments, the anti-Sortilin antibody increases cellular levels of Progranulin, increases extracellular levels of Progranulin, inhibits the interaction between Sortilin and Progranulin, and does not decrease cellular levels of Sortilin. In certain embodiments that may be combined with any of the preceding embodiments, the anti-Sortilin antibody decreases cellular levels of Sortilin, increases extracellular levels of Progranulin, does not increase cellular levels of Progranulin, and does not inhibit the interaction between Sortilin and Progranulin. In certain embodiments that may be combined with any of the preceding embodiments, the anti-Sortilin antibody decreases cellular levels of Sortilin, increases cellular levels of Progranulin, increases extracellular levels of Progranulin, and inhibits the interaction between Sortilin and Progranulin. In certain embodiments that may be combined with any of the preceding embodiments, the cellular levels of Progranulin, extracellular levels of Progranulin, cellular levels of Sortilin, or any combination thereof are measured utilizing an in vitro assay. In certain embodiments that may be combined with any of the preceding embodiments, the cellular levels of Progranulin, extracellular levels of Progranulin, cellular levels of Sortilin, or any combination thereof are measured utilizing a cell assay. In certain embodiments that may be combined with any of the preceding embodiments, the cellular levels of Progranulin, extracellular levels of Progranulin, cellular levels of Sortilin, or any combination thereof are measured utilizing an in vivo model. In certain embodiments that may be combined with any of the preceding embodiments, the anti-Sortilin antibody further inhibits interaction between Sortilin and pro-nerve growth factor (pro-NGF). In certain embodiments that may be combined with any of the preceding embodiments, the anti-Sortilin antibody further inhibits interaction between Sortilin and one or more proteins selected from the group consisting of a pro-neurotrophin, a neurotrophin, nerve growth factor (NGF), pro-brain-derived neurotrophic factor (pro-BDNF), brain-derived neurotrophic factor (BDNF), pro-neurotrophin-3, neurotrophin-3, pro-neurotrophin-4/5, neurotrophin-4/5, neurotensin, neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and receptor associated protein (RAP). In certain embodiments that may be combined with any of the preceding embodiments, the anti-Sortilin antibody further inhibits interaction between Sortilin and one or more proteins by: a) reducing the effective levels of Sortilin available for interacting with the one or more proteins; b) inducing degradation of Sortilin; or both. In certain embodiments that may be combined with any of the preceding embodiments, the anti-Sortilin antibody inhibits cellular secretion of PCSK9, inhibits A beta peptide production, or both. In certain embodiments that may be combined with any of the preceding embodiments, the anti-Sortilin antibody binds specifically to human Sortilin, mouse Sortilin, or both. In certain embodiments that may be combined with any of the preceding embodiments, the anti-Sortilin antibody is a human antibody, a humanized antibody, a bispecific antibody, a monoclonal antibody, a multivalent antibody, a conjugated antibody, or a chimeric antibody. In certain embodiments that may be combined with any of the preceding embodiments, the anti-Sortilin antibody is a bispecific antibody recognizing a first antigen and a second antigen. In certain embodiments that may be combined with any of the preceding embodiments, the first antigen is Sortilin and the second antigen is an antigen facilitating transport across the blood-brain-barrier. In certain embodiments that may be combined with any of the preceding embodiments, the second antigen is selected from the group consisting of Sortilin, transferring receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, THEM 30(A), a protein transduction domain, TAT, Syn-B, penetratin, a poly-arginine peptide, an angiopep peptide, basigin, Ghn1, and CD98 hc, and ANG1005. In certain embodiments that may be combined with any of the preceding embodiments, the anti-Sortilin antibody is an antibody fragment that binds to an epitope comprising amino acid residues on human Sortilin or a mammalian Sortilin protein. In certain embodiments that may be combined with any of the preceding embodiments, the fragment is an Fab, Fab', Fab'-SH, F(ab')2, Fv, or scFv fragment. In certain embodiments that may be combined with any of the preceding embodiments, the anti-Sortilin antibody further comprises one or more activities selected from the group consisting of: (a) inducing one or more Progranulin activities; (b) reducing endosomal internalization of Progranulin, or fragments thereof; and (c) increasing the effective concentration of Progranulin.

In certain embodiments that may be combined with any of the preceding embodiments, the anti-Sortilin antibody binds a discontinuous Sortilin epitope. In certain embodiments that may be combined with any of the preceding embodiments, the discontinuous Sortilin epitope comprises two or more peptides, three or more peptides, four or more peptides, five or more peptides, six or more peptides, seven or more peptide, eight or more peptides, nine or more peptides, or 10 or more peptides. In certain embodiments that may be combined with any of the preceding embodiments, each of the peptides comprise five or more, six or more, seven or more, eight or more, nine or more, 10 or more, 11 or more, 12 or more, 13 or more 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid residues of the amino acid sequence of SEQ ID NO: 1; or five or more, six or more, seven or more, eight or more, nine or more, 10 or more, 11 or more, 12 or more, 13 or more 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid residues on a mammalian Sortilin protein corresponding to the amino acid sequence of SEQ ID NO: 1. In certain embodiments that may be combined with any of the preceding embodiments, the anti-Sortilin antibody binds to a conformational epitope of Sortilin. In certain embodiments that may be combined with any of the preceding embodiments, the anti-Sortilin antibody binds to one or more amino acids within amino acid residues selected from the group consisting of: i, amino acid residues 740-749 of SEQ ID NO: 1, or amino acid residues on a mammalian Sortilin protein corresponding to amino acid residues 740-749 of SEQ ID NO: 1; ii. amino acid residues 623-632 of SEQ ID NO: 1, or amino acid residues on a mammalian Sortilin protein corresponding to amino acid residues 623-632 of SEQ ID NO: 1; iii. amino acid residues 429-443 of SEQ ID NO: 1, or amino acid residues on a mammalian Sortilin protein corresponding to amino acid residues 429-443 of SEQ ID NO: 1; iv. amino acid residues 367-391 of SEQ ID NO: 1, or amino acid residues on a mammalian Sortilin protein corresponding to amino acid residues 367-391 of SEQ ID NO: 1; v. amino acid residues 314-338 of SEQ ID NO: 1, or amino acid residues on a mammalian Sortilin protein corresponding to amino acid residues 314-338 of SEQ ID NO: 1; vi. amino acid residues 297-317 of SEQ ID NO: 1, or amino acid residues on a mammalian Sortilin protein corresponding to amino acid residues 297-317 of SEQ ID NO: 1; vii. amino acid residues 237-260 of SEQ ID NO: 1, or amino acid residues on a mammalian Sortilin protein corresponding to amino acid residues 237-260 of SEQ ID NO: 1; viii. amino acid residues 237-260 and 297-317 of SEQ ID NO: 1, or amino acid residues on a mammalian Sortilin protein corresponding to amino acid residues 237-260 and 297-317 of SEQ ID NO: 1; ix. amino acid residues 237-247 of SEQ ID NO: 1, or amino acid residues on a mammalian Sortilin protein corresponding to amino acid residues 237-247 of SEQ ID NO: 1; x. amino acid residues 237-247 and 314-338 of SEQ ID NO: 1, or amino acid residues on a mammalian Sortilin protein corresponding to amino acid residues 237-247 and 314-338 of SEQ ID NO: 1; xi. amino acid residues 233-243 of SEQ ID NO: 1, or amino acid residues on a mammalian Sortilin protein corresponding to amino acid residues 233-243 of SEQ ID NO: 1; xii. amino acid residues 212-221 of SEQ ID NO: 1, or amino acid residues on a mammalian Sortilin protein corresponding to amino acid residues 212-221 of SEQ ID NO: 1; xiii. amino acid residues 207-227 of SEQ ID NO: 1, or amino acid residues on a mammalian Sortilin protein corresponding to amino acid residues 207-227 of SEQ ID NO: 1; xiv. amino acid residues 207-227 and 237-260 of SEQ NO: 1, or amino acid residues on a mammalian Sortilin protein corresponding to amino acid residues 207-227 and 237-260 of SEQ ID NO: 1; xv. amino acid residues 207-231 of SEQ ID NO: 1, or amino acid residues on a mammalian Sortilin protein corresponding to amino acid residues 207-231 of SEQ ID NO: 1; xvi. amino acid residues 175-181 of SEQ ID NO: 1, or amino acid residues on a mammalian Sortilin protein corresponding to amino acid residues 175-181 of SEQ ID NO: 1; and xvii. amino acid residues 131-138 of SEQ ID NO: 1, or amino acid residues on a mammalian Sortilin protein corresponding to amino acid residues 131-138 of SEQ ID NO: 1. In certain embodiments that may be combined with any of the preceding embodiments, the anti-Sortilin antibody binds to one or more amino acid residues selected from the group consisting of H131, V132, P133, L134, V135, I136, M137, T138, T210, T218, Y222, S223, S227, S242, K243, K248, K254, S305, R311, S316, R325, S379, R382, Y386, and S595 of SEQ ID NO: 1, or one or more amino acid residues on a mammalian Sortilin protein corresponding to an amino acid residue selected from the group consisting of H131, V132, P133, L134, V135, I136, M137, T138, T210, T218, Y222, S223, S227, S242, K243, K248, K254, S305, R311, S316, R325, S379, R382, Y386, and S595 of SEQ ID NO: 1. In certain embodiments that may be combined with any of the preceding embodiments, the anti-Sortilin antibody binds to one or more amino acid residues selected from the group consisting of R88, F105, L108, R109, G110, D403, D449, T451, H461, G495, Y513, S530, I537, D552, F569, E590, F592, L593, S595, W597, I619, L621, E628, D632, L636, Q642, R646, and Y679 of SEQ ID NO: 1, or one or more amino acid residues on a mammalian Sortilin protein corresponding to an amino acid residue selected from the group consisting of R88F105, L108, R109, G110, D403, D449, T451, H461, G495, Y513, S530, I537, D552, F569, E590, F592, L593, S595, W597, I619, L621, E628, D632, L636, Q642, R646, and Y679.

In certain embodiments that may be combined with any of the preceding embodiments, the anti-Sortilin antibody comprises at least one, two, three, four, five, or six HVRs of an antibody selected from the group consisting of: S-5, S-6, S-8, S-45, S-49, S-60, S-63, S-64, S-65, S-72, and S-83. In certain embodiments that may be combined with any of the preceding embodiments, the anti-Sortilin antibody comprises: (a) an HVR-L1 comprising an amino acid sequence selected from the group consisting of SEQ ID NOs:6, 9-12, 14, and 15; (b) an HVR-L2 comprising an amino acid sequence selected from the group consisting of SEQ ID NOs:26, 27, 29, 30, and 32; (c) an HVR-L3 comprising an amino acid sequence selected from the group consisting of SEQ ID NOs:45, 46, 48, 85, 89, 100, 103-105, 112, and 123; (d) an comprising an amino acid sequence selected from the group consisting of SEQ ID NOs:126, 127, 136, 140, 142, 145, and 148; (e) an HVR-H2 comprising an amino acid sequence selected from the group consisting of SEQ ID NOs:151, 152, 163, 166, 169, 170, 173, and 175; or (f) an HVR-H3 comprising an amino acid sequence selected from the group consisting of SEQ ID NOs:182, 183, 185, 219, 223, 233, 236, 237, 244, and 254. In certain embodiments that may be combined with any of the preceding embodiments, the anti-Sortilin antibody comprises a light chain variable domain and a heavy chain variable domain, wherein the light chain variable domain comprises: (a) an HVR-L1 comprising an amino acid sequence selected from the group consisting of SEQ ID NOs:6, 9-12, 14, and 15, or an amino acid sequence with at least about 95% homology to an amino acid sequence selected from the group consisting of SEQ ID NOs:6, 9-12, 14, and 15; (b) an HVR-L2 comprising an amino acid sequence selected from the group consisting of SEQ ID NOs:26, 27, 29, 30, and 32, or an amino acid sequence with at least about 95% homology to an amino acid sequence selected from the group consisting of SEQ ID NOs:26, 27, 29, 30, and 32; and (c) an HVR-L3 comprising an amino acid sequence selected from the group consisting of SEQ ID NOs:45, 46, 48, 85, 89, 100, 103-105, 112, and 123, or an amino acid sequence with at least about 95% homology to an amino acid sequence selected from the group consisting of SEQ ID NOs:45, 46, 48, 85, 89, 100, 103-105, 112, and 123; and wherein the heavy chain variable domain comprises: (a) an HVR-H1 comprising an amino acid sequence selected from the group consisting of SEQ ID NOs:126, 127, 136, 140, 142, 145, and 148, or an amino acid sequence with at least about 95% homology to an amino acid sequence selected from the group consisting of SEQ ID NOs:126, 127, 136, 140, 142, 145, and 148; (b) HVR-H2 comprising an amino acid sequence selected from the group consisting of SEQ ID NOs:151, 152, 163, 166, 169, 170, 173, and 175, or an amino acid sequence with at least about 95% homology to an amino acid sequence selected from the group consisting of SEQ NOs:151, 152, 163, 166, 169, 170, 173, and 175; and (c) an HVR-H3 comprising an amino acid sequence selected from the group consisting of SEQ ID NOs:182, 183, 185, 219, 223, 233, 236, 237, 244, and 254 or an amino acid sequence with at least about 95% homology to an amino acid sequence selected from the group consisting of SEQ ID NOs:182, 183, 185, 219, 223, 233, 236, 237, 244, and 254. In certain embodiments that may be combined with any of the preceding embodiments, the anti-Sortilin antibody comprises a light chain variable domain comprising an amino acid sequence selected from the group consisting of SEQ ID NOs:324, 326, 330, 401, 409, 430, 436, 438, 439, 453, and 474; and/or a heavy chain variable domain comprising an amino acid sequence selected from the group consisting of SEQ NOs:325, 327, 331, 402, 410, 431, 437, 440, 454, and 475.

In certain embodiments that may be combined with any of the preceding embodiments, the anti-Sortilin antibody comprises at least one, two, three, four, five, or six HVRs of an antibody selected from the group consisting of: S-2, S-14, S-15, S-18, S-19, S-20, S-21, S-22, S-29, S-51, S57, S-61, and S-82. In certain embodiments that may be combined with any of the preceding embodiments, the anti-Sortilin antibody comprises: (a) an HVR-L1 comprising an amino acid sequence selected from the group consisting of SEQ ID NOs:7-10, 13, and 14; (b) an HVR-L2 comprising an amino acid sequence selected from the group consisting of SEQ NOs:26-31 and 33-35; (c) an HVR-L3 comprising an amino acid sequence selected from the group consisting of SEQ ID NOs:42, 54, 55, 58, 59, 60, 61, 62, 69, 91, 97, 101, and 122; (d) an HVR-H1 comprising an amino acid sequence selected from the group consisting of SEQ ID NOs:126, 129, 130, 135, 140, 142, and 147; (e) an HVR-H2 comprising an amino acid sequence selected from the group consisting of SEQ ID NOs:150, 155-158, 162, 166, 169, and 173; or (f) an HVR-H3 comprising an amino acid sequence selected from the group consisting of SEQ ID NOs:180, 190, 193-197, 203, 225, 231, 234, and 253. In certain embodiments that may be combined with any of the preceding embodiments, the anti-Sortilin antibody comprises a light chain variable domain and a heavy chain variable domain, wherein the light chain variable domain comprises: (a) an HVR-1-1 comprising an amino acid sequence selected from the group consisting of SEQ ID NOs:7-10, 13, and 14, or an amino acid sequence with at least about 95% homology to an amino acid sequence selected from the group consisting of SEQ ID NOs:7-10, 13, and 14; (b) an HVR-L2 comprising an amino acid sequence selected from the group consisting of SEQ ID NOs:26-31 and 33-35, or an amino acid sequence with at least about 95% homology to an amino acid sequence selected from the group consisting of SEQ ID NOs:26-31 and 33-35; and (c) an HVR-L3 comprising an amino acid sequence selected from the group consisting of SEQ NOs: 42, 54, 55, 58, 59, 60, 61, 62, 69, 91, 97, 101, and 122, or an amino acid sequence with at least about 95% homology to an amino acid sequence selected from the group consisting of SEQ ID NOs:42, 54, 55, 58, 59, 60, 61, 62, 69, 91, 97, 101, and 122; and wherein the heavy chain variable domain comprises: (a) an HVR-H1 comprising an amino acid sequence selected from the group consisting of SEQ ID NOs:126, 129, 130, 135, 140, 142, and 147, or an amino acid sequence with at least about 95% homology to an amino acid sequence selected from the group consisting of SEQ ID NOs:126, 129, 130, 135, 140, 142, and 147; (b) an HVR-H2 comprising an amino acid sequence selected from the group consisting of SEQ ID NOs:150, 155-158, 162, 166, 169, and 173, or an amino acid sequence with at least about 95% homology to an amino acid sequence selected from the group consisting of SEQ ID NOs:150, 155-158, 162, 166, 169, and 173; and (c) an HVR-H3 comprising an amino acid sequence selected from the group consisting of SEQ ID NOs:180, 190, 193-197, 203, 225, 231, 234, and 253, or an amino acid sequence with at least about 95% homology to an amino acid sequence selected from the group consisting of SEQ ID NOs:180, 190, 193-197, 203, 225, 231, 234, and 253. In certain embodiments that may be combined with any of the preceding embodiments, the anti-Sortilin antibody comprises a light chain variable domain comprising an amino acid sequence selected from the group consisting of SEQ ID NOs:319, 341, 343, 348, 350, 352, 354, 356, 370, 413, 425, 430, and 472; and/or a heavy chain variable domain comprising an amino acid sequence selected from the group consisting of SEQ ID NOs:320, 342, 349, 351, 353, 355, 357, 369, 414, 426, 431, and 473.

In certain embodiments that may be combined with any of the preceding embodiments, the anti-Sortilin antibody comprises at least one, two, three, four, five, or six HVRs of an antibody selected from the group consisting of: S-5, S-30, S-60-1, S-60-2, S-60-3, S-60-4, S-60-5, S-60-6, S-60-7, S-60-8, and S-60-9. In certain embodiments that may be combined with any of the preceding embodiments, the anti-Sortilin antibody comprises: (a) an HVR-L1 comprising the amino acid sequence of SEQ ID NO:10; (b) an HVR-L2 comprising the amino acid sequence of SEQ ID NO:30; (c) an HVR-L3 comprising an amino acid sequence selected from the group consisting of SEQ ID NOs:45, 70, and 100; (d) an HVR-H1 comprising an amino acid sequence selected from the group consisting of SEQ ID NOs:126, 136, and 142; (e) an HVR-H2 comprising an amino acid sequence selected from the group consisting of SEQ NOs:151, 163, and 170; or (f) an HVR-H3 comprising an amino acid sequence selected from the group consisting of SEQ ID NOs:182, 204, and 233. In certain embodiments that may be combined with any of the preceding embodiments, the anti-Sortilin antibody comprises a light chain variable domain and a heavy chain variable domain, wherein the light chain variable domain comprises: (a) an HVR-L1 comprising the amino acid sequence of SEQ ID NOs:10, or an amino acid sequence with at least about 95% homology to comprising the amino acid sequence of SEQ ID NO:10; (b) an HVR-L2 comprising the amino acid sequence of SEQ ID NOs:30, or an amino acid sequence with at least about 95% homology to comprising the amino acid sequence of SEQ ID NO:30; and (c) an HVR-L3 comprising an amino acid sequence selected from the group consisting of SEQ ID NOs:45, 70, and 100, or an amino acid sequence with at least about 95% homology to an amino acid sequence selected from the group consisting of SEQ ID NOs:45, 70, and 100; and wherein the heavy chain variable domain comprises: (a) an HVR-H1 comprising an amino acid sequence selected from the group consisting of SEQ ID NOs:126, 136, and 142, or an amino acid sequence with at least about 95% homology to an amino acid sequence selected from the group consisting of SEQ ID NOs:126, 136, and 142; (b) an HVR-112 comprising an amino acid sequence selected from the group consisting of SEQ ID NOs:151, 163, and 170, or an amino acid sequence with at least about 95% homology to an amino acid sequence selected from the group consisting of SEQ NOs:151, 163, and 170; and (c) an HVR-H3 comprising an amino acid sequence selected from the group consisting of SEQ ID NOs:182, 204, and 233, or an amino acid sequence with at least about 95% homology to an amino acid sequence selected from the group consisting of SEQ NOs:182, 204, and 233. In certain embodiments that may be combined with any of the preceding embodiments, the anti-Sortilin antibody comprises a light chain variable domain comprising an amino acid sequence selected from the group consisting of SEQ ID NOs:324, 371, and 430; and/or a heavy chain variable domain comprising an amino acid sequence selected from the group consisting of SEQ ID NOs:325, 372, and 431.

In certain embodiments that may be combined with any of the preceding embodiments, the anti-Sortilin antibody comprises a light chain variable domain and a heavy chain variable domain, wherein the light chain variable domain comprises: (a) an HVR-L1 comprising an amino acid sequence selected from the group consisting of SEQ ID NOs:6-16, 20-22, and 24-25, or an amino acid sequence with at least about 95% homology to an amino acid sequence selected from the group consisting of SEQ ID NOs:6-16, 20-22, and 24-25; (b) an HVR-L2 comprising an amino acid sequence selected from the group consisting of SEQ ID NOs:26-40, or an amino acid sequence with at least about 95% homology to an amino acid sequence selected from the group consisting of SEQ ID NOs:26-40; and (c) an HVR-L3 comprising an amino acid sequence selected from the group consisting of SEQ ID NOs:41-50, 52, 54-56, 58-62, 64-66, 68-70, 72, 74, 79-80, 82-85, 88-91, 95, 97-101, 103-107, 109, 111-116, 118, and 121-125, or an amino acid sequence with at least about 95% homology to an amino acid sequence selected from the group consisting of SEQ ID NOs:41-50, 52, 54-56, 58-62, 64-66, 68-70, 72, 74, 79-80, 82-85, 88-91, 95, 97-101, 103-107, 109, 111-116, 118, and 121-125; and wherein the heavy chain variable domain comprises: (a) an HVR-H1 comprising an amino acid sequence selected from the group consisting of SEQ ID NOs:126-127, 129-130, 133-140, 142, 144-145, and 147-149, or an amino acid sequence with at least about 95% homology to an amino acid sequence selected from the group consisting of SEQ ID NOs:126-127, 129-130, 133-140, 142, 144-145, and 147-149; (b) an HVR-H2 comprising an amino acid sequence selected from the group consisting of SEQ ID NOs:150-153, 155-158, 160-166, 169-175, and 177-178, or an amino acid sequence with at least about 95% homology to an amino acid sequence selected from the group consisting of SEQ ID NOs:150-153, 155-158, 160-166, 169-175, and 177-178; and (c) an HVR-H3 comprising an amino acid sequence selected from the group consisting of SEQ ID NOs:179-186, 188, 190-191, 193-197, 199-201, 203-204, 206, 208, 213-214, 216-219, 222-225, 229, 231-234, 236-239, 241, 243-247, 249, and 252-256 or an amino acid sequence with at least about 95% homology to an amino acid sequence selected from the group consisting of SEQ ID NOs:179-186, 188, 190-191, 193-197, 199-201, 203-204, 206, 208, 213-214, 216-219, 222-225, 229, 231-234, 236-239, 241, 243-247, 249, and 252-256.

In certain embodiments that may be combined with any of the preceding embodiments, the anti-Sortilin antibody competes with one or more antibodies selected from the group consisting of S-6, S-8, S-49, S-60, S-63, S-72, S-83, and any combination thereof for binding to Sortilin. In certain embodiments that may be combined with any of the preceding embodiments, the anti-Sortilin antibody competes with one or more antibodies selected from the group consisting of S-5, S-45, S-64, S-65, and any combination thereof for binding to Sortilin. In certain embodiments that may be combined with any of the preceding embodiments, the anti-Sortilin antibody competes with one or more antibodies selected from the group consisting of S-5, S-30. S-60, and any combination thereof for binding to Sortilin.

Other aspects of the present disclosure relate to an isolated (e.g., monoclonal) anti-Sortilin antibody, wherein the anti-Sortilin antibody comprises at least one, two, three, four, five, or six HVRs of an antibody selected from the group consisting of: S-1, S-2, S-3, S-4, S-5, S-6, S-7, S-8, S-9, S-10, S-12, S-14, S-15, S-16, S-18, S-19, S-20, S-21, S-22, S-24, S-25, S-26, S-28, S-29, S-30, S-32, S-34, S-39, S-40, S-42. S-43, S-44, S-45, S-48, S-49, S-50, S-51, S-55, S-57, S-58, S-59, S-60, S-61, S-63, S-64, S-65, S-66, S-67, S-69, S-71, S-72, S-73, S-74, S-75, S-76, S-78, S-81, S-82, S-83, S-84, and S-85. In certain embodiments that may be combined with any of the preceding embodiments, the anti-Sortilin antibody comprises: (a) an HVR-L1 comprising an amino acid sequence selected from the group consisting of SEQ NOs:6-16, 20-22, and 24-25; (b) an HVR-L2 comprising an amino acid sequence selected from the group consisting of SEQ ID NOs:26-40; (c) an HVR-L3 comprising an amino acid sequence selected from the group consisting of SEQ ID NOs:41-50, 52, 54-56, 58-62, 64-66, 68-70, 72, 74, 79-80, 82-85, 88-91, 95, 97-101, 103-107, 109, 111-116, 118, and 121-125; (d) an HVR-H1 comprising an amino acid sequence selected from the group consisting of SEQ ID NOs:126-127, 129-130, 133-140, 142, 144-145, and 147-149; (e) an HVR-H2 comprising an amino acid sequence selected from the group consisting of SEQ ID NOs:150-153, 155-158, 160-166, 169-175, and 177-178; or (f) an HVR-H3 van amino acid sequence selected from the group consisting of SEQ ID NOs:179-186, 188, 190-191, 193-197, 199-201, 203-204, 206, 208, 213-214, 216-219, 222-225, 229, 231-234, 236-239, 241, 243-247, 249, and 252-256. In certain embodiments that may be combined with any of the preceding embodiments, the anti-Sortilin antibody comprises a light chain variable domain and a heavy chain variable domain, wherein the light chain variable domain comprises: (a) an HVR-L1 comprising an amino acid sequence selected from the group consisting of SEQ ID NOs:6-16, 20-22, and 24-25, or an amino acid sequence with at least about 95% homology to an amino acid sequence selected from the group consisting of SEQ ID NOs:6-16, 20-22, and 24-25; (b) an HVR-L2 comprising an amino acid sequence selected from the group consisting of SEQ ID NOs:26-40, or an amino acid sequence with at least about 95% homology to an amino acid sequence selected from the group consisting of SEQ ID NOs:26-40; and (c) an HVR-L3 comprising an amino acid sequence selected from the group consisting of SEQ ID NOs:41-50, 52, 54-56, 58-62, 64-66, 68-70, 72, 74, 79-80, 82-85, 88-91, 95, 97-101, 103-107, 109, 111-116, 118, and 121-125, or an amino acid sequence with at least about 95% homology to an amino acid sequence selected from the group consisting of SEQ ID NOs:41-50, 52, 54-56, 58-62, 64-66, 68-70, 72, 74, 79-80, 82-85, 88-91, 95, 97-101, 103-107, 109, 111-116, 118, and 121-125; and wherein the heavy chain variable domain comprises: (a) an HVR-H1 comprising an amino acid sequence selected from the group consisting of SEQ ID NOs:126-127, 129-130, 133-140, 142, 144-145, and 147-149, or an amino acid sequence with at least about 95% homology to an amino acid sequence selected from the group consisting of SEQ NOs:126-127, 129-130, 133-140, 142, 144-145, and 147-149; (b) an HVR-1712 comprising an amino acid sequence selected from the group consisting of SEQ ID NOs:150-153, 155-158, 160-166, 169-175, and 177-178, or an amino acid sequence with at least about 95% homology to an amino acid sequence selected from the group consisting of SEQ ID NOs:150-153, 155-158, 160-166, 169-175, and 177-178; and (c) an HVR-H3 comprising an amino acid sequence selected from the group consisting of SEQ ID NOs:179-186, 188, 190-191, 193-197, 199-201, 203-204, 206, 208, 213-214, 216-219, 222-225, 229, 231-234, 236-239, 241, 243-247, 249, and 252-256 or an amino acid sequence with at least about 95% homology to an amino acid sequence selected from the group consisting of SEQ ID NOs:179-186, 188, 190-191, 193-197, 199-201, 203-204, 206, 208, 213-214, 216-219, 222-225, 229, 231-234, 236-239, 241, 243-247, 249, and 252-256. Other aspects of the present disclosure relate to an isolated (e.g., monoclonal) anti-Sortilin antibody, wherein the anti-Sortilin antibody comprises a light chain variable domain and/or a heavy chain variable domain comprising an amino acid sequence selected from the group consisting of SEQ ID NOs:317-334, 337-338, 341-345, 348-357, 360-365, 368-372, 375-376, 379-380, 389-392, 395-402, 407-414, 421-422, 425-433, 436-444, 447-448, 451-461, 464-465, and 470-479.

Other aspects of the present disclosure relate to an isolated (e.g., monoclonal) anti-Sortilin antibody, wherein the anti-Sortilin antibody competes with one or more antibodies selected from the group consisting of S-2, S-16, S-18, S-19, S-20, S-21, S-22, S-28, S-29, S-82, and any combination thereof for binding to Sortilin. Other aspects of the present disclosure relate to an isolated (e.g., monoclonal) anti-Sortilin antibody, wherein the anti-Sortilin antibody competes with one or more antibodies selected from the group consisting of S-1, S-3, S-4, S-6, S-7, S-9, S-10, S-14, S-15, S-26, S-32, S-48, S-51, S-55, S57, S-58, S-59, S-61, S-69, S-71, S-73, S-74, S-75, S-85, and any combination thereof for binding to Sortilin. Other aspects of the present disclosure relate to an isolated (e.g., monoclonal) anti-Sortilin antibody, wherein the anti-Sortilin antibody competes with one or more antibodies selected from the group consisting of S-5, S-12, S-24, S-25, S26, S-34, S-39, S-40, S-42, S-43, S-44, S-45, S-60, S-63, S-64, S-65, S-66, S-67, S-72, S-76, S-78, S-81, S-83, S-84, and any combination thereof for binding to Sortilin. Other aspects of the present disclosure relate to an isolated (e.g., monoclonal) anti-Sortilin antibody, wherein the anti-Sortilin antibody competes with one or more antibodies selected from the group consisting of S-8, S-49, S-50, and any combination thereof for binding to Sortilin. Other aspects of the present disclosure relate to an isolated (e.g., monoclonal) anti-Sortilin antibody which binds essentially the same Sortilin epitope as an antibody selected from the group consisting of S-1, S-2, S-3, S-4, S-5, S-6, S-7, S-8, S-9, S-10, S-12, S-14, S-15, S-16, S-18, S-19, S-20, S-21, S-22, S-24, S-25, S-26, S-28, S-29, S-30, S-32, S-34S-39, S-40, S-42, S-43S-44, S-45, S-48, S-49, S-50, S-51, S-55, S-57, S-58, S-59, S-60, S-61, S-63, S-64, S-65, S-66, S-67, S-69, S-71, S-72, S-73, S-74, S-75, S-76, S-78, S-81, S-82, S-83, S-84, and S-85.

Other aspects of the present disclosure relate to an isolated (e.g., monoclonal) anti-Sortilin antibody, wherein the anti-Sortilin antibody comprises a light chain variable domain and a heavy chain variable domain, wherein the light chain variable domain comprises: (a) an HVR-L1 comprising an amino acid sequence selected from the group consisting of SEQ ID NOs:6-16, 20-22, and 24-25, or an amino acid sequence with at least about 95% homology to an amino acid sequence selected from the group consisting of SEQ ID NOs:6-16, 20-22, and 24-25; (b) an HVR-112 comprising an amino acid sequence selected from the group consisting of SEQ ID NOs:26-40, or an amino acid sequence with at least about 95% homology to an amino acid sequence selected from the group consisting of SEQ ID NOs:26-40; and (c) an HVR-L3 comprising an amino acid sequence selected from the group consisting of SEQ ID NOs:41-50, 52, 54-56, 58-62, 64-66, 68-70, 72, 74, 79-80, 82-85, 88-91, 95, 97-101, 103-107, 109, 111-116, 118, and 121-125, or an amino acid sequence with at least about 95% homology to an amino acid sequence selected from the group consisting of SEQ ID NOs:41-50, 52, 54-56, 58-62, 64-66, 68-70, 72, 74, 79-80, 82-85, 88-91, 95, 97-101, 103-107, 109, 111-116, 118, and 121-125; or wherein the heavy chain variable domain comprises: (a) an HVR-H1 comprising an amino acid sequence selected from the group consisting of SEQ ID NOs:126-127, 129-130, 133-140, 142, 144-145, and 147-149, or an amino acid sequence with at least about 95% homology to an amino acid sequence selected from the group consisting of SEQ ID NOs:126-127, 129-130, 133-140, 142, 144-145, and 147-149; (b) an HVR-H2 comprising an amino acid sequence selected from the group consisting of SEQ ID NOs:150-153, 155-158, 160-166, 169-175, and 177-178, or an amino acid sequence with at least about 95% homology to an amino acid sequence selected from the group consisting of SEQ ID NOs:150-153, 155-158, 160-166, 169-175, and 177-178; and (c) an HVR-H3 comprising an amino acid sequence selected from the group consisting of SEQ ID NOs:179-186, 188, 190-191, 193-197, 199-201, 203-204, 206, 208, 213-214, 216-219, 222-225, 229, 231-234, 236-239, 241, 243-247, 249, and 252-256 or an amino acid sequence with at least about 95% homology to an amino acid sequence selected from the group consisting of SEQ ID NOs:179-186, 188, 190-191, 193-197, 199-201, 203-204, 206, 208, 213-214, 216-219, 222-225, 229, 231-234, 236-239, 241, 243-247, 249, and 252-256.

Other aspects of the present disclosure relate to an isolated (e.g., monoclonal) anti-Sortilin antibody that inhibits interaction between Sortilin and Progranulin, increases levels of Progranulin, and decreases cellular levels of Sortilin, wherein the anti-Sortilin antibody comprises at least one, two, three, four, five, or six HVRs of an antibody selected from the group consisting of: S-8, S-49, and S-60. In some embodiments, the antibody comprises a light chain variable domain and a heavy chain variable domain, wherein the light chain variable domain comprises: (a) an HVR-L1 comprising the amino acid sequence of SEQ NO:11, (b) comprising the amino acid sequence of SEQ ID NO:26; and (c) an HVR-13 comprising the amino acid sequence of SEQ ID NO:48; and wherein the heavy chain variable domain comprises: (a) an HVR-H1 comprising the amino acid sequence of SEQ ID NO:127; (b) an HVR-H2 comprising the amino acid sequence of SEQ ID NO:152; and (c) an HVR-H3 comprising the amino acid sequence of SEQ ID NO:185. In some embodiments, the antibody comprises a light chain variable domain and a heavy chain variable domain, wherein the light chain variable domain comprises: (a) an HVR-L1 comprising the amino acid sequence of SEQ ID NO:6; (b) comprising the amino acid sequence of SEQ ID NO:26; and (c) an HVR-L3 comprising the amino acid sequence of SEQ NO:89; and wherein the heavy chain variable domain comprises: (a) an HVR-H1 comprising the amino acid sequence of SEQ ID NO:140; (b) an HVR-H2 comprising the amino acid sequence of SEQ ID NO:166; and (c) an HVR-143 comprising the amino acid sequence of SEQ ID NO:223. In some embodiments, the antibody comprises a light chain variable domain and a heavy chain variable domain, wherein the light chain variable domain comprises: (a) an HVR-L1 comprising the amino acid sequence of SEQ ID NO:10; (b) comprising the amino acid sequence of SEQ ID NO: 30; and (c) an HVR-L3 comprising the amino acid sequence of SEQ ID NO:100; and wherein the heavy chain variable domain comprises: (a) an HVR-H1 comprising the amino acid sequence of SEQ ID NO:142, (b) an HVR-H2 comprising the amino acid sequence of SEQ NO:147; and (c) an HVR-H3 comprising the amino acid sequence of SEQ ID NO:233. Other aspects of the present disclosure relate to an isolated (e.g., monoclonal) anti-Sortilin antibody that inhibits interaction between Sortilin and Progranulin, increases levels of Progranulin, and decreases cellular levels of Sortilin, wherein the anti-Sortilin antibody competes with one or more antibodies selected from the group consisting of S-8, S-49, S-60, and any combination thereof for binding to Sortilin. Other aspects of the present disclosure relate to an isolated (e.g., monoclonal) anti-Sortilin antibody that inhibits interaction between Sortilin and Progranulin, increases levels of Progranulin, and decreases cellular levels of Sortilin, wherein the anti-Sortilin antibody binds to one or more amino acids within amino acid residues selected from the group consisting of: i, amino acid residues 429-443 of SEQ ID NO: 1, or amino acid residues on a mammalian Sortilin protein corresponding to amino acid residues 429-443 of SEQ ID NO: 1; ii. amino acid residues 232-243 of SEQ ID NO: 1, or amino acid residues on a mammalian Sortilin protein corresponding to amino acid residues 232-243 of SEQ ID NO: 1; and iii. amino acid residues 207-231 of SEQ ID NO: 1, or amino acid residues on a mammalian Sortilin protein corresponding to amino acid residues 207-231 of SEQ ID NO: 1.

Other aspects of the present disclosure relate to an isolated (e.g., monoclonal) anti-Sortilin antibody that increases levels of Progranulin and decreases cellular levels of Sortilin without inhibiting interaction between Sortilin and Progranulin, wherein the anti-Sortilin antibody comprises at least one, two, three, four, five, or six HVRs of an antibody selected from the group consisting of: S-2, S-19, and S-22. In some embodiments, the antibody comprises a light chain variable domain and a heavy chain variable domain, wherein the light chain variable domain comprises: (a) an HVR-L1 comprising the amino acid sequence of SEQ ID NO:7; (b) comprising the amino acid sequence of SEQ ID NO:27; and (c) an HVR-L3 comprising the amino acid sequence of SEQ ID N0:42, and wherein the heavy chain variable domain comprises: (a) an HVR-H1 comprising the amino acid sequence of SEQ ID NO:126; (b) an HVR-H2 comprising the amino acid sequence of SEQ ID NO:150; and (c) an HVR-H3 comprising the amino acid sequence of SEQ ID NO:180. In some embodiments, the antibody comprises a light chain variable domain and a heavy chain variable domain, wherein the light chain variable domain comprises: (a) an HVR-L1 comprising the amino acid sequence of SEQ ID NO:7; (b) comprising the amino acid sequence of SEQ ID NO: 35; and (c) an HVR-L3 comprising the amino acid sequence of SEQ ID NO:59; and wherein the heavy chain variable domain comprises: (a) an HVR-H1 comprising the amino acid sequence of SEQ ID NO:130; (b) an HVR-H2 comprising the amino acid sequence of SEQ ID NO:158; and (c) an HVR-H3 comprising the amino acid sequence of SEQ ID NO:194. In some embodiments, the antibody comprises a light chain variable domain and a heavy chain variable domain, wherein the light chain variable domain comprises: (a) an HVR-L1 comprising the amino acid sequence of SEQ ID NO:7; (b) comprising the amino acid sequence of SEQ ID NO:27; and (c) an HVR-1-3 comprising the amino acid sequence of SEQ NO:61; and wherein the heavy chain variable domain comprises: (a) an HVR-H1 comprising the amino acid sequence of SEQ ID NO:130; (b) an HVR-H2 comprising the amino acid sequence of SEQ ID NO:157; and (c) an HVR-H3 comprising the amino acid sequence of SEQ ID NO:196. Other aspects of the present disclosure relate to an isolated (e.g., monoclonal) anti-Sortilin antibody that increases levels of Progranulin and decreases cellular levels of Sortilin without inhibiting interaction between Sortilin and Progranulin, wherein the anti-Sortilin antibody competes with one or more antibodies selected from the group consisting of S-2, S-19, S-22, and any combination thereof for binding to Sortilin. Other aspects of the present disclosure relate to an isolated (e.g., monoclonal) anti-Sortilin antibody that increases levels of Progranulin and decreases cellular levels of Sortilin without inhibiting interaction between Sortilin and Progranulin, wherein the anti-Sortilin antibody binds to one or more amino acids within amino acid residues selected from the group consisting of: i. amino acid residues 237-260 and 297-317 of SEQ ID NO: 1, or amino acid residues on a mammalian Sortilin protein corresponding to amino acid residues 237-260 and 297-317 of SEQ ID NO: 1; and ii. amino acid residues 207-227 and 237-260 of SEQ ID NO: 1, or amino acid residues on a mammalian Sortilin protein corresponding to amino acid residues 207-227 and 237-260 of SEQ NO: 1.

Other aspects of the present disclosure relate to an isolated (e.g., monoclonal) anti-Sortilin antibody that inhibiting interaction between Sortilin and Progranulin without increasing levels of Progranulin and without decreasing cellular levels of Sortilin, wherein the anti-Sortilin antibody comprises at least one, two, three, four, five, or six HVRs of an antibody selected from the group consisting of: S-5 and S-64. In some embodiments, the antibody comprises a light chain variable domain and a heavy chain variable domain, wherein the light chain variable domain comprises: (a) an HVR-L1 comprising the amino acid sequence of SEQ ID NO:10; (b) comprising the amino acid sequence of SEQ ID NO:30; and (c) an HVR-L3 comprising the amino acid sequence of SEQ ID NO:45; and wherein the heavy chain variable domain comprises: (a) an HVR-H1 comprising the amino acid sequence of SEQ ID NO:126; (b) an HVR-H2 comprising the amino acid sequence of SEQ ID NO:151; and (c) an HVR-H3 comprising the amino acid sequence of SEQ ID NO:182. In some embodiments, the antibody comprises a light chain variable domain and a heavy chain variable domain, wherein the light chain variable domain comprises: (a) an HVR-L1 comprising the amino acid sequence of SEQ ID NO:15; (b) comprising the amino acid sequence of SEQ ID NO:27; and (c) an HVR-L3 comprising the amino acid sequence of SEQ ID NO:104; and wherein the heavy chain variable domain comprises: (a) an HVR-H1 comprising the amino acid sequence of SEQ ID NO:142; (b) an HVR-H2 comprising the amino acid sequence of SEQ ID NO:169; and (c) an HVR-H3 comprising the amino acid sequence of SEQ ID NO:236. Other aspects of the present disclosure relate to an isolated (e.g., monoclonal) anti-Sortilin antibody that inhibiting interaction between Sortilin and Progranulin without increasing levels of Progranulin and without decreasing cellular levels of Sortilin, wherein the anti-Sortilin antibody competes with one or more antibodies selected from the group consisting of S-5, S-64, and any combination thereof for binding to Sortilin.

Other aspects of the present disclosure relate to an isolated (e.g., monoclonal) anti-Sortilin antibody that inhibiting interaction between Sortilin and Progranulin and increases levels of Progranulin without decreasing cellular levels of Sortilin, wherein the anti-Sortilin antibody comprises at least one, two, three, four, five, or six HVRs of antibody S-30. In some embodiments, the antibody comprises a light chain variable domain and a heavy chain variable domain, wherein the light chain variable domain comprises: (a) an HVR-1-1 comprising the amino acid sequence of SEQ ID NO:10; (b) comprising the amino acid sequence of SEQ ID NO:30; and (c) an HVR-L3 comprising the amino acid sequence of SEQ ID NO:70; and wherein the heavy chain variable domain comprises: (a) an HVR-H1 comprising the amino acid sequence of SEQ ID NO:136; (b) an HVR-H2 comprising the amino acid sequence of SEQ ID NO:163; and (c) an HVR-H3 comprising the amino acid sequence of SEQ ID NO:204. Other aspects of the present disclosure relate to an isolated (e.g., monoclonal) anti-Sortilin antibody that inhibiting interaction between Sortilin and Progranulin and increases levels of Progranulin without decreasing cellular levels of Sortilin, wherein the anti-Sortilin antibody competes with antibody S-30 for binding to Sortilin.

Other aspects of the present disclosure relate to an isolated (e.g., monoclonal) anti-Sortilin antibody, wherein the anti-Sortilin antibody comprises a light chain variable domain and a heavy chain variable domain, wherein the light chain variable domain comprises: (a) an HVR-L1 comprising the amino acid sequence of RASQSISSYLN (SEQ NO:7); (b) an HVR-L2 comprising the amino acid sequence of AASSLQS (SEQ ID NO:27); and (c) an HVR-L3 comprising the amino acid sequence of QQSDVSPIT (SEQ ID NO:42); and/or wherein the heavy chain variable domain comprises: (a) an HVR-H1 comprising the amino acid sequence of YTFX$_1$X$_2$YX$_3$MX$_4$ (SEQ ID NO:480), wherein X$_1$ is T, G, V, P, L, F, A, or R, X$_2$ is G, A, or S, X$_3$ is Y, M, or L, and X$_4$ is H or W; (b) an HVR-H2 comprising the amino acid sequence of X$_1$X$_2$X$_3$PX$_4$X$_5$GX$_6$TX$_7$YAQKFQG (SEQ ID NO:481), wherein X$_1$ is W, I, or G, X$_2$ is I, V, or I, X$_3$ is N, G, or L, X$_4$ is N, S, V, or M, X$_5$ is S, G, W, or Q, X$_6$ is G, F, A, Y, S, N, or R, and X$_7$ is N, R, S, or M; and (c) an HVR-H3 comprising the amino acid sequence of ARGKRSSGWYEGYGMDV (SEQ ID NO:180). In certain embodiments, the anti-Sortilin antibody has at least one, two, three, four, five, or six HVRs selected from (i) HVR-L 1 comprising the amino acid sequence of any of the HVR-L1 sequences from an antibody selected from the group consisting of S-2, S-2-1, S-2-2, S-2-3, S-2-4, S-2-5, S-2-6, S-2-7, S-2-8, S-2-9, S-2-10, S-2-11, S-2-12, S- 2-13, S-2-14, and S-2-15; (ii) HVR-L2 comprising the amino acid sequence of any of the HVR-L2 sequences from an antibody selected from the group consisting of S-2, S-2-1, S-2-2, S-2-3, S-2-4, S-2-5, S-2-6, S-2-7, S-2-8, S-2-9, S-2-10, S-2-11, S-2-12, S-2-13, S-2-14, and S-2-15; (iii) HVR-L3 comprising the amino acid sequence of any of the HVR-L3 sequences from an antibody selected from the group consisting of S-2, S-2-1, S-2-2, S-2-3, S-2-4, S-2-5, S-2-6, S-2-7, S-2-8, S-2-9, S-2-10, S-2-11, S-2-12, S- 2-13, S-2-14, and S-2-15; (iv) HVR-H1 comprising the amino acid sequence of any of the HVR-H1 sequences from an antibody selected from the group consisting of S-2, S-2-1, S-2-2, S-2-3, S-2-4, S-2-5, S-2-6, S-2-7, S-2-8, S-2-9, S-2-10, S-2-11, S-2-12, S-2-13, S-2-14, and S-2-15; (v) HVR-H2 comprising the amino acid sequence of any of the HVR-H2 sequences from an antibody selected from the group consisting of S-2, S-2-1, S-2-2, S-2-3, S-2-4, S-2-5, S-2-6, S-2-7, S-2-8, S-2-9, S-2-10, S-2-11, S-2-12, S- 2-13, S-2-14, and S-2-15; and (vi) HVR-H3 comprising the amino acid sequence of any of the HVR-H3 sequences from an antibody selected from the group consisting of S-2, S-2-1, S-2-2, S-2-3, S-2-4, S-2-5, S-2-6, S-2-7, S-2-8, S-2-9, S-2-10, S-2-11, S-2-12, S-2-13, S-2-14, and S-2-15. In certain embodiments, anti-Sortilin antibody comprises a light chain variable region of any one of the antibodies sequences from an antibody selected from the group consisting of S-2, S-2-1, S-2-2, S-2-3, S-2-4, S-2-5, S-2-6, S-2-7, S-2-8, S-2-9, S-2-10, S-2-11, S-2-12, S-2-13, S-2-14, and S-2-15; and/or a heavy chain variable region of any one of the antibodies sequences from an antibody selected from the group consisting of S-2, S-2-1, S-2-2, S-2-3, S-2-4, S-2-5, S-2-6, S-2-7, S-2-8, S-2-9, S-2-10, S-2-11, S-2-12, S-2-13, S-2-14, and S-2-15. Other aspects of the present disclosure relate to an isolated (e.g., monoclonal) anti-Sortilin antibody, wherein the anti-Sortilin antibody comprises a light chain variable domain and a heavy chain variable domain, wherein the light chain variable domain comprises: (a) an HVR-L1 comprising the amino acid sequence of RASQSX$_1$X$_2$SNLA (SEQ ID NO:508), wherein X$_1$ is V or I and X$_2$ is S or G; (b) an HVR-L2 comprising the amino acid sequence of GASTRAT (SEQ ID NO:29); and (c) an HVR-L3 comprising the amino acid sequence of QQARLGPWT (SEQ ID NO:55); and/or wherein the heavy chain variable domain comprises: (a) an HVR-H1 comprising the amino acid sequence of YTX$_1$X$_2$X$_3$X$_4$X$_5$X$_6$S (SEQ ID NO:509), wherein X$_1$ is F or L, X$_2$ is T or A, X$_3$ is S or K, X$_4$ is Y, I, R, L, T, G, Q, or H, X$_5$ is Y, T, or L, and X$_6$ is M or I; (b) an HVR-H2 comprising the amino acid sequence of X$_1$INPx$_2$GGX$_3$X$_4$SYAX$_5$X$_6$FX$_7$G (SEQ ID NO:510), wherein X$_1$ is I or V, X$_2$ is S, W, Y, V, F, L, or I, X$_3$ is S or T, X$_4$ is T or A, X$_5$ is Q or R, X$_6$ is K, or R, and X$_7$ is Q or R, and (c) an HVR-H3 comprising the amino acid sequence of X$_1$RDPX$_2$GX$_3$X$_4$X$_5$X$_6$X$_7$PX$_8$X$_9$RX$_{10}$X$_{11}$X$_{12}$GX$_{13}$DV (SEQ NO:511), wherein X$_1$ is A, V, or T, X$_2$ is S, F, or G, X$_3$ is I or A, X$_4$ is A. or G, X$_5$ is A, L, or V, X$_6$ is A, L, or P, X$_7$ is G, F, or Y, X$_8$ is A, G, or F, X$_9$ is S, G, or A, X$_{10}$ is Y, G, P, H, or S, X$_{11}$ is Y or N, X$_{12}$ is Y, L, Q, or R, and X$_{13}$ is M or L. In certain embodiments, the anti-Sortilin antibody has at least one, two, three, four, five, or six HVRs selected from (i) HVR-L1 comprising the amino acid sequence of any of the HVR-L1 sequences from an antibody selected from the group consisting of S-15S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-10, S-15-6-11, S-15-6-12, S-15-6-13, S-15-7, S-15-8, S-15-9, S-15-10, S-15- 10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, and S-15-16; (ii) HVR-L2 comprising the amino acid sequence of any of the HVR-L2 sequences from an antibody selected from the group consisting of S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, and S-15-16; (iii) HVR-13 comprising the amino acid sequence of any of the HVR-13 sequences from an antibody selected from the group consisting of S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-S-15-11, S-15-12, S-15-13, S-15-14, S-15-15, and S-15-16; (iv) HVR-H1 comprising the amino acid sequence of any of the HVR-H1 sequences from an antibody selected from the group consisting of S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, and S-15-16; (v) HVR-H2 comprising the amino acid sequence of any of the HVR-H2 sequences from an antibody selected from the group consisting of S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S- 15-10-20, S- 15-10-21, S-15-11, S-15-12, S-15-13, S-15-14, S-15-15, and S-15-16; and (vi) HVR-H3 comprising the amino acid sequence of any of the HVR-H3 sequences from an antibody selected from the group consisting of S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13S-15-7, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, and S-15-16. In certain embodiments, anti-Sortilin antibody comprises a light chain variable region of any one of the antibodies sequences from an antibody selected from the group consisting of S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, and S-15-16; and/or a heavy chain variable region of any one of the antibodies sequences from an antibody selected from the group consisting of S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6 S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S- 15-12, S-15-13, S-15-14, S-15-15, and S-15-16. Other aspects of the present disclosure relate to an isolated (e.g., monoclonal) anti-Sortilin antibody, wherein the anti-Sortilin antibody comprises a light chain variable domain and a heavy chain variable domain, wherein the light chain variable domain comprises: (a) an HVR-L1 comprising the amino acid sequence of RASQSISSWLA (SEQ ID NO:8); (b) an HVR-L2 comprising the amino acid sequence of KASSLES (SEQ ID NO:28); and (c) an HVR-L3 comprising the amino acid sequence of QQADGHIT (SEQ ID NO:62); and/or wherein the heavy chain variable domain comprises: (a) an HVR-H1 comprising the amino acid sequence of $X_1TFX_2X_3YAX_4X_5$ (SEQ ID NO:565), wherein $X_1$ is G or Y, $X_2$ is S, R, G, or T, $X_3$ is S, G, or N, $X_4$ is I or M, and $X_5$ is S or A; (b) an HVR-H2 comprising the amino acid sequence of $GIX_1PX_2X_3GX_4AX_5YAQKFQG$ (SEQ ID NO:566), wherein $X_1$ is I or V, $X_2$ is I, R, G, A, S, T, or Q, $X_3$ is F or G, $X_4$ is T, R, or W, and $X_5$ is S, N, Q, or W; and (c) an HVR-H3 comprising the amino acid sequence of: RQGRKTGYYYYYGMDV (SEQ NO:197). In certain embodiments, the anti-Sortilin antibody has at least one, two, three, four, five, or six HVRs selected from (i) HVR-L1 comprising the amino acid sequence of any of the HVR-L1 sequences from an antibody selected from the group consisting of S-22, S-22-1, S-22-2, S-22-3, S-22-4, S-22-5, S-22-6, S-22-7, S-22-8, and S-22-9; (ii) HVR-L2 comprising the amino acid sequence of any of the HVR-L2 sequences from an antibody selected from the group consisting of S-22, S-22-1, S-22-2, S-22-3, S-22-4, S-22-5, S-22-6, S-22-7, S-22-8, and S-22-9; (iii) HVR-L3 comprising the amino acid sequence of any of the HVR-L3 sequences from an antibody selected from the group consisting of S-22, S-22-1, S-22-2, S-22-3, S-22-4, S-22-5, S-22-6, S-22-7, S-22-8, and S-22-9; (iv) HVR-H1 comprising the amino acid sequence of any of the HVR-H1 sequences from an antibody selected from the group consisting of S-22, S-22-1, S-22-2, S-22-3, S-22-4, S-22-5, S-22-6, S-22-7, S-22-8, and S-22-9; (v) HVR-H2 comprising the amino acid sequence of any of the HVR-H2 sequences from an antibody selected from the group consisting of S-22, S-22-1, S-22-2, S-22-3, S-22-4, S-22-5, S-22-6, S-22-7, S-22-8, and S-22-9; and (vi) HVR-H3 comprising the amino acid sequence of any of the HVR-H3 sequences from an antibody selected from the group consisting of S-22, S-22-1, S-22-2, S-22-3, S-22-4, S-22-5, S-22-6, S-22-7, S-22-8, and S-22-9. In certain embodiments, anti-Sortilin antibody comprises a light chain variable region of any one of the antibodies sequences from an antibody selected from the group consisting of S-22, S-22-1, S-22-2, S-22-3, S-22-4, S-22-5, S-22-6, S-22-7, S-22-8, and S-22-9; and/or a heavy chain variable region of any one of the antibodies sequences from an antibody selected from the group consisting of S-22, S-22-1, S-22-2, S-22-3, S-22-4, S-22-5, S-22-6, S-22-7, S-22-8, and S-22-9. Other aspects of the present disclosure relate to an isolated (e.g., monoclonal) anti-Sortilin antibody, wherein the anti-Sortilin antibody comprises a light chain variable domain and a heavy chain variable domain, wherein the light chain variable domain comprises: (a) an HVR-L1 comprising the amino acid sequence of $RSSQX_1LLX_2SNGYNYLD$ (SEQ ID NO:580), wherein $X_1$ is S or G and $X_2$ is H or R; (b) an HVR-L2 comprising the amino acid sequence of LGSNRXS (SEQ ID NO:581), wherein X is A or V; and (c) an HVR-L3 comprising the amino acid sequence of MQQQETPLT (SEQ NO:100); and/or wherein the heavy chain variable domain comprises; (a) an HVR-H1 comprising the amino acid sequence of $YSISSX_1X_2YWG$ (SEQ ID NO:582), wherein $X_1$ is G or V and $X_2$ is Y or R; (b) an HVR-H2 comprising the amino acid sequence of $X_1IYX_2SGSTYYNPSLKS$ (SEQ ID NO:583), wherein $X_1$ is T, S, or A and $X_2$ is H or P; and (c) an HVR-H3 comprising the amino acid sequence of ARQGSIKQGYYGMDV (SEQ ID NO:233). In certain embodiments, the anti-Sortilin antibody has at least one, two, three, four, five, or six HVRs selected from (i) HVR-L1 comprising the amino acid sequence of any of the HVR-L1 sequences from an antibody selected from the group consisting of S-60, S-60-1, S-60-2, S-60-3, S-60-4, S-60-5, S-60-6, S-60-7, S-60-8, and S-60-9; (ii) HVR-L2 comprising the amino acid sequence of any of the HVR-L2 sequences from an antibody selected from the group consisting of S-60, S-60-1, S-60-2, S-60-3, S-60-4, S-60-5, S-60-6, S-60-7, S-60-8, and S-60-9; (iii) HVR-L3 comprising the amino acid sequence of any of the HVR-L3 sequences from an antibody selected from the group consisting of S-60, S-60-1, S-60-2, S-60-3, S-60-4, S-60-5, S-60-6, S-60-7, S-60-8, and S-60-9; (iv) HVR-H1 comprising the amino acid sequence of any of the HVR-H1 sequences from an antibody selected from the group consisting of S-60, S-60-1, S-60-2, S-60-3, S-60-4, S-60-5, S-60-6, S-60-7, S-60-8, and S-60-9; (v) HVR-H2 comprising the amino acid sequence of any of the HVR-H2 sequences from an antibody selected from the group consisting of S-60, S-60-1, S-60-2, S-60-3, S-60-4, S-60-5, S-60-6, S-60-7, S-60-8, and S-60-9; and (vi) HVR-H3 comprising the amino acid sequence of any of the HVR-H3 sequences from an antibody selected from the group consisting of S-60, S-60-1, S-60-2, S-60-3, S-60-4, S-60-5, S-60-6, S-60-7, S-60-8, and S-60-9. In certain embodiments, anti-Sortilin antibody comprises a light chain variable region of any one of the antibodies sequences from an antibody selected from the group consisting of S-60, S-60-1, S-60-2, S-60-3, S-60-4, S-60-5, S-60-6, S-60-7, S-60-8, and S-60-9; and/or a heavy chain variable region of any one of the antibodies sequences from an antibody selected from the group consisting of S-60, S-60-1, S-60-2, S-60-3, S-60-4, S-60-5, S-60-6, S-60-7, S-60-8, and S-60-9. Other aspects of the present disclosure relate to an isolated (e.g., monoclonal) anti-Sortilin antibody, wherein the anti-Sortilin antibody comprises a light chain variable domain and a heavy chain variable domain, wherein the light chain variable domain comprises: (a) an HVR-L1 comprising the amino acid sequence of RASQSVSSSYLA (SEQ ID NO:14); (b) an HVR-L2 comprising the amino acid sequence of GASSRAT (SEQ ID NO:26); and (c) an HVR-L3 comprising the amino acid sequence of QQSHVSPWT (SEQ ID NO:122); and/or wherein the heavy chain variable domain comprises: (a) an HVR-H1 comprising the amino acid sequence of $X_1SIX_2SX_3X_4YYWG$ (SEQ ID NO:589), wherein $X_1$ is G or Y, $X_2$ is S, V, Y, K, or P, $X_3$ is S or R, and $X_4$ is D or E; (b) an HVR-H2 comprising the amino acid sequence of $X_1IYX_2X_3GSTX_4YNPSILKS$ (SEQ ID NO:590), wherein $X_1$ is S, G, Q, or L, $X_2$ is Y, W, or R, $X_3$ is S, R, K, or A, and $X_4$ is Y or V; and (c) an HVR-H3 comprising the amino acid sequence of ARGVGSGYSYGYRYFDY (SEQ ID NO:253). In certain embodiments, the anti-Sortilin antibody has at least one, two, three, four, five, or six HVRs selected from (i) HVR-L1 comprising the amino acid sequence of any of the HVR-L1 sequences from an antibody selected from the group consisting of S-82, S-82-1, S-82-2, S-82-3, S-82-4, S-82-5, S-82-6. S-82-7, and S-82-8; (ii) comprising the amino acid sequence of any of the HVR-L2 sequences from an antibody selected from the group consisting of S-82, S-82-1, S-82-2, S-82-3, S-82-4, S-82-5, S-82-6, S-82-7, and S-82-8; (iii) HVR-L3 comprising the amino acid sequence of any of the HVR-L3 sequences from an antibody selected from the group consisting of S-82, S-82-1, S-82-2, S-82-3, S-82-4, S-82-5, S-82-6, S-82-7, and S-82-8; (iv) HVR-H1 comprising the amino acid sequence of any of the HVR-H1 sequences from an antibody selected from the group consisting of S-82, S-82-1, S-82-2, S-82-3, S-82-4, S-82-5, S-82-6, S-82-7, and S-82-8; (v) HVR-H2 comprising the amino acid sequence of any of the HVR-H2 sequences from an antibody selected from the group consisting of S-82, S-82-1, S-82-2, S-82-3, S-82-4, S-82-5, S-82-6, S-82-7, and S-82-8; and (vi) HVR-H3 comprising the amino acid sequence of any of the HVR-H3 sequences from an antibody selected from the group consisting of S-82, S-82-1, S-82-2, S-82-3, S-82-4, S-82-5, S-82-6, S-82-7, and S-82-8. In certain embodiments, anti-Sortilin antibody comprises a light chain variable region of any one of the antibodies sequences from an antibody selected from the group consisting of S-82, S-82-1, S-82-2, S-82-3, S-82-4, S-82-5, S-82-6, S-82-7, and S-82-8; and/or a heavy chain variable region of any one of the antibodies sequences from an antibody selected from the group consisting of S-82, S-82-1, S-82-2, S-82-3, S-82-4, S-82-5, S-82-6, S-82-7, and S-82-8.

In certain embodiments that may be combined with any of the preceding embodiments, the anti-Sortilin antibody has an IgG1, IgG2, IgG3, or IgG4 isotype. In certain embodiments that may be combined with any of the preceding embodiments, (a) the anti-Sortilin antibody has a human or mouse IgG1 isotype and comprises one or more amino acid substitutions in the Fc region at a residue position selected from the group consisting of: N297A, N297Q, D265A, L234A, L235A, C226S, C229S, P238S, E233P, L234V, P238A, A327Q, A327G, P329A, K322A, L234F, L235E, P331S, T394, A330L, M252Y, S254T, T256E, and any combination thereof, wherein the numbering of the residues is according to EU or Kabat numbering; (b) the anti-Sortilin antibody has an IgG2 isotype and comprises one or more amino acid substitutions in the Fc region at a residue position selected from the group consisting of: P238S, V234A, G237A, H268A, H268Q, H268E, V309L, N297A, N297Q, A330S, P331S, C232S, C233S, M252Y, S254T, T256E, and any combination thereof, wherein the numbering of the residues is according to EU or Kabat numbering; or (c) the anti-Sortilin antibody has an IgG4 isotype and comprises one or more amino acid substitutions in the Fc region at a residue position selected from the group consisting of E233P, F234V, L234A/F234A, L235A, G237A, E318A, S228P, L236E, S241P, L248E, T394D, M252Y, S254T, T256E, N297A, N297Q, and any combination thereof, wherein the numbering of the residues is according to EU or Kabat numbering. In certain embodiments that may be combined with any of the preceding embodiments, (a) the Fc region further comprises one or more additional amino acid substitutions at a position selected from the group consisting of A330L, L234F; L235E, P331S, and any combination thereof, wherein the numbering of the residues is according to EU or Kabat numbering; (b) the Fc region further comprises one or more additional amino acid substitutions at a position selected from the group consisting of M252Y, S254T, T256E, and any combination thereof, wherein the numbering of the residues is according to EU or Kabat numbering; or (c) the Fc region further comprises a S228P amino acid substitution according to EU or Kabat numbering. In certain embodiments that may be combined with any of the preceding embodiments, the anti-Sortilin antibody decreases expression of one or more pro-inflammatory mediators selected from the group consisting of IL-6, IL12p70, IL12p40, IL-1β, TNF-α, CXCL1, CCL2, CCL3, CCL4, and CCL5. In certain embodiments that may be combined with any of the preceding embodiments, the anti-Sortilin antibody has a dissociation constant ($K_D$) for human Sortilin, mouse Sortilin, or both, that ranges from about 100 nM to about 0.005 nM, or less than 0.005 nM. In certain embodiments that may be combined with any of the preceding embodiments, the anti-Sortilin antibody has dissociation constant ($K_D$) for human Sortilin that ranges from about 70.4 nM to about 0.005 nM, or less than 0.005 nM. In certain embodiments that may be combined with any of the preceding embodiments, the anti-Sortilin antibody has dissociation constant ($K_D$) for mouse Sortilin that ranges from about 40.3 nM to about 0.07 nM, or less than 0.07 nM.

Other aspects of the present disclosure relate to an isolated (e.g., monoclonal) anti-Sortilin antibody, wherein the anti-Sortilin antibody hinds to one or more amino acid residues selected from the group consisting of R88, F105, L108, R109, G110, D403, D449, T451, H461, G495, Y513, S530, I537, D552, F569, E590, F592, L593, S595, W597, I619, L621, E628, D632, L636, Q642, R646, and Y679 of SEQ ID NO: 1, or one or more amino acid residues on a mammalian Sortilin protein corresponding to an amino acid residue selected from the group consisting of R88, F105, L108, R109, G110, D403, D449, T451, H461, G495, Y513, S530, I537, D552, F569, E590, F592, L593, S595, W597, I619, L621, E628, D632, L636, Q642. R646, and Y679. In certain embodiments, wherein the anti-Sortilin antibody binds to amino acid residue R88, or to amino acid residue D552, or to amino acid residues R88 and D552 of SEQ ID NO: 1, or to an amino acid residue on a mammalian Sortilin protein corresponding to an amino acid residue R88, or to an amino acid residue on a mammalian Sortilin protein corresponding to an amino acid residue D552, or to an amino acid residues on a mammalian Sortilin protein corresponding to an amino acid residues R88 and D552. In certain embodiments, wherein the anti-Sortilin antibody binds to one or more amino acid residues selected from the group consisting of D403, D449, T451, H461, and G495 of SEQ ID NO: 1, or one or more amino acid residues on a mammalian Sortilin protein corresponding to an amino acid residue selected from the group consisting of D403, D449, T451, H461, and G495. In certain embodiments, wherein the anti-Sortilin antibody binds to amino acid residues D403, D449, T451, H-461, and G495 of SEQ ID NO: 1, or to amino acid residues on a mammalian Sortilin protein corresponding to amino acid residues D403, D449, T451, H461, and G495. In certain embodiments, wherein the anti-Sortilin antibody binds to one or more amino acid residues selected from the group consisting of S530, L621, and D632 of SEQ ID NO: 1, or one or more amino acid residues on a mammalian Sortilin protein corresponding to an amino acid residue selected from the group consisting of S530, L621, and D632. In certain embodiments, wherein the anti-Sortilin antibody binds to amino acid residues S530, L621, and D632 of SEQ ID NO: 1, or amino acid residues on a mammalian Sortilin protein corresponding to amino acid residues S530, L621, and D632. In certain embodiments, wherein the anti-Sortilin antibody binds to one or more amino acid residues selected from the group consisting of F105, L108, R109, G110, I537, F569, E590, F592, L593, S595, and W597 of SEQ ID NO: 1, or one or more amino acid residues on a mammalian Sortilin protein corresponding to an amino acid residue selected from the group consisting of F105, L108, R109, G110, I537, F569, E590, F592, L593, S595, and W597. In certain embodiments, wherein the anti-Sortilin antibody binds to amino acid residues F105, L108, R109, G110, I537, F569, E590, F592, L593, S5595, and W597 of SEQ ID NO: 1, or amino acid residues on a mammalian Sortilin protein corresponding to an amino acid residues F105, L108, R109, G110, I537, F569, E590, F592, L593, S595, and W597. In certain embodiments, wherein the anti-Sortilin antibody binds to one or more amino acid residues selected from the group consisting of Y513; I619; E628; D632; L636; Q641; R646; and Y679 of SEQ ID NO: 1, or one or more amino acid residues on a mammalian Sortilin protein corresponding to an amino acid residue selected from the group consisting of Y513; I1619; E628; D632; L636, Q641; R646; and Y679. In certain embodiments, wherein the anti-Sortilin antibody binds to amino acid residues Y513; I619; E628; D632; L636; Q641; R646; and Y679 of SEQ ID NO: 1, or amino acid residues on a mammalian Sortilin protein corresponding to an amino acid residues Y513; I619; E628; D632; L636; Q641; R646; and Y679.

In certain embodiments that may be combined with any of the preceding embodiments, wherein the anti-Sortilin antibody has a property selected from the group consisting of: increasing extracellular levels of Progranulin, increasing cellular levels of Progranulin, decreasing cellular levels of Sortilin, inhibiting interaction between Sortilin and Progranulin, and any combination thereof. In certain embodiments that may be combined with any of the preceding embodiments, wherein the antibody decreases cell surface levels of Sortilin, decreases intracellular levels of Sortilin, decreases total levels of Sortilin, or any combination thereof. In certain embodiments that may be combined with any of the preceding embodiments, wherein the anti-Sortilin antibody induces Sortilin degradation, Sortilin cleavage, Sortilin internalization, Sortilin down regulation, or any combination thereof. In certain embodiments that may be combined with any of the preceding embodiments, wherein the anti-Sortilin antibody decreases cellular levels of Sortilin and does not inhibit the interaction between Sortilin and Progranulin. In certain embodiments that may be combined with any of the preceding embodiments, wherein the anti-Sortilin antibody decreases cellular levels of Sortilin and inhibits the interaction between Sortilin and Progranulin. In certain embodiments that may be combined with any of the preceding embodiments, wherein the anti-Sortilin antibody decreases cellular levels of Sortilin and increases cellular levels of Progranulin. In certain embodiments that may be combined with any of the preceding embodiments, wherein the anti-Sortilin antibody increases cellular levels of Progranulin and does not inhibit the interaction between Sortilin and Progranulin. In certain embodiments that may be combined with any of the preceding embodiments, wherein the anti-Sortilin antibody inhibits the interaction between Sortilin and Progranulin and increases cellular levels of Progranulin. In certain embodiments that may be combined with any of the preceding embodiments, wherein the anti-Sortilin antibody increases levels of Progranulin in vivo. In certain embodiments that may be combined with any of the preceding embodiments, wherein the anti-Sortilin antibody increases levels of Progranulin in viva without decreasing cellular levels of Sortilin. In certain embodiments that may be combined with any of the preceding embodiments, wherein the anti-Sortilin antibody increases levels of Progranulin in brain, blood, one or more peripheral organs, or any combination thereof. In certain embodiments that may be combined with any of the preceding embodiments, wherein the anti-Sortilin antibody decreases cellular levels of Sortilin in vivo. In certain embodiments that may be combined with any of the preceding embodiments, wherein the anti-Sortilin antibody decreases cellular levels of Sortilin in brain, one or more peripheral organs, or any combination thereof. In certain embodiments that may be combined with any of the preceding embodiments, wherein the anti-Sortilin antibody inhibits the interaction between Sortilin and Progranulin and does not decrease cellular levels of Sortilin. In certain embodiments that may be combined with any of the preceding embodiments, wherein the anti-Sortilin antibody increases cellular levels of Progranulin and does not decrease cellular levels of Sortilin. In certain embodiments that may be combined with any of the preceding embodiments, wherein the anti-Sortilin antibody further inhibits interaction between Sortilin and pro-nerve growth factor (pro-NGF). In certain embodiments that may be combined with any of the preceding embodiments, wherein the anti-Sortilin antibody further inhibits interaction between Sortilin and one or more proteins by: a) reducing the effective levels of Sortilin available for interacting with the one or more proteins; b) inducing degradation of Sortilin; or both. In certain embodiments that may be combined with any of the preceding embodiments, wherein the anti-Sortilin antibody binds specifically to human Sortilin, mouse Sortilin, or both. In certain embodiments that may be combined with any of the preceding embodiments, wherein the anti-Sortilin antibody is a human antibody, a humanized antibody, a bispecific antibody, a monoclonal antibody, a multivalent antibody, a conjugated antibody, or a chimeric antibody. In certain embodiments that may be combined with any of the preceding embodiments, wherein the anti-Sortilin antibody is a bispecific antibody recognizing a first antigen and a second antigen. In certain embodiments that may be combined with any of the preceding embodiments, wherein the first antigen is Sortilin and the second antigen is an antigen facilitating transport across the blood-brain-barrier. In certain embodiments that may be combined with any of the preceding embodiments, wherein the second antigen is selected from the group consisting of Sortilin, transferring receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, basigin, Glut1, CD98 hc, and ANG1005. In certain embodiments that may be combined with any of the preceding embodiments, wherein the anti-Sortilin antibody is an antibody fragment that binds to an epitope comprising amino acid residues on human Sortilin or a mammalian Sortilin protein. In certain embodiments that may be combined with any of the preceding embodiments, wherein the fragment is an Fab, Fab', Fab'-SH, F(ab')2, Fv, or scFv fragment. In certain embodiments that may be combined with any of the preceding embodiments, wherein the anti-Sortilin antibody further comprises one or more activities selected from the group consisting of: (a) inducing one or more Progranulin activities; (b) reducing endosomal internalization of Progranulin, or fragments thereof; and (c) increasing the effective concentration of Progranulin. In certain embodiments that may be combined with any of the preceding embodiments, herein the anti-Sortilin antibody comprises at least one, two, three, four, five, or six HVRs of an antibody selected from the group consisting of S-2-2, S-15-6, S-22-9, S-60, and S-82-8. In certain embodiments that may be combined with any of the preceding embodiments, wherein the anti-Sortilin antibody comprises at least one, two, three, four, five, or six HVRs of antibody S-2-2. In certain embodiments that may be combined with any of the preceding embodiments, wherein the anti-Sortilin antibody comprises a light chain variable domain and a heavy chain variable domain, wherein the light chain variable domain comprises an HVR-L1 comprising the amino acid sequence of SEQ ID NO:7, an HVR-L2 comprising the amino acid sequence of SEQ ID NO:27, and an HVR-L3 comprising the amino acid sequence of SEQ ID NO:42, and wherein the heavy chain variable domain comprises an HVR-H1 comprising the amino acid sequence of SEQ ID NO:483, an HVR-H2 comprising the amino acid sequence of SEQ ID NO:494, and an HVR-H3 comprising the amino acid sequence of SEQ ID NO:180. In certain embodiments that may be combined with any of the preceding embodiments, wherein the anti-Sortilin antibody comprises a light chain variable domain comprising the amino acid sequence of SEQ ID NO:319, and a heavy chain variable domain comprising the amino acid sequence of SEQ ID NO:606. In certain embodiments that may be combined with any of the preceding embodiments, wherein the anti-Sortilin antibody comprises at least one, two, three, four, five, or six HVRs of antibody S-15-6. In certain embodiments that may be combined with any of the preceding embodiments, wherein the anti-Sortilin antibody comprises a light chain variable domain and a heavy chain variable domain, wherein the light chain variable domain comprises an HVR-L1 comprising the amino acid sequence of SEQ NO:9, an HVR-L2 comprising the amino acid sequence of SEQ ID NO:29, an HVR-L3 comprising the amino acid sequence of SEQ ID NO:55, and wherein the heavy chain variable domain comprises an HVR-H1 comprising the amino acid sequence of SEQ ID NO:516, an HVR-H2 comprising the amino acid sequence of SEQ ID NO:527, and an HVR-H3 comprising the amino acid sequence of SEQ ID NO:190. In certain embodiments that may be combined with any of the preceding embodiments, wherein the anti-Sortilin antibody comprises a light chain variable domain comprising the amino acid sequence of SEQ ID NO:343, and a heavy chain variable domain comprising the amino acid sequence of SEQ ID NO:624. In certain embodiments that may be combined with any of the preceding embodiments, wherein the anti-Sortilin antibody comprises at least one, two, three, four, five, or six HVRs of antibody S-22-9. In certain embodiments that may be combined with any of the preceding embodiments, wherein the anti-Sortilin antibody comprises a light chain variable domain and a heavy chain variable domain, wherein the light chain variable domain comprises an HVR-L1 comprising the amino acid sequence of SEQ ID NO:8, an HVR-L2 comprising the amino acid sequence of SEQ ID NO:28, an HVR-L3 comprising the amino acid sequence of SEQ ID NO:62, and wherein the heavy chain variable domain comprises an HVR-H1 comprising the amino acid sequence of SEQ ID NO:570, an HVR-H2 comprising the amino acid sequence of SEQ ID NO:579, and anti HVR-H3 comprising the amino acid sequence of SEQ ID NO:197. In certain embodiments that may be combined with any of the preceding embodiments, wherein the anti-Sortilin antibody comprises a light chain variable domain comprising the amino acid sequence of SEQ ID NO:356, and a heavy chain variable domain comprising the amino acid sequence of SEQ ID NO:678. In certain embodiments that may be combined with any of the preceding embodiments, wherein the anti-Sortilin antibody comprises at least one, two, three, four, five, or six HVRs of antibody S-60. In certain embodiments that may be combined with any of the preceding embodiments, wherein the anti-Sortilin antibody comprises a light chain variable domain and a heavy chain variable domain, wherein the light chain variable domain comprises an HVR-L1 comprising the amino acid sequence of SEQ ID NO:10, an HVR-L2 comprising the amino acid sequence of SEQ ID NO:30, an HVR-L3comprising the amino acid sequence of SEQ ID NO:100, and wherein the heavy chain variable domain comprises an HVR-H1 comprising the amino acid sequence of SEQ ID NO:142, an HVR-H2 comprising the amino acid sequence of SEQ ID NO:170, and an HVR-H3 comprising the amino acid sequence of SEQ ID NO:233. In certain embodiments that may be combined with any of the preceding embodiments, wherein the anti-Sortilin antibody comprises a light chain variable domain comprising the amino acid sequence of SEQ ID NO:430, and a heavy chain variable domain comprising the amino acid sequence of SEQ ID NO:431. In certain embodiments that may be combined with any of the preceding embodiments, wherein the anti-Sortilin antibody comprises at least one, two, three, four, five, or six HVRs of antibody S-82-8. In certain embodiments that may be combined with any of the preceding embodiments, wherein the anti-Sortilin antibody comprises a light chain variable domain and a heavy chain variable domain, wherein the light chain variable domain comprises an HVR-L1 comprising the amino acid sequence of SEQ ID NO:14, an HVR-L2 comprising the amino acid sequence of SEQ ID NO:26, an HVR-L3 comprising the amino acid sequence of SEQ ID NO:122, and wherein the heavy chain variable domain comprises an HVR-H1 comprising the amino acid sequence of SEQ ID NO:596, an HVR-H2 comprising the amino acid sequence of SEQ ID NO:603, and an HVR-H3 comprising the amino acid sequence of SEQ ID NO:253. In certain embodiments that may be combined with any of the preceding embodiments, wherein the anti-Sortilin antibody comprises a light chain variable domain comprising the amino acid sequence of SEQ ID NO:472, and a heavy chain variable domain comprising the amino acid sequence of SEQ ID NO:692. In certain embodiments that may be combined with any of the preceding embodiments, wherein the anti-Sortilin antibody competes with one or more antibodies selected from the group consisting of S-2-2, S-15-6, S-22-9, S-60, and S-82-8, and any combination thereof for binding to Sortilin. In certain embodiments that may be combined with any of the preceding embodiments, wherein the anti-Sortilin antibody competes with antibody S-2-2 for binding to Sortilin. In certain embodiments that may be combined with any of the preceding embodiments, wherein the anti-Sortilin antibody competes with antibody S-15-6 for binding to Sortilin. In certain embodiments that may be combined with any of the preceding embodiments, wherein the anti-Sortilin antibody competes with antibody S-22-9 for binding to Sortilin. In certain embodiments that may be combined with any of the preceding embodiments, wherein the anti-Sortilin antibody competes with antibody S-60 for binding to Sortilin. In certain embodiments that may be combined with any of the preceding embodiments, wherein the anti-Sortilin antibody competes with antibody S-82-8 for binding to Sortilin. In certain embodiments that may be combined with any of the preceding embodiments, wherein the anti-Sortilin antibody binds essentially the same Sortilin epitope as an antibody selected from the group consisting of S-2-2, S-15-6, S-22-9, S-60, and S-82-8. In certain embodiments that may be combined with any of the preceding embodiments, wherein the anti-Sortilin antibody binds essentially the same Sortilin epitope as antibody S-2-2. In certain embodiments that may be combined with any of the preceding embodiments, wherein the anti-Sortilin antibody binds essentially the same Sortilin epitope as antibody S-15-6. In certain embodiments that may be combined with any of the preceding embodiments, wherein the anti-Sortilin antibody binds essentially the same Sortilin epitope as antibody S-22-9. In certain embodiments that may be combined with any of the preceding embodiments, wherein the anti-Sortilin antibody binds essentially the same Sortilin epitope as antibody S-60. In certain embodiments that may be combined with any of the preceding embodiments, herein the anti-Sortilin antibody binds essentially the same Sortilin epitope as antibody S-82-8. In certain embodiments that may be combined with any of the preceding embodiments, wherein the anti-Sortilin antibody has an IgG1, IgG2, IgG3, or IgG4 isotype. In certain embodiments that may be combined with any of the preceding embodiments, wherein (a) the anti-Sortilin antibody has a human or mouse IgG1 isotype and comprises one or more amino acid substitutions in the Fc region at a residue position selected from the group consisting of: N297A, N297Q, D265A, L234A, L235A, C226S, C229S, P238S, E233P, L234V, P238A, A327Q, A327G, P329A, K322A, L234F, L235E, P331S, T394D, A330L, M252Y, S254T, T256E, and any combination thereof, wherein the numbering of the residues is according to EU numbering; (b) the anti-Sortilin antibody has an IgG2 isotype and comprises one or more amino acid substitutions in the Fc region at a residue position selected from the group consisting of P238S, V234A, G237A, H268A, H268Q, H268E, V309L, N297A, N297Q, A330S, P331S, C232S, C233S, M252Y, S254T, T256E, and any combination thereof, wherein the numbering of the residues is according to EU numbering; or (c) the anti-Sortilin antibody has an IgG4 isotype and comprises one or more amino acid substitutions in the Fc region at a residue position selected from the group consisting of: E233P, F234V, L234A/F234A, L235A, G237A, E318A, S228P, L236E, S241P, L248E, T394D, M252Y, S254T, T256E, N297A, N297Q, and any combination thereof, wherein the numbering of the residues is according to EU numbering. In certain embodiments that may be combined with any of the preceding embodiments, wherein: (a) the Fc region further comprises one or more additional amino acid substitutions at a position selected from the group consisting of A330L, L234F; L235E, P331 S, and any combination thereof, wherein the numbering of the residues is according to EU numbering; (b) the Fc region further comprises one or more additional amino acid substitutions at a position selected from the group consisting of M252Y, S254T, T256E, and any combination thereof, wherein the numbering of the residues is according to EU numbering; or (c) the Fc region further comprises a S228P amino acid substitution according to EU numbering. In certain embodiments that may be combined with any of the preceding embodiments, wherein the anti-Sortilin antibody has an IgG4 isotype. In certain embodiments that may be combined with any of the preceding embodiments, wherein the anti-Sortilin antibody comprises an S228P amino acid substitution at residue position 228, an F234A amino acid substitution at residue position 234, and an L235A amino acid substitution at residue position 235, wherein the numbering of the residue position is according to EU numbering. In certain embodiments that may be combined with any of the preceding embodiments, wherein the anti-Sortilin antibody decreases expression of one or more pro-inflammatory mediators selected from the group consisting of IL-6, IL12p70, IL12p40, IL-1β, TNF-α, CXCL1, CCL2, CCL3, CCL4, and CCL5. In certain embodiments that may be combined with any of the preceding embodiments, wherein the anti-Sortilin antibody has a dissociation constant ($K_D$) for human Sortilin, mouse Sortilin, or both, that ranges from about 100 nM to about 0.005 nM, or less than 0.005 nM. In certain embodiments that may be combined with any of the preceding embodiments, wherein the anti-Sortilin antibody has dissociation constant ($K_D$) for human Sortilin that ranges from about 70.4 nM to about 0.005 nM, or less than 0.005 nM. In certain embodiments that may be combined with any of the preceding embodiments, wherein the anti-Sortilin antibody has dissociation constant ($K_D$) for mouse Sortilin that ranges from about 40.3 nM to about 0.07 nM, or less than 0.07 nM.

Other aspects of the present disclosure relate to an isolated nucleic acid comprising a nucleic acid sequence encoding the anti-Sortilin antibody of any of the preceding embodiments. Other aspects of the present disclosure relate to a vector comprising the nucleic acid of any of the preceding embodiments. Other aspects of the present disclosure relate to an isolated host cell comprising the vector of any of the preceding embodiments. Other aspects of the present disclosure relate to a method of producing an anti-Sortilin antibody, comprising culturing the host cell of any of the preceding embodiments so that the anti-Sortilin antibody is produced. In certain embodiments, the method further comprises recovering the anti-Sortilin antibody produced by the host cell. Other aspects of the present disclosure relate to an isolated anti-Sortilin antibody produced by the method of any of the preceding embodiments. Other aspects of the present disclosure relate to a pharmaceutical composition comprising the anti-Sortilin antibody of any of the preceding embodiments, and a pharmaceutically acceptable carrier.

Other aspects of the present disclosure relate to a method of increasing Progranulin levels in the brain of an individual in need thereof, comprising administering to the individual a therapeutically effective amount of an anti-Sortilin antibody. Other aspects of the present disclosure relate to an anti-Sortilin antibody for use in increasing Progranulin levels in the brain of an individual in need thereof. Other aspects of the present disclosure relate to use of an anti-Sortilin antibody in the manufacture of a medicament for increasing Progranulin levels in the brain of an individual in need thereof. Other aspects of the present disclosure relate to a method of increasing Progranulin levels in an individual in need thereof, comprising administering to the individual a therapeutically effective amount of an anti-Sortilin antibody. Other aspects of the present disclosure relate to an anti-Sortilin antibody for use in increasing Progranulin levels in an individual in need thereof. Other aspects of the present disclosure relate to use of an anti-Sortilin antibody in the manufacture of a medicament for increasing Progranulin levels in an individual in need thereof. In certain embodiments that may be combined with any of the preceding embodiments, levels of Progranulin are increased in the brain, blood, and/or or one or more peripheral organs of the individual. In certain embodiments that may be combined with any of the preceding embodiments, levels of Progranulin are increased without decreasing cellular levels of Sortilin.

Other aspects of the present disclosure relate to a method of increasing extracellular levels of Progranulin from one or more cells, comprising contacting one or more cells with an anti-Sortilin antibody. Other aspects of the present disclosure relate to an anti-Sortilin antibody for use in increasing extracellular levels of Progranulin from one or more cells. Other aspects of the present disclosure relate to use of an anti-Sortilin antibody in the manufacture of a medicament for increasing extracellular levels of Progranulin from one or more cells. In certain embodiments that may be combined with any of the preceding embodiments, levels of Progranulin are increased without decreasing cellular levels of Sortilin. Other aspects of the present disclosure relate to a method of decreasing cellular levels of Sortilin in an individual in need thereof, comprising administering to the individual a therapeutically effective amount of an anti-Sortilin antibody. Other aspects of the present disclosure relate to an anti- Sortilin antibody for use in decreasing cellular levels of Sortilin in an individual in need thereof. Other aspects of the present disclosure relate to use of an anti-Sortilin antibody in the manufacture of a medicament for decreasing cellular levels of Sortilin in an individual in need thereof. In certain embodiments that may be combined with any of the preceding embodiments, levels of Sortilin are decreased in the brain, and/or one or more peripheral organs of the individual. Other aspects of the present disclosure relate to a method of decreasing cellular levels of Sortilin of one or more cells, comprising contacting one or more cells with an anti-Sortilin antibody. Other aspects of the present disclosure relate to an anti-Sortilin antibody for use in decreasing cellular levels of Sortilin of one or more cells. Other aspects of the present disclosure relate to use of an anti-Sortilin antibody in the manufacture of a medicament for decreasing cellular levels of Sortilin of one or more cells.

Other aspects of the present disclosure relate to a method for inhibiting one or more interactions between a Sortilin protein and one or more proteins selected from the group consisting of Progranulin, neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and receptor associated protein (RAP), the method comprising: contacting the Sortilin protein with an anti-Sortilin antibody that binds to an epitope comprising SEQ ID NO: 4. Other aspects of the present disclosure relate to an anti-Sortilin antibody that binds to an epitope comprising SEQ ID NO: 4 for use in inhibiting one or more interactions between a Sortilin protein and one or more proteins selected from the group consisting of Progranulin, neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and receptor associated protein (RAP). Other aspects of the present disclosure relate to use of an anti-Sortilin antibody that binds to an epitope comprising SEQ ID NO: 4 in the manufacture of a medicament for inhibiting one or more interactions between a Sortilin protein and one or more proteins selected from the group consisting of Progranulin, neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and receptor associated protein (RAP).

In certain embodiments that may be combined with any of the preceding embodiments, (a) the anti-Sortilin antibody has a property selected from the group consisting of: increasing extracellular levels of Progranulin, increasing cellular levels of Progranulin, decreasing cellular levels of Sortilin, inhibiting interaction between Sortilin and Progranulin, and any combination thereof; (b) the anti-Sortilin antibody decreases cell surface levels of Sortilin, decreases intracellular levels of Sortilin, decreases total levels of Sortilin, or any combination thereof; (c) the anti-Sortilin antibody induces Sortilin degradation, Sortilin cleavage, Sortilin internalization, Sortilin down regulation, or any combination thereof; (d) the anti-Sortilin antibody decreases cellular levels of Sortilin and does not inhibit the interaction between Sortilin and Progranulin; (e) the anti-Sortilin antibody decreases cellular levels of Sortilin and inhibits the interaction between Sortilin and Progranulin; (f) the anti-Sortilin antibody decreases cellular levels of Sortilin and increases cellular levels of Progranulin; (g) the anti-Sortilin antibody increases cellular levels of Progranulin and does not inhibit the interaction between Sortilin and Progranulin; (h) the anti-Sortilin antibody inhibits the interaction between Sortilin and Progranulin and increases cellular levels of Progranulin, (i) the anti-Sortilin antibody inhibits the interaction between Sortilin and Progranulin and does not decrease cellular levels of Sortilin; (j) the anti-Sortilin antibody increases cellular levels of Progranulin and does not decrease cellular levels of Sortilin; (k) the anti-Sortilin antibody further inhibits interaction between Sortilin and pro-nerve growth factor (pro-NGF); (1) the anti-Sortilin antibody further inhibits interaction between Sortilin and one or more proteins selected from the group consisting of a pro-neurotrophin, a neurotrophin, nerve growth factor (NGF), pro-brain-derived neurotrophic factor (pro-BDNF), brain-derived neurotrophic factor (BDNF), pro-neurotrophin-3, neurotrophin-3, pro-neurotrophin-4/5, neurotrophin-4/5, neurotensin, neurotensin, p75, Sortilin propeptide (Sort-pro), amyloid precursor protein (APP), the A beta peptide, lipoprotein lipase (LpL), apolipoprotein AV (APOA5). apolipoprotein E (APOE), PCSK9, and receptor associated protein (RAP); (m) the anti-Sortilin antibody further inhibits interaction between Sortilin and one or more proteins selected from the group consisting of a pro-neurotrophin, a neurotrophin, nerve growth factor (NGF), pro-brain-derived neurotrophic factor (pro-BDNF), brain-derived neurotrophic factor (BDNF), pro-neurotrophin-3, neurotrophin-3, pro-neurotrophin-4/5, neurotrophin-4/5, neurotensin, neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and receptor associated protein (RAP) by: a) reducing the effective levels of Sortilin available for interacting with the one or more proteins; b) inducing degradation of Sortilin; or both; (n) the anti-Sortilin antibody inhibits cellular secretion of PCSK9, inhibits A beta peptide production, or both; (o) the anti-Sortilin antibody induces one or more Progranulin activities; (p) the anti-Sortilin antibody reduces endosomal internalization of Progranulin, or fragments thereof; and/or (q) the anti-Sortilin antibody increases the effective concentration of Progranulin. In certain embodiments that may be combined with any of the preceding embodiments, (a) the anti-Sortilin antibody binds specifically to human Sortilin, mouse Sortilin, or both; (b) the anti-Sortilin antibody is a human antibody; (c) the anti-Sortilin antibody is a humanized antibody; (d) the anti-Sortilin antibody is a bispecific antibody; (e) the anti-Sortilin antibody is a bispecific antibody recognizing a first antigen and a second antigen; (f) the anti-Sortilin antibody is a bispecific antibody recognizing a first antigen and a second antigen, wherein the first antigen is a Sortilin protein and the second antigen is an antigen facilitating transport across the blood-brain-barrier, and, optionally, wherein the second antigen is selected from the group consisting of Sortilin, transferring receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, basigin, Glut1, CD98 hc, and ANG1005; (g) the anti-Sortilin antibody is a multivalent antibody; (h) the anti-Sortilin antibody is a conjugated antibody; (i) the anti-Sortilin antibody is a chimeric antibody; (j) the anti-Sortilin antibody is an antibody; (k) the anti-Sortilin antibody is an antibody fragment that binds to an epitope comprising amino acid residues on human Sortilin, or a mammalian Sortilin protein; or (l) the anti-Sortilin antibody is an antibody fragment that binds to an epitope comprising amino acid residues on human Sortilin or a mammalian Sortilin protein, and optionally, wherein the fragment is an Fab, Fab', Fab'-SH, F(ab')2, Fv, or scFv fragment.

In certain embodiments that may be combined with any of the preceding embodiments, the anti-Sortilin antibody binds a discontinuous Sortilin epitope. In certain embodiments that may be combined with any of the preceding embodiments, the discontinuous Sortilin epitope comprises two or more peptides, three or more peptides, four or more peptides, five or more peptides, six or more peptides, seven or more peptide, eight or more peptides, nine or more peptides, or 10 or more peptides. In certain embodiments that may be combined with any of the preceding embodiments, each of the peptides comprise five or more, six or more, seven or more, eight or more, nine or more, 10 or more, 11 or more, 12 or more, 13 or more 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid residues of the amino acid sequence of SEQ ID NO: 1; or five or more, six or more, seven or more, eight or more, nine or more, 10 or more, 11 or more, 12 or more, 13 or more 14 or more, 15 or more, 16 or more, 17 or more 18 or more, 19 or more, 20 or more, 21 or more, 22 or more, 23 or more, 24 or more, 25 or more, 26 or more, 27 or more, 28 or more, 29 or more, or 30 or more amino acid residues on a mammalian Sortilin protein corresponding to the amino acid sequence of SEQ ID NO: 1. In certain embodiments that may be combined with any of the preceding embodiments, the anti-Sortilin antibody binds to a conformational epitope of Sortilin. In certain embodiments that may be combined with any of the preceding embodiments, the anti-Sortilin antibody binds to one or more amino acids within amino acid residues selected from the group consisting of: i. amino acid residues 740-749 of SEQ ID NO: 1, or amino acid residues on a mammalian Sortilin protein corresponding to amino acid residues 740-749 of SEQ ID NO: 1; ii. amino acid residues 623-632 of SEQ ID NO: 1, or amino acid residues on a mammalian Sortilin protein corresponding to amino acid residues 623-632 of SEQ ID NO: 1; iii. amino acid residues 429-443 of SEQ ID NO: 1, or amino acid residues on a mammalian Sortilin protein corresponding to amino acid residues 429-443 of SEQ ID NO: 1; iv. amino acid residues 367-391 of SEQ ID NO: 1, or amino acid residues on a mammalian Sortilin protein corresponding to amino acid residues 367-391 of SEQ ID NO: 1; v. amino acid residues 314-338 of SEQ ID NO: 1, or amino acid residues on a mammalian Sortilin protein corresponding to amino acid residues 314-338 of SEQ ID NO: 1; vi. amino acid residues 297-317 of SEQ ID NO: 1, or amino acid residues on a mammalian Sortilin protein corresponding to amino acid residues 297-317 of SEQ ID NO: 1; vii. amino acid residues 237-260 of SEQ ID NO: 1, or amino acid residues on a mammalian Sortilin protein corresponding to amino acid residues 237-260 of SEQ ID NO: 1; viii. amino acid residues 237-260 and 297-317 of SEQ ID NO: 1, or amino acid residues on a mammalian Sortilin protein corresponding to amino acid residues 237-260 and 297-317 of SEQ ID NO: 1; ix, amino acid residues 237-247 of SEQ ID NO: 1, or amino acid residues on a mammalian Sortilin protein corresponding to amino acid residues 237-247 of SEQ ID NO: 1; x. amino acid residues 237-247 and 314-338 of SEQ ID NO: 1, or amino acid residues on a mammalian Sortilin protein corresponding to amino acid residues 237-247 and 314-338 of SEQ ID NO: 1; xi. amino acid residues 233-243 of SEQ ID NO: 1, or amino acid residues on a mammalian Sortilin protein corresponding to amino acid residues 233-243 of SEQ ID NO: 1; xii. amino acid residues 212-221 of SEQ ID NO: 1, or amino acid residues on a mammalian Sortilin protein corresponding to amino acid residues 212-221 of SEQ ID NO: 1; xiii. amino acid residues 207-227 of SEQ ID NO: 1, or amino acid residues on a mammalian Sortilin protein corresponding to amino acid residues 207-227 of SEQ ID NO: 1; xiv. amino acid residues 207-227 and 237-260 of SEQ ID NO: 1, or amino acid residues on a mammalian Sortilin protein corresponding to amino acid residues 207-227 and 237-260 of SEQ ID NO: 1; xv. amino acid residues 207-231 of SEQ ID NO: 1, or amino acid residues on a mammalian Sortilin protein corresponding to amino acid residues 207-231 of SEQ ID NO: 1; xvi. amino acid residues 175-181 of SEQ ID NO: 1, or amino acid residues on a mammalian Sortilin protein corresponding to amino acid residues 175-181 of SEQ ID NO: 1; and vii. amino acid residues 131-138 of SEQ ID NO: 1, or amino acid residues on a mammalian Sortilin protein corresponding to amino acid residues 131-138 of SEQ ID NO: 1. In certain embodiments that may be combined with any of the preceding embodiments, the anti-Sortilin antibody binds to one or more amino acid residues selected from the group consisting of H131, V132, P133, L134, V135, I136, M137, T138, T210, T218, Y222, S223, S227, S242, K243, K248, K254, S305, R311, S316, R325, S379, R382, Y386, and S595 of SEQ ID NO: 1, or one or more amino acid residues on a mammalian Sortilin protein corresponding to amino acid residues H131, V132, P133, L134, V135, I136, M137, T138, T210, T218, Y222, S223, S227, S242, K243, K248, K254, S305, R311, S316, R325, S379, R382, Y386, and S595 of SEQ ID NO: 1. In certain embodiments that may be combined with any of the preceding embodiments, the anti-Sortilin antibody binds to one or more amino acid residues selected from the group consisting of R88, F105, L108, R109, G110, D403, D449, T451, H461, G495, Y513, S530, I537, D552, F569, E590, F592, L593, S595, W597, I619, L621, E628, D632, L636, Q642, R646, and Y679 of SEQ ID NO: 1, or one or more amino acid residues on a mammalian Sortilin protein corresponding to an amino acid residue selected from the group consisting of R88, F105, L108, R109, G110, D403, D449, T451, H461, G495, Y513, S530, I537, D552, F569, E590, F592, L593, S595, W597, I619, L621, E628, D632, L636, Q642, R646, and Y679. In certain embodiments that may be combined with any of the preceding embodiments, the anti-Sortilin antibody comprises at least one, two, three, four, five, or six HVRs of an antibody selected from the group consisting of: S-1, S-2, S-3, S-4, S-5, S-6, S-7, S-8, S-9, S-10, S-12, S-14S-15, S-16, S-18, S-19, S-20, S-21, S-22, S-24, S-25, S-26, S-28, S-29, S-30, S-32, S-34, S-39, S-40, S-42, S-43, S-44, S-45, S-48, S-49, S-50, S-51, S-55, S-57, S-58, S-59, S-60, S-61, S-63, S-64, S-65, S-66, S-67, S-69, S-71, S-72, S-73, S-74, S-75, S-76, S-78, S-81, S-82, S-83, S-84, and S-85. In certain embodiments that may be combined with any of the preceding embodiments, the anti-Sortilin antibody comprises: (a) an HVR-L1 comprising an amino acid sequence selected from the group consisting of SEQ ID NOs:6-16, 20-22, and 24-25; (b) an HVR-L2 comprising an amino acid sequence selected from the group consisting of SEQ ID NOs:26-40; (c) an HVR-L3 comprising an amino acid sequence selected from the group consisting of SEQ ID NOs:41-50, 52, 54-56, 58-62, 64-66, 68-70, 72, 74, 79-80, 82-85, 88-91, 95, 97-101, 103-107, 109, 111-116, 118, and 121-125; (d) an HVR-H1 comprising an amino acid sequence selected from the group consisting of SEQ ID NOs:126-127, 129-130, 133-140, 142, 144-145, and 147-149; (e) an HVR-H2 comprising an amino acid sequence selected from the group consisting of SEQ ID NOs:150-153, 155-158, 160-166, 169-175, and 177-178; or (f) an HVR-H3 comprising an amino acid sequence selected from the group consisting of SEQ ID NOs:179-186, 188, 190-191, 193-197, 199-201, 203-204, 206, 208, 213-214, 216-219, 22. In certain embodiments that may be combined with any of the preceding embodiments, the anti-Sortilin antibody comprises a light chain variable domain and a heavy chain variable domain, wherein the light chain variable domain comprises: (a) an HVR-L1 comprising an amino acid sequence selected from the group consisting of SEQ ID NOs:6-16, 20-22, and 24-25, or an amino acid sequence with at least about 95% homology to an amino acid sequence selected from the group consisting of SEQ ID NOs:6-16, 20-22, and 24-25; (b) an HVR-L2 comprising an amino acid sequence selected from the group consisting of SEQ ID NOs:26-40, or an amino acid sequence with at least about 95% homology to an amino acid sequence selected from the group consisting of SEQ ID NOs:26-40; and (c) an HVR-L3 comprising an amino acid sequence selected from the group consisting of SEQ ID NOs:41-50, 52, 54-56, 58-62, 64-66, 68-70, 72, 74, 79-80, 82-85, 88-91, 95, 97-101, 103-107, 109, 111-116, 118, and 121-125, or an amino acid sequence with at least about 95% homology to an amino acid sequence selected from the group consisting of SEQ ID NOs:41-50, 52, 54-56, 58-62, 64-66, 68-70, 72, 74, 79-80, 82-85, 88-91, 95, 97-101, 103-107, 109, 111-116, 118, and 121-125; and wherein the heavy chain variable domain comprises: (a) an HVR-H1 comprising an amino acid sequence selected from the group consisting of SEQ ID NOs:126-127, 129-130, 133-140, 142, 144-145, and 147-149, or an amino acid sequence with at least about 95% homology to an amino acid sequence selected from the group consisting of SEQ ID NOs:126-127, 129-130, 133-140, 142, 144-145, and 147-149; (b) an HVR-H2 comprising an amino acid sequence selected from the group consisting of SEQ ID NOs:150-153, 155-158, 160-166, 169-175, and 177-178, or an amino acid sequence with at least about 95% homology to an amino acid sequence selected from the group consisting of SEQ ID NOs:150-153, 155-158, 160-166, 169-175, and 177-178; and (c) an HVR-H3 comprising an amino acid sequence selected from the group consisting of SEQ ID NOs:179-186, 188, 190-191, 193-197, 199-201, 203-204, 206, 208, 213-214, 216-219, 222-225, 229, 231-234, 236-239, 241, 243-247, 249, and 252-256 or an amino acid sequence with at least about 95% homology to an amino acid sequence selected from the group consisting of SEQ ID NOs:179-186, 188, 190-191, 193-197, 199-201, 203-204, 206, 208, 213-214, 216-219, 222-225, 229, 231-234, 236-239, 241, 243-247, 249, and 252-256.

In certain embodiments that may be combined with any of the preceding embodiments, the anti-Sortilin antibody comprises a light chain variable domain and a heavy chain variable domain, wherein: (a) the light chain variable domain comprises an HVR-L1 comprising the amino acid sequence of RASQSISSYLN (SEQ ID NO:7); an HVR-L2 comprising the amino acid sequence of AASSLQS (SEQ ID NO:27); and an HVR-L3 comprising the amino acid sequence of QQSDVSPIT (SEQ ID NO:42); and/or the heavy chain variable domain comprises an HVR-H1 comprising the amino acid sequence of YTFX$_1$X$_2$YX$_3$MX$_4$ (SEQ ID NO:480), wherein X$_1$ is T, G, V, P, L, F, A, or R, X$_2$ is G, A, or S, X$_3$ is Y, M, or L, and X$_4$ is H or W; HVR-H2 comprising the amino acid sequence of X$_1$X$_2$X$_3$PX$_4$X$_5$GX$_6$TX$_7$YAQKFQG (SEQ ID NO:481), wherein X$_1$ is W, I, or G, X$_2$ is I, V, or T, X$_3$ is N, G, or L, X$_4$ is N, S, V, or M, X$_5$ is S, G, W, or Q, X$_6$ is G, F, A, Y, S, N, or R, and X$_7$ is N, R, S, or M; and an HVR-H3 comprising the amino acid sequence of ARGKRSSGWYEGYGMDV (SEQ ID NO:180); (b) the light chain variable domain comprises an HVR-L1 comprising the amino acid sequence of RASQSX$_1$X$_2$SNLA (SEQ ID NO:508), wherein X$_1$ is V or I and X$_2$ is S or G; an HVR-L2 comprising the amino acid sequence of GASTRAT (SEQ ID NO:29); and an HVR-L3 comprising the amino acid sequence of QQARLGPWT (SEQ ID NO:55); and/or the heavy chain variable domain comprises an HVR-H1 comprising the amino acid sequence of YTX$_1$X$_2$X$_3$X$_4$X$_5$X$_6$S (SEQ ID NO:509), wherein X$_1$ is F or L, X$_2$ is T or A, X$_3$ is S or K, X$_4$ is Y, T, R, L, T, G, Q, or H, X$_5$ is Y, T, or L, and X$_6$ M or I; an HVR-H2 comprising the amino acid sequence of X$_1$INPx$_2$GGX$_3$X$_4$SYAX$_5$X$_6$FX$_7$G (SEQ ID NO:510), wherein X$_1$ is I or V, X$_2$ is S, W, Y, F, L, or I, X$_3$ is S or T, X$_4$ is T or A, X$_5$ is Q or R, X$_6$ is K, or R, and X$_7$ is Q or R; and an HVR-H3 comprising the amino acid sequence of X$_1$RDPX$_2$GX$_3$X$_4$X$_5$X$_6$X$_7$PX$_8$X$_9$RX$_{10}$X$_{11}$X$_{12}$GX$_{13}$DV (SEQ ID NO:511), wherein X$_1$ is A, V, or T, X$_2$ is S, F, or G, X$_3$ is I or A, X$_4$ is A or G, X$_5$ is A, L, or V, X$_6$ is A, L, or P, X$_7$ is G, F, or Y, X$_8$ is A, G, or F, X$_9$ is S, G, or A, X$_{10}$ is Y, G, P, H, or S, X$_{11}$ is Y or N, X$_{12}$ is Y, L, Q, or R, and X$_{13}$ is M or L; (c) the light chain variable domain comprises an HVR-L1 comprising the amino acid sequence of RASQSISSWLA (SEQ ID NO:8); an HVR-L2 comprising the amino acid sequence of KASSLES (SEQ ID NO:28); and an HVR-L3 comprising the amino acid sequence of QQADGHIT (SEQ ID NO:62); and/or the heavy chain variable domain comprises an HVR-H1 comprising the amino acid sequence of X$_1$TFX$_2$X$_3$YAX$_4$X$_5$ (SEQ ID NO:565), wherein X$_1$ is G or Y, X$_2$ is S, R, G, or T, X$_3$ is S, G, or N, X$_4$ is I or M, and X$_5$ is S or A; an HVR-H2 comprising the amino acid sequence of GIX$_1$PX$_2$X$_3$GX$_4$AX$_5$YAQKFQG (SEQ ID NO:566), wherein X$_1$ is I or V, X$_2$ is I, R, G, A, S, T, or Q, X$_3$ is G, X$_4$ is T, R, or W, and X$_5$ is S, N, Q, or W, and an HVR-H3 comprising the amino acid sequence of ARQGRKTGYYYYYGMDV (SEQ ID NO:197); (d) the light chain variable domain comprises an HVR-L1 comprising the amino acid sequence of RSSQX$_1$LLX$_2$SNGYNYLD (SEQ ID NO:580), wherein X$_1$ is S or G and X$_2$ is H or R; an HVR-L2 comprising the amino acid sequence of LGSNRXS (SEQ ID NO:581), wherein X is A or V; and an HVR-L3 comprising the amino acid sequence of MQQQETPLT (SEQ NO:100); and/or the heavy chain variable domain comprises an HVR-H1 comprising the amino acid sequence of YSISSX$_1$X$_2$YWG (SEQ ID NO:582), wherein X$_1$ is G or V and X$_2$ is Y or R; an HVR-H2 comprising the amino acid sequence of X$_1$IYX$_2$SGSTYYNPSLKS (SEQ ID NO:583), wherein X$_1$ is T, S, or A and X$_2$ is H or P; and an HVR-H3 comprising the amino acid sequence of ARQGSIKQGYYGMDV (SEQ ID NO:233); or (e) the light chain variable domain comprises an HVR-L1 comprising the amino acid sequence of RASQSVSSSYLA (SEQ ID NO:14), an HVR-L2 comprising the amino acid sequence of GASSRAT (SEQ ID NO:26), and an HVR-L3 comprising the amino acid sequence of QQSHVSPWT (SEQ ID NO:122); and/or the heavy chain variable domain comprises an HVR-H1 comprising the amino acid sequence of X$_1$ SIX$_2$SX$_3$X$_4$YYWG (SEQ ID NO:589), wherein X$_1$ is G or Y, X$_2$ is S, V, Y, K, or P, X$_3$ is S or R, and X$_4$ is D or E; an HVR-H2 comprising the amino acid sequence of X$_1$IYX$_2$X$_3$GSTX$_4$YNPSLKS (SEQ ID NO:590), wherein X$_1$ is S, G, Q, or L, X$_2$ is Y, W, or R, X$_3$ is S, R, K, or A, and X$_4$ is Y or V; and an HVR-H3 comprising the amino acid sequence of ARGVGSGYSYGYRYFDY (SEQ ID NO:253). In certain embodiments that may be combined with any of the preceding embodiments, (a) the anti-Sortilin antibody competes with one or more antibodies selected from the group consisting of S-6, S-8, S-49, S-60, S-63, S-72, S-83, and any combination thereof for binding to Sortilin; (b) the anti-Sortilin antibody competes with one or more antibodies selected from the group consisting of S-5, S-45, S-64, S-65, and any combination thereof for binding to Sortilin; (c) the anti-Sortilin antibody competes with one or more antibodies selected from the group consisting of S-5, S-30, S-60, and any combination thereof for binding to Sortilin; (d) the anti-Sortilin antibody competes with one or more antibodies selected from the group consisting of S-2, S-16, S-18, S-19, S-20, S-21, S-22, S-28, S-29, S-82, and any combination thereof for binding to Sortilin; (e) the anti-Sortilin antibody competes with one or more antibodies selected from the group consisting of S-1, S-3, S-4, S-6, S-7, S-9, S-10, S-14, S-15, S-26, S-32, S-48, S-51, S-55, S57, S-58, S-59, S-61, S-69, S-71, S-73, S-74, S-75, S-85, and any combination thereof for binding to Sortilin; (f) the anti-Sortilin antibody competes with one or more antibodies selected from the group consisting of S-5, S-12, S-24, S-25, S-30, S-34, S-39, S-40, S-42, S-43, S-44, S-45, S-60, S-63, S-64, S-65, S-66, S-67, S-72, S-76, S-78, S-81, S-83, S-84, and any combination thereof for binding to Sortilin; (g) the anti-Sortilin antibody competes with one or more antibodies selected from the group consisting of S-8, S-49, S-50, and any combination thereof for binding to Sortilin; or (h the anti-Sortilin antibody which binds essentially the same Sortilin epitope as an antibody selected from the group consisting of: S-1, S-2, S-3, S-4, S-5, S-6, S-7, S-8, S-9, S-10, S-12, S-14, S-15, S-16, S-18, S-19, S-20, S-21, S-22, S-24, S-25, S-26, S-28, S-29, S-30, S-32, S-34, S-39, S-40, S-42, S-43, S-44, S-45, S-48, S-49, S-50, S-51, S-55, S-57, S-58, S-59, S-60, S-61, S-63, S-64, S-65, S-66, S-67, S-69, S-71, S-72, S-73, S-74, S-75, S-76, S-78, S-81, S-82, S-83, S-84, and S-85. In certain embodiments that may be combined with any of the preceding embodiments, the anti-Sortilin antibody comprises a light chain variable domain and/or a heavy chain variable domain comprising an amino acid sequence selected from the group consisting of SEQ ID NOs:317-334, 337-338, 341-345, 348-357, 360-365, 368-372, 375-376, 379-380, 389-392, 395-402, 407-414, 421-422, 425-433, 436-444, 447-448, 451-461, 464-465, and 470-479. In certain embodiments that may be combined with any of the preceding embodiments, (a) the anti-Sortilin antibody is of the IgG class the IgM class, or the IgA class; or (b) the anti-Sortilin antibody has an IgG1, IgG2, IgG3, or IgG4 isotype; (c) the anti-Sortilin antibody has a human or mouse IgG1 isotype and comprises one or more amino acid substitutions in the Fc region at a residue position selected from the group consisting of: N297A, N297Q, D265A, L234A, L235A, C226S, C229S, P238S, E233P, L234V, P238A, A327Q, A327G, P329A, K322A, L234F, L235E, P331S, T394D, A330L, M252Y, S254T, T256E, and any combination thereof, wherein the numbering of the residues is according to EU or Kabat numbering; (d) the anti-Sortilin antibody has an IgG2 isotype and comprises one or more amino acid substitutions in the Fc region at a residue position selected from the group consisting of: P238S, V234A, G237A, H268A, H268Q H268E, V309L, N297A, N297Q, A330S, P331S, C232S, C233S, M252Y, S254T, T256E, and any combination thereof, wherein the numbering of the residues is according to EU or Kabat numbering; or (e) the anti-Sortilin antibody has an IgG4 isotype and comprises one or more amino acid substitutions in the Fc region at a residue position selected from the group consisting of: E233P, F234V, L234A/F234A, L235A, G237A, E318A, S228P, L236E, S241P, L248E, T394D, M252Y, S254T, T256E, N297A N297Q, and any combination thereof, wherein the numbering of the residues is according to EU or Kabat numbering. In certain embodiments that may be combined with any of the preceding embodiments, the Fc region of one or more of (c), (d), and (e) further comprises: (a) one or more additional amino acid substitutions at a position selected from the group consisting of A330L, L234F; L235E, P331S, and any combination thereof, wherein the numbering of the residues is according to EU or Kabat numbering; (b) one or more additional amino acid substitutions at a position selected from the group consisting of M252Y, S254T, T256E, and any combination thereof, wherein the numbering of the residues is according to EU or Kabat numbering; or (c) a S228P amino acid substitution according to EU or Kabat numbering. In certain embodiments that may be combined with any of the preceding embodiments, (a) the anti-Sortilin antibody has a dissociation constant ($K_D$) for human Sortilin, mouse Sortilin, or both, that ranges from about 100 nM to about 0.005 nM, or less than 0.005 nM; (b) the anti-Sortilin antibody has dissociation constant ($K_D$) for human Sortilin that ranges from about 70.4 nM to about 0.005 nM, or less than 0.005 nM; or (c) the anti-Sortilin antibody has dissociation constant ($K_D$) for mouse Sortilin that ranges from about 40.3 nM to about 0.07 nM, or less than 0.07 nM. In certain embodiments that may be combined with any of the preceding embodiments, the anti-Sortilin antibody is the anti-Sortilin antibody of any of the preceding embodiments.

Other aspects of the present disclosure relate to a method of preventing, reducing risk, or treating an individual having a disease, disorder, or injury selected from the group consisting of frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotriphic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arforitis, multiple sclerosis, metabolic disorder, obesity, insulin resistance, type 2 diabetes, tissue or vascular damage, an injury, and one or more undesirable symptoms of normal aging, comprising administering to the individual a therapeutically effective amount of the anti-Sortilin antibody of any of the preceding embodiments. Other aspects of the present disclosure relate to an anti-Sortilin antibody of any of the preceding embodiments for use in preventing, reducing risk, or treating an individual having a disease, disorder, or injury selected from the group consisting of frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotriphic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arforitis, multiple sclerosis, metabolic disorder, obesity, insulin resistance, type 2 diabetes, tissue or vascular damage, an injury, and one or more undesirable symptoms of normal aging. Other aspects of the present disclosure relate to use of an anti-Sortilin antibody of any of the preceding embodiments in the manufacture of a medicament for preventing, reducing risk, or treating an individual having a disease, disorder, or injury selected from the group consisting of frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotriphic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arforitis, multiple sclerosis, metabolic disorder, obesity, insulin resistance, type 2 diabetes, tissue or vascular damage, an injury, and one or more undesirable symptoms of normal aging. Other aspects of the present disclosure relate to a method of preventing, reducing risk, or treating an individual having a disease, disorder, or injury selected from the group consisting of frontotemporal dementia, progressive supranuclear palsy, Alzheimer's disease, vascular dementia, seizures, retinal dystrophy, amyotriphic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arforitis, and osteoarthritis, comprising administering to the individual a therapeutically effective amount of the anti-Sortilin antibody of any of the preceding embodiments. Other aspects of the present disclosure relate to an anti-Sortilin antibody of any of the preceding embodiments for use in preventing, reducing risk, or treating an individual having a disease, disorder, or injury selected from the group consisting of frontotemporal dementia, progressive supranuclear palsy, Alzheimer's disease, vascular dementia, seizures, retinal dystrophy, amyotriphic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arforitis, and osteoarthritis. Other aspects of the present disclosure relate to use of an anti-Sortilin antibody of any of the preceding embodiments in the manufacture of a medicament for preventing, reducing risk, or treating an individual having a disease, disorder, or injury selected from the group consisting of frontotemporal dementia, progressive supranuclear palsy, Alzheimer's disease, vascular dementia, seizures, retinal dystrophy, amyotriphic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arforitis, and osteoarthritis.

Other aspects of the present disclosure relate to a method of inhibiting one or more of neuroinflammation, axonopathy characterized by short axonal outgrowth and aberrant branching, microglial activation, and inflammatory response, comprising administering to the individual a therapeutically effective amount of the anti-Sortilin antibody of any of the preceding embodiments. Other aspects of the present disclosure relate to an anti-Sortilin antibody of any of the preceding embodiments for use in inhibiting one or more of neuroinflammation, axonopathy characterized by short axonal outgrowth and aberrant branching, microglial activation, and inflammatory response. Other aspects of the present disclosure relate to use of an anti-Sortilin antibody of any of the preceding, embodiments in the manufacture of a medicament for inhibiting one or more of neuroinflammation, axonopathy characterized by short axonal outgrowth and aberrant branching microglial activation, and inflammatory response. Other aspects of the present disclosure relate to a method of promoting one or more of wound healing, autophagy, and clearance of aggregate proteins, comprising administering to the individual a therapeutically effective amount of the anti-Sortilin antibody of any of the preceding embodiments. Other aspects of the present disclosure relate to an anti-Sortilin antibody of any of the preceding embodiments for use in promoting one or more of wound healing, autophagy, and clearance of aggregate proteins. Other aspects of the present disclosure relate to use of an anti-Sortilin antibody of any of the preceding embodiments in the manufacture of a medicament for promoting one or more of wound healing, autophagy, and clearance of aggregate proteins. Other aspects of the present disclosure relate to a method of preventing, reducing risk, or treating an individual having arforitis, comprising administering to the individual a therapeutically effective amount of the anti-Sortilin antibody of any of the preceding embodiments. Other aspects of the present disclosure relate to an anti-Sortilin antibody of any of the preceding embodiments for use in preventing, reducing risk, or treating an individual having arforitis. Other aspects of the present disclosure relate to use of an anti-Sortilin antibody of any of the preceding embodiments in the manufacture of a medicament for preventing, reducing risk, or treating an individual having arforitis. Other aspects of the present disclosure relate to a method of decreasing expression of one or more pro-inflammatory mediators, comprising administering to the individual a therapeutically effective amount of the anti-Sortilin antibody of any of the preceding embodiments. Other aspects of the present disclosure relate to an anti-Sortilin antibody of any of the preceding embodiments for use in decreasing expression of one or more pro-inflammatory mediators. Other aspects of the present disclosure relate to use of an anti-Sortilin antibody of any of the preceding embodiments in the manufacture of a medicament for decreasing expression of one or more pro-inflammatory mediators. In certain embodiments, the one or more pro-inflammatory mediators are selected from the group consisting of IL-6, IL12p70, IL 1p40, IL-1β, TNF-α, CXCL1, CCL2, CCL3, CCL4, and CCL5.

In certain embodiments that may be combined with any of the preceding embodiments, the anti-Sortilin antibody comprises two or more anti-Sortilin antibodies.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A shows kinetic analysis of Progranulin (PGRN) binding to His-captured Sortilin 1(SORT1) using Biacore SPR. FIG. 2B shows binding of biotinylated human PGRN to immobilized human SORT1 on an ELISA plate. FIG. 2C shows binding of biotinylated mouse PGRN to immobilized mouse SORT1 on an ELISA plate.

FIG. 5A shows FACS plots showing binding levels of human PGRN-Bio to HEK293Tcells expressing human SORT. FIG. 5B shows FACS plots showing binding levels of human PGRN-Bio to control cells. FIG. 5C shows mean fluorescent intensity (MFI) plotted against concentration of human PGRN binding to HEK293Tcells expressing human SORT (circles) or control cells (squares). FIG. 5D shows MFI plotted against concentration of mouse PGRN binding to HEK293Tcells expressing mouse SORT (circles) or control cells (squares).

FIG. 6A and FIG. 6B depict antibody inhibition of human Progranulin binding to human Sortilin, FIG. 6C and FIG. 6D depict antibody inhibition of mouse Progranulin binding to mouse Sortilin. FIG. 6E depicts inhibition of binding of biotinylated human Progranulin to cells that express human Sortilin by 67 nM of anti Sortilin antibodies.

FIG. 9A depicts results of U-251 cells incubated with 50 nM of anti Sortilin antibodies for 72 h. FIG. 9B depicts results of U-251 cells incubated with 5 nM of anti Sortilin antibodies for 72 h. FIG. 9C depicts results of U-251 cells incubated with 50 nM of anti Sortilin antibodies for 72 h. FIG. 9D depicts results of U-251 cells incubated with 5 nM of anti Sortilin antibodies for 72 h. Progranulin levels in the media were quantified by ELISA analysis. Shown are averages of two independent experiments. Statistics were performed using ANOVA and stars show antibodies that significantly elevate Progranulin levels.

FIG. 10A shows cell surface expression of Sortilin on U-251 cells as percent (%) of control levels that were pre-treated with test the antibodies listed on the X-axis. Grey bars indicate antibodies that showed a significant decrease in Sortilin (ANOVA, p<0.05), while white bars indicate antibodies that did not show a decrease in Sortilin. Black bars denote control IgG. FIG. 10B shows cell surface expression of Sortilin on N2A cells as percent (%) of control levels that were pre-treated with test the antibodies listed on the X-axis. Grey bars indicate antibodies that showed a significant decrease in Sortilin (ANOVA, p<0.05), while white bars indicate antibodies that did not show a decrease in Sortilin. Black bars denote control IgG. FIG. 10C and FIG. 10D depict the levels of cell surface Sortilin in U-251 cells that were incubated with different concentration of the anti-Sortilin antibodies for 72 h. The anti-Sortilin antibodies induce a dose-dependent decrease in cell surface expression of Sortilin. The decrease in Sortilin levels is depicted by decreased fluorescent intensity (MFI) of S-20 antibody binding to Sortilin. FIG. 10E depicts ELISA-based quantification of the corresponding levels of PGRN in the media of the U-251 cells in FIG. 10B that were incubated with the listed anti-Sortilin antibodies for 72 h. The anti-Sortilin antibodies that decrease Sortilin cell surface levels also cause a dose-dependent increase in the levels of extracellular PGRN. FIG. 10F shows the correlation between the reduction in cell surface levels of Sortilin induced by the anti-Sortilin antibodies and the increase in extracellular levels of Progranulin (PGRN).

FIG. 11A depicts Progranulin levels in different brain regions contralateral to site of ICV infusion. FIG. 11B depicts Progranulin levels in different brain regions ipsilateral to site of ICV infusion. The different brain regions are the hippocampus (Hip), the frontal cortex (F Ctx), and the occipital cortex (R Ctx). 14-month-old Tg2576 mice were ICV infused with buffer, goat IgG, or goat anti-Sortilin polyclonal antibody (n=3/group). FIG. 11C depicts levels of anti-Sortilin antibody in the three different brain regions. FIG. 11D depicts the strong positive correlation between anti-Sortilin antibody levels and endogenous Progranulin (PGRN) levels ($r^2$=0.92). Higher levels of anti-Sortilin antibody lead to an increase in brain PGRN in a dose dependent manner. FIG. 11F depicts levels of Abeta42 peptide in the soluble protein fraction after ICV infusion with anti-Sortilin antibody.

FIG. 13A, FIG. 13B, FIG. 13C, and FIG. 13D depict Sortilin cell surface expression on human U-251 cells. FIG. 13E, FIG. 13F, and FIG. 13G depict Sortilin cell surface expression on mouse N2A cells. The results indicate that affinity-matured antibodies induced an increased reduction in cell surface levels of Sortilin, especially when use at the lowest concentration of 1.25 nM.

FIG. 16D depicts binding reactivity in percentage to wild-type Sortilin (% WT) of antibodies of the present disclosure to the indicated Sortilin mutants.

FIG. 17A shows levels of binding of Progranulin (PGRN) to Sortilin in the presence or absence of Neurotensin (NTS). FIG. 17B shows levels of binding of anti-Sortilin antibody S-15 to Sortilin in the presence or absence of NTS. FIG. 17C shows levels of binding of anti-Sortilin antibody S-22 to Sortilin in the presence or absence of NTS. FIG. 17D shows levels of binding of anti-Sortilin antibody S-49 to Sortilin in the presence or absence of NTS. FIG. 17E shows levels of binding of anti-Sortilin antibody S-60 to Sortilin in the presence or absence of NTS. NTS did not affect binding of the antibodies to Sortilin, indicating that the anti-Sortilin antibodies do not bind to the NTS binding site.

FIG. 19A depicts injection of human anti-Sortilin IgG1 N297A antibodies, n=4-5 animals/group, FIG. 19B depicts injections of mouse anti-Sortilin IgG1 N297A antibody. Data was fit using a one phase decay function (Graph Pad Prism), Anti-Sortilin antibodies have a shorter half-life than the control IgG.

FIG. 20A and FIG. 20B depict results with mouse anti-Sortilin IgG1 N297A antibodies. FIG. 20C and FIG. 20D depict results with human anti-Sortilin IgG1 N297A antibody. FIG. 20B and FIG. 20D summarize statistical analysis using One-Way Anova with a Tukey posthoc test. Stars indicate significance level compared to the ms or hu IgG1 isotype control group: *$p<0.05$, $p<0.01$, *$p<0.001$, ****$p<0.0001$. The anti-Sortilin antibodies induce an increase in plasma PGRN protein levels, with the duration of the effect correlated to antibody half-life.

FIG. 21A and FIG. 21B show protein levels at day 5. FIG. 21C and FIG. 21D show protein levels at day 12. Anti-Sortilin antibodies S-20, S-15-6, and S-2-11 induce a significant reduction in Sortilin protein levels on day 5 (One Way Anova with Tukey posthoc test. Stars indicate significance level: $p<0.01$, *$p<0.001$). Antibody S-15-6 induced reduced Sortilin protein levels on day 12 in 2 out of 3 mice. FIGS. 21E and 21F shows protein levels in white blood cells after a chronic six-week course of weekly IP injections in mice with 20, 40, or 80 mg/kg of anti-Sortilin antibody S15-6. All three doses result in a strong and statistically significant downregulation of Sortilin in white blood cells (****$p<0.0001$ compared to control IgG, one-way ANOVA).

FIG. 22A depicts antibody S-15. FIG. 22B depicts antibody S-20. FIG. 22C depicts antibody S-30. FIG. 22D depicts isotype control antibody.

FIG. 27A depicts serum levels of CXCL1 after 1.5 hours of LPS treatment wild type mice and Sortilin knock-out (Sortilin -/-) mice. FIG. 27B depicts serum levels of CCL2 after 1.5 hours of LPS treatment wild type mice and Sortilin knock-out (Sortilin -/-) mice. FIG. 27C depicts serum levels of CCL3 after 1.5 hours of LYS treatment wild type mice and Sortilin knock-out (Sortilin -/-) mice. FIG. 27D depicts serum levels of CCL4 after 1.5 hours of LPS treatment wild type mice and Sortilin knock-out (Sortilin -/-) mice. FIG. 27E depicts serum levels of CCL5 after 1.5 hours of LPS treatment wild type mice and Sortilin knock-out (Sortilin -/-) mice. Open circles represent wild type mice and open squares represent Sortilin knock-out mice. n=8-10 mice/group. *$p<0.01$, $p<0.001$, *$p<0.001$, and ****$p<0.0001$ by 1-way ANOVA with Tukey's multiple comparisons test.

FIG. 29A depicts serum levels of CXCL1 after 6 hours of LPS treatment wild type mice and Sortilin knock-out (Sortilin −/−) mice. FIG. 29B depicts serum levels of CCL2 after 6 hours of LPS treatment wild type mice and Sortilin knock-out (Sortilin −/−) mice. FIG. 29C depicts serum levels of CCL3 after 6 hours of LPS treatment wild type mice and Sortilin knock-out (Sortilin −/−) mice. FIG. 29D depicts serum levels of CCL4 after 6 hours of LPS treatment wild type mice and Sortilin knock-out (Sortilin −/−) mice. FIG. 29E depicts serum levels of CCL5 after 6 hours of LPS treatment wild type mice and Sortilin knock-out (Sortilin −/−) mice. Open circles represent wild type mice and open squares represent Sortilin knock-out mice. n=8-10 mice/group. *$p<0.01$, $p<0.001$, *$p<0.001$, and ****$p<0.0001$. by 1-way ANOVA with Tukey's multiple comparisons test.

DETAILED DESCRIPTION OF THE INVENTION

General Techniques

Figure 1:
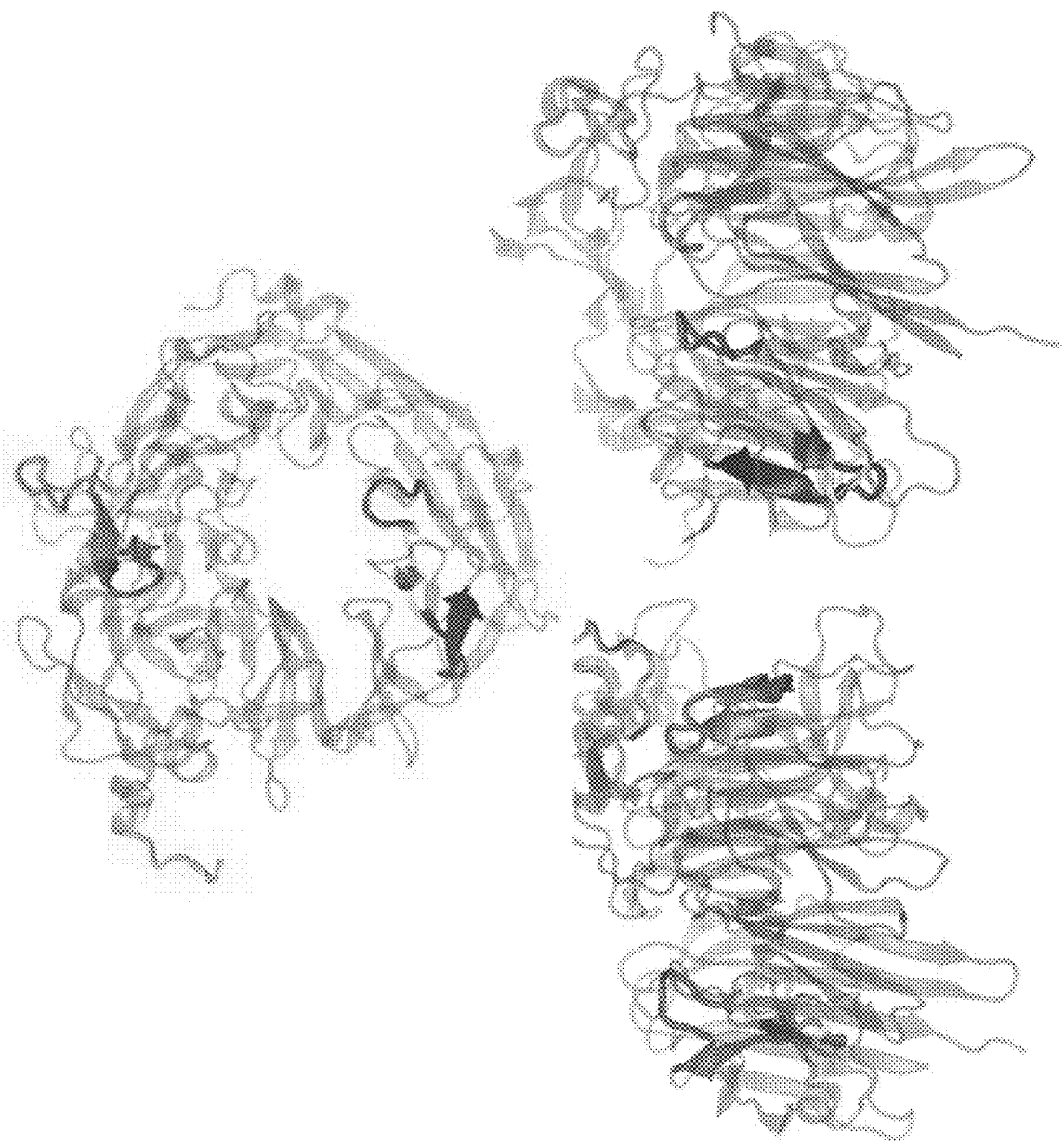
FIG. 1 depicts several views of human Sortilin protein showing the Sortilin binding sites of anti-Sortilin antibodies S-1, S-65, S-49, S-78, S-44, and S-8. The Sortilin backbone is rendered in a transparent grey representation. Highlighted in colors are linear binding regions identified for antibodies S-1 (green), S-65 (red), S-49 (blue), S-78 (yellow), S-44 (pink), and S-8 (purple). The binding sites are found within flexible loop regions of Sortilin.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach*(D. Catty, ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

Definitions

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations.

A "therapeutically effective amount" is at least the minimum concentration required to effect a measurable improvement of a particular disease, disorder, or condition. A therapeutically effective amount herein may vary according to factors such as the disease state, age, sex, and weight of the patient, and the ability of the Sortilin protein antagonist to elicit a desired response in the individual. A therapeutically effective amount is also one in which any toxic or detrimental effects of the Sortilin protein antagonist are outweighed by the therapeutically beneficial effects.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. Preferably, the individual is human.

The term "immunoglobulin" (Ig) is used interchangeably with "antibody" herein. The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

The basic 4-chain antibody unit is a heterotetrameric glycoprotein composed of two identical light (L) chains and two identical heavy (H) chains. The pairing of a $V_H$ and $V_L$ together forms a single antigen-binding site. For the structure and properties of the different classes of antibodies, see, e.g., *Basic and Clinical Immunology*, 8th Ed., Daniel P. Stites, Abba I. Terr and Tristram G. Parslow (eds.), Appleton & Lange, Norwalk, Conn., 1994. page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ") and mu ("μ"), respectively. The γ and γ classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three dimensional configurations of different classes of immunoglobulins are well known and described generally in, for example, Abbas et al., Cellular and Molecular Immunology, $4^{th}$ ed. (W.B. Saunders Co., 2000).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

An "isolated" antibody, such as an anti-Sortilin antibody of the present disclosure, is one that has been identified, separated and/or recovered from a component of its production environment (e.g., naturally or recombinantly). Preferably, the isolated polypeptide is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T-cells since at least one component of the antibody's natural environment will not be present. Ordinarily, however, an isolated polypeptide or antibody will be prepared by at least one purification step.

The "variable region" or "variable domain" of an antibody, such as an anti-Sortilin antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-Sortilin antibodies of the present disclosure. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as an anti-Sortilin antibody of the present disclosure, obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against one or more antigenic sites. In some embodiments, an antibody of the present disclosure can be a bispecific antibody. In contrast to polyclonal antibody preparations which typically include different antibodies directed against different determinants (epitopes), each monoclonal antibody is directed against a single determinant on the one or more antigenic sites. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, phage-display technologies (see, e.g., Clackson et al., *Nature,* 352:624-628 (1991); Marks et *J. Mol. Biol.* 222:581-597 (1992); Sidhu et al *J. Mol. Biol.* 338(2): 299-310 (2004); Lee et al., *J. Mol. Biol.* 340(5):1073-1093 (2004); Fellouse, *Proc. Nat'l Acad. Sci. USA* 101(34):12467-472 (2004); and Lee et al., *J. Immunol. Methods* 284(1-2):119-132 (2004), the hybridoma method (e.g., Kohler and Milstein, *Nature,* 256:495-97 (1975); Hongo et al., *Hybridoma,* 14 (3):253-260 (1995), Harlow et al., *Antibodies: A Laboratory Manual,* (Cold Spring Harbor Laboratory Press, 2d ed. 1988); Hammerling et al., in: *Monoclonal Antibodies and T-Cell Hybridomas* 563-681 (Elsevier, N. Y., 1981)), recombinant DNA methods (see, e.g., U.S. Pat. No. 4,816,567), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Nat'l Acad. Sci. USA* 90:2551 (1993); Jakobovits et al. *Nature* 362:255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10:779-783 (1992); Lonberg et al., *Nature* 368:856-859 (1994); Morrison, *Nature* 368:812-813 (1994); Fishwild et al. *Nature Biotechnol.* 14:845-851 (1996); Neuberger, *Nature Biotechnol.* 14:826 (1996); and Lonberg and Huszar, *Intern. Rev, Immunol.* 13:65-93 (1995).

The terms "full-length antibody," "intact antibody" or "whole antibody" are used interchangeably to refer to an antibody, such as an anti-Sortilin antibody of the present disclosure, in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al, *Protein Eng.* 8(10):1057-1062 (1995)); single-chain antibody molecules and multispecific antibodies formed from antibody fragments.

Papain digestion of antibodies, such as anti-Sortilin antibodies of the present disclosure, produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue (s) of the constant domains hear a free thiol group. F(ab')$_2$, antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and—binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies,* vol. 113, Rosenburg and Moore eds., Springer-Verlag, New York, pp. 269-315 (1994).

"Functional fragments" of antibodies, such as anti-Sortilin antibodies of the present disclosure, comprise a portion of an intact antibody, generally including the antigen binding or variable region of the intact antibody or the F region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Nat'l Acad. Sci. USA* 90:6444-48 (1993).

As used herein, a "chimeric antibody" refers to an antibody (immunoglobulin), such as an anti-Sortilin antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat'l Acad.*

Sci. USA, 81:6851-55 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as anti-Sortilin antibodies of the present disclosure, are chimeric antibodies that contain minimal sequence derived from non-human immunoglobulin. In one embodiment, a humanized antibody is a. human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, and the like. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see. e.g., Jones et al., *Nature* 321:522-525 (1986); Riechmann et al., *Nature* 332:323-329 (1988); and Presta, *Curr. Op. Struct, Biol.* 2:593-596 (1992). See also, for example, Vaswani and Hamilton, *Ann. Allergy, Asthma & Immunol.* 1:105-115 (1998), Harris, Biochem. *Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one that possesses an amino-acid sequence corresponding to that of an antibody, such as an anti-Sortilin antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.* 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology), See also, for example, Li et al., *Proc. Nat'l Acad. Sci. USA,* 103:3557-3562 (2006) regarding human antibodies generated via a human B-cell hybridoma technology.

The term "hypervariable region," "HVR," or "HV," when used herein refers to the regions of an antibody-variable domain, such as that of an anti-Sortilin antibody of the present disclosure, that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu in *Methods in Molecular Biology* 248:1-25 (Lo, ed., Human Press, Totowa, N.J., 2003)), indeed, naturally occurring camelid antibodies consisting of a heavy chain only are functional and stable in the absence of light chain. See, e.g., Hamers-Castennan et al., *Nature* 363:446-448 (1993) and Sheriff et al., *Nature Struct. Biol.* 3:733-736 (1996).

A number of HVR delineations are in use and are encompassed herein. The HVRs that are EU or Kabat complementarity-determining regions (CDRs) are based on sequence variability and are the most commonly used (Kabat et al., supra). Chothia refers instead to the location of the structural loops (Chothia and Lesk *J. Mol. Biol.* 196:901-917 (1987)). The AbM HVRs represent a compromise between the EU or Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31 -H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to EU or Kabat et al., supra, for each of these extended-HVR definitions.

"Framework" or "FR" residues are those variable-domain residues other than the HVR residues as herein defined.

The phrase "variable-domain residue-numbering as in EU or Kabat" or "amino-acid-position numbering as in EU or Kabat," and variations thereof, refers to the numbering system used for heavy-chain variable domains or light-chain variable domains of the compilation of antibodies in EU or Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g., residues 82a, 82b, and 82c, etc. according to Kabat) after heavy-chain FR residue 82. The EU or Kabat numbering of residues may be determined for a given antibody by alignment at regions of homology of the sequence of the antibody with a "standard" Kabat numbered sequence.

The EU or Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU or Kabt numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU or Kabat numbering system (e.g., see United States Patent Publication No. 2010-280227).

An "acceptor human framework" as used herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the VL human immunoglobulin framework sequence or human consensus framework sequence.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, 5th Ed. Public Health Service, National Institutes of Health, Bethesda, Md. (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra.

An "amino-acid modification" at a specified position, e.g., of an anti-Sortilin antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody, such as an anti-Sortilin antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically recognizes" or "specifically binds" refers to measurable and reproducible interactions such as attraction or binding between a target and an antibody, such as an anti-Sortilin antibody of the present disclosure, that is determinative of the presence of the target in the presence of a heterogeneous population of molecules including biological molecules. For example, an antibody, such as an anti-Sortilin antibody of the present disclosure, that specifically or preferentially binds to a target or an epitope is an antibody that binds this target or epitope with greater affinity, avidity, more readily, and/or with greater duration than it hinds to other targets or other epitopes of the target. It is also understood by reading this definition that, for example, an antibody (or a moiety) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3$ $M^{-1}$ or $10^4$ $M^{-1}$, sometimes about $10^5$ $M^{-1}$ or $10^6$ $M^{-1}$, in other instances about $10^6$ $M^{-1}$ or $10^7$ $M^{-1}$, about $10^8$ $M^{-1}$ to $10^9$ $M^{-1}$, or about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, an "interaction" between a Sortilin protein and a second protein encompasses, without limitation, protein-protein interaction, a physical interaction, a chemical interaction, binding, covalent binding, and ionic binding. As used herein, an antibody "inhibits interaction" between two proteins when the antibody disrupts, reduces, or completely eliminates an interaction between the two proteins. An antibody of the present disclosure, or fragment thereof, "inhibits interaction" between two proteins when the antibody or fragment thereof binds to one of the two proteins.

A "blocking" antibody, an "antagonist" antibody, or an "inhibitory" antibody is an antibody, such as an anti-Sortilin antibody of the present disclosure, that inhibits or reduces one or more biological activities of the antigen it binds, such as interactions with one or more proteins. In some embodiments, blocking antibodies, antagonist antibodies, or inhibitory antibodies substantially or completely inhibit one or more biological activities or interactions of the antigen.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU or Kabat numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. (see, e.g., M. Daëron, *Annu. Rev. Immunol.* 15:203-234 (1997)). FcRs are reviewed in Ravetch and Kinet, *Annu. Rev. Immunol.* 9:457-92 (1991); Capel et al., *Immunomethods* 4:25-34 (1994); and de Haas et al., *J. Lab. Clin. Med.* 126: 330-41 (1995). Other FcRs, including those to be identified in the future, are encompassed by the term "FcR" herein. FcRs can also increase the serum half-life of antibodies.

Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants with improved or diminished binding to FcRs. See also, e.g., Shields et al., *J. Biol. Chem.* 9(2):6591-6604 (2001).

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full length of the sequences being compared.

An "isolated" nucleic acid molecule encoding an antibody, such as an anti-Sortilin antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of the present disclosure.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

As used herein, the term "apoptosis" refers to gene-directed process of intracellular cell destruction. Apoptosis is distinct from necrosis; it includes cytoskeletal disruption, cytoplasmic shrinkage and condensation, expression of phosphatidylserine on the outer surface of the cell membrane and blebbing, resulting in the formation of cell membrane bound vesicles or apoptotic bodies. The process is also referred to as "programmed cell death." During apoptosis, characteristic phenomena such as curved cell surfaces, condensation of nuclear chromatin, fragmentation of chromosomal DNA, and loss of mitochondrial function are observed. Various known technologies may be used to detect apoptosis, such as staining cells with Annexin V, propidium iodide, DNA fragmentation assay and YO-PRO-1 (Invitrogen). In some embodiments, staining with Annexin V and propidium iodide may be used, and the combined percentages of the Annexin V+/PI+, Annexin V+/PI− and Annexin V−/PI+ populations are considered as dead cells.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the present disclosure described herein include "comprising," "consisting," and "consisting essentially of" aspects and embodiments.

Sortilin Proteins

In one aspect, the present disclosure provides isolated (e.g., monoclonal) antibodies that bind to an epitope within a Sortilin protein of the present disclosure. Sortilin proteins of the present disclosure include, without limitation, a mammalian Sortilin protein, human Sortilin protein, mouse Sortilin protein, and rat Sortilin protein.

Sortilin is variously referred to as sortilin 1, sort1, 100 kDa NT receptor, glycoprotein 95 (GP95), Progranulin receptor (PGRN-R), and neurotensin receptor 3 (NT-3 or NTR-3). Sortilin is an 831 amino acid protein that encodes a type 1 membrane receptor. Various Sortilin homologs are known, including without limitation, human Sortilin, rat Sortilin, and mouse Sortilin. The amino acid sequence of human Sortilin is set forth below as SEQ 1D NO: 1 (with key amino acid residues predicted to participate in Progranulin binding depicted in bold and, and the predicted pro-NGF binding region underlined):

```
        10         20         30         40         50
MERPWGAADG LSRWPHGLGL LLLLQLLPPS TLSQDRLDAP PPPAAPLPRW 60         70         80         90        100
SGPIGVSWGL RAAAAGGAFP RGGRWRRSAP GEDEECGRVR DFVAKLANNT 110        120        130        140        150
HQHVFDDLRG SVSLSWVGDS TGVILVLTTF HVPLVIMTFG QSKLYRSEDY 160        170        180        190        200
GKNFKDITDL INNTFIRTEF GMAIGPENSG KVVLTAEVSG GSRGGRIFRS 210        220        230        240        250
SDFAKNFVQT DLPFHPLTQM MYSPQNSDYL LALSTENGLW VSKNFGGKWE 260        270        280        290        300
EIHKAVCLAK WGSDNTIFFT TYANGSCKAD LGALELWRTS DLGKSEKTIG 310        320        330        340        350
VKIYSFGLGG RFLFASVMAD KDTTRRIHVS TDQGDTWSMA QLPSVGQEQF 360        370        380        390        400
YSILAANDDM VFMHVDEPGD TGFGTIFTSD DRGIVYSKSL DRHLYTTTGG 410        420        430        440        450
ETDFTNVTSL RGVYITSVLS EDNSIQTMIT FDQGGRWTHL RKPENSECDA 460        470        480        490        500
TAKNKNECSL HIHASYSISQ KLNVPMAPLS EPNAVGIVIA HGSVGDAISV 510        520        530        540        550
MVPDVYISDD GGYSWTKMLE GPHYYTILDS GGIIVAIEHS SRPINVIKFS 560        570        580        590        600
TDEGQCWQTY TFTRDPIYFT GLASEPGARS MNISIWGFTE SFLTSQWVSY 610        620        630        640        650
TIDFKDILER NCEEKDYTIW LAHSTDPEDY EDGCILGYEE QFLRLRKSSV 660        670        680        690        700
CQNGRDYVVT KQPSICLCSL EDFLCDFGYY RPENDSKCVE QPELKGHDLE 710        720        730        740        750
FCLYGREEHL TTNGYRKIPG DKCQGGVNPV REVKDLKKKC TSNFLSPEKQ 760        770        780        790        800
NSKSNSVPII LAIVGLMLVT VVAGVLIVKK YVCGGRFLVH RYSVLQQHAE 810        820        830
ANGVDGVDAL DTASHTNKSG YHDDSDEDLL E
```

Additionally, the amino acid sequence of mouse Sortilin is set forth in SEQ ID NO: 2:
MERPRGAADG LLRWPLGLLL LLQLLPPAAV GQDRLDAPPP PAPPLLRWAG PVGVSWGLRA AAPGGPVPRA

GRWRRGAPAE DQDCGRLPDF IAKLTNNTHQ HVFDDLSGSV SLSWVGDSTG VILVLTTFQV PLVIVSFGQS

KLYRSEDYGK NFKDITNLIN NTFIRTEFGM AIGPENSGKV ILTAEVSGGS RGGRVFRSSD FAKNFVQTDL

PFHPLTQMMY SPQNSDYLLA LSTENGLWVS KNFGEKWEEI HKAVCLAKWG PNNIIFFTTH VNGSCKADLG

ALELWRTSDL GKTFKTIGVK IYSFGLGGRF LFASVMADKD TTRRIHVSTD QGDTWSMAQL PSVGQEQFYS

ILAANEDMVF MHVDEPGDTG FGTIFTSDDR GIVYSKSLDR HLYTTTGGET DFTNVTSLRG VYITSTLSED

NSIQSMITFD QGGRWEHLRK PENSKCDATA KNKNECSLHI HASYSISQKL NVPMAPLSEP NAVGIVIAHG

SVGDAISVMV PDVYISDDGG YSWAKMLEGP HYYTILDSGG IIVAIEHSNR PINVIKFSTD EGQCWQSYVF

TQEPIYFTGL ASEPGARSMN ISIWGFTESF ITRQWVSYTV DFKDILERNC EEDDYTTWLA HSTDPGDYKD

GCILGYKEQF LRLRKSSVCQ NGRDYVVAKQ PSVCPCSLED FLCDFGYFRP ENASECVEQP ELKGHELEFC

LYGKEEHLTT NGYRKIPGDK CQGGMNPARE VKDLKKKCTS NFLNPTKQNS KSNSVPIILA IVGLMLVTW

AGVLIVKKYV CGGRFLVHRY SVLQQHAEAD GVEALDSTSH AKSGYHDDSD EDLLE

Additionally, the amino acid sequence of rat Sortilin is set forth in SEQ ID NO: 3.
MERPRGAADG LLRWPLGILL LLQLLPPAAV GQDRLDAPPP PAPPLLRWAG PVGVSWGLRA AAPGGPVPRA

GRWRRGAPAE DQDCGRLPDF IAKLTNNTHQ HVFDDLSGSV SLSWVGDSTG VILVLTTFQV PLVIVSFGQS

-continued

```
KLYRSEDYGK NFKDITNLIN NTFIRTEFGM AIGPENSGKV ILTAEVSGGS RGGRVFRSSD FAKNFVQTDL

PFHPLTQMMY SPQNSDYLLA LSTENGLWVS KNFGEKWEEI HKAVGLAKWG PNNIIFFTTH VNGSCKADLG

ALELWRTSDL GKTFKTIGVK IYSFGLGGRF LFASVMADKD TTRRIHVSTD QGDTWSMAQL PSVGQEQFYS

ILAANDDMVF MHVDEPGDTG FGTIFTSDDR GIVYSKSLDR HLYTTTGGET DFTNVTSLRG VYITSTLSED

NSIQSMITFD QGGRWEHLQK PENSKCDATA KNKNECSLHI HASYSISQKL NVPMAPLSEP NAVGIVIAHG

SVGDAISVMV PDVYISDDGG YSWAKMLEGP HYYTILDSGG IIVAIEHSNR PINVIKFSTD EGQCWQSYVF

SQEPVYFTGL ASEPGARSMN ISIWGFTESF LTRQWVSYTI DFKDILERNC EENDYTTWLA HSTDPGDYKD

GCILGYKEQF LRLRKSSVCQ NGPDYVVAKQ PSICPCSLED FLCDFGYFRP ENASECVEQP ELKGHELEFC

LYGKEEHLTT NGYRKIPGDR CQGGMNPARE VKDLKKKCTS NFLNPKKQNS KSSSVPIILA IVGLMLVTVV

AGVLIVKKYV CGGRFLVHRY SVLQQHAEAD GVEALDTASH AKSGYHDDSD EDLIE
```

In some embodiments, the Sortilin is a preprotein that includes a signal sequence. In some embodiments, the Sortilin is a mature protein. In some embodiments, the mature Sortilin protein does not include a signal sequence. In some embodiments, the mature Sortilin protein is expressed on a cell, Sortilin proteins of the present disclosure include several domains, including without limitation, a signal sequence, a propeptide, a luminal domain, a Vps10p domain, a 10 CC domain, a transmembrane domain and a cytoplasmic domain. Additionally, proteins of the present disclosure are expressed at high levels in a number of tissues, including without limitation, the brain, spinal cord, heart and skeletal muscle, thyroid, placenta, and testis.

Sortilin is a member of the Vps10p family of sorting receptors, which also includes, without limitation, sorting protein-related receptor with A-type repeats (SorLA), sortilin-related receptor CNS expressed 1 (SorCS1), sortilin-related receptor CNS expressed 2 (SorCS2), and sortilin-related receptor CNS expressed 3 (SorCS3). The luminal region of Sortilin aligns with each of the two luminal domains in yeast Vps10p (Vps10p domains). The hallmark of the Vps10p domain is an amino-terminal propeptide and a carboxy-terminal segment that contains 10 conserved cysteine (10CC) residues. Other receptors of the Vps10p family share a Vps10p domain, which is situated at the amino-terminus, and contain additional ectodomains.

The Vps10p family of sorting receptors has diverse functions both within the nervous system and elsewhere. The receptors have been shown to be multifunctional, binding several different ligands, including without limitation, Progranulin (PGRN), pro-nerve growth factor (Pro-NGF), nerve growth factor (NGF), PCSK9, pro-neurotrophins, neurotrophins, pro-neurotrophin-3 (pro-NT3), pro-neurotrophin-4/5, pro-brain-derived neurotrophic factor (Pro-BDNF), brain-derived neurotrophic factor (BDNF), neurotrophin-3 (NT3), neurotrophin-4/5, neurotensin, p75NTR, Sortilin propeptide (Sort-pro), amyloid precursor protein (APP), lipoprotein lipase (LpL), apolipoproteins, apolipoprotein AV (APOA5), apolipoprotein E (APOE 2, 3, 4). receptor-associated protein (RAP), and elements of the plasminogen activator system; and engaging in intracellular sorting, endocytosis, and signal transduction. Sortilin proteins of the present disclosure have been shown to mediate rapid endocytosis of lipoprotein lipase. neurotensin, and the pro-form of nerve growth factor; and to target proteins for transport from the Golgi to late endosomes. Further, Sortilin proteins of the present disclosure have been shown to form a complex with p75 on the cell membrane and be essential to pro-nerve growth factor (NGF)-induced neuronal death. It has also been recently shown that members of the lips Vps10p receptor family interact with members of the neurotrophin family, which includes NGF, brain derived neurotrophic factor, neurotrophin-3, and neurotrophin-4/5, or the pro-domain form of a neurotrophin (pro-neurotrophin). Sortilin proteins of the present disclosure have also been shown to bind to and regulate extracellular levels of PCSK9, which destines low-density lipoprotein receptor for degradation in lysosomes, resulting in increased levels of LDL cholesterol, Accordingly, as used herein a "Sortilin" protein of the present disclosure includes, without limitation, a mammalian Sortilin protein, human Sortilin protein, primate Sortilin protein, mouse Sortilin protein, and rat Sortilin protein. Additionally, anti-Sortilin antibodies of the present disclosure may bind an epitope within one or more of a mammalian Sortilin protein, human Sortilin protein, primate Sortilin, mouse Sortilin protein, and rat Sortilin protein.

Sortilin Protein Domains

Sortilin proteins of the present disclosure contain several domains, such as a Vps10p domain that contains an Asp-box motif, a ten-bladed beta-propeller structure, and a hydrophobic loop; and a 10 CC domain.

As disclosed herein, interactions between Sortilin proteins of the present disclosure and pro-neurotrophins or neurotrophins are mediated by the Vps10p domain that contains a ten-bladed beta-propeller structure and an Asp-box motif. In certain embodiments, Sortilin proteins of the present disclosure contain a Vps10p domain that includes a ten-bladed beta-propeller structure and is located within amino acid residues 78-611 of human Sortilin (SEQ ID NO: 1) or amino acid residues of a mammalian Sortilin that correspond to amino acid residues 78-611 of SEQ ID NO: 1. In certain embodiments, amino acid residues 190-220 of human Sortilin (SEQ ID NO: 1) or amino acid residues of a mammalian Sortilin that correspond to amino acid residues 190-220 of SEQ ID NO: 1 are located within the Vps10p domain.

Vps10p domains of the present disclosure may include an Asp-box motif. As used herein, Asp-box motifs have the following sequence: (S/T)-X-(D/N)-X-X-X-X-(W/F/Y) (SEQ ID NO: 4), or X-X-(S/T)-X-(D/N)-X-G-X-(T/S)-(W/F/Y)-X (SEQ NO: 5), where X represents any amino acid. In human Sortilin, the Asp-box motif is located at amino acid residues 200-207 (SSDFAKNF (SEQ ID NO:694)). Accordingly, in certain embodiments, an Asp-box motif is located at amino acid residues 200-207 of human Sortilin (SEQ ID NO:1) or amino acid residues of a mammalian Sortilin that correspond to amino acid residues 200-207 of SEQ ID NO: 1.

As disclosed herein, interactions between Sortilin proteins of the present disclosure and p75 are mediated by the 10CC domain of the hydrophobic loop of the Vps10p domain.

In certain embodiments, Sortilin proteins of the present disclosure contain a 10CC domain that is located within amino acid residues 610-757 of human Sortilin (SEQ ID NO: 1) or amino acid residues of a mammalian Sortilin that correspond to amino acid residues 610-757 of SEQ ID NO: 1. In preferred embodiments, amino acid residues 592-593, 610-660, and/or 667-749 of human Sortilin (SEQ ID NO: 1) or amino acid residues of a mammalian Sortilin that correspond to amino acid residues 592-593, 610-660, and/or 667-749 of SEQ ID NO: 1 are located within the 10CC domain of Sortilin.

In other embodiments, Sortilin proteins of the present disclosure contain a hydrophobic loop within the Vps10p domain that is located within amino acid residues 130-141 of human Sortilin (SEQ ID NO: 1) or amino acid residues of a mammalian Sortilin that correspond to amino acid residues 130-141 of SEQ ID NO: 1.

As one of skill in the art will appreciate, the beginning and ending residues of the domains of the present disclosure may vary depending upon the computer modeling program used or the method used for determining the domain.

Sortilin Binding Partners

Sortilin proteins of the present disclosure can interact with (e.g., bind to) one or more proteins including, without limitation, Progranulin protein; neurotrophins, such as pro-neurotrophins, pro-neurotrophin-3, neurotrophin-3, pro-neurotrophin-4/5, neurotrophin-4/5, pro-nerve growth factor (Pro-NGF), nerve growth factor (NGF), pro-brain-derived neurotrophic factor (Pro-BDNF), and brain-derived neurotrophic factor (BDNF); neurotensin, p75, lipoprotein lipase (LpL), apolipoprotein AV (APOA5), apolipoprotein E (APOE), amyloid precursor protein, A beta peptide, PCSK9, p75NTR, and receptor associated protein (RAP).

Progranulin

Sortilin proteins of the present disclosure have been shown to interact (e.g., bind to) directly with Progranulin and mediate the degradation of Progranulin (e.g., Zheng, Y et al., (2011) PLoS ONE 6(6): e21023).

Progranulin is variously referred to as PGRN, proepithelin, granulin-epithelin precursor, PC (prostate cancer) cell-derived growth factor (PCDGF), and acrogranin. Progranulin is a 593 amino acid protein that encodes a 68.5 kD a secreted glycoprotein that has 7.5 repeats of smaller granulin (epithelia) motifs, ranging from 6-25 kDa, which can be proteolytically cleaved from the precursor PGRN. Examples of Progranulin cleavage products include, without limitation, granulin A/Epithelins 1, granulin B Epithelins 2, granulin C, granulins D, granulin E, granulin F, granulin G and any other known peptide products derived from Progranulin.

Progranulin is widely expressed, and in non-neuronal cells has been associated with a variety of events, such as cell cycle regulation and cell motility, wound repair, inflammation, induction of growth factors such as vascular endothelial growth factor (VEGF), and tumorigenesis. Progranulin is also widely expressed in early neural development, but becomes restricted in later development to defined neuronal populations, such as cortical neurons, hippocampal pyramidal neurons, and Purkinje cells. However, the role of Progranulin in neuronal cells was unclear until patients suffering from frontotemporal dementia (FTD) were shown to carry mutations in the Progranulin gene on chromosome 17. Subsequently, Progranulin has been shown to promote neuronal survival and enhance neurite outgrowth in cortical and motor neurons. Thus, although Progranulin is not a neurotrophin, or a member of the neurotrophin family, it has been referred to as a neurotrophic factor because of its ability to promote neuronal survival.

Further, it has been shown that haploinsufficiency of Progranulin (which include over 70 different mutations, such as loss-of-function mutations) is associated with frontotemporal dementia (FTD) with TDP-43 pathology. Furthermore, Progranulin levels in plasma are reduced with patients with FTD mutations. Progranulin mutations account for 25% of familial FTD. Additionally, low levels of Progranulin are seen in some FTD patients without Progranulin mutations, and Progranulin levels are altered in Alzheimer's disease and ALS. Thus, it is believed that Progranulin may be generally involved in degenerative diseases.

It has also been shown that complete loss of Progranulin leads to a Neuronal Lipoid Fuscinosis (NPL) phenotype. Accordingly, it is believe that individuals with various lysosomal storage disorders may respond to increased levels of Progranulin. Progranulin is widely expressed, and in the central nervous system is produced by neurons and microglia. Progranulin is also generally thought to have an anti-inflammatory role in macrophages and microglia, and a pro-survival role in neurons.

Accordingly, anti-Sortilin antibodies of the present disclosure that increase Progranulin levels, decrease cell surface levels of Sortilin, and/or block the interaction (e.g., binding) between Sortilin and Progranulin would be beneficial for preventing, lowering the risk of, or treating conditions and/or diseases associated with decreased levels of Progranulin expression and/or activity, cell death (e.g., neuronal cell death), frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotriphic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, intervertebral disc degeneration, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arforitis, multiple sclerosis, metabolic disorder, obesity, insulin resistance, type 2 diabetes, tissue or vascular damage, an injury, and/or one or more undesirable symptoms of normal aging. Additionally, anti-Sortilin antibodies of the present disclosure that increase Progranulin levels, decrease cell surface levels of Sortilin, and/or block the interaction e.g., binding) between Sortilin and Progranulin may inhibit interaction between Sortilin and Progranulin, may induce one or more Progranulin activities, may reduce the endosomal internalization of Progranulin, or fragments thereof, and/or may increase the effective concentration of Progranulin.

In some embodiments, anti-Sortilin antibodies of the present disclosure that increase Progranulin levels, decrease cell surface levels of Sortilin, and/or block the interaction (e.g., binding) between Sortilin and Progranulin bind to one or more amino acids within amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of human Sortilin (SEQ ID NO: 1); or within amino acid residues of a mammalian Sortilin that corresponds to amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of SEQ ID NO: 1. In other embodiments, anti-Sortilin antibodies of the present disclosure that increase Progranulin levels, decrease cell surface levels of Sortilin, and/or block the interaction (e.g., binding) between Sortilin and Progranulin may bind one or more amino acids of amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of human Sortilin (SEQ ID NO: 1); or of amino acid residues of a mammalian Sortilin that corresponds to one or more amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379Arg382, Tyr386, Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of SEQ ID NO: 1.

Neurotrophins

Sortilin proteins of the present disclosure have been shown to interact (e.g., bind) directly with pro-neurotrophins (e.g., pro-NGF), which harbor a pro-domain and are typically pro-apoptotic (e.g., Andersen, O S et al. (2010) The Journal of Biological Chemistry, 285, 12210-12222). Such pro-NGF precursors are released during stress, and Sortilin proteins have been shown to be involved in regulating their release as well as binding on the receiving cell. This binding may be mediated through a linear epitope on Sortilin that corresponds to amino acid residues 163-174 of SEQ ID NO: 1.

Neurotrophins are a family of dimeric peptide hormone proteins that induce neuronal cell survival, development, and function. Neurotrophins belong to a class of growth factors, which are secreted proteins that are capable of signaling particular cells to survive, differentiate, or grow. Growth factors such as neurotrophins that promote the survival of neurons are known as neurotrophic factors. Neurotrophic factors are secreted by target tissues and act by preventing the associated neuron from initiating programmed cell death. Neurotrophins can also induce differentiation of progenitor cells to form neurons. Neurotrophins of the present disclosure are synthesized intracellularly as 30-35 kDa precursor proteins, containing a signal peptide and glycosylation sites. During processing precursor proteins are also cleaved at a di-basic cleavage site by the calcium-dependent serine protease furin and other members of the prohormone convertase family, within the Golgi apparatus. The N-terminal part of this cleavage is the mature neurotrophin of 118-120 amino acids and a biologically active 12-14 kDa C-terminal product (Seidah et al, Biochem. J. (1996) 314:951-960). As used herein, "neurotrophin" and "neurotrophic factor" may be used interchangeably. Neurotrophins of the present disclosure include, without limitation, the structurally related factors nerve growth factor (NGF), brain-derived neurotrophic factor (BDNF), neurotrophin-3 (NT-3), and neurotrophin-4 (NT-4). As used herein a "pro-neurotrophin" may refer to any pro-peptide of the neurotrophin family, including; without limitation, pro-NGF, pro-BDNF, pro-neurotrophin-3 and pro-neurotrophin-4/5.

It has been shown that pro-neurotrophins play a pathological role in aging, seizures, retinal dystrophy, traumatic brain injury, spinal cord injury, and long-term depression (e.g., Beattie, M S et al., (2002) Neuron 36, 375-386; Volosin, M et al. (2006) J. Neurosci. 26, 7756-7766 Nykjaer, A et al., (2005) Curr. Opin. Neurobiol. 15, 49-57; Jansen, P et al., (2007) Nat. Neurosci. 10, 1449-1457; Volosin, M et al., (2008) J. Neurosci. 28, 9870-9879; Fahnestock, M et al., (2001) Mol. Cell Neurosci. 18, 210-220; Nakamura, K et al., (2007) Cell Death. Differ. 14, 1552-1554; Yune, T et al. (2007) J. Neurosci. 27, 7751-7761, Arnett, M G et al., (2007) Brain Res. 1183, 32-42; Wei, Y et al., (2007) Neurosci. Lett. 429, 169-174; Provenzano, M J et al., (2008) Laryngoscope 118, 87-93; and Pang, P T et al., (2004) Science 306, 487-491).

Nerve growth factor (NGF) is a small, secreted protein that homodimerizes and is incorporated into a larger complex. NGF has nerve growth stimulating activity and the complex is involved in the regulation of growth, maintenance, survival, and the differentiation of sympathetic and certain sensory neurons. Mutations in NGF have been associated with hereditary sensory and autonomic neuropathy, type 5 (HSAN5), and dysregulation of NGF expression is associated with allergic rhinitis. Without wishing to be bound by theory, it is also believed that pro-NGF can induce apoptosis and long-term depression.

Brain-derived neurotrophic factor (BDNF) is a secreted protein induced by cortical neurons, and is necessary for survival of striatal neurons in the brain. Expression of BDNF is reduced in both Alzheimer's disease and Huntington disease patients. BDNF may play a role in the regulation of stress response and in the biology of mood disorders. Multiple transcript variants encoding distinct isoforms have been described for this gene. Without wishing to be bound by theory, it is also believed that pro-BDNF can induce apoptosis and long term depression.

Neurotrophin-3 is a secreted protein that is necessary for survival and function of multiple peripheral and central nervous system neurons. A neurotrophin-3 gene variant is associated with severe forms of schizophrenia and pro-neurotrophin-3 (pro-NT3) induces sympathetic neuron death.

Accordingly, anti-Sortilin antibodies of the present disclosure may also inhibit (e.g., block) the interaction between Sortilin and neurotrophies of the present disclosure (e.g., pro-neurotrophins). Such antibodies may be beneficial for preventing, lowering the risk of, or treating conditions and/or diseases associated with decreased levels of neurotrophin expression and/or activity, cell death (e.g., neuronal cell death), ffrontotemparal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotriphic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, intervertebral disc degeneration, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arforitis, multiple sclerosis, metabolic disorder, obesity, insulin resistance, type 2 diabetes, tissue or vascular damage, an injury, and/or one or more undesirable symptoms of normal aging. Anti-Sortilin antibodies of the present disclosure that inhibit (e.g., block) the interaction between Sortilin and neurotrophins of the present disclosure (e.g., pro-neurotrophins) may also prevent cell death (e.g., apoptosis) induced by pro-neurotrophins.

In some embodiments, anti-Sortilin antibodies of the present disclosure that inhibit (e.g., block) the interaction between Sortilin and a neurotrophin of the present disclosure bind one or more amino acids within amino acid residues within amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of human Sortilin (SEQ ID NO: 1); or within amino acid residues of a mammalian Sortilin that corresponds to amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of SEQ ID NO: 1. In other embodiments, anti-Sortilin antibodies of the present disclosure that inhibit (e.g., block) the interaction between Sortilin and a neurotrophin of the present disclosure bind one or more amino acids of amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of human Sortilin (SEQ ID NO: 1); or of amino acid residues of a mammalian Sortilin that corresponds to one or more amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of SEQ ID NO: 1.

Neurotensin

Sortilin proteins of the present disclosure have been shown to interact (e.g., bind) with neurotensin within the beta-propeller structure of Sortilin, and an important contact has been shown to at serine 283 of human Sortilin (e.g., Quistgaard, E M, et al. (2009) Nature Structural and Molecular Biology, 16 p96-98). This residue is also has also been shown to be important for Progranulin binding. The neurotensin binding site is within the centrally located tunnel of the beta-propeller structure of Sortilin, whereas the pro-neurotrophin domain is on the surface of the beta-propeller structure. Pro-neurotrophin binding to Sortilin is partly inhibited by neurotensin, as the binding regions are not very far apart.

Neurotensin is a 13 amino acid neuropeptide that is implicated in the regulation of luteinizing hormone and prolactin release. Neurotensin has been shown to have significant interaction with the dopaminergic system. Neurotensin is synthesized as part of a 169-170 amino acid precursor protein that also contains the related neuropeptide neuromedin N. The peptide coding domains are located in tandem near the carboxyl terminal end of the precursor and are bounded and separated by paired basic amino acid (lysine-arginine) processing sites. Neurotensin shares significant sequence similarity in its 6 C-terminal amino acid residues with several other neuropeptides, including neuromedin N. This C-terminal region is responsible for the full biological activity, while the N-terminal portion has a modulatory role. In the central nervous system, neurotensin has the dual function of a neuromodulator of dopamine transmission and of anterior pituitary hormone secretion. It also shows potent hypothermic and analgesic effects in the brain. Neurotensin has also been implicated in the pathophysiology of schizophrenia, Huntington, and Parkinson diseases. Neurotensin has also been shown to provide neuroprotection in experimental models of cerebral ischemia.

Accordingly, anti-Sortilin antibodies of the present disclosure may also inhibit e.g., block) the interaction between Sortilin and neurotensin. Such antibodies would be beneficial for preventing, lowering the risk of, or treating conditions and/or diseases associated with decreased levels of neurotensin expression and/or activity, cell death (e.g., neuronal cell death), frontotemporal dementia, Alzheimer's disease, vascular dementia, seizures, retinal dystrophy, a traumatic brain injury, a spinal cord injury, long-term depression, atherosclerotic vascular diseases, and/or undesirable symptoms of normal aging.

In some embodiments, anti-Sortilin antibodies of the present disclosure that inhibit (e.g., block) the interaction between Sortilin and neurotensin bind one or more amino acids within amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of human Sortilin (SEQ ID NO: 1); or within amino acid residues of a mammalian Sortilin that corresponds to amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of SEQ ID NO: 1. In other embodiments, anti-Sortilin antibodies of the present disclosure that inhibit (e.g., block) the interaction between Sortilin and neurotensin bind one or more amino acids of amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of human Sortilin (SEQ ID NO: 1); or of amino acid residues of a mammalian Sortilin that corresponds to one or more amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of SEQ ID NO: 1.

Low Affinity Nerve Growth Factor Receptor (p75)

Sortilin proteins of the present disclosure have been shown to interact (e.g., bind) with the low affinity nerve growth factor (NGF) receptor (p75) within the 10CC domain of Sortilin or the hydrophobic loop of the Vps10p domain of Sortilin. As disclosed herein, Sortilin proteins of the present disclosure can function as a co-receptor with p75 for pro-neurotrophins, which induce apoptotic signaling.

Low affinity NGF receptor variously referred to as p75, p75 neurotrophin receptor, p75 NGF receptor, $p75^{NTR}$, LNGFR, NGFR, CD271, Gp80-LNGFR, and TNTRSF16, and $p75^{NTR}$. P75 is one of the two receptor types for neurotrophins of the present disclosure. P75 has been shown that binds and serves as a "sink" for neurotrophins. It has also been shown, however, that, in the absence of a co-expressed TrkA (the other receptor type for neurotrophins), p75 can induce cell death (e.g., apoptosis) in cells. As such and without wishing to be bound by theory, it is believed that blocking the interaction between Sortilin and p75 reduces the production of a p75 immunogenic cell death-dependent cell death signal.

Thus, inhibiting interaction (e.g., binding) of Sortilin to p75 would decrease the effective concentration of pro-neurotrophins and thus the resulting neuronal cell death.

Accordingly, anti-Sortilin antibodies of the present disclosure may also inhibit (e.g., block) the interaction between Sortilin and p75. Such antibodies would be beneficial for preventing, lowering the risk of, or treating conditions and/or diseases associated with decreased levels of p75 expression and/or activity, cell death (e.g., neuronal cell death), frontotemporal dementia, Alzheimer's disease, vascular dementia, seizures, retinal dystrophy, a traumatic brain injury, a spinal cord injury, long-term depression, atherosclerotic vascular diseases, and/or undesirable symptoms of normal aging. Anti-Sortilin antibodies of the present disclosure that inhibit (e.g., block) the interaction between Sortilin and p75 would also decrease the effective concentrations of pro-neurotrophins required for apoptotic signaling by p75, reduce the internalization of p75, or fragments thereof, destined for endosomes, reduce the production of a p75 immunogenic cell death-dependent cell death signal in cells, and prevent cell death (e.g., apoptosis) induced by p75.

In some embodiments, anti-Sortilin antibodies of the present disclosure that inhibit (e.g., block) the interaction between Sortilin and p75 bind one or more amino acids within amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of human Sortilin (SEQ ID NO: 1); or within amino acid residues of a mammalian Sortilin that corresponds to amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of SEQ ID NO: 1. In other embodiments, anti-Sortilin antibodies of the present disclosure that inhibit (e.g., block) the interaction between Sortilin and p75 bind one or more amino acids of amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe:314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of human Sortilin (SEQ ID NO: 1); or of amino acid residues of a mammalian Sortilin that corresponds to one or more amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of SEQ ID NO: 1.

Amyloid Precursor Protein (APP)

Sortilin proteins of the present disclosure have been shown to interact (e.g., bind) with amyloid precursor protein (APP). As disclosed herein, Sortilin proteins of the present disclosure can function to change the subcellular localization of APP and to increase its processing to the A beta peptides and intra-cellular fragments which are associated with Alzheimer's disease.

Amyloid precursor protein (APP) is an integral membrane protein expressed in many tissues and concentrated in the synapses of neurons. Its primary function is not known, though it has been implicated as a regulator of synapse formation, neural plasticity and iron export. APP is best known as the precursor molecule whose proteolysis generates beta amyloid (Aβ), a 37 to 49 amino acid peptide whose amyloid fibrillar form is the primary component of amyloid plaques found in the brains of Alzheimer's disease patients.

Thus, inhibiting interaction (e.g., binding) of Sortilin to APP would increase the effective concentration of pro-neurotrophins. Moreover, blocking the interaction between Sortilin and APP would result in reduced endosomal internalization of APP and its processing to the A beta peptide.

Accordingly, anti-Sortilin antibodies of the present disclosure may also inhibit (e.g., block) the interaction between Sortilin and APP. Such antibodies would be beneficial for preventing, lowering the risk of, or treating conditions and/or diseases associated with abnormal levels or processing of APP expression and/or activity, cell death (e.g., neuronal cell death), frontotemporal dementia, Alzheimer's disease, vascular dementia, seizures, retinal dystrophy, a traumatic brain injury, a spinal cord injury, long-term depression, atherosclerotic vascular diseases, and/or undesirable symptoms of normal aging.

In some embodiments, anti-Sortilin antibodies of the present disclosure that inhibit (e.g., block) the interaction between Sortilin and APP bind one or more amino acids within amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of human Sortilin (SEQ ID NO: 1); or within amino acid residues of a mammalian Sortilin that corresponds to amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of SEQ ID NO: 1. In other embodiments, anti-Sortilin antibodies of the present disclosure that inhibit (e.g., block) the interaction between Sortilin and APP bind one or more amino acids of amino acid residues Arg88, Phe105, Leu108, Arg109, Gly110, His131, Val132, Pro133, Leu134, Val135, Ile136, Met137, Thr138, Arg196, Phe198, Arg199Phe203, Lys205, Phe207, Thr210, Thr218, Tyr222, Ser223, Ser227, Ser242, Lys243, Lys248, Lys254, Lys260, Ser305, Phe306, Gly307, Arg 311, Phe314, Ser316, Arg325, Arg326, Ile327, Phe350, Tyr351, Ser352, Ile353, Asn373, Ser379, Arg382, Tyr386Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of human Sortilin (SEQ ID NO: 1); or of amino acid residues of a mammalian Sortilin that corresponds to one or more amino acid residues Arg88, Phe105, Leu108, Arg109, Gly110, His131, Val132Pro133, Leu134, Val135, Ile136, Met137, Thr138, Arg196Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of SEQ ID NO: 1.

Lipoprotein Lipase

Sortilin proteins of the present disclosure have been shown to interact (e.g., bind) with the lipoprotein lipase (LpL). As disclosed herein, Sortilin proteins of the present disclosure bind to and modify the degradation of LpL.

Lipoprotein lipase is a secreted enzyme that has EC 3.1.1.34 activity. Lipoprotein lipase is a member of the lipase gene family, which includes pancreatic lipase, hepatic lipase, and endothelial lipase. It is a water-soluble enzyme that hydrolyzes triglycerides in lipoproteins, such as those found in chylomicrons and very low-density lipoproteins (VLDL), into two free fatty acids and one monoacylglycerol molecule. Lipoprotein lipase is also involved in promoting the cellular uptake of chylomicron remnants, cholesterol-rich lipoproteins, and free fatty acids. Lipoprotein lipase is attached to the luminal surface of endothelial cells in capillaries, and is most widely distributed in adipose, heart, and skeletal muscle tissue. Lipoprotein lipase is secreted from parenchymal cells as a glycosylated homodimer, and is then translocated through the extracellular matrix and across endothelial cells to the capillary lumen.

Accordingly, an Sortilin antibodies of the present disclosure may also inhibit (e.g., block) the interaction between Sortilin and lipoprotein lipase. Such antibodies would be beneficial for preventing, lowering the risk of, or treating conditions and/or diseases associated with decreased levels of lipoprotein lipase expression and/or activity, vascular dementia, and/or atherosclerotic vascular diseases.

In some embodiments, anti-Sortilin antibodies of the present disclosure that inhibit (e.g., block) the interaction between Sortilin and lipoprotein lipase bind one or more amino acids within amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of human Sortilin (SEQ ID NO: 1); or within amino acid residues of a mammalian Sortilin that corresponds to amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of SEQ ID NO: 1. In other embodiments, anti-Sortilin antibodies of the present disclosure that inhibit (e.g., block) the interaction between Sortilin and lipoprotein lipase bind one or more amino acids of amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350Tyr351, Ser352, Ile353Asn373, Ser379, Arg382, Tyr386, Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of human Sortilin (SEQ ID NO: 1); or of amino acid residues of a mammalian Sortilin that corresponds to one or more amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of SEQ ID NO: 1.

Apolipoprotein AV

Sortilin proteins of the present disclosure have been shown to interact (e.g., bind) with the apolipoprotein AV (APOA5). As disclosed herein, Sortilin proteins of the present disclosure bind to and modify the degradation of APOA5.

Apolipoprotein AV is variously referred to as apolipoprotein A-V, APOA5, APOAV, and RAP3. Apolipoprotein AV is an important regulator of plasma triglyceride levels, which is a major risk factor for atherosclerotic vascular diseases, such as coronary artery disease. It is a component of several lipoprotein fractions including VLDL HDL, and chylomicrons. Apolipoprotein AV may affect lipoprotein metabolism by interacting with LDL-R gene family receptors.

Accordingly, anti-Sortilin antibodies of the present disclosure may also inhibit (e.g., block) the interaction between Sortilin and apolipoprotein AV. Such antibodies would be beneficial for preventing, lowering the risk of, or treating conditions and/or diseases associated with abnormal levels of apolipoprotein AV expression and/or activity, vascular dementia, and/or atherosclerotic vascular diseases.

In some embodiments, anti-Sortilin antibodies of the present disclosure that inhibit (e.g., block) the interaction between Sortilin and apolipoprotein AV bind one or more amino acids within amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of human Sortilin (SEQ ID NO: 1); or within amino acid residues of a mammalian Sortilin that corresponds to amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of SEQ ID NO: 1. In other embodiments, anti-Sortilin antibodies of the present disclosure that inhibit (e.g., block) the interaction between Sortilin and apolipoprotein AV bind one or more amino acid of amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of human Sortilin (SEQ ID NO: 1); or of amino acid residues of a mammalian Sortilin that corresponds to one or more amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of SEQ ID NO: 1.

Apolipoprotein E

Sortilin proteins of the present disclosure have been shown to interact (e.g., bind) with the apolipoprotein E (APOE2, APOE3, APOE4). As disclosed herein, Sortilin proteins of the present disclosure bind to and modify the degradation and transport of APOE as well as agents that APOE carries such as the A beta peptide.

Apolipoprotein E (APOE) is a class of apolipoprotein found in the chylomicron and Intermediate-density lipoprotein (IDLs) that is essential for the normal catabolism of triglyceride-rich lipoprotein constituents. In peripheral tissues, APOE is primarily produced by the liver and macrophages, and mediates cholesterol metabolism in an isoform-dependent manner. In the central nervous system, APOE is mainly produced by astrocytes, and transports cholesterol to neurons via ApoE receptors, which are members of the low density lipoprotein receptor gene family. APOE variants are associates with increased risk of Alzheimer's disease and Cardio vascular disorders, as well as with damage to the blood brain barrier. APOE was also shown to transport the A beta peptide into neurons via the Sortilin receptor.

Accordingly, anti-Sortilin antibodies of the present disclosure may also inhibit (e.g., block) the interaction between Sortilin and apolipoprotein E. Such antibodies would be beneficial for preventing, lowering the risk of, or treating conditions and/or diseases associated with abnormal levels of apolipoprotein E expression and/or activity, vascular dementia, and/or atherosclerotic vascular diseases.

In some embodiments, anti-Sortilin antibodies of the present disclosure that inhibit (e.g., block) the interaction between Sortilin and apolipoprotein E bind one or more amino acids within amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of human Sortilin (SEQ ID NO: 1); or within amino acid residues of a mammalian Sortilin that corresponds to amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of SEQ ID NO: 1. In other embodiments, anti-Sortilin antibodies of the present disclosure that inhibit (e.g., block) the interaction between Sortilin and apolipoprotein E bind one or more amino acid of amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of human Sortilin (SEQ ID NO: 1); or of amino acid residues of a mammalian Sortilin that corresponds to one or more amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552, Phe569, Glu590, Phe592, Leu593, Ser595, Trp597, Ile619 Leu621, Glu628, Asp632, Leu636, Gln642, Arg646, and Tyr679, and/or Glu700 of SEQ ID NO: 1.

Receptor-Associated Protein

Sortilin proteins of the present disclosure have been shown to interact (e.g., bind) with receptor-associate protein (RAP).

Receptor-associate protein is variously referred to as RAP, low-density lipoprotein receptor-related protein associated protein 1, LRPAP1, A2MRAP, A2RAP, HBP44, and MRAP. Receptor-associate protein is a chaperone protein involved in trafficking certain members of the LDL receptor family, including without limitation, LRP1 and LRP2. Receptor-associate protein is a glycoprotein that binds to the alpha-2-macroglobulin receptor, as well as to other members of the low-density lipoprotein receptor family. It acts to inhibit the binding of all know ligands for such receptors, and can prevent receptor aggregation and degradation in the endoplasmic reticulum, thereby acting as a molecular chaperone. Receptor-associate protein may also be under the regulatory control of calmodulin.

Accordingly, anti-Sortilin antibodies of the present disclosure may also inhibit (e.g., block) the interaction between Sortilin and RAP. Such antibodies would be beneficial for preventing, lowering the risk of, or treating conditions and/or diseases associated with decreased levels of RAP expression and/or activity, vascular dementia, and/or atherosclerotic vascular diseases.

In some embodiments, anti-Sortilin antibodies of the present disclosure that inhibit (e.g., block) the interaction between Sortilin and RAP bind one or more amino acids within amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of human Sortilin (SEQ ID NO: 1); or within amino acid residues of a mammalian Sortilin that corresponds to amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of SEQ ID NO: 1. In other embodiments, anti-Sortilin antibodies of the present disclosure that inhibit (e.g., block) the interaction between Sortilin and RAP bind one or more amino acids of amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile137, Asp552, Phe569, Glu590, Phe592, Leu593, Ser595, Trp597, Ile619, Leu621, Glu628, Asp632, Leu636, Gln642, Arg646, and Tyr679, and/or Glu700 of human Sortilin (SEQ ID NO: 1); or of amino acid residues of a mammalian Sortilin that corresponds to one or more amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Ser305, Phe306, Gly307, Arg311, Phe314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of SEQ ID NO: 1.

PCSK9

Sortilin proteins of the present disclosure have been shown to interact (e.g., bind) with Proprotein convertase subtilisin/kexin type 9 (PCSK9), and secrete it to the circulation.

PCSK9 is a member of the proteinase K subfamily of secretory proteases. PCSK9 plays a major regulatory role in cholesterol homeostasis. It binds to the low-density lipoprotein receptor (LDLR), inducing LDLR degradation and a reduction in the ability of LDLR to remove cholesterol, which may lead to hypercholesterolemia.

Accordingly, anti-Sortilin antibodies of the present disclosure may also inhibit (e.g., block) the interaction between Sortilin and PCSK9 and secretion of PCSK9. Such antibodies would be beneficial for preventing, lowering the risk of, or treating; conditions and/or diseases associated with increased levels of PCSK9 expression and/or activity, vascular dementia, and/or atherosclerotic vascular diseases.

In some embodiments, anti-Sortilin antibodies of the present disclosure that inhibit (e.g., block) the interaction between Sortilin and PCSK9 bind one or more amino acids within amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of human Sortilin (SEQ ID NO: 1); or within amino acid residues of a mammalian Sortilin that corresponds to amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of SEQ ID NO: 1. In other embodiments, anti-Sortilin antibodies of the present disclosure that inhibit (e.g., block) the interaction between Sortilin and PCSK9 bind one or more amino acids of amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of human Sortilin (SEQ ID NO: 1); or of amino acid residues of a mammalian Sortilin that corresponds to one or more amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of SEQ ID NO: 1.

Anti-Sortilin Antibodies

Anti-Sortilin antibodies of the present disclosure can inhibit one or more activities of a Sortilin protein, including, but not limited to, increasing Progranulin levels (e.g., extracellular levels of Progranulin and/or cellular levels of Progranulin), decreasing cellular levels of Sortilin (e.g., cell surface levels of Sortilin, intracellular levels of Sortilin, and/or total levels of Sortilin), inhibiting the interaction (e.g., binding) with Progranulin, and/or inhibiting interaction (e.g., binding) with one or more of pro-neurotrophins of the present disclosure (pro-neurotrophin-3, pro-neurotrophin-4/5, pro-NGF, pro-BDNF, etc.), neurotrophins of the present disclosure (neurotrophin-3, neurotrophin-4/5, NGF, BDNF, etc.), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), and receptor associated protein (RAP), decreasing secretion of PCSK9, decreasing production of beta amyloid peptide.

In some embodiments, anti-Sortilin antibodies of the present disclosure increase extracellular levels of Progranulin and/or cellular levels of Progranulin in vitro or in vivo (e.g., in the brain, blood, and/or peripheral organs of an individual). As used herein, an anti-Sortilin antibody increases extracellular levels of Progranulin if it induces an increase of 20% or more in extracellular levels of Progranulin as measured by any in vitro cell-based, assays or in tissue-based (such as brain tissue-based) assays described herein or known in the art. As used herein, an anti-Sortilin antibody increases cellular levels of Progranulin if it induces an increase of 20% or more in cellular levels of Progranulin as measured by any in vitro cell-based assays or in tissue-based (such as brain tissue-based) assays described herein or known in the art.

In some embodiments, anti-Sortilin antibodies of the present disclosure decrease cellular levels of Sortilin in vitro or in vivo (e.g., in the brain, and/or peripheral organs of an individual). In some embodiments, a decrease in cellular levels of Sortilin comprises a decrease in cell surface levels of Sortilin. As used herein, an anti-Sortilin antibody decreases cell surface levels of Sortilin if it induces a decrease of 20% or more in cell surface levels of Sortilin as measured by any in vitro cell-based assays or suitable in vivo model described herein or known in the art. In some embodiments, a decrease in cellular levels of Sortilin comprises a decrease in intracellular levels of Sortilin. As used herein, an anti-Sortilin antibody decreases intracellular levels of Sortilin if it induces a decrease of 20% or more in intracellular levels of Sortilin as measured by any in vitro cell-based assays or suitable in vivo model described herein or known in the art. In some embodiments, a decrease in cellular levels of Sortilin comprises a decrease in total levels of Sortilin. As used herein, an anti-Sortilin antibody decreases total levels of Sortilin if it induces a decrease of 20% or more in total levels of Sortilin as measured by any in vitro cell-based assays or suitable in vivo model described herein or known in the art.

In certain embodiments, anti-Sortilin antibodies of the present disclosure increase Progranulin levels and/or decrease cellular levels of Sortilin without inhibiting the interaction (e.g., binding) between Sortilin and Progranulin. Accordingly, in some embodiments, anti-Sortilin antibodies of the present disclosure do not inhibit the interaction (e.g., binding) between Sortilin and Progranulin. As used herein, an anti-Sortilin antibody does not inhibit the interaction (e.g., binding) between Sortilin and Progranulin if it decreases Progranulin binding to Sortilin by 20% or less at saturating antibody concentrations (e.g., 67 nM) any in vitro assay or cell-based culture assay described herein or known in the art.

In certain embodiments, anti-Sortilin antibodies of the present disclosure may decrease cellular levels of Sortilin (e.g., cell surface levels of Sortilin, intracellular levels of Sortilin, and/or total levels of Sortilin) by inducing Sortilin degradation. Accordingly, in some embodiments, anti-Sortilin antibodies of the present disclosure induce Sortilin degradation.

As used herein, levels of Progranulin may refer to expression levels of the gene encoding Progranulin; to expression levels of one or more transcripts encoding Progranulin; to expression levels of Progranulin protein; and/or to the amount of Progranulin protein secreted from cells and/or present within cells. As used herein, levels of Sortilin may refer to expression levels of the gene encoding Sortilin; to expression levels of one or more transcripts encoding Sortilin; to expression levels of Sortilin protein; and/or to the amount of Sortilin protein present within cells and/or on the cell surface. Any methods known in the art for measuring levels of gene expression, transcription, translation, and/or protein abundance or localization may be used to determine the levels of Progranulin and Sortilin.

Additionally, anti-Sortilin antibodies of the present disclosure can be used to prevent, reduce risk of, or treat cell death (e.g., neuronal cell death), frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotriphic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, intervertebral disc degeneration, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arforitis, multiple sclerosis, metabolic disorder, obesity, insulin resistance, type 2 diabetes, tissue or vascular damage, an injury, and/or one or more undesirable symptoms of normal aging. In some embodiments, anti-Sortilin antibodies of the present disclosure are monoclonal antibodies.

Certain aspects of the preset disclosure provide anti-Sortilin antibodies that bind a discontinuous Sortilin epitope. In some embodiments, the discontinuous Sortilin epitope comprises two or more peptides, three or more peptides, four or more peptides, five or more peptides, six or more peptides, seven or more peptide, eight or more peptides, nine or more peptides, or 10 or more peptides. In some embodiments, each of the peptides comprise five or more, six or more, seven or more, eight or more, nine or more, 10 or more, 11 or more, 12 or more, 13 or more 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid residues of the amino acid sequence of SEQ ID NO: 1, or five or more, six or more, seven or more, eight or more, nine or more, 10 or more, 11 or more, 12 or more, 13 or more 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid residues on a mammalian Sortilin protein corresponding to the amino acid sequence of SEQ ID NO: 1. Other aspects of the preset disclosure provide anti-Sortilin antibodies that bind to a conformational epitope of Sortilin.

Certain aspects of the preset disclosure provide anti-Sortilin antibodies that bind to one or more amino acids within amino acid residues 131-138 of human Sortilin (SEQ ID NO: 1); or within amino acid residues on a mammalian Sortilin corresponding to amino acid residues 131-138 of SEQ NO: 1; one or more amino acids within amino acid residues 175-181 of human Sortilin (SEQ ID NO: 1); or within amino acid residues on a mammalian Sortilin corresponding to amino acid residues 175-181 of SEQ ID NO: 1; one or more amino acids within amino acid residues 207-231 of human Sortilin (SEQ ID NO: 1); or within amino acid residues on a mammalian Sortilin corresponding to amino acid residues 207-231 of SEQ ID NO: 1; one or more amino acids within amino acid residues 207-227 of human Sortilin (SEQ ID NO: 1); or within amino acid residues on a mammalian Sortilin corresponding to amino acid residues 207-227 of SEQ ID NO: 1; one or more amino acids within amino acid residues 207-227 and 237-260 of human Sortilin (SEQ ID NO: 1); or within amino acid residues on a mammalian Sortilin corresponding to amino acid residues 207-227 and 237-260 of SEQ ID NO: 1; one or more amino acids within amino acid residues 212-221 of human Sortilin (SEQ ID NO: 1); or within amino acid residues on a mammalian Sortilin corresponding to amino acid residues 212-221 of SEQ ID NO: I; one or more amino acids within amino acid residues 233-243 of human Sortilin (SEQ ID NO: 1); or within amino acid residues on a mammalian Sortilin corresponding to amino acid residues 233-243 of SEQ ID NO: 1; one or more amino acids within amino acid residues 237-247 of human Sortilin (SEQ ID NO: 1); or within amino acid residues on a mammalian Sortilin corresponding to amino acid residues 237-247 of SEQ ID NO: 1; one or more amino acids within amino acid residues 237-247 and 314-338 of human Sortilin (SEQ ID NO: 1); or within amino acid residues on a mammalian Sortilin corresponding to amino acid residues 237-247 and 314-338 of SEQ ID NO: 1; one or more amino acids within amino acid residues 237-260 of human Sortilin (SEQ ID NO: 1); or within amino acid residues on a mammalian Sortilin corresponding to amino acid residues 237-260 of SEQ ID NO: 1; one or more amino acids within amino acid residues 237-260 and 297-317 of human Sortilin (SEQ ID NO: 1); or within amino acid residues on a mammalian Sortilin corresponding to amino acid residues 237-260 and 297-317 of SEQ ID NO: 1; one or more amino acids within amino acid residues 297-317 of human Sortilin (SEQ ID NO: 1); or within amino acid residues on a mammalian Sortilin corresponding to amino acid residues 297-317 of SEQ NO: 1; one or more amino acids within amino acid residues 314-338 of human Sortilin (SEQ ID NO: 1); or within amino acid residues on a mammalian Sortilin corresponding to amino acid residues 314-338 of SEQ ID NO: 1; one or more amino acids within amino acid residues 367-391 of human Sortilin (SEQ ID NO: 1); or within amino acid residues on a mammalian Sortilin corresponding to amino acid residues 367-391 of SEQ ID NO: 1; one or more amino acids within amino acid residues 429-443 of human Sortilin (SEQ ID NO: 1); or within amino acid residues on a mammalian Sortilin corresponding to amino acid residues 429-443 of SEQ ID NO: 1; one or more amino acids within amino acid residues 623-632 of human Sortilin (SEQ ID NO: 1); or within amino acid residues on a mammalian Sortilin corresponding to amino acid residues 623-632 of SEQ ID NO: 1; and/or one or more amino acids within amino acid residues 740-749 of human Sortilin (SEQ ID NO: 1); or within amino acid residues on a mammalian Sortilin corresponding to amino acid residues 740-749 of SEQ ID NO: 1.

In some embodiments, anti-Sortilin antibodies of the present disclosure bind to one or more amino acids within amino acid residues 190-220 of human Sortilin (SEQ ID NO: 1); or within amino acid residues on a mammalian Sortilin corresponding to amino acid residues 190-220 of SEQ ID NO: 1, In some embodiments, the anti-Sortilin antibodies bind to one or more amino acids within amino acid residues 199-220, 190-211, 196-207, 196-199, 200-207, and/or 203-207 of human Sortilin; or within amino acid residues on a mammalian Sortilin corresponding to amino acid residues 199-220, 190-211, 196-207, 196-199, 200-207, and/or 203-207 of SEQ ID NO: 1. In some embodiments, the anti-Sortilin antibodies bind to one or more amino acids of amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305Phe306, Gly307, Arg311, Phe314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of human Sortilin (SEQ NO: 1); or of amino acid residues of a mammalian Sortilin that corresponds to one or more amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306Gly307, Arg311, Phe314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of SEQ NO: 1. Other aspects of the present disclosure provide anti-Sortilin antibodies that bind to an epitope having amino acid residues (S/T)-X-(D/N)-X-X-X-X-(W/F/Y), where X represents any amino acid (SEQ ID NO: 4).

In certain embodiments, anti-Sortilin antibodies of the present disclosure increase extracellular levels of Progranulin, increase cellular levels of Progranulin, and/or decrease cell surface levels of Sortilin. In certain embodiments, the anti-Sortilin antibodies decrease cellular levels of Sortilin and do not inhibit the interaction between Sortilin and Progranulin. In certain embodiments, the anti-Sortilin antibodies decrease cellular levels of Sortilin and inhibit the interaction between Sortilin and Progranulin. In certain embodiments, the anti-Sortilin antibodies decrease cellular levels of Sortilin and increase cellular levels of Progranulin. In certain embodiments, the anti-Sortilin antibodies increase cellular levels of Progranulin and do not inhibit the interaction between Sortilin and Progranulin. In certain embodiments, the anti-Sortilin antibodies inhibit the interaction between Sortilin and Progranulin and increase cellular levels of Progranulin. In certain embodiments, the anti-Sortilin antibodies increase levels of Progranulin in vivo. In certain embodiments, the anti-Sortilin antibodies increase levels of Progranulin in vivo without decreasing cellular levels of Sortilin. In certain embodiments, the anti-Sortilin antibodies increase lends of Progranulin in brain. In certain embodiments, the anti-Sortilin antibodies increase cellular levels of Progranulin in blood. In certain embodiments, the anti-Sortilin antibodies increase cellular levels of Progranulin in one or more peripheral organs. In certain embodiments, the anti-Sortilin antibodies decrease cellular levels of Sortilin in vivo. In certain embodiments, the anti-Sortilin antibodies decrease cellular levels of Sortilin in brain. In certain embodiments, the anti-Sortilin antibodies decrease cellular levels of Sortilin in one or more peripheral organs. In certain embodiments, the anti-Sortilin antibodies inhibit the interaction between Sortilin and Progranulin and do not decrease cellular levels of Sortilin. In certain embodiments, the anti-Sortilin antibodies increase cellular levels of Progranulin and do not decrease cellular levels of Sortilin. In certain embodiments, the anti-Sortilin antibodies increase extracellular levels of Progranulin and do not inhibit the interaction between Sortilin and Progranulin. In certain embodiments, the anti-Sortilin antibodies increase extracellular levels of Progranulin and inhibit the interaction between Sortilin and Progranulin. In certain embodiments, the anti-Sortilin antibodies decrease cellular levels of Sortilin, increase extracellular levels of Progranulin, and do not inhibit the interaction between Sortilin and Progranulin. In certain embodiments, the anti-Sortilin antibodies decrease cellular levels of Sortilin, increase extracellular levels of Progranulin, and inhibit the interaction between Sortilin and Progranulin. In certain embodiments, the anti-Sortilin antibodies decrease cellular levels of Sortilin, increase cellular levels of Progranulin, and do not inhibit the interaction between Sortilin and Progranulin. In certain embodiments, the anti-Sortilin antibodies decrease cellular levels of Sortilin, increase cellular levels of Progranulin, and inhibit the interaction between Sortilin and Progranulin. In certain embodiments, the anti-Sortilin antibodies decrease cellular levels of Sortilin, increase extracellular levels of Progranulin, increase cellular levels of Progranulin, and do not inhibit the interaction between Sortilin and Progranulin. In certain embodiments, the anti-Sortilin antibodies decrease cellular levels of Sortilin, increase extracellular levels of Progranulin, inhibit the interaction between Sortilin and Progranulin, and do not increase cellular levels of Progranulin. In certain embodiments, the anti-Sortilin antibodies decrease cellular levels of Sortilin, increase cellular levels of Progranulin, inhibit the interaction between Sortilin and Progranulin, and do not increase extracellular levels of Progranulin. In certain embodiments, the anti-Sortilin antibodies increase cellular levels of Progranulin, increase extracellular levels of Progranulin, inhibit the interaction between Sortilin and Progranulin, and do not decrease cellular levels of Sortilin. In certain embodiments, the anti-Sortilin antibodies decrease cellular levels of Sortilin, increase extracellular levels of Progranulin, do not increase cellular levels of Progranulin, and do not inhibit the interaction between Sortilin and Progranulin. In certain embodiments, the anti-Sortilin antibodies decrease cellular levels of Sortilin, increase cellular levels of Progranulin, increase extracellular levels of Progranulin, and inhibit the interaction between Sortilin and Progranulin. Extracellular levels of Progranulin, cellular levels of Progranulin, cell surface levels of Sortilin, or both may be measured by any cell-based assay known in the art and/or disclosed herein. In certain embodiments, extracellular levels of Progranulin, cell surface levels of Sortilin, or both can be measured by utilizing an in vitro cell assay. In some embodiments, the anti-Sortilin antibodies also inhibit interaction (e.g., binding) between Sortilin and Progranulin. In some embodiments, the anti-Sortilin antibodies also inhibit the transport and secretion of PCSK9. In some embodiments, the anti-Sortilin antibodies also inhibit the production of the beta amyloid peptide. In some embodiments, the anti-Sortilin antibodies also inhibit interaction (e.g., binding) between Sortilin and pro-nerve growth factor (pro-NGF). In some embodiments, the anti-Sortilin antibodies also inhibit interaction (e.g., binding) between Sortilin and one or more proteins selected from a pro-neurotrophin, a neurotrophin, nerve growth factor (NGF), pro-brain-derived neurotrophic factor (pro-BDNF), brain-derived neurotrophic factor (BINF), pro-neurotrophin-3, neurotrophin-3, pro-neurotrophin-4/5, neurotrophin-4/5, neurotensin, neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and receptor associated protein (RAP).

Other aspects of the preset disclosure provide anti-Sortilin antibodies that bind to one or more amino acids within amino acid residues 130-141 or 592-757 of human Sortilin (SEQ ID NO: 1); or within amino acid residues on a mammalian Sortilin corresponding to amino acid residues 130-141 or 592-757 of SEQ ID NO: 1. In some embodiments, the anti-Sortilin antibodies bind to one or more amino acids within amino acid residues 610-666, 592-593, and/or 667-749 of human Sortilin; or within amino acid residues on a mammalian Sortilin corresponding to amino acid residues 610-666, 592-593, and/or 667-749 of SEQ ID NO: 1. In some embodiments, the anti-Sortilin antibodies bind to one or more amino acids within amino acid residues 130-141 of human Sortilin; or within amino acid residues on a mammalian Sortilin corresponding to amino acid residues 130-141 of SEQ ID NO: 1, in some embodiments, the anti-Sortilin antibodies bind to one or more amino acids of amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of human Sortilin (SEQ ID NO: 1); or of amino acid residues of a mammalian Sortilin that corresponds to one or more amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222Ser223, Ser227, Ser242, Lys243, Lys248, Lys254, Lys260Ser305, Phe306, Gly307, Arg311, Phe314Ser316, Arg325, Arg326, Ile327, Phe350, Tyr351, Ser352, Ile353, Asn373, Ser379, Arg382, Tyr386, Asp403, Asp449Thr451, His461, Gly495, Tyr513, Ser530, Ile537, Asp552, Phe569, Glu590, Phe592, Leu593, Ser595, Trp597, Ile619, Leu621, Glu628, Asp632, Leu636, Gln642, Arg646, and Tyr679, and/or Glu700 of SEQ ID NO: 1. In certain embodiment, the anti-Sortilin antibodies inhibit interaction (e.g., binding) between a Sortilin protein of the present disclosure and one or more proteins selected from Progranulin, a pro-neurotrophin, a neurotrophin, pro-neurotrophin-3, neurotrophin-3, pro-neurotrophin-4/5, neurotrophin-4/5, pro-nerve growth factor (pro-NGF), nerve growth factor (NGF), pro-brain-derived neurotrophic factor (pro-BDNF), brain-derived neurotrophic factor (BDNF), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and receptor associated protein (RAP), and/or naturally occurring variants. Preferably, the anti-Sortilin antibodies inhibit interaction (e.g., binding) between a Sortilin protein of the present disclosure and p75.

Other aspects of the preset disclosure provide anti-Sortilin antibodies that bind to an epitope having one or more amino acids of amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248Lys254, Lys260, Ser305, Phe306, Gly307, Arg311, Phe 314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552Phe569, Glu590, Phe592, Leu593, Ser595, Trp597, Ile619, Leu621, Glu628, Asp632, Leu636, Gln642, Arg646, and Tyr679, and/or Glu700 of human Sortilin (SEQ ID NO: 1); or of amino acid residues of a mammalian Sortilin that corresponds to one or more amino acid residues Arg88, Phe105, Leu108, Arg109, Gly110, His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Asp403, Asp449, Thr451, His461, Gly495, Tyr513, Ser530, Ile537, Asp552Phe569, Glu590, Phe592, Leu593, Ser595, Trp597, Ile619, Leu621, Glu628, Asp632, Leu636, Gln642, Arg646, and Tyr679, and/or Glu700 of SEQ ID NO: 1. In certain embodiments, the anti-Sortilin antibodies inhibit interaction (e.g., binding) between a Sortilin protein of the present disclosure and one or more proteins selected from Progranulin, a pro-neurotrophin, a neurotrophin, pro-neurotrophin-3, neurotrophin-3, pro-neurotrophin-4/5, neurotrophin-4/5, pro-nerve growth factor (pro-NGF), nerve growth factor (NGF), pro-brain-derived neurotrophic factor (pro-BDNF), brain-derived neurotrophic factor (BDNF), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and receptor associated protein (RAP). Preferably, the anti-Sortilin antibodies inhibit interaction (e.g., binding) between a Sortilin protein of the present disclosure and Progranulin. In certain embodiments, the anti-Sortilin antibodies induce one or more Progranulin activities. In some embodiments, the anti-Sortilin antibodies reduce endosomal internalization of Progranulin, or fragments thereof. In some embodiments, the anti-Sortilin antibodies increase the effective concentration of Progranulin.

In some embodiments, the anti-Sortilin antibodies inhibit interaction e.g., binding) between a Sortilin protein of the present disclosure and a neurotrophin of the present disclosure, such as a pro-neurotrophin, pro-neurotrophin-3, pro-neurotrophin-4/5, pro-NGF, pro-BDNF, neurotrophin-3, neurotrophin-4/5, NGF, and BDNF. In other embodiments, the anti-Sortilin antibodies inhibit interaction (e.g., binding) between a Sortilin protein of the present disclosure and neurotensin. In other embodiments, the anti-Sortilin antibodies inhibit interaction (e.g., binding) between a Sortilin protein of the present disclosure and p75. In other embodiments, the anti-Sortilin antibodies inhibit interaction (e.g., binding) between a Sortilin protein of the present disclosure and a Sort-pro. In other embodiments, the anti-Sortilin antibodies inhibit interaction (e.g., binding) between a Sortilin protein of the present disclosure and APP. In other embodiments, the anti-Sortilin antibodies inhibit the production of the A beta peptide. In other embodiments, the anti-Sortilin antibodies inhibit the transport and secretion of PCSK9. In other embodiments, the anti-Sortilin antibodies inhibit interaction (e.g., binding) between a Sortilin protein of the present disclosure and LpL. In other embodiments, the anti-Sortilin antibodies inhibit interaction (e.g., binding) between a Sortilin protein of the present disclosure and APOA5. In other embodiments, the anti-Sortilin antibodies inhibit interaction (e.g., binding) between a Sortilin protein of the present disclosure and APOE. In other embodiments, the anti-Sortilin antibodies inhibit interaction (e.g., binding) between a Sortilin protein of the present disclosure and RAP.

In some embodiments, anti-Sortilin antibodies of the present disclosure bind to a Sortilin protein of the present disclosure and/or naturally occurring variants. In certain preferred embodiments, the anti-Sortilin antibodies bind to human Sortilin.

In some embodiments, anti-Sortilin antibodies of the present disclosure bind to a Sortilin protein of the present disclosure expressed on the surface of cell and the naked antibodies inhibit interaction (e.g., binding) between the Sortilin protein and Progranulin, a pro-neurotrophin, a neurotrophin, pro-neurotrophin-3, neurotrophin-3, pro-neurotrophin-4/5, neurotrophin-4/5, pro-nerve growth factor (pro-NGF), nerve growth factor (NGF), pro-brain-derived neurotrophic factor (pro-BDNF), brain-derived neurotrophic factor (BDNF), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and receptor associated protein (RAP).

In some embodiments, anti-Sortilin antibodies of the present disclosure that bind to a Sortilin protein of the present inhibit interaction (e.g., binding) between the Sortilin protein and Progranulin, a pro-neurotrophin, a neurotrophin, pro-neurotrophin-3, neurotrophin-3, pro-neurotrophin-4/5, neurotrophin-415, pro-nerve growth factor (pro-NGF), nerve growth factor (NGF), pro-brain-derived neurotrophic factor (pro-BDNF), brain-derived neurotrophic factor (BDNF), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and receptor associated protein (RAP) by reducing the effective levels of Sortilin that is available to interact with these proteins either on the cell surface or inside the cell.

In some embodiments, anti-Sortilin antibodies of the present disclosure that bind to a Sortilin protein of the present inhibit interaction (e.g., binding) between the Sortilin protein and Progranulin, a pro-neurotrophin, a neurotrophin, pro-neurotrophin-3, neurotrophin-3, pro-neurotrophin-4/5, neurotrophin-4/5, pro-nerve growth factor (pro-NGF), nerve growth factor (NGF), pro-brain-derived neurotrophic factor (pro-BDNF), brain-derived neurotrophic factor (BDNF), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and receptor associated protein (RAP) by inducing degradation of Sortilin.

In some embodiments, anti-Sortilin antibodies of the present disclosure competitively inhibit binding of at least one antibody selected from any of the antibodies listed in Tables 1-3 and 11-15. In some embodiments, anti-Sortilin antibodies of the present disclosure competitively inhibit binding of at least one antibody selected from S-1, S-2, S-2-1, S-2-2, S-2-3, S-2-4, S-2-5, S-2-6, S-2-7, S-2-8, S-2-9, S- 2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-83, S-84, and S-85. In some embodiments, an anti-Sortilin antibody of the present disclosure competes with one or more antibodies selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S- 15-6-13, S-15-7, S-15-8, S-15-9, S-15-10, S-15-10-1, S-15-10-2, S-15-10-3, S-15-10-4, S-15-10-5, S-15-10-6, S-15-10-7 S-15-10-8, S-15-10-9, S-15-10-10, S-15-10-11, S-15-10-12, S-15-10-13, S-15-10-14, S-15-10- 15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2 S-22-3, S-22-4, S-22-5, S-22-6, S-22-7, S-22-8, S-22-9, S-23, S-24, S-25, S-26, S-27S-28, S-29, S-30, S-31, S-32, S-33, S-34, S-35, S-36, S-37, S-38, S-39, S-40, S-41, S-42 S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85, and any combination thereof, for binding to Sortilin when the anti-Sortilin antibody reduces the binding of one or more antibodies selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S- 15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-102, S-15-10-13, S-15-10-14, S-15-10-15, S-15-10-16, S-15-10-17, S-15-10-18, S-15-10-19, S-15-10-20, S-15-10-21, S-15- 11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-32 S-32, S-33, S-34, S-35, S-36, S-37, S-38 S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S- 82-6, S-82-7, S-82-8, S-83, S-84, and S-85, and any combination thereof to Sortilin by an amount the ranges from about 50% to 100%, as compared to binding to Sortilin in the absence of the anti-Sortilin antibody. In some embodiments, an anti-Sortilin antibody of the present disclosure competes with one or more antibodies selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S- 83, S-84, and S-85, and any combination thereof for binding to Sortilin when the anti-Sortilin antibody reduces the binding of one or more antibodies selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S- 15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S- 72, S-73, S-74, S-75, S-76, S-77, S-78, S-79, S-80, S-81, S-82, S-82-1, S-82-2, S-82-3, S-82-4, S-82-5, S- 82-6, S-82-7, S-82-8, S-83, S-84, and S-85, and any combination thereof to Sortilin by at least 50%, at least 55%, by at least 60%, at least 65%, at least 70%, at least 75%, at least 80%, at least 85%, at least 90%, at least 95%, or 100%, as compared to binding to Sortilin in the absence of the anti-Sortilin antibody. In some embodiments, an anti-Sortilin antibody of the present disclosure that reduces the binding of one or more antibodies selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S- 15-6-12, S-15-6-13, S-15-7, S-15-8, S-15-9, S-15-10, S-15-10-1, S-15-10-2, S-15-10-3, S-15-10-4, S-15-10-5, S- 15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85, and any combination thereof to Sortilin by 100% indicates that the anti-Sortilin antibody essential completely blocks the binding of one or more antibodies selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15- 10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14 S-15-15, S-15-16, S-16, S-17, S-18, S- 19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85, and any combination thereof to Sortilin. In some embodiments, the anti-Sortilin antibody and the one or more antibodies selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39S-40, S-41, S-42, S-43, S-44, S-45, S-46S-47, S-48, S-49, S-50, S-51, S-52, S-53S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85, and any combination thereof are present in an amount that corresponds to a 10:1 ratio, 9:1 ratio, 8:1 ratio, 7:1 ratio, 6:1 ratio, 5:1 ratio, 4:1 ratio, 3:1 ratio, 2:1 ratio, 1:1 ratio, 0.75:1 ratio, 0.5:1 ratio, 0.25:1 ratio, 0.1:1 ratio, 0.075:1 ratio, 0.050:1 ratio, 0.025:1 ratio, 0.01:1 ratio, 0.0075: ratio, 0.0050:1 ratio, 0.0025:1 ratio, 0.001: ratio, 0.00075:1 ratio, 0.00050:1 ratio, 0.00025:1 ratio, 0.0001: ratio, 1:10 ratio, 1:9 ratio, 1:8 ratio, 1:7 ratio, 1:6 ratio, 1:5 ratio, 1:4 ratio, 1:3 ratio, 1:2 ratio, 1:0.75 ratio, 1:0.5 ratio, 1:0.25 ratio, 1:0.1 ratio, 1:0.075 ratio, 1:0.050 ratio, 1:0.025 ratio, 1:0.01 ratio, 1:0.0075 ratio, 1:0.0050 ratio, 1:0.0025 ratio, 1:0.001 ratio, 1:0.00075 ratio, 1:0.00050 ratio, 1:0.00025 ratio, or 1:0.0001ratio of anti-Sortilin antibody to one or more antibodies selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85, and any combination thereof. In some embodiments, the anti-Sortilin antibody is present in excess by an amount that ranges from about 1.5-fold to 100-fold, or greater than 100-fold compared to the amount of the one or more antibodies selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12S-15-13, S-15-14, S-15-15S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-3, S-82-4, S-82-5, S-82-6, S-82-7, S-82-8, S-83, S-84, and S-85, and any combination thereof. In some embodiments, the anti-Sortilin antibody is present in an amount that is about a 2-fold, 3-fold, 4-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold excess compared to the amount of the one or more antibodies selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-5-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-7S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85, and any combination thereof.

In some embodiments, anti-Sortilin antibodies of the present disclosure bind to an epitope of human Sortilin that is the same as or overlaps with the Sortilin epitope bound by at least one antibody selected from any of the antibodies listed in Tables 1-3 and 11-15. In some embodiments, anti-Sortilin antibodies of the present disclosure bind to an epitope of human Sortilin that is the same as or overlaps with the Sortilin epitope bound by at least one antibody selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13S-15-7, S-15-8S-15-9, S-15-10S-15-10-1, S-15-10-2, S-15-10-3, S-15-10-4, S-15-10-5, S-15-10-6, S-15-10-7, S-15-10-8, S-15-10-9, S-15-10-10, S-15-10-11S-15-10-12S-15- 10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S- 71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85. In some embodiments, anti-Sortilin antibodies of the present disclosure bind essentially the same Sortilin epitope bound by at least one antibody selected from any of the antibodies listed in Tables 1-3 and 11-15. In some embodiments, anti-Sortilin antibodies of the present disclosure bind essentially the same Sortilin epitope bound by at least one antibody selected from S-1, S-2, S-2-1, S-2-2, S-2-3, S-2-4, S-2-5, S-2-6, S-2-7, S-2-8, S-2-9, S-2-10, S-2- 11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S- 15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In some embodiments, anti-Sortilin antibodies of the present disclosure compete with one or more antibodies selected from S-6, S-8, S-49, S-60, S-60-1, S-60-2, S-60-3, S-60-4, S-60-5, S-60-6, S-60-7, S-60-8, S-60-9, S-63, S-72, S-83, and any combination thereof for binding to Sortilin. In some embodiments, anti-Sortilin antibodies of the present disclosure compete with one or more antibodies selected from S-5, S-45, S-64, S-65, and any combination thereof for binding to Sortilin. In some embodiments, anti-Sortilin antibodies of the present disclosure compete with one or more antibodies selected from S-5, S-30, S-60, S-60-1, S-60-2, S-60-3, S-60-4, S-60-5, S-60-6, S-60-7, S-60-8, S-60-9, and any combination thereof for binding to Sortilin. In some embodiments, anti-Sortilin antibodies of the present disclosure compete with one or more antibodies selected from S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-16, S-17, S-18, S-19, S-20, S-21, S-22, S-22-1, S-22-2, S-22-3, S-22-4, S-22-5, S-22-6, S-22-7, S-22-8, S-22-9, S-28, S-29, S-53, S-56, S-82, and any combination thereof for binding to Sortilin. In some embodiments, anti-Sortilin antibodies of the present disclosure compete with one or more antibodies selected from S-1, S-3, S-4, S-6, S-7, S-9, S-10, S-11, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15- 11, S-15-12, S-15-13, S-15-14, S-15-15, S-15-16, S-23, S-26, S-27, S-31, S-32, S-38, S-46, S-48, S-51, S-52, S-54, S-55, S57, S-58, S-59, S-61, S-62, S-68, S-69, S-70, S-71, S-73, S-74, S-75, S-77, S-79, S-80, S-85, and any combination thereof for binding to Sortilin. In some embodiments, anti-Sortilin antibodies of the present disclosure compete with one or more antibodies selected from S-5, S-12, S-24, S-25, S-30, S-33, S-34, S-35, S-36, S-37, S-39, S-40, S-41, S-42, S-43, S-44, S-45, S-47, S-60, S-60-1, S-60-2, S-60-3, S-60-4, S-60-5, S-60-6, S-60-7, S-60-8, S-60-9, S-63, S-64, S-65, S-66, S-67, S-72, S-76, S-78, S-81, S-83, S-84, and any combination thereof for binding to Sortilin. In some embodiments, anti-Sortilin antibodies of the present disclosure compete with one or more antibodies selected from S-8, S-49, S-50, and any combination thereof for binding to Sortilin. In some embodiments, anti-Sortilin antibodies of the present disclosure compete with one or more antibodies selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S- 72, S-73, S-74, S-75, S-76, S-77, S-78, S-79, S-80, S-81, S-82, S-82-1, S-82-2, S-82-3, S-82-4, S-82-5, S- 82-6, S-82-7, S-82-8, S-83, S-84, and S-85, and any combination thereof for binding to Sortilin.

Any suitable competition assay or Sortilin binding assay known in the art, such as BIAcore analysis, ELISA assays, or flow cytometry, may be utilized to determine whether an anti-Sortilin antibody competes with one or more antibodies selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85; and any combination thereof for binding to Sortilin. In an exemplary competition assay, immobilized Sortilin or cells expressing Sortilin on the cell surface are incubated in a solution comprising a first labeled antibody that binds to Sortilin (e.g., human or non-human primate) and a second unlabeled antibody that is being tested for its ability to compete with the first antibody for binding to Sortilin. The second antibody may be present in a hybridoma supernatant. As a control, immobilized Sortilin or cells expressing Sortilin is incubated in a solution comprising the first labeled antibody but not the second unlabeled antibody. After incubation under conditions permissive for binding of the first antibody to Sortilin, excess unbound antibody is removed, and the amount of label associated with immobilized Sortilin or cells expressing Sortilin is measured. If the amount of label associated with immobilized Sortilin or cells expressing Sortilin is substantially reduced in the test sample relative to the control sample, then that indicates that the second antibody is competing with the first antibody for binding to Sortilin. See, Harlow and Lane (1988) *Antibodies: A Laboratory Manual* ch. 14 (Cold Spring Harbor Laboratory, Cold Spring Harbor, N.Y.). In some embodiments, the competition assay that is utilized is one or more of the competition assays described in Examples 1, 3, or 4.

In some embodiments, anti-Sortilin antibodies of the present disclosure comprise (a) a light chain variable region comprising at least one, two, or three HVRs selected from HVR-L1, HVR-L2, and HVR-L3 of any one of the antibodies listed in Tables 1-3 and 11-15, or selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85; and/or (b) a heavy chain variable region comprising at least one, two, or three HVRs selected from HVR-H1, HVR-H2, and HVR-H3 of any one of the antibodies listed in Tables 1-3 and 11-15, or selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-10-5, S-15-10-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85. In some embodiments, the HVR-L1, HVR-L2, HVR-H1, HVR-H2, and HVR-H3 comprise EU Kabat CDR, Chothia CDR, or Contact CDR sequences as shown in Tables 1-3 and 11-15, or from an antibody selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85.

In some embodiments, anti-Sortilin antibodies of the present disclosure comprise at least one, two, three, four, five, or six HVRs selected from (i) HVR-L1 comprising the amino acid sequence of any of the HVR-L1 sequences listed in Tables 1-3 and 11-15, or from an antibody selected from S-1, S-2, S-2-1, S-2-2, S-2-3, S-2-4, S-2-5, S-2-6, S-2-7, S-2-8, S-2-9, S-2-10, S-2-11, S-2-12, S- 2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4 S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85; (ii) HVR-L2 comprising the amino acid sequence of any of the HVR-L2 sequences listed in Tables 1-3 and 11-15, or from an antibody selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10S-15-10-1, S-15-10-2, S-15-10-3, S-15-10-4, S-15-10-5, S-15-10-6, S-15-10-7, S-15-10-8, S-15-10-9S-15-10-10S-15-10-11S-15-10-12S-15-10-13S-15-10-14, S-15-10-15S-15-10-16, S-15-10-17, S-15-10-18, S-15-10-19, S-15-10-20, S-15-10-21, S-15-11, S-15-12, S-15-13, S-15-14, S15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85; (iii) HVR-L3 comprising the amino acid sequence of any of the HVR-L3 sequences listed in Tables 1-3 and 11-15, or from an antibody selected from S-1, S-2, S-2-1, S-2-2, S-2-3, S-2-4, S-2-5, S-2-6, S-2-7, S-2-8, S-2-9S-2-10, S-2-11S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S- 15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S- 72, S-73, S-74, S-75, S-76, S-77, S-78, S-79, S-80, S-81, S-82, S-82-1, S-82-2, S-82-3, S-82-4, S-82-5, S- 82-6, S-82-7, S-82-8, S-83, S-84, and S-85; (iv) HVR-H1 comprising the amino acid sequence of any of the HVR-H1 sequences listed in Tables 1-3 and 11-15, or from an antibody selected from S-1, S-2, S-2-1, S-2-2, S-2-3, S-2-4, S-2-5, S-2-6, S-2-7, S-2-8, S-2-9, S-2-10, S-2-11, S-2-12, S-2- 13, S-2-14, S-2-15S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-1, S-15- 10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20S-21, S-22, S-22-1, S-22-2, S-22-3, S-22-4, S-22-5, S-22-6, S-22-7, S-22-8, S-22-9, S-23, S-24, S-25S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85; (v) HVR-H2 comprising the amino acid sequence of any of the HVR-H2 sequences listed in Tables 1-3 and 11-15, or from an antibody selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85; and (vi) HVR-H3 comprising the amino acid sequence of any of the HVR-H3 sequences listed in Tables 1-3 and 11-15, or from an antibody selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S- 15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1 S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S- 72, S-73, S-74S-75, S-76, S-77, S-78, S-79, S-80, S-81, S-82, S-82-1, S-82-2, S-82-3. S-82-4, S-82-5, S-82-6, S-82-7, S-82-8, S-83, S-84, and S-85.

In some embodiments, anti-Sortilin antibodies of the present disclosure comprise a light chain variable domain and a heavy chain variable domain, wherein the light chain variable domain comprises one or more of: (a) an HVR-L 1 comprising an amino acid sequence selected from the group consisting of SEQ ID NOs:6-16, 20-22, 24-25, 512, 584, and 585, or an amino acid sequence with at least about 95% homology to an amino acid sequence selected from the group consisting of SEQ NOs: 6-16, 20-22, 24-25, 512, 584, and 585; (b) an HVR-L2 comprising an amino acid sequence selected from the group consisting of SEQ ID NOs:26-40 and 586, or an amino acid sequence with at least about 95% homology to an amino acid sequence selected from the group consisting of SEQ ID NOs:26-40 and 586; and (c) an HVR-L3 comprising an amino acid sequence selected from the group consisting of SEQ ID NOs:41-50, 52, 54-56, 58-62, 64-66, 68-70, 72, 74, 79-80, 82-85, 88-91, 95, 97-101, 103-107, 109, 111-116, 118, and 121-125, or an amino acid sequence with at least about 95% homology to an amino acid sequence selected from the group consisting of SEQ ID NOs:41-50, 52, 54-56, 58-62, 64-66, 68-70, 72, 74, 79-80, 82-85, 88-91, 95, 97-101, 103-107, 109, 111-116, 118, and 121-125; and/or wherein the heavy chain variable domain comprises one or more of: (a) an HVR-141 comprising an amino acid sequence selected from the group consisting of SEQ ID NOs:126-127, 129-130, 133-140, 142, 144-145, 147-149, 482-492, 513-524, 567-570, 587, and 591-596, or an amino acid sequence with at least about 95% homology to an amino acid sequence selected from the group consisting of SEQ ID NOs:126-127, 129-130, 133-140, 142, 144-145, 147-149, 482-492, 513-524, 567-570, 587, and 591-596; (b) an HVR-H2 comprising an amino acid sequence selected from the group consisting of SEQ ID NOs:150-153, 155-158, 160-166, 169-175, 177-178, 493-507, 525-539, 571-579, 588, and 597-603, or an amino acid sequence with at least about 95% homology to an amino acid sequence selected from the group consisting of SEQ ID NOs:150-153, 155-158, 160-166, 169-175, 177-178, 493-507, 525-539, 571-579, 588, and 597-603; and (c) an HVR-H3 comprising an amino acid sequence selected from the group consisting of SEQ ID NOs:179-186, 188, 190-191, 193-197, 199-201, 203-204, 206, 208, 213-214, 216-219, 222-225, 229, 231-234, 236-239, 241, 243-247, 249, 252-256, and 540-564, or an amino acid sequence with at least about 95% homology to an amino acid sequence selected from the group consisting of SEQ ID NOs:179-186, 188, 190-191, 193-197, 199-201, 203-204, 206, 208, 213-214, 216-219, 222-225, 229, 231-234, 236-239, 241, 243-247, 249, 252-256, and 540-564.

In some embodiments, anti-Sortilin antibodies of the present disclosure comprise a light chain variable region of any one of the antibodies listed in Tables 1-3 and 11-15, or selected from S-1, S-2, S-2-1, S-2-2, S-2-3, S-2-4, S-2-5, S-2-6, S-2-7, S-2-8, S-2-9, S-2-10, S-2-11, S-2-12, S- 2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-5-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85; and/or a heavy chain variable region of any one of the antibodies listed in Tables 1-3 and 11-15, or selected from S-1, S-2, S-2-1, S-2-2, S-2-3, S-2-4, S-2-5, S-2-6, S-2-7, S-2-8, S-2-9, S-2-10, S-2-11, S-2-12, S- 2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10S-15-10-11S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-2S, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85. In some embodiments, anti-Sortilin antibodies of the present disclosure comprise a light chain variable region and/or a heavy chain variable domain comprising an amino acid sequence selected from any of SEQ ID NOs:317-334, 337-338, 341-345, 348-357, 360-365, 368-372, 375-376, 379-380, 389-392, 395-402, 407-414, 421-422, 425-433, 436-444, 447-448, 451-461, 464-465, 470-479, 604-692.

Any of the antibodies of the present disclosure may be produced by a cell line. In some embodiments, the cell line may be a yeast cell line. In other embodiments, the cell line may be a mammalian cell line. In certain embodiments, the cell line may be a hybridoma cell line. Any cell line known in the art suitable for antibody production may be used to produce an antibody of the present disclosure. Exemplary cell lines for antibody production are described throughout the present disclosure.

In some embodiments, the anti-Sortilin antibody is an anti-Sortilin monoclonal antibody selected from S-1, S-2, S-2-1, S-2-2, S-2-3, S-2-4, S-2-5, S-2-6, S-2-7, S-2-8, S-2-9, S-2-10, S- 2-11, S-2-12, S-2-13S-2-14, S-2-15, S-3, S-4, S-5, S-6, S-7, S-8, S-9, S-10, S-11, S-12S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6- 13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85. In certain embodiments, the anti-Sortilin antibody is an antagonist antibody.

In some embodiments, anti-Sortilin antibodies of the present disclosure competitively inhibit binding of at least one antibody selected from S-5, S-6, S-8, S-45, S-49, S-60, S-60-1, S-60-2, S-60-3, S-60-4, S-60-5, S-60-6, S-60-7, S-60-8, S-60-9, S-63, S-64, S-65, S-72, and S-83. In some embodiments, anti-Sortilin antibodies of the present disclosure bind to an epitope of human Sortilin that is the same as or overlaps with the Sortilin epitope bound by at least one antibody selected from S-5, S-6, S-8, S-45, S-49, S-60, S-60-1, S-60-2, S-60-3, S-60-4, S-60-5, S-60-6, S-60-7, S-60-8, S-60-9, S-63, S-64, S-65, S-72, and S-83. In some embodiments, anti-Sortilin antibodies of the present disclosure bind essentially the same Sortilin epitope bound by at least one antibody selected from S-5, S-6, S-8, S-45, S-49, S-60, S-60-1, S-60-2, S-60-3, S-60-4, S-60-5, S-60-6, S-60-7, S-60-8, S-60-9, S-63, S-64, S-65, S-72, and S-83. In some embodiments, anti-Sortilin antibodies of the present disclosure comprise (a) a light chain variable region comprising at least one, two, or three HVRs selected from HVR-L1, HVR-L2, and HVR-L3 selected from S-5, S-6, S-8, S-45, S-49, S-60, S-60-1, S-60-2, S-60-3, S-60-4, S-60-5, S-60-6, S-60-7, S-60-8, S-60-9, S-63, S-64, S-65, S-72, and S-83; and/or (b) a heavy chain variable region comprising at least one, two, or three HVRs selected from HVR-H1, HVR-H2, and HVR-H3 selected from S-5, S-6, S-8, S-45, S-49, S-60, S-60-1, S-60-2, S-60-3, S-60-4, S-60-5, S-60-6, S-60-7, S-60-8, S-60-9, S-63, S-64, S-65, S-72, and S-83. In some embodiments, the HVR-L1, HVR-L2, HVR-L3, HVR-H1, HVR-H2, and HVR-H3 comprise EU or Kabat CDR, Chothia CDR, or Contact CDR sequences from an antibody selected from S-5, S-6, S-8, S-45, S-49, S-60, S-60-1, S-60-2, S-60-3, S-60-4, S-60-5, S-60-6, S-60-7, S-60-8, S-60-9, S-63, S-64. S-65, S-72, and S-83. In some embodiments, anti-Sortilin antibodies of the present disclosure comprise at least one, two, three, four, five, or six HVRs selected from (i) HVR-L1 comprising the amino acid sequence of any of the HVR-L1 sequences from an antibody selected from S-5, S-6, S-8, S-45, S-49, S-60, S-60-1, S-60-2, S-60-3, S-60-4, S-60-5, S-60-6, S-60-7, S-60-8, S-60-9, S-63, S-64, S-65, S-72, and S-83; (ii) HVR-L2 comprising the amino acid sequence of any of the HVR-L2 sequences from an antibody selected from S-5, S-6, S-8, S-45, S-49, S-60, S-60-1, S-60-2, S-60-3, S-60-4, S-60-5, S-60-6, S-60-7, S-60-8, S-60-9, S-63, S-64, S-65, S-72, and S-83; (iii) HVR-L3 comprising the amino acid sequence of any of the HVR-L3 sequences from an antibody selected from S-5, S-6, S-8, S-45, S-49, S-60, S-60-1, S-60-2, S-60-3, S-60-4, S-60-5, S-60-6, S-60-7, S-60-8, S-60-9, S-63, S-64, S-65, S-72, and S-83; (iv) HVR-141 comprising the amino acid sequence of any of the HVR-H1 sequences from an antibody selected from S-5, S-6, S-8, S-45, S-49, S-60, S-60-1, S-60-2, S-60-3, S-60-4, S-60-5, S-60-6, S-60-7, S-60-8, S-60-9, S-63, S-64, S-65, S-72, and S-83; (v) HVR-H2 comprising the amino acid sequence of any of the HVR-H2 sequences from an antibody selected from S-5, S-6, S-8, S-45, S-49, S-60, S-60-1, S-60-2, S-60-3, S-60-4, S-60-5, S-60-6, S-60-7, S-60-8, S-60-9, S-63, S-64, S-65, S-72, and S-83; and (vi) HVR-H3 comprising the amino acid sequence of any of the HVR-H3 sequences from an antibody selected from S-5, S-6, S-8, S-45, S-49, S-60, S-60-1, S-60-2, S-60-3, S-60-4, S-60-5, S-60-6, S-60-7, S-60-8, S-60-9, S-63, S-64, S-65, S-72, and S-83. In some embodiments, anti-Sortilin antibodies of the present disclosure comprise a light chain variable region of any one of the antibodies selected from S-5, S-6, S-8, S-45, S-49, S-60, S-60-1, S-60-2, S-60-3, S-60-4, S-60-5, S-60-6, S-60-7, S-60-8, S-60-9, S-63, S-64, S-65, S-72, and S-83; and/or a heavy chain variable region of any one of the antibodies selected from S-5, S-6, S-8, S-45, S-49, S-60, S-60-1, S-60-2, S-60-3, S-60-4, S-60-5S-60-6, S-60-7, S-60-8, S-60-9, S-63, S-64, S-65, S-72, and S-83. In some embodiments, the anti-Sortilin antibody is an anti-Sortilin monoclonal antibody selected from S-5, S-6, S-8, S-45, S-49, S-60, S-60-1, S-60-2, S-60-3, S-60-4, S-60-5, S-60-6, S-60-7, S-60-8, S-60-9, S-63, S-64, S-65, S-72, and S-835.

In some embodiments, anti-Sortilin antibodies of the present disclosure comprise a light chain variable domain and a heavy chain variable domain, wherein the light chain variable domain comprises one or more of: (a) an HVR-L1 comprising an amino acid sequence selected from the group consisting of SEQ ID NOs:6, 9-12, 14, and 15, or an amino acid sequence with at least about 95% homology to an amino acid sequence selected from the group consisting of SEQ ID NOs:6, 9-12, 14, and 15; (b) an HVR-L2 comprising an amino acid sequence selected from the group consisting of SEQ ID NOs:26, 27, 29, 30, and 32, or an amino acid sequence with at least about 95% homology to an amino acid sequence selected from the group consisting of SEQ ID NOs:26, 27, 29, 30, and 32; and (c) an HVR-L3 comprising an amino acid sequence selected from the group consisting of SEQ ID NOs:45, 46, 48, 85, 89, 100, 103-105, 112, and 123, or an amino acid sequence with at least about 95% homology to an amino acid sequence selected from the group consisting of SEQ ID NOs:45, 46, 48, 85, 89, 100, 103-105, 112, and 123; and/or wherein the heavy chain variable domain comprises one or more of: (a) an HVR-H1 comprising an amino acid sequence selected from the group consisting of SEQ ID NOs:126, 127, 136, 140, 142, 145, and 148, or an amino acid sequence with at least about 95% homology to an amino acid sequence selected from the group consisting of SEQ ID NOs:126, 127, 136, 140, 142, 145, and 148; (b) an HVR-H2 comprising an amino acid sequence selected from the group consisting of SEQ ID NOs:151, 152, 163, 166, 169, 170, 173, and 175, or an amino acid sequence with at least about 95% homology to an amino acid sequence selected from the group consisting of SEQ ID NOs:151, 152, 163, 166, 169, 170, 173, and 175;

and (c) an HVR-H3 comprising an amino acid sequence selected from the group consisting of SEQ ID NOs:182, 183, 185, 219, 223, 233, 236, 237, 244, and 254 or an amino acid sequence with at least about 95% homology to an amino acid sequence selected from the group consisting of SEQ NOs: 182, 183, 185, 219, 223, 233, 236, 237, 244, and 254.

In some embodiments, anti-Sortilin antibodies of the present disclosure competitively inhibit binding of at least one antibody selected from S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-18, S-19, S-20, S-21, S-22, S-22-1, S-22-2, S-22-3, S-22-4, S-22-5, S-22-6, S-22-7, S-22-8, S-22-9, S-29, S-51, S57, S-61, S-82, S-82-1, S-82-2, S-82-3, S-82-4, S-82-5, S-82-6, S-82-7, and S-82-8.

In some embodiments, anti-Sortilin antibodies of the present disclosure bind to an epitope of human Sortilin that is the same as or overlaps with the Sortilin epitope bound by at least one antibody selected from S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-18, S-19, S-20, S-21, S-22, S-22-1, S-22-2, S-22-3, S-22-4, S-22-5, S-22-6, S-22-7, S-22-8, S-22-9, S-29, S-51, S57, S-61, S-82, S-82-1, S-82-2, S-82-3, S-82-4, S-82-5, S-82-6, S-82-7, and S-82-8. In some embodiments, anti-Sortilin antibodies of the present disclosure bind essentially the same Sortilin epitope bound by at least one antibody selected from S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-18, S-15-10-19, S-15-10-20, S-15-10-21 S-15-11, S-15-12, S-15-13, S-15-14, S-15-15, S-15-16, S-18 S-19, S-20, S-21, S-22, S-22-1, S-22-2, S-22-3, S-22-4, S-22-5, S-22-6, S-22-7, S-22-8, S-22-9, S-29, S-51, S57 S-61, S-82, S-82-1, S-82-2, S-82-3, S-82-4, S-82-5, S-82-6, S-82-7, and S-82-8. In some embodiments, anti-Sortilin antibodies of the present disclosure comprise (a) a light chain variable region comprising at least one, two, or three HVRs selected from HVR-L1, HVR-L2, and HVR-L3 selected from S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S45-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-18, S-19, S-20, S-21, S-22, S-22-1, S-22-2, S-22-3, S-22-4, S-22-5, S-22-6, S-22-7, S-22-8, S- 22-9, S-29, S51, S57, S-61 S-82, S-8 S-82-2, S-82-3, S-82-4, S-82-5, S-82-6, S-82-7, and S-82-8; and/or (b) a heavy chain variable region comprising at least one, two, or three HVRs selected from HVR-H1, HVR-H2, and HVR-H3 selected from S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-14, S-15, S-15-1, S-15-2, S-15-3, S-15- 4, S-15-5, S-15-6, S-15-6-1, S-15-6-2, S-15-6-3, S-15-6-4S-15-6-5, S-15-6-6, S-15-6-7, S-15-6-8, S-15-6-9, S-15-6-10, S-15-6-11S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15- 10-20, S-15-10-21, S-15-11, S-15-12, S-15-13, S-15-14, S-15-15, S-15-16, S-18, S-19, S-20, S-21, S-22, S-22-1, S-22-2, S-22-3, S-22-4, S-22-5, S-22-6, S-22-7, S-22-8, S-22-9, S-29, S-51, S7, S-61, S-82, S-82- 1, S-82-2, S-82-3, S-82-4, S-82-5, S-82-6, S-82-7, and S-82-8. In some embodiments, the HVR-L1, HVR-L2, HVR-L3, HVR-H2, and HVR-H3 comprise EU or Kabat CDR, Chothia CDR, or Contact CDR sequences from an antibody selected from S-2, S-2-1, S-2-2, S-2-3, S-2-4, S-2-5, S-2-6, S-2-7, S-2-8, S-2-9, S-2-10S-2-11, S-2-12, S-2-13, S-2-14, S-2-15, S-14, S-15S-15-1, S-15-2, S-15-3, S-15-4, S- 15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-18, S-19, S-20, S-21, S-22, S-22-1, S-22-2, S-22-3, S-22-4, S-22-5, S-22-6, S-22-7, S-22-8, S-22-9, S-29, S-51, S57, S-61, S-82, S-82-1, S-82-2, S-82-3, S-82-4, S-82-5, S-82-6, S-82-7, and S-82-8. In some embodiments, anti-Sortilin antibodies of the present disclosure comprise at least one, two, three, four, five, or six HVRs selected from (i) HVR-L1 comprising the amino acid sequence of any of the HVR-L1 sequences from an antibody selected from S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10- 4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17S-15-10-18S-15-10-19S-15-10-21, S-15-11, S-15-12, S-15-13, S-15-14, S-15-15, S-15-16, S-18, S-19, S-20, S-21, S-22, S-22-1, S-22-2, S-22-3, S-22-4, S-22-5, S-22- 6, S-22-7, S-22-8, S-22-9, S-29, S-51, S57, S-61, S-82, S-82-1, S-82-2, S-82-3, S-82-4, S-82-5, S-82-6, S-82-7, and S-82-8; (ii) HVR-L2 comprising the amino acid sequence of any of the HVR-L2 sequences from an antibody selected from S-2, S-2-1, S-2-2, S-2-3, S-2-4, S-2-5, S-2-6, S-2-7, S-2-8, S-2-9, S-2-10, S-2-11S-2-12, S-2-13S-2-14, S-2-15, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-16, S-18, S-19, S-20, S-21, S-22, S-22-1, S-22-2, S-22-3, S-22-4, S-22-5, S-22-6, S-22-7, S-22-8, S-22-9, S-29, S-51, S57, S-61, S-82, S-82-1, S-82-2, S-82-3, S-82-4, S-82-5, S-82-6, S-82-7, and S-82-8; (iii) HVR-L3 comprising the amino acid sequence of any of the HVR-L3 sequences from an antibody selected from S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11S-15-10-12, S-15-10-13, S-15-10-14, S-15-10-15S-15-10-16, S-15-10-17, S-15-10-18, S-15-10-19, S-15-10-20, S-15-10-21, S-15-11, S-15-12, S-15-13, S-15-14, S-15-15, S-15-16, S-18, S-19, S-20, S-21, S-22, S-22-1, S-22-2, S-22-3, S-22-4, S-22-5, S-22-6, S-22-7, S-22-8, S-22-9, S-29, S-51, S57, S-61, S-82, S-82-1, S-82-2, S-82-3, S-82-4, S-82-5, S-82-6, S-82-7, and S-82-8; (iv) HVR-H1 comprising the amino acid sequence of any of the HVR-H1 sequences from an antibody selected from S-2, S-2-1, S-2-2, S-2-3, S-2-4S-2-5, S-2-6, S-2-7, S-2-8, S-2-9, S-2-10, S-2-11, S-2-12, S-2-13, S-2-14, S-2-15, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18S-15-10-19, S-15-10-20, S-15-10-21, S-15-11, S-15-12, S-15-13, S-15-14, S-15-15, S-15-16, S-18, S-19, S-20, S-21, S-22, S-22-1, S-22-2, S-22-3, S-22-4, S-22-5, S-22-6, S-22-7, S-22-8, S-22-9, S-29, S-51, S57, S-61, S-82, S-82-1, S-82-2, S-82-3, S-82-4, S-82-5, S-82-6, S-82-7, and S-82-8; (v) HVR-H2 comprising the amino acid sequence of any of the HVR-H2 sequences from an antibody selected from S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-18, S-19, S-20, S-21, S-22, S-22-1, S-22-2, S-22-3, S-22-4, S-22-5, S-22-6, S-22-7, S-22-8, S-22-9, S-29, S-51, S57, S-61, S-82, S-82-1S-82-2, S-82-3, S-82-4, S-82-5, S-82-6, S-82-7, and S-82-8; and (vi) HVR-H3 comprising the amino acid sequence of any of the HVR-H3 sequences from an antibody selected from S-2, S-2-1, S-2-2, S-2-3, S-2-4, S-2-5, S-2-6, S-2-7, S-2-8, S-2-9, S-2-10, S-2-11, S-2-12, S-2-13S-2-14, S-2-15S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-18, S-19, S-20, S-21, S-22, S-22-1, S-22-2, S-22-3, S-22-4, S-22-5, S-22-6, S-22-7, S-22-8, S-22-9, S-29S-51, S57, S-61, S-82, S-82-1, S-82-2, S-82-3, S-82-4, S-82-5, S-82-6, S-82-7, and S-82-8. In some embodiments, anti-Sortilin antibodies of the present disclosure comprise a light chain variable region of any one of the antibodies selected from S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-18, S-19, S-20, S-21, S-22, S-22-1, S-22-2, S-22-3, S-22-4, S-22-5, S-22-6, S-22-7, S-22-8, S-22-9, S-29, S-51, S57, S-61, S-82, S-82-1, S-82-2, S-82-3, S-82-4, S-82-5, S-82-6, S-82-7, and S-82-8; and/or a heavy chain variable region of any one of the antibodies selected from S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19 S-15-11S-15-12, S-15-13, S-15-14, S-15-15, S-15-16, S-18, S-19, S-20, S-21, S-22, S-22-1, S-22-2, S-22-3, S-22-4, S-22-5, S-22-6, S-22-7, S-22-8, S-22-9, S-29, S-51, S57, S-61, S-82, S-82-1, S-82-2, S-82-3, S-82-4, S-82-5, S-82-6, S-82-7, and S-82-8. In some embodiments, the anti-Sortilin antibody is an anti-Sortilin monoclonal antibody selected from S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-18, S-19, S-20, S-21, S-22, S-22-1, S-22-2, S-22-3, S-22-4, S-22-5, S-22-6, S-22-7, S-22-8, S-22-9, S-29, S-51, S57, S-61, S-82, S-82-1, S-82-2, S-82-3, S-82-4, S-82-5, S-82-6, S-82-7, and S-82-8.

In some embodiments, anti-Sortilin antibodies of the present disclosure comprise a light chain variable domain and a heavy chain variable domain, wherein the light chain variable domain comprises one or more of: (a) an HVR-L1 comprising an amino acid sequence selected from the group consisting of SEQ ID NOs:7-10, 13, and 14, or an amino acid sequence with at least about 95% homology to an amino acid sequence selected from the group consisting of SEQ ID NOs:7-10, 13, and 14; (b) an HVR-L2 comprising an amino acid sequence selected from the group consisting of SEQ ID NOs:26-31 and 33-35, or an amino acid sequence with at least about 95% homology to an amino acid sequence selected from the group consisting of SEQ ID NOs:26-31 and 33-35; and (c) an HVR-L3 comprising an amino acid sequence selected from the group consisting of SEQ ID NOs:42, 54, 55, 58, 59, 60, 61, 62, 69, 91, 97, 101, and 122, or an amino acid sequence with at least about 95% homology to an amino acid sequence selected from the group consisting of SEQ ID NOs:42, 54, 55, 58, 59, 60, 61, 62, 69, 91, 97, 101, and 122; and/or wherein the heavy chain variable domain comprises one or more of: (a) an HVR-H1 comprising an amino acid sequence selected from the group consisting of SEQ ID NOs:126, 129, 130, 135, 140, 142, and 147, or an amino acid sequence with at least about 95% homology to an amino acid sequence selected from the group consisting of SEQ ID NOs:126, 129, 130, 135, 140, 142, and 147; (b) art HVR-H2 comprising an amino acid sequence selected from the group consisting of SEQ ID NOs:150, 155-158, 162, 166, 169, and 173, or an amino acid sequence with at least about 95% homology to an amino acid sequence selected from the group consisting of SEQ ID NOs:150, 155-158, 162, 166, 169, and 173; and (c) an HVR-H3 comprising an amino acid sequence selected from the group consisting of SEQ ID NOs:180, 190, 193-197, 203, 225, 231, 234, and 253 or an amino acid sequence with at least about 95% homology to an amino acid sequence selected from the group consisting of SEQ ID NOs:180, 190, 193-197, 203, 225, 231, 234, and 253.

In some embodiments, anti-Sortilin antibodies of the present disclosure competitively inhibit binding of at least one antibody selected from S-5, S-30, S-60-1, S-60-2, S-60-3, S-60-4, S-60-5, S-60-6, S-60-7, S-60-8, and S-60-9. In some embodiments, anti-Sortilin antibodies of the present disclosure bind to an epitope of human Sortilin that is the same as or overlaps with the Sortilin epitope bound by at least one antibody selected from S-5, S-30, S-60-1, S-60-2, S-60-3, S-60-4, S-60-5, S-60-6, S-60-7, S-60-8, and S-60-9. In some embodiments, anti-Sortilin antibodies of the present disclosure bind essentially the same Sortilin epitope bound by at least one antibody selected from S-5, S-30, S-60-1, S-60-2, S-60-3, S-60-4, S-60-5, S-60-6, S-60-7, S-60-8, and S-60-9. In some embodiments, anti-Sortilin antibodies of the present disclosure comprise (a) a light chain variable region comprising at least one, two, or three HVRs selected from HVR-L1, HVR-L2, and HVR-L3 selected from S-5, S-30, S-60-1, S-60-2, S-60-3, S-60-4, S-60-5, S-60-6, S-60-7, S-60-8, and S-60-9; and/or (b) a heavy chain variable region comprising at least one, two, or three HVRs selected from HVR-H1, HVR-H2, and HVR-H3 selected from S-5, S-30, S-60-1, S-60-2, S-60-3, S-60-4, S-60-5, S-60-6, S-60-7, S-60-8, and S-60-9. In some embodiments, the HVR-L1, HVR-L2, HVR-L3, HVR-H1, HVR-H2, and HVR-L3 comprise EU or Kabat CDR, Chothia CDR, or Contact CDR sequences from an antibody selected from S-5, S-30, S-60-1, S-60-2, S-60-3, S-60-4, S-60-5, S-60-6, S-60-7, S-60-8, and S-60-9. In some embodiments, anti-Sortilin antibodies of the present disclosure comprise at least one, two, three, four, five, or six HVRs selected from (i) HVR-L1 comprising the amino acid sequence of any of the HVR-L1 sequences from an antibody selected from S-5, S-30, S-60-1, S-60-2, S-60-3, S-60-4, S-60-5, S-60-6, S-60-7, S-60-8, and S-60-9; (ii) HVR-L2 comprising the amino acid sequence of any of the HVR-L2 sequences from an antibody selected from S-5, S-30, S-60-1, S-60-2, S-60-3, S-60-4, S-60-5, S-60-6, S-60-7, S-60-8, and S-60-9; (iii) HVR-L3 comprising the amino acid sequence of any of the HVR-L3 sequences from an antibody selected from S-5, S-30, S-60-1, S-60-2, S-60-3, S-60-4, S-60-5, S-60-6, S-60-7, S-60-8, and S-60-9; (iv) HVR-H1 comprising the amino acid sequence of any of the HVR-H1 sequences from an antibody selected from S-5, S-30, S-60-1, S-60-2, S-60-3, S-60-4, S-60-5, S-60-6, S-60-7, S-60-8, and S-60-9; (v) HVR-H2 comprising the amino acid sequence of any of the HVR-H2 sequences from an antibody selected from S-5, S-30, S-60-1, S-60-2, S-60-3, S-60-4, S-60-5, S-60-6, S-60-7, S-60-8, and S-60-9; and (vi) HVR-H3 comprising the amino acid sequence of any of the HVR-H3 sequences from an antibody selected from S-5, S-30, S-60-1, S-60-2, S-60-3, S-60-4, S-60-5, S-60-6, S-60-7, S-60-8, and S-60-9. In some embodiments, anti-Sortilin antibodies of the present disclosure comprise a light chain variable region of any one of the antibodies selected from S-5, S-30, S-60-1, S-60-2, S-60-3, S-60-4, S-60-5, S-60-6, S-60-7, S-60-8, and S-60-9; and/or a heavy chain variable region of any one of the antibodies selected from S-5, S-30, S-60-1, S-60-2, S-60-3, S-60-4, S-60-5, S-60-6, S-60-7, S-60-8, and S-60-9. In some embodiments, the anti-Sortilin antibody is an anti-Sortilin monoclonal antibody selected from S-5, S-30, S-60-1, S-60-2, S-60-3, S-60-4, S-60-5, S-60-6, S-60-7, S-60-8, and S-60-9.

In some embodiments, anti-Sortilin antibodies of the present disclosure comprise a light chain variable domain and a heavy chain variable domain, wherein the light chain variable domain comprises one or more of: (a) an HVR-L1 comprising the amino acid sequence of SEQ ID NO:10, or an amino acid sequence with at least about 95% homology to the amino acid sequence of SEQ ID NO:10; (b) an HVR-L2 comprising the amino acid sequence of SEQ ID NO:30, or an amino acid sequence with at least about 95% homology to the amino acid sequence of SEQ ID NO:30; and (c) an HVR-L3 comprising an amino acid sequence selected from the group consisting of SEQ ID NOs:45, 70, and 100, or an amino acid sequence with at least about 95% homology to an amino acid sequence selected from the group consisting of SEQ ID NOs:45, 70, and 100; and/or wherein the heavy chain variable domain comprises one or more of: (a) an HVR-H1 comprising an amino acid sequence selected from the group consisting of SEQ ID NOs:126, 136, and 142, or an amino acid sequence with at least about 95% homology to an amino acid sequence selected from the group consisting of SEQ ID NOs:126, 136, and 142; (b) an HVR-H2 comprising an amino acid sequence selected from the group consisting of SEQ ID NOs:151, 163, and 170, or an amino acid sequence with at least about 95% homology to an amino acid sequence selected from the group consisting of SEQ ID NOs:151, 163, and 170; and (c) an HVR-H3 comprising an amino acid sequence selected from the group consisting of SEQ ID NOs:182, 204, and 233, or an amino acid sequence with at least about 95% homology to an amino acid sequence selected from the group consisting of SEQ ID NOs:182, 204, and 233.

The dissociation constants ($K_D$) of anti-Sortilin antibodies for human Sortilin, mouse Sortilin, or both, may be less than 100 nM, less than 90 nM, less than 80 nM, less than 70 nM, less than 60 nM, less than 50 nM, less than 40 nM, less than 30 nM, less than 20 nM, less than 10 nM, less than 9 nM, less than 8 nM, less than 7 nM, less than 6 nM, less than 5 nM, less than 4 nM, less than 3 nM, less than 2 nM, less than 1 nM, less than 0.5 nM, less than 0.1 nM, less than 0.09 nM, less than 0.08 nM, less than 0.07 nM, less than 0.06 nM, less than 0.05 nM, less than 0.04 nM, less than 0.03 nM, less than 0.02 nM, less than 0.01 nM, less than 0.009 nM, less than 0.008 nM, less than 0.007 nM, less than 0.006 nM, less than 0.005 nM, less than 0.004 nM, less than 0.003 nM, less than 0.002 nM, less than 0.001 nM, or less than 0.001 nM. In some embodiments, the antibody has a dissociation constant ($K_D$) for human Sortilin, mouse Sortilin, or both, that ranges from about 100 nM to about 0.005 nM, or less than 0.005 nM. Preferably, the dissociation constant is less than 50 nM. In some embodiments, the dissociation constant ($K_D$) is measured at 4° C. or room temperature utilizing, for example, a cell binding assay, ForteBio assay, or MSD-SET assay as described herein (see, e.g., Examples 1 and 23).

The dissociation constants ($K_D$) of anti-Sortilin antibodies for human Sortilin and mouse Sortilin may be less than 71 nM, less than 70.9 nM, less than 70.8 nM, less than 70.7 nM, less than 70.6 nM, less than 70.5 nM, less than 70.4 nM, less than 70.3 nM, less than 70.2 nM, less than 70.1 nM, less than 70 nM, less than 60 nM, less than 50 nM, less than 40 nM, less than 30.5 nM, less than 30 nM, less than 29.9 nM, less than 29.8 nM, less than 29.7 nM, less than 29.6 nM, less than 29.5 nM, less than 29.4 nM, less than 29.3 nM, less than 29.2 nM, less than 29.1 nM, less than 29 nM, less than 28.5 nM, less than 28 nM, less than 27.5 nM, less than 27 nM, less than 26.5 nM, less than 26 nM, less than 25.5 nM, less than 25 nM, less than 24.5 nM, less than 24 nM, less than 23.5 nM, less than 23 nM, less than 22.5 nM, less than 22 nM, less than 21.5 nM, less than 21 nM, less than 20.5 nM, less than 20 nM, less than 19.5 nM, less than 19 nM, less than 18.9 nM, less than 18.8 nM, less than 18.7 nM, less than 18.6 nM, less than 18.5 nM, less than 18.4 nM, less than 18.3 nM, less than 18.2 nM, less than 1.8.1 nM, less than 18 nM, less than 17.5 nM, less than 17 nM, less than 16.5 nM, less than 16 nM, less than 15.5 nM, less than 15 nM, less than 14.5 nM, less than 14 nM, less than 13.5 nM, less than 13 nM, less than 12.5 nM, less than 12 nM, less than 11.5 nM, less than 11 nM, less than 10.5 nM, less than 10 nM, less than 9.5 nM, less than 9 nM, less than 8.5 nM, less than 8 nM, less than 7.5 nM, less than 7 nM, less than 6.9 nM, less than 6.8 nM, less than 6.7 nM, less than 6.6 nM, less than 6.5 nM, less than 6.4 nM, less than 6.3 nM, less than 6.2 nM, less than 6.1 nM, less than 6 nM, less than 5.5 nM, less than 5 nM, less than 4.5 nM, less than 4 nM, less than 3.5 nM, less than 3 nM, less than 2.5 nM, less than 2 nM, less than 1.5 nM, less than 1 nM, less than 0.95 nM, less than 0.9 nM, less than 0.89 nM, less than 0.88 nM, less than 0.87 nM, less than 0.86 nM, less than 0.85 nM, less than 0.84 nM, less than 0.83 nM, less than 0.82 nM, less than 0.81 nM, less than 0.8 nM, less than 0.75 nM, less than 0.7 nM, less than 0.65 nM, less than 0.64 nM, less than 0.63 nM, less than 0.62 nM, less than 0.61 nM, less than 0.6 nM, less than 0.55 nM, less than 0.5 nM, less than 0.45 nM less than 0.4 nM, less than 0.35 nM, less than 0.3 nM, less than 0.29 nM, less than 0.28 nM, less than 0.27 nM, less than 0.26 nM, less than 0.25 nM, less than 0.24 nM, less than 0.23 nM, less than 0.22 nM, less than 0.21 nM, less than 0.2 nM, less than 0.15 nM, less than 0.1 nM, less than 0.09 nM, less than 0.08 nM, less than 0.07 nM, less than 0.06 nM, less than 005 nM, less than 0.04 nM, less than 0.03 nM, less than 0.02 nM, less than 0.01 nM, less than 0.009 nM, less than 0.008 nM, less than 0.007 nM, less than 0.006 nM, less than 0.005 nM, less than 0.004 nM, less than 0003 nM, less than 0.002 nM, or less than 0.001 nM. In some embodiments, dissociation constants of anti-Sortilin antibodies for human Sortilin proteins range from less than about 70.4 nM to less than about 0.29 nM, or from less than about 18.7 nM to less than about 0.89 nM. In some embodiments, dissociation constants of anti-Sortilin antibodies for human Sortilin proteins range from about 70.4 nM to about 0.005 nM, or less than 0.005 nM. In some embodiments, dissociation constants of anti-Sortilin antibodies for mouse Sortilin proteins range from less than about 40.3 nM to less than about 0.61 nM, or from less than about 29.6 nM to less than about 0.61 nM. In some embodiments, dissociation constants of anti-Sortilin antibodies for mouse Sortilin proteins range from about 40.3 nM to about 0.07 nM, or less than 0.07 nM. In some embodiments, dissociation constants of anti-Sortilin antibodies for both human and mouse Sortilin proteins range front less than about 70.4 nM to less than about 0.29 nM, or from less than about 29.6 nM to less than about 0.61 nM. Dissociation constants may be determined through any analytical technique, including any biochemical or biophysical technique such as ELISA, surface plasmon resonance (SPR), bio-layer interferometry (see, e.g., Octet System by ForteBio), meso scale discover (see, e.g., MSD-SET), isothermal titration calorimetry (ITC), differential scanning calorimetry (DSC), circular dichroism (CD), stopped-flow analysis, and colorimetric or fluorescent protein melting analyses; or a cell binding assay. Accordingly, in some embodiments, the dissociation constant ($K_D$) is measured at 4° C. or room temperature utilizing, for example, a cell binding assay, ForteBio assay, or MSD-SET assay as described herein (see, e.g., Examples 1 and 23).

Additional anti-Sortilin antibodies, e.g., antibodies that specifically bind to a Sortilin protein of the present disclosure, may be identified, screened, and/or characterized for their physical/chemical properties and/or biological activities by various assays known in the art.

Decreased Expression of Pro-Inflammatory Mediators

In some embodiments, anti-Sortilin antibodies of the present disclosure may decrease the expression of pro-inflammatory mediators after binding to a Sortilin protein expressed in a cell.

As used herein, pro-inflammatory mediators are proteins involved either directly or indirectly (e.g., by way of pro-inflammatory signaling pathways) in a mechanism that induces, activates, promotes, or otherwise decreases an inflammatory response. Any method known in the art for identifying and characterizing pro-inflammatory mediators may be used.

Examples of pro-inflammatory mediators include, without limitation, cytokines, such as type I and II interferons, IL-6, IL12p70, IL12p40, IL-1β, TNF-α, IL-8, CRP, IL-20 family members, IL-33, LIF OSM, CNTF, GM-CSF, IL-11, IL-12, IL-17, IL-18, and CRP. Further examples of pro-inflammatory mediators include, without limitation, chemokines, such as CXCL1, CCL2, CCL3, CCL4, and CCL5.

In some embodiments, the anti-Sortilin antibodies of the present disclosure may decrease functional expression and/or secretion of pro-inflammatory mediators, IL-6, IL12p70, IL12p40, IL-1β, TNT-α, CXCL1, CCL2, CCL3, CCL4, and CCL5. In certain embodiments, decreased expression of the pro-inflammatory mediators occurs in macrophages, dendritic cells, monocytes, osteoclasts, Langerhans cells of skin, Kupffer cells, T cells, and/or microglial cells. Decreased expression may include, without limitation, a decrease in gene expression, a decrease in transcriptional expression, or a decrease in protein expression. Any method known in the art for determining gene, transcript (e.g., mRNA), and/or protein expression may be used. For example, Northern blot analysis may be used to determine pro-inflammatory mediator gene expression levels, RT-PCR may be used to determine the level of pro-inflammatory mediator transcription, and Western blot analysis may be used to determine pro-inflammatory mediator protein levels.

As used herein, a pro-inflammatory mediator may have decreased expression if its expression in one or more cells of a subject treated with a Sortilin agent, such as an agonist anti-Sortilin antibody of the present disclosure is more than the expression of the same pro-inflammatory mediator expressed in one or more cells of a corresponding subject that is not treated with the agonist anti-Sortilin antibody. In some embodiments, the anti-Sortilin antibody of the present disclosure may decrease pro-inflammatory mediator expression in one or more cells of a subject by at least 10%, at least 15%, at least 20%, at least 25%, at least 30%, at least at least 40%, at least 45%, at least 50%, at least 55%, at least 60%, at least 65%, at least 70%, at least 75%, at least 80%, at least 85%, at least 90%, at least 95%, at least 100%, at least 110%, at least 115% at least 120%, at least 125%, at least 130%, at least 135%, at least 140%, at least 145%, at least 150%, at least 160%, at least 170%, at least 180%, at least 190%, or at least 200% for example, as compared to pro-inflammatory mediator expression in one or more cells of a corresponding subject that is not treated with the anti-Sortilin antibody. In other embodiments, the anti-Sortilin antibody may decrease pro-inflammatory mediator expression in one or more cells of a subject by at least at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to pro-inflammatory mediator expression in one or more cells of a corresponding subject that is not treated with the anti-Sortilin antibody.

Anti-Sortilin Antibody Fc Isotypes

In some embodiments, antibodies of the present disclosure include antagonist antibodies. In some embodiments, antibodies that bind a Sortilin protein may include antagonist antibodies that bind Sortilin and inhibit one or more Sortilin activities, either by preventing interaction between Sortilin and one or more of its ligands (e.g., Progranulin, pro-neurotrophins, neurotrophins, neurotensin, p75, Sortilin propeptide, APP, A beta peptide, LpL, APOA5, APOE, and RAP). In some embodiments, antagonist antibodies of the present disclosure may have an Fc domain that is not capable of binding Fcg receptors.

Exemplary blocking and/or antagonist antibody Fc isotypes and modifications are provided in Table A below. In some embodiments, an anti-Sortilin antibody of the present disclosure has an Fc isotype listed in Table A below.

TABLE A

Exemplary anti-Sortilin antibody Fc isotypes

| Fc Isotype | Mutation (EU or Kabat numbering scheme) |
|---|---|
| IgG1 | N297A or N297Q |
| IgG1 | D265A and N297A |
| IgG1 | L234A and L235A |
| IgG2 | V234A and G237A |
| IgG4 | F235A and G237A and E318A |
| | E233P and/or F234V |
| | N297A or N297Q |
| IgG4 | S228P and L236E |
| | S241P |
| | S241P and L248E |
| | S228P and F234A and L235A |
| IgG2 | H268Q and V309L and A330S and P331S |
| IgG1 | C220S and C226S and C229S and P238S |

TABLE A-continued

Exemplary anti-Sortilin antibody Fc isotypes

| Fc Isotype | Mutation (EU or Kabat numbering scheme) |
|---|---|
| IgG1 | C226S and C229S and E233P and L234V, and L235A |
| IgG1 | E233P and L234V and L235A and G236-deleted |
| | P238A |
| | D265A |
| | N297A |
| | A327Q or A327G |
| | P329A |
| IgG1 | K322A and L234A and L235A |
| IgG1 | L234F and L235E and P331S |
| IgG1 or IgG4 | T394D |
| IgG2 | C232S or C233S |
| | N297A or N297Q |
| IgG2 | V234A and G237A and P238S and H268A and V309L and A330S and P331S |
| IgGl, IgG2, or IgG4 | delta a, b, c, ab, ac, g modifications |
| IgG1 | Any of the above listed mutations together with A330L or L234F and/or L235E and/or P331S |
| IgG1, IgG2, or IgG4 | Any of the above listed mutations together with M252Y and/or S254T and/or T256E |

In certain embodiments, the anti-Sortilin antibody has an IgG1 isotype. In some embodiments, the anti-Sortilin antibody contains a mouse IgG1 constant region. In some embodiments, the anti-Sortilin antibody contains a human IgG1 constant region. In some embodiments, the human IgG1 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from N297A, N297Q (Bolt S et al. (1993) *Eur J Immunol* 23:403-411), D265A, L234A, L235A (McEarchern et al., (2007) *Blood,* 109:1185-1192), C226S, C229S (McEarchern et al., (2007) *Blood,* 109:1185-1192), P238S (Davis et al., (2007) *J Rheumatol,* 34:2204-2210), E233P, L234V (McEarchern et al., (2007) *Blood,* 109:1185-1192), P238A, A327Q, A327G, P329A (Shields R L. et al., (2001) *J Biol Chem.* 276(9):6591-604), K:322A, L234F, L235E (Hezareh, et al., (2001) J Virol 75, 12161-12168; Oganesyan et al., (2008). *Acta Crystallographica* 64, 700-704), P331S (Oganesyan et al., (2008) *Acta Crystallographica* 64, 700-704), T394D (Wilkinson et al. (2013) *MAbs* 5(3): 406-417), A330L, M252Y, S254T, and/or T256E, where the amino acid position is according to the EU or Kabat numbering convention. In certain embodiments, the Fc region further includes an amino acid deletion at a position corresponding to glycine 236 according to the EU or Kabat numbering convention.

In some embodiments, the anti-Sortilin antibody has an IgG1 isotype with a heavy chain constant region that contains a C220S amino acid substitution according to the EU or Kabat numbering convention.

In some embodiments, the Fc region further contains one or more additional amino acid substitutions selected from t A330L, L234F; L235E, and/or P331S according to EU or Kabat numbering convention.

In certain embodiments, the anti-Sortilin antibody has an IgG2 isotype. In some embodiments, the anti-Sortilin antibody contains a human IgG2 constant region. In some embodiments, the human IgG2 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from P238S, V234A, G237A, H268A, H268Q, H268E, V309L, N297A, N297Q, V309L, A330S, P331S, C232S, C233S, M252Y, S254T, and/or T256E, where the amino acid position is according to the EU or Kabat numbering convention (Vafa O. et al., (2014) Methods 65:114-126).

In certain embodiments, the anti-Sortilin in antibody has an IgG4 isotype. In some embodiments, the anti-Sortilin antibody contains a human IgG4 constant region. In some embodiments, the human IgG4 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from E233P, F234V, L235A, G237A, E318A (Hutchins et al. (1995) *Proc Natl Acad Sci USA*, 92:11980-11984), S228P, L234A/F234A, L236E, S241P, L248E (Reddy et al., (2000) *J Immunol*, 164:1925-1933: Angal et al., (1993) *Mol Immunol*. 30(1):105-8; U.S. Pat. No. 8,614,299 B2; Vafa O. et al., (2014) Methods 65:114-126), T394D, M252Y, S254T, T256E, N297A, and/or N297Q, where the amino acid position is according to the EU or Kabat numbering convention.

In some embodiments, the Fc region further contains one or more additional amino acid substitutions selected from a M252Y, S254T, and/or T256E, where the amino acid position is according to the EU or Kabat numbering convention.

Further IgG Mutations

In some embodiments, one or more of the IgG1 variants described herein may be combined with an A330L mutation (Lazar et al., (2006) Proc Natl Acad Sci USA, 103:4005-4010), or one or more of L234F, L235E, and/or P331S mutations (Sazinsky et al., (2008) Proc Natl Acad Sci. USA, 105:20167-20172), where the amino acid position is according to the EU or Kabat numbering convention, to eliminate complement activation. In some embodiments, the IgG variants described herein may be combined with one or more mutations to enhance the anti-Sortilin antibody half-life in human serum (e.g. M252Y, S254T, T256E mutations according to the EU or Kabat numbering convention) (Dall'Acqua et al., (2006) J Biol Chem, 281:23514-23524; and Strohl e al., (2009) Current Opinion in Biotechnology, 20:685-691).

In some embodiments, an IgG4 variant of the present disclosure may be combined with an S228P mutation according to the EU or Kabat numbering convention (Angal et al., (1993) Mol Immunol, 30:105-108) and/or with one or more mutations described in Peters et al., (2012) J Biol Chem. 13; 287(29):24525-33) to enhance antibody stabilization.

Bispecific Antibodies

Certain aspects of the present disclosure relate to bispecific antibodies that bind to one or more domains on a Sortilin protein of the present disclosure and a second antigen. Methods of generating bispecific antibodies are well known in the art and described herein. In some embodiments, bispecific antibodies of the present disclosure bind to one or more amino acid residues of a Sortilin protein of the present disclosure. In some embodiments, bispecific antibodies of the present disclosure recognize a first antigen and a second antigen. In some embodiments, the first antigen is a Sortilin protein or a naturally occurring variant thereof. In some embodiments, the second antigen is also a Sortilin protein, or a naturally occurring variant thereof. In some embodiments, the second antigen is an antigen facilitating transport across the blood-brain-barrier (see, e.g., Gabathuler R., *Neurobiol. Dis.* 37 (2010) 48-57). Such second antigens include, without limitation, transferring receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, Angiopep peptides such as ANG1005 (see, e.g., Gabathuler, 2010), basigin, Glut1, CD98hc, and other cell surface proteins that are enriched on blood-brain barrier endothelial cells (see, e.g., Daneman et al., PLoS One. 2010 Oct. 29; 5(10):e13741).

Antibody Combinations

Certain aspects of the present disclosure relate to the use of two or more anti-Sortilin antibodies that when utilized together display additive or synergistic effects, as compared to utilization of a corresponding single anti-Sortilin antibody.

Antibody Fragments

Certain aspects of the present disclosure relate to antibody fragments that bind to a Sortilin protein of the present disclosure. In some embodiments, the antibody fragment is an Fab, Fab', Fab'-SH, F(ab')2, Fv or scFv fragment. In some embodiments, the antibody fragment is used in combination with a second Sortilin antibody and/or with one or more antibodies that specifically bind a disease-causing protein selected from: amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, media, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, proline-arginine (PR) repeat peptides, and any combination thereof.

In some embodiments, antibody fragments of the present disclosure may be functional fragments that bind the same epitope as any of the anti-Sortilin antibodies of the present disclosure. In some embodiments, the antibody fragments are miniaturized versions of the anti-Sortilin antibodies or antibody fragments of the present disclosure that have the same epitope of the corresponding full-length antibody, but have much smaller molecule weight. Such miniaturized anti-Sortilin antibody fragments may have better brain penetration ability and a shorter half-life, which is advantageous for imaging and diagnostic utilities (see e.g., Lüje S et al., *Bioconjug Chem.* 2014 Feb. 19; 25(2):335-41; Tavaré R et al., *Proc Natl Acad Sci USA*. 2014 Jan. 21; 111(3):1108-13; and Wiehr S et al., *Prostate*, 2014 May; 74(7):743-55). Accordingly, in some embodiments, anti-Sortilin antibody fragments of the present disclosure have better brain penetration as compared to their corresponding full-length antibodies and/or have a shorter half-life as compared to their corresponding full-length antibodies.

Antibody Frameworks

Any of the antibodies described herein further include a framework. In some embodiments, the framework is a human immunoglobulin framework. For example, in some embodiments, an antibody (e.g., an anti-Sortilin antibody) comprises HVRs as in any of the above embodiments and further comprises an acceptor human framework, e.g., a human immunoglobulin framework or a human consensus framework. Human immunoglobulin frameworks may be part of the human antibody, or a non-human antibody may be humanized by replacing one or more endogenous frameworks with human framework region(s). Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J Biol. Chem.* 272:10678-10684 (1997) and Rosok et al., *J. Biol. Chem.* 271:22611-22618 (1996)).

In some embodiments, an antibody comprises a light chain variable region comprising an HVR-L1, an HVR-L2, and an HVR-L3 of the present disclosure and one, two, three or four of the light chain framework regions as shown in Table 2 and SEQ ID NOs:630, 667, and 641-684. In some embodiments, an antibody comprises a heavy chain variable region comprising an HVR-H1, an HVR-H2, and an HVR-H3 of the present disclosure and one, two, three or four of the heavy chain framework regions as shown in Table 3 and SEQ ID NOs:604-618, 619-629, 631-666, 668, 669, 670-678-680, and 685-692. In some embodiments, an antibody comprises a light chain variable region comprising an HVR-L1, an HVR-L2, and an HVR-L3 of the present disclosure and one, two, three or four of the light chain framework regions as shown in Table 2 and SEQ ID NOs:630, 667, and 641-684 and further comprises a heavy chain variable region comprising an HVR-H1, an HVR-H2, and an HVR-H3 of the present disclosure and one, two, three or four of the heavy chain framework regions as shown in Table 3 and SEQ ID NOs:604-618, 619-629, 631-666, 668, 669, 670-678-680, and 685-692.

Antibody Preparation

Anti-Sortilin antibodies of the present disclosure can encompass polyclonal antibodies, monoclonal antibodies, humanized and chimeric antibodies, human antibodies, antibody fragments (e.g., Fab, Fab'-SH, Fv, scFv, and F(ab')$_2$), bispecific and polyspecific antibodies, multivalent antibodies, heteroconjugate antibodies, conjugated antibodies, library derived antibodies, antibodies having modified effector functions, fusion proteins containing an antibody portion, and any other modified configuration of the immunoglobulin molecule that includes an antigen recognition site, such as an epitope having amino acid residues of a Sortilin protein of the present disclosure, including glycosylation variants of antibodies, amino acid sequence variants of antibodies, and covalently modified antibodies. The anti-Sortilin antibodies may be human, murine, rat, or of any other origin (including chimeric or humanized antibodies).

(1) Polyclonal Antibodies

Polyclonal antibodies, such as polyclonal anti-Sortilin antibodies, are generally raised in animals by multiple subcutaneous (sc) or intraperitoneal (ip) injections of the relevant antigen and an adjuvant. It may be useful to conjugate the relevant antigen (e.g., a purified or recombinant Sortilin protein of the present disclosure) to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the desired antigen, immunogenic conjugates, or derivatives by combining, e.g., 100 µg (for rabbits) or 5 µg (for mice) of the protein or conjugate with 3 volumes of Freund's complete adjuvant and injecting the solution intradermally at multiple sites. One month later, the animals are boosted with ⅕ to ¹⁄₁₀ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant-cell culture as protein fusions. Also, aggregating agents such as alum are suitable to enhance the immune response.

(2) Monoclonal Antibodies

Monoclonal antibodies, such as monoclonal anti-Sortilin antibodies, are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal anti-Sortilin antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization (e.g., a purified or recombinant Sortilin protein of the present disclosure). Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986)).

The immunizing agent will typically include the antigenic protein (e.g., a purified or recombinant Sortilin protein of the present disclosure) or a fusion variant thereof. Generally peripheral blood lymphocytes ("PBLs") are used if cells of human origin are desired, while spleen or lymph node cells are used if non-human mammalian sources are desired. The lymphoctyes are then fused with an immortalized cell line using a suitable fusing agent, such as polyethylene glycol, to form a hybridoma cell. Goding, *Monoclonal Antibodies: Principles and Practice,* Academic Press (1986), pp. 59-103.

Immortalized cell lines are usually transformed mammalian cells, particularly myeloma cells of rodent, bovine or human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient-cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors (available from the Salk Institute Cell Distribution Center, San Diego, Calif. USA), as well as SP-2 cells and derivatives thereof (e.g., X63-Ag8-653) (available from the American Type Culture Collection, Manassas, Va. USA). Human myeloma and mouse-human heteromyeloma cell lines have also been described for the production of human monoclonal antibodies (Kozbor, *J Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen (e.g., a Sortilin protein of the present disclosure). Preferably, the binding specificity of monoclonal antibodies produced by hybridoma cells is determined by immunoprecipitation or by an in vitro binding assay, such as radioimmunoassay (RIA) or enzyme-linked immunosorbent, assay (ELISA).

The culture medium in which the hybridoma cells are cultured can be assayed for the presence of monoclonal antibodies directed against the desired antigen (e.g., a Sortilin protein of the present disclosure). Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose chromatography, hydroxylapatite chromatography, gel electrophoresis, dialysis, affinity chromatography, and other methods as described above.

Anti-Sortilin monoclonal antibodies may also be made by recombinant DNA methods, such as those disclosed in U.S. Pat. No. 4,816,567, and as described above. DNA encoding the monoclonal antibodies is readily isolated and sequenced using conventional procedures (e.g., by using oligonucleotide probes that specifically bind to genes encoding the heavy and light chains of nimble antibodies). The hybridoma cells sere as a preferred source of such DNA. Once isolated, the DNA may be placed into expression vectors, which are then transfected into host-cells such as *E. coli* cells, simian CO S cells, Chinese hamster ovary (CHO) cells, or myeloma cells that do not otherwise produce immunoglobulin protein, in order to synthesize monoclonal antibodies in such recombinant host-cells. Review articles on recombinant expression in bacteria of DNA encoding the antibody include Skerra et al., *Curr. Opin. Immunol.*, 5:256-262 (1993) and Plückthun, *Immunol. Rev.* 130; 151-188 (1992).

In certain embodiments, anti-Sortilin antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) described the isolation of murine and human antibodies, respectively, from phage libraries. Subsequent publications describe the production of high affinity (nanomolar ("nM") range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nucl. Acids Res.*, 21:2265-2266 (1993)). Thus, these techniques are viable alternatives to traditional monoclonal antibody hybridoma techniques for isolation of monoclonal antibodies of desired specificity (e.g., those that bind a Sortilin protein of the present disclosure).

The DNA encoding antibodies or fragments thereof may also be modified, for example, by substituting the coding sequence for human heavy- and light-chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein (e.g., anti-Sortilin antibodies of the present disclosure or fragments thereof) may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid anti-Sortilin antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(3) Humanized Antibodies

Anti-Sortilin antibodies of the present disclosure or antibody fragments thereof may further include humanized or human antibodies. Humanized forms of non-human (e.g., murine) antibodies are chimeric immunoglobulins, immunoglobulin chains or fragments thereof (such as Fab, Fab'-SH, Fv, scFv, F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally will also comprise at least a portion of an immunoglobulin constant region (Fc), typically that of a human immunoglobulin. Jones et al., Nature 321: 522-525 (1986); Riechmann et al., Nature 332: 323-329 (1988) and Presta, Curr. Opin. Struct. Biol. 2: 593-596 (1992).

Methods for humanizing non-human anti-Sortilin antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., Nature 321:522-525 (1986); Riechmann et al., Nature 332: 323-327 (1988); Verhoeyen et al., Science 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., J. Immunol., 151:2296 (1993); Chothia et al., J. Mol. Biol., 196:901 (1987). Another method uses a particular framework derived from the consensus sequence of all human antibodies of a particular subgroup of light or heavy chains. The same framework may be used for several different humanized antibodies. Carter et al., Proc. Nat'l Acad. Sci. USA 89:4285 (1992); Presta et al., J. Immunol. 151:2623 (1993).

Furthermore, it is important that antibodies be humanized with retention of high affinity for the antigen and other favorable biological properties. To achieve this goal, according to a preferred method, humanized antibodies are prepared by a process of analyzing the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen or antigens (e.g., Sortilin proteins of the present disclosure), is achieved. In general, the CDR residues are directly and most substantially involved in influencing antigen binding.

Various forms of the humanized anti-Sortilin antibody are contemplated. For example, the humanized anti-Sortilin antibody may be an antibody fragment, such as an Fab, which is optionally conjugated with one or more cytotoxic agent(s) in order to generate an immunoconjugate. Alternatively, the humanized anti-Sortilin antibody may be an intact antibody, such as an intact IgG1 antibody.

(4) Human Antibodies

Alternatively, human anti-Sortilin antibodies can be generated. For example, it is now possible to produce transgenic animals (e.g., mice) that are capable, upon immunization, of producing a full repertoire of human antibodies in the absence of endogenous immunoglobulin production. The homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Nat'l Acad. Sci. USA, 90:2551 (1993); Jakobovits et al., Nature, 362:255-258 (1993); Bruggemann et al., Year in Immunol., 7:33 (1993); U.S. Pat. No. 5,591,669 and WO 97/17852.

Alternatively, phage display technology can be used to produce human anti-Sortilin antibodies and antibody fragments in vitro, from immunoglobulin variable (V) domain gene repertoires from unimmunized donors. McCafferty et al., Nature 348:552-553 (1990); Hoogenboom and Winter, J. Mol. Biol. 227: 381 (1991). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David. J., Curr. Opin Struct. Biol. 3:564-571 (1993). Several sources of V-gene segments can be used for phage display. Clackson et al., Nature 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See also U.S. Pat. Nos. 5,565,332 and 5,573,905. Additionally, yeast display technology can be used to produce human anti-Sortilin antibodies and antibody fragments in vitro (e.g., WO 2009/036379; WO 2010/105256; WO 2012/009568; US 2009/0181855; US 2010/0056386; and Feldhaus and Siegel (2004) J. Immunological Methods 290:69-80). In other embodiments, ribosome display technology can be used to produce human anti-Sortilin antibodies and antibody fragments in vitro (e.g., Roberts and Szostak (1997) Proc Natl Acad Sci 94:12297-12302; Schaffitzel et al. (1999) J. Immunolical Methods 231:119-135; Lipovsek and Plückthun (2004) J. Immunological Methods 290:51-67).

The techniques of Cole et al., and Boerner et al., are also available for the preparation of human anti-Sortilin monoclonal antibodies (Cole et al., Monoclonal Antibodies and Cancer Therapy, Alan R. Liss, p. 77 (1985) and Boerner et al., *J. Immunol.* 147(1): 86-95 (1991). Similarly, human anti-Sortilin antibodies can be made by introducing human immunoglobulin loci into transgenic animals, e.g., mice in which the endogenous immunoglobulin genes have been partially or completely inactivated. Upon challenge, human antibody production is observed, which closely resembles that seen its humans in all respects, including gene rearrangement, assembly and antibody repertoire. This approach is described, for example, in U.S. Pat. Nos. 5,545,807; 5,545,806, 5,569,825, 5,625,126, 5,633,425, 5,661,016 and in the following scientific publications: Marks et al., *Bio/Technology* 10: 779-783 (1992); Lonberg et al. *Nature* 368: 856-859 (1994); Morrison, *Nature* 368: 812-13 (1994), Fishwild et al., *Nature Biotechnology* 14: 845-51 (1996), Neuberger, *Nature Biotechnology* 14: 826 (1996) and Lonberg and Huszar, *Intern. Rev. Immunol.* 13: 65-93 (1995).

Finally, human anti-Sortilin antibodies may also be generated in vitro by activated B-cells (see U.S. Pat. Nos. 5,567,610 and 5,229,275).

(5) Antibody Fragments

In certain embodiments there are advantages to using anti-Sortilin antibody fragments, rather than whole anti-Sortilin antibodies. Smaller fragment sizes allow for rapid clearance and better brain penetration.

Various techniques have been developed for the production of antibody fragments. Traditionally, these fragments were derived via proteolytic digestion of intact antibodies (see, e.g., Morimoto et al., *J. Biochem. Biophys. Method.* 24:107-117 (1992); and Brennan et al., *Science* 229:81 (1985)). However, these fragments can now be produced directly by recombinant host-cells, for example, using nucleic acids encoding anti-Sortilin antibodies of the present disclosure. Fab, Fv and scFv antibody fragments can all be expressed in and secreted from *E. coli*, thus allowing the straightforward production of large amounts of these fragments. A anti-Sortilin antibody fragments can also be isolated from the antibody phage libraries as discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host-cell culture. Production of Fab and F(ab')$_2$ antibody fragments with increased in vivo half-lives are described in U.S. Pat. No. 5,869,046. In other embodiments, the antibody of choice is a single chain Fv fragment (scFv). See WO 93/16185; U.S. Pat. Nos. 5,571,894 and 5,587,458. The anti-Sortilin antibody fragment may also be a "linear antibody," e.g., as described in U.S. Pat. No. 5,641,870. Such linear antibody fragments may be monospecific or bispecific.

(6) Bispecific and Polyspecific Antibodies

Bispecific antibodies (BsAbs) are antibodies that have binding specificities for at least two different epitopes, including those on the same or another protein (e.g., one or more Sortilin proteins of the present disclosure). Alternatively, one part of a BsAb can be armed to bind to the target Sortilin antigen, and another can be combined with an arm that binds to a second protein. Such antibodies can be derived from full length antibodies or antibody fragments (e.g., F(ab')$_2$ bispecific antibodies)

Methods for making bispecific antibodies are known in the art. Traditional production of full length bispecific antibodies is based on the coexpression of two immunoglobulin heavy-chain/light chain pairs, where the two chains have different specificities. Millstein et al., *Nature,* 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only half of the bispecific molecules provides for an easy way of separation. This approach is disclosed in WO 94/04690. For further details of generating bispecific antibodies, see, for example, Suresh et al., *Methods in Enzymology* 121: 210 (1986).

According to another approach described in WO 96/27011 or U.S. Pat. No. 5,731,168, the interface between a pair of antibody molecules can be engineered to maximize the percentage of heterodimers which are recovered from recombinant-cell culture. The preferred interface comprises at least a part of the $C_H3$ region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shabby et al., *J. Exp. Med.* 175: 217-225 (1992) describes the production of fully humanized bispecific antibody F(ab')$_2$ molecules. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T-cells, as well as trigger the lytic activity of human cytotoxic lymphocytes against human breast tumor targets.

Various techniques for making and isolating bivalent antibody fragments directly from recombinant-cell culture have also been described. For example, bivalent heterodimers have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Nat'l Acad. Sci. USA*, 90: 6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (sFv) dimers has also been reported. See Gruber et al., *J. Immunol.*, 152:5368 (1994).

Antibodies with more than two valencies are also contemplated. For example, trispecific antibodies can be prepared. Tutt et al., *J. Immunol.* 147:60 (1991).

Exemplary bispecific antibodies may bind to two different epitopes on a given molecule (e.g., a Sortilin protein of the present disclosure). Alternatively, an arm targeting a Sortilin signaling component may be combined with an arm which binds to a triggering molecule on a leukocyte such as a T-cell receptor molecule (e.g., CD2, CD3, CD28 or B7), or Fc receptors for IgG (FcγR), such as FcγRI (CD64), FcγRII (CD32) and FcγRIII (CD16) so as to focus cellular defense mechanisms to the cell expressing the particular protein. Bispecific antibodies may also be used to localize cytotoxic agents to cells which express a particular protein. Such antibodies possess a protein-binding arm and an arm which binds a cytotoxic agent or a radionuclide chelator, such as EOTUBE, DPTA, DOTA or TETA. Another bispecific antibody of interest binds the protein of interest and further binds tissue factor (IF).

(7) Multivalent Antibodies

A multivalent antibody may be internalized (and/or catabolized) faster than a bivalent antibody by a cell expressing an antigen to which the antibodies bind. The anti-Sortilin antibodies of the present disclosure or antibody fragments thereof can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises an Fc region or a hinge region. In this scenario, the antibody will comprise an Fc region and three or more antigen binding sites amino-terminal to the Fc region. The preferred multivalent antibody herein contains three to about eight, but preferably four, antigen binding sites. The multivalent antibody contains at least one polypeptide chain (and preferably two polypeptide chains), wherein the polypeptide chain or chains comprise two or more variable domains. For instance, the polypeptide chain or chains may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. Similarly, the polypeptide chain or chains may comprise $V_H$-$C_H$1-flexible linker-$V_H$-$C_H$1-Fc region chain; or $V_H$-$C_H$1-$V_H$-$C_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain. The multivalent antibodies may recognize the Sortilin antigen as well as, without limitation, additional antigens A beta peptide, antigen or an alpha synuclain protein antigen or, Tau protein antigen or, TDP-43 protein antigen or, prion protein antigen or, huntingtin protein antigen, or RAN, translation Products antigen, including the DiPeptide Repeats, (DPRs peptides) composed of glycine-alanine (GA), glycine-proline (GP), glycine-arginine (GR), proline-alanine (PA), or proline-arginine (PR), insulin receptor, insulin like growth factor receptor, transferring receptor, or any other antigen that facilitates antibody transfer across the blood brain barrier.

(8) Heteroconjugate Antibodies

Heteroconjugate antibodies are also within the scope of the present disclosure. Heteroconjugate antibodies are composed of two covalently joined antibodies (e.g., anti-Sortilin antibodies of the present disclosure or antibody fragments thereof). For example, one of the antibodies in the heteroconjugate can be coupled to avidin, the other to biotin. Such antibodies have, for example, been proposed to target immune system cells to unwanted cells, U.S. Pat. No. 4,676,980, and have been used to treat HIV infection. International Publication Nos. WO 91/00360, WO 92/200373 and EP 0308936. It is contemplated that the antibodies may be prepared in vitro using known methods in synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may be made using any convenient cross-linking methods. Suitable cross-linking agents are well known in the art, and are disclosed in U.S. Pat. No. 4,676,980, along with a number of cross-linking techniques.

(9) Effector Function Engineering

It may also be desirable to modify an anti-Sortilin antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII. In some embodiments, the effector function is impaired by removing N-glycosylation of the Fc region (e.g., in the CH 2 domain of IgG) of the antibody. In some embodiments, the effector function is impaired by modifying regions such as 233-236, 297, and/or 327-331 of human IgG as described in PCT WO 99/58572 and Armour et al., *Molecular Immunology* 40: 585-593 (2003); Reddy et al., *J. Immunology* 164:1925-1933 (2000).

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

(10) Other Amino Acid Sequence Modifications

Amino acid sequence modifications of anti-Sortilin antibodies of the present disclosure, or antibody fragments thereof, are also contemplated. For example, it may be desirable to improve the binding affinity and/or other biological properties of the antibodies or antibody fragments. Amino acid sequence variants of the antibodies or antibody fragments are prepared by introducing appropriate nucleotide changes into the nucleic acid encoding the antibodies or antibody fragments, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics (i.e., the ability to bind or physically interact with a Sortilin protein of the present disclosure). The amino acid changes also may alter post-translational processes of the antibody, such as changing the number or position of glycosylation sites.

A useful method for identification of certain residues or regions of the anti-Sortilin antibody that are preferred locations for mutagenesis is called "alanine scanning mutagenesis" as described by Cunningham and Wells in *Science*, 244:1081-1085 (1989). Here, a residue or group of target residues are identified (e.g., charged residues such as arg, asp, his, lys, and glu) and replaced by a neutral or negatively charged amino acid (most preferably Amine of polyalanine) to affect the interaction of the amino acids with the target antigen. Those amino acid locations demonstrating functional sensitivity to the substitutions then are refilled by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning; or random mutagenesis is conducted at the target codon or region and the expressed antibody variants are screened for the desired activity.

Amino acid sequence insertions include amino-("N") and/or carboxy-("C") terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table B below under the heading of "preferred substitutions". If such substitutions result in a change in biological activity, then more substantial changes, denominated "exemplary substitutions" in Table B, or as further described below in reference to amino acid classes, may be introduced and the products screened.

TABLE B

Amino Acid Substitutions

| Original Residue | Exemplary Substitutions | Preferred Substitutions |
|---|---|---|
| Ala (A) | val; leu; ile | val |
| Arg (R) | lys; gln; asn | lys |
| Asn (N) | gln: his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: up, tyr, phe.

Non-conservative substitutions entail exchanging a member of one of these classes for another class.

Any cysteine residue not involved in maintaining the proper conformation of the antibody also may be substituted, generally with serine, to improve the oxidative stability of the molecule and prevent aberrant crosslinking.

Conversely, cysteine bond(s) may be added to the antibody to improve its stability (particularly where the antibody is an antibody fragment, such as an Fv fragment).

A particularly preferred type of substitutional variant involves substituting one or more hypervariable region residues of a parent antibody (e.g. a humanized or human anti-Sortilin antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen (e.g., a Sortilin protein of the present disclosure). Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-IgE antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibodies (e.g., anti-Sortilin antibodies of the present disclosure) or antibody fragments.

(11) Other Antibody Modifications

Anti-Sortilin antibodies of the present disclosure, or antibody fragments thereof, can be further modified to contain additional non-proteinaceous moieties that are known in the art and readily available. Preferably, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in *Remington: the Science and Practice of Pharmacy*, 20th Ed., Alfonso Gennaro, Ed., Philadelphia College of Pharmacy and Science (2000).

Binding Assays and Other Assays

Anti-Sortilin antibodies of the present disclosure may be tested for antigen binding activity, e.g., by known methods such as ELISA, surface plasmon resonance (SPR), Western blot, etc.

In some embodiments, competition assays may be used to identify an antibody that competes with any of the antibodies listed in Tables 1-3 and 11-15, or selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S-5, S-6, S-7, S-8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S-15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S-72, S-73, S-74, S-75, S-76, S-77, S-78, S-79, S-80, S-81, S-82, S-82-1, S-82-2, S-82-3, S-82-4, S-82-5, S-82-6, S-82-7, S-82-8, S-83, S-84, and S-85. In certain embodiments, such a competing antibody binds to the same epitope (e.g., a linear or a conformational epitope) that is bound by any of the antibodies listed in Tables 1-3 and 11-15, or selected from S-1, S-2, S-2-1, S-2-2, S-2-3, S-2-4, S-2-5, S-2-6, S-2-7, S-2-8, S-2-9, S-2-10, S-2-11, S-2-12, S-2-13, S-2-14, S-2-15, S-3, S-4, S5, S-6, S-7, S8, S-9, S-10, S-11, S-12, S-13, S-14, S-15, S-15-1, S-15-2, S-15-3, S-15-4, S-15-5, S-15-6, S-15-6-1, S-15-6-2, S-15-6-3, S-15-6-4, S-15-6-5, S-15-6-6, S-15-6-7, S-15-6-8, S-15-6-9, S-15-6-10, S-15-6-11, S-15-6-12, S-15-6-13, S-15-7, S-15-8, S-15-9, S-15-10, S-15-10-1, S-15-10-2, S-15-10-3, S-15-10-4, S- 15-10-5, S-15-10-6, S-15-10-7, S-15-10-8, S-15-10-9, S-15-10-10, S-15-10-11, S-15-10-12, S-15-10-13, S-15-10-14, S-15-10-15, S-15-10-16, S-15-10-17, S-15-10-18, S-15-10-19, S-15-10-20, S-15-10-21, S-15-11, S-15-12, S-15-13, S-15-14, S-15-15, S-15-16, S-16, S-17, S-18, S-19, S-20, S-21, S-22, S-22-1, S-22-2, S-22-3, S-22-4, S-22-5, S-22-6, S-22-7, S-22-8, S-22-9, S-23, S-24, S-25, S-26, S-27, S-28, S-29, S-30, S-31, S-32, S-33, S-34, S-35, S-36, S-37, S-38, S-39, S-40, S-41, S-42, S-43, S-44, S-45, S-46, S-47, S-48, S-49, S-50, S-51, S-52, S-53, S-54, S-55, S-56, S-57, S-58, S-59, S-60, S-60-1, S-60-2, S-60-3, S-60-4, S-60-5, S-60-6, S-60-7, S-60-8, S-60-9, S-61, S-62, S-63, S-64, S-65, S-66, S-67, S-68, S-69, S-70, S-71, S- 72S-73, S-74, S-75, S-76, S-77, S-78, S-79S-80, S-81, S-82, S-82-1, S-82-2, S-82-3, S-82-4, S-82-5, S-82-6, S-82-7, S-82-8, S-83, S-84, and S-85. Detailed exemplary methods for mapping an epitope to which an antibody binds are provided in Morris (1996) "Epitope Mapping Protocols," in *Methods in Molecular Biology* vol. 66 (Humana Press, Totowa. N.J.).

In an exemplary competition assay, immobilized Sortilin or cells expressing Sortilin on a cell surface are incubated in a solution comprising a first labeled antibody that binds to Sortilin (e.g., human or non-human primate) and a second unlabeled antibody that is being tested for its ability to compete with the first antibody for binding to Sortilin. The second antibody may be present in a hybridoma supernatant. As a control, immobilized Sortilin or cells expressing Sortilin is incubated in a solution comprising the first labeled antibody but not the second unlabeled antibody. After incubation under conditions permissive for binding of the first antibody to Sortilin, excess unbound antibody is removed, and the amount of label associated with immobilized Sortilin or cells expressing Sortilin is measured. If the amount of label associated with immobilized Sortilin or cells expressing Sortilin is substantially reduced in the test sample relative to the control sample, then that indicates that the second antibody is competing with the first antibody for binding to Sortilin. See, Harlow and Lane (1988) *Antibodies: A Laboratory Manual* ch. 14 (Cold Spring Harbor Laboratory, Cold Spring Harbor, N.Y.).

Ligand Binding Assays

Further provided herein are methods of screening for anti-Sortilin antibodies that bind Lys260, Phe314, Ser316, Ile329, Arg325, Arg326, Tyr351, Ser352, and/or, Ile353 of human Sortilin, and that block the interactions between Sortilin and a Sortilin ligand (e.g. Progranulin, pro-neurotrophin, pro-NGF, pro-BDNF, pro-NT3, p75, APP, LpL, APOA5, APOE). In some embodiments, a peptide library can be synthesized in which a Sortilin protein is dissected into consecutive 15-mer and 25-mer peptides separated by one amino acid residue and subsequently spotted onto filters. Binding of a Sortilin ligand can then then tested for its ability to interact with the receptor peptide or with peptides that are, for example, mutated at Lys260, Phe 314, Ser316, Ile329, Arg325, Arg326, Tyr351, Ser352, and/or, Ile353 of human Sortilin libraries in the presence or absence of the anti-Sortilin antibodies by SPOT binding analysis (e.g., Frank, R and Overwin, H (1996) Methods. Mol. Biol. 66, 149-169; Reineke, U et al., (2002) J. Immunol. Methods 267, 13-26; and Andersen, O S et al., (2010) J, BIOLOGICAL CHEMISTRY 285, 12210-12222). In some embodiments, peptide libraries for members of the VPS 10p-domain receptor gene family members or specific peptide variations in terms of substitution or length analyses of identified ligand binding peptides can be constructed on a cellulose membrane. In some embodiments, a total of 2181 peptides may be used for representation of the Sortilin gene family, including 273 peptides for Sortilin (Accession No. CAA66904), with a I3-amino acid overlap between 16-mer peptides (Frank, R (1992) Tetrahedron 48, 9217-9232). In some embodiments, a cellulose support can be prepared as an N-modified cellulose-aminohydroxylpropyl ether membrane, and all rounds of synthesis are started with spot definition by 9-fluorenylmethoxycar-bonyalanine-pentafluoophenyl ester that creates an alanine linker between peptide and membrane. For example, an automated linear synthesis of stepwise addition of the different amino acids protected at their N-terminal by 9-fluorenyl-methoxycarbonyl and appropriate side-chain protection for the growing peptide chain. In some embodiments, the pattern of deprotection, activation, and coupling is continued until 16-mer peptides are produced, resulting in an equally distributed array of covalently anchored peptides to the cellulose support at their C-terminal ends with N-terminal free ends (Scharn, D et al., (2000) J. Comb. Chem. 2, 361-369). In some embodiments, removal of the side protection group can be performed in two steps. First, the membrane can be treated with 90% trifluoroacetic acid (in dichlormethane, containing 3% triisobutylsilane and 2% H2O); and secondly with, for example, 60% trifluoroacetic acid (in dichlormethane, containing 3% triisobutylsilane and 2% H2O). To remove trifluoroacetic acid salts, the membrane can be washed several times with $H_2O$, ethanol, Tris-buffered saline, and ethanol, and then dried. Finally, the membrane is blocked in blocking buffer dilated in Tris-buffered saline (pH 8.0) and supplemented with 5% sac-charose for 2 h before the predefined peptide library is ready for ligand binding analysis. In some embodiments, for binding studies of cellulose-bound peptides, membrane-bound libraries can be incubated with combined S-peptide and polyhistidine-tagged ligands in the presence or absence of the anti-Sortilin antibodies, for example, in blocking buffer overnight at 4° C., followed by a second incubation with 1 mg/ml of HRP-conjugated S-protein also in blocking buffer but for 3 h at room temperature. Subsequently, the membrane can be washed, for example, three times for 10 min with Tris-buffered saline before quantitative characterization of bound ligand may be carried out using the UptiLight chemiluminescence substrate and a LumiImager instrument, providing the spot signal intensities in Boehringer light units. Alternatively, detection of bound ligand can be performed by an immunochemical assay with an antibody against a histidine tag from and a secondary HRP-conjugated anti-mouse antibody. Incubations can be performed utilizing standard Western blotting procedures and spot detection.

Further provided herein are methods of screening for anti-Sortilin antibodies that block interactions (e.g., binding) Sortilin and a Sortilin ligand (e.g., Progranulin, pro-neurotrophin, pro-NGF, pro-BDNF, pro-NT3, p75, APP, LpL, APOA5, APOE).

In some embodiments, tagged forms of the Sortilin ligands for detection, constructs can be prepared for each protein that allow for the addition of an N-terminal S-peptide and polyhistidine tags. Template cDNA for human NGF and BDNF includes the ATCC clones used for generation of fragments spanning residues $Glu^1$-$Arg^{102}$ of NGF and $Ala^1$-

Arg[110] of BDNF using the primer pair 5'-GGTATT-GAGGGTCGCGAAC-CACACTCAGAGAGCAATGTCCC-3' (SEQ ID NO:695) and 3'-GGGGGAAGTTGTCCTGAGTGTCCTCGTTCGC-CACTCCGAG ATTGAGAGGAGA-5' (SEQ ID NO:696); and the primer pair 5'-GGTATTGAGGGTCGCGC CCC-CATGAAAGAAGCAAACAT CCGAGG-3' (SEQ ID NO:697) and 3'-CACGTTTGTAC AGGTACTCCCAGGCCGCGACTCCGAGATTGA GAG-GAGA-5' (SEQ ID NO:698). The cDNA can include compatible overhangs for ligation-independent cloning into the pET-30 Xa/LIC vector, and amplification using Phusion DNA polymerase and following the protocol as provided by the manufacturer. Proteins can be expressed in the BL21/DE3 strain of *Escherichia coli*, efficiently extracted from bacterial inclusion bodies using Bugbuster reagent with added benzonase, and purified by standard nickel-nitrilotriacetic acid affinity chromatography, for example, in 500 mM NaCl, 5 mM Imidazole, and 20 mM Tris-HCl, pH 8.0. Protein elution is done in buffer supplemented with 20 mM EDTA. Verification of intact tagged versions of HisS-NGFpro and HisS-BDNFpro can be carried out by SDS-PAGE analysis followed by Coomassie staining or Western blot analysis using either antibody against the histidine tag from Sigma (H-1029) and secondary HRP-conjugated anti-mouse antibody, or alternatively by direct binding of HRP-conjugated S-protein from Novagen (catalog no. 69047-3) (e.g., Andersen, O S et al., P (2010) THE JOURNAL OF BIOLOGICAL CHEMISTRY, 285, 12210-12222). Similar methods can also be used to generate GST-tagged Sortilin ligands (e.g., Quistgaard, E M et al., (2009) Nat. Struct. Mol. Biol. 16, 96-98).

In some embodiments, the interaction between Sortilin and Sortilin ligands (e.g., Progranulin, pro-neurotrophin, pro-NGF, pro-BDNF, pro-NT3, p75, APP, LpL, APOA5, APOE) may be characterized using surface Plasmon resonance analysis (e.g., Skeldal, S et al., (2012) J Biol Chem., 287:43798; and Andersen, O S et al., (2010) THE JOURNAL OF BIOLOGICAL CHEMISTRY, 285, 12210-12222). Determination of direct binding of Sortilin ligand to immobilized Sortilin in the presence or absence of blocking anti-Sortilin antibodies can be performed, for example, on a Biacore2000 instrument (Biacore, Sweden) using CaHBS as standard running buffer (10 mM HEPES, pH 7.4, 140 mM NaCl, 2 mM CaCl$_2$, 1 mM EGTA, and 0.005% Tween 20). In some embodiments, a biosensor chip from Biacore (CM5) can be activated using the NHS/EDC method followed by coating with Sortilin to a protein density of 79 fmol/mm$^2$ and used for affinity measurements of the recombinant prodomains of NGF, BDNF, and NT3. Preparation of a biosensor surface with pro-Sortilin will follow an equal procedure. Regeneration of the flow cell after each cycle of ligand binding experiment can be done by two 10-µl pulses of regeneration buffer (10 mM glycine-HCl, pH 4.0, 500 nM NaCl, 20 mM EDTA, and 0.005% Tween 20) and a single injection of 0.001% SDS. Fitting of sensorgrams for affinity estimations can be done, for example, by using BIAevaluation version 3.1. Following similar protocols, immobilization of HisS-NGFpro or HisS-BDNFpro may also done on a CM5 biosensor chip using the NHS/EDC coupling kit, giving similar surface densities of immobilized protein (~300 fmol/mm$^2$). A biosensor chip with immobilized NGF-pro or BDNFpro can also used to examine the binding of Sortilin in the absence or presence of competing Sortilin antibodies. Unprocessed versions of pro-NGF and pro-BDNF, as well as another Sortilin ligand (e.g., receptor-associated protein (RAP), neurotensin, Progranulin, p75, LpL, APOA5, APOE, or APP) can also be applied to immobilized Sortilin and the binding in absence or presence of competing antibodies can be measured.

In some embodiments, the interaction between Sortilin and Sortilin ligands (e.g., Progranulin, pro-neurotrophin, pro-NGF, pro-BDNF, pro-NT3, p75, APP, LpL, APOA5, APOE) can be characterized using a pulldown assay (e.g., Andersen, O S et al., (2010) THE JOURNAL OF BIOLOGICAL CHEMISTRY, 285, 12210-12222). For example, expressed extracellular domains of Sortilin can be incubated with tagged Sortilin ligands in the absence or presence of Sortilin blocking antibodies and are precipitated using 100 µl of glutathione (GSH)-Sepharose beads (Amersham Biosciences, catalog no. 17-0756-01). The amount of applied receptor domains can be determined by precipitation using Talon beads as control. Bound proteins can be separated by SDS-PAGE analysis and visualized using anti-histidine antibody by standard Western blotting analysis.

In some embodiments, the interaction between Sortilin and Sortilin ligands (e.g., Progranulin, pro-neurotrophin, pro-NGF, pro-BDNF, pro-NT3, p75, APP, LpL, APOA5, APOE) may be characterized using cellulose-bound proteins (e.g., Andersen, O S et al., (2010) THE JOURNAL OF BIOLOGICAL CHEMISTRY, 285, 12210-12222). For example, membrane-bound proteins can be incubated with S-peptide and polyhistidine-tagged pro-NGF, pro-BDNF, Progranulin, or another Sortilin ligand, such as Progranulin, pro-neurotrophin, pro-NT3, p75, APP, LpL, APOA5, or APOE; in blocking buffer overnight at 4° C., followed by a second incubation with 1 µg/ml of HRP-conjugated S-protein also in blocking buffer but for 3 h at room temperature. Subsequently, the membrane may be washed three times for 10 min with Tris-buffered saline before quantitative characterization of bound ligand is carried out using the UptiLight chemiluminescence substrate and a LumiImager instrument, providing the spot signal intensities in Boehringer light units. Alternatively, detection of bound ligand can be performed by an immunochemical assay with an antibody against the histidine tag and a secondary HRP-conjugated anti-mouse antibody. Incubations can be followed by standard Western blotting analysis and spot detection.

In some embodiments, the interaction between Sortilin and Sortilin ligands (e.g., Progranulin, pro-neurotrophin, pro-NGF, pro-BDNF, pro-NT3, p75, APP, LpL, APOA5, APOE) may be characterized using a proximity ligation assay (e.g., Gustafsen, C et al., (2013) The Journal of Neuroscience, 33:64-71). For example, proximity ligation assay (PLA) (DuolinkII) on cells expressing or exposed to Sortilin and its binding partner can be performed with the primary antibodies anti-Sortilin/F11, anti-SorLA/20C11, and antibodies against the binding partner, such as anti-APP/AF1168 antibodies, followed by incubation with secondary antibodies conjugated to oligonucleotides, which hybridize to subsequently added circle-forming oligonucleotides and prime a rolling circle amplification when the antigens are located within proximity of 40 nm. The amplified DNA can be visualized by addition of complementary fluorescent-labeled oligonucleotides.

In some embodiments, the interaction between Sortilin and Sortilin ligands (e.g., Progranulin, pro-neurotrophin, pro-NGF, pro-BDNF, pro-NT3, p75, APP, LpL, APOA5, APOE) may be characterized using alkaline phosphatase-tagged ligands in cell binding assays (e.g., Hu, F et al., (2005) J. Neurosci. 25, 5298-5304; Fournier, A E et al., (2001) Nature 409, 341-346; Lauren, J et al., (2009) Nature 457, 1128-1132; and Hu, F et al., (2010) Neuron 68, 654-667). For example, alkaline phosphatase (AP)-tagged ligands can be made to assess binding to Sortilin on transfected cells or primary neurons. To detect AP tagged ligand binding to cells expressing sortilin, cultures can be washed with, for example, Hanks balanced salt solution containing 20 mM sodium HEPES, pH 7.05, and 1 mg ml-1 bovine serum albumin (BSA) (HBH). Then, the plates can be incubated with AP tagged ligands in the presence or absence of sortilin blocking antibodies, for example, in HBH for 2 h at 23° C. AP bound ligand can be detected and quantified according to methods well-known in the art.

Cell-Based Assays

Further provided herein are methods of screening for a Sortilin binding antagonist, such as an anti-Sortilin antibody, that include contacting an agent (e.g., an anti-Sortilin antibody) with a cell expressing a Sortilin protein on its cell surface. In some embodiments, the agent and cell are further contacted with a Sortilin ligand of the present disclosure. In some embodiments, the cell itself expresses a Sortilin ligand of the present disclosure. The cell-based methods are particularly suited for screening and validating Sortilin binding antagonists (e.g., anti-Sortilin antibodies) by assessing the effect on the interaction between Sortilin and a Sortilin ligand in the context of a cell.

Accordingly, certain aspects of the present disclosure relate to a cell expressing a Sortilin protein of the present disclosure on its cell surface. In some embodiments, the cell endogenously expresses a Sortilin protein of the present disclosure. In some embodiments, the cell is recombinantly engineered to express a Sortilin protein of the present disclosure. In any of these embodiments, the Sortilin protein of the present disclosure (whether endogenous or recombinant) encoded by the polynucleotide will preferably include at least protein domains required for post-translational processing, membrane translocation, and targeting to the cell surface, including without limitation a signal peptide and a transmembrane domain. In some embodiments, the signal peptide and/or transmembrane domain may refer to the endogenous Sortilin signal peptide and/or transmembrane domain. In other embodiments, the signal peptide and/or transmembrane domain may refer to an exogenous signal peptide and/or transmembrane domain known to promote cell surface expression in the desired host cell. In preferred embodiments, the Sortilin protein will also contain a domain sufficient for binding a Sortilin ligand of the present disclosure.

Standard molecular biological techniques well known in the an, such as those described and referenced in the present disclosure, may be used to recombinantly engineer a cell (e.g., a host cell of the present disclosure) to express a Sortilin protein of the present disclosure. In some embodiments, the methods include culturing a host cell of the present disclosure containing a polynucleotide encoding the Sortilin protein of the present disclosure, under conditions suitable for expression of the antibody.

For recombinant production of a Sortilin protein of the present disclosure, a nucleic acid encoding the Sortilin protein is isolated and inserted into one or more vectors for further cloning and/or expression in a host cell. Such nucleic acid may be readily isolated and sequenced using conventional procedures (e.g., by using oligonucleotide probes that are capable of binding specifically to a gene encoding the Sortilin protein).

Suitable vectors containing a nucleic acid sequence encoding any of the Sortilin proteins of the present disclosure, or cell-surface-expressed fragments thereof, described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC9, Bluescript (e.g., pBS SK+) and its derivatives, mpl8, mpl19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a nucleic acid of the present disclosure. The expression vector may replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the nucleic acids of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell. In some embodiments, the vector contains a nucleic acid containing one or more amino acid sequences encoding a Sortilin protein of the present disclosure.

Suitable host cells for cloning or expression of antibody-encoding vectors include eukaryotic cells. In preferred embodiments, the host cell of the present disclosure is a mammalian cell, including without limitation monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV 1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. In some embodiments, the host cell is a human cell. In some embodiments, the host cell is a HEK293T cell.

In addition to mammalian cells, eukaryotic microorganisms, such as filamentous fungi or yeast, are also suitable cloning or expression hosts for protein-encoding vectors, including fungi and yeast strains whose glycosylation pathways have been "humanized," resulting in the production of a protein with a partially or fully human glycosylation pattern (e.g., Gerngross, *Nat. Biotech.* 22:1409-1414 (2004); and Li et al., *Nat. Biotech.* 24:210-215 (2006)). Suitable host cells for the expression of glycosylated protein can also be derived from multicellular organisms (invertebrates and vertebrates). Examples of invertebrate cells include plant and insect cells (e.g., Sf9 or S2 cells). Numerous baculoviral strains have been identified which may be used in conjunction with insect cells, particularly for transfection of *Spodoptera frugiperda* cells.

In some embodiments, the methods of the present disclosure include contacting a cell expressing a Sortilin protein on its cell surface with an agent (e.g., an anti-Sortilin antibody) and a Sortilin ligand under conditions in which the Sortilin protein is capable of binding to the Sortilin ligand. As used herein, a condition in which a Sortilin protein is capable of binding to a Sortilin ligand may refer to a parameter or aspect of the environment in which the Sortilin protein and Sortilin ligand exist (e.g., temperature, pH, a solution, etc.), and conditions may refer to the environment in which the Sortilin protein and Sortilin ligand exist (e.g., the sum-total of multiple individual conditions). These conditions will allow for the Sortilin-Sortilin ligand interaction to occur, as described above. In preferred embodiments, these methods are also permissive for maintaining cell viability over the timescale of the assay.

In some embodiments, the Sortilin ligand is attached to a fluorophore. Any fluorophore known in the art may be used. In some embodiments, the fluorophore may be a fluorescent protein or peptide, including without limitation GFP, RFP, YFP, CFP, derivatives thereof, and the like. In some embodiments, the fluorophore may be a non-protein organic fluorophore, including without limitation a xanthene derivative (e.g., rhodamine, fluorescein, Texas red, etc.), a squaraine derivative, a naphthalene derivative, a cyanine derivative (e.g., cyanine, indocarbocyanine, oxacarbocyanin, etc.), a coumarin derivative, a pyrene derivative, an anforacene derivative, an oxadiazole derivative, an acridine derivative, a tetrapyrrole derivative, an arylmethine derivative, or an oxazine derivative. In some embodiments, the fluorophore may be a quantum dot. Lists of suitable fluorophores and their properties (e.g., absorption and emission spectra, molar extinction coefficient, photobleaching properties, brightness, photostability, and so forth) are commonly obtained through manufacturers, e.g. *The Molecular Probes® Handbook*, 11$^{th}$ ed. (Life Technologies, Carlsbad, Calif.). In some embodiments, the Sortilin ligand is attached to a non-fluorescent detection moiety, such as a luminescent or bioluminescent moiety (e.g., a luciferase such as *Renilla* luciferase or a derivative thereof), and a bioluminogenic substrate is further included (e.g., a luciferin such as a coelenterazine or coelenterazine derivative, including without limitation DeepatueC™).

In some embodiments, the fluorophore attached to the Sortilin ligand is associated with the cell upon binding of the Sortilin ligand to the Sortilin protein. The fluorophore attached to the Sortilin ligand may be associated with the cell, for example, if it can be detected on the cell surface and/or detected inside of the cell (e.g., in an endocytic, endosomal, or lysosomal compartment). In this way, detection of emitted fluorescence associated with the cell (e.g., fluorescence on the surface of the cell or inside the cell) allows for detection of an interaction between Sortilin and the Sortilin ligand in the context of the cell expressing the Sortilin. Preferably, the fluorophore itself, and the fluorophore attachment to the Sortilin ligand, do not disrupt binding between the Sortilin ligand and the Sortilin protein expressed by the cell.

In some embodiments, a fluorophore associated with the cell is treated with light of a wavelength sufficient to cause the fluorophore to emit fluorescence. In some embodiments, subsequent fluorescence emitted by the fluorophore associated with the cell is detected. In some embodiments, the wavelength sufficient to cause the fluorophore to emit fluorescence is within the absorption spectrum of the fluorophore. In some embodiments, the wavelength with which the cell is treated is the wavelength of maximum absorption or the excitation maximum. In some embodiments, the wavelength detected is within the emission spectrum of the fluorophore. In some embodiments, the wavelength detected is the emission maximum. As a non-limiting example, DyLight-650 attached to a Progranulin protein of the present disclosure may be excited at 652 nm, and emitted fluorescence may be detected at 672 nm. Information on the wavelengths of light sufficient to cause a fluorophore of the present disclosure to emit fluorescence and the wavelengths of light emitted by the fluorophore is widely available in the art and typically supplied by the manufacturer (e.g., Life Technologies, Pierce Biotechnology, Thermo Scientific, abeam, etc.).

Any suitable method for detecting fluorescence emitted at the appropriate wavelength (e.g., a wavelength described supra) may be used. Fluorescence detection techniques may employ a plate reader (e.g., a PHERAstar plate reader from BMG LABTECH, Ortenberg, Germany), fluorescence microscope, flow cytometer or any other equipment known in the art for fluorescence detection.

In some embodiments, the fluorophore is directly coupled to the Sortilin ligand. In some embodiments, the Sortilin ligand is coupled to biotin, and the fluorophore is coupled to streptavidin, which is attached to the Sortilin ligand by binding to the biotin. Similar to fluorescence donor/acceptor attachments techniques known in the art, the fluorophore may be attached to the Sortilin ligand by direct coupling, or they may be indirectly coupled through an intermediary (e.g., antibody binding, biotin:streptavidin binding, an affinity tag, etc.). For example and without limitation, if the fluorophore is a fluorescent protein, the Sortilin ligand may be translated with the coding sequence of the fluorescent protein attached (e.g., by a peptide linker) in-frame with the coding sequence of the Sortilin ligand, such that a fusion protein is produced. For example and without limitation, if the fluorophore is a non-protein organic fluorophore, the fluorophore may be chemically attached (e.g., through a covalent bond) to the Sortilin ligand. Labeling kits for attaching a fluorophore to a protein of interest (e.g., a Sortilin ligand of the present disclosure) are commercially available and typically employ a chemical reaction between a primary airline of the protein and an amine-reactive fluorophore or crosslinker. A member of a fluorescence donor/acceptor pair may be attached at the N-terminus, C-terminus, or any suitable position along the amino acid sequence of the Sortilin ligand. Typically, a fluorescent protein may be attached to the N- or C-terminus of the Sortilin ligand.

In some embodiments, a cell expressing a Sortilin protein on its cell surface is contacted with an agent (e.g., an anti-Sortilin antibody) and a Sortilin ligand under conditions in which the Sortilin protein is capable of binding to the Sortilin ligand, the Sortilin ligand is attached to a fluorophore, and the fluorophore is associated with the cell upon binding of the Sortilin ligand to the Sortilin protein. The fluorophore associated with the cell is treated with light of a wavelength sufficient to cause the fluorophore to emit fluorescence; and a decrease in the fluorescence emitted by the fluorophore associated with the cell is detected, as compared to the fluorescence emitted by the fluorophore associated with the cell in the absence of the agent. The decrease in emitted fluorescence indicates that the agent is a Sortilin binding antagonist. Without wishing to be bound to theory, it is thought that an interaction between a Sortilin protein of the present disclosure expressed on the surface of a cell and a Sortilin ligand of the present disclosure labeled with a fluorophore of the present disclosure will lead to detectable fluorescence associated with the cell (e.g., on the surface of the cell and/or in the interior of the cell, if the Sortilin ligand is internalized by the cell). A Sortilin binding antagonist is thought to decrease the fluorescence signal emitted by the fluorophore associated with the cell by reducing this interaction.

In some embodiments, a cell-based assay that operates without emitted fluorescence is used. For example, in some embodiments, a cell expressing a Sortilin protein on its cell surface is contacted with an agent (e.g., an anti-Sortilin antibody) and a Sortilin ligand under conditions in which the Sortilin protein is capable of binding to the Sortilin ligand; and a failure of decrease in the level of the Sortilin ligand, as compared to the decrease in the level of the Sortilin ligand in the absence of the agent, is detected. The failure of decrease in the level of the Sortilin ligand indicates that the agent is a Sortilin binding antagonist. Without wishing to be bound to theory, it is thought that contacting a Sortilin-expressing cell with a Sortilin ligand of the present disclosure leads to reduction of extracellular Sortilin ligand through binding to Sortilin, endocytosis, and lysosomal degradation. It is thought that incubating a Sortilin-expressing cell with a certain level of the Sortilin ligand will lead to a decrease in Sortilin ligand over time, and that a Sortilin binding antagonist of the present disclosure (e.g., an anti-Sortilin antibody) is able to reduce this decrease (e.g., a failure to decrease). Thus, in comparison with a control treatment, treatment with a Sortilin binding antagonist of the present disclosure leads to a failure of decrease in Sortilin ligand.

In these embodiments, any cell that expresses a Sortilin protein of the present disclosure on its cell surface may be used. In some embodiments, the cell endogenously expresses a Sortilin protein of the present disclosure on its cell surface. In some embodiments, the cell is recombinantly engineered to express a Sortilin protein of the present disclosure on its cell surface. Any suitable Sortilin ligand of the present disclosure may be used, such that it retains the ability to bind to the Sortilin protein expressed on the cell surface. The Sortilin ligand need not be fluorescently labeled. Levels of Sortilin ligand may be detected by any assay known in the art, including without limitation ELISA, SPR, Western blotting, mass spectrometry, immunoprecipitation, peptide microarray, and so forth.

In some embodiments, a cell that expresses a Sortilin protein of the present disclosure on its cell surface is cultured in a cell culture medium containing a level of a Sortilin ligand of the present disclosure. In some embodiments, a known amount of the Sortilin ligand is added to the cell culture medium. In some embodiments, a conditioned cell culture medium (e.g., a Sortilin ligand-conditioned cell culture medium) may be used, e.g., in which a Sortilin ligand of the present disclosure was expressed and secreted into the cell culture medium by a Sortilin ligand-producing cell (upon which the Sortilin ligand-conditioned cell culture medium is separated from the Sortilin ligand-producing cell and subsequently added to the cell that expresses a Sortilin protein).

Any suitable cell culture medium useful for culturing a cell that expresses a Sortilin protein of the present disclosure on its cell surface may be used. Cell culture media useful for culturing a variety of cell types are known in the art and commercially available. Commercially available media such as Ham's F10 (Sigma), Minimal Essential Medium ((MEM), (Sigma), RPMI-1640 (Sigma), and Dulbecco's Modified Eagle's Medium ((DMEM), Sigma) may be suitable for culturing a cell that expresses a Sortilin protein of the present disclosure. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media. Any of these media may be supplemented as necessary with salts (such as sodium chloride, calcium, magnesium, and phosphate), buffers (such as HEPES), growth factors or hormones (such as insulin, transferring, or epidermal growth factor), nucleotides, antibiotics, trace elements (defined as inorganic compounds usually present at a final concentration in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to one of ordinary skill in the art.

In some embodiments, the methods disclosed herein involve culturing a cell that expresses both a Sortilin protein on its cell surface and a Sortilin ligand in a media under conditions in which the Sortilin protein and the Sortilin ligand are expressed and the Sortilin ligand is released into the media; contacting the cell with an agent (e.g., an anti-Sortilin antibody) under conditions in which the Sortilin protein is capable of binding to the Sortilin ligand; and detecting an increase in the level of the Sortilin ligand in the media, as compared to the level of the Sortilin ligand in the media in the absence of the agent. An increase in the level of the Sortilin ligand indicates that the agent is a Sortilin binding antagonist. Without wishing to be bound to theory, it is thought that the interaction between the Sortilin protein expressed on the cell surface and the secreted Sortilin ligand will result in endocytosis and lysosomal degradation of the Sortilin ligand. Therefore, it is thought that decreasing this interaction (e.g., by addition of a Sortilin binding antagonist of the present disclosure) leads to an increase in the level of the Sortilin ligand in the media over time.

In these embodiments, any cell that expresses a Sortilin protein of the present disclosure on its cell surface and expresses and secretes a Sortilin ligand of the present disclosure may be used. In some embodiments, the cell may endogenously express a Sortilin protein of the present disclosure on its cell surface. In some embodiments, the cell may endogenously express and secrete a Sortilin ligand of the present disclosure. In some embodiments, the cell is a U-251 cell, and the Sortilin ligand is a Progranulin protein. In some embodiments, the cell may be recombinantly engineered to express a Sortilin protein of the present disclosure on its cell surface. In some embodiments, the cell may be recombinantly engineered to express and secrete a Sortilin ligand of the present disclosure.

In any of the cell-based assays described herein, a Sortilin ligand of the present disclosure may be used. In some embodiments, the Sortilin ligand is a Progranulin protein.

The Sortilin ligand may be a full-length protein, or it may be a Sortilin-binding peptide fragment thereof.

Nucleic Adds, Vectors, and Host Cells

Anti-Sortilin antibodies of the present disclosure may be produced using recombinant methods and compositions, e.g., as described in U.S. Pat. No. 4,816,567. In some embodiments, isolated nucleic acids having a nucleotide sequence encoding any of the anti-Sortilin antibodies of the present disclosure are provided. Such nucleic acids may encode an amino acid sequence containing the VL and/or an amino acid sequence containing the VH of the anti-Sortilin antibody (e.g., the light and/or heavy chains of the antibody). In some embodiments, one or more vectors (e.g., expression vectors) containing such nucleic acids are provided. In some embodiments, a host cell containing such nucleic acid is also provided. In some embodiments, the host cell contains (e.g., has been transduced with): (1) a vector containing a nucleic acid that encodes an amino acid sequence containing the VL of the antibody and an amino acid sequence containing the VH of the antibody, or (2) a first vector containing a nucleic acid that encodes an amino acid sequence containing the VL of the antibody and a second vector containing a nucleic acid that encodes an amino acid sequence containing the VH of the antibody. In some embodiments, the host cell is eukaryotic, e.g., a Chinese Hamster Ovary (CHO) cell or lymphoid cell (e.g., Y0, NS0, Sp20 cell).

Methods of making an anti-Sortilin antibody of the present disclosure are provided. In some embodiments, the method includes culturing a host cell of the present disclosure containing a nucleic acid encoding the anti-Sortilin antibody, under conditions suitable for expression of the antibody. In some embodiments, the antibody is subsequently recovered from the host cell (or host cell culture medium).

For recombinant production of an anti-Sortilin antibody of the present disclosure, a nucleic acid encoding the anti-Sortilin antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors containing a nucleic acid sequence encoding any of the anti-Sortilin antibodies of the present disclosure, or fragments thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mpl8, mpl9, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a nucleic acid of the present disclosure. The expression vector may replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87104462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the nucleic acids of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell. In some embodiments, the vector contains a nucleic acid containing one or more amino acid sequences encoding an anti-Sortilin antibody of the present disclosure.

Suitable host cells for cloning or expression of antibody-encoding vectors include prokaryotic or eukaryotic cells. For example, anti-Sortilin antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523; and Charlton, *Methods in Molecular Biology, Vol.* 248 (B. K. C. Lo, ed., Humana Press, Totowa, N.J., 2003), pp. 245-254, describing expression of antibody fragments in *E. coli.*). After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gemgross, *Nat. Biotech.* 22:1409-1414 (2004); and Li et al., *Nat. Biotech.* 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants.).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol,* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

Pharmaceutical Compositions

Anti-Sortilin antibodies of the present disclosure can be incorporated into a variety of formulations for therapeutic administration by combining the antibodies with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents and detergents.

A pharmaceutical composition of the present disclosure can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, and enhance solubility or uptake). Examples of such modifications or complexing agents include, without limitation, sulfate, gluconate, citrate and phosphate. The polypeptides of a composition can also be complexed with molecules that enhance their in vivo attributes. Such molecules include, without limitation, carbohydrates, polyamines, amino acids, other peptides, ions (e.g., sodium, potassium, calcium, magnesium, manganese), and lipids.

Further examples of formulations that are suitable for various types of administration can be found in Remington's *Pharmaceutical Sciences*, Mace Publishing Company, Philadelphia, Pa., 17th ed. (1985). For a brief review of methods for drug delivery, see. Langer, *Science* 249:1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the antibody, such as an anti-Sortilin antibody of the present disclosure, in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the present disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing an anti-Sortilin antibody of the present disclosure may be administered to an individual in need of treatment with the anti-Sortilin antibody, preferably a human, in accord with known methods, such as intravenous administration as a bolus or by continuous infusion over a period of time, by intramuscular, intraperitoneal, intracerobrospinal, intracranial, intraspinal, subcutaneous, intra-articular, intrasynovial, intrathecal, oral, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," in *Toxicokinetics and New Drug Development*, Yacobi et al., Eds, Pergamon Press, New York 1989, pp. 42-46.

For in vivo administration of any of the anti-Sortilin antibodies of the present disclosure, normal dosage amounts may vary from about 10 ng/kg up to about 100 mg/kg of an individual's body weight or more per day, preferably about 1 mg/kg/day to 10 mg/kg/day, depending upon the route of administration. For repeated administrations over several days or longer, depending on the severity of the disease, disorder, or condition to be treated, the treatment is sustained until a desired suppression of symptoms is achieved.

An exemplary dosing regimen may include administering an initial dose of an anti-Sortilin antibody, of about 2 mg/kg, followed by a weekly maintenance dose of about 1 mg/kg every other week. Other dosage regimens may be useful, depending on the pattern of pharmacokinetic, decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, and about 2/mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the anti-Sortilin antibody administered, can vary over time independently of the dose used.

Dosages for a particular anti-Sortilin antibody may be determined empirically in individuals who have been given one or more administrations of the anti-Sortilin antibody. Individuals are given incremental doses of an anti-Sortilin antibody. To assess efficacy of an anti-Sortilin antibody, a clinical symptom of ay of the diseases, disorders, or conditions of the present disclosure (e.g., frontotemporal dementia, Alzheimer's disease, vascular dementia, seizures, retinal dystrophy, a traumatic brain injury, a spinal cord injury, long-term depression, atherosclerotic vascular diseases, and undesirable symptoms of normal aging) can be monitored.

Administration of an anti-Sortilin antibody of the present disclosure can be continuous or intermittent, depending, for example, on the recipient's physiological condition, whether the purpose of the administration is therapeutic or prophylactic, and other factors known to skilled practitioners. The administration of an anti-Sortilin antibody may be essentially continuous over a preselected period of time or may be in a series of spaced doses.

Guidance regarding particular dosages and methods of delivery is provided in the literature; see, for example, U.S. Pat. Nos. 4,657,760; 5,206,344; or 5,225,212, it is within the scope of the present disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Therapeutic Uses

Further aspects of the present disclosure provide methods of increasing Progranulin levels in an individual in need thereof, such as in the brain, blood, and/or peripheral organs of the individual, by administering to the individual a therapeutically effective amount of one or more anti-Sortilin antibodies of the present disclosure. Other aspects of the present disclosure provide methods of increasing extracellular levels of Progranulin, by contacting one or more cells with one or more anti-Sortilin antibodies of the present disclosure. In some embodiments, levels of Progranulin are increased without decreasing cellular levels of Sortilin. Other aspects of the present disclosure provide methods of decreasing cellular levels of Sortilin in an individual in need thereof, such as in the brain and/or peripheral organs of the individual, by administering to the individual a therapeutically effective amount of one or more anti-Sortilin antibodies of the present disclosure. Other aspects of the present disclosure provide methods of decreasing cellular levels of Sortilin of one or more cells, comprising contacting one or more cells with one or more anti-Sortilin antibodies of the present disclosure.

Further aspects of the present disclosure provide methods for increasing the effective concentrations of Progranulin and/or reducing the effective concentrations of a neurotrophin of the present disclosure (e.g., pro-neurotrophin-3, pro-neurotrophin-4/5, pro-neurotrophins, pro-NGF, pro-BDNF, neurotrophin-3, neurotrophin-4/5, NGF, BDNF, etc.), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and receptor associated protein (RAP) in an individual in need thereof, by administering to the individual a therapeutically effective amount of an anti-Sortilin antibody of the present disclosure to inhibit the interaction between Sortilin and Progranulin, a neurotrophin of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), and/or receptor associated protein (RAP).

The present disclosure also provides methods of inhibiting the interaction between Sortilin and Progranulin, a neurotrophin of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and/or receptor associated protein (RAP); as well as one or more activities of Sortilin, Progranulin, a neurotrophin of the present disclosure e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), and/or receptor associated protein (RAP) in an individual by administering to the individual a therapeutically effective amount of an anti-Sortilin antibody of the present disclosure.

As disclosed herein, anti-Sortilin antibodies of the present disclosure may also be used for preventing, reducing risk, or treating frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotriphic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, intervertebral disc degeneration, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arforitis, multiple sclerosis, metabolic disorder, obesity, insulin resistance, type 2 diabetes, tissue or vascular damage, an injury, and one or more undesirable symptoms of normal aging.

In some embodiments, the present disclosure provides methods of preventing, reducing risk, or treating an individual having frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia. Creutzfeldt-Jakob disease, normal pressure hydrocephalus, amyotriphic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, intervertebral disc degeneration, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arforitis, multiple sclerosis, metabolic disorder, obesity, insulin resistance, type 2 diabetes, tissue or vascular damage, an injury, and one or more undesirable symptoms of normal aging, in an individual in need thereof by administering to the individual a therapeutically effective amount of an anti-Sortilin antibody of the present disclosure to: (i) inhibit the interaction between Sortilin and Progranulin, a neurotrophin of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), and/or receptor associated protein (RAP); and/or (ii) inhibit one or more activities of Sortilin, Progranulin, a neurotrophin of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), and/or receptor associated protein (RAP). In some embodiments, the present disclosure provides methods of inducing wound healingin an individual in need thereof by administering to the individual a therapeutically effective amount of an anti-Sortilin antibody of the present disclosure.

The present disclosure also provides methods of promoting cell survival, such as neuronal cell survival, by administering an anti-Sortilin antibody of the present disclosure to inhibit the interaction between Sortilin and Progranulin, a neurotrophin of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, amyloid precursor protein (APP), and the A beta peptide. The anti-Sortilin antibody may be administered to cells in vitro to promote cell survival. Alternatively, the anti-Sortilin antibody may be administered in vivo (e.g., administering the antibody to an individual) to promote cell survival.

The present disclosure also provides methods of inhibiting neuroinflammation, axonopathy characterized by short axonal outgrowth and aberrant branching, microglial activation, and inflammatory response and promoting wound healing, autophagy and the clearance of aggregate proteins by administering an anti-Sortilin antibody of the present disclosure to inhibit the interaction between Sortilin and Progranulin, a neurotrophin. of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, amyloid precursor protein (APP), and the A beta peptide. The anti-Sortilin antibody may be administered to cells in vitro. Alternatively, the anti-Sortilin antibody may be administered in vivo (e.g., by administering the antibody to an individual).

The present disclosure also provides methods of decreasing expression of one or more pro-inflammatory mediators by administering to an individual in need thereof an anti-Sortilin antibody of the present disclosure. In some embodiments, the one or more pro-inflammatory mediators are selected from IL-6, IL12p70, IL12p40, IL-1β, TNF-α, CXCL1, CCL2, CCL3, CCL4, and CCL5.

Dementia

Dementia is a non-specific syndrome (i.e., a set of signs and symptoms) that presents as a serious loss of global cognitive ability in a previously unimpaired person, beyond what might be expected from normal ageing. Dementia may be static as the result of a unique global brain injury. Alternatively, dementia may be progressive, resulting in long-term decline due to damage or disease in the body. While dementia is much more common in the geriatric population, it can also occur before the age of 65. Cognitive areas affected by dementia include, without limitation, memory, attention span, language, and problem solving. Generally, symptoms must be present for at least six months to before an individual is diagnosed with dementia.

Exemplary forms of dementia include, without limitation, frontotemporal dementia, Alzheimer's disease, vascular dementia, semantic dementia, and dementia with Lewy bodies.

Without wishing to be bound by theory, it is believed that administering an anti-Sortilin antibody of the present disclosure can prevent, reduce the risk, and/or treat dementia. In some embodiments, administering an anti-Sortilin antibody may induce one or more Progranulin activities in an individual having dementia (e.g., neurotrophic and/or survival activity on neurons, and anti-inflammatory activity Frontotemporal Dementia Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. The clinical features of FTD include memory deficits, behavioral abnormalities, personality changes, and language impairments (Carts, M. & Van Broeckhoven, C., Trends Genet. 24:186-194 (2008); Neary, D., et al., Neurology 51:1546-1554 (1998); Ratnavalli, E., Wayne, C., Dawson, K. & Hodges, J. R., Neurology 58:1615-1621 (2002)).

A substantial portion of FTD cases are inherited in an autosomal dominant fashion, but even in one family, symptoms can span a spectrum from FTD with behavioral disturbances, to Primary Progressive Aphasia, to Cortico-Basal Ganglionic Degeneration. FTD, like most neurodegenerative diseases, can be characterized by the pathological presence of specific protein aggregates in the diseased brain. Historically, the first descriptions of FTD recognized the presence of intraneuronal accumulations of hyperphosphorylated Tau protein in neurofibrillary tangles or Pick bodies. A causal role for the microtubule associated protein Tau was supported by the identification of mutations in the gene encoding the Tau protein in several families (Hutton, M., et al., Nature 393:702-705 (1998). However, the majority of FTD brains show no accumulation of hyperphosphorylated Tau but do exhibit immunoreactivity to ubiquitin (Ub) and TAR DNA binding protein (TDP43) (Neumann, M., et al., Arch. Neurol. 64:1388-1394 (2007)), A majority of those ETD cases with Ub inclusions (FTD-U) were shown to carry mutations in the Progranulin gene.

Progranulin mutations result in haploinsufficiency and are known to be present in nearly 50% of familial FTD cases, making Progranulin mutation a major genetic contributor to FTD. Without wishing to be bound by theory, it is believed that the loss-of-function heterozygous character of Progranulin mutations indicates that in healthy individuals, Progranulin expression plays a dose-dependent, critical role in protecting healthy individuals from the development of FTD.

Accordingly, increasing levels of Progranulin by inhibiting the interaction between Sortilin and Progranulin, can prevent, reduce the risk, and/or treat FTD.

Alzheimer's Disease

Alzheimer's disease (AD), is the most common form of dementia. There is no cure for the disease, which worsens as it progresses, and eventually leads to death. Most often, AD is diagnosed in people over 65 years of age. However, the less-prevalent early-onset Alzheimer's can occur much earlier.

Common symptoms of Alzheimer's disease include, behavioral symptoms, such as difficulty in remembering recent events; cognitive symptoms, confusion, irritability and aggression, mood swings, trouble with language, and long-term memory loss. As the disease progresses bodily functions are lost, ultimately leading to death. Alzheimer's disease develops for an unknown and variable amount of time before becoming fully apparent, and it can progress undiagnosed for years.

It has been shown that Sortilin binds to amyloid precursor protein (APP) and the APP processing enzyme BACE1. Without wishing to be bound by theory, it is believed that these interactions are involved in Alzheimer's disease. Accordingly, and without wishing to be bound by theory, it is believed that anti-Sortilin antibodies of the present disclosure can be utilized to inhibit such interactions and prevent, reduce the risk of, or treat Alzheimer's disease in individuals in need thereof.

Recent studies have also shown that the levels of pro-neurotrophins (e.g., pro-NGF, pro-BDNF, etc.) increase in the early stages of Alzheimer's disease (e.g., Fahnestock, M et al., (2001) Cell Neurosci. 18, 210-220; Michalski B et al., (2003) Brain Res. Mol. Brain Res. 111, 148-154; Pedraza, C E et al., (2005) Am. J. Pathol. 166, 533-543; and Peng, S et al., (2005) J. Neurochem. 93, 1412-1421). Moreover, pro-neurotrophins undergo glycation and lipoxidation in the hippocampus and entorhinal cortex of Alzheimer's disease patients (Counts, S E et al., (2004) Ann. Neurol. 56, 520-531; and Counts, S E et al., (2005) J. Neuropathol. Exp. Neurol. 64, 263-272). This renders the pro-neurotrophins less susceptible to processing into mature neurotrophins.

Furthermore, in Alzheimer's disease patient TrkA expression is decreased, whereas the expression of p75 and Sortilin are unchanged. Accordingly, and without wishing to be bound by theory, it is believed that anti-Sortilin antibodies of the present disclosure that inhibit the interaction between Sortilin and neurotrophins of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), p75, amyloid precursor protein (APP), and/or the A beta peptide; or that inhibit one or more activities of Sortilin can be utilized to prevent, reduce the risk of, or treat Alzheimer's disease in individuals in need thereof.

Vascular Dementia

Vascular dementia (VaD) is a subtly progressive worsening of memory and other cognitive functions that is believed to be due to cerebrovascular disease (vascular disease within the brain). Cerebrovascular disease is the progressive change in our blood vessels (vasculature) the brain (cerebrum). The most common vascular change associated with age is the accumulation of cholesterol and other substances in the blood vessel walls. This results in the thickening and hardening of the walls, as well as narrowing of the vessels, which can result in a reduction or even a complete stopping of blood flow to brain regions supplied by the affected artery. Vascular dementia patients often present with similar symptoms to Alzheimer's disease (AD) patients. However, the related changes in the brain are not due to AD pathology but to chronic reduced blood flow in the brain, eventually resulting in dementia. VaD is considered one of the most common types of dementia in older adults. Symptoms of VaD include difficulties with memory, difficulty with organization and solving complex problems, slowed thinking, distraction or "absent mindedness," difficulty retrieving words from memory, changes in mood or behavior such as depression, irritability, or apathy, and hallucinations or delusions.

Without wishing to be bound by theory, it is believed that one or more activities of Sortilin, or one or more interactions between Sortilin and Progranulin, neurotrophins of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, lipoprotein lipase, apolipoprotein AV, and/or receptor-associated protein are involved in vascular dementia. Accordingly, and without wishing to be bound by theory, it is believed that anti-Sortilin antibodies of the present disclosure that inhibit the interaction between Sortilin and neurotrophins of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), and/or receptor associated protein (RAP); or that inhibit one or more activities of Sortilin can be utilized to prevent, reduce the risk of, or treat vascular dementia in individuals in need thereof.

Seizures, Retinal Dystrophy, Traumatic Brain Injuries, Spinal Cord Injuries, and Long-Term Depression As used herein, retinal dystrophy refers to any disease or condition that involves the degeneration of the retinal. Such diseases or conditions may lead to loss of vision or complete blindness.

As used herein, seizures also include epileptic seizures, and refer to a transient symptom of abnormal excessive or synchronous neuronal activity in the brain. The outward effect can be as dramatic as a wild thrashing movement or as mild as a brief loss of awareness. Seizures can manifest as an alteration in mental state, tonic or clonic movements, convulsions, and various other psychic symptoms.

Traumatic brain injuries (TBI), may also be known as intracranial injuries. Traumatic brain injuries occur when an external force traumatically injures the brain. Traumatic brain injuries can be classified based on severity, mechanism (closed or penetrating head injury), or other features (e.g., occurring in a specific location or over a widespread area).

Spinal cord injuries (SCI) include any injury to the spinal cord that is caused by trauma instead of disease. Depending on where the spinal cord and nerve roots are damaged, the symptoms can vary widely, from pain to paralysis to incontinence. Spinal cord injuries are described at various levels of "incomplete", which can vary from having no effect on the patient to a "complete" injury which means a total loss of function.

Long-term depression (LTD) is an activity-dependent reduction in the efficacy of neuronal synapses lasting hours or longer following a long patterned stimulus. Long-term depression can occur in many areas of the central nervous system with varying mechanisms depending upon brain region and developmental progress. Long-term depression can occur in the hippocampus, cerebellum, and in different types of neurons that release various neurotransmitters. Without wishing to be bound by theory, it is believed that long-term depression may be associated with neurodegeneration, dementia, and Alzheimer's disease.

It has been shown that pro-neurotrophins (e.g., pro-neurotrophin-4/5, neurotrophin-4/5, pro-NGF, pro-BDNF, etc.) play a role in seizures, retinal dystrophy, traumatic brain injury, spinal cord injury, and long-term depression (e.g., Beattie, M S et al., (2002) Neuron 36, 375-386; Volosin, M et al. (2006) J. Neurosci. 26, 7756-7766; Nykjaer, A et al., (2005) Curr. Opin. Neurobiol. 15, 49-57; Jansen, P et al., (2007) Nat. Neurosci. 10, 1449-1457; Volosin, M et al., (2008) J. Neurosci. 28, 9870-9879; Fahnestock, M et al., (2001) Mol. Cell Neurosci. 18, 210-220; Nakamura, K et al., (2007) Cell Death. Differ. 14, 1552-1554; Yune, T et al. (2007) J. Neurosci. 27, 7751-7761; Arnett, M G et al., (2007) Brain Res. 1183, 32-42; Wei, Y et al., (2007) Neurosci. Len. 429, 169-174; Provenzano, M J et al., (2008) Laryngoscope 118, 87-93; and Pang, P T et al., (2004) Science 306, 487-491).

Accordingly, and without wishing to be bound by theory, it is believed that anti-Sortilin antibodies of the present disclosure that inhibit the interaction between Sortilin and neurotrophins of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.); or that inhibit one or more activities of Sortilin can be utilized to prevent, reduce the risk of, or treat seizures, retinal dystrophy, traumatic brain injuries, spinal cord injuries, and/or long-term depression in individuals in need thereof.

Atherosclerotic Vascular Diseases

As used herein, "arteriosclerotic vascular disease," "ASVD," and "atherosclerosis" are used interchangeably and refer to any condition in which an artery wall thickens as a result of the accumulation of fatty materials such as cholesterol, lipids, and triglyceride. "Arteriosclerotic vascular diseases" include, without limitation, any ASVD-associated condition, disorder, or disease, including without limitation, thromboembolism, stroke, ischemia, infarctions, coronary thrombosis, myocardial infarction (e.g., heart attack), and claudication.

Arteriosclerotic vascular disease is a syndrome affecting arterial blood vessels, a chronic inflammatory response in the walls of arteries, caused largely by the accumulation of macrophage white blood cells and promoted by low-density lipoproteins (LDL) without adequate removal of fats and cholesterol from the macrophages by functional high-density lipoproteins (HDL). Arteriosclerotic vascular disease is commonly referred to as a hardening or furring of the arteries, and is caused by the formation of multiple plaques within the arteries.

As disclosed herein, Sortilin proteins of the present disclosure are involved in lipid regulation, by binding lipid-associated proteins, such as receptor associated protein, lipoprotein lipase and apopolipoproteins APOA5 and APOE (e.g., Nisson, S K et al., (2007) Biochemistry 46: 3896-3904; Nisson, S K et al., (2008) J Biol Chem 283: 25920-25927; and Klinger, S C et al., J Cell Sci 124: 1095-1105). It has also been shown that Sortilin-deficient mice have reduced plaque load in the aorta, and reduced cholesterols levels in plasma in the context of LDL receptor deficiency (e.g., Kjolby, M et al., Cell Metab 12: 213-223). Consistent with similar roles of the Sortilin receptors in lipid metabolism, SorLA has been shown to have a similar effect as Sortilin on lipid metabolism, as loss of SorLA is protective (e.g., Guo, Z et al, Mediators Inflamm 2012: 540794). SorLA is upregulated in atheromatous plaques in rabbits and mice, and knockout mice are protected from vascular cuff injury (e.g., Guo, Z et al., Mediators Inflamm 2012: 540794).

Accordingly, and without wishing to be bound by theory, it is believed that anti-Sortilin antibodies of the present disclosure that inhibit the interaction between Sortilin and lipoprotein lipase (LpL), apolipoprotein AV (APOA5), apolipoprotein E (APOE), and/or receptor associated protein (RAP); or that inhibit one or more activities of Sortilin can be utilized to prevent, reduce the risk of, or treat one or more arteriosclerotic vascular disease in individuals in need thereof.

Undesirable Symptoms of Aging

As used herein, undesirable symptoms of aging include, without limitation, memory loss, behavioral changes, dementia, Alzheimer's disease, retinal degeneration, atherosclerotic vascular diseases, hearing loss, and cellular breakdown.

It has been shown that pro-neurotrophins (e.g., pro-neurotrophin-3, pro-neurotrophin-4/5, pro-NGF, pro-BDNF, etc.) play a role in aging and aging-related symptoms (e.g., Beattie, M S et al., (2002) Neuron 36, 375-386; Volosin, M et al. (2006) J. Neurosci. 26, 7756-7766; Nykjaer, A et al., (2005) Curr. Opin. Neurobiol. 15, 49-57; Jansen, P et al., (2007) Nat. Neurosci. 10, 1449-1457; Volosin, M et al., (2008) J. Neurosci, 28, 9870-9879; Fahnestock, M et al., (2001) Mol. Cell Neurosci. 18, 210-220; Nakamura, K et al., (2007) Cell Death. Differ, 14, 1552-1554; Yune, T et al., (2007) J. Neurosci. 27, 7751-7761; Arnett, M G et al., (2007) Brain Res. 1183, 32-42; Wei, Y et al., (2007) Neurosci. Lett. 429, 169-174; Provenzano, M J et al., (2008) Laryngoscope 118, 87-93; Pang, P T et al., (2004) Science 306, 487-491; and Al-Shawi, R et al., Ann N Y Acad Sci. 2007; 1119:208-15).

In some embodiments, anti-Sortilin antibodies of the present disclosure that inhibit the interaction between Sortilin and Progranulin, neurotrophins of the present disclosure e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, lipoprotein lipase (LpL), apolipoprotein AV (APOA5), and/or receptor associated protein (RAP); or that inhibit one or more activities of Sortilin can be utilized to prevent, reduce the risk of, or treat one or more undesirable symptoms of aging.

Amyotriphic Lateral Sclerosis (ALS)

As used herein, amyotriphic lateral sclerosis (ALS) or, motor neuron disease or, Lou Gehrig's disease are used interchangeably and refer to a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

It has been shown that Progranulin play a role in ALS (Schymick, J C et al., (2007) J Neurol Neurosurg Psychiatry; 78:754-6) and protects again the damage caused by ALS causing proteins such as TDP-43 (Laird, A S et al., (2010). PLoS ONE 5: e13368). It was also demonstrated that pro-NGF induces p75 mediated death of oligodendrocytes and corticospinal neurons following spinal cord injury (Beatty et al., Neuron (2002), 36, pp. 375-386; Giehl et al, Proc. Natl. Acad. Sci LISA (2004), 101, pp 6226-30).

In some embodiments, anti-Sortilin antibodies of the present disclosure that inhibit the interaction between Sortilin and Progranulin, neurotrophins of the present disclosure e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, lipoprotein lipase (LpL), apolipoprotein AV (APOA5), and/or receptor associated protein (RAP); or that inhibit one or more activities of Sortilin can be utilized to prevent, or treat one or more undesirable symptoms of ALS.

Depression

As used herein, depression or, major depressive disorder (MDD), clinical depression, major depression, unipolar depression, unipolar disorder, recurrent depression or, dysthymia, are used interchangeably and refer to a mental disorder characterized by episodes of all-encompassing low mood accompanied by low self-esteem and loss of interest or pleasure in normally enjoyable activities. This cluster of symptoms (syndrome) was named, described and classified as one of the mood disorders in the 1980 edition of the American Psychiatric Association's diagnostic manual. The term "depression" is ambiguous. It is often used to denote this syndrome but may refer to other mood disorders or to lower mood states lacking clinical significance. Major depressive disorder is a disabling condition that adversely affects a person's family, work or school life, sleeping and eating habits, and general health. In the United States, around 3.4% of people with major depression commit suicide, and up to 60% of people who commit suicide had depression or another mood disorder.

Neurotrophins have been shown to be involved in depression and antidepressant action (Duman et al., Arch Gen Psychiatry (1997) 54:597-606); for example, infusion of BDNF into the hippocampus has produced an antidepressant effect in two behavioral models of depression (Shirayama et al., (2002), J Neurosci 22: 3251-3261). Moreover, a single nucleotide polymorphism in the bdnf gene leading to a valine (Val) to methionine (Met) substitution at codon 66 in the pro-domain ($BDNF_{Met}$) was found to be associated with increased susceptibility in humans heterozygous for the polymorphism to neuropsychiatric disorders including Alzheimer's disease, Parkinson's disease, depression, and bipolar disorder (Chen et al, J. Neuroscience (2005), 25:6156-6166; Kuipers and Bramham, Curr. Opin. Drug Discov. Devel. (2006) 9(5):580-6; and Bath and Lee, Cogn, Affect. Behav. Neurosci (2006) 1:79-85). In addition, humans heterozygous for BDNF$_{met}$ were shown to have memory impairments (Egan et al., Cell (2003). 112, pp 257-269).

In some embodiments, anti-Sortilin antibodies of the present disclosure that inhibit the interaction between Sortilin and Progranulin, neurotrophins of the present disclosure e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, lipoprotein lipase (LpL), apolipoprotein AV (APOA5), and/or receptor associated protein (RAP); or that inhibit one or more activities of Sortilin can be utilized to prevent, or treat one or more undesirable symptoms of depression.

Parkinson's Disease

Parkinson's disease, which may be referred to as idiopathic or primary parkinsonism, hypokinetic rigid syndrome (HRS), or paralysis agitans, is a neurodegenerative brain disorder that affects motor system control. The progressive death of dopamine-producing cells in the brain leads to the major symptoms of Parkinson's. Most often, Parkinson's disease is diagnosed in people over 50 years of age. Parkinson's disease is idiopathic (having no known cause) in most people. However, genetic factors also play a role in the disease.

Symptoms of Parkinson's disease include, without limitation, tremors of the hands, arms, legs, jaw, and face, muscle rigidity in the limbs and trunk, slowness of movement (bradykinesia), postural instability, difficulty walking, neuropsychiatric problems, changes in speech or behavior, depression, anxiety, pain, psychosis, dementia, hallucinations, and sleep problems.

Without wishing to be bound by theory, it is believed that administering an anti-Sortilin antibody of the present disclosure can prevent, reduce the risk, and/or treat Parkinson's disease. In some embodiments, administering an anti-Sortilin antibody may induce one or more Progranulin activities in an individual having Parkinson's disease.

Huntington's Disease

Huntington's disease (HD) is an inherited neurodegenerative disease caused by an autosomal dominant mutation in the Huntingtin gene (HTT). Expansion of a cytokine-adenine-guanine (CAG) triplet repeat within the Huntingtin gene results in production of a mutant form of the Huntingtin protein (Htt) encoded by the gene. This mutant Huntingtin protein (mHtt) is toxic and contributes to neuronal death. Symptoms of Huntington's disease most commonly appear between the ages of 35 and 44, although they can appear at any age.

Symptoms of Huntington's disease, include, without limitation, motor control problems, jerky, random movements (chorea), abnormal eye movements, impaired balance, seizures, difficulty chewing, difficulty swallowing, cognitive problems, altered speech, memory deficits, thinking difficulties, insomnia, fatigue, dementia, changes in personality, depression, anxiety, and compulsive behavior.

Without wishing to be bound by theory, it is believed that administering an anti-Sortilin antibody of the present disclosure can prevent, reduce the risk, and/or treat Huntington's disease (HD). In some embodiments, administering an anti-Sortilin antibody may induce one or more Progranulin activities in an individual having HD Taupathy Disease Taupathy diseases, or Tauopathies, are a class of neurodegenerative disease caused by aggregation of the microtubule-associated protein tau within the brain. Alzheimer's disease (AD) is the most well-known Taupathy disease, and involves an accumulation of tau protein within neurons in the form of insoluble neurofibrillary tangles (NFTs). Other Taupathy diseases and disorders include progressive supranuclear palsy, dementia pugilistica (chromic traumatic encephalopathy), Frontotemporal dementia and parkinsonism linked to chromosome 17, Lytico-Bodig disease (Parkinson-dementia complex of Guam), Tangle-predominant dementia, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), Huntington's disease, frontotemporal dementia, and frontotemporal lobar degeneration.

Without wishing to be bound by theory, it is believed that administering an anti-Sortilin antibody of the present disclosure can prevent, reduce the risk, and/or treat Taupathy disease. In some embodiments, administering an anti-Sortilin antibody may induce one or more Progranulin activities in an individual having Taupathy disease.

Multiple Sclerosis

Multiple sclerosis (MS) can also be referred to as disseminated sclerosis or encephalomyelitis disseminata. MS is an inflammatory disease in which the fatty myelin sheaths around the axons of the brain and spinal cord are damaged, leading to demyelination and scarring as well as a broad spectrum of signs and symptoms. MS affects the ability of nerve cells in the brain and spinal cord to communicate with each other effectively. Nerve cells communicate by sending electrical signals called action potentials down long fibers called axons, which are contained within an insulating substance called myelin. In MS, the body's own immune system attacks and damages the myelin. When myelin is lost, the axons can no longer effectively conduct signals. MS onset usually occurs in young adults, and is more common in women.

Symptoms of MS include, without limitation, changes in sensation, such as loss of sensitivity or tingling; pricking or numbness, such as hypoesthesia and paresthesia; muscle weakness; clonus; muscle spasms; difficulty in moving; difficulties with coordination and balance, such as ataxia; problems in speech, such as dysarthria, or in swallowing, such as dysphagia; visual problems, such as nystagmus, optic neuritis including phosphenes, and diplopia; fatigue; acute or chronic pain; and bladder and bowel difficulties; cognitive impairment of varying degrees; emotional symptoms of depression or unstable mood; Uhthoff's phenomenon, which is an exacerbation of extant symptoms due to an exposure to higher than usual ambient temperatures; and Lhermitte's sign, which is an electrical sensation that runs down the back when bending the neck.

Without wishing to be bound by theory, it is believed that administering an anti-Sortilin antibody of the present disclosure can prevent, reduce the risk, and/or treat multiple sclerosis. In some embodiments, administering an anti-Sortilin antibody may induce one or more Progranulin activities in an individual having multiple sclerosis.

Glaucoma and Macular Degeneration

Glaucoma describes, without limitation, a group of diseases that are characterized by a damaged optic nerve, resulting in vision loss and blindness. Glaucoma is usually caused by increased fluid pressure (=intraocular pressure) in the anterior chamber underneath the cornea. Glaucoma results in the successive loss of retinal ganglion cells that are important for vision. Age-related macular degeneration usually affects older people and primarily causes loss of vision in the macula, the central field of vision. Macular degeneration causes, without limitation, drusen, pigmentary changes, distorted vision, hemorrhages of the eye, atrophy, reduced visual acuity, blurred vision, central scotomas, reduced color vision and reduced contrast sensitivity.

Without wishing to be bound by theory, it is believed that administering an anti-Sortilin antibody of the present disclosure can prevent, reduce the risk, and/or treat glaucoma and macular degeneration. In some embodiments, administering an anti-Sortilin antibody may induce one or more Progranulin activities in an individual having glaucoma or macular degeneration.

Degenerative Disc Disease (DDD)

Degenerative disc disease (DDD) describes, without limitation, a group of diseases in which intervertebral disc (IVD) undergoes extensive morphological as well as biomechanical changes, and usually manifests clinically in patients with lower back pain. Degenerative discs typically show degenerative fibrocartilage and clusters of chondrocytes, suggestive of repair. Inflammation may or may not be present. The pathologic findings in DDD include protrusion, spondylolysis, and/or subluxation of vertebrae (sponylolisthesis) and spinal stenosis.

Kits/Articles of Manufacture

The present disclosure also provides kits containing an isolated antibody of the present disclosure (e.g., an anti-Sortilin antibody described herein), or a functional fragment thereof. Kits of the present disclosure may include one or more containers comprising a purified antibody of the present disclosure. In some embodiments, the kits further include instructions for use in accordance with the methods of this disclosure. In some embodiments, these instructions comprise a description of administration of the isolated antibody of the present disclosure e.g., an anti-Sortilin antibody described herein) to prevent, reduce risk, or treat an individual having a disease, disorder, or injury selected from frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotriphic lateral sclerosis, Huntington's disease, Taupathy disease, Nasu-Hakola disease, stroke, acute trauma, chronic trauma, lupus, acute and chronic colitis, wound healing, Crohn's disease, inflammatory bowel disease, ulcerative colitis, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, lupus, arforitis, multiple sclerosis, and wound healing, according to any methods of this disclosure.

In some embodiments, the instructions comprise a description of how to detect a Sartain protein, for example in an individual, in a tissue sample, or in a cell. The kit may further comprise a description of selecting an individual suitable for treatment based on identifying whether that individual has the disease and the stage of the disease.

In some embodiments, the kits may further include another antibody of the present disclosure (e.g., at least one antibody that specifically binds to an inhibitory checkpoint molecule, at least one antibody that specifically binds to an inhibitory cytokine, and/or at least one agonistic antibody that specifically binds to a stimulatory checkpoint protein) and/or at least one stimulatory cytokine. In some embodiments, the kits may further include instructions for using the antibody and/or stimulatory cytokine in combination with an isolated antibody of the present disclosure (e.g., an anti-Sortilin antibody described herein), instructions for using the isolated antibody of the present disclosure in combination with an antibody and/or stimulatory cytokine, or instructions for using an isolated antibody of the present disclosure and an antibody and/or stimulatory cytokine, according to any methods of this disclosure.

The instructions generally include information as to dosage, dosing schedule, and route of administration for the intended treatment. The containers may be unit doses, bulk packages multi-dose packages) or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a disease of the present disclosure. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). At least one active agent in the composition is an isolated antibody of the present disclosure (e.g., an anti-Sortilin antibody described herein). The container may further comprise a second pharmaceutically active agent.

Kits may optionally provide additional components such as buffers and interpretive information. Normally, the kit comprises a container and a label or package insert(s) on or associated with the container.

Diagnostic Uses

The isolated antibodies of the present disclosure (e.g., an anti-Sortilin antibody described herein) also have diagnostic utility. This disclosure therefore provides for methods of using the antibodies of this disclosure, or functional fragments thereof, for diagnostic purposes, such as the detection of a Sortilin protein in an individual or in tissue samples derived from an individual.

In some embodiments, the individual is a human. In some embodiments, the individual is a human patient suffering from, or at risk for developing a disease, disorder, or injury of the present disclosure. In some embodiments, the diagnostic methods involve detecting a Sortilin protein in a biological sample, such as a biopsy specimen, a tissue, or a cell. An isolated antibody of the present disclosure (e.g., an anti-Sortilin antibody described herein) is contacted with the biological sample and antigen-bound antibody is detected. For example, a biopsy specimen may be stained with an anti-Sortilin antibody described herein in order to detect and/or quantify disease-associated cells. The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with $^{18}$F and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

In other embodiments, an isolated antibody of the present disclosure (e.g., an anti-Sortilin antibody described herein) may be used to detect and/or quantify, for example, microglia in a brain specimen taken from a preclinical disease model (e.g., a non-human disease model). As such, an isolated antibody of the present disclosure (e.g., an anti-Sortilin antibody described herein) may be useful in evaluating therapeutic response after treatment in a model for a nervous system. disease or injury such as frontotemporal dementia, Alzheimer's disease, vascular dementia, seizures, retinal dystrophy, atherosclerotic vascular diseases, Nasu-Hakola disease, or multiple sclerosis, as compared to a control.

The present disclosure will be more fully understood by reference to the following Examples. They should not, however, be construed as limiting the scope of the present disclosure. All citations throughout the disclosure are hereby expressly incorporated by reference.

Enumerated Embodiments

The following enumerated embodiments are representative of some aspects of the invention.

1. An isolated anti-Sortilin antibody, wherein the anti-Sortilin antibody has a property selected from the group consisting of: increasing extracellular levels of Progranulin, increasing cellular levels of Progranulin, decreasing cellular levels of Sortilin, inhibiting interaction between Sortilin and Progranulin, and any combination thereof.
2. The anti-Sortilin antibody of embodiment 1, wherein the antibody decreases cell surface levels of Sortilin, decreases intracellular levels of Sortilin, decreases total levels of Sortilin, or any combination thereof.
3. The anti-Sortilin antibody of embodiment 1 or embodiment 2, wherein the anti-Sortilin antibody induces Sortilin degradation, Sortilin cleavage, Sortilin internalization, Sortilin down regulation, or any combination thereof.
4. The anti-Sortilin antibody of any one of embodiments 1-3, wherein the anti-Sortilin antibody decreases cellular levels of Sortilin and does not inhibit the interaction between Sortilin and Progranulin.
5. The anti-Sortilin antibody of any one of embodiments 1-3, wherein the anti-Sortilin antibody decreases cellular levels of Sortilin and inhibits the interaction between Sortilin and Progranulin.
6. The anti-Sortilin antibody of any one of embodiments 1-3, wherein the anti-Sortilin antibody decreases cellular levels of Sortilin and increases cellular levels of Progranulin.
7. The anti-Sortilin antibody of any one of embodiments 1-3, wherein the anti-Sortilin antibody increases cellular levels of Progranulin and does not inhibit the interaction between Sortilin and Progranulin.
8. The anti-Sortilin antibody of any one of embodiments 1-3, wherein the anti-Sortilin antibody inhibits the interaction between Sortilin and Progranulin and increases cellular levels of Progranulin.
9. The anti-Sortilin antibody of any one of embodiments 1-8, wherein the anti-Sortilin antibody increases levels of Progranulin in vivo.
10. The anti-Sortilin antibody of any one of embodiments 1-8, wherein the anti-Sortilin antibody increases levels of Progranulin in vivo without decreasing cellular levels of Sortilin.
11. The anti-Sortilin antibody of embodiment 9 or embodiment 10, wherein the anti-Sortilin antibody increases levels of Progranulin in brain, blood, one or more peripheral organs, or any combination thereof.
12. The anti-Sortilin antibody of any one of embodiments 1-9, wherein the anti-Sortilin antibody decreases cellular levels of Sortilin in vivo.
13. The anti-Sortilin antibody of embodiment 12, wherein the anti-Sortilin antibody decreases cellular levels of Sortilin in brain, one or more peripheral organs, or any combination thereof.
14. The anti-Sortilin antibody of embodiment 1, wherein the anti-Sortilin antibody inhibits the interaction between Sortilin and Progranulin and does not decrease cellular levels of Sortilin.
15. The anti-Sortilin antibody of embodiment 1, wherein the anti-Sortilin antibody increases cellular levels of Progranulin and does not decrease cellular levels of Sortilin.
16. The anti-Sortilin antibody of any one of embodiments 1-15, wherein the anti-Sortilin antibody further inhibits interaction between Sortilin and pro-nerve growth factor (pro-NGF).
17. The anti-Sortilin antibody of embodiment 16, wherein the anti-Sortilin antibody further inhibits interaction between Sortilin and one or more proteins by: a) reducing the effective levels of Sortilin available for interacting with the one or more proteins; b) inducing degradation of Sortilin; or both.
18. The anti-Sortilin antibody of any one of embodiments 1-17, wherein the anti-Sortilin antibody binds specifically to human Sortilin, mouse Sortilin, or both.
19. The anti-Sortilin antibody of any one of embodiments 1-18, wherein the anti-Sortilin antibody is a human antibody, a humanized antibody, a bispecific antibody, a monoclonal antibody, a multivalent antibody, a conjugated antibody, or a chimeric antibody.
20. The anti-Sortilin antibody of any one of embodiments 1-19, wherein the anti-Sortilin antibody is a bispecific antibody recognizing a first antigen and a second antigen.
21. The anti-Sortilin antibody of embodiment 20, wherein the first antigen is Sortilin and the second antigen is an antigen facilitating transport across the blood-brain-barrier.
22. The anti-Sortilin antibody of embodiment 21, wherein the second antigen is selected from the group consisting of Sortilin, transferring receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, basigin, Glut1, CD98hc, and ANG1005.
23. The anti-Sortilin antibody of any one of embodiments 1-22, wherein the anti-Sortilin antibody is an antibody fragment that binds to an epitope comprising amino acid residues on human Sortilin or a mammalian Sortilin protein.
24. The anti-Sortilin antibody of embodiment 23, wherein the fragment is an Fab, Fab', Fab'-SH, F(ab')2, Fv, or scFv fragment.

25. The anti-Sortilin antibody of any one of embodiments 1-24, wherein the anti-Sortilin antibody further comprises one or more activities selected from the group consisting of:
(a) inducing one or more Progranulin activities;
(b) reducing endosomal internalization of Progranulin, or fragments thereof; and
(c) increasing the effective concentration of Progranulin.

26. The anti-Sortilin antibody of any one of embodiments 1-25, wherein the anti-Sortilin antibody binds a discontinuous Sortilin epitope.

27. The anti-Sortilin antibody of embodiment 26, wherein the discontinuous Sortilin epitope comprises two or more peptides, three or more peptides, four or more peptides, five or more peptides, six or more peptides, seven or more peptide, eight or more peptides, nine or more peptides, or 10 or more peptides.

28. The anti-Sortilin antibody of embodiment 27, wherein each of the peptides comprise five or more, six or more, seven or more, eight or more, nine or more, 10 or more, 11 or more, 12 or more, 13 or more 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid residues of the amino acid sequence of SEQ ID NO: 1; or five or more, six or more, seven or more, eight or more, nine or more, 10 or more, 11 or more, 12 or more, 13 or more 1'-1 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid residues on a mammalian Sortilin protein corresponding to the amino acid sequence of SEQ ID NO: 1.

29. The anti-Sortilin antibody of any one of embodiments 1-25, wherein the anti-Sortilin antibody binds to a conformational epitope of Sortilin.

30. The anti-Sortilin antibody of any one of embodiments 1-25, wherein the anti-Sortilin antibody binds to one or more amino acids within amino acid residues selected from the group consisting of
  i. amino acid residues 740-749 of SEQ NO: 1, or amino acid residues on a mammalian Sortilin protein corresponding to amino acid residues 740-749 of SEQ ID NO: 1;
  ii. amino acid residues 623-632 of SEQ ID NO: 1, or amino acid residues on a mammalian Sortilin protein corresponding to amino acid residues 623-632 of SEQ ID NO: 1;
  iii. amino acid residues 429-443 of SEQ ID NO: 1, or amino acid residues on a mammalian Sortilin protein corresponding to amino acid residues 429-443 of SEQ ID NO: 1;
  iv. amino acid residues 367-391 of SEQ ID NO: 1, or amino acid residues on a mammalian Sortilin protein corresponding to amino acid residues 367-391 of SEQ ID NO: 1;
  v. amino acid residues 314-338 of SEQ ID NO: 1, or amino acid residues on a mammalian Sortilin protein corresponding to amino acid residues 314-338 of SEQ ID NO: 1;
  vi. amino acid residues 297-317 of SEQ ID NO: 1, or amino acid residues on a mammalian Sortilin protein corresponding to amino acid residues 297-317 of SEQ ID NO: 1;
  vii. amino acid residues 237-260 of SEQ ID NO: 1, or amino acid residues on a mammalian Sortilin protein corresponding to amino acid residues 237-260 of SEQ ID NO: 1;
  viii. amino acid residues 237-260 and 297-317 of SEQ ID NO: 1, or amino acid residues on a mammalian Sortilin protein corresponding to amino acid residues 237-260 and 297-317 of SEQ ID NO: 1;
  ix. amino acid residues 237-247 of SEQ ID NO: 1, or amino acid residues on a mammalian Sortilin protein corresponding to amino acid residues 237-247 of SEQ ID NO: 1;
  x. amino acid residues 237-247 and 314-338 of SEQ ID NO: 1, or amino acid residues on a mammalian Sortilin protein corresponding to amino acid residues 237-247 and 314-338 of SEQ ID NO: 1;
  xi. amino acid residues 233-243 of SEQ ID NO: 1, or amino acid residues on a mammalian Sortilin protein corresponding to amino acid residues 233-243 of SEQ ID NO: 1;
  xii. amino acid residues 212-221 of SEQ ID NO: 1, or amino acid residues on a mammalian Sortilin protein corresponding to amino acid residues 212-221 of SEQ ID NO: 1;
  xiii. amino acid residues 207-227 of SEQ ID NO: 1, or amino acid residues on a mammalian Sortilin protein corresponding to amino acid residues 207-227 of SEQ ID NO: 1;
  xiv. amino acid residues 207-227 and 237-260 of SEQ ID NO: 1, or amino acid residues on a mammalian Sortilin protein corresponding to amino acid residues 207-227 and 237-260 of SEQ ID NO: 1;
  xv. amino acid residues 207-231 of SEQ NO: 1, or amino acid residues on a mammalian Sortilin protein corresponding to amino acid residues 207-231 of SEQ ID NO: 1;
  xvi. amino acid residues 175-181 of SEQ ID NO: 1, or amino acid residues on a mammalian Sortilin protein corresponding to amino acid residues 175-181 of SEQ ID NO: 1; and
  xvii. amino acid residues 131-138 of SEQ ID NO: 1, or amino acid residues on a mammalian Sortilin protein corresponding to amino acid residues 131-138 of SEQ ID NO: 1.

31. The anti-Sortilin antibody of any one of embodiments 1-25, wherein the anti-Sortilin antibody binds to one or more amino acid residues selected from the group consisting of H131, V132, P133, L134, V135, I136, M137, T138, T210, T218, Y222, S223, S227, S242, K243, K248, K254, S305, R311, S316, R325, S379, R382, Y386, and S595 of SEQ ID NO: 1, or one or more amino acid residues on a mammalian Sortilin protein corresponding to an amino acid residue selected from the group consisting of H131, V132, P133, L134, V135, I136, M137, T138, T210, T218, Y222, S223, S227, S242, K243, K248, K254, S305, R311, S316, R325, S379, R382, Y386, and S595 of SEQ ID NO: 1.

32. The anti-Sortilin antibody of any one of embodiments 1-25, wherein the anti-Sortilin antibody binds to one or more amino acid residues selected from the group consisting of R88, F105, L108, R109, G110, D403, D449, T451, H461, G495, Y513, S530, I537, D552, F569, E590, F592, L593, S595, W597, I619, L621, E628, D632, L636, Q642, R646, and Y679 of SEQ ID NO: 1, or one or more amino acid residues on a mammalian Sortilin protein corresponding to an amino acid residue selected from the group consisting of R88, F105, L108, R109, G110, D403, D449, T451, H461, G495, Y513, S530, I537, D552, F569, E590, F592, L593, S595, W597, I619, L621, E628, D632, L636, Q642, R646, and Y679.

33. The anti-Sortilin antibody of any one of embodiments 1-32, wherein the anti-Sortilin antibody comprises at least one, two, three, four, five, or six HVRs of an antibody selected from the group consisting of: S-5, S-6, S-8, S-45, S-49, S-60, S-63, S-64, S-65, S-72, and S-83.

34. The anti-Sortilin antibody of any one of embodiments 1-32, wherein the anti-Sortilin antibody comprises at least one, two, three, four, five, or six HVRs of an antibody selected from the group consisting of: S-2, S-14, S-15, S-18, S-19, S-20, S-21, S-22, S-29, S-51, S-57, S-61, and S-82.

35. The anti-Sortilin antibody of any one of embodiments 1-32, wherein the anti-Sortilin antibody comprises at least one, two, three, four, five, or six HVRs of an antibody selected from the group consisting of: S-5, S-30 and S-60.

36. The anti-Sortilin antibody of any one of embodiments 1-32, wherein the anti-Sortilin antibody competes with one or more antibodies selected from the group consisting of S-6, S-8, S-49, S-60, S-63, S-72, S-83, and any combination thereof for binding to Sortilin.

37. The anti-Sortilin antibody of any one of embodiments 1-32, wherein the anti-Sortilin antibody competes with one or more antibodies selected from the group consisting of S-5, S-45, S-64, S-65, and any combination thereof for binding to Sortilin.

38. The anti-Sortilin antibody of any one of embodiments 1-32, wherein the anti-Sortilin antibody competes with one or more antibodies selected from the group consisting of S-5, S-30, S-60, and any combination thereof for binding to Sortilin.

39. An isolated anti-Sortilin antibody, wherein the anti-Sortilin antibody comprises at least one, two, three, four, five, or six HVRs of an antibody selected from the group consisting of: S-1, S-2, S-3, S-4, S-5, S-6, S-7, S-8, S-9, S-10, S-12, S-14, S-15, S-16, S-18, S-19, S-20, S-21, S-22, S-24, S-25, S-26, S-28, S-29, S-30, S-32, S-34, S-39, S-40, S-42, S-43, S-44, S-45, S-48, S-49, S-50, S-51, S-55, S-57, S-58, S-59, S-60, S-61, S-63, S-64, S-65, S-66, S-67, S-69, S-71, S-72, S-73, S-74, S-75, S-76, S-78, S-81, S-82, S-83, S-84, and S-85.

40. The anti-Sortilin antibody of embodiment 39, wherein the anti-Sortilin antibody comprises:
   (a) an HVR-L1 comprising an amino acid sequence selected from the group consisting of SEQ ID NOs:6-16, 20-22, and 24-25;
   (b) an HVR-L2 comprising an amino acid sequence selected from the group consisting of SEQ ID NOs: 26-40;
   (c) an HVR-L3 comprising an amino acid sequence selected from the group consisting of SEQ ID NOs: 41-50, 52, 54-56, 58-62, 64-66, 68-70, 72, 74, 79-80, 82-85, 88-91, 95, 97-101, 103-107, 109, 111-116, 118, and 121-125;
   (d) an HVR-H1 comprising an amino acid sequence selected from the group consisting of SEQ ID NOs: 126-127, 129-130, 133-140, 142, 144-145, and 147-149;
   (e) HVR-H2 comprising an amino acid sequence selected from the group consisting of SEQ ID NOs:150-153, 155-158, 160-166, 169-175, and 177-178; or
   (f) an HVR-H3 v an amino acid sequence selected from the group consisting of SEQ ID NOs:179-186, 188, 190-191, 193-197, 199-201, 203-204, 206, 208, 213-214, 216-219, 222-225, 229, 231-234, 236-239, 241, 243-247, 249, and 252-256.

41. The anti-Sortilin antibody of embodiment 39, wherein the anti-Sortilin antibody comprises a light chain variable domain and a heavy chain variable domain, wherein the light chain variable domain comprises:
   (a) an HVR-L1 comprising an amino acid sequence selected from the group consisting of SEQ ID NOs:6-16, 20-22, and 24-25, or an amino acid sequence with at least about 95% homology to an amino acid sequence selected from the group consisting of SEQ ID NOs:6-16, 20-22. and 24-25;
   (b) an HVR-L2 comprising an amino acid sequence selected from the group consisting of SEQ ID NOs: 26-40, or an amino acid sequence with at least about 95% homology to an amino acid sequence selected from the group consisting of SEQ ID NOs:26-40; and
   (c) an HVR-L3 comprising an amino acid sequence selected from the group consisting of SEQ ID NOs: 41-50, 52, 54-56, 58-62, 64-66, 68-70, 72, 74, 79-80, 82-85, 88-91, 95, 97-101, 103-107, 109, 111-116, 118, and 121-125, or an amino acid sequence with at least about 95% homology to an amino acid sequence selected from the group consisting of SEQ ID NOs: 41-50, 52, 54-56, 58-62, 64-66, 68-70, 72, 74, 79-80, 82-85, 88-91, 95, 97-101, 103-107, 109, 111-116, 118, and 121-125; and
wherein the heavy chain variable domain comprises:
   (a) an HVR-H1 comprising an amino acid sequence selected from the group consisting of SEQ ID NOs: 126-127, 129-130, 133-140, 142, 144-145, and 147-149, or an amino acid sequence with at least about 95% homology to an amino acid sequence selected from the group consisting of SEQ ID NOs:126-127, 129-130, 133-140, 142, 144-145, and 147-149,
   (b) an HVR-H2 comprising an amino acid sequence selected from the group consisting of SEQ ID NOs: 150-153, 155-158, 160-166, 169-175, and 177-178, or an amino acid sequence with at least about 95% homology to an amino acid sequence selected from the group consisting of SEQ ID NOs:150-153, 155-158, 160-166, 169-175, and 177-178; and
   (c) an HVR-H3 comprising an amino acid sequence selected from the group consisting of SEQ ID NOs: 179-186, 188, 190-191, 193-197, 199-201, 203-204, 206, 208, 213-214, 216-219, 222-225, 229, 231-234, 236-239, 241, 243-247, 249, and 252-256 or an amino acid sequence with at least about 95% homology to an amino acid sequence selected from the group consisting of SEQ ID NOs:179-186, 188, 190-191, 193-197, 199-201, 203-204, 206, 208, 213-214, 216-219, 222-225, 229, 231-234, 236-239, 241, 243-247, 249, and 252-256.

42. An isolated anti-Sortilin antibody, wherein the anti-Sortilin antibody comprises a light chain variable domain and/or a heavy chain variable domain comprising an amino acid sequence selected from the group consisting of SEQ ID NOs:317-334, 337-338, 341-345, 348-357, 360-365, 368-372, 375-376, 379-380, 389-392, 395-402, 407-414, 421-422, 425-433, 436-444, 447-448, 451-461, 464-465, and 470-479.

43. An isolated anti-Sortilin antibody, wherein the anti-Sortilin antibody competes with one or more antibodies selected from the group consisting of S-2, S-16, S-18, S-19, S-20, S-21, S-22, S-28, S-29, S-82, and any combination thereof for binding to Sortilin.

44. An isolated anti-Sortilin antibody, wherein the anti-Sortilin antibody competes with one or more antibodies selected from the group consisting of S-1, S-3, S-4, S-6, S-7, S-9, S-10, S-14, S-15, S-26, S-32, S-48, S-51, S-55, S57, S-58, S-59, S-61, S-69, S-71, S-73, S-74, S-75, S-85, and any combination thereof for binding to Sortilin.

45. An isolated anti-Sortilin antibody, wherein the anti-Sortilin antibody competes with one or more antibodies selected from the group consisting of S-5, S-12, S-24, S-25, S-30, S-34, S-39, S-40, S-42, S-43, S-44, S-45, S-60, S-63, S-64, S-65, S-66, S-67, S-72, S-76, S-78, S-81, S-83, S-84, and any combination thereof for binding to Sortilin.

46. An isolated anti-Sortilin antibody, wherein the anti-Sortilin antibody competes with one or more antibodies selected from the group consisting of S-8, S-49, S-50, and any combination thereof for binding to Sortilin.

47. An isolated anti-Sortilin antibody which binds essentially the same Sortilin epitope as an antibody selected from the group consisting of: S-1, S-2, S-3, S-4, S-5, S-6, S-7, S-8, S-9, S-10, S-12, S-14, S-15, S-16, S-18, S-19, S-20, S-21, S-22, S-24, S-25, S-26, S-28, S-29, S-30, S-32, S-34, S-39, S-40, S-42, S-43, S-44, S-45, S-48, S-49, S-50, S-51, S-55, S-57, S-58, S-59, S-60, S-61, S-63, S-64, S-65, S-66, S-67, S-69, S-71, S-72, S-73, S-74, S-75, S-76, S-78, S-81, S-82, S-83, S-84, and S-85.

48. An isolated anti-Sortilin antibody, wherein the anti-Sortilin antibody comprises a light chain variable domain and a heavy chain variable domain, wherein the light chain variable domain comprises:
  (a) an HVR-L1 comprising an amino acid sequence selected from the group consisting of SEQ ID NOs:6-16, 20-22, and 24-25, or an amino acid sequence with at least about 95% homology to an amino acid sequence selected from the group consisting of SEQ ID NOs:6-16, 20-22, and 24-25;
  (b) an HVR-L2 comprising an amino acid sequence selected from the group consisting of SEQ ID NOs: 26-40, or an amino acid sequence with at least about 95% homology to an amino acid sequence selected from the group consisting of SEQ ID NOs:26-40; and
  (c) an HVR-L3 comprising an amino acid sequence selected from the group consisting of SEQ ID NOs: 41-50, 52, 54-56, 58-62, 64-66, 68-70, 72, 74, 79-80, 82-85, 88-91, 95, 97-101, 103-107, 109, 111-116, 118, and 121-125, or an amino acid sequence with at least about 95% homology to an amino acid sequence selected from the group consisting of SEQ ID NOs: 41-50, 52, 54-56, 58-62, 64-66, 68-70, 72, 74, 79-80, 82-85, 88-91, 95, 97-101, 103-107, 109, 111-116, 118, and 121-125; and/or
wherein the heavy chain variable domain comprises:
  (a) an HVR-H1 comprising an amino acid sequence selected from the group consisting of SEQ ID NOs: 126-127, 129-130, 133-140, 142, 144-145, and 147-149, or an amino acid sequence with at least about 95% homology to an amino acid sequence selected from the group consisting of SEQ ID NOs:126-127, 129-130, 133-140, 142, 144-145, and 147-149;
  (b) an HVR-H2 comprising an amino acid sequence selected from the group consisting of SEQ ID NOs: 150-153, 155-158, 160-166, 169-175, and 177-178, or an amino acid sequence with at least about 95% homology to an amino acid sequence selected from the group consisting of SEQ ID NOs:150-153, 155-158, 160-166, 169-175, and 177-178; and
  (c) an HVR-H3 comprising an amino acid sequence selected from the group consisting of SEQ ID NOs: 179-186, 188, 190-191, 193-197, 199-201, 203-204, 206, 208, 213-214, 216-219, 222-225, 229, 231-234, 236-239, 241, 243-247, 249, and 252-256 or an amino acid sequence with at least about 95% homology to an amino acid sequence selected from the group consisting of SEQ ID NOs:179-186, 188, 190-191, 193-197, 199-201, 203-204, 206, 208, 213-214, 216-219, 222-225, 229, 231-234, 236-239, 241, 243-247, 249, and 252-256.

49. An isolated anti-Sortilin antibody, wherein the anti-Sortilin antibody comprises a light chain variable domain and a heavy chain variable domain, wherein the light chain variable domain comprises:
  (a) an HVR-L1 comprising the amino acid sequence of RASQSISSYLN (SEQ ID NO:7);
  (b) an HVR-L2 comprising the amino acid sequence of AASSLQS (SEQ ID NO:27); and
  (c) an HVR-L3 comprising the amino acid sequence of QQSDVSPIT (SEQ ID NO:42); and/or
wherein the heavy chain variable domain comprises:
  (a) an HVR-H1 comprising the amino acid sequence of YTFX$_1$X$_2$YX$_3$MX$_4$ (SEQ ID NO:480), wherein X$_1$ is T, G, V, P, L, F, A, or R, X$_2$ is G, A, or S, X$_3$ is Y, M, or L, and X$_4$ is H or W;
  (b) an HVR-H2 comprising the amino acid sequence of X$_1$X$_2$X$_3$PX$_4$X$_5$GX$_6$TX$_7$YAQKFQG (SEQ ID NO:481), wherein X$_1$ is W, I, or G, X$_2$ is I, V, or T, X$_3$ is N, G, or L, X$_4$ is N, S, V, or M, X$_5$ S, G, W, or Q, X$_6$ is G, F, Y, S, N, or R, and X$_7$ is N, R, S, or M; and
  (c) an HVR-H3 comprising the amino acid sequence of ARGKRSSGWYEGYGMDV (SEQ ID NO:180).

50. An isolated anti-Sortilin antibody, wherein the anti-Sortilin antibody comprises a light chain variable domain and a heavy chain variable domain, wherein the light chain variable domain comprises:
  (a) an HVR-L1 comprising the amino acid sequence of RASQSX$_1$X$_2$SNLA (SEQ NO:508), wherein X$_1$ is V or I and X$_2$ is S or G;
  (b) an HVR-L2 comprising the amino acid sequence of GASTRAT (SEQ ID NO:29); and
  (c) an HVR-L3 comprising the amino acid sequence of QQARLGPWT (SEQ ID NO:55); and/or
wherein the heavy chain variable domain comprises:
  (a) an HVR-H1 comprising the amino acid sequence of YTX$_1$X$_2$X$_3$X$_4$X$_5$X$_6$S (SEQ ID NO:509), wherein X$_1$ is F or L, X$_2$ is I or A, X$_3$ is S or K, X$_4$ is Y, T, R. T, G, Q, or H, X$_5$ is Y, T, or L, and X$_6$ is M or I;
  (b) an HVR-H2 comprising the amino acid sequence of X$_1$INPx$_2$GGX$_3$X$_4$SYAX$_5$X$_6$FX$_7$G (SEQ ID NO:510), wherein X$_1$ is I or V, X$_2$ is S, W, Y, V, F, L, or I, X$_3$ is S or T, X$_4$ is T or A, X$_5$ is Q or R, X$_6$ is K, or R, and X$_7$ is Q or R; and
  (c) an HVR-H3 comprising the amino acid sequence of X$_1$RDPX$_2$GX$_3$X$_4$X$_5$X$_6$X$_7$PX$_8$X$_9$RX$_{10}$X$_{11}$X$_{12}$GX$_{13}$DV (SEQ ID NO:511), wherein X$_1$ is A, V, or T, X$_2$ is S, F, or G, X$_3$ is I or A, X$_4$ is A or G, X$_5$ is A, L, or V, X$_6$ is A, L, or P, X$_7$ is G, F, or Y, X$_8$ is A, G, or F, X$_9$ is S, G, or A, X$_{10}$ is Y, G, P, H, or S, is Y or N, X$_{12}$ is Y, L, Q, or R, and X$_{13}$ is M or L.

51. An isolated anti-Sortilin antibody, wherein the anti-Sortilin antibody comprises a light chain variable domain and a heavy chain variable domain, wherein the light chain variable domain comprises:
  (a) an HVR-L1 comprising the amino acid sequence of RASQSISSWLA (SEQ ID NO:8);
  (b) an HVR-L2 comprising the amino acid sequence of KASSLES (SEQ ID NO:28); and
  (c) an HVR-L3 comprising the amino acid sequence of QQADGHIT (SEQ ID NO:62); and/or wherein the heavy chain variable domain comprises:
  (a) an HVR-H1 comprising the amino acid sequence of X₁TFX₂X₃YAX₁X₅ (SEQ ID NO:565), wherein X₁ is G or Y, X₂ is S, R, G, or T, X₃ is S, G, or N, X₄ is I or M, and X₅ is S or A;
  (b) an HVR-H2 comprising the amino acid sequence of GIX₁PX₂X₃GX₄AX₅YAQKFQG-(SEQ ID NO:566), wherein X₁ is I or V, X₂ is I, R, G, A, S, or Q, X₃ is F or G, X₄ is T, R, or W, and X₅ is S, N, Q, or W; and
  (c) an HVR-H3 comprising the amino acid sequence of: ARQGRKGYYYYYGMDV (SEQ ID NO:197).

52. An isolated anti-Sortilin antibody, wherein the anti-Sortilin antibody comprises a light chain variable domain and a heavy chain variable domain, wherein the light chain variable domain comprises:
  (a) an HVR-L1 comprising the amino acid sequence of RSSQX₁LLX₂SNGYNYLD (SEQ ID NO:580), wherein X₁ is S or G and X₂ is H or R;
  (b) an HVR-L2 comprising the amino acid sequence of LGSNRXS (SEQ ID NO:581), wherein X is A or V; and
  (c) an HVR-L3 comprising the amino acid sequence of MQQQETPLT (SEQ ID NO:100); and/or
wherein the heavy chain variable domain comprises:
  (a) an HVR-H1 comprising the amino acid sequence of YSISSX₁X₂YWG (SEQ ID NO:582), wherein X₁ is G or V and X₂ is Y or R;
  (b) an HVR-H2 comprising the amino acid sequence of X₁YX₂SGSTYYNPSLKS (SEQ ID NO:583), wherein X₁ is T, S, or A and X₂ is H or P; and
  (c) an HVR-H3 comprising the amino acid sequence of ARQGSIKQGYYGMDV (SEQ ID NO:233).

53. An isolated anti-Sortilin antibody, wherein the anti-Sortilin antibody comprises a light chain variable domain and a heavy chain variable domain, wherein the light chain variable domain comprises:
  (a) an HVR-L1 comprising the amino acid sequence of RASQSVSSSYLA (SEQ ID NO:14);
  (b) art HVR-L2 comprising the amino acid sequence of GASSRAT (SEQ ID NO:26); and
  (c) art HVR-L3 comprising the amino acid sequence of QQSHVSPWT (SEQ ID NO:122); and/or
wherein the heavy chain variable domain comprises:
  (a) an HVR-H1 comprising the amino acid sequence of X₁SIX₂SX₃X₄YYWG (SEQ NO:589), wherein X₁ is G or Y, X₂ is S, V, Y, K, or P, X₃ is S or R, and X₄ is D or E;
  (b) an HVR-H2 comprising the amino acid sequence of X₁YX₂X₃GSTX₄YNPSLKS (SEQ ID NO:590), wherein X₁ is S, G, Q, or L, X₂ is Y, W, or R, X₃ is S, R, K, or A, and X₄ is Y or V; and
  (c) an HVR-H3 comprising the amino acid sequence of ARGVGSGYSYGYRYFDY (SEQ ID NO:253).

54. The anti-Sortilin antibody of any one of embodiments 1-53, wherein the anti-Sortilin antibody has an IgG1, IgG2, IgG3, or IgG4 isotype.

55. The anti-Sortilin antibody of embodiment 54, wherein:
  (a) the anti-Sortilin antibody has a human or mouse IgG1 isotype and comprises one or more amino acid substitutions in the Fc region at a residue position selected from the group consisting of: N297A, N297Q, D265A, L234A, L235A, C226S, C229S, P238S, E233P, L234V, P238A, A327Q, A327G, P329A, K322A, L234F, L235E, P331S, T394D, A330L, M252Y, S254T, T256E, and any combination thereof, wherein the numbering of the residues is according to EU or Kabat numbering;
  (b) the anti-Sortilin antibody has an IgG2 isotype and comprises one or more amino acid substitutions in the Fc region at a residue position selected from the group consisting of: P238S, V234A, G237A, H268A, H268Q, H268E, V309L, N297A, N297Q, A330S, P331 S, C232S, C233S, M252Y, S254T, T256E, and any combination thereof, wherein the numbering of the residues is according to EU or Kabat numbering; or
  (c) the anti-Sortilin antibody has an IgG4 isotype and comprises one or more amino acid substitutions in the Fc region at a residue position selected from the group consisting of: E233P, F234V, L234A/F234A, L235A, G237A, E318A, S228P, L236E, S241P, L248E, T394D, M252Y, S254T, T256E, N297A, N297Q, and any combination thereof, wherein the numbering of the residues is according to EU or Kabat numbering.

56. The anti-Sortilin antibody of embodiment 55, wherein:
  (a) the Fc region further comprises one or more additional amino acid substitutions at a position selected from the group consisting of A330L, L234F; L235E, P331S, and any combineution thereof, wherein the numbering of the residues is according to EU or Kabat numbering;
  (b) the Fc region further comprises one or more additional amino acid substitutions at a position selected from the group consisting of M252Y, S254T, T256E, and any combination thereof, wherein the numbering of the residues is according to EU or Kabat numbering; or
  (c) the Fc region further comprises a S228P amino acid substitution according to EU or Kabat numbering.

57. The anti-Sortilin antibody of any one of the preceding embodiments, wherein the anti-Sortilin antibody decreases expression of one or more pro-inflammatory mediators selected from the group consisting of IL-6, IL12p70, IL12p40, IL-1β, TNF-α, CXCL1, CCL2, CCL3, CCL4, and CCL5.

58. The anti-Sortilin antibody of any one of the preceding embodiments, wherein the anti-Sortilin antibody has a dissociation constant ($K_D$) for human Sortilin, mouse Sortilin, or both, that ranges from about 100 nM to about 0.005 nM, or less than 0.005 nM.

59. The anti-Sortilin antibody of any one of the preceding embodiments, wherein the anti-Sortilin antibody has dissociation constant ($K_D$) for human Sortilin that ranges from about 70.4 nM to about 0.005 nM, or less than 0.005 nM.

60. The anti-Sortilin antibody of any one of the preceding embodiments, wherein the anti-Sortilin antibody has dissociation constant ($K_D$) for mouse Sortilin that ranges from about 40.3 nM to about 0.07 nM, or less than 0.07 nM.

61. An isolated nucleic acid comprising a nucleic acid sequence encoding the anti-Sortilin antibody of any one of the preceding embodiments.

62. A vector comprising the nucleic acid of embodiment 61.

63. An isolated host cell comprising the vector of embodiment 62.

64. A method of producing an anti-Sortilin antibody, comprising culturing the host cell of embodiment 63 so that the anti-Sortilin antibody is produced.

65. The method of embodiment 64, further comprising recovering the anti-Sortilin antibody produced by the host cell 66. An isolated anti-Sortilin antibody produced by the method of embodiment 64 or embodiment 65.

67. A pharmaceutical composition comprising the anti-Sortilin antibody of any one of embodiments 1-60, and a pharmaceutically acceptable carrier.

68. A method of increasing Progranulin levels an individual in need thereof, comprising administering to the individual a therapeutically effective amount of an anti-Sortilin antibody.

69. The method of embodiment 68, wherein levels of Progranulin are increased in the brain, blood, and/or or one or more peripheral organs of the individual.

70. A method of increasing extracellular levels of Progranulin from one or more cells, comprising contacting one or more cells with an anti-Sortilin antibody.

71. The method of any one of embodiments 68-70, wherein levels of Progranulin are increased without decreasing cellular levels of Sortilin.

72. A method of decreasing cellular levels of Sortilin in an individual in need thereof, comprising administering to the individual a therapeutically effective amount of an anti-Sortilin antibody.

73. The method of embodiment 72, wherein levels of Sortilin are decreased in the brain, and/or one or more peripheral organs of the individual.

74. A method of decreasing cellular levels of Sortilin of one or more cells, comprising contacting one or more cells with an anti-Sortilin antibody.

75. The method of any one of embodiments 68-74, wherein:
  (a) the anti-Sortilin antibody has a property selected from the group consisting of: increasing extracellular levels of Progranulin, increasing cellular levels of Progranulin, decreasing cellular levels of Sortilin, inhibiting interaction between Sortilin and Progranulin, and any combination thereof;
  (b) the anti-Sortilin antibody decreases cell surface levels of Sortilin, decreases intracellular levels of Sortilin, decreases total levels of Sortilin, or any combination thereof;
  (c) the anti-Sortilin antibody induces Sortilin degradation, Sortilin cleavage, Sortilin internalization, Sortilin down regulation, or any combination thereof;
  (d) the anti-Sortilin antibody decreases cellular levels of Sortilin and does not inhibit the interaction between Sortilin and Progranulin;
  (e) the anti-Sortilin antibody decreases cellular levels of Sortilin and inhibits the interaction between Sortilin and Progranulin;
  (f) the anti-Sortilin antibody decreases cellular levels of Sortilin and increases cellular levels of Progranulin;
  (g) the anti-Sortilin antibody increases cellular levels of Progranulin and does not inhibit the interaction between Sortilin and Progranulin;
  (h) the anti-Sortilin antibody inhibits the interaction between Sortilin and Progranulin and increases cellular levels of Progranulin;
  (i) the anti-Sortilin antibody inhibits the interaction between Sortilin and Progranulin and does not decrease cellular levels of Sortilin;
  (j) the anti-Sortilin antibody increases cellular levels of Progranulin and does not decrease cellular levels of Sortilin;
  (k) the anti-Sortilin antibody further inhibits interaction between Sortilin and pro-nerve growth factor (pro-NGF);
  (l) the anti-Sortilin antibody further inhibits interaction between Sortilin and pro-nerve growth factor (pro-NGF) by: a) reducing the effective levels of Sortilin available for interacting with the one or more proteins; b) inducing degradation of Sortilin; or both;
  (m) the anti-Sortilin antibody induces one or more Progranulin activities;
  (n) the anti-Sortilin antibody reduces endosomal internalization of Progranulin, or fragments thereof; and/or
  (o) the anti-Sortilin antibody increases the effective concentration of Progranulin.

76. The method of any one of embodiments 68-75, wherein:
  (a) the anti-Sortilin antibody binds specifically to human Sortilin, mouse Sortilin, or both;
  (b) the anti-Sortilin antibody is a human antibody;
  (c) the anti-Sortilin antibody is a humanized antibody;
  (d) the anti-Sortilin antibody is a bispecific antibody;
  (e) the anti-Sortilin antibody is a bispecific antibody recognizing a first antigen and a second antigen;
  (f) the anti-Sortilin antibody is a bispecific antibody recognizing a first antigen and a second antigen, wherein the first antigen is a Sortilin protein and the second antigen is an antigen facilitating transport across the blood-brain-harrier, and, optionally, wherein the second antigen is selected from the group consisting of Sortilin, transferring receptor (TR), insulin receptor (HIR), insulin-like growth factor receptor (CFR), low-density lipoprotein receptor related proteins 1 and 2 (LPR-1 and 2), diphtheria toxin receptor, CRM197, llama single domain antibody, TMEM 30(A), a protein transduction domain, TAT, Syn-B, penetratin, a poly-arginine peptide, an angiopep peptide, basigin, Glut1, CD98 hc, and ANG1005;
  (g) the anti-Sortilin antibody is a multivalent antibody;
  (h) the anti-Sortilin antibody is a conjugated antibody;
  (i) the anti-Sortilin antibody is a chimeric antibody;
  (j) the anti-Sortilin antibody is a monoclonal antibody;
  (k) the anti-Sortilin antibody is an antibody fragment that binds to an epitope comprising amino acid residues on human Sortilin, or a mammalian Sortilin protein; or
  (l) the anti-Sortilin antibody is an antibody fragment that binds to an epitope comprising amino acid residues on human Sortilin or a mammalian Sortilin protein, and optionally, wherein the fragment is an Fab, Fab', Fab'-SH, F(ab)2, Fv, or say fragment, 77. The method of any one of embodiments 68-76, wherein the anti-Sortilin antibody binds a discontinuous Sortilin epitope.

78. The method of embodiment 77, wherein the discontinuous Sortilin epitope comprises two or more peptides, three or more peptides, four or more peptides, five or more peptides, six or more peptides, seven or more peptide, eight or more peptides, nine or more peptides, or 10 or more peptides.

79. The method of embodiment 78, wherein each of the peptides comprise five or more, six or more, seven or more, eight or more, nine or more, 10 or more, 11 or more, 12 or more, 13 or more 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid residues of the amino acid sequence of SEQ NO: 1; or five or more, six or more, seven or more, eight or more, nine or more, 10 or more, 11 or more, 12 or more, 13 or more 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid residues on a mammalian Sortilin protein corresponding to the amino acid sequence of SEQ ID NO: 1.

80. The method of any one of embodiments 68-76, wherein the anti-Sortilin antibody binds to a conformational epitope of Sortilin.

81. The method of any one of embodiments 68-76, wherein the anti-Sortilin antibody binds to one or more amino acids within amino acid residues selected from the group consisting of:
  i. amino acid residues 740-749 of SEQ ID NO: 1, or amino acid residues on a mammalian Sortilin protein corresponding to amino acid residues 740-749 of SEQ ID NO: 1;
  ii. amino acid residues 623-632 of SEQ ID NO: 1, or amino acid residues on a mammalian Sortilin protein corresponding to amino acid residues 623-632 of SEQ ID NO: 1;
  iii. amino acid residues 429-443 of SEQ ID NO: 1, or amino acid residues on a mammalian Sortilin protein corresponding to amino acid residues 429-443 of SEQ ID NO: 1;
  iv. amino acid residues 367-391 of SEQ NO: 1, or amino acid residues on a mammalian Sortilin protein corresponding to amino acid residues 367-391 of SEQ ID NO: 1;
  v. amino acid residues 314-338 of SEQ ID NO: 1, or amino acid residues on a mammalian Sortilin protein corresponding to amino acid residues 314-338 of SEQ ID NO: 1;
  vi. amino acid residues 297-317 of SEQ ID NO: 1, or amino acid residues on a mammalian Sortilin protein corresponding to amino acid residues 297-317 of SEQ ID NO: 1;
  vii. amino acid residues 237-260 of SEQ ID NO: 1, or amino acid residues on a mammalian Sortilin protein corresponding to amino acid residues 237-260 of SEQ ID NO: 1;
  viii. amino acid residues 237-260 and 297-317 of SEQ ID NO: 1, or amino acid residues on a mammalian Sortilin protein corresponding to amino acid residues 237-260 and 297-317 of SEQ ID NO: 1;
  ix. amino acid residues 237-247 of SEQ ID NO: 1, or amino acid residues on a mammalian Sortilin protein corresponding to amino acid residues 237-247 of SEQ ID NO: 1;
  x. amino acid residues 237-247 and 314-338 of SEQ ID NO: 1, or amino acid residues on a mammalian Sortilin protein corresponding to amino acid residues 237-247 and 314-338 of SEQ ID NO: 1;
  xi. amino acid residues 233-243 of SEQ NO: 1, or amino acid residues on a mammalian Sortilin protein corresponding to amino acid residues 233-243 of SEQ ID NO: 1;
  xii. amino acid residues 212-221 of SEQ ID NO: 1, or amino acid residues on a mammalian Sortilin protein corresponding to amino acid residues 212-221 of SEQ ID NO: 1;
  xiii. amino acid residues 207-227 of SEQ ID NO: 1, or amino acid residues on a mammalian Sortilin protein corresponding to amino acid residues 207-227 of SEQ ID NO: 1;
  xiv. amino acid residues 207-227 and 237-260 of SEQ ID NO: 1, or amino acid residues on a mammalian Sortilin protein corresponding to amino acid residues 207-227 and 237-260 of SEQ ID NO: 1;
  xv. amino acid residues 207-231 of SEQ ID NO: 1, or amino acid residues on a mammalian Sortilin protein corresponding to amino acid residues 207-231 of SEQ ID NO: 1;
  xvi. amino acid residues 175-181 of SEQ ID NO: 1, or amino acid residues on a mammalian Sortilin protein corresponding to amino acid residues 175-181 of SEQ ID NO: 1; and
  xvii. amino acid residues 131-138 of SEQ ID NO: 1, or amino acid residues on a mammalian Sortilin protein corresponding to amino acid residues 131-138 of SEQ ID NO: 1.

82. The method of any one of embodiments 68-76, wherein the anti-Sortilin antibody binds to one or more amino acid residues selected from the group consisting of H131, V132, P133, L134, V135, I136, M137, T138, T210, T218, Y222, S223, S227, S242, K243, K248, K254, S305, S311, S316, R325, S379, R382, Y386, and S595 of SEQ ID NO: 1, or one or more amino acid residues on a mammalian Sortilin protein corresponding to an amino acid residue selected from the group consisting of H131, V132, P133, L134, V135, I136, M137, T138, T210, T218, Y222, S223, S227, S242, K243, K248, K254, S305, R311, S316, R325, S379, R382, Y386, and S595 of SEQ ID NO: 1.

83. The method of any one of embodiments 68-76, wherein the anti-Sortilin antibody binds to one or more amino acid residues selected from the group consisting of R88, F105, L108, R109, G110, D403, D449, T451, H461, G495, Y513, S530, I537, D552, F569, E590, F592, L593, S595, W597, I619, L621, E628, D632, L636, Q642, R646, and Y679 of SEQ ID NO: 1, or one or more amino acid residues on a mammalian Sortilin protein corresponding to an amino acid residue selected from the group consisting of R88, F105, L108, R109, G110, D403, D449, T451, H461, G495, Y513, S530, I537, D552, F569, E590, F592, L593, S595, W597, I619, L621, E628, D632, L636, Q642, R646, and Y679.

84. The method of any one of embodiments 68-83, wherein the anti-Sortilin antibody comprises at least one, two, three, four, five, or six HVRs of an antibody selected from the group consisting of: S-1, S-2, S-3, S-4, S-5, S-6, S-7, S-8, S-9, S-10, S-12, S-14, S-15, S-16, S-18, S-19, S-20, S-21, S-22, S-24, S-25, S-26, S-28, S-29, S-30, S-32, S-34, S-39, S-40, S-42, S-43, S-44, S-45, S-48, S-49, S-50, S-51, S-55, S-57, S-58, S-59, S-60, S-61, S-63, S-64, S-65, S-66, S-67, S-69, S-71, S-72, S-73, S-74, S-75, S-76, S-78, S-81, S-82, S-83, S-84, and S-85, 85. The method of embodiment 84, wherein the anti-Sortilin antibody comprises:
  (a) an HVR-L1 comprising an amino acid sequence selected from the group consisting of SEQ ID NOs:6-16, 20-22, and 24-25;
  (b) an HVR-L2 comprising an amino acid sequence selected from the group consisting of SEQ ID NOs: 26-40;
  (c) an HVR-L3 comprising an amino acid sequence selected from the group consisting of SEQ ID NOs: 41-50, 52, 54-56, 58-62, 64-66, 68-70, 72, 74, 79-80, 82-85, 88-91, 95, 97-101, 103-107, 109, 111-116, 118, and 121-125;
  (d) an HVR-H1 comprising an amino acid sequence selected from the group consisting of SEQ ID NOs: 126-127, 129-130, 133-140, 142, 144-145, and 147-149;
  (e) an HVR-H2 comprising an amino acid sequence selected from the group consisting of SEQ ID NOs: 150-153, 155-158, 160-166, 169-175, and 177-178; or
  (f) an HVR-H3 comprising an amino acid sequence selected from the group consisting of SEQ ID NOs: 179-186, 188, 190-191, 193-197, 199-201, 203-204, 206, 208, 213-214, 216-219, 222-225, 229, 231-234, 236-239, 241, 243-247, 249, and 252-256.

86. The method of any one of embodiments 68-82, wherein the anti-Sortilin antibody comprises a light chain variable domain and a heavy chain variable domain, wherein the light chain variable domain comprises:
  (a) an HVR-L1 comprising an amino acid sequence selected from the group consisting of SEQ ID NOs:6-16, 20-22, and 24-25, or an amino acid sequence with at least about 95% homology to an amino acid sequence selected from the group consisting of SEQ ID NOs:6-16, 20-22, and 24-25;
  (b) an HVR-L2 comprising an amino acid sequence selected from the group consisting of SEQ ID NOs: 26-40, or an amino acid sequence with at least about 95% homology to an amino acid sequence selected from the group consisting of SEQ ID NOs:26-40; and
  (c) an HVR-L3 comprising an amino acid sequence selected from the group consisting of SEQ ID NOs: 41-50, 52, 54-56, 58-62, 64-66, 68-70, 72, 74, 79-80, 82-85, 88-91, 95, 97-101, 103-107, 109, 111-116, 118, and 121-125, or an amino acid sequence with at least about 95% homology to an amino acid sequence selected from the group consisting of SEQ ID NOs: 41-50, 52, 54-56, 58-62, 64-66, 68-70, 72, 74, 79-80, 82-85, 88-91, 95, 97-101, 103-107, 109, 111-116, 118, and 121-125; and wherein the heavy chain variable domain comprises:
  (a) an HVR-H1 comprising an amino acid sequence selected from the group consisting of SEQ ID NOs: 126-127, 129-130, 133-140, 142, 144-145, and 147-149, or an amino acid sequence with at least about 95% homology to an amino acid sequence selected from the group consisting of SEQ ID NOs:126-127, 129-130, 133-140, 142, 144-145, and 147-149;
  (b) an HVR-H2 comprising an amino acid sequence selected from the group consisting of SEQ ID NOs: 150-153, 155-158, 160-166, 169-175, and 177-178, or an amino acid sequence with at least about 95% homology to an amino acid sequence selected from the group consisting of SEQ ID NOs:150-153, 155-158, 160-166, 169-175, and 177-178; and
  (c) an HVR-H3 comprising an amino acid sequence selected from the group consisting of SEQ ID NOs: 179-186, 188, 190-191, 193-197, 199-201, 203-204, 206, 208, 213-214, 216-219, 222-225, 229, 231-234, 236-239, 241, 243-247, 249, and 252-256 or an amino acid sequence with at least about 95% homology to an amino acid sequence selected from the group consisting of SEQ ID NOs:179-186, 188, 190-191, 193-197, 199-201, 203-204, 206, 208, 213-214, 216-219, 222-225, 229, 231-234, 236-239, 241, 243-247, 249, and 252-256.

87. The method of any one of embodiments 68-82, wherein the anti-Sortilin antibody comprises a light chain variable domain and a heavy chain variable domain, wherein:
  (a) the light chain variable domain comprises an HVR-L1 comprising the amino acid sequence of RASQSIS-SYLN (SEQ ID NO:7); an HVR-L2 comprising the amino acid sequence of AASSLQS (SEQ ID NO:27); and an HVR-L3 comprising the amino acid sequence of QQSDVSPIT (SEQ ID NO:42); and/or the heavy chain variable domain comprises an HVR-H1 comprising the amino acid sequence of YTFX$_1$X$_2$YX$_3$MX$_4$ (SEQ ID NO:480), wherein X$_1$ is T, G, V, P, L, F, A, or R, X$_2$ is G, A, or S, X$_3$ is Y, M, or L, and X$_4$ is H or W; an HVR-H2 comprising the amino acid sequence of X$_1$X$_2$X$_3$PX$_4$X$_5$GX$_6$TX$_7$YAQKFQG (SEQ ID NO:481), wherein X$_1$ is W, I, or G, X$_2$ is V, or T, X$_3$ is N, G, or L, X$_4$ is N, S, V, or M, X$_5$ is S, G W, or Q, X$_6$ is G, F, A, Y, S, N, or R, and X$_7$ is N, R, S, or M; and an HVR-H3 comprising the i acid sequence of ARGKRSSGWYEGYGMDV (SEQ ID NO:180);
  (b) the light chain variable domain comprises an HVR-L1 comprising the amino acid sequence of RASQSX$_1$X$_2$SNLA (SEQ NO:508), wherein X$_1$ is V or I and X$_2$ is S or G; an HVR-L2 comprising the amino acid sequence of GASTRAT (SEQ ID NO:29); and an HVR-L3 comprising the amino acid sequence of QQARLGPWT (SEQ ID NO:55); and/or the heavy chain variable domain comprises an HVR-H1 comprising the amino acid sequence of YTX$_1$X$_2$X$_3$X$_4$X$_5$X$_6$S (SEQ ID NO:509), wherein X$_1$ is F or L, X$_2$ is T or A, X$_3$ is S or K, X$_4$ is Y, T, R, L, T, G, Q, or H, X$_5$ is Y, T, or L, and X$_6$ is M or I; an HVR-H2 comprising the amino acid sequence of X$_1$INPx$_2$GGX$_3$X$_4$SYAX$_5$X$_6$FX$_7$G (SEQ ID NO:510), wherein X$_1$ is I or V, X$_2$ is S, W, Y, V, F, L, or I, X$_3$ is S or T X$_4$ is T or A, X$_5$ is Q or R, X$_6$ is K, or R, and X$_7$ is Q or R; and an HVR-H3 comprising the amino acid sequence of X$_1$RDPX$_2$GX$_3$X$_4$X$_5$X$_6$X$_7$PX$_8$X$_9$RX$_{10}$X$_{11}$X$_{12}$GX$_{13}$DV (SEQ ID NO:511), wherein X$_1$ is A, V, or T, X$_2$ is S, F, or G, X$_3$ is I or A, X$_4$ is A or G, X$_5$ is A, L, or V, X$_6$ is A, L, or P, X$_7$ is G, F, or Y, X$_8$ is A, G, or F, is S, G, or A, X$_{10}$ is Y, G, P, H, or S, X$_{11}$ is Y or N, X$_{12}$ is Y, L, Q, or R, and X$_{13}$ is M or L;
  (c) the light chain variable domain comprises an HVR-L1 comprising the amino acid sequence of RASQSISS-WLA (SEQ ID NO:8); an HVR-L2 comprising the amino acid sequence of KASSLES (SEQ ID NO:28); and an HVR-L3 comprising the amino acid sequence of QQADGHIT (SEQ ID NO:62); and/or the heavy chain variable domain comprises an HVR-H1 comprising the amino acid sequence of X$_1$TFX$_2$X$_3$YAX$_4$X$_5$ (SEQ ID NO:565), wherein X$_1$ is G or Y, X$_2$ is S, R, G, or T, X$_3$ is S, G, or N, X$_4$ is I or M, and X$_5$ is S or A; an HVR-H2 comprising the amino acid sequence of GIX$_1$PX$_2$X$_3$GX$_4$AX$_5$YAQKFQG (SEQ ID NO:566), wherein X$_1$ is I or V, X$_2$ is I, R, G, A, S, T, or Q, X$_3$ is F or G, X$_4$ is T, R, or W, and X$_5$ is S, N, Q, or W; and an HVR-H3 comprising the amino acid sequence of ARQGRKTGYYYYYGMDV (SEQ ID NO:197);
  (d) the light chain variable domain comprises an HVR-1 comprising the amino acid sequence of RSSQX$_1$LLX$_2$SNGYNYLD (SEQ ID NO:580), wherein X$_1$ is S or G and X$_2$ is H or R; an HVR-L2 comprising the amino acid sequence of LGSNRXS (SEQ NO:581), wherein X is A or V; and an HVR-L3 comprising the amino acid sequence of MQQQETPLT (SEQ ID NO:100); and/or the heavy chain variable domain comprises an HVR-H1 comprising the amino acid sequence of YSISSX$_1$X$_2$YWG (SEQ ID NO:582), wherein X$_1$ is G or V and X$_2$ is Y or R; an HVR-H2 comprising the amino acid sequence of X$_{11}$YX$_2$SGSTYYNPSLKS (SEQ ID NO:583), wherein X$_1$ is T, S, or A and X$_2$ is H or P; and an HVR-H3 comprising the amino acid sequence of ARQGSIKQGYYGMDV (SEQ ID NO:233); or
  (e) the light chain variable domain comprises an HVR-L1 comprising the amino acid sequence of RASQSVSS-SYLA (SEQ ID NO:14); an HVR-112 comprising the amino acid sequence of GASSRAT (SEQ ID NO:26); and an HVR-L3 comprising the amino acid sequence of QQSHVSPWT (SEQ ID NO:122); and/or the heavy chain variable domain comprises an HVR-H1 comprising the amino acid sequence of $X_1SIX_2SX_3X_4YYWG$ (SEQ ID NO:589), wherein $X_1$ is G or Y, $X_2$ is S, V, Y, K, or P, $X_3$ is S or R, and $X_4$ is D or E; an HVR-H2 comprising the amino acid sequence of $X_1IYX_2X_3GSTX_4YNPSLKS$ (SEQ ID NO:590), wherein $X_1$ is S, G, Q, or L, $X_2$ is Y, W, R, $X_3$ is S, R, K, or A, and $X_4$ is Y or V; and an HVR-H3 comprising the amino acid sequence of ARGVGSGYSYGYRYFDY (SEQ ID NO:253).

88. The method of any one of embodiments 68-82, wherein:
    (a) the anti-Sortilin antibody competes with one or more antibodies selected from the group consisting of S-6, S-8, S-49, S-60, S-63, S-72, S-83, and any combination thereof for binding to Sortilin;
    (b) the anti-Sortilin antibody competes with one or more antibodies selected from the group consisting of S-5, S-45, S-64, S-65, and any combination thereof for binding to Sortilin;
    (c) the anti-Sortilin antibody competes with one or more antibodies selected from the group consisting of S-5, S-30, S-60, and any combination thereof for binding to Sortilin;
    (d) the anti-Sortilin antibody competes with one or more antibodies selected from the group consisting of S-2, S-16, S-18, S-19, S-20, S-21, S-22, S-28. S-29, S-82, and any combination thereof for binding to Sortilin;
    (e) the anti-Sortilin antibody competes with one or more antibodies selected from the group consisting of S-1, S-3, S-4, S-6, S-7, S-9, S-10, S-14, S-15, S-26, S-32, S-48, S-51, S-55, S57, S-58, S-59, S-61, S-69, S-71, S-73, S-74, S-75, S-85, and any combination thereof for binding to Sortilin;
    (f) the anti-Sortilin antibody competes with one or more antibodies selected from the group consisting of S-5, S-12, S-24, S-25, S-30, S-34, S-39, S-40, S-42, S-43, S-44, S-45, S-60, S-63, S-64, S-65, S-66, S-67, S-72, S-76, S-78, S-81, S-83, S-84, and any combination thereof for binding to Sortilin;
    (g) the anti-Sortilin antibody competes with one or more antibodies selected from the group consisting of S-8, S-49, S-50, and any combination thereof for binding to Sortilin; or
    (h) the anti-Sortilin antibody which binds essentially the same Sortilin epitope as an antibody selected from the group consisting of: S-1, S-2, S-3, S-4, S-5, S-6, S-7, S-8, S-9, S-10, S-12, S-14, S-15, S-16, S-18, S-19, S-20, S-21, S-22, S-24, S-25, S-26, S-28, S-29, S-30, S-32, S-34, S-39, S-40, S-42, S-43, S-44, S-45, S-48, S-49, S-50, S-51, S-55, S-57, S-58, S-59, S-60, S-61, S-63, S-64, S-65, S-66, S-67, S-69, S-71, S-72, S-73, S-74, S-75, S-76, S-78, S-81, S-82, S-83, S-84, and S-85.

89. The method of any one of embodiments 68-82, wherein the anti-Sot/inn antibody comprises a light chain variable domain and/or a heavy chain variable domain comprising an amino acid sequence selected from the group consisting of SEQ ID NOs:317-334, 337-338, 341-345, 348-357, 360-365, 368-372, 375-376, 379-380, 389-392, 395-402, 407-414, 421-422, 425-433, 436-444, 447-448, 451-461, 464-465, and 470-479.

90. The method of any one of embodiments 68-89, wherein:
    (a) the anti-Sortilin antibody is of the IgG class the IgM class, or the IgA class;
    (b) the anti-Sortilin antibody has an IgG1, IgG2, IgG3, or IgG4 isotype;
    (c) the anti-Sortilin antibody has a human or mouse IgG1 isotype and comprises one or more amino acid substitutions in the Fc region at a residue position selected from the group consisting of: N297A, N297Q, D265A, L234A, L235A, C226S, C229S, P238S, E233P, L234V, P238A, A327Q, A327G, P329A, K322A, L234F, L235E, P331S, T394D, A330L, M252Y, 5254T, T256E, and any combination thereof, wherein the numbering of the residues is according to EU or Kabat numbering;
    (d) the anti-Sortilin antibody has an IgG2 isotype and comprises one or more amino acid substitutions in the Fc region at a residue position selected from the group consisting of P238S, V234A, G237A, H268A, H268Q H268E, V309L, N297A, N297Q, A330S, P331S, C232S, C233S, M252Y, S254T, T256E, and any combination thereof, wherein the numbering of the residues is according to EU or Kabat numbering; or
    (e) the anti-Sortilin antibody has an IgG4 isotype and comprises one or more amino acid substitutions in the Fc region at a residue position selected from the group consisting of: E233P, F234V, L234A/F234A, L235A, G237A, E318A, S228P, L236E, S241P, L248E, T394D, M252Y, S254T, T256E, N297A, N297Q, and any combination thereof, wherein the numbering of the residues is according to EU or Kabat numbering.

91. The method of embodiment 90, wherein the Fc region of one or more of (c), (d), and (e) further comprises:
    (a) one or more additional amino acid substitutions at a position selected from the group consisting of A330L, L234F; L235E, P331S, and any combination thereof, wherein the numbering of the residues is according to EU or Kabat numbering;
    (b) one or more additional amino acid substitutions at a position selected from the group consisting of M252Y, S254T, T256E, and any combination thereof, wherein the numbering of the residues is according to EU or Kabat numbering; or
    (c) a S228P amino acid substitution according to EU or Kabat numbering.

92. The method of any one of embodiments 68-91, wherein:
    (a) the anti-Sortilin antibody has a dissociation constant ($K_D$) for human Sortilin, mouse Sortilin, or both, that ranges from about 100 nM to about 0.005 nM, or less than 0.005 nM;
    (b) the anti-Sortilin antibody has dissociation constant ($K_D$) for human Sortilin that ranges from about 70.4 nM to about 0.005 nM, or less than 0.005 nM; or
    (c) the anti-Sortilin antibody has dissociation constant ($K_D$) for mouse Sortilin that ranges from about 40.3 nM to about 0.07 nM, or less than 0.07 nM.

93. A method of preventing, reducing risk, or treating an individual having a disease, disorder, or injury selected from the group consisting of frontotemporal dementia, progressive supranuclear palsy, Alzheimer's disease, vascular dementia, seizures, retinal dystrophy, amyotriphic lateral sclerosis, traumatic brain injury a spinal cord injury, dementia, stroke, Parkinson's disease, acute disseminated encephalomyelitis, retinal degeneration, age related macular degeneration, glaucoma, multiple sclerosis, septic shock, bacterial infection, arforitis, and osteoarthritis, comprising administering to the individual a therapeutically effective amount of the anti-Sortilin antibody of any one of embodiments 1-60.

94. A method of inhibiting one or more of neuroinflammation, axonopathy characterized by short axonal outgrowth and aberrant branching, microglial activation, and inflammatory response, comprising administering to the individual a therapeutically effective amount of the anti-Sortilin antibody of any one of embodiments 1-60.

95. A method of promoting one or more of wound healing, autophagy, and clearance of aggregate proteins, comprising administering to the individual a therapeutically effective amount of the anti-Sortilin antibody of any one of embodiments 1-60.

96. A method of preventing, reducing risk, or treating an individual having arforitis, comprising administering to the individual a therapeutically effective amount of the anti-Sortilin antibody of any one of embodiments 1-60.

97. A method of decreasing expression of one or more pro-inflammatory mediators, comprising administering to the individual a therapeutically effective amount of the anti-Sortilin antibody of any one of embodiments 1-60.

98. The method of embodiment 97, wherein the one or more pro-inflammatory mediators are selected from the group consisting of IL-6, 1L12p70, IL12p40, IL-1β, TNF-α, CXCL1, CCL2, CCL3, CCL4, and CCL5.

99. The method of any one of embodiment 68-98, wherein the anti-Sortilin antibody comprises two or more anti-Sortilin antibodies.

EXAMPLES

Example 1: Production Identification, and Characterization of Anti-Sortilin Antibodies
Introduction Anti-Sortilin antibodies may be identified using established yeast-based antibody presentation libraries, for example, as disclosed in WO 2009/036379, WO 2010/105256, WO 2012/009568, US 2009/0181855, and US 2010/0056386. Such libraries can be used to identify anti-Sortilin antibodies that block the interaction between Sortilin and a Sortilin ligand, such as Progranulin and/or pro-NGF, and/or anti-Sortilin antibodies that cross-react with other mammalian Sortilin proteins, such as mouse Sortilin, rat Sortilin, and/or primate Sortilin.

Alternatively, standard yeast display screening protocols, as described in Patrick Chames (ed.), *Antibody Engineering: Methods and Protocols, Second Edition*, Methods in Molecular Biology, vol. 907, Springer Science+Business Media, LLC 2012 Chapter 15, Selection of Antibody Fragments by Yeast Display by Nathalie Scholler, may be used.

The antibodies can also be generated by any other established method of antibody production, such as those described in *Antibody Engineering: Methods and Protocols, Second Edition*, Methods in Molecular Biology, vol. 907, Springer Science+Business Media, LLC 2012.

The ability of antibodies to inhibit interactions between Sortilin and its ligands can then be validated in multiple, established biochemical and/or cell-based assays, including but not limited to surface plasmon resonance analysis, co-immunoprecipitation, pulldown assays, cellulose-bound protein assays, β-galactosidase complementation assays, cell population FRET assays, proximity ligation assays, and cell binding assays.

As described herein, 85 anti-Sortilin antibodies were identified and characterized.

Materials and Methods

Production of Monomeric and Fc-Conjugated Human and Mouse Sortilin

Mammalian expression of Sortilin antigen was performed by cloning synthetic genes based on cDNA into mammalian expression vectors, followed by transient transfection and expression in HEK293Tcells. Constructs included a heterologous signal peptide and human IgG1 Fc for Fc fusion constructs. Briefly, expression vectors containing the antigen of interest were transfected by complexing with a transfection reagent followed by exposure to HEK293Tcells for one hour followed by dilution of culture media to a final density of 4 million cells per mL. The cells were then cultured for 7 days with fresh feed media every 48 hours. After 7 days, the supernatant was collected following centrifugation and purification was performed using protein Ni-sepharose and if necessary a SEC column purification to reach >95% non-aggregated monomer content. Sortilin monomer antigens were prepared by fragmenting a Sortilin Fc fusion antigen with modified hinge region (Lynaugh et al., MAbs. 2013 October; 5(5):641-45) with FabRICATOR (IdeS) protease (Genovis, Cat #A2-FR2-1000), followed by Protein A affinity purification to remove undigested Fc fusion protein and SEC to remove aggregated monomer.

Biotinylated Sortilin and Progranulin

Protein reagent biotinylation was performed using the EZ-Link Sulfo-NHS-Biotinylation Kit, Thermo Scientific, Cat #21425.

Sortilin and Progranulin were concentrated to ~1 mg/mL and buffer exchanged into PBS before addition of 1:7.5 molar ratio biotinylation reagent (EZ-Link Sulfo-NHS-Biotinylation Kit, Thermo Scientific, Cat #21425.). The mixture was held at 4° C. overnight prior to another buffer exchange to remove free biotin in the solution. Biotinylation was confirmed through Streptavidin sensor binding of the labeled proteins on a ForteBio.

Sortilin Antibody Screen

Eight nave human synthetic yeast libraries each of ~$10^9$ diversity were designed, generated, and propagated as described previously (see, e.g., Xu et al, 2013; WO2009036379; WO2010105256; WO2012009568; Xu et al., Protein Eng Des Sel. 2013 October; 26(10):663-70). Ten parallel selections were performed, using the eight naïve libraries for human Sortilin Fc fusion antigen selections and two pools of the eight libraries for human Sortilin monomer selections. For the first two rounds of selection, a magnetic bead sorting technique utilizing the Miltenyi MACs system was performed, essentially as described (Siegel et al., J Immunol Methods. 2004 March; 286(1-2):141-53). Briefly, yeast cells (~$10^{10}$ cells/library) were incubated with 3 ml of 10 nM biotinylated Sortilin Fc fusion antigen or 100 nM biotinylated Sortilin monomer antigen for 15 min at room temperature in FACS wash buffer PBS with 0.1% BSA. After washing once with 50 ml ice-cold wash buffer, the cell pellet was resuspended in 40 mL wash buffer, and 500 µl Streptavidin MicroBeads (Miltenyi Biotec, Bergisch Gladbach, Germany. Cat #130-048-101) were added to the yeast and incubated for 15 min at 4° C. Next, the yeast were pelleted, resuspended in 5 mL wash buffer, and loaded onto a MACS LS column (Miltenyi Biotec, Bergisch Gladbach, Germany, Cat#130-042-401). After the 5 mL was loaded, the column was washed 3 times with 3 ml FACS wash buffer. The column was then removed from the magnetic field, and the yeast were eluted with 5 mL of growth media and then grown overnight. The following four rounds of sorting were performed using flow cytometry. Approximately 1×$10^8$ yeast were pelleted, washed three times with wash buffer, and incubated with 10 nM biotinylated Sortilin Fc fusion antigen or 100 nM biotinylated Sortilin monomer antigen for 10 min at room temperature. Yeast were then washed twice and stained with goat anti-human F(ab')$_2$ kappa-FITC diluted 1:100 (Southern Biotech, Birmingham, Ala., Cat #2062-0) and either streptavidin-Alexa Fluor 633 (Life Technologies, Grand Island, N.Y., Cat #S21375) diluted 1:500, or Extravidin-phycoerthyrin (Sigma-Aldrich, St Louis, Cat 4 E4011) diluted 1:50, secondary reagents for 15 min at 4° C. After washing twice with ice-cold wash buffer, the cell pellets were resuspended in 0.4 mL wash buffer and transferred to strainer-capped sort tubes. Sorting was performed using a FACS ARIA sorter (BD Biosciences) and sort gates were determined to select only Sortilin binding clones for one round and the second round was a negative sort to decrease reagent binders, polyspecific binders (Xu et al., PEDS. 2013 October; 26(10):663-70), and binders to control protein human SorCS1 HIS tagged monomer. The third round utilized labeling with 10 nM human and mouse Sortilin Fc fusion antigens, 100 nM human Sortilin monomer antigen, and competition with Progranulin using Sortilin antigens (10 nM) pre-complexed with 500 nM Progranulin. For yeast competitive with Progranulin, a final round to enrich Sortilin Fc fusion antigen binders was performed. After the final round of sorting, yeast were plated and individual colonies were picked for characterization.

Heavy chains from the second and fourth FACS sorting selection round outputs were used to prepare light chain diversification libraries used for additional selections. For these selections, the first selection round utilized Miltenyi MACs beads and labeling with 10 nM human Sortilin Fc fusion antigen. Four rounds of FACS sorting followed. The first round used 100 nM human Sortilin monomer antigen. The second FACS round was a negative sort to decrease binding to reagent binders, polyspecific binders, and binders to control protein human SorCS1 HIS tagged monomer. The last two rounds utilized human Sortilin monomer titration (100 nM, 10 nM, and 1 nM) to select highest affinity binders, 100 nM mouse Sortilin monomer, and competition with control 3E3 antibody to assess competitor representation in the enriched population. After the final round of sorting, yeast were plated and individual colonies were picked for characterization.

Antibody IgG and Fab Production and Purification

Yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over CaptureSelect IgG-CH1 affinity matrix (LifeTechnologies, Cat #1943200250).

ForteBio Binding Experiments

The affinity for the Sortilin antibodies was determined by measuring their $K_D$ by ForteBio. ForteBio affinity measurements were performed generally as previously described (Estep et al., MAbs. 2013 March-April; 5(2):270-8). Briefly, ForteBio affinity measurements were performed by loading IgGs on-line onto AHQ sensors. Sensors were equilibrated off-line in assay buffer for 30 min and then monitored on-line for 60 seconds for baseline establishment. For avid binding measurement, sensors with loaded IgGs were exposed to 100 nM antigen (human or mouse Sortilin Fc fusion) for 3, afterwards they were transferred to assay buffer for 3 min for off-rate measurement. Additional avid binding was determined by loading biotinylated Sortilin monomer on SA sensors and exposure to ~100 nM IgG in solution. Monovalent binding measurements were obtained by loading human or mouse Sortilin Fc fusion antigens to AHQ sensor and followed by exposure to 100 nM Sortilin antibody Fab. Additional monovalent measurements were made by loading biotinylated human or mouse Sortilin monomer to SA sensor followed by exposure to 100 nM Fab in solution.

Kinetics data were fit using a 1:1 binding model in the data analysis software provided by ForteBio.

Epitope Binning

Epitope binning of the anti-Sortilin antibodies was performed on a ForteBio Octet Red384 system (ForteBio, Menlo Park, Calif.) using a standard sandwich format binning assay. Control anti-target IgG was loaded onto AHQ sensors and unoccupied Fc-binding sites on the sensor were blocked with a non-relevant human IgG1 antibody. The sensors were then exposed to 100 nM target antigen followed by a second anti-target antibody. Data was processed using ForteBio's Data Analysis Software 7.0. Additional binding by the second antibody after antigen association indicates an unoccupied epitope (non-competitor), while no binding indicates epitope blocking (competitor). This process was iterated for four control antibodies: (i) 3E3, which binds to Domain 1 of Sortilin (bin 1); (ii) S-29, which hinds to Domain 2 of Sortilin (bin 2_, (iii) S-3, which binds to Domain 3 of Sortilin (bin 3); and S-40, which binds to Domain 4 of Sortilin (bin 4). Antibody bins are listed in TABLE 5 below. Similar binning methods may be used to determine competition between anti-Sortilin antibodies and full length human or mouse Progranulin, as well as between anti-Sortilin antibodies and a C-terminal Progranulin peptide.

Progranulin Competition Assays

All experiments were performed on a ForteBio HTX instrument. All samples were diluted into PBSF (0.1% BSA in PBS). All dip and read ForteBio steps involved shaking at 1000 rpm.

Competition for Progranulin was assessed utilizing three ForteBio assays.

Assay 1: Progranulin Competition Experiments with Biotinylated Progranulin C-Terminal Peptide:

SA sensors were soaked in PBS for 10 min prior to analysis. The blank sensors were dipped into biotinylated Progranulin (PGRN) C-terminal peptide (Bio-TKCLR-REAPRWDAPLRDPA LRQLL (SEQ ID NO:693)) at 100 nM and then soaked in PBSF for at least 10 min prior to analysis. The peptide-loaded tips were sequentially dipped into PBSF (60 s), human Sortilin monomer (100 nM) for 3 min, and finally 100 nM antibody. The data was prepared for analysis with ForteBio Data Analysis Software version 8.1.0.36 as follows. The data was y-axis aligned and inter-step corrected to the beginning of the Sortilin capture step and then cropped to show only the Sortilin capture and antibody interaction steps. Assays in which no binding signal was observed upon addition of a given test Sortilin antibody solution indicated that the test Sortilin antibody binding site overlaps with the PRGN-peptide binding site on the surface of Sortilin. Assays in which a binding signal was observed upon addition of a given test Sortilin antibody solution indicated that the test Sortilin antibody does not block PRGN peptide binding to Sortilin.

Assay 2: Progranulin Competition Experiments with Biotinylated Human Sortilin Monomer:

SA sensors were soaked in PBS for 10 min prior to analysis. The blank sensors were dipped into biotinylated human Sortilin monomer (100 nM) and were then soaked in PBSF for 10 min prior to the analysis. The Sortilin-loaded tips were sequentially dipped into PBSF (1 min), Progranulin (1.0 uM) for 3 min and finally 100 nM antibody. The data was prepared for analysis with ForteBio Data Analysis Software version 8.1.0.36 as follows. The data was y-axis aligned and inter-step corrected to the beginning of the Progranulin capture step and then cropped to show only the Progranulin capture and antibody interaction steps. Assays in which no binding signal was observed upon addition of a given test Sortilin antibody solution indicated that the test Sortilin antibody binding site overlaps with the Progranulin binding site on the surface of Sortilin. Assays in which a binding signal was observed upon addition of a given test Sortilin antibody solution indicated that the Sortilin antibody does not block Progranulin binding to Sortilin.

Assay 3: Progranulin Competition Experiments with Biotinylated-Progranulin:

SA sensors were soaked in PBS for 10 min prior to analysis. The blank sensors were dipped into biotinylated Progranulin (100 nM) and were then soaked in PBSF for 10 min prior to the analysis. The Progranulin loaded tips were sequentially dipped into PBSF (1 min), 100 nM human Sortilin monomer (3 min) and finally 100 nM antibody. The data was prepared for analysis with ForteBio Data Analysis Software version 8.1.0.36 as follows. The data was y-axis aligned and inter-step corrected to the beginning of the Sortilin capture step and then cropped to show only the Sortilin capture and antibody interaction steps. Assays in which no binding signal was observed upon addition of a given test Sortilin antibody solution indicated that the Sortilin antibody binding site overlaps the Progranulin binding site on the surface of Sortilin. Assays in which a binding signal was observed upon addition of a given test Sortilin antibody solution indicated that the Sortilin antibody does not block Progranulin binding to Sortilin.

Results

Anti-Sortilin Antibody Production

Antibodies that bind to Sortilin, particularly within the Vps10p domain located at amino acid residues 78-611 of human Sortilin (SEQ ID NO: 1), were identified from eight naïve human synthetic yeast libraries, as described above. A total of 85 antibodies were generated (S-1 through S-85). The antibodies were then screened for Sortilin binding.

Antibody Heavy Chain and Light Chain Variable Domain Sequences

Using standard techniques, the amino acid sequences encoding the heavy chain variable and the light chain variable domains of the generated antibodies were determined. The EU or Kabat CDR sequences of the antibodies are set forth in Table 1. The EU or Kabat light chain framework sequences of the antibodies are set forth in Table 2. The Kabat heavy chain framework sequences of the antibodies are set forth in Table 3.

TABLE 1

EU or Kabat CDR sequences of anti-Sorillin antibodies

| Antibody | CDR L1 | CDR L2 | CDR L3 | CDR H1 | CDR H2 | CDR H3 |
|---|---|---|---|---|---|---|
| S-1 | RASQSVRSSYLA (SEQ ID NO: 6) | GASSRAT (SEQ ID NO: 26) | QQSPWT (SEQ ID NO: 41) | YTFTGYYMH (SEQ ID NO: 126) | WINPNSGGTNYAQKFQG (SEQ ID NO: 150) | ARSPGGATDGLVYYYYYGMDV (SEQ ID NO: 179) |
| S-2 | RASQSISSYLN (SEQ ID NO: 7) | AASSLQS (SEQ ID NO: 27) | QQSDVSPIT (SEQ ID NO: 42) | YTFTGYYMH (SEQ ID NO: 126) | WINPNSGGTNYAQKFQG (SEQ ID NO: 150) | ARGKRSSGWYEGYGMDV (SEQ ID NO: 180) |
| S-3 | RASQSISSWLA (SEQ ID NO: 8) | KASSLES (SEQ ID NO: 28) | QQYKSYPIT (SEQ ID NO: 43) | YTFTGYYMH (SEQ ID NO: 126) | WINPNSGGTNYAQKFQG (SEQ ID NO: 150) | ARGGPQLRVAEYFQH (SEQ ID NO: 181) |
| S-4 | RASQSVSSNLA (SEQ ID NO: 9) | GASTRAT (SEQ ID NO: 29) | QQFRVLPPT (SEQ ID NO: 44) | YTFTGYYMH (SEQ ID NO: 126) | WINPNSGGTNYAQKFQG (SEQ ID NO: 150) | ARGGPQLRVAEYFQH (SEQ ID NO: 181) |
| S-5 | RSSQLLHSNGYNLD (SEQ ID NO: 10) | LGSNRAS (SEQ ID NO: 30) | MQVSTEPPT (SEQ ID NO: 45) | YTFTGYYMH (SEQ ID NO: 126) | SINPNSGGTNYAQKFQG (SEQ ID NO: 151) | ARRHRSSTYGMDV (SEQ ID NO: 182) |
| S-6 | RASQSVSSNLA (SEQ ID NO: 9) | GASTRAT (SEQ ID NO: 29) | QQVANYPRT (SEQ ID NO: 46) | YTFTGYYMH (SEQ ID NO: 126) | SINPNSGGTNYAQKFQG (SEQ ID NO: 151) | ARGVFSTVTLAYYYYGMDV (SEQ ID NO: 183) |
| S-7 | RASQSVRSSYLA (SEQ ID NO: 6) | GASSRAT (SEQ ID NO: 26) | DQLGSSPRT (SEQ ID NO: 47) | YTFTSYGIS (SEQ ID NO: 127) | SISAYNGNTNYAQKLGQ (SEQ ID NO: 152) | ARDPSGGTTLHYYYGMDV (SEQ ID NO: 184) |
| S-8 | RASQSVSSSFLA (SEQ ID NO: 11) | GASSRAT (SEQ ID NO: 26) | QQAKVWPYT (SEQ ID NO: 48) | YTFTSYGIS (SEQ ID NO: 127) | SISAYNGNTNYAQKLGQ (SEQ ID NO: 152) | ARQGGHDSPTLYYYYGMDV (SEQ ID NO: 185) |
| S-9 | RASQSVSSNLA (SEQ ID NO: 9) | GASTRAT (SEQ ID NO: 29) | QQYNIYPLT (SEQ ID NO: 49) | YTFTSYGIS (SEQ ID NO: 127) | WISAYNGNTNYAQKLG (SEQ ID NO: 153) | ARDPGGYGPTLYYYYGMDV (SEQ ID NO: 186) |
| S-10 | RASQSVSSNLA (SEQ ID NO: 9) | GASTRAT (SEQ ID NO: 29) | QQYADWPPIT (SEQ ID NO: 50) | YTFTSYGIS (SEQ ID NO: 127) | WISAYNGNTNYAQKLG (SEQ ID NO: 153) | ARDPGGYGPTLYYYYGMDV (SEQ ID NO: 186) |
| S-12 | RASQSVSSNLA (SEQ ID NO: 9) | GASTRAT (SEQ ID NO: 29) | QQYNNHPPT (SEQ ID NO: 52) | YTFTSYGIS (SEQ ID NO: 127) | WISAYNGNTNYAQKLG (SEQ ID NO: 153) | ARDLPKYKWGWFDP (SEQ ID NO: 188) |
| S-14 | RASQSISSYLN (SEQ ID NO: 7) | GASSLQS (SEQ ID NO: 31) | QQHYVGPFT (SEQ ID NO: 54) | YTFTSYYMS (SEQ ID NO: 129) | IINPSGGSTSYAQKFQG (SEQ ID NO: 155) | ARDPSGIAAAGPASRYYYGMDV (SEQ ID NO: 190) |

TABLE 1-continued

EU or Kabat CDR sequences of anti-Sorillin antibodies

| Antibody | CDR L1 | CDR L2 | CDR L3 | CDR H1 | CDR H2 | CDR H3 |
|---|---|---|---|---|---|---|
| S-15 | RASQSVSSNLA (SEQ ID NO: 9) | GASTRAT (SEQ ID NO: 29) | QQARLGPWT (SEQ ID NO: 55) | YTFTSYYMS (SEQ ID NO: 129) | IINPSGGSTSYAQKFQG (SEQ ID NO: 155) | ARDPSGIAAAGPASRYYYGMDV (SEQ ID NO: 190) |
| S-16 | RASQGISSWLA (SEQ ID NO: 12) | AASNLQS (SEQ ID NO: 32) | QQGNSYPIT (SEQ ID NO: 56) | GTFSSYAIS (SEQ ID NO: 130) | GIIPIFGTANYAQKFQG (SEQ ID NO: 156) | ARSPYSGTRDFDL (SEQ ID NO: 191) |
| S-18 | RASQSVSSYLA (SEQ ID NO: 13) | DASNRAT (SEQ ID NO: 34) | QQGANAFPRT (SEQ ID NO: 58) | GTFSSYAIS (SEQ ID NO: 130) | SIIPIFGTANYAQKFQG (SEQ ID NO: 157) | ARDKHGRRGYYYYMDV (SEQ ID NO: 193) |
| S-19 | RASQSISSYLN (SEQ ID NO: 7) | SASSKQS (SEQ ID NO: 35) | QQTDGKPPT (SEQ ID NO: 59) | GTFSSYAIS (SEQ ID NO: 130) | GIIPIFGTASYAQKRQG (SEQ ID NO: 158) | ARESRIPGSGYYYYYGMDV (SEQ ID NO: 194) |
| S-20 | RASQSVSSSYLA (SEQ ID NO: 14) | GASSRAT (SEQ ID NO: 26) | QQYDGFPIT (SEQ ID NO: 60) | GTFSSYAIS (SEQ ID NO: 130) | GIIPIFGTANYAQKFQG (SEQ ID NO: 156) | AREGRMSGWYYAYGMDV (SEQ ID NO: 195) |
| S-21 | RASQSISSYLN (SEQ ID NO: 7) | AASSLQS (SEQ ID NO: 27) | QQKASLPFT (SEQ ID NO: 61) | GTFSSYAIS (SEQ ID NO: 130) | SIIPIFGTANYAQKFQG (SEQ ID NO: 157) | ARERRYDGYYYYYGMDV (SEQ ID NO: 196) |
| S-22 | RASQSISSWLA (SEQ ID NO: 8) | GASSRAT (SEQ ID NO: 28) | QQADGHIT (SEQ ID NO: 62) | GTFSSYAIS (SEQ ID NO: 130) | GIIPIFGTASYAQKFQG (SEQ ID NO: 158) | ARQGRKTGYYYYYGMDV (SEQ ID NO: 197) |
| S-24 | RASQSVSSSYLA (SEQ ID NO: 14) | GASSRAT (SEQ ID NO: 26) | QQVAVSPIT (SEQ ID NO: 64) | FTFGDYAMH (SEQ ID NO: 133) | GISWNSGSIGYADSVKG (SEQ ID NO: 160) | AKPLYRGGPFDI (SEQ ID NO: 199) |
| S-25 | RASQSVSSSYLA (SEQ ID NO: 14) | GASSRAT (SEQ ID NO: 26) | QQYDSAPIT (SEQ ID NO: 65) | FTFDDYAMH (SEQ ID NO: 134) | GISWNSGSIGYADSVKG (SEQ ID NO: 160) | AKGVGQVPASVAFDI (SEQ ID NO: 200) |
| S-26 | RASQGIDSWLA (SEQ ID NO: 16) | AASSLQS (SEQ ID NO: 27) | QQGNSLPPIT (SEQ ID NO: 66) | FTFSSYSMN (SEQ ID NO: 135) | SISSSSYIYYADSVKG (SEQ ID NO: 161) | ARDRLGRFYKWNWFDP (SEQ ID NO: 201) |
| S-28 | RSSQLLHSNGYNLD (SEQ ID NO: 10) | LGSNRAS (SEQ ID NO: 30) | MQRLQSPLRT (SEQ ID NO: 68) | FTFSSYSMN (SEQ ID NO: 135) | SISSSSNYIYYADSVKG (SEQ ID NO: 162) | ARGGLDRWGSFDI (SEQ ID NO: 203) |
| S-29 | RSSQLLHSNGYNLD (SEQ ID NO: 10) | LGSNRAS (SEQ ID NO: 30) | MQRIQGPPRT (SEQ ID NO: 69) | FTFSSYSMN (SEQ ID NO: 135) | SISSSSNYIYYADSVKG (SEQ ID NO: 162) | ARGGLDRWGSFDI (SEQ ID NO: 203) |
| S-30 | RSSQLLHSNGYNLD (SEQ ID NO: 10) | LGSNRAS (SEQ ID NO: 30) | MQALGPPIT (SEQ ID NO: 70) | FTFSSYAMS (SEQ ID NO: 136) | AISGSGGSTYYADSVKG (SEQ ID NO: 163) | ARGDGMDV (SEQ ID NO: 204) |
| S-32 | RSSQLLHSNGYNLD (SEQ ID NO: 10) | LGSNRAS (SEQ ID NO: 30) | MQGIETPPT (SEQ ID NO: 72) | FTFSSYAMS (SEQ ID NO: 136) | AISASGGSTYYADSVKG (SEQ ID NO: 164) | AKRGYPGYPAFDI (SEQ ID NO: 206) |
| S-34 | RASQSVSSSFLA (SEQ ID NO: 11) | GASSRAT (SEQ ID NO: 26) | QQYGSPPLT (SEQ ID NO: 74) | FTFSSYAMS (SEQ ID NO: 136) | SISGSGGSTYYADSVKG (SEQ ID NO: 165) | AKTGGTYGMDV (SEQ ID NO: 208) |
| S-39 | RSSQLLHSNGYNLD (SEQ ID NO: 10) | LGSNRAS (SEQ ID NO: 30) | MQAIQGPIT (SEQ ID NO: 79) | FTFSNYAMS (SEQ ID NO: 138) | AISGSGGSTYYADSVKG (SEQ ID NO: 163) | AKPLSSTGGGNI (SEQ ID NO: 213) |
| S-40 | RASQSVSSYLA (SEQ ID NO: 13) | DASNRAT (SEQ ID NO: 34) | QQRSALPFT (SEQ ID NO: 80) | FTFSSYAMS (SEQ ID NO: 136) | AISGSGGSTYYADSVKG (SEQ ID NO: 163) | AREVMARARTYGMDV (SEQ ID NO: 214) |
| S-42 | RASQSVSSSYLA (SEQ ID NO: 14) | GASSRAT (SEQ ID NO: 26) | QQALRSPLT (SEQ ID NO: 82) | FTFSNYAMS (SEQ ID NO: 138) | AISGSGGSTYYADSVKG (SEQ ID NO: 163) | AKLYQGTPDFDL (SEQ ID NO: 216) |

TABLE 1-continued

EU or Kabat CDR sequences of anti-Sorillin antibodies

| Antibody | CDR L1 | CDR L2 | CDR L3 | CDR H1 | CDR H2 | CDR H3 |
|---|---|---|---|---|---|---|
| S-43 | RASQSVSSSYLA (SEQ ID NO: 14) | GASSRAT (SEQ ID NO: 26) | QQLGSHPPT (SEQ ID NO: 83) | FTFSSYAMS (SEQ ID NO: 136) | AISGSGGSTYYADSVKG (SEQ ID NO: 163) | AKVGGMYDGGVYYYGMDV (SEQ ID NO: 217) |
| S-44 | RASQSVRSSYLA (SEQ ID NO: 6) | GASSRAT (SEQ ID NO: 26) | QQLDSSPIT (SEQ ID NO: 84) | FTFSTYAMS (SEQ ID NO: 139) | AISGSGGSTYYADSVKG (SEQ ID NO: 163) | AKTPSSIYAAGMDV (SEQ ID NO: 218) |
| S-45 | RASQSVSSSYLA (SEQ ID NO: 14) | GASSRAT (SEQ ID NO: 26) | QQSGSVPPIT (SEQ ID NO: 85) | FTFSSYAMS (SEQ ID NO: 136) | AISGSGGSTYYADSVKG (SEQ ID NO: 163) | ARVRGYGGSNYFDY (SEQ ID NO: 219) |
| S-48 | RASQSVSSNLA (SEQ ID NO: 9) | SASTRAT (SEQ ID NO: 37) | QQYNSWPIT (SEQ ID NO: 88) | FTFSSYGMH (SEQ ID NO: 140) | VISYDGSNKYYADSVKG (SEQ ID NO: 166) | ARESGDRATLVYYYYGMDV (SEQ ID NO: 222) |
| S-49 | RASQSVRSSYLA (SEQ ID NO: 6) | GASSRAT (SEQ ID NO: 26) | QQAGDYPPT (SEQ ID NO: 89) | FTFSSYGMH (SEQ ID NO: 140) | VISYDGSNKYYADSVKG (SEQ ID NO: 166) | ARDRGGYSSLLPYYYYMDV (SEQ ID NO: 223) |
| S-50 | RSSQLLHSNGYNLD (SEQ ID NO: 10) | LGSNRAS (SEQ ID NO: 30) | MQALERPPT (SEQ ID NO: 90) | FTFSSYGMH (SEQ ID NO: 140) | VISYDGSNKYYADSVKG (SEQ ID NO: 166) | ARDAYEGRVDV (SEQ ID NO: 224) |
| S-51 | RASQSVSSYLA (SEQ ID NO: 13) | DASKRAT (SEQ ID NO: 33) | QQRSNYPIT (SEQ ID NO: 91) | FTFSSYGMH (SEQ ID NO: 140) | VISYDGSNKYYADSVKG (SEQ ID NO: 166) | AKGLEYYDSSRLYYPYYYYMDV (SEQ ID NO: 225) |
| S-55 | RASQGISRWLA (SEQ ID NO: 21) | AASSLQS (SEQ ID NO: 27) | QQANALPT (SEQ ID NO: 95) | YSISSGYYWG (SEQ ID NO: 142) | SIYHSGSTYYNPSLKS (SEQ ID NO: 169) | ARGRPELGWDKYFQH (SEQ ID NO: 229) |
| S-57 | RASQSVSSSYLA (SEQ ID NO: 14) | GASSRAT (SEQ ID NO: 26) | EQYGGSPIT (SEQ ID NO: 97) | YSISSGYYWG (SEQ ID NO: 142) | SIYHSGSTYYNPSLKS (SEQ ID NO: 169) | QRGPLKFYYGSGSYGFFDY (SEQ ID NO: 231) |
| S-58 | RASQSVSSNLA (SEQ ID NO: 9) | GASTRAT (SEQ ID NO: 29) | QQDRKGPLT (SEQ ID NO: 98) | YSISSGYYWG (SEQ ID NO: 142) | SIYHSGNTYYNPSLKS (SEQ ID NO: 171) | ARGPPELGKMYFQH (SEQ ID NO: 232) |
| S-59 | RASQSVSSSYLA (SEQ ID NO: 14) | GASSRAT (SEQ ID NO: 26) | QQHGRLPPWT (SEQ ID NO: 99) | YSISSGYYWG (SEQ ID NO: 142) | SIYHSGNTYYNPSLKS (SEQ ID NO: 171) | ARGPPELGKMYFQH (SEQ ID NO: 232) |
| S-60 | RSSQLLHSNGYNLD (SEQ ID NO: 10) | LGSNRAS (SEQ ID NO: 30) | MQQQETPLT (SEQ ID NO: 100) | YSISSGYYWG (SEQ ID NO: 142) | TIYHSGSTYYNPSLKS (SEQ ID NO: 170) | ARQGSIKQGYYGMDV (SEQ ID NO: 233) |
| S-61 | RASQSVSSNLA (SEQ ID NO: 9) | GASTRAT (SEQ ID NO: 29) | QEYLNYPIT (SEQ ID NO: 101) | YSISSGYYWG (SEQ ID NO: 142) | SIYHSGSTYYNPSLKS (SEQ ID NO: 169) | ARGSPRFYYGSGSYLDLFDI (SEQ ID NO: 234) |
| S-63 | RASQSVSSSFLA (SEQ ID NO: 11) | GASSRAT (SEQ ID NO: 26) | QQLGIAPIT (SEQ ID NO: 103) | YSISSGYYWG (SEQ ID NO: 142) | SIYHSGSTYYNPSLKS (SEQ ID NO: 169) | ARAEHRGPRYFDL (SEQ ID NO: 236) |
| S-64 | RASQSINSYLN (SEQ ID NO: 15) | AASSLQS (SEQ ID NO: 27) | QQLDSTPIT (SEQ ID NO: 104) | YSISSGYYWG (SEQ ID NO: 142) | SIYHSGSTYYNPSLKS (SEQ ID NO: 169) | ARAEHRGPRYFDL (SEQ ID NO: 236) |
| S-65 | RSSQLLHSNGYNLD (SEQ ID NO: 10) | LGSNRAS (SEQ ID NO: 30) | MQARDGPIT (SEQ ID NO: 105) | YSISSGYYWG (SEQ ID NO: 142) | SIYHSGSTYYNPSLKS (SEQ ID NO: 169) | AREGQLPTGTFDY (SEQ ID NO: 237) |
| S-66 | RASQDISSWLA (SEQ ID NO: 22) | AASSLQS (SEQ ID NO: 27) | EQANSLPPIT (SEQ ID NO: 106) | GSISSGGYYWS (SEQ ID NO: 144) | YIYYSGSTVYNPSLKS (SEQ ID NO: 172) | ARDVGRTGPHYYGMDV (SEQ ID NO: 238) |
| S-67 | RSSQLLHSNGYNLD (SEQ ID NO: 10) | LGSHRAS (SEQ ID NO: 38) | MQRLEAPLT (SEQ ID NO: 107) | GSISSGGYYWS (SEQ ID NO: 144) | AIYYSGSTYYNPSLKS (SEQ ID NO: 173) | ARLHSDYSVLYYGMDV (SEQ ID NO: 239) |

TABLE 1-continued

EU or Kabat CDR sequences of anti-Sorillin antibodies

| Antibody | CDR L1 | CDR L2 | CDR L3 | CDR H1 | CDR H2 | CDR H3 |
|---|---|---|---|---|---|---|
| S-69 | RASQSVSSSLS (SEQ ID NO: 20) | GASTRAT (SEQ ID NO: 29) | QQAADWPIT (SEQ ID NO: 109) | GSISSGGYYWS (SEQ ID NO: 144) | YIYYSGSTYYNPSLKS (SEQ ID NO: 175) | ARDRGGTHFGADHYYYGMDV (SEQ ID NO: 241) |
| S-71 | RASQSVSSSYLA (SEQ ID NO: 14) | GASSRAT (SEQ ID NO: 26) | QQAASSPIT (SEQ ID NO: 111) | GSISSGGYYWS (SEQ ID NO: 144) | YIYYSGSTVYNPSLKS (SEQ ID NO: 172) | ARLPGYPLGLFDI (SEQ ID NO: 243) |
| S-72 | RASQGISSWLA (SEQ ID NO: 12) | AASNLQA (SEQ ID NO: 32) | QQAPSVPPIT (SEQ ID NO: 112) | GSISSGTYYWS (SEQ ID NO: 145) | YIYYSGSTYYNPSLKS (SEQ ID NO: 175) | ARDRGRTESYYYGMDV (SEQ ID NO: 244) |
| S-73 | RASQSVSSYLA (SEQ ID NO: 13) | DASNRAT (SEQ ID NO: 34) | QQASVYPPIT (SEQ ID NO: 113) | GSISSGTYYWS (SEQ ID NO: 145) | YIYYSGSTYYNPSLKS (SEQ ID NO: 175) | ARGVGRYRVADY (SEQ ID NO: 245) |
| S-74 | RASQSVSSYLA (SEQ ID NO: 13) | DSSNRAT (SEQ ID NO: 39) | QQETNMPPIT (SEQ ID NO: 114) | GSISSGTYYWS (SEQ ID NO: 145) | YIYYSGSTYYNPSLKS (SEQ ID NO: 175) | ARGVGRYRVADY (SEQ ID NO: 245) |
| S-75 | RASQSVSSNLA (SEQ ID NO: 9) | SASTRAT (SEQ ID NO: 37) | QQYNALPRT (SEQ ID NO: 115) | GSISSGGYYWS (SEQ ID NO: 144) | NIYYSGSTYYNPSLKS (SEQ ID NO: 174) | ARDRGMGPKLYYYYGMDV (SEQ ID NO: 246) |
| S-76 | RASQSISSFLN (SEQ ID NO: 24) | AASSLQS (SEQ ID NO: 27) | QQSYREPIT (SEQ ID NO: 116) | GSISSGGYYWS (SEQ ID NO: 144) | SIYYSGSTYYNPSLKS (SEQ ID NO: 173) | ARGVGIQQQLVLGFDP (SEQ ID NO: 247) |
| S-78 | KSSQSVLYSSNNKNYLA (SEQ ID NO: 25) | WASTRES (SEQ ID NO: 36) | QQYANAPIT (SEQ ID NO: 118) | GSISSSDYYWG (SEQ ID NO: 147) | SIYYSGSTYYNPSLKS (SEQ ID NO: 173) | QRSLAMSGAYFDL (SEQ ID NO: 249) |
| S-81 | RSSQLLHSNGYNLD (SEQ ID NO: 10) | LGSNRAS (SEQ ID NO: 30) | MQALDVPLT (SEQ ID NO: 121) | GSISSSSYYWG (SEQ ID NO: 148) | SIYYSGSTYYNPSLKS (SEQ ID NO: 173) | ARERWDLGHGMDV (SEQ ID NO: 252) |
| S-82 | RASQSVSSSYLA (SEQ ID NO: 14) | GASSRAT (SEQ ID NO: 26) | QQSHVSPWT (SEQ ID NO: 122) | GSISSSDYYWG (SEQ ID NO: 147) | SIYYSGSTYYNPSLKS (SEQ ID NO: 173) | ARGVGSGYSYGYRYFDV (SEQ ID NO: 253) |
| S-83 | RASQSVSSNLA (SEQ ID NO: 9) | GASTRAT (SEQ ID NO: 29) | QQYNAFPPT (SEQ ID NO: 123) | GSISSSSYYWG (SEQ ID NO: 148) | SIYYSGSTYYNPSLKS (SEQ ID NO: 173) | ARGSPTWLRDYYMDV (SEQ ID NO: 254) |
| S-84 | RSSQLLHSNGYNLD (SEQ ID NO: 10) | GASTRAT (SEQ ID NO: 29) | MQAIDTPPT (SEQ ID NO: 124) | GSISSSSYYWG (SEQ ID NO: 148) | SISYSGSTYYNPSLKS (SEQ ID NO: 177) | ARGGTTWLVADV (SEQ ID NO: 255) |
| S-85 | RASQSVSSSFLA (SEQ ID NO: 11) | GASSRAT (SEQ ID NO: 26) | EQYASSPYT (SEQ ID NO: 125) | YSFTSYWIG (SEQ ID NO: 149) | IIYPGDSDTTYSPSFQG (SEQ ID NO: 178) | ARGRGRYSYGYHKAAFDI (SEQ ID NO: 256) |

TABLE 2

EU or Kabat Light Chain Framework sequences of anti-Sortilin antibodies

| Antibody | VL FR1 | VL FR2 | VL FR3 | VL FR4 |
|---|---|---|---|---|
| S-1 | EIVLTQSPGTLSLSPGERATLSC (SEQ ID NO: 257) | WYQQKPGQAPRLLIY (SEQ ID NO: 269) | GIPDRFSGSGSGTDFTLTISRLEPEDFAVYYC (SEQ ID NO: 276) | FGGGTKVEIK (SEQ ID NO: 283) |
| S-2 | DIQMTQSPSSLSASVGDRVTITC (SEQ ID NO: 258) | WYQQKPGKAPKLLIY (SEQ ID NO: 270) | GVPSRFSGSGSGTDFTLTISSLQPEDFATYYC (SEQ ID NO: 277) | GFFFTKVEIK (SEQ ID NO: 283) |
| S-3 | DIQMTQSPSTLSASVGDRVTITC (SEQ ID NO: 259) | WYQQKPGKAPKLLIY (SEQ ID NO: 270) | GVPSRFSGSGSGTEFTLTISSLQPDDFATYYC (SEQ ID NO: 278) | GFFFTKVEIK (SEQ ID NO: 283) |
| S-4 | EIVMTQSPATLSVSPGERATLSC (SEQ ID NO: 260) | WYQQKPGQAPRLLIY (SEQ ID NO: 269) | GIPARFSGSGSGTEFTLTISSLQSEDFAVYYC (SEQ ID NO: 279) | GFFFTKVEIK (SEQ ID NO: 283) |
| S-5 | DIVMTQSPLSLPVTPGEPASISC (SEQ ID NO: 261) | WYLQKPGQSPQLLIY (SEQ ID NO: 270) | GVPDRFSGSGSGTDFTLKISRVEAEDVGVYYC (SEQ ID NO: 280) | GFFFTKVEIK (SEQ ID NO: 283) |
| S-6 | EIVMTQSPATLSVSPGERATLSC (SEQ ID NO: 260) | WYQQKPGQAPRLLIY (SEQ ID NO: 269) | GIPARFSGSGSGTEFTLTISSLQSEDFAVYYC (SEQ ID NO: 279) | GFFFTKVEIK (SEQ ID NO: 283) |
| S-7 | EIVLTQSPGTLSLSPGERATLSC (SEQ ID NO: 257) | WYQQKPGQAPRLLIY (SEQ ID NO: 269) | GIPDRFSGSGSGTDFTLTISRLEPEDFAVYYC (SEQ ID NO: 276) | GFFFTKVEIK (SEQ ID NO: 283) |
| S-8 | EIVLTQSPGTLSLSPGERATLSC (SEQ ID NO: 257) | WYQQKPGQAPRLLIY (SEQ ID NO: 269) | GIPDRFSGSGSGTDFTLTISRLEPEDFAVYYC (SEQ ID NO: 276) | GFFFTKVEIK (SEQ ID NO: 283) |
| S-9 | EIVMTQSPATLSVSPGERATLSC (SEQ ID NO: 260) | WYQQKPGQAPRLLIY (SEQ ID NO: 269) | GIPARFSGSGSGTEFTLTISSLQSEDFAVYYC (SEQ ID NO: 279) | GFFFTKVEIK (SEQ ID NO: 283) |
| S-10 | EIVMTQSPATLSVSPGERATLSC (SEQ ID NO: 260) | WYQQKPGQAPRLLIY (SEQ ID NO: 269) | GIPARFSGSGSGTEFTLTISSLQSEDFAVYYC (SEQ ID NO: 279) | GFFFTKVEIK (SEQ ID NO: 283) |
| S-12 | EIVLTQSPATLSVSPGERATLSC (SEQ ID NO: 262) | WYQQKPGQAPRLLIY (SEQ ID NO: 269) | GIPARFSGSGSGTEFTLTISSLQSEDFAVYYC (SEQ ID NO: 279) | GFFFTKVEIK (SEQ ID NO: 283) |
| S-14 | DIQMTQSPSSLSASVGDRVTITC (SEQ ID NO: 258) | WYQQKPGKAPKLLIY (SEQ ID NO: 270) | GVPSRFSGSGSGTDFTLTISSLQPEDFATYYC (SEQ ID NO: 277) | GFFFTKVEIK (SEQ ID NO: 283) |
| S-15 | EIVMTQSPATLSVSPGERATLSC (SEQ ID NO: 260) | WYQQKPGQAPRLLIY (SEQ ID NO: 269) | GIPARFSGSGSGTEFTLTISSLQSEDFAVYYC (SEQ ID NO: 279) | GFFFTKVEIK (SEQ ID NO: 283) |
| S-16 | DIQMTQSPSSVSASVGDRVTITC (SEQ ID NO: 263) | WYQQKPGKAPKLLIY (SEQ ID NO: 270) | GVPSRFSGSGSGTDFTLTISSLQPEDFATYYC (SEQ ID NO: 277) | GFFFTKVEIK (SEQ ID NO: 283) |
| S-18 | EIVLTQSPATLSLSPGERATLSC (SEQ ID NO: 264) | WYQQKPGQAPRLLIY (SEQ ID NO: 269) | GIPARFSGSGSGTDFTLTISSLEPEDFAVYYC (SEQ ID NO: 281) | GFFFTKVEIK (SEQ ID NO: 283) |
| S-19 | DIQMTQSPSSLSASVGDRVTITC (SEQ ID NO: 258) | WYQQKPGKAPKLLIY (SEQ ID NO: 270) | GVPSRFSGSGSGTDFTLTISSLQPEDFATYYC (SEQ ID NO: 277) | GFFFTKVEIK (SEQ ID NO: 283) |

TABLE 2-continued

EU or Kabat Light Chain Framework sequences of anti-Sortilin antibodies

| Antibody | VL FR1 | VL FR2 | VL FR3 | VL FR4 |
|---|---|---|---|---|
| S-20 | EIVMTQSPGTLSLSPGERATLSC (SEQ ID NO: 265) | WYQQKPGQAPRLLIY (SEQ ID NO: 269) | GIPDRFSGSGSGTDFTLTISRLEPEDFAVYYC (SEQ ID NO: 276) | GFFFTKVEIK (SEQ ID NO: 283) |
| S-21 | DIQMTQSPSSLSASVGDRVTITC (SEQ ID NO: 258) | WYQQKPGKAPKLLIY (SEQ ID NO: 270) | GVPSRFSGSGSGTDFTLTISSLQPEDFATYYC (SEQ ID NO: 277) | GFFFTKVEIK (SEQ ID NO: 283) |
| S-22 | DIQMTQSPSTLSASVGDRVTITC (SEQ ID NO: 259) | WYQQKPGKAPKLLIY (SEQ ID NO: 270) | GVPSRFSGSGSGTEFTLTISSLQPDDFATYYC (SEQ ID NO: 278) | GFFFTKVEIK (SEQ ID NO: 283) |
| S-24 | EIVLTQSPGTLSLSPGERATLSC (SEQ ID NO: 257) | WYQQKPGQAPRLLIY (SEQ ID NO: 269) | GIPDRFSGSGSGTDFTLTISRLEPEDFAVYYC (SEQ ID NO: 276) | GFFFTKVEIK (SEQ ID NO: 283) |
| S-25 | EIVLTQSPGTLSLSPGERATLSC (SEQ ID NO: 257) | WYQQKPGQAPRLLIY (SEQ ID NO: 269) | GIPDRFSGSGSGTDFTLTISRLEPEDFAVYYC (SEQ ID NO: 276) | GFFFTKVEIK (SEQ ID NO: 283) |
| S-26 | DIQMTQSPSSVSASVGDRVTITC (SEQ ID NO: 263) | WYQQKPGKAPKLLIY (SEQ ID NO: 270) | GVPSRFSGSGSGTDFTLTISSLQPEDFATYYC (SEQ ID NO: 277) | GFFFTKVEIK (SEQ ID NO: 283) |
| S-28 | DIVMTQSPLSLPVTGEPASISC (SEQ ID NO: 261) | WYLQKPGQSPQLLIY (SEQ ID NO: 271) | GVPDRFSGSGSGTDFTLKISRVEAEDVGVYYC (SEQ ID NO: 280) | GFFFTKVEIK (SEQ ID NO: 283) |
| S-29 | DIVMTQSPLSLPVTPGEPASISC (SEQ ID NO: 261) | WYLQKPGQSPQLLIY (SEQ ID NO: 271) | GVPDRFSGSGSGTDFTLKISRVEAEDVGVYYC (SEQ ID NO: 280) | GFFFTKVEIK (SEQ ID NO: 283) |
| S-30 | DIVMTQSPLSLPVTPGEPASISC (SEQ ID NO: 261) | WYLQKPGQSPQLLIY (SEQ ID NO: 271) | GVPDRFSGSGSGTDFTLKISRVEAEDVGVYYC (SEQ ID NO: 280) | GFFFTKVEIK (SEQ ID NO: 283) |
| S-32 | DIVMTQSPLSLPVTPGEPASISC (SEQ ID NO: 261) | WYLQKPGQSPQLLIF (SEQ ID NO: 272) | GVPDRFSGSGSGTDFTLKISRVEAEDVGVYYC (SEQ ID NO: 280) | GFFFTKVEIK (SEQ ID NO: 283) |
| S-34 | EIVLTQSPGTLSLSPGERATLSC (SEQ ID NO: 257) | WYQQKPGQAPRLLIY (SEQ ID NO: 269) | GIPDRFSGSGSGTDFTLTISRLEPEDFAVYYC (SEQ ID NO: 276) | GFFFTKVEIK (SEQ ID NO: 283) |
| S-39 | DIVMTQSPLSLPVTPGEPASISC (SEQ ID NO: 261) | WYLQKPGQSPQLLIF (SEQ ID NO: 272) | GVPDRFSGSGSGTDFTLKISRVEAEDVGVYYC (SEQ ID NO: 280) | GFFFTKVEIK (SEQ ID NO: 283) |
| S-40 | EIVMTQSPATLSLSPGERATLSC (SEQ ID NO: 266) | WYQQKPGQAPRLLIY (SEQ ID NO: 269) | GIPARFSGSGSGTDFTLTISSLEPEDFAVYYC (SEQ ID NO: 281) | GFFFTKVEIK (SEQ ID NO: 283) |
| S-42 | EIVLTQSPGTLSLSPGERATLSC (SEQ ID NO: 257) | WYQQKPGQAPRLLIY (SEQ ID NO: 269) | GIPDRFSGSGSGTDFTLTISRLEPEDFAVYYC (SEQ ID NO: 276) | GFFFTKVEIK (SEQ ID NO: 283) |
| S-43 | EIVLTQSPGTLSLSPGERATLSC (SEQ ID NO: 257) | WYQQKPGQAPRLLIY (SEQ ID NO: 269) | GIPDRFSGSGSGTDFTLTISRLEPEDFAVYYC (SEQ ID NO: 276) | GFFFTKVEIK (SEQ ID NO: 283) |
| S-44 | EIVLTQSPGTLSLSPGERATLSC (SEQ ID NO: 257) | WYQQKPGQAPRLLIY (SEQ ID NO: 269) | GIPDRFSGSGSGTDFTLTISRLEPEDFAVYYC (SEQ ID NO: 276) | GFFFTKVEIK (SEQ ID NO: 283) |

TABLE 2-continued

EU or Kabat Light Chain Framework sequences of anti-Sortilin antibodies

| Antibody | VL FR1 | VL FR2 | VL FR3 | VL FR4 |
|---|---|---|---|---|
| S-45 | EIVLTQSPGTLSLSPGERATLSC (SEQ ID NO: 257) | WYQQKPGQAPRLLIY (SEQ ID NO: 269) | GIPDRFSGSGSGTDFTLTISRLEPEDFAVYYC (SEQ ID NO: 276) | GFFFTKVEIK (SEQ ID NO: 283) |
| S-48 | EIVMTQSPATLSVSPGERATLSC (SEQ ID NO: 260) | WYQQKPGQAPRLLIY (SEQ ID NO: 269) | GIPARFSGSGSGTDFTLTISSLQSEDFAVYYC (SEQ ID NO: 279) | GFFFTKVEIK (SEQ ID NO: 283) |
| S-49 | EIVLTQSPGTLSLSPGERATLSC (SEQ ID NO: 257) | WYQQKPGQAPRLLIY (SEQ ID NO: 269) | GIPDRFSGSGSGTDFTLTISRLEPEDFAVYYC (SEQ ID NO: 276) | GFFFTKVEIK (SEQ ID NO: 283) |
| S-50 | DIVMTQSPLSLPVTPGEPASISC (SEQ ID NO: 261) | WYLQKPGQSPQLLIY (SEQ ID NO: 271) | GVPDRFSGSGSGTDFTLKISRVEAEDVGVYYC (SEQ ID NO: 280) | GFFFTKVEIK (SEQ ID NO: 283) |
| S-51 | EIVLTQSPATLSLSPGERATLSC (SEQ ID NO: 264) | WYQQKPGQAPRLLIY (SEQ ID NO: 269) | GIPARFSGSGSGTDFTLTISSLEPEDFAVYYC (SEQ ID NO: 281) | GFFFTKVEIK (SEQ ID NO: 283) |
| S-55 | DIQMTQSPSSVSASVGDRVTITC (SEQ ID NO: 263) | WYQQKPGKAPKLLIY (SEQ ID NO: 270) | GVPSRFSGSGSGTDFTLTISSLQPEDFATYYC (SEQ ID NO: 277) | GFFFTKVEIK (SEQ ID NO: 283) |
| S-57 | EIVLTQSPGTLSLSPGERATLSC (SEQ ID NO: 257) | WYQQKPGQAPRLLIY (SEQ ID NO: 269) | GIPDRFSGSGSGTDFTLTISRLEPEDFAVYYC (SEQ ID NO: 276) | GFFFTKVEIK (SEQ ID NO: 283) |
| S-58 | EIVLTQSPATLSVSPGERATLSC (SEQ ID NO: 262) | WYQQKPGQAPRLLIY (SEQ ID NO: 269) | GIPARFSGSGSGTEFTLTISSLQSEDFAVYYC (SEQ ID NO: 279) | GFFFTKVEIK (SEQ ID NO: 283) |
| S-59 | EIVLTQSPGTLSLSPGERATLSC (SEQ ID NO: 257) | WYQQKPGQAPRLLIY (SEQ ID NO: 269) | GIPDRFSGSGSGTDFTLTISRLEPEDFAVYYC (SEQ ID NO: 276) | GFFFTKVEIK (SEQ ID NO: 283) |
| S-60 | DIVMTQSPLSLPVTPGEPASISC (SEQ ID NO: 261) | WYLQKPGQSPQLLIY (SEQ ID NO: 271) | GVPDRFSGSGSGTDFTLKISRVEAEDVGVYYC (SEQ ID NO: 280) | GFFFTKVEIK (SEQ ID NO: 283) |
| S-61 | EIVMTQSPATLSVSPGERATLSC (SEQ ID NO: 260) | WYQQKPGQAPRLLIY (SEQ ID NO: 269) | GIPARFSGSGSGTEFTLTISSLQSEDFAVYYC (SEQ ID NO: 279) | GFFFTKVEIK (SEQ ID NO: 283) |
| S-63 | EIVLTQSPGTLSLSPGERATLSC (SEQ ID NO: 257) | WYQQKPGQAPRLLIY (SEQ ID NO: 269) | GIPDRFSGSGSGTDFTLTISRLEPEDFAVYYC (SEQ ID NO: 276) | GFFFTKVEIK (SEQ ID NO: 283) |
| S-64 | DIQMTQSPSSLSASVGDRVTITC (SEQ ID NO: 258) | WYQQKPGKAPKLLIY (SEQ ID NO: 270) | GVPSRFSGSGSGTDFTLTISSLQPEDFATYYC (SEQ ID NO: 277) | GFFFTKVEIK (SEQ ID NO: 283) |
| S-65 | DIVMTQSPLSLPVTPGEPASISC (SEQ ID NO: 261) | WYLQKPGQSPQLLIY (SEQ ID NO: 271) | GVPDRFSGSGSGTDFTLKISRVEAEDVGVYYC (SEQ ID NO: 280) | GFFFTKVEIK (SEQ ID NO: 283) |
| S-66 | DIQLTQSPSSVSASVGDRVTITC (SEQ ID NO: 268) | WYQQKPGKAPKLLIY (SEQ ID NO: 270) | GVPSRFSGSGSGTDFTLTISSLQPEDFATYYC (SEQ ID NO: 277) | GFFFTKVEIK (SEQ ID NO: 283) |
| S-67 | DIVMTQSPLSLPVTPGEPASISC (SEQ ID NO: 261) | WYLQKPGQSPQLLIY (SEQ ID NO: 271) | GVPDRFSGSGSGTDFTLKISRVEAEDVGVYYC (SEQ ID NO: 280) | GFFFTKVEIK (SEQ ID NO: 283) |

TABLE 2-continued

EU or Kabat Light Chain Framework sequences of anti-Sortilin antibodies

| Antibody | VL FR1 | VL FR2 | VL FR3 | VL FR4 |
|---|---|---|---|---|
| S-69 | EIVMTQSPATLSVSPGERATLSC (SEQ ID NO: 260) | WYQQKPGQAPRLLIY (SEQ ID NO: 269) | GIPARFSGSGSGTEFTLTISSLQSEDFAVYYC (SEQ ID NO: 279) | GFFFTKVEIK (SEQ ID NO: 283) |
| S-71 | EIVLTQSPGTLSLSPGERATLSC (SEQ ID NO: 257) | WYQQKPGQAPRLLIY (SEQ ID NO: 269) | GIPDRFSGSGSGTDFTLTISRLEPEDFAVYYC (SEQ ID NO: 276) | GFFFTKVEIK (SEQ ID NO: 283) |
| S-72 | DIQMTQSPSSVSASVGDRVTITC (SEQ ID NO: 263) | WYQQKPGKAPKLLIY (SEQ ID NO: 270) | GVPSRFSGSGSGTDFTLTISSLQPEDFATYYC (SEQ ID NO: 277) | GFFFTKVEIK (SEQ ID NO: 283) |
| S-73 | EIVLTQSPATLSLSPGERATLSC (SEQ ID NO: 264) | WYQQKPGQAPRLLIY (SEQ ID NO: 269) | GIPARFSGSGSGTDFTLTISSLEPEDFAVYYC (SEQ ID NO: 281) | GFFFTKVEIK (SEQ ID NO: 283) |
| S-74 | EIVMTQSPATLSLSPGERATLSC (SEQ ID NO: 266) | WYQQKPGQAPRLLIY (SEQ ID NO: 269) | GIPARFSGSGSGTDFTLTISSLEPEDFAVYYC (SEQ ID NO: 281) | GFFFTKVEIK (SEQ ID NO: 283) |
| S-75 | EIVMTQSPATLSVSPGERATLSC (SEQ ID NO: 260) | WYQQKPGQAPRLLIY (SEQ ID NO: 269) | GIPARFSGSGSGTEFTLTISSLQSEDFAVYYC (SEQ ID NO: 279) | GFFFTKVEIK (SEQ ID NO: 283) |
| S-76 | DIQMTQSPSSLSASVGDRVTITC (SEQ ID NO: 258) | WYQQKPGKAPKLLIS (SEQ ID NO: 274) | GVPSRFSGSGSGTDFTLTISSLQPEDFATYYC (SEQ ID NO: 277) | GFFFTKVEIK (SEQ ID NO: 283) |
| S-78 | DIVMTQSPDSLAVSLGERATINC (SEQ ID NO: 267) | WYQQKPGQPPKLLIY (SEQ ID NO: 273) | GVPDRFSGSGSGTDFTLTISSLQAEDVAVYYC (SEQ ID NO: 282) | GFFFTKVEIK (SEQ ID NO: 283) |
| S-81 | DIVMTQSPLSLPVTPGEPASISC (SEQ ID NO: 261) | WYLQKPGQSPQVLIY (SEQ ID NO: 275) | GVPDRFSGSGSGTDFTLKISRVEAEDVGVYYC (SEQ ID NO: 280) | GFFFTKVEIK (SEQ ID NO: 283) |
| S-82 | EIVLTQSPGTLSLSPGERATLSC (SEQ ID NO: 257) | WYQQKPGQAPRLLIY (SEQ ID NO: 269) | GIPDRFSGSGSGTDFTLTISRLEPEDFAVYYC (SEQ ID NO: 276) | GFFFTKVEIK (SEQ ID NO: 283) |
| S-83 | EIVLTQSPATLSVSPGERATLSC (SEQ ID NO: 262) | WYQQKPGQAPRLLIY (SEQ ID NO: 269) | GIPARFSGSGSGTEFTLTISSLQSEDFAVYYC (SEQ ID NO: 279) | GFFFTKVEIK (SEQ ID NO: 283) |
| S-84 | DIVMTQSPLSLPVTPGEPASISC (SEQ ID NO: 261) | WYLQKPGQSPQLLIY (SEQ ID NO: 271) | GVPDRFSGSGSGTDFTLKISRVEAEDVGVYYC (SEQ ID NO: 280) | GFFFTKVEIK (SEQ ID NO: 283) |
| S-85 | EIVLTQSPGTLSLSPGERATLSC (SEQ ID NO: 257) | WYQQKPGQAPRLLIY (SEQ ID NO: 269) | GIPDRFSGSGSGTDFTLTISRLEPEDFAVYYC (SEQ ID NO: 276) | GFFFTKVEIK (SEQ ID NO: 283) |

TABLE 3

EU or Kabat Heavy Chain Framework sequences of anti-Sortilin antibodies

| Antibody | VH FR1 | VH FR2 | VH FR3 | VH FR4 |
|---|---|---|---|---|
| S-1 | QVQLVQSGAEVKKPGASVKVSCKASG (SEQ ID NO: 284) | WVRQAPGQGLEWMG (SEQ ID NO: 296) | RVTMTRDTSISTAYMELSRLRSDDTAVYYC (SEQ ID NO: 302) | WGQGTTVTVSS (SEQ ID NO: 311) |
| S-2 | QVQLVQSGAEVKKPGASVKVSCKASG (SEQ ID NO: 284) | WVRQAPGQGLEWMG (SEQ ID NO: 296) | RVTMTRDTSISTAYMELSRLRSDDTAVYYC (SEQ ID NO: 302) | WGQGTTVTVSS (SEQ ID NO: 311) |
| S-3 | QVQLVQSGAEVKKPGASVKVSCKASG (SEQ ID NO: 284) | WVRQAPGQGLEWMG (SEQ ID NO: 296) | RVTMTRDTSISTAYMELSRLRSDDTAVYYC (SEQ ID NO: 302) | WGQGTLVTVSS (SEQ ID NO: 312) |
| S-4 | QVQLVQSGAEVKKPGASVKVSCKASG (SEQ ID NO: 284) | WVRQAPGQGLEWMG (SEQ ID NO: 296) | RVTMTRDTSISTAYMELSRLRSDDTAVYYC (SEQ ID NO: 302) | WGQGTLVTVSS (SEQ ID NO: 312) |
| S-5 | QVQLVQSGAEVKKPGASVKVSCKASG (SEQ ID NO: 284) | WVRQAPGQGLEWMG (SEQ ID NO: 296) | RVTMTRDTSISTAYMELSRLRSDDTAVYYC (SEQ ID NO: 302) | WGQGTTVTVSS (SEQ ID NO: 311) |
| S-6 | QVQLVQSGAEVKKPGASVKVSCKASG (SEQ ID NO: 284) | WVRQAPGQGLEWMG (SEQ ID NO: 296) | RVTMTRDTSISTAYMELSRLRSDDTAVYYC (SEQ ID NO: 302) | WGQGTTVTVSS (SEQ ID NO: 311) |
| S-7 | QVQLVQSGAEVKKPGASVKVSCKASG (SEQ ID NO: 284) | WVRQAPGQGLEWMG (SEQ ID NO: 296) | RVTMTTDTSTSTAYMELRSLRSDDTAVYYC (SEQ ID NO: 303) | WGQGTTVTVSS (SEQ ID NO: 311) |
| S-8 | QVQLVQSGAEVKKPGASVKVSCKASG (SEQ ID NO: 284) | WVRQAPGQGLEWMG (SEQ ID NO: 296) | RVTMTTDTSTSTAYMELRSLRSDDTAVYYC (SEQ ID NO: 303) | WGQGTTVTVSS (SEQ ID NO: 311) |
| S-9 | QVQLVQSGAEVKKPGASVKVSCKASG (SEQ ID NO: 284) | WVRQAPGQGLEWMG (SEQ ID NO: 296) | RVTMTTDTSTSTAYMELRSLRSDDTAVYYC (SEQ ID NO: 303) | WGQGTTVTVSS (SEQ ID NO: 311) |
| S-10 | QVQLVQSGAEVKKPGASVKVSCKASG (SEQ ID NO: 284) | WVRQAPGQGLEWMG (SEQ ID NO: 296) | RVTMTTDTSTSTAYMELRSLRSDDTAVYYC (SEQ ID NO: 303) | WGQGTTVTVSS (SEQ ID NO: 311) |
| S-12 | QVQLVQSGAEVKKPGASVKVSCKASG (SEQ ID NO: 284) | WVRQAPGQGLEWMG (SEQ ID NO: 296) | RVTMTTDTSTSTAYMELRSLRSDDTAVYYC (SEQ ID NO: 303) | WGQGTLVTVSS (SEQ ID NO: 312) |
| S-14 | QVQLVQSGAEVKKPGASVKVSCKASG (SEQ ID NO: 284) | WVRQAPGQGLEWMG (SEQ ID NO: 296) | RVTMTRDTSTSTVYMELSSLRSEDTAVYYC (SEQ ID NO: 304) | WGQGTTVTVSS (SEQ ID NO: 311) |
| S-15 | QVQLVQSGAEVKKPGASVKVSCKASG (SEQ ID NO: 284) | WVRQAPGQGLEWMG (SEQ ID NO: 296) | RVTMTRDTSTSTVYMELSSLRSEDTAVYYC (SEQ ID NO: 304) | WGQGTTVTVSS (SEQ ID NO: 311) |
| S-16 | QVQLVQSGAEVKKPGSSVKVSCKASG (SEQ ID NO: 285) | WVRQAPGQGLEWMG (SEQ ID NO: 296) | RVTITADESTSTAYMELSSLRSEDTAVYYC (SEQ ID NO: 305) | WGRGTLVTVSS (SEQ ID NO: 314) |
| S-18 | QVQLVQSGAEVKKPGSSVKVSCKASG (SEQ ID NO: 285) | WVRQAPGQGLEWMG (SEQ ID NO: 296) | RVTITADESTSTAYMELSSLRSEDTAVYYC (SEQ ID NO: 305) | WGKGTTVTVSS (SEQ ID NO: 315) |
| S-19 | QVQLVQSGAEVKKPGSSVKVSCKASG (SEQ ID NO: 285) | WVRQAPGQGLEWMG (SEQ ID NO: 296) | RVTITADESTSTAYMELSSLRSEDTAVYYC (SEQ ID NO: 305) | WGQGTTVTVSS (SEQ ID NO: 311) |
| S-20 | QVQLVQSGAEVKKPGSSVKVSCKASG (SEQ ID NO: 285) | WVRQAPGQGLEWMG (SEQ ID NO: 296) | RVTITADESTSTAYMELSSLRSEDTAVYYC (SEQ ID NO: 305) | WGQGTTVTVSS (SEQ ID NO: 311) |
| S-21 | QVQLVQSGAEVKKPGSSVKVSCKASG (SEQ ID NO: 285) | WVRQAPGQGLEWMG (SEQ ID NO: 296) | RVTITADESTSTAYMELSSLRSEDTAVYYC (SEQ ID NO: 305) | WGQGTTVTVSS (SEQ ID NO: 311) |
| S-22 | QVQLVQSGAEVKKPGSSVKVSCKASG (SEQ ID NO: 285) | WVRQAPGQGLEWMG (SEQ ID NO: 296) | RVTITADESTSTAYMELSSLRSEDTAVYYC (SEQ ID NO: 305) | WGQGTTVTVSS (SEQ ID NO: 311) |
| S-24 | EVQLVESGGGLVQPGRSLRLSCAASG (SEQ ID NO: 287) | WVRQAPGKGLEWVS (SEQ ID NO: 298) | RFTISRDNAKNSLYLQMNSLRAEDTALYYC (SEQ ID NO: 307) | WGQGTMVTVSS (SEQ ID NO: 313) |
| S-25 | EVQLVESGGGLVQPGRSLRLSCAASG (SEQ ID NO: 287) | WVRQAPGKGLEWVS (SEQ ID NO: 298) | RFTISRDNAKNSLYLQMNSLRAEDTALYYC (SEQ ID NO: 307) | WGQGTMVTVSS (SEQ ID NO: 313) |
| S-26 | EVQLVESGGGLVKPGGSLRLSCAASG (SEQ ID NO: 288) | WVRQAPGKGLEWVS (SEQ ID NO: 298) | RFTISRDNAKNSLYLQMNSLRAEDTAVYYC (SEQ ID NO: 306) | WGQGTLVTVSS (SEQ ID NO: 312) |
| S-28 | EVQLVESGGGLVKPGGSLRLSCAASG (SEQ ID NO: 288) | WVRQAPGKGLEWVS (SEQ ID NO: 298) | RFTISRDNAKNSLYLQMNSLRAEDTAVYYC (SEQ ID NO: 306) | WGQGTMVTVSS (SEQ ID NO: 313) |
| S-29 | EVQLVESGGGLVKPGGSLRLSCAASG (SEQ ID NO: 288) | WVRQAPGKGLEWVS (SEQ ID NO: 298) | RFTISRDNAKNSLYLQMNSLRAEDTAVYYC (SEQ ID NO: 306) | WGQGTMVTVSS (SEQ ID NO: 313) |
| S-30 | EVQLLESGGGLVQPGGSLRLSCAASG (SEQ ID NO: 289) | WVRQAPGKGLEWVS (SEQ ID NO: 298) | RFTISRDNSKNTLYLQMNSLRAEDTAVYYC (SEQ ID NO: 308) | WGQGTTVTVSS (SEQ ID NO: 311) |

TABLE 3-continued

EU or Kabat Heavy Chain Framework sequences of anti-Sortilin antibodies

| Antibody | VH FR1 | VH FR2 | VH FR3 | VH FR4 |
|---|---|---|---|---|
| S-32 | EVQLLESGGGLVQPGGSLRLSCAASG (SEQ ID NO: 289) | WVRQAPGKGLEWVS (SEQ ID NO: 298) | RFTISRDNSKNTLYLQMNSLRAEDTAVYYC (SEQ ID NO: 308) | WGQGTMVTVSS (SEQ ID NO: 313) |
| S-34 | EVQLLESGGGLVQPGGSLRLSCAASG (SEQ ID NO: 289) | WVRQAPGKGLEWVS (SEQ ID NO: 298) | RFTISRDNSKNTLYLQMNSLRAEDTAVYYC (SEQ ID NO: 308) | WGQGTTVTVSS (SEQ ID NO: 311) |
| S-39 | EVQLLESGGGLVQPGGSLRLSCAASG (SEQ ID NO: 289) | WVRQAPGKGLEWVS (SEQ ID NO: 298) | RFTISRDNSKNTLYLQMNSLRAEDTAVYYC (SEQ ID NO: 308) | WGQGTMVTVSS (SEQ ID NO: 313) |
| S-40 | EVQLLESGGGLVQPGGSLRLSCAASG (SEQ ID NO: 289) | WVRQAPGKGLEWVS (SEQ ID NO: 298) | RFTISRDNSKNTLYLQMNSLRAEDTAVYYC (SEQ ID NO: 308) | WGQGTTVTVSS (SEQ ID NO: 311) |
| S-42 | EVQLLESGGGLVQPGGSLRLSCAASG (SEQ ID NO: 289) | WVRQAPGKGLEWVS (SEQ ID NO: 298) | RFTISRDNSKNTLYLQMNSLRAEDTAVYYC (SEQ ID NO: 308) | WGRGTLVTVSS (SEQ ID NO: 314) |
| S-43 | EVQLLESGGGLVQPGGSLRLSCAASG (SEQ ID NO: 289) | WVRQAPGKGLEWVS (SEQ ID NO: 298) | RFTISRDNSKNTLYLQMNSLRAEDTAVYYC (SEQ ID NO: 308) | WGQGTTVTVSS (SEQ ID NO: 311) |
| S-44 | EVQLLESGGGLVQPGGSLRLSCAASG (SEQ ID NO: 289) | WVRQAPGKGLEWVS (SEQ ID NO: 298) | RFTISRDNSKNTLYLQMNSLRAEDTAVYYC (SEQ ID NO: 308) | WGQGTTVTVSS (SEQ ID NO: 311) |
| S-45 | EVQLLESGGGLVQPGGSLRLSCAASG (SEQ ID NO: 289) | WVRQAPGKGLEWVS (SEQ ID NO: 298) | RFTISRDNSKNTLYLQMNSLRAEDTAVYYC (SEQ ID NO: 308) | WGQGTLVTVSS (SEQ ID NO: 312) |
| S-48 | QVQLVESGGGVVQPGRSLRLSCAASG (SEQ ID NO: 290) | WVRQAFGKGLEWVA (SEQ ID NO: 297) | RFTISRDNSKNTLYLQMNSLRAEDTAVYYC (SEQ ID NO: 308) | WGQGTTVTVSS (SEQ ID NO: 311) |
| S-49 | QVQLVESGGGVVQPGRSLRLSCAASG (SEQ ID NO: 290) | WVRQAFGKGLEWVA (SEQ ID NO: 297) | RFTISRDNSKNTLYLQMNSLRAEDTAVYYC (SEQ ID NO: 308) | WGQGTTVTVSS (SEQ ID NO: 311) |
| S-50 | QVQLVESGGGVVQPGRSLRLSCAASG (SEQ ID NO: 290) | WVRQAFGKGLEWVA (SEQ ID NO: 297) | RFTISRDNSKNTLYLQMNSLRAEDTAVYYC (SEQ ID NO: 308) | WGQGTMVTVSS (SEQ ID NO: 313) |
| S-51 | QVQLVESGGGVVQPGRSLRLSCAASG (SEQ ID NO: 290) | WVRQAFGKGLEWVA (SEQ ID NO: 297) | RFTISRDNSKNTLYLQMNSLRAEDTAVYYC (SEQ ID NO: 308) | WGKGTTVTVSS (SEQ ID NO: 315) |
| S-55 | QVQLQESGPGLVKPSETLSLTCAVSG (SEQ ID NO: 291) | WIRQPPGKGLEWIG (SEQ ID NO: 299) | RVTISVDTSKNQFSLKLSSVTAADTAVYYC (SEQ ID NO: 309) | WGQGTLVTVSS (SEQ ID NO: 312) |
| S-57 | QVQLQESGPGLVKPSETLSLTCAVSG (SEQ ID NO: 291) | WIRQPPGKGLEWIG (SEQ ID NO: 299) | RVTISVDTSKNQFSLKLSSVTAADTAVYYC (SEQ ID NO: 309) | WGQGTLVTVSS (SEQ ID NO: 312) |
| S-58 | QVQLQESGPGLVKPSETLSLTCAVSG (SEQ ID NO: 291) | WIRQPPGKGLEWIG (SEQ ID NO: 299) | RVTISVDTSKNQFSLKLSSVTAADTAVYYC (SEQ ID NO: 309) | WGQGTLVTVSS (SEQ ID NO: 312) |
| S-59 | QVQLQESGPGLVKPSETLSLTCAVSG (SEQ ID NO: 291) | WIRQPPGKGLEWIG (SEQ ID NO: 299) | RVTISVDTSKNQFSLKLSSVTAADTAVYYC (SEQ ID NO: 309) | WGQGTLVTVSS (SEQ ID NO: 312) |
| S-60 | QVQLQESGPGLVKPSETLSLTCAVSG (SEQ ID NO: 291) | WIRQPPGKGLEWIG (SEQ ID NO: 299) | RVTISVDTSKNQFSLKLSSVTAADTAVYYC (SEQ ID NO: 309) | WGQGTTVTVSS (SEQ ID NO: 311) |
| S-61 | QVQLQESGPGLVKPSETLSLTCAVSG (SEQ ID NO: 291) | WIRQPPGKGLEWIG (SEQ ID NO: 299) | RVTISVDTSKNQFSLKLSSVTAADTAVYYC (SEQ ID NO: 309) | WGQGTMVTVSS (SEQ ID NO: 313) |
| S-63 | QVQLQESGPGLVKPSETLSLTCAVSG (SEQ ID NO: 291) | WIRQPPGKGLEWIG (SEQ ID NO: 299) | RVTISVDTSKNQFSLKLSSVTAADTAVYYC (SEQ ID NO: 309) | WGRGTLVTVSS (SEQ ID NO: 314) |
| S-64 | QVQLQESGPGLVKPSETLSLTCAVSG (SEQ ID NO: 291) | WIRQPPGKGLEWIG (SEQ ID NO: 299) | RVTISVDTSKNQFSLKLSSVTAADTAVYYC (SEQ ID NO: 309) | WGRGTLVTVSS (SEQ ID NO: 314) |
| S-65 | QVQLQESGPGLVKPSETLSLTCAVSG (SEQ ID NO: 291) | WIRQPPGKGLEWIG (SEQ ID NO: 299) | RVTISVDTSKNQFSLKLSSVTAADTAVYYC (SEQ ID NO: 309) | WGQGTLVTVSS (SEQ ID NO: 312) |
| S-66 | QVQLQESGPGLVKPSQTLSLTCTVSG (SEQ ID NO: 292) | WIRQHPGKGLEWIG (SEQ ID NO: 300) | RVTISVDTSKNQFSLKLSSVTAADTAVYYC (SEQ ID NO: 309) | WGQGTTVTVSS (SEQ ID NO: 311) |
| S-67 | QVQLQESGPGLVKPSQTLSLTCTVSG (SEQ ID NO: 292) | WIRQHPGKGLEWIG (SEQ ID NO: 300) | RVTISVDTSKNQFSLKLSSVTAADTAVYYC (SEQ ID NO: 309) | WGQGTTVTVSS (SEQ ID NO: 311) |
| S-69 | QVQLQESGPGLVKPSQTLSLTCTVSG (SEQ ID NO: 292) | WIRQHPGKGLEWIG (SEQ ID NO: 300) | RVTISVDTSKNQFSLKLSSVTAADTAVYYC (SEQ ID NO: 309) | WGQGTMVTVSS (SEQ ID NO: 313) |
| S-71 | QVQLQESGPGLVKPSQTLSLTCTVSG (SEQ ID NO: 292) | WIRQHPGKGLEWIG (SEQ ID NO: 300) | RVTISVDTSKNQFSLKLSSVTAADTAVYYC (SEQ ID NO: 309) | WGQGTLVTVSS (SEQ ID NO: 312) |

TABLE 3-continued

EU or Kabat Heavy Chain Framework sequences of anti-Sortilin antibodies

| Antibody | VH FR1 | VH FR2 | VH FR3 | VH FR4 |
|---|---|---|---|---|
| S-72 | QVQLQESGPGLVKPSQTLSLTCTVSG (SEQ ID NO: 292) | WIRQHPGKGLEWIG (SEQ ID NO: 300) | RVTISVDTSKNQFSLKLSSVTAADTAVYYC (SEQ ID NO: 309) | WGQGTTVTVSS (SEQ ID NO: 311) |
| S-73 | QVQLQESGPGLVKPSQTLSLTCTVSG (SEQ ID NO: 292) | WIRQHPGKGLEWIG (SEQ ID NO: 300) | RVTISVDTSKNQFSLKLSSVTAADTAVYYC (SEQ ID NO: 309) | WGQGTLVTVSS (SEQ ID NO: 312) |
| S-74 | QVQLQESGPGLVKPSQTLSLTCTVSG (SEQ ID NO: 292) | WIRQHPGKGLEWIG (SEQ ID NO: 300) | RVTISVDTSKNQFSLKLSSVTAADTAVYYC (SEQ ID NO: 309) | WGQGTLVTVSS (SEQ ID NO: 312) |
| S-75 | QVQLQESGPGLVKPSQTLSLTCTVSG (SEQ ID NO: 292) | WIRQHPGKGLEWIG (SEQ ID NO: 300) | RVTISVDTSKNQFSLKLSSVTAADTAVYYC (SEQ ID NO: 309) | WGQGTTVTVSS (SEQ ID NO: 311) |
| S-76 | QVQLQESGPGLVKPSQTLSLTCTVSG (SEQ ID NO: 292) | WIRQHPGKGLEWIG (SEQ ID NO: 300) | RVTISVDTSKNQFSLKLSSVTAADTAVYYC (SEQ ID NO: 309) | WGQGTLVTVSS (SEQ ID NO: 312) |
| S-78 | QLQLQESGPGLVKPSETLSLTCTVSG (SEQ ID NO: 294) | WIRQPPGKGLEWIG (SEQ ID NO: 299) | RVTISVDTSKNQFSLKLSSVTAADTAVYYC (SEQ ID NO: 309) | WGRGTLVTVSS (SEQ ID NO: 314) |
| S-81 | QLQLQESGPGLVKPSETLSLTCTVSG (SEQ ID NO: 294) | WIRQPPGKGLEWIG (SEQ ID NO: 299) | RVTISVDTSKNQFSLKLSSVTAADTAVYYC (SEQ ID NO: 309) | WGQGTTVTVSS (SEQ ID NO: 311) |
| S-82 | QLQLQESGPGLVKPSETLSLTCTVSG (SEQ ID NO: 294) | WIRQPPGKGLEWIG (SEQ ID NO: 299) | RVTISVDTSKNQFSLKLSSVTAADTAVYYC (SEQ ID NO: 309) | WGQGTLVTVSS (SEQ ID NO: 312) |
| S-83 | QLQLQESGPGLVKPSETLSLTCTVSG (SEQ ID NO: 294) | WIRQPPGKGLEWIG (SEQ ID NO: 299) | RVTISVDTSKNQFSLKLSSVTAADTAVYYC (SEQ ID NO: 309) | WGKGTTVTVSS (SEQ ID NO: 315) |
| S-84 | QLQLQESGPGLVKPSETLSLTCTVSG (SEQ ID NO: 294) | WIRQPPGKGLEWIG (SEQ ID NO: 299) | RVTISVDTSKNQFSLKLSSVTAADTAVYYC (SEQ ID NO: 309) | WGQGTMVTVSS (SEQ ID NO: 313) |
| S-85 | EVQLVQSGAEVKKPGESLKISCKGSG (SEQ ID NO: 295) | WVRQMPGKGLEWMG (SEQ ID NO: 301) | QVTISADKSISTAYLQWSSLKASDTAMYYC (SEQ ID NO: 310) | WGQGTMVTVSS (SEQ ID NO: 313) |

Characterization of Sortilin Antibody Binding

Initial characterization of anti-Sortilin antibodies involved determining their ability to bind Sortilin expressed on human embryonic kidney (293) cells expressing either recombinant human Sortilin (hSort) or recombinant mouse Sortilin (mSort). Cells were harvested, plated at $10^5$/ml in a 96 well plate, washed, and incubated in 100 μl PBS containing 10 μg/ml Mab and 2% FBS for 1 hour in ice. Cells were then washed twice and incubated in 100 μl PBS+2% FBS containing 5 μg/ml PE-conjugated anti-human secondary antibody for 30 minutes in ice. Cells were washed twice in cold PBS and data was acquired on a BD FACS Canto. Data analysis and calculation of MFI values was performed with FlowJo (TreeStar) software version 10.0.7.

Median fluorescent intensities (MFI) values for cell types bound by Sortilin antibodies S1-S85 are listed in Table 4. Binding is compared to the parental cell line (293). The results in Table 4 indicate that S1-S85 bind specifically to cell lines overexpressing human and mouse Sortilin on the cell membrane, but not to control cell lines that do not express Sortilin.

TABLE 4

Sortilin Antibody Binding to Human and Mouse Cells

| Antibody | MFI binding hSort on 293 cells | MRI binding mSort on 293 cells | MFI binding to 293 parental cells |
|---|---|---|---|
| S-1 | 10019 | 23720 | 68 |
| S-2 | 8427 | 22413 | 96 |
| S-3 | 8863 | 18775 | 62 |
| S-4 | 9124 | 15696 | 38 |
| S-5 | 10566 | 8817 | 133 |
| S-6 | 11089 | 25632 | 45 |
| S-7 | 10657 | 23714 | 88 |
| S-8 | 14184 | 28089 | 41 |
| S-9 | 10272 | 22166 | 40 |
| S-10 | 8661 | 19377 | 98 |
| S-11 | 2286 | 7064 | 106 |
| S-12 | 9759 | 18830 | 38 |
| S-13 | 5439 | 8692 | 134 |
| S-14 | 8008 | 16531 | 106 |
| S-15 | 8745 | 17598 | 34 |
| S-16 | 6279 | 1777 | 131 |
| S-17 | 2409 | 2011 | 74 |
| S-18 | 9347 | 21722 | 46 |
| S-19 | 11724 | 28245 | 107 |
| S-20 | 9390 | 23831 | 129 |
| S-21 | 9382 | 22946 | 109 |
| S-22 | 8935 | 23188 | 52 |
| S-23 | 6682 | 8635 | 65 |
| S-24 | 4381 | 10520 | 63 |
| S-25 | 8376 | 5818 | 68 |
| S-26 | 9018 | 20856 | 77 |
| S-27 | 4302 | 9828 | 82 |
| S-28 | 8564 | 21616 | 123 |
| S-29 | 9604 | 21845 | 131 |
| S-30 | 9433 | 19598 | 108 |
| S-31 | 6082 | 9899 | 69 |
| S-32 | 7898 | 4679 | 107 |
| S-33 | 5996 | 4896 | 95 |
| S-34 | 6217 | 8974 | 101 |
| S-35 | 5798 | 5891 | 52 |
| S-36 | 6331 | 8183 | 36 |
| S-37 | 5949 | 4931 | 41 |

TABLE 4-continued

Sortilin Antibody Binding to Human and Mouse Cells

| Antibody | MFI binding hSort on 293 cells | MRI binding mSort on 293 cells | MFI binding to 293 parental cells |
|---|---|---|---|
| S-38 | 4678 | 11706 | 82 |
| S-39 | 8178 | 8436 | 66 |
| S-40 | 7411 | 2628 | 68 |
| S-41 | 6498 | 963 | 34 |
| S-42 | 7153 | 8247 | 66 |
| S-43 | 6950 | 2016 | 64 |
| S-44 | 6510 | 12288 | 42 |
| S-45 | 8812 | 7788 | 41 |
| S-46 | 6363 | 1459 | 43 |
| S-47 | 5639 | 1785 | 47 |
| S-48 | 8145 | 11921 | 114 |
| S-49 | 11561 | 24088 | 34 |
| S-50 | 7628 | 17540 | 33 |
| S-51 | 12196 | 21931 | 137 |
| S-52 | 5652 | 1380 | 115 |
| S-53 | 4813 | 1456 | 136 |
| S-54 | 6021 | 12448 | 52 |
| S-55 | 9478 | 21359 | 46 |
| S-56 | 6059 | 4343 | 39 |
| S-57 | 9126 | 20843 | 97 |
| S-58 | 7773 | 15090 | 52 |
| S-59 | 7970 | 14213 | 111 |
| S-60 | 7978 | 858 | 105 |
| S-61 | 7476 | 21797 | 61 |
| S-62 | 6534 | 20619 | 74 |
| S-63 | 7689 | 19361 | 41 |
| S-64 | 7932 | 3672 | 146 |
| S-65 | 8072 | 17890 | 30 |
| S-66 | 9010 | 7452 | 67 |
| S-67 | 9129 | 2563 | 48 |
| S-68 | 3872 | 1886 | 144 |
| S-69 | 8585 | 1893 | 43 |
| S-70 | 3544 | 1141 | 152 |
| S-71 | 7505 | 2472 | 62 |
| S-72 | 8992 | 7746 | 24 |
| S-73 | 8073 | 7673 | 79 |
| S-74 | 9207 | 7296 | 50 |
| S-75 | 7131 | 12415 | 139 |
| S-76 | 9680 | 4175 | 142 |
| S-77 | 6224 | 13030 | 127 |
| S-78 | 7117 | 7931 | 79 |
| S-79 | 4294 | 1308 | 116 |
| S-80 | 5110 | 579 | 112 |
| S-81 | 8935 | 16565 | 108 |
| S-82 | 10087 | 5196 | 35 |
| S-83 | 9298 | 484 | 77 |
| S-84 | 9242 | 15364 | 105 |
| S-85 | 8356 | 20416 | 69 |
| Isotype control 1 | 44 | 43.6 | 21 |
| Isotype control 2 | 38 | 41.7 | 22 |

The binding affinity of each anti-Sortilin antibody was determined by measuring their Ku by ForteBio or MSD-SET at room temperature. ForteBio affinity measurements were performed as previously described (Estep et al, (2013), Mabs 5(2):270-8). Briefly, ForteBio affinity measurements were performed by loading IgGs on-line onto AHQ sensors. Sensors were equilibrated off-line in assay buffer for 30 min and then monitored on-line for 60 seconds for baseline establishment. Sensors with loaded IgGs were exposed to 100 nM antigen for 5 minutes, then transferred to assay buffer for 5 min for off-rate measurement. Kinetics were analyzed using the 1:1 binding model.

Equilibrium affinity measurements were performed as previously described (Estep et al., (2013) MAbs 5(2):270-8). Solution equilibrium titrations (SET) were performed in PBS+0.1% IgG-Free BSA (PBSF) with antigen held constant at 50 psi and incubated with 3- to 5-fold serial dilutions of antibody starting at 10 nM. Antibodies (20 nM in PBS) were coated onto standard bind MSD-ECL plates overnight at 4° C. or at room temperature for 30 min. Plates were then blocked for 30 mum with shaking at 700 rpm, followed by three washes with wash buffer (PBSF+0.05% Tween 20). SET samples were applied and incubated on the plates for 150 s with shaking at 700 rpm followed by one wash. Antigen captured on a plate was detected with 250 ng/mL sulfotag-labeled streptavidin in PBSF by incubation on the plate for 3 min. The plates were washed three times with wash buffer and then read on the MSD Sector Imager 2400 instrument using 1× Read Buffer T with surfactant. The percent free antigen was plotted as a function of titrated antibody in Prism and fit to a quadratic equation to extract the K0. To improve throughput, liquid handling robots were used throughout MSD-SET experiments, including SET sample preparation.

Table 5 lists values representing the binding affinity ($K_D$) of antibodies S1-S85 to a human Sortilin Fc fusion protein (hSort-Fc), and a mouse Sortilin Fc fusion protein (mSort-Fc), as well as the bin to which they belong. Antibodies that belong to the same bin compete with each other on binding to Sortilin. In Table 5, "N.B." corresponds to no binding; and "P.F." corresponds to poor curve fit.

TABLE 5

Binding affinity of Sortilin antibodies

| Antibody | Bin Number | IgG KD hSort-Fc (M) Avid | IgG KD mSort-Fc (M) Avid |
|---|---|---|---|
| S-1 | 3/4 | 1.87E−08 | 1.22E−08 |
| S-2 | 1/2 | 5.17E−10 | 1.07E−09 |
| S-3 | 3/4 | 1.24E−08 | 3.29E−09 |
| S-4 | 3/4 | 4.50E−09 | 1.55E−09 |
| S-5 | 4 | 2.46E−09 | P.F. |
| S-6 | 3/4 | 3.55E−09 | 1.21E−09 |
| S-7 | 3 | 4.20E−09 | 1.26E−09 |
| S-8 |  | 3.25E−09 | 1.09E−09 |
| S-9 | 3/4 | 6.98E−09 | 2.16E−09 |
| S-10 | 3/4 | 1.10E−08 | 2.29E−09 |
| S-11 | 3/4 | 7.04E−08 | 3.63E−08 |
| S-12 | 4 | 9.35E−09 | N.B. |
| S-13 | 3/4 | 1.53E−08 | N.B. |
| S-14 | 3 | 5.74E−09 | 2.74E−09 |
| S-15 | 3 | 2.30E−09 | 1.40E−09 |
| S-16 | 1 | 3.80E−09 | N.B. |
| S-17 | 1/2 | 7.59E−09 | N.B. |
| S-18 | 2 | 4.75E−10 | 2.30E−09 |
| S-19 | 2 | 8.43E−10 | 7.33E−10 |
| S-20 | 2 | 1.00E−09 | 9.57E−10 |
| S-21 | 2 | 1.87E−09 | 2.80E−09 |
| S-22 | 2 | 9.90E−10 | 1.12E−09 |
| S-23 | 3/4 | 2.22E−08 | P.F. |
| S-24 | 4 | 2.74E−08 | 1.32E−08 |
| S-25 | 4 | 7.07E−09 | N.B. |
| S-26 | 3/4 | 2.88E−09 | 6.81E−10 |
| S-27 | 3/4 | 1.28E−08 | 2.17E−08 |
| S-28 | 2 | 2.99E−10 | 1.25E−09 |
| S-29 | 2 | 3.70E−10 | 1.37E−09 |
| S-30 | 4 | 1.55E−09 | 6.11E−10 |
| S-31 | 3/4 | 1.17E−08 | P.F. |
| S-32 | 3/4 | 9.39E−09 | P.F. |
| S-33 | 4 | 1.19E−08 | P.F. |
| S-34 | 4 | 1.24E−08 | P.F. |
| S-35 | 4 | 9.87E−09 | P.F. |
| S-36 | 4 | 9.93E−09 | P.F. |

TABLE 5-continued

Binding affinity of Sortilin antibodies

| Antibody | Bin Number | IgG KD hSort-Fc (M) Avid | IgG KD mSort-Fc (M) Avid |
|---|---|---|---|
| S-37 | 4 | 7.69E−09 | N.B. |
| S-38 | 3/4 | 1.32E−08 | 1.09E−08 |
| S-39 | 4 | 5.15E−09 | 1.83E−08 |
| S-40 | 4 | 2.43E−09 | P.F. |
| S-41 | 4 | 6.51E−09 | 2.38E−08 |
| S-42 | 4 | 5.86E−09 | P.F. |
| S-43 | 4 | 1.13E−08 | P.F. |
| S-44 | 4 | 7.81E−09 | 7.96E−09 |
| S-45 | 4 | 2.07E−09 | 2.96E−08 |
| S-46 | 3/4 | 4.31E−09 | N.B. |
| S-47 | 4 | 5.08E−09 | 2.66E−08 |
| S-48 | 3 | 4.96E−09 | 1.53E−09 |
| S-49 | | 1.34E−09 | 1.09E−09 |
| S-50 | | 2.14E−09 | 1.92E−09 |
| S-51 | 3 | 4.12E−09 | 1.21E−09 |
| S-52 | 3/4 | 7.81E−09 | 4.03E−08 |
| S-53 | 1/2 | 8.76E−09 | 2.29E−08 |
| S-54 | 3/4 | 5.40E−09 | 2.48E−09 |
| S-55 | 3 | 2.28E−09 | 1.13E−09 |
| S-56 | 1/2 | 2.08E−08 | 3.31E−08 |
| S-57 | 3 | 2.97E−09 | 1.62E−09 |
| S-58 | 3 | 2.59E−09 | 8.00E−10 |
| S-59 | 3 | 6.01E−09 | 1.21E−09 |
| S-60 | 4 | 9.97E−10 | N.B. |
| S-61 | 3 | 4.26E−09 | 2.45E−09 |
| S-62 | 3/4 | 1.16E−08 | 3.24E−09 |
| S-63 | 4 | 8.95E−10 | 7.23E−09 |
| S-64 | 4 | 1.24E−09 | 2.42E−08 |
| S-65 | 4 | 2.92E−09 | 6.90E−09 |
| S-66 | 4 | 2.37E−09 | 1.78E−08 |
| S-67 | 4 | 2.66E−09 | 2.01E−08 |
| S-68 | 3/4 | 2.26E−08 | P.F. |
| S-69 | 3/4 | 4.29E−09 | 2.01E−08 |
| S-70 | 3/4 | 9.17E−09 | N.B. |
| S-71 | 3/4 | 2.82E−09 | 1.75E−08 |
| S-72 | 4 | 1.32E−09 | 1.25E−08 |
| S-73 | 3/4 | 3.33E−09 | 1.97E−08 |
| S-74 | 3/4 | 3.05E−09 | N.B. |
| S-75 | 3/4 | 7.07E−09 | 1.01E−08 |
| S-76 | 4 | 1.58E−09 | 1.90E−08 |
| S-77 | 3/4 | 5.31E−09 | 4.33E−09 |
| S-78 | 4 | 3.51E−09 | 1.06E−08 |
| S-79 | 3/4 | 2.36E−08 | N.B. |
| S-80 | 3/4 | 1.95E−08 | N.B. |
| S-81 | 4 | 2.20E−09 | 1.59E−09 |
| S-82 | 2 | 3.94E−10 | 1.87E−08 |
| S-83 | 4 | 1.79E−09 | N.B. |
| S-84 | 4 | 4.40E−09 | N.B. |
| S-85 | 3/4 | 7.63E−09 | 3.99E−09 |
| Isotype control 1 | | NA | NA |
| Isotype control 2 | | NA | NA |

Example 2: Epitope Mapping of Sortilin Antibodies

Sortilin antibodies were tested for their ability to bind 15-mer or 25-mer peptides spanning the entire human Sortilin protein.

Linear 15-mer peptides were synthesized based on the sequence of human Sortilin (SEQ ID NO:1), with a 14 residue overlap. in addition, linear 25-mer peptides were synthesized based on sequence of human Sortilin (SEQ ID NO:1), with a 24 residue overlap. The peptides were synthesized using standard Fmoc-chemistry and deprotected using trifluoric acid with scavengers. The binding of Sortilin antibodies to each of the synthesized peptides was tested in an ELISA-based method. In this assay, the peptide arrays were incubated with primary antibody solution (overnight at 4° C.). After washing, the peptide arrays were incubated with a 1/1000 dilution of an antibody peroxidase conjugate (SBA, cat. nr. 2010-05) for one hour at 25° C. After washing, the peroxidase substrate 2,2'-azino-di-3-ethylbenzthiazoline sulfonate (ARTS) and 2 µl/ml of 3% $H_2O_2$ were added. After one hour, the color development was measured. The color development was quantified with a charge coupled device (CCD) camera and an image processing system.

The Sortilin binding region was determined for six anti-Sortilin antibodies: S-1, S-8, S-44, 5-49, S-65, and S-78. The binding regions are listed in Table 6. FIG. 1 shows a schematic representation of human Sortilin, indicating the regions bound by the six anti-Sortilin antibodies.

TABLE 6A

Sortilin antibody binding regions

| Antibody | Sortilin binding region | Amino acid region of SEQ ID: 1 |
|---|---|---|
| S-1 | $^{623}$HSTDPEDYIED$^{632}$ (SEQ ID NO: 708) | 623-632 |
| S-8 | $^{429}$ITFDQGGRWTHLRKP$^{443}$ (SEQ ID NO: 709) | 429-443 |
| S-44 | $^{740}$CTSNFLSPEK$^{749}$ (SEQ ID NO: 710) | 740-749 |
| S-49 | $^{233}$LSTENGLWVSK$^{243}$ (SEQ ID NO: 711) | 233-243 |
| S-65 | $^{175}$GPENSGK$^{181}$ (SEQ ID NO: 712) | 175-181 |
| S-78 | $^{212}$LPFHPLTQMM$^{221}$ (SEQ ID NO: 713) | 212-221 |

As indicated in Table 6, the peptide recognized by antibody S-1 corresponds to amino acid residues 623-632 of SEQ ID NO: 1 and has the amino acid sequence of: HSTDPEDYED (SEQ ID NO:708). The peptide recognized by antibody S-8 corresponds to amino acid residues 429-443 of SEQ ID NO: 1 and has the amino acid sequence of ITFDQGGRWTHLRKP (SEQ ID NO:709). The peptide recognized by antibody S-44 corresponds to amino acid residues 740-749 of SEQ ID NO: 1 and has the amino acid sequence of: CTSNFLSPEK (SEQ ID NO:710). The peptide recognized by antibody S-49 corresponds to amino acid residues 233-243 of SEQ ID NO: I and has the amino acid sequence of: LSTENGLWVSK (SEQ ID NO:711). The peptide recognized by antibody S-65 corresponds to amino acid residues 175-181 of SEQ ID NO: I and has the amino acid sequence of: GPENSGK (SEQ ID NO: 712). The peptide recognized by antibody S-78 corresponds to amino acid residues 212-221 of SEQ ID NO: 1 and has the amino acid sequence of: LPFHPLTQMM (SEQ ID NO:713). The peptides bound by each antibody are depicted in FIG. 1. The peptide recognized by S-1 is shown in green, the peptide recognized by S-65 is shown in red, the peptide recognized by S-49 shown in blue, the peptide recognized by S-78 is shown in yellow, the peptide recognized by S-44 is shown in pink, and the peptide recognized by S-8 is shown in purple.

Example 3: Characterization of Interactions Between Sortilin and Progranulin Introduction The interaction between Sortilin and Progranulin was characterized using ForteBio and surface plasmon resonance analysis (e.g., Skeldal, S et al., (2012) J Biol Chem., 287:43798; and Andersen, O S et al., (2010) THE JOURNAL OF BIOLOGICAL CHEMISTRY, 285, 122111-12222)

Materials and Methods

The interaction between Sortilin (SORT1) and Progranulin (PGRN) was characterized using surface plasmon resonance (SPR) analysis (see, e.g., Skeldal, S et al., (2012) J Biol Chem., 287:43798; and Andersen, O S et al., (2010) THE JOURNAL OF BIOLOGICAL CHEMISTRY, 285, 12210-12222).

Determination of direct binding of human or mouse Progranulin to immobilized Sortilin, as well as binding of human or mouse Sortilin to immobilized Progranulin, in the presence or absence of blocking anti-Sortilin antibodies was performed on a Biacore2000 instrument (Biacore, Sweden) using CaHBS as standard running buffer (10 mM HEPES, pH 7.4, 140 mM NaCl, 2 mM $CaCl_2$, 1 mM EGTA, and 0.005% Tween 20).

A biosensor chip from Biacore (CM5, catalog no. BR-1000-14) was activated using the NHS/EDC: method as described by the supplier followed by coating with Sortilin to a protein density of 79 $fmol/mm^2$ and used for affinity measurements of native Progranulin protein. Regeneration of the flow cell after each cycle of ligand binding experiment was done by two 10-µl pulses of regeneration buffer (10 mM glycine-HCl, pH 4.0, 500 mM NaCl, 20 mM EDTA, and 0.005% Tween 20) and a single injection of 0.001% SDS. Fitting of sensorgrams for affinity estimations was done using BIAevaluation version 3.1. Following similar protocols, immobilization of His-Progranulin was also done on a CM5 biosensor chip using the NHS/EDC coupling kit according to the manufacturer's instructions (Biacore, Sweden), giving similar surface densities of immobilized protein (~300 $fmol/mm^2$). A biosensor chip with immobilized Progranulin was also used to examine the binding of Sortilin in the absence or presence of competing Sortilin antibodies.

Figure 2A:
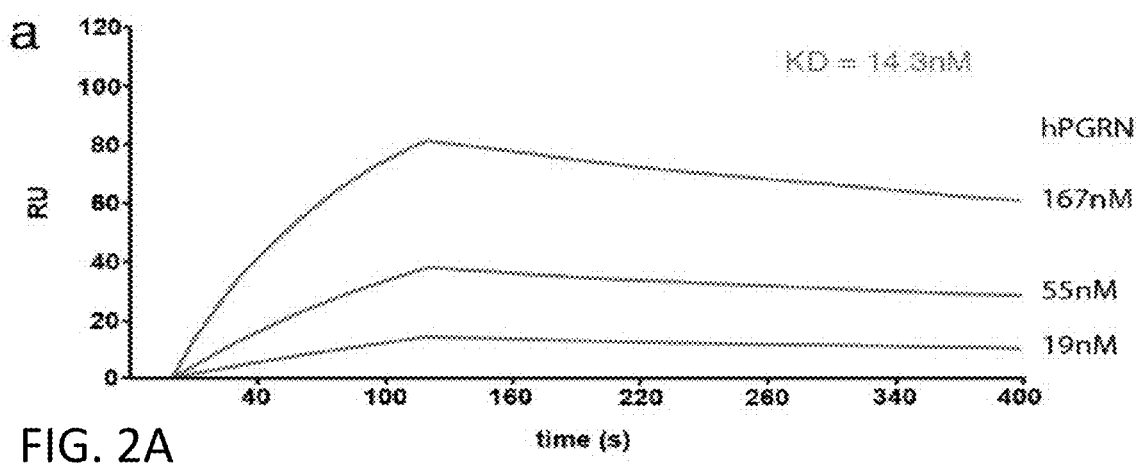
FIG. 2A-2C show the characterization of interactions between Sortilin and Progranulin using surface plasmon resonance (SPR) and ELISA.

Ligand competition between Progranulin and anti-Sortilin antibodies was performed similarly to the epitope binning of Sortilin antibodies described in Example 1 above. Briefly, the competition assay was performed on a Forte Bio Octet Red384 system (Pall Forte Bio Corporation, Menlo Park, Calif.) using a standard sandwich format binning assay. Control anti-target IgG was loaded onto AHQ sensors and unoccupied Fc-binding sites on the sensor were blocked with a non-relevant human IgG1 antibody. The sensors were then exposed to 100 nM target antigen followed by a second anti-target antibody. Data was processed using ForteBio's Data Analysis Software 7.0. Additional binding by the second antibody after antigen association indicates an unoccupied epitope (non-competitor), while no binding indicates epitope blocking (competitor), Results Characterization of Progranulin binding with Sortilin The interactions between Sortilin and Progranulin were first characterized using SPR and ELISA analysis. FIG. 2A shows a kinetic analysis of PGRN binding to His-captured SORT1 was performed using Biacore SPR. Briefly, Sortilin was captured on a CMS sensor chip that was immobilized with an anti-His antibody (kit from GE). Progranulin was flowed over in HBS binding buffer at various concentrations. Fitting of sensorgrams for affinity estimations was done using BIAevaluation version 3.1, The results indicate that human Progranulin binds to human Sortilin with a $K_D$ of 14.3 nM.

Binding between Sortilin and Progranulin was also confirmed by ELISA. Briefly, human or mouse Sortilin (R&D Systems) was immobilized overnight on an ELBA plate (2 µg/ml in PBS). The plates were washed in wash buffer (PBS+0.05% TWEEN20) and blocked for one hour at 37° C. with binding buffer (PBS+1% BSA). Recombinant human or mouse Progranulin (Adipogen) was biotinylated with a EZ-Link Micro NFIS-PEG4 kit from ThermoScientific/Pierce. Biotinylated Progranulin was added at various concentrations to immobilized Sortilin and incubated at RT for 30 min. Plates were washed thrice in wash buffer and incubated with Streptavidin-HRP (1:200 in binding buffer, R&D Systems) for 20 min. Plates were washed thrice again and incubated with TMB substrate solution until color developed. The reaction was stopped by adding 50 ul of 2N sulfuric acid and color was quantified using a Biotek Synergy H1 plate reader. Data was analyzed and fitted in Prism.

Figure 2B:
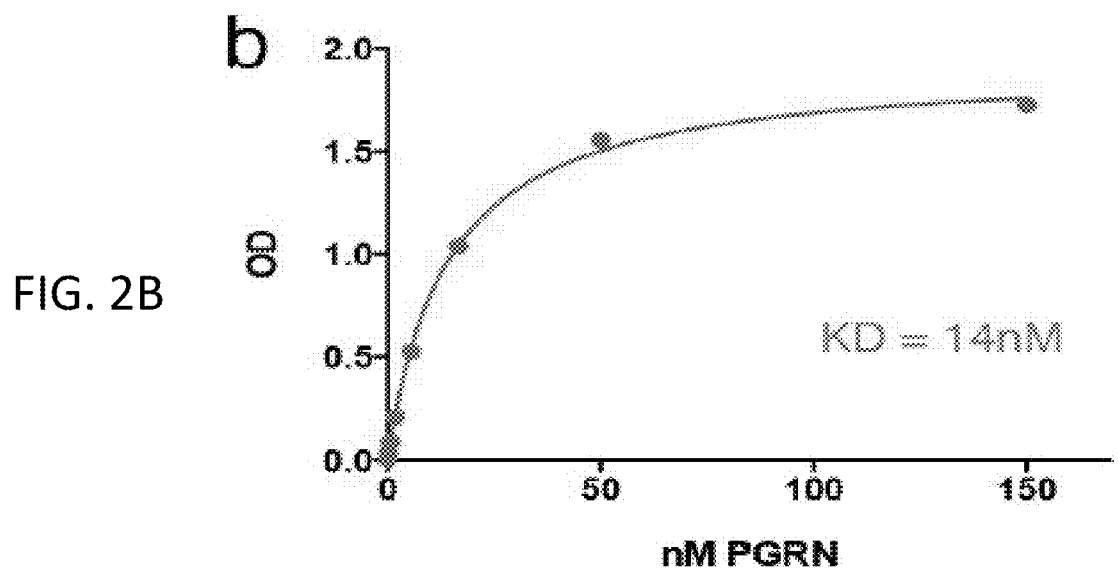
Figure 2C:
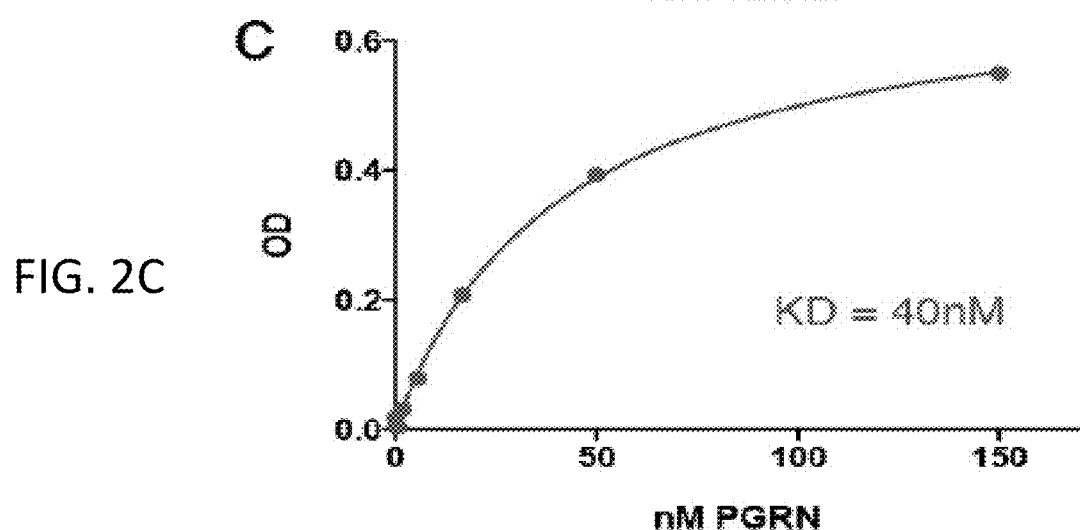

FIG. 2B shows binding of biotinylated human Progranulin to immobilized human Sortilin on anti ELISA plate (OD=optical density), and FIG. 2C shows binding of biotinylated mouse Progranulin to immobilized mouse Sortilin on an ELISA plate. The results indicate that human Progranulin binds to human Sortilin with a $K_D$ of 14 nM, and mouse Progranulin binds to mouse Sortilin with a $K_D$ of 40 nM.

Antibody Competition Assays with Progranulin Peptides

Figure 3A:
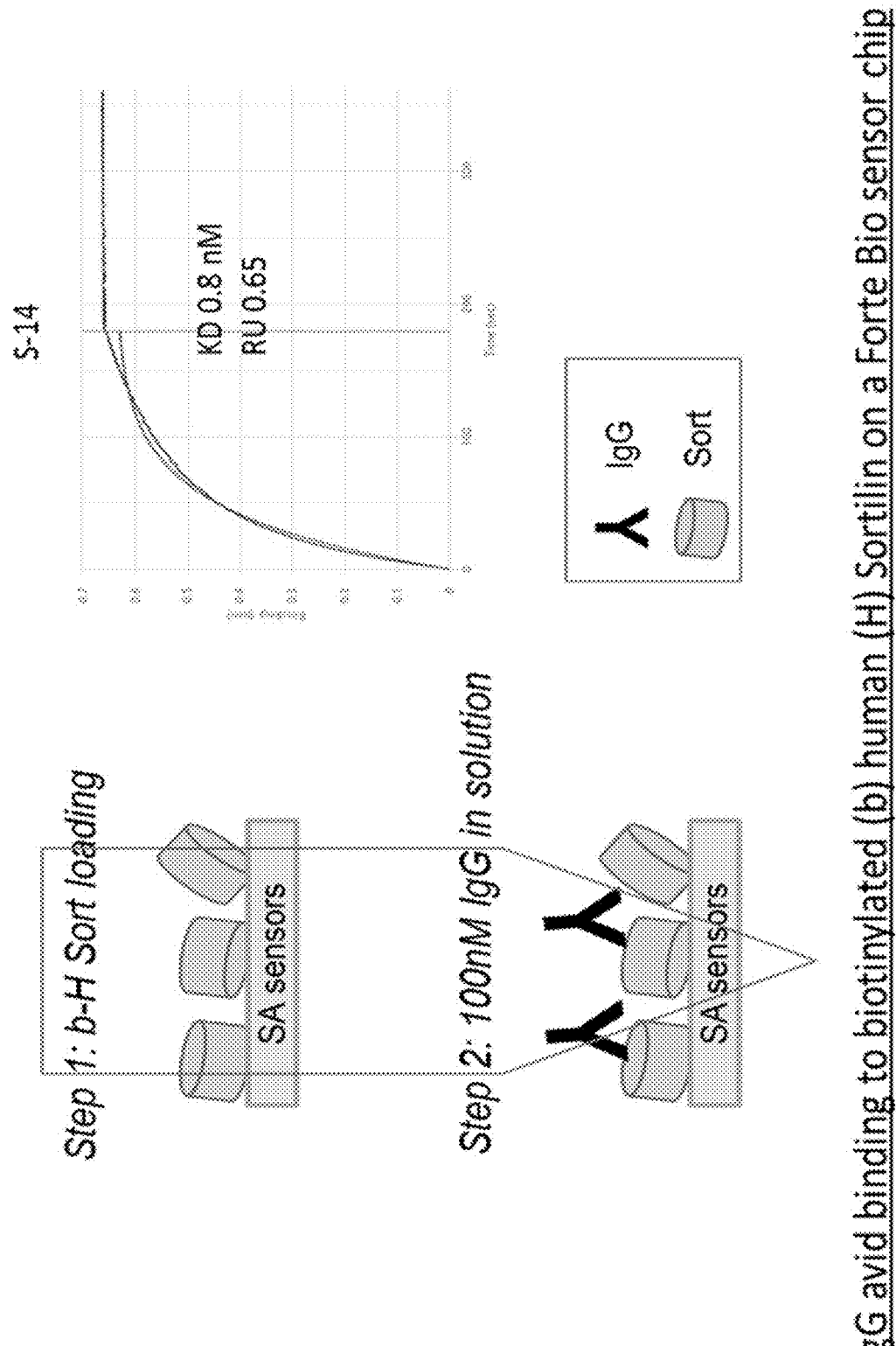
FIG. 3A shows antibody avidity binding to human Sortilin (b-H Sort) on a sensor chip and competition with anti-Sortilin antibodies (IgG).

FIG. 3A depicts a ForteBio analysis scheme for determining the ability of anti-Sortilin antibodies to bind Sortilin and for quantifying the binding (i.e., $K_D$). In the figure, "RU" refers to response units. Exemplary results are shown with antibody S-14, which was calculated to have a $K_D$ of 0.8 nM.

Antibody Competition Assays with Sortilin Protein

FIG. 38 depicts different ForteBio competition analysis schemes. The left column depicts ForteBio competition analysis using biotinylated Progranulin peptides bound on SA sensors and recombinant human Sortilin (monomeric)

and anti-Sortilin IgG antibodies (see left column; SORT=Sortilin PGRN Progranulin, b=biotinylated, H=human, mono=monomeric).

The middle column of FIG. 38 depicts ForteBio competition analysis using biotinylated monomeric human Sortilin protein bound on SA sensors and human native full-length Progranulin and anti-Sortilin antibodies.

Figure 3B:
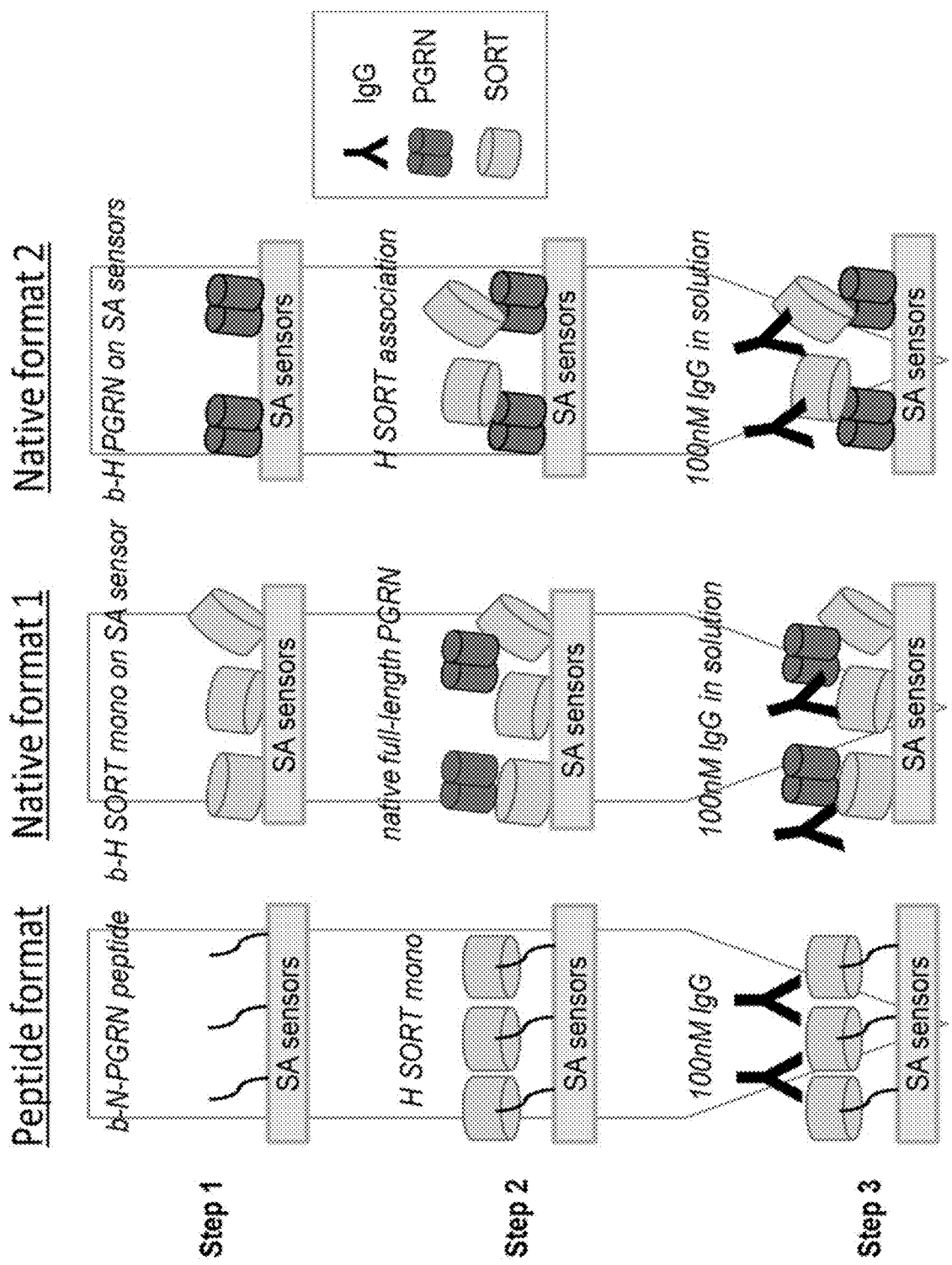
FIG. 3B shows the characterization of interactions between Sortilin (SORT) and Progranulin (PGRN) using Forte Bio analysis and competition with anti-Sortilin antibodies (IgG). Left column: biotinylated Progranulin peptide is immobilized on the sensor chip and SORT added in solution, followed by IgG. Center column: biotinylated recombinant human SORT is immobilized on a sensor chip and recombinant PGRN is added in solution followed by the IgG. Right column: biotinylated recombinant PGRN is immobilized on a sensor chip and human SORT is added in solution, followed by IgG. (SORT=Sortilin, PGRN=Progranulin, b=biotinylated, H=human, mono=monomeric).

The right column of FIG. 3B depicts ForteBio competition analysis using biotinylated human Progranulin protein bound on SA sensors and human Sortilin monomers and anti-Sortilin antibodies.

Results of Antibody Competition Assays

Figure 4A:
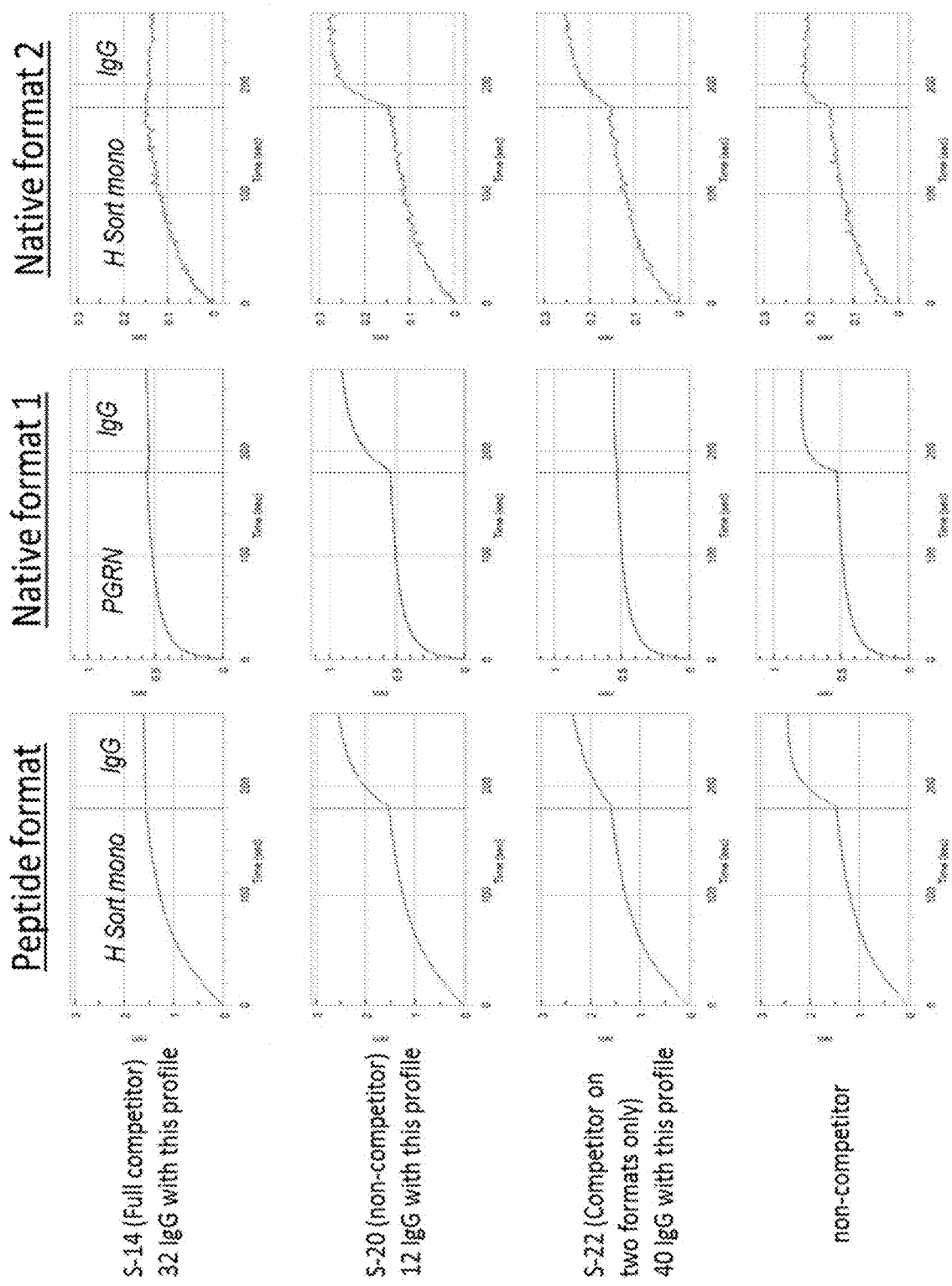
FIG. 4A shows examples of different classes of anti-Sortilin antibodies that block Progranulin binding in different ForteBio orientations (described in FIG. 3B). The left column depicts competition binding using human SORT that binds a PGRN peptide immobilized on a sensor chip. The middle column depicts competition binding using native PGRN protein that binds human SORT immobilized on a sensor chip. The right column depicts competition binding using native SORT protein that hinds native PGRN protein immobilized on a SensorChip.

FIG. 4A depicts results from the three different ForteBio analyses depicted in FIGS. 3A and 3B, and shows several examples of anti-Sortilin antibodies that block Progranulin (PGRN) binding to Sortilin (SORT1).

The left column of FIG. 4A shows the binding setup described in the left column of FIG. 38, where a PGRN peptide that binds SORT1 was immobilized on a SensorChip. SORT1 was bound and then it was tested whether the test anti-Sortilin antibody could bind. The antibodies that were able to bind Sortilin were considered to be non-competitors. The results indicate that antibodies S-20 and S-22 are non-competitors, while antibody S-14 is a competitor.

The middle column of FIG. 4A shows the binding setup described in the middle column of FIG. 3B, where biotinylated SORT1 monomer was immobilized on a SensorChip. Full-length PGRN protein was bound and then it was tested whether the test anti-Sortilin antibody could bind. The antibodies that were able to bind Sortilin were considered to be non-competitors. The results indicate that antibody S-20 is a non-competitor, while antibodies S-14 and S-22 are competitors.

The right column of FIG. 4A shows the binding setup described in the right column of FIG. 38, where biotinylated PGRN protein was immobilized on a SensorChip. SORT1 was bound and then it was tested whether the test anti-Sortilin antibody could bind. The antibodies that were able to bind Sortilin were considered to be non-competitors. The results indicate that antibodies S-20 and S-22 are non-competitors, while antibody S-14 is a competitor.

The results in FIG. 4A indicate that not all anti-Sortilin antibodies are competitors, and that some, such as antibody S-22, can act as a non-competitor in one or two formats, while acting as competitor in other format(s).

Figure 4B:
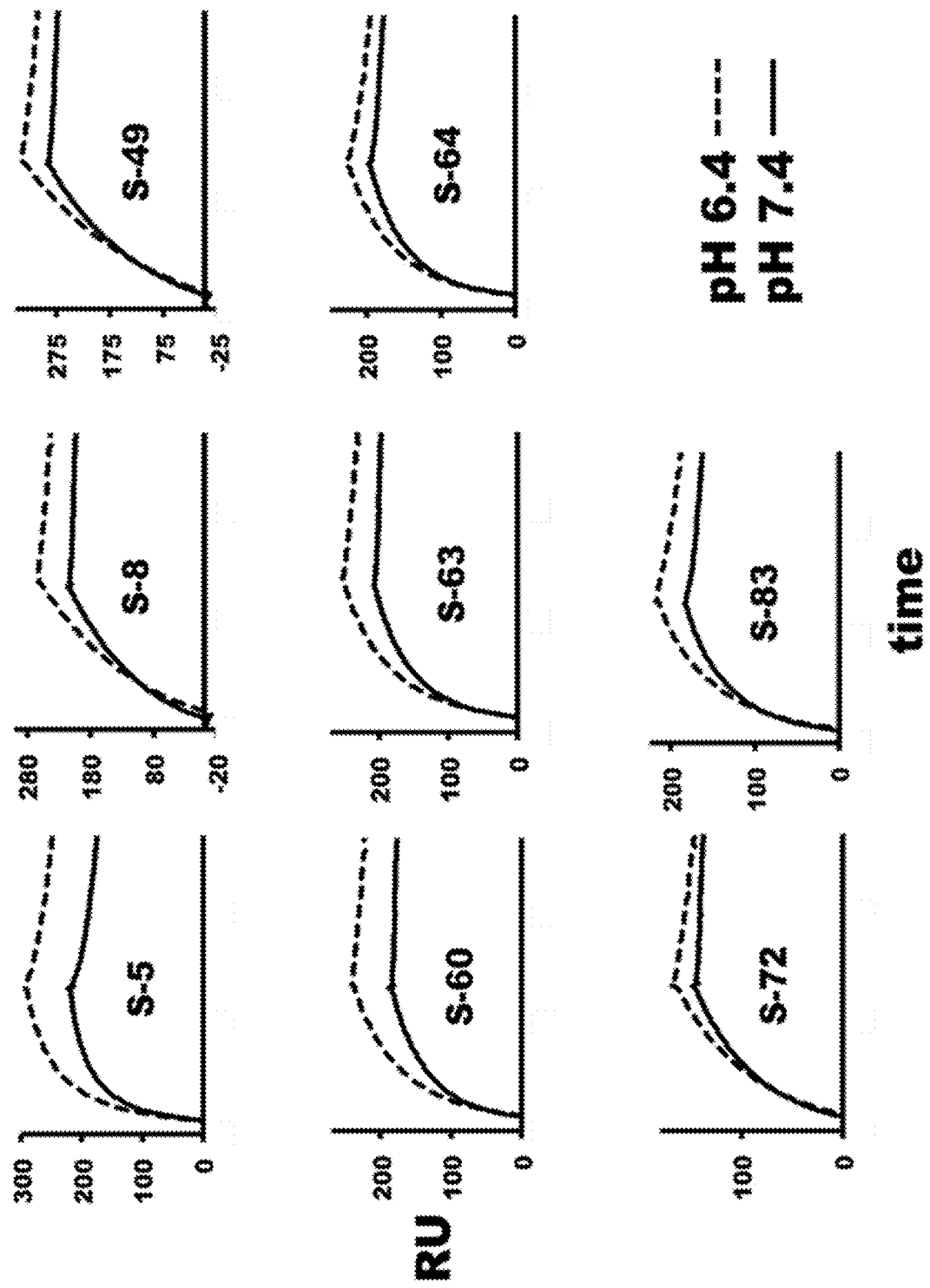
FIG. 4B shows binding of anti-Sortilin antibodies to His-captured Sortilin (SORT1) using Biacore SPR at pH6.4 and pH7.4.

FIG. 4B shows binding of anti-Sortilin antibodies (S-5, S-8, S-49, S-60, S-63, S-64, S-72, and S-83) to His-captured Sortilin (SORT1) using Biacore SPR at pH6.4 and pH7.4, Table 7 shows the results of SPR competition assays performed with antibodies S1-S85. Column 2 of Table 7 corresponds to the assay described in the left column of FIG. 38. Column 3 of Table 7 corresponds to the assay described in the middle column of FIG. 38. Column 4 of Table 7 correspond to the assay described in the right column of FIG. 3B. In Table 7, "hPGRN" refers to human Progranulin; a "Yes" indicates that the antibody blocked in the given format, and a "No" indicates that the antibody did not block in the given format.

TABLE 7

ForteBio Antibody Competition Assays

| Antibody | Competition with hPGRN peptide ForteBio, Peptide Format | Competition with native hPGRN ForteBio, Native Format 1 | Competition with native hPGRN, ForteBio, Native Format 2 |
|---|---|---|---|
| S-1 | Yes | Yes | Yes |
| S-2 | No | No | No |
| S-3 | Yes | Yes | Yes |
| S-4 | No | No | Yes |
| S-5 | Yes | No | Yes |
| S-6 | No | No | Yes |
| S-7 | No | No | No |
| S-8 | No | No | No |
| S-9 | No | No | No |
| S-10 | Y? | Yes | Yes |
| S-11 | No | Yes | Yes |
| S-12 | Yes | No | Yes |
| S-13 | Yes | Yes | Yes |
| S-14 | Yes | Yes | Yes |
| S-15 | Yes | No | Yes |
| S-16 | No | No | No |
| S-17 | No | No | No |
| S-18 | No | No | No |
| S-19 | No | No | No |
| S-20 | No | No | No |
| S-21 | No | No | No |
| S-22 | No | No | No |
| S-23 | Yes | Yes | Yes |
| S-24 | Yes | Yes | Yes |
| S-25 | Yes | No | Yes |
| S-26 | Yes | No | Yes |
| S-27 | Yes | No | Yes |
| S-28 | No | No | No |
| S-29 | No | No | No |
| S-30 | Yes | No | Yes |
| S-31 | Yes | Yes | Yes |
| S-32 | Yes | Yes | Yes |
| S-33 | Yes | Yes | Yes |
| S-34 | Yes | Yes | Yes |
| S-35 | Yes | Yes | Yes |
| S-36 | Yes | Yes | Yes |
| S-37 | Yes | Yes | Yes |
| S-38 | Yes | Yes | Yes |
| S-39 | Yes | Yes | Yes |
| S-40 | Yes | No | Yes |
| S-41 | Yes | Yes | Yes |
| S-42 | Yes | Yes | Yes |
| S-43 | Yes | Yes | Yes |
| S-44 | Yes | Yes | Yes |
| S-45 | Y? | No | Yes |
| S-46 | Yes | Yes | Yes |
| S-47 | Yes | Yes | Yes |
| S-48 | No | No | No |
| S-49 | No | No | No |
| S-50 | No | Yes | No |
| S-51 | No | No | No |
| S-52 | Yes | Yes | Yes |
| S-53 | No | No | No |
| S-54 | Yes | Yes | Yes |
| S-55 | Yes | No | Yes |
| S-56 | No | Yes | Yes |
| S-57 | No | No | Yes |
| S-58 | No | No | Yes |
| S-59 | No | Yes | Yes |
| S-60 | Yes | No | Yes |
| S-61 | Yes | Yes | Yes |
| S-62 | Yes | Yes | Yes |
| S-63 | Yes | No | Yes |
| S-64 | Yes | No | Yes |
| S-65 | Yes | No | Yes |
| S-66 | Yes | No | Yes |
| S-67 | Yes | No | Yes |
| S-68 | Yes | Yes | Yes |
| S-69 | Yes | No | Yes |
| S-70 | Yes | Yes | Yes |
| S-71 | Yes | No | Yes |
| S-72 | Yes | No | Yes |
| S-73 | Yes | Yes | Yes |

TABLE 7-continued

ForteBio Antibody Competition Assays

| Antibody | Competition with hPGRN peptide ForteBio, Peptide Format | Competition with native hPGRN ForteBio, Native Format 1 | Competition with native hPGRN, ForteBio, Native Format 2 |
|---|---|---|---|
| S-74 | Yes | Yes | Yes |
| S-75 | No | No | Yes |
| S-76 | Yes | No | Yes |
| S-77 | No | Yes | Yes |
| S-78 | Yes | Yes | Yes |
| S-79 | Yes | Yes | Yes |
| S-80 | Yes | Yes | Yes |
| S-81 | Yes | No | Yes |
| S-82 | No | No | No |
| S-83 | Yes | No | Yes |
| S-84 | Yes | Yes | Yes |
| S-85 | Y? | Yes | Yes |
| Isotype control 1 | No | No | No |
| Isotype control 2 | N/D | N/D | N/D |

Example 4: Characterization of Interactions Between Sortilin and Progranulin Cell-Based Assays Materials and Methods Recombinant human or mouse Progranulin (Adipogen) was biotinylated with an EZ-Link Micro NHS-PEG4 kit from ThermoScientific/Pierce according to the manufacturer's instructions. A stable cell line expressing full-length untagged human Sortilin was established by viral infection of HEK293Tcells, and positive selection with hygromycin (Genscript custom project). Full-length mouse Sortilin was cloned into pCMV-AC-IRES-GFP (Origene) and HEK293Tcells were transiently transfected with this plasmid using Eugene HD (Promega). As control cells, either parental HEK293Tcells or HEK293Tcells expressing fill-length human SORCS1 (cloned into pCMV-AC-IRES-GFP) were utilized.

Sortilin-expressing cells or control cells were harvested and washed in PBS. Biotinylated human or mouse Progranulin was added in PBS+2% FBS with or without anti-Sortilin antibodies (10 µg/ml) or control human IgG 1 isotype antibodies, and incubated on ice for 2 h. After washing cells 3 times in PBS+2% FBS, cells were incubated in Streptavidin-APC (BD Biosciences, 1:100) on ice for 30 min. Then cells were washed again, resuspended in PBS+2% FBS and analyzed on a FACSCanto™ flow cytometer (BD Biosciences, Mississauga, ON). PGRN binding was measured as the median fluorescence intensity of APC of the Sortilin expressing cell population.

Results

Program/in Binding to Sortilin

The ability of biotinylated human Progranulin (PGRN) or of biotinylated mouse PGRN to bind to human or mouse Sortilin (SORT1) expressed on the surface of HEK293Tcells was analyzed. Biotinylated Progranulin was added at increasing concentrations (0 nM-100 nM) to HEK293Tcells expressing Sortilin, or control cells, and binding was analyzed using a FACSCanto™.

Figure 5B:
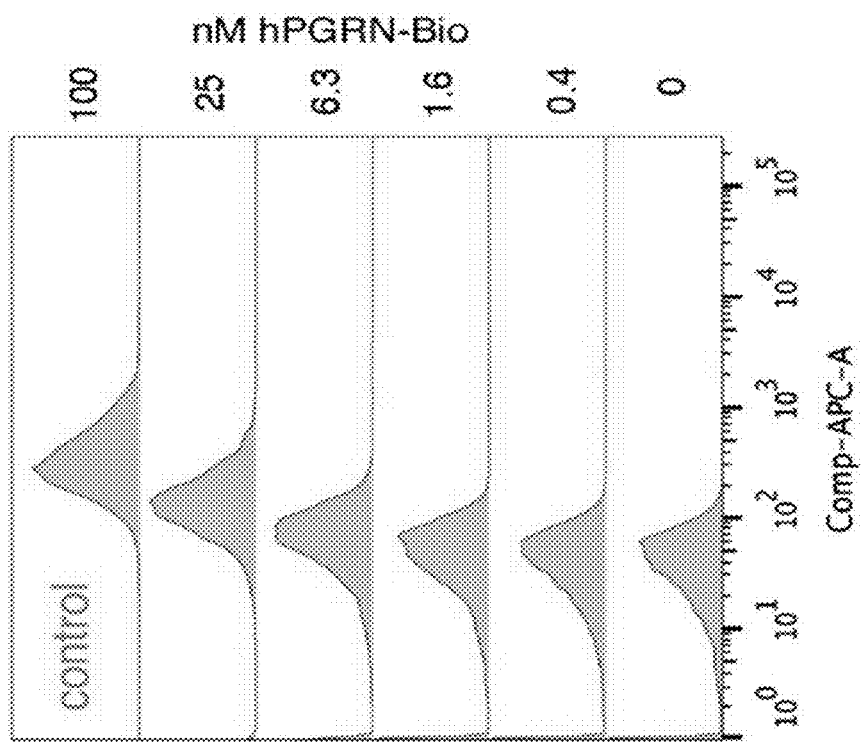
FIG. 5A-5D show characterization of interactions between Sortilin and Progranulin on cells.
Figure 5A:
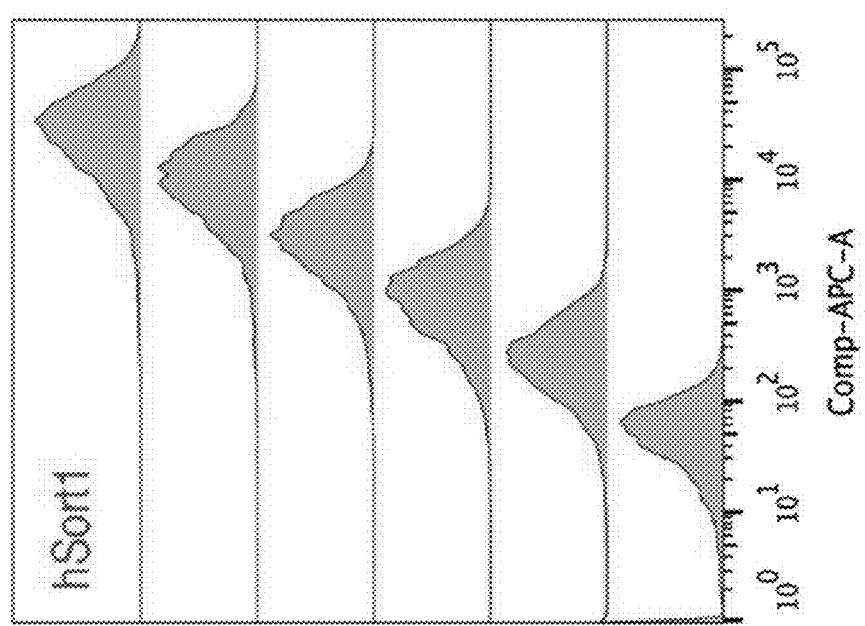

FIG. 5A is a FACS plot demonstrating dose-dependent binding of human PGRN to recombinant SORT1 expressed on HEK293Tcells. As shown FIG. 5B, PGRN does not show much binding to control cells.

Figure 5C:
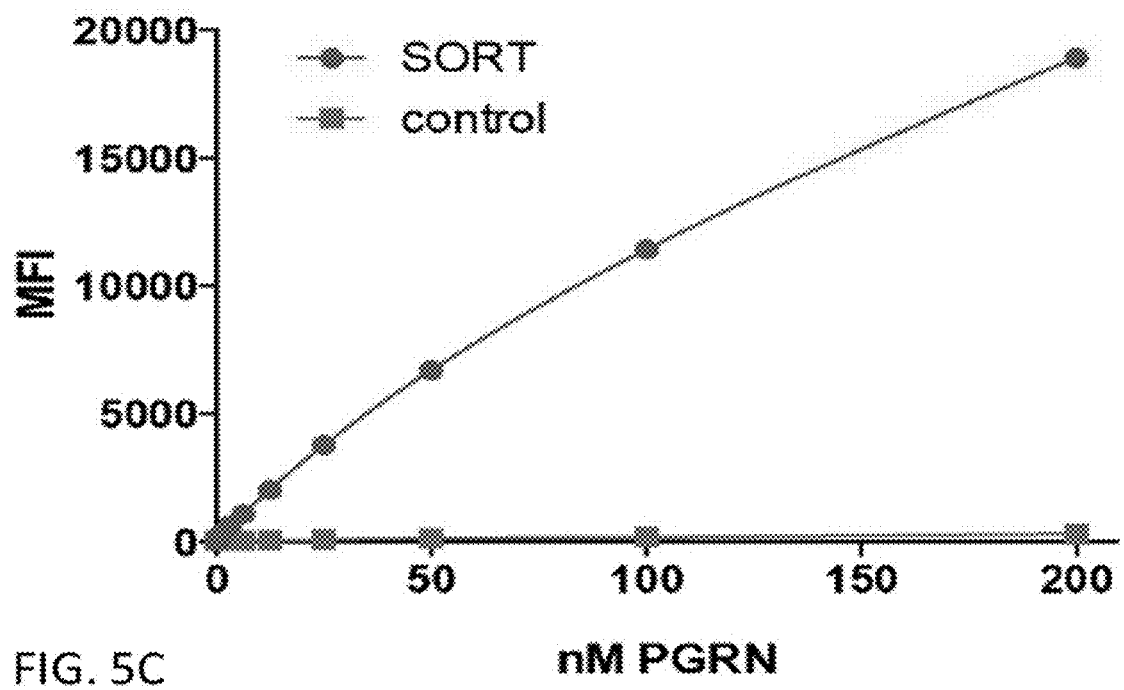
Figure 5D:
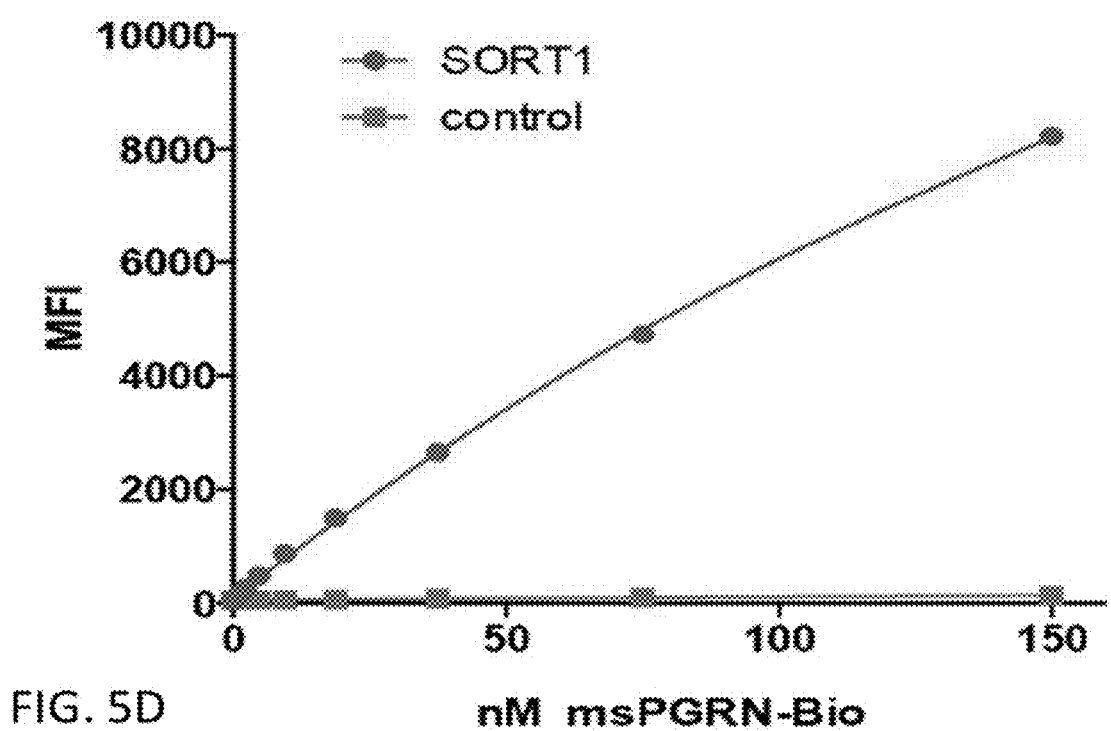

FIGS. 5C and 5D show median fluorescent intensity (MFI) plotted against concentration of human PGRN binding to recombinant human Sortilin (SORT) expressed on HEK293Tcells (FIG. 5C) or mouse PGRN binding to mouse Sortilin (SORT1) expressed on HEK293Tcells (FIG. 5D), as compared to control cells that do not express recombinant Sortilin. The results demonstrate that PGRN binds to Sortilin in a dose-dependent manner.

Sortilin Antibodies Capable of Blocking Progranulin Binding

To test whether anti-Sortilin antibodies can block binding of Progranulin to Sortilin, human or mouse Sortilin-expressing cells were incubated with 15 nM biotinylated human or mouse Progranulin together with 67 nM of anti-Sortilin antibodies. Results of the cell based Progranulin competition assay are shown in Table 8. Anti-Sortilin antibodies show a range in ability to block Progranulin. Antibodies S-64, S-63, S-60, S-05, S-49, S-72, S-06, S-76, S-83, and S-65 were identified as the top Progranulin blocking antibodies.

In Table 8, "hPGRN" refers to human Progranulin, "mPGRN" refers to mouse Progranulin, "hSort" refers to human Sortilin, and "mSort" refers to mouse Sortilin.

TABLE 8

Cell-based Antibody Competition

| Antibody | Competition with FL hPGRN on hSort expressing cells (% blocking of hPGRN binding) | Competition with FL mPGRN on mSort expressing cells (% blocking of mPGRN binding) |
|---|---|---|
| S-1 | 57.05 | 61.54 |
| S-2 | 17.88 | −10.83 |
| S-3 | 26.26 | 11.25 |
| S-4 | 30.06 | 11.06 |
| S-5 | 81.22 | 31.30 |
| S-6 | 69.54 | 71.66 |
| S-7 | 9.30 | N/D |
| S-8 | 58.02 | 26.53 |
| S-9 | 4.58 | −9.97 |
| S-10 | 5.14 | −7.84 |
| S-11 | 7.25 | N/D |
| S-12 | 55.04 | −7.06 |
| S-13 | 41.49 | −0.22 |
| S-14 | 35.93 | 15.56 |
| S-15 | 35.71 | 23.87 |
| S-16 | 29.17 | N/D |
| S-17 | 18.83 | N/D |
| S-18 | 9.07 | 6.99 |
| S-19 | 19.69 | 10.60 |
| S-20 | 11.74 | −5.70 |
| S-21 | 11.12 | −2.99 |
| S-22 | 15.51 | −1.90 |
| S-23 | 37.09 | 15.56 |
| S-24 | 28.41 | 66.57 |
| S-25 | 41.55 | 2.35 |
| S-26 | 57.05 | 75.88 |
| S-27 | 18.35 | N/D |
| S-28 | 7.42 | 5.72 |
| S-29 | 11.32 | 1.24 |
| S-30 | 63.75 | 94.58 |
| S-31 | 27.31 | N/D |
| S-32 | 41.61 | −1.00 |
| S-33 | 38.13 | −3.01 |
| S-34 | 52.37 | 26.06 |
| S-35 | 43.53 | 6.03 |
| S-36 | 45.14 | 7.60 |
| S-37 | 23.29 | N/D |
| S-38 | 26.50 | 45.86 |
| S-39 | 52.00 | 50.17 |
| S-40 | 46.60 | 0.24 |
| S-41 | 43.14 | −1.29 |
| S-42 | 41.66 | 27.39 |
| S-43 | 52.86 | −7.75 |
| S-44 | 37.39 | 63.67 |
| S-45 | 53.05 | 23.18 |
| S-46 | 43.93 | −2.68 |

TABLE 8-continued

Cell-based Antibody Competition

| Antibody | Competition with FL hPGRN on hSort expressing cells (% blocking of hPGRN binding) | Competition with FL mPGRN on mSort expressing cells (% blocking of mPGRN binding) |
|---|---|---|
| S-47 | 36.72 | −7.65 |
| S-48 | 18.36 | −20.32 |
| S-49 | 74.62 | −43.64 |
| S-50 | 12.47 | −26.16 |
| S-51 | 49.71 | −9.22 |
| S-52 | 28.25 | N/D |
| S-53 | 31.77 | −4.41 |
| S-54 | 31.83 | 18.15 |
| S-55 | 36.68 | 8.32 |
| S-56 | 19.77 | N/D |
| S-57 | 44.46 | 37.02 |
| S-58 | 39.91 | 18.13 |
| S-59 | 30.64 | 13.27 |
| S-60 | 81.61 | −7.93 |
| S-61 | 23.81 | 9.05 |
| S-62 | 4.47 | −10.15 |
| S-63 | 81.81 | 15.90 |
| S-64 | 82.11 | 8.32 |
| S-65 | 68.27 | 26.10 |
| S-66 | 60.52 | 7.75 |
| S-67 | 54.12 | 11.41 |
| S-68 | 22.98 | N/D |
| S-69 | 67.10 | 9.72 |
| S-70 | 12.75 | N/D |
| S-71 | 55.05 | 6.16 |
| S-72 | 70.56 | 6.22 |
| S-73 | 48.53 | 3.86 |
| S-74 | 61.72 | 6.67 |
| S-75 | 12.92 | −0.67 |
| S-76 | 69.39 | 7.21 |
| S-77 | 12.33 | 23.35 |
| S-78 | 45.95 | 42.58 |
| S-79 | 31.10 | 5.63 |
| S-80 | 17.07 | N/D |
| S-81 | 64.24 | 81.99 |
| S-82 | 8.32 | N/D |
| S-83 | 68.67 | 4.64 |
| S-84 | 49.76 | 9.22 |
| S-85 | 46.41 | 75.33 |
| Isotype control 1 | −6.06 | 1.73 |
| Isotype control 2 | −2.95 | 5.67 |

To test the blocking ability of the top Progranulin blocking anti-Sortilin antibodies, Sortilin expressing HEK293Tcells were incubated with 15 nM biotinylated human or mouse Progranulin together with increasing concentrations of anti-Sortilin or control antibodies. Median fluorescent intensity was measured and curves were fit in Prism (nonlinear regression: log inhibitor vs. dose response with three parameters) to determine blocking constants.

Figure 6A:
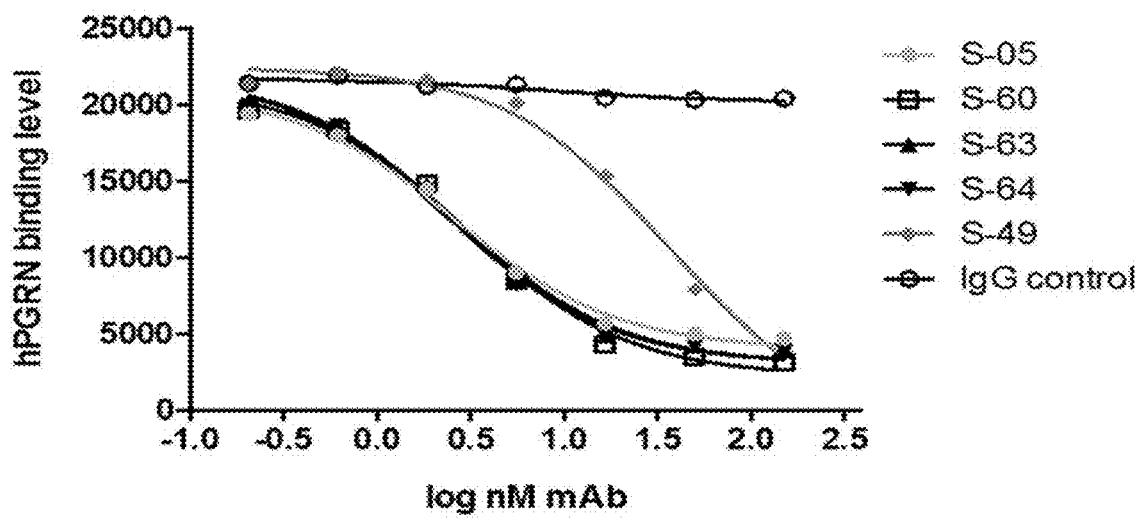
FIG. 6A-6E show dose dependent inhibition of binding of biotinylated Progranulin to cells that express Sortilin by anti-Sortilin antibodies.
Figure 6B:
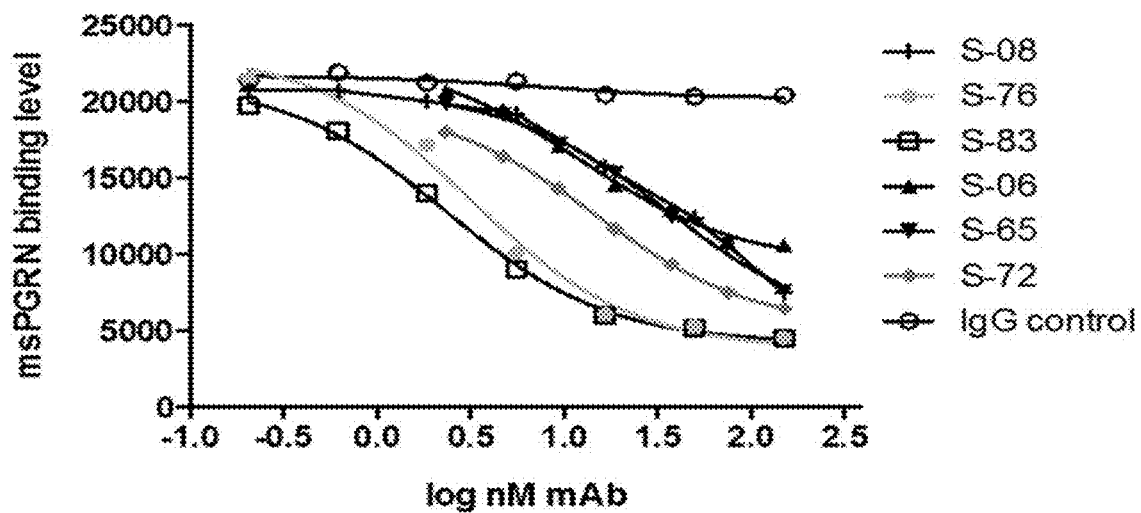
Figure 6C:
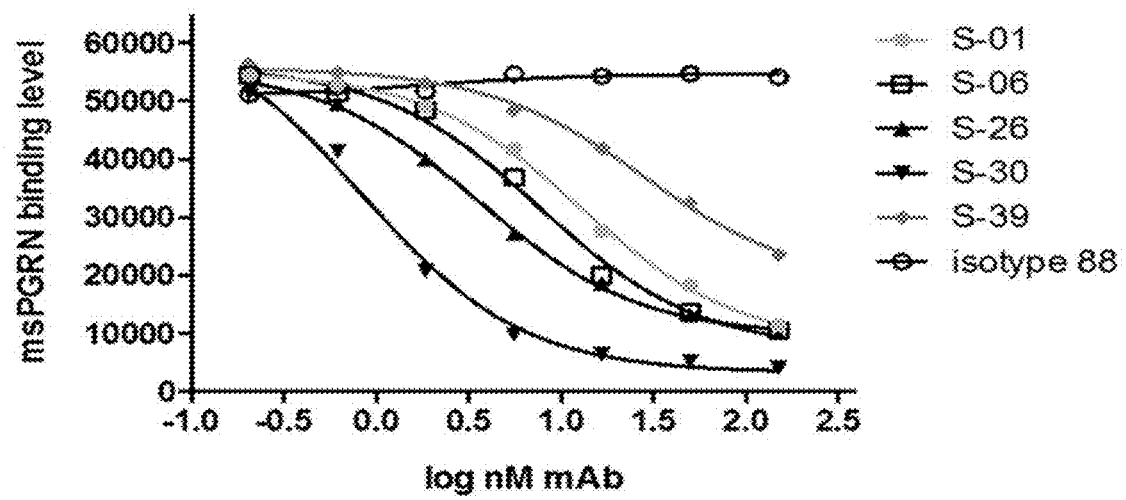
Figure 6D:
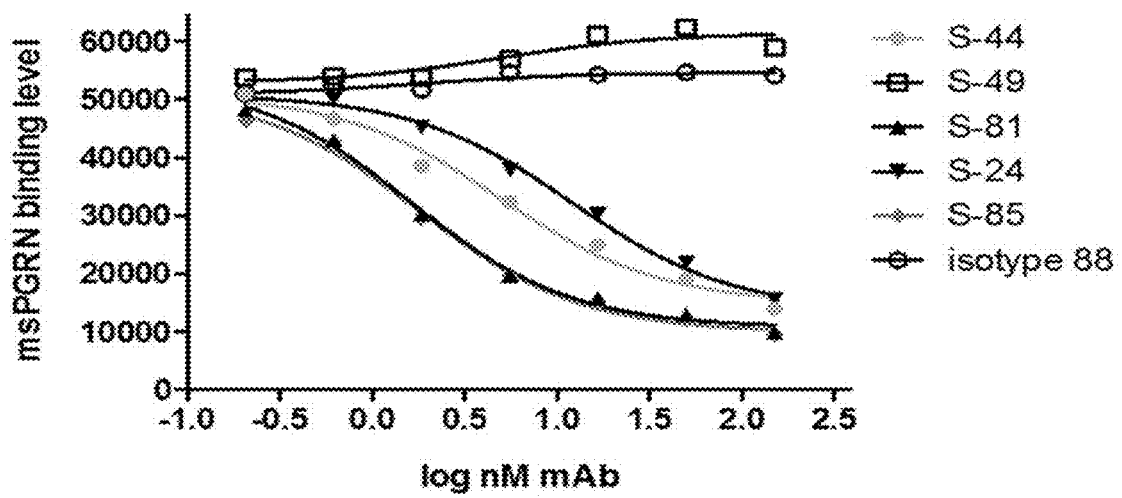

FIG. 6A-6D demonstrate that anti-Sortilin antibodies inhibit the binding of human Progranulin to human Sortilin and mouse Progranulin to mouse Sortilin expressed on HEK293Tcells in a dose-dependent manner. FIGS. 6A and 6B show that antibodies S-5, S-60, S-63, S-64, S-49, S-8, S-76, S-83, S-6, S-65, and S-72 inhibit the binding of human Progranulin to human Sortilin. FIGS. 6C and 6D show that antibodies S-1, S-6, S-26, S-30, S-39, S-44, S-24, S-81, and S-85 inhibit the binding of mouse Progranulin to mouse Sortilin, while antibody S-49 was not able to inhibit the binding of mouse Progranulin to mouse Sortilin but instead increased binding of Progranulin to Sortilin. The results in FIG. 6A-6D indicate that certain anti-Sortilin antibodies, such as antibody S-6, are capable of inhibiting binding of both human and mouse Progranulin to the respective Sortilin protein.

Figure 6E:
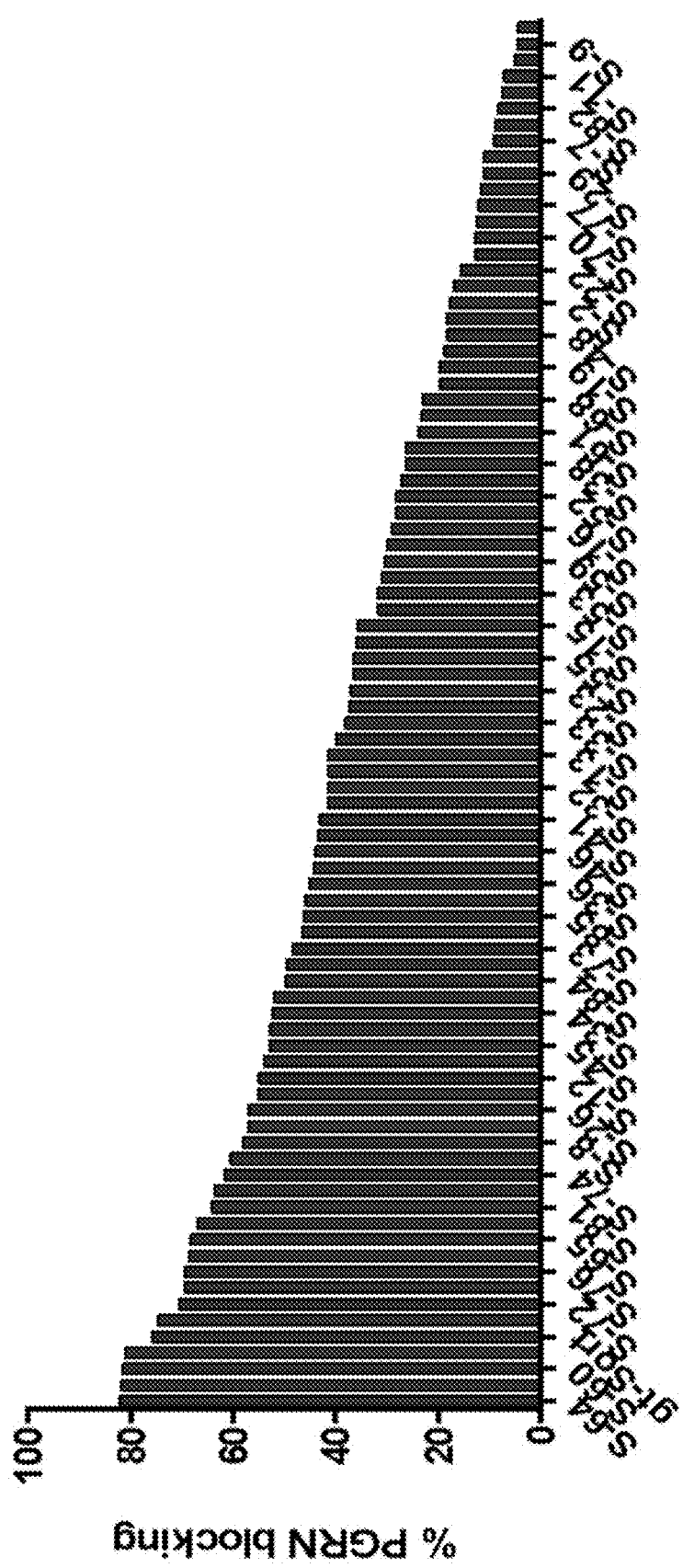

FIG. 6E depicts that there is a gradual range in the ability of anti-Sortilin antibodies to block binding of PGRN to Sortilin. Anti-Sortilin antibodies that decrease Progranulin binding to Sortilin by 20% or less at a saturating antibody concentration (67 nM) were designated non-Progranulin blocking antibodies.

Table 9 quantifies the ability of anti-Sortilin antibodies to inhibit the binding of Progranulin (PGRN) to Sortilin based on the data depicted in FIG. 6. Table 9 depicts the half-maximal ($IC_{50}$) blocking and percent maximal blocking of Sortilin: Progranulin binding by the indicated anti-Sortilin antibodies (at 150 nM IgG). "NT" refers to antibodies that were not tested.

TABLE 9

Blocking Antibodies that Inhibit PGRN/SORT1 Interaction

| Antibody | $IC_{50}$ block Bio-hPGRN (nM) | % max block at 150 nM Bio-hPGRN | $IC_{50}$ block Bio-mPGRN (nM) | max block at 150 nM Bio-mPGRN |
|---|---|---|---|---|
| S-83 | 2.4 | 77.4 | NT | NT |
| S-64 | 2.6 | 82.5 | NT | NT |
| S-5 | 2.7 | 78.5 | NT | NT |
| S-63 | 2.8 | 82.4 | NT | NT |
| S-60 | 3.2 | 85.6 | NT | NT |
| S-76 | 3.2 | 79.2 | NT | NT |
| S-6 | 12.2 | 50.1 | 7.7 | 79.8 |
| S-72 | 14.7 | 68.7 | NT | NT |
| S-65 | 36.2 | 63.4 | NT | NT |
| S-49 | 36.6 | 82.3 | NT | NT |
| S-8 | 47.3 | 62.73 | NT | NT |
| S-1 | NT | NT | 12.9 | 77.9 |
| S-24 | NT | NT | 12.1 | 70.1 |
| S-26 | NT | NT | 3.6 | 80.6 |
| S-30 | NT | NT | 0.8 | 92.2 |
| S-39 | NT | NT | 28.2 | 54.4 |
| S-44 | NT | NT | 5.0 | 73.0 |
| S-81 | NT | NT | 1.6 | 80.8 |
| S-85 | NT | NT | 1.8 | 81.6 |

Progranulin Blocking is Increased with Combinations of Sortilin Antibodies

Figure 7:
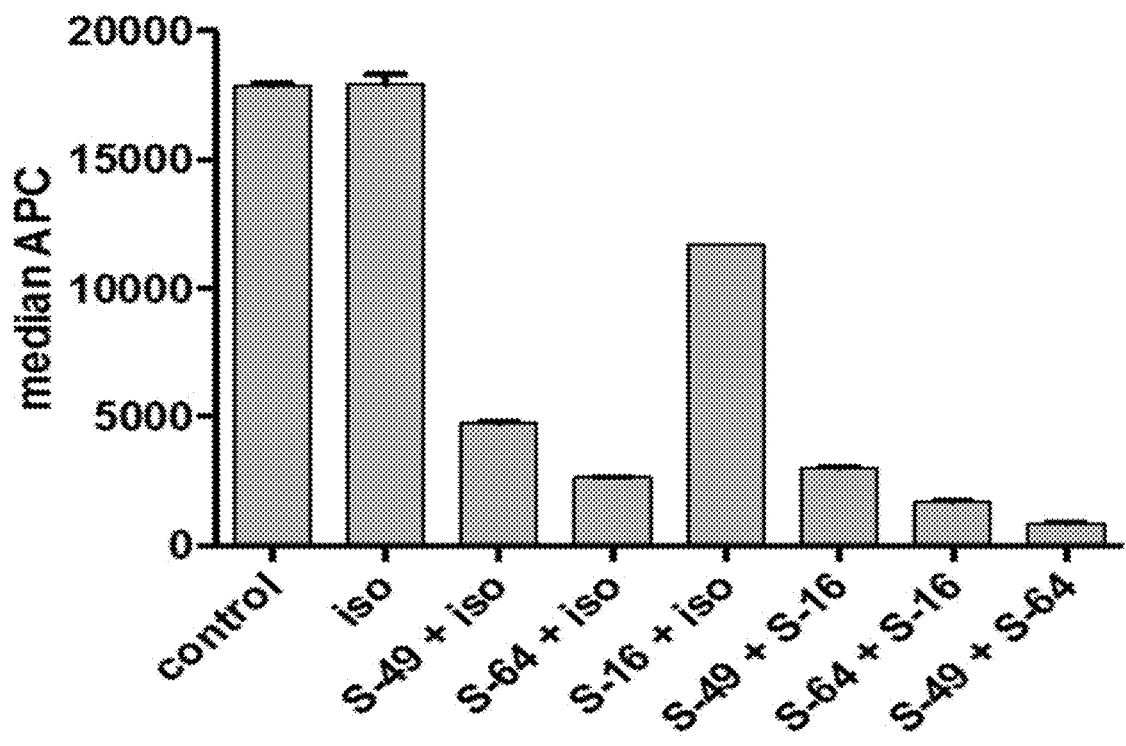
FIG. 7 depicts testing of synergistic effects of antibody combinations on binding of biotinylated Progranulin to Sortilin expressed on HEK293Tcells. S-49, S-64 (bin 4), and S-16 (bin 1) were either combined with an isotype control antibody or with each other.

FIG. 7 shows the synergistic effects of combinations of anti-Sortilin antibodies that block Progranulin binding. Briefly, HEK293Tcells expressing recombinant human Sortilin were incubated with 15 nM biotinylated Progranulin with 67 nM of S-49 or S-64 or S-16 antibodies, together with 67 nM of isotype control antibody or different combinations of S-49 or S-64 with each other or S-16 (each antibody as 67 nM). Bound Progranulin was detected by streptavidin-APC (1:100, BD Biosciences) and quantified as median fluorescent intensity of APC. The results in FIG. 7 demonstrate that blocking of human Progranulin was increased by the combination of S-49 and S-16 antibodies, the combination of S-64 and S-16 antibodies, and the combination of S-49 and S-64 antibodies, as compared to the Progranulin blocking ability of either antibody alone. These results indicate that combinations of anti-Sortilin antibodies may be more efficacious than single anti-Sortilin antibodies.

Sortilin Expressing Cells Bind and Endocytose Progranulin

For results depicted in FIG. 8, HEK293Tcells expressing Sortilin or LacZ (control) were incubated with Progranulin (PGRN) for up to 60 minutes at 37° C. Time-dependent binding and endocytosis of PGRN were observed by fluorescence microscopy. Recombinant human Progranulin (Adipogen) was labeled with DyLight 650 (Life Technologies, Carlsbad, Calif.). Cells were transiently transfected with human Sortilin or lacZ (control) and GFP using Fugene and harvested after 24 h. GFP was either expressed by a second vector (Topo3.3, Invitrogen) or located on the same vector, separated by an IRES (pCMV6-AC-IRES-GFP, Origene). Full-length Sortilin was used either untagged (Topo3.3) or with a C-terminal myc tag (pCMV6-AC-IRES-GFP). Cells were then plated on microscopy chambered glass slides coated with poly-1-lysine. After 4-6 h, cells were washed in OptiMem serum-free media, and 40 nM Progranulin-650 was added with or without 10 uM Sortilin pro-peptide as a blocker. Cells were incubated at 37° C. for up to 60'. Subsequently, cells were fixed in 4% paraformaldehyde, washed in PBS and imaged on a Nikon fluorescent microscope.

Figure 8A:
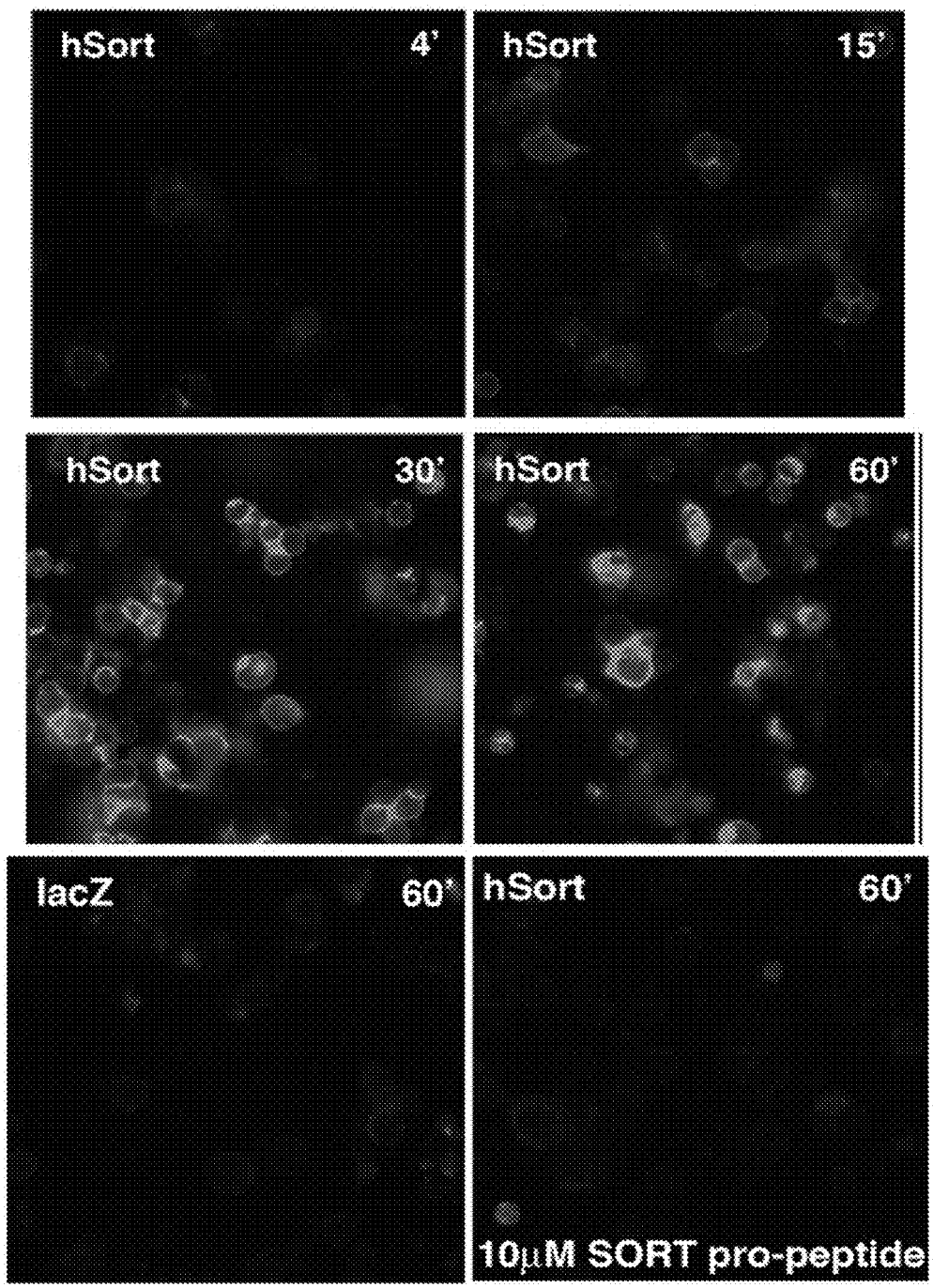
FIG. 8A shows results of an imaging assay for time dependent binding and endocytosis of fluorescently labeled Progranulin (PGRN) and its blockade by 10 μM of Sortilin pro-peptide that competes with PGRN. Cells transfected either with human Sortilin (hSort) or lacZ were incubated with Progranulin (PGRN) for 4, 15, 30 or 60 minutes and imaged thereafter. The assay is designed to test the ability of anti-Sortilin antibodies to prevent binding and endocytosis of Progranulin (PGRN) by Sortilin (Sort).
Figure 8B:
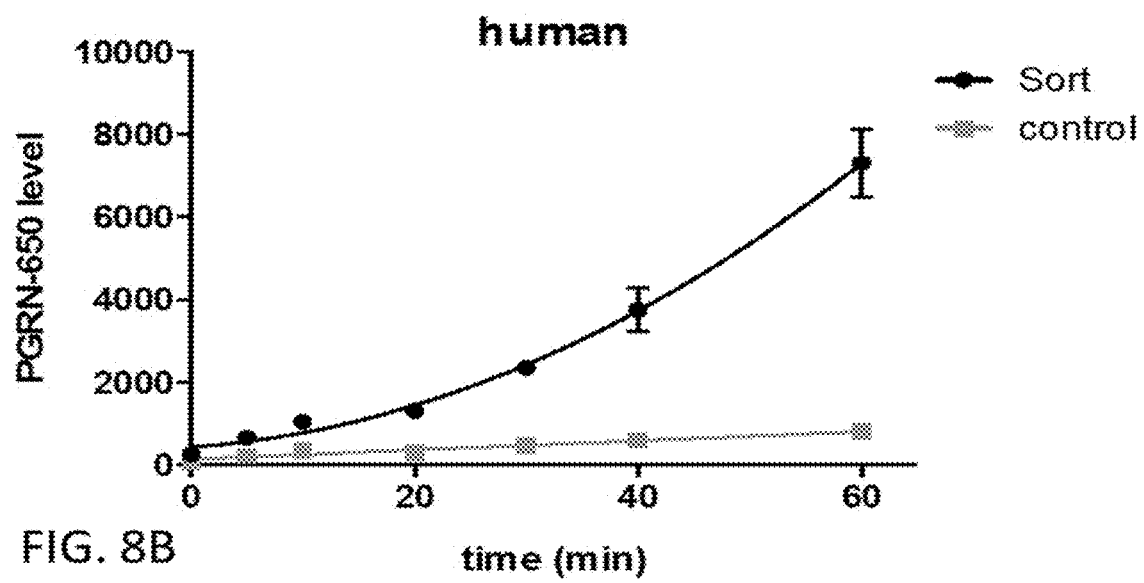
FIG. 8B shows results of a FACS graph depicting time dependent binding and endocytosis of PGRN-DyLight650 by cells that expresses human Sortilin. The assay is designed to test the ability of anti-Sortilin antibodies to prevent binding and endocytosis of fluorescently labeled Progranulin by human Sortilin.
Figure 8C:
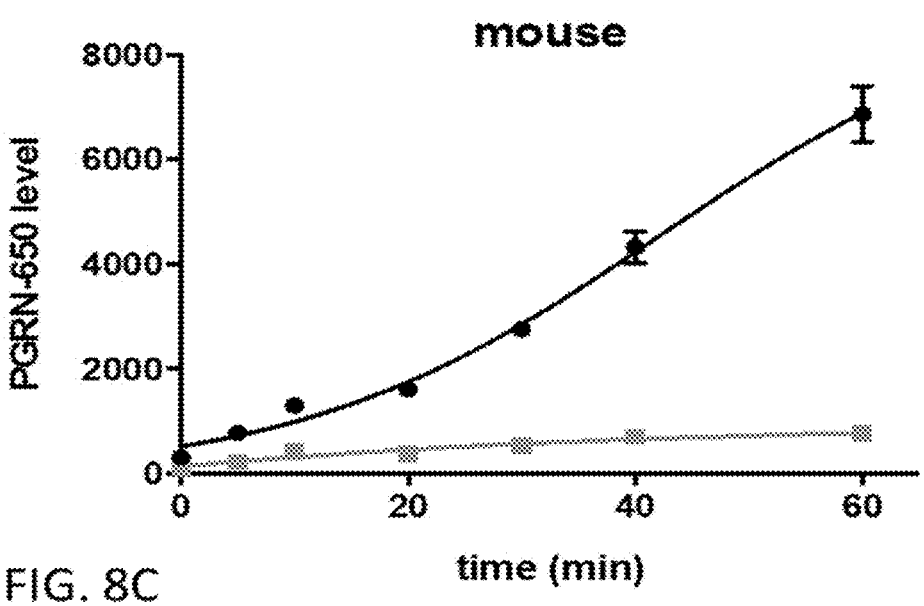
FIG. 8C shows results of a FACS graph depicting time dependent binding and endocytosis of PGRN-DyLight650 by cells that expresses mouse Sortilin. The assay is designed to test the ability of anti-Sortilin antibodies to prevent binding and endocytosis of fluorescently labeled Progranulin by mouse Sortilin. Human PGRN-DyLight650 was added to human Sort (FIG. 8B) or mouse Sort (FIG. 8C), or control HEK293Tcells, and the amount of bound and endocytosed PGRN is quantified by FACS.

FIG. 8A shows increased binding and endocytosis of Progranulin to Sortilin expressing cells with increased incubation time, as assayed by DyLight-650 fluorescence. Only negligible Progranulin binding was observed when cells expressed control LacZ protein, or when cells were co-incubated with 10 μM of blocking Sortilin pro-peptide.

Figure 8D:
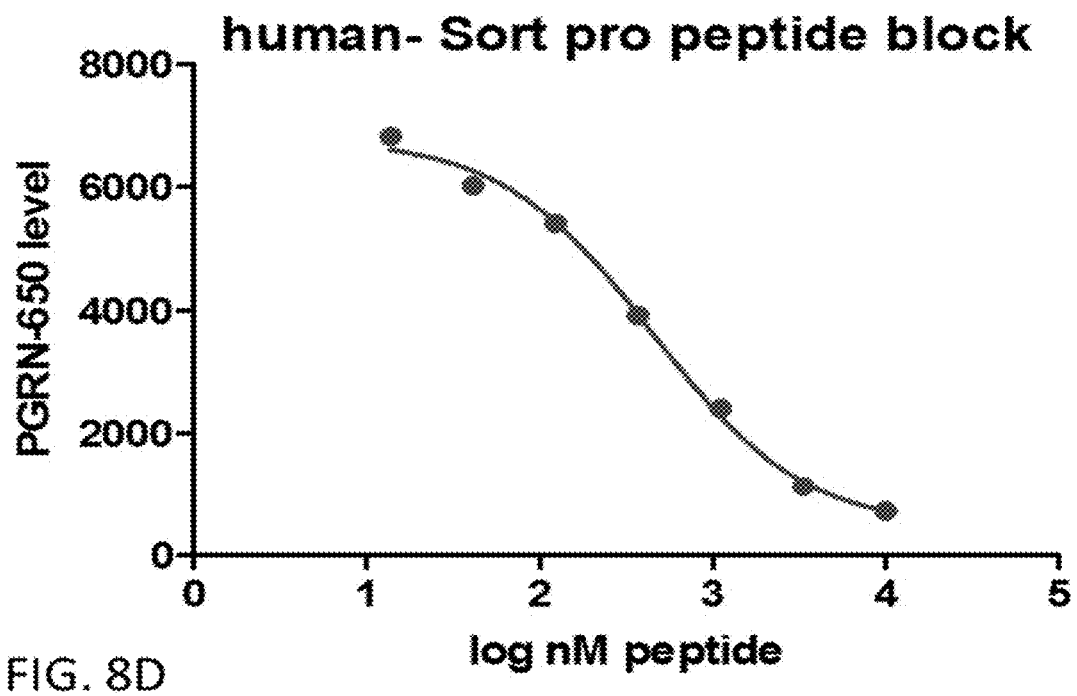
FIG. 8D shows results of a FACS assay demonstrating the ability of the human PGRN inhibitor Sort pro-peptide to prevent binding and endocytosis of fluorescently labeled PGRN by human Sortilin.
Figure 8E:
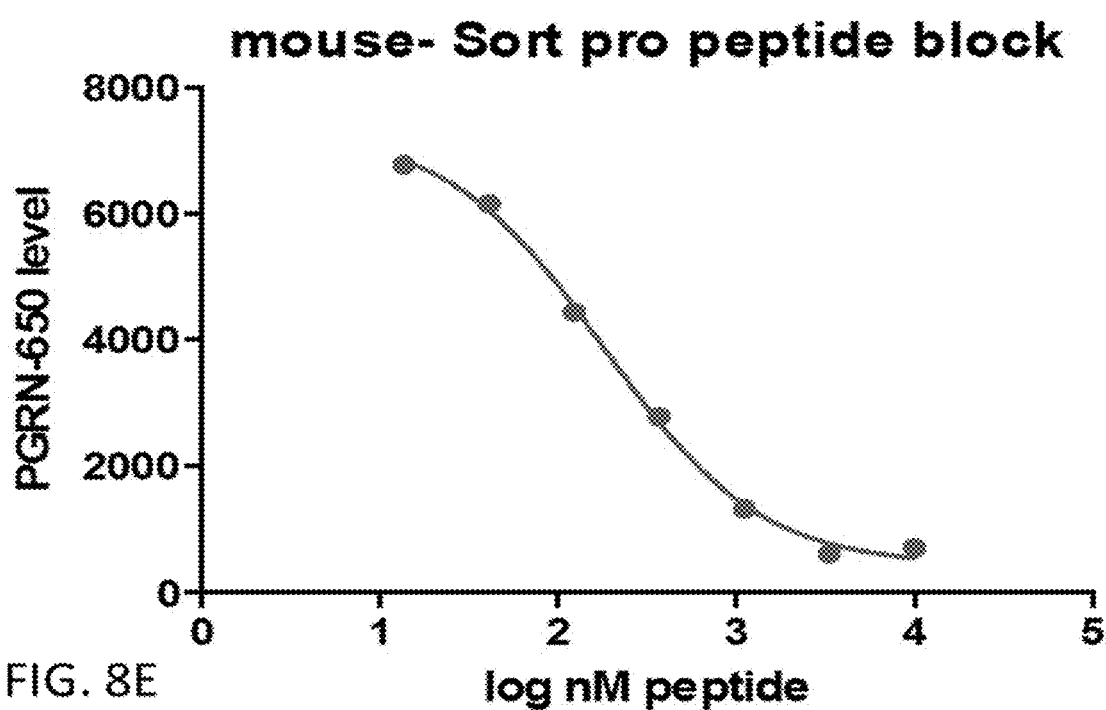
FIG. 8E shows results of a FACS assay demonstrating the ability of the mouse PGRN inhibitor Sort pro-peptide to prevent binding and endocytosis of fluorescently labeled PGRN by mouse Sortilin.

FIG. 8B-8E depict a FACS assay quantifying Progranulin endocytosis and the ability of blocking Sortilin pro-peptide to inhibit Progranulin endocytosis. Fluorescently labeled human Progranulin (PGRN-DyLight650) was added to human Sortilin (Sort) (FIG. 8B) or mouse Sortilin (Sort) (FIG. 8C) or control HEK293Tcells and the amount of bound and endocytosed Progranulin was quantified by FACS by measuring the median fluorescence intensity of Sortilin expressing cells. FIGS. 8D and 8E demonstrate quantifies the ability of Sortilin pro-peptide to inhibit endocytosis of Progranulin by human Sort (FIG. 8D) or mouse Sort (FIG. 8E).

Example 5: Increased Levels of Secreted Progranulin in Cells Treated with Sortilin Antibodies Increased Extracellular Levels of Progranulin U-251 human astrocytoma cells were seeded in 96-well dishes and incubated overnight. The next morning, blocking anti-Sortilin antibodies (S-1 to S-10, S-12, S-14 to S-16, S-18 to S-22, S-24 to S-26, S-28 to S-30, S-32, S-34, S-39, S-40, S-42 to S-45, S-48 to S-51, S-55, S-57 to S-61, S-63, S-64, S-65, S-67, S-69, S-71 to S-76, S-78, and S-81 to S-85), as well as a positive blocking antibody (goat anti-human Sortilin (gtSort) from R&D Systems AF3154) and isotype control antibodies (goat (gt) IgG, ADI-88 (human IgG1), and ADI-89 (human IgG1), were added at 50 nM or 5 nM final dilution and the cells were thus incubated for 72 h. The media was then collected and the concentration of Progranulin in the media samples was measured using an R&D Systems human Progranulin Duoset ELISA kit.

Figure 9A:
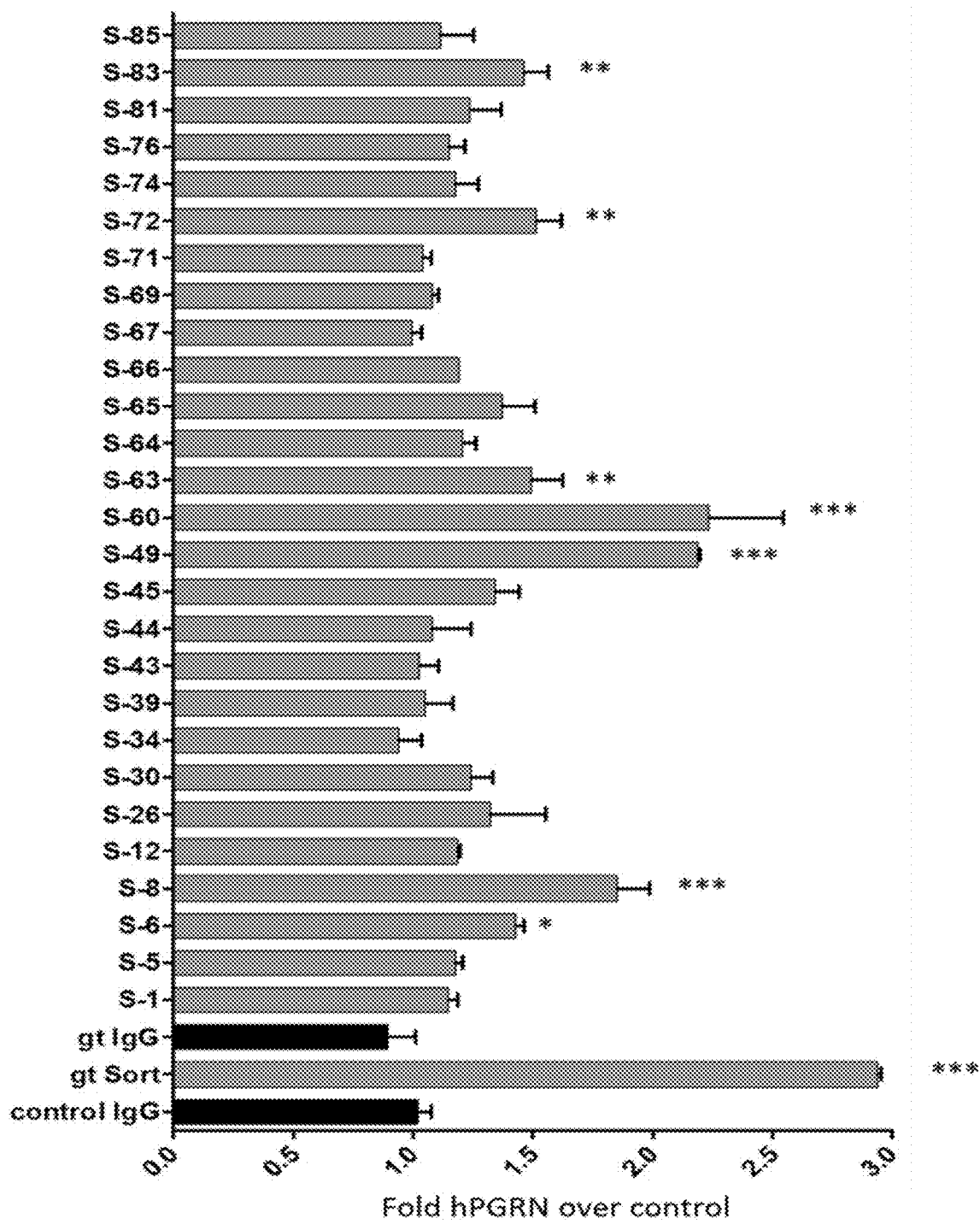
FIG. 9A-9D show the results of assays demonstrating the ability of anti-Sortilin antibodies to increase endogenous secreted levels of Progranulin in the media of the human astrocyte cell line U-251, which expresses endogenous human Sortilin.
Figure 9B:
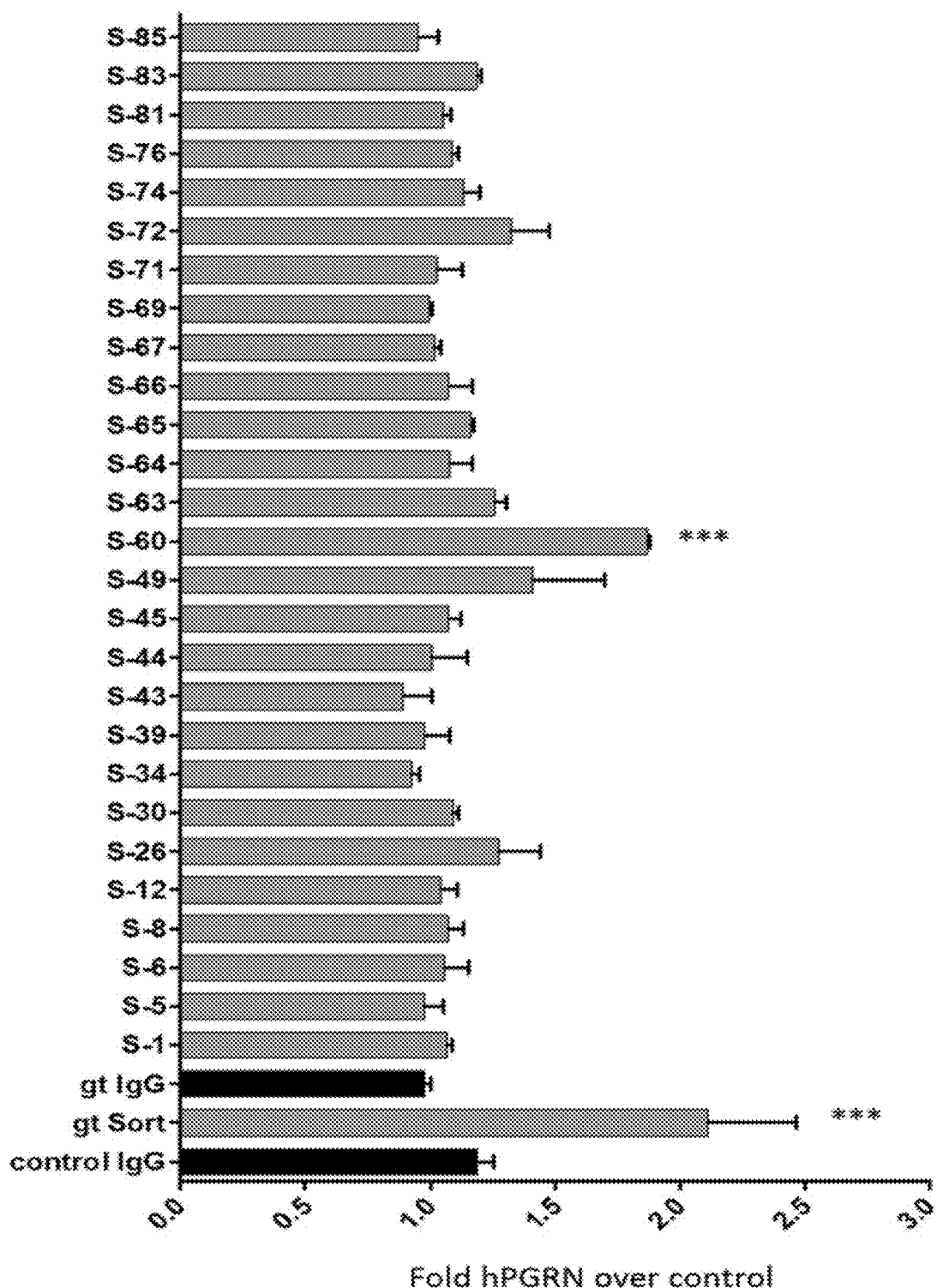
Figure 9C:
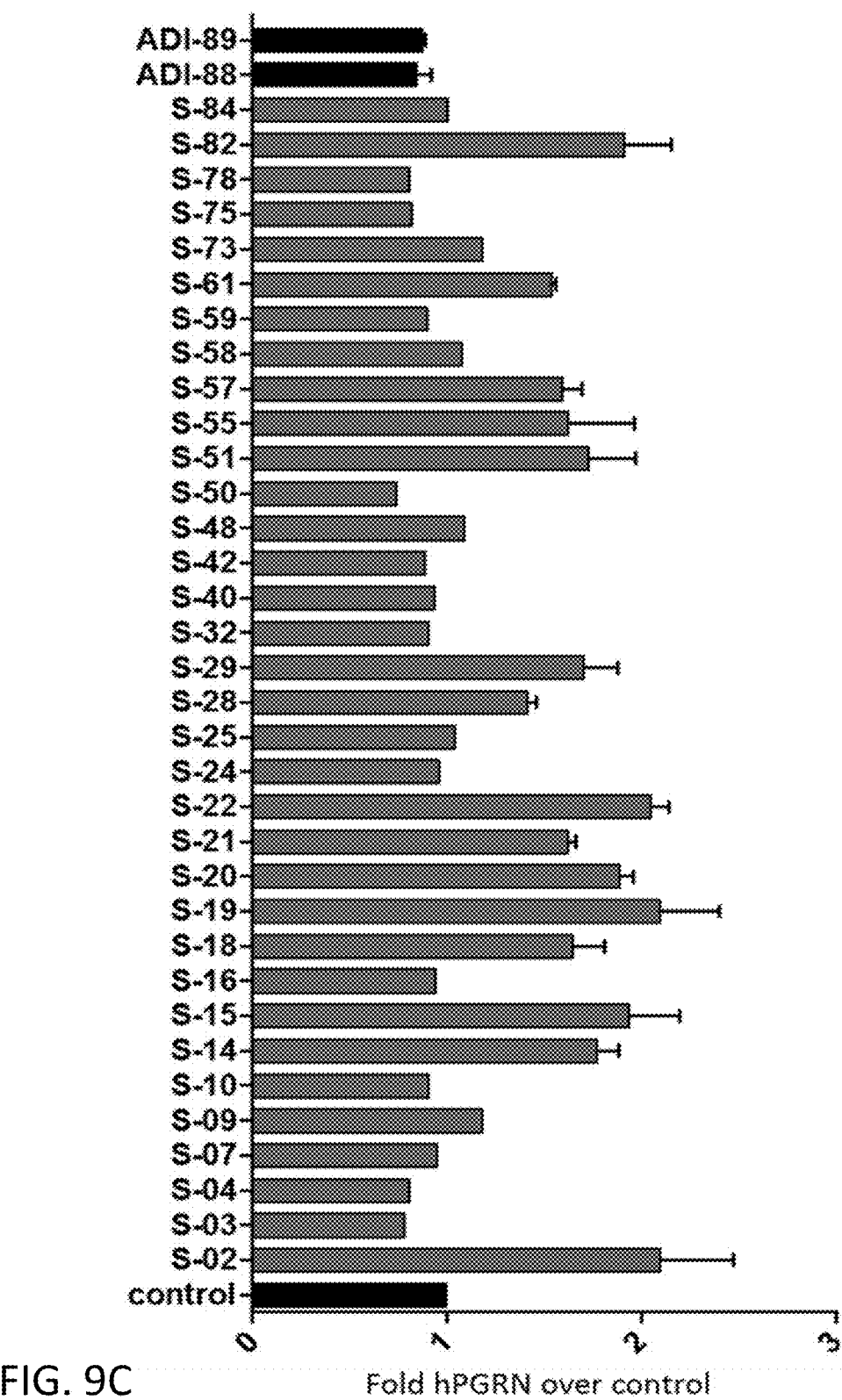
Figure 9D:
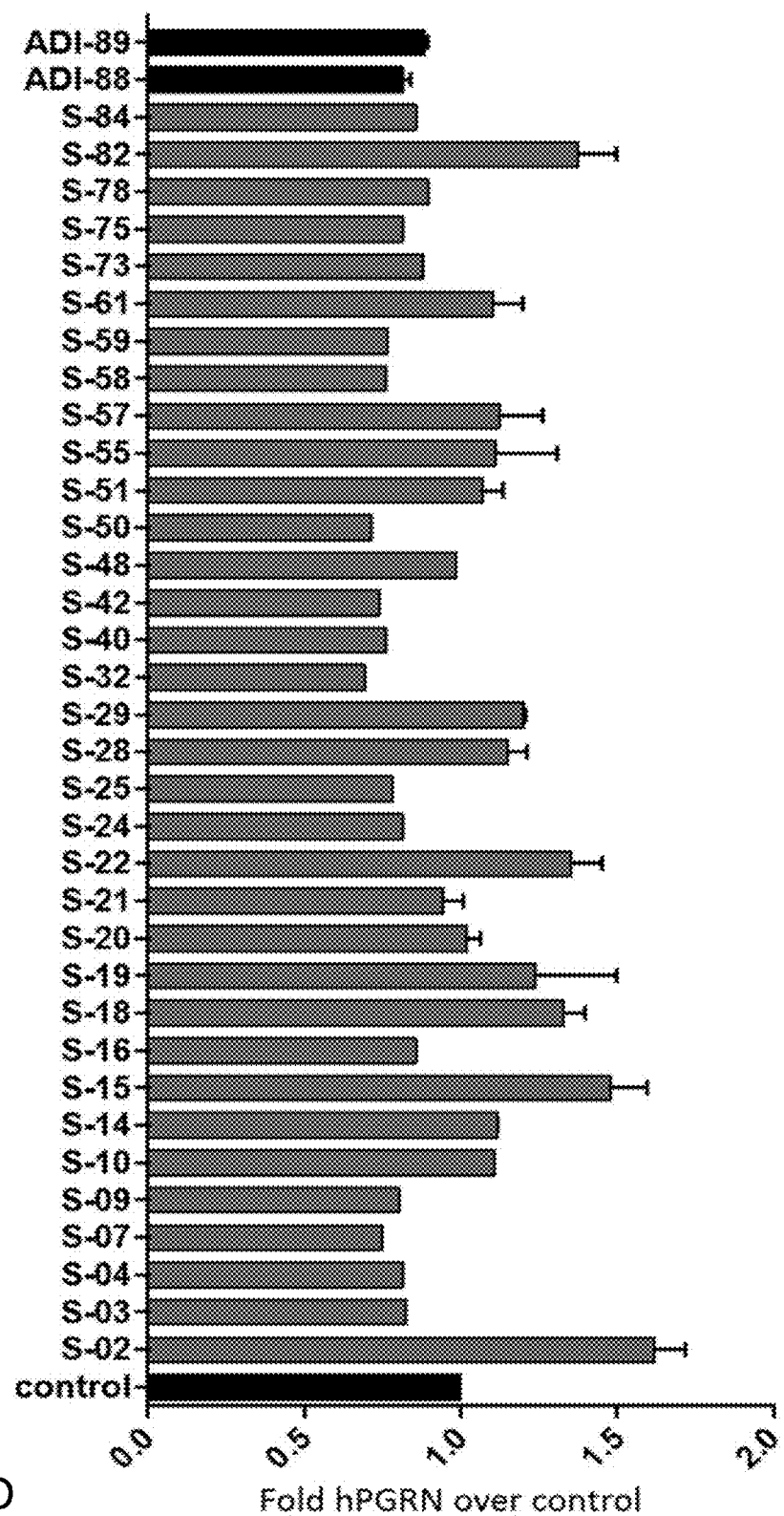

As shown in FIG. 9A-9D, blocking of Progranulin binding to Sortilin using various anti-Sortilin antibodies resulted in an up to 3-fold increase in the level of Progranulin secreted into the media of the U-251 cells. FIGS. 9A and 9C shows results for 50 nM added antibodies and FIGS. 9B and 9D shows results for 5 nM added antibodies. The results in FIGS. 9A and 9B demonstrate that a subset of one class of anti-Sortilin antibodies belonging to bins ¾ and 4 (including, e.g., S-8, S-49, and S-60) not only block the binding of Progranulin to Sortilin, but actually increase the level of endogenous Progranulin in the U-251 cells, which naturally express both Sortilin and Progranulin. Moreover, the results in FIGS. 9C and 9D further demonstrate that a second class of anti-Sortilin antibodies belonging to bins ½, 2, and 3 (including, e.g., S-2, S-14, S-15, S-18, S-19, S-20, S-21, S-22, S-29, S-51, S-57, S-61, and S-82) that do not block Progranulin binding to Sortilin, or only weakly block Progranulin binding to Sortilin, are also able to induce increase the level of endogenous Progranulin in the U-251 cells.

Decreased Cell Surface Levels of Sortilin

After U-251 cells were incubated with 50 nM anti-Sortilin antibodies for 72 h as above, cells were harvested with Trypsin, washed in PBS and labeled with anti-Sortilin antibody S-20 (whose binding is not significantly competed by the Progranulin blocking antibodies). After cells were incubated with 5 μg/ml S-20 for one hour on ice, cells were washed three times in PBS+2% FBS and then incubated with 5 μg/ml anti-human PE secondary antibody (Southern Biotech). Cells were then washed again and S-20 binding was quantified using a FACSCanto™, as median fluorescence intensity of PE.

Figure 10A:
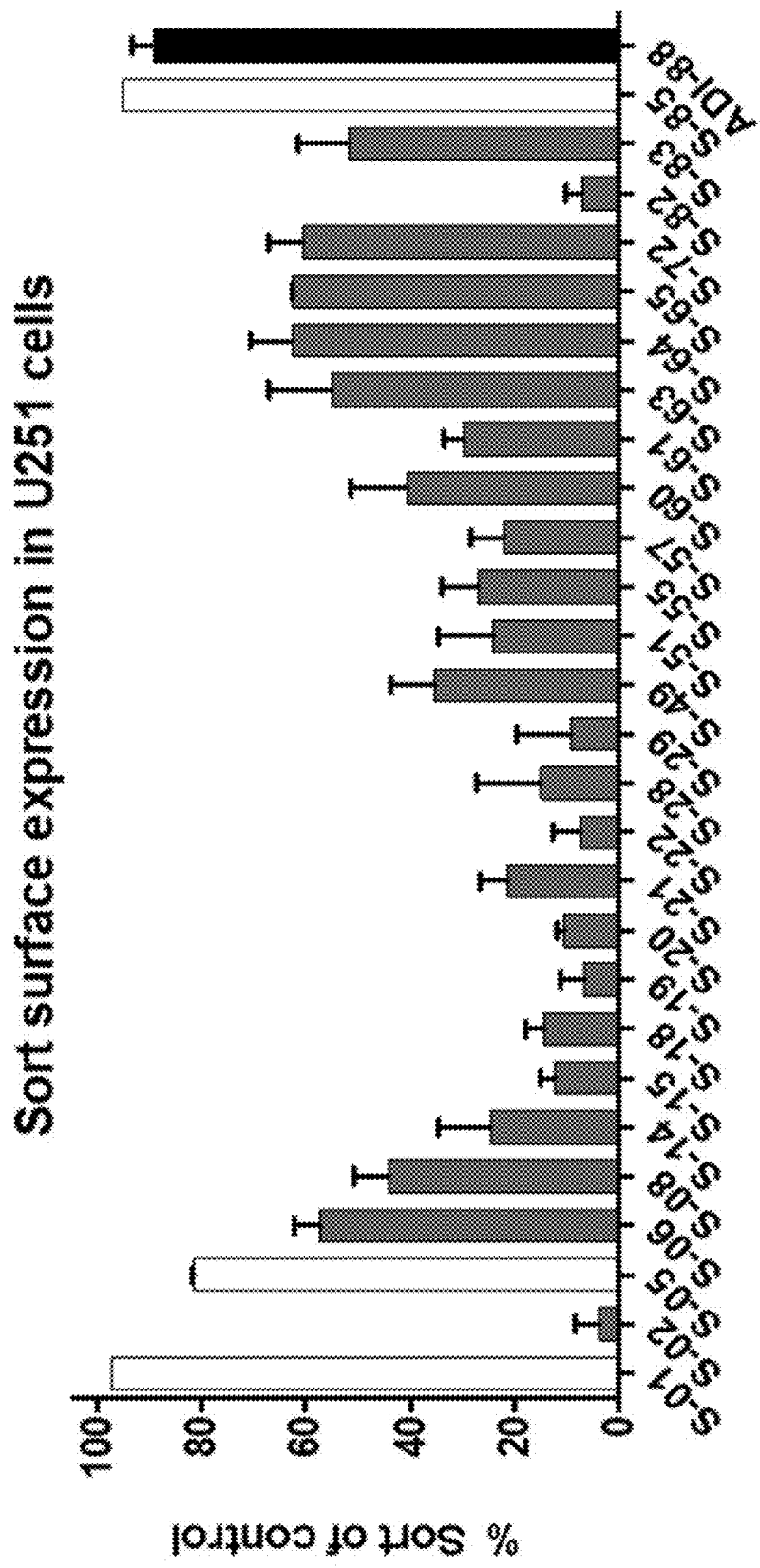
FIG. 10A-10F show the effect of anti-Sortilin antibodies on cell surface levels of Sortilin on human U-251 cells or murine N2A cells, and the corresponding ability of the antibodies to increase secreted levels of endogenous Progranulin (PGRN) in a dose dependent manner. Cells were incubated for 72 h with 50 nM blocking IgG, harvested and stained with an anti-Sortilin antibody that binds a different region on Sortilin than the test antibodies.
Figure 10B:
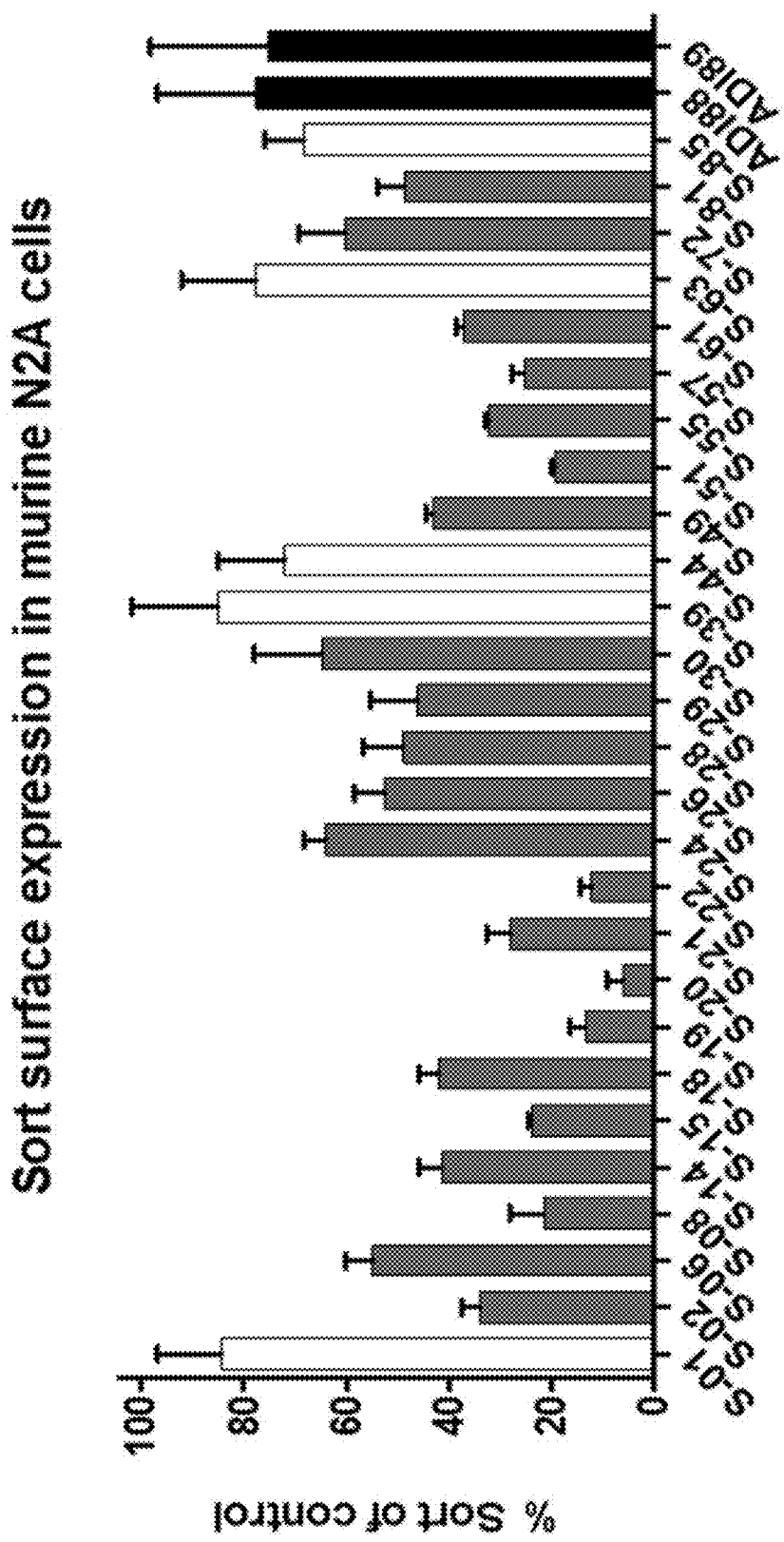

FIG. 10A shows that certain anti-Sortilin antibodies reduce cell surface levels of Sortilin in human U-251 cells, with the antibodies that induce the strongest increase of secreted Progranulin S-2, S-19, and S-22) also inducing the strongest decrease in cell surface levels of Sortilin. Antibodies such as S-64 and S-5, which do not decrease cell surface levels of Sortilin, were not able to increase extracellular levels of Progranulin, despite their ability to block Progranulin binding to Sortilin being as good as, or better, than the Progranulin blocking ability of antibodies S-49, S-60. FIG. 10B shows that certain anti-Sortilin antibodies reduce cell surface levels of Sortilin in murine Neuro-2A (N2A) cells. Overall, antibodies that reduce cell surface levels of Sortilin in human U-251 cells also reduce cell surface levels of Sortilin in murineN2A cells. These results indicate that reducing cell surface levels of Sortilin is a universal activity of these antibodies and thus the antibodies may also be able to reduce cell surface levels of Sortilin in other cell types both in vitro and in vivo.

Figure 10D:
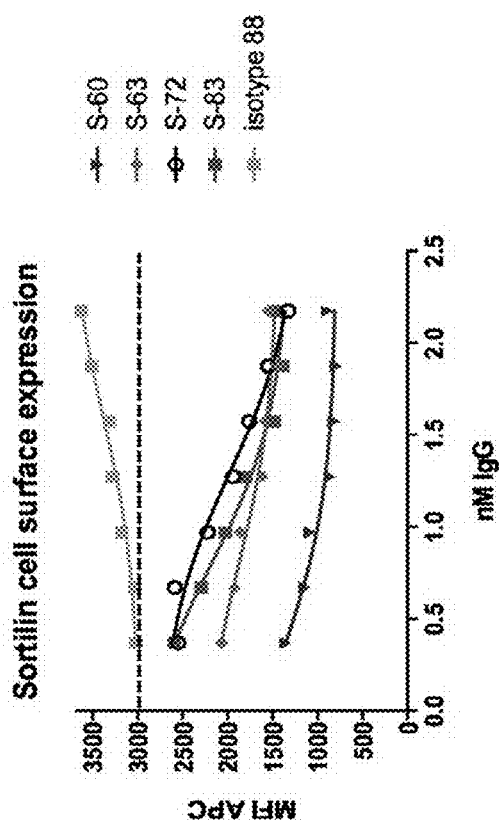
Figure 10C:
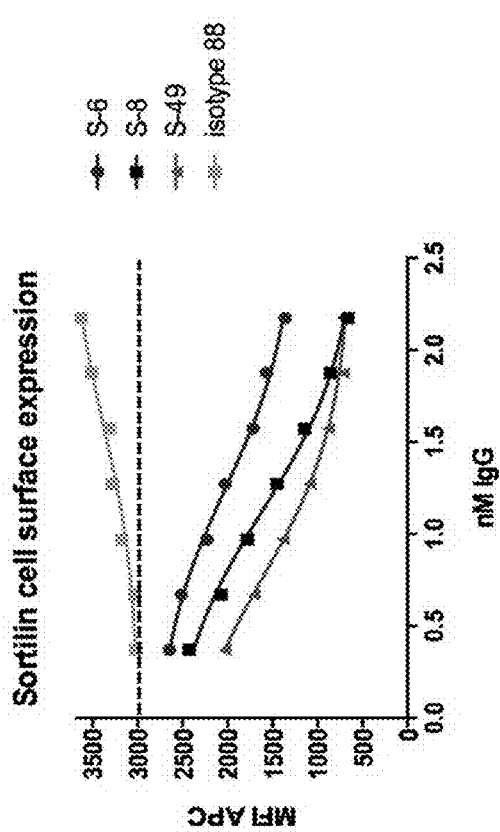
Figure 10E:
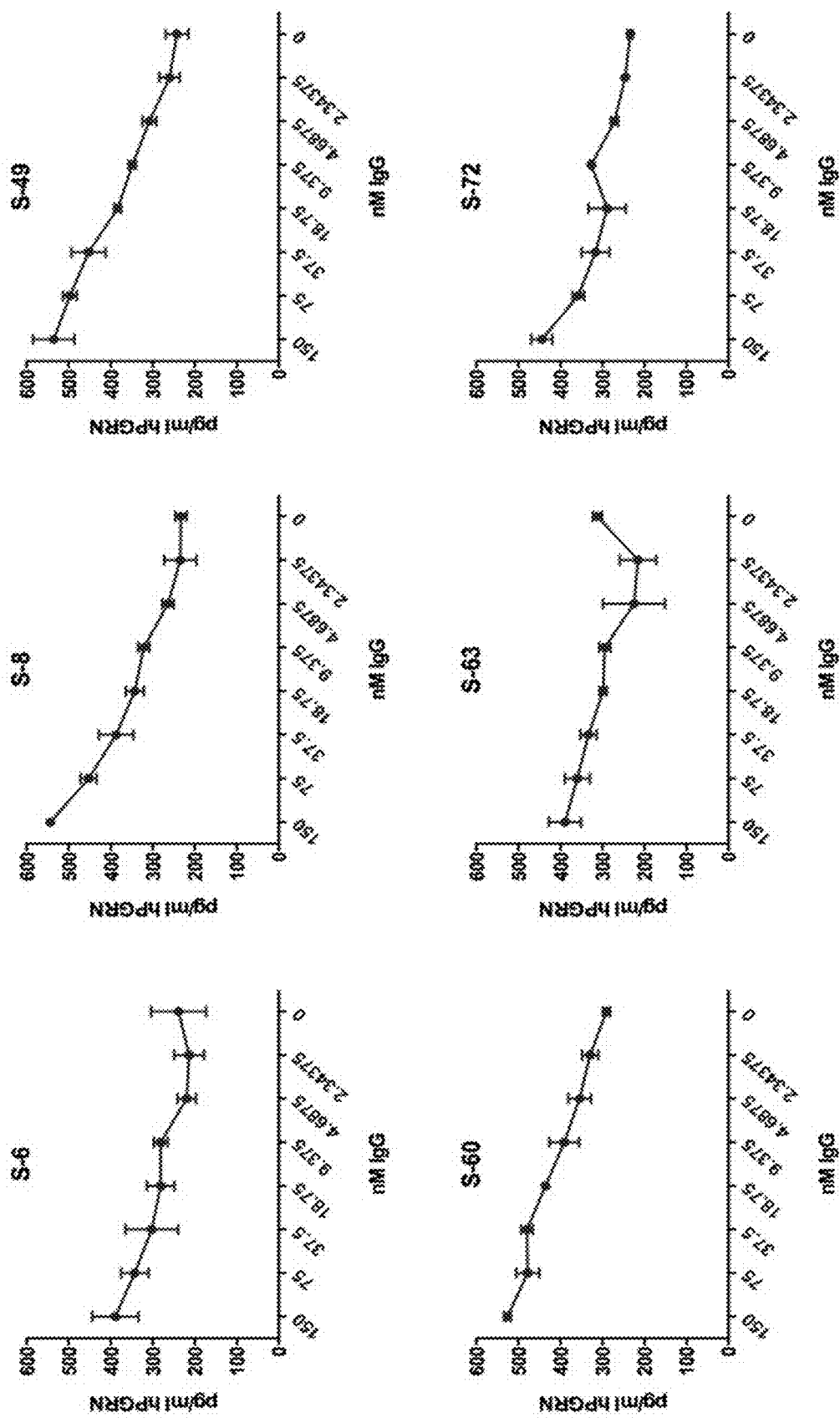
Figure 10E:
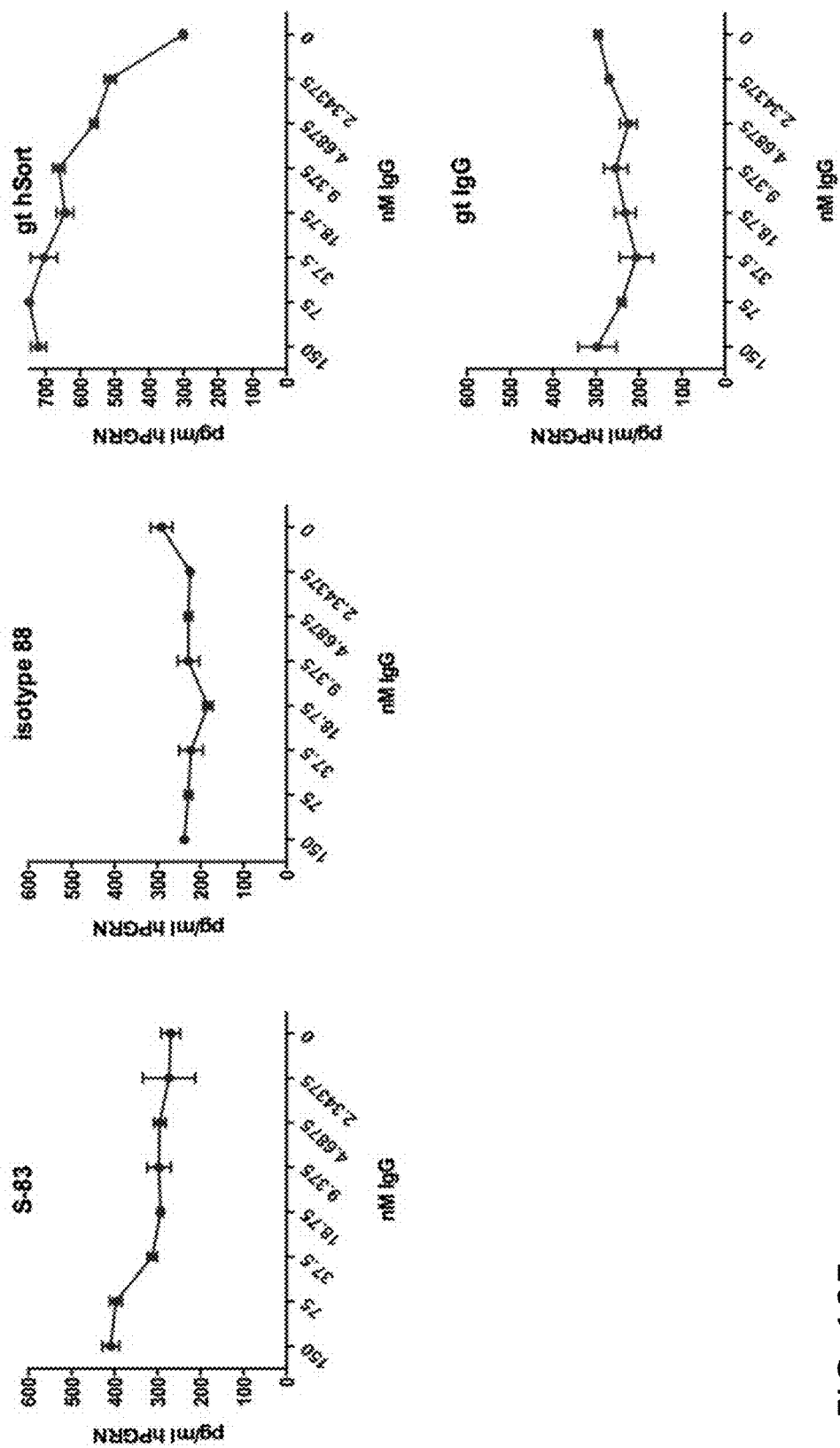

FIGS. 10C and 10D show the levels of cell surface Sortilin in U-251 cells that were incubated with different concentration of the anti-Sortilin antibodies for 72 h. The anti-Sortilin antibodies induce a dose-dependent decrease in cell surface expression of Sortilin. The decrease in Sortilin levels is depicted by decreased fluorescent intensity (MFI) of 5-20 antibody binding to Sortilin. FIG. 10E shows quantification (utilizing ELISA analysis) of the corresponding levels of PGRN in the media of the U-251 cells that were incubated with the listed anti-Sortilin antibodies for 72 h. The anti-Sortilin antibodies that decrease Sortilin cell surface levels also cause a dose-dependent increase in the levels of extracellular PGRN.

Figure 10F:
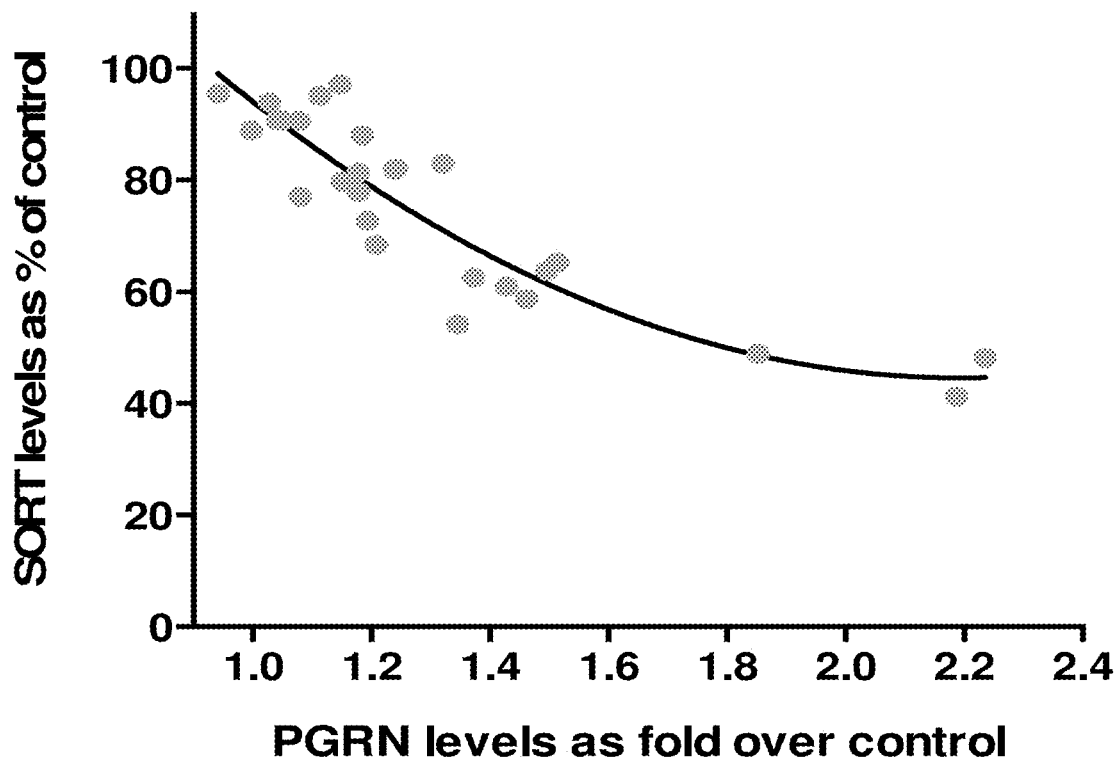

FIG. 10F shows that cell surface levels of Sortilin (SORT) are strongly and inversely correlated with the fold increase in extracellular levels of Progranulin (PGRN). Based on these results, anti-Sortilin antibodies that decrease cell surface levels of Sortilin also increase extracellular levels of Progranulin. Moreover, anti-Sortilin antibodies that decrease cell surface levels of Sortilin and increase extracellular levels of Progranulin (e.g., S-49, S-60, and S-8) belong to antibody bins 2, 3, 4 or uncategorized bins (Table 5). Thus, the results indicate that additional anti-Sortilin antibodies that belong to the same bins as antibodies S-49, S-60, and S-8 (antibodies that belong to the same bin compete with each other on binding to Sortilin) will also be able to decrease cell surface levels of Sortilin and increase extracellular levels of Progranulin, Table 10 indicates antibodies that are able to decrease cell surface levels of Sortilin in human U-251 cells and/or murine N2A cells, and/or increase extracellular levels of Progranulin. The antibodies are listed in orger form strongest to weakest activity. "N.T." refers to antinodies that were not tested.

TABLE 10

Anti-Sortilin Antibody Activities

| Antibody | Percent reduction of Sortilin levels in U251 cells | Percent reduction of Sortilin levels in N2A cells | Fold increase in Progranulin levels in U251 cells |
|---|---|---|---|
| S-02 | 96.24 | 65.95 | 2.07 |
| S-19 | 93.37 | 86.51 | 1.64 |
| S-82 | 92.95 | N.T. | 1.79 |
| S-22 | 92.74 | 87.68 | 1.68 |
| S-29 | 90.76 | 53.81 | 1.50 |
| S-20 | 89.54 | 94.01 | 1.80 |
| S-15 | 87.82 | 76.08 | 1.90 |
| S-18 | 85.69 | 57.95 | 1.44 |
| S-28 | 85.00 | 51.14 | 1.40 |
| S-21 | 78.70 | 71.88 | 1.57 |
| S-57 | 77.86 | 74.55 | 1.79 |
| S-51 | 75.92 | 80.67 | 1.60 |
| S-14 | 75.38 | 58.54 | 1.62 |
| S-55 | 73.02 | 67.72 | 1.45 |
| S-61 | 70.33 | 62.68 | 1.51 |
| S-49 | 64.59 | 56.74 | 2.19 |
| S-60 | 59.45 | N.T. | 2.24 |
| S-08 | 55.82 | 78.42 | 1.85 |
| S-83 | 48.11 | N.T. | 1.46 |
| S-45 | 45.80 | N.T. | 1.35 |
| S-63 | 45.03 | 22.21 | 1.50 |
| S-06 | 42.47 | 45.14 | 1.43 |
| S-72 | 39.29 | 39.57 | 1.51 |
| S-64 | 37.43 | N.T. | 1.21 |
| S-65 | 37.34 | N.T. | 1.37 |
| S-66 | 27.22 | N.T. | 1.19 |
| S-69 | 23.04 | N.T. | 1.08 |
| S-74 | 22.11 | N.T. | 1.18 |
| S-76 | 20.32 | N.T. | 1.15 |
| S-05 | 18.52 | N.T. | 1.18 |
| S-81 | 18.23 | 51.26 | 1.24 |
| S-30 | 17.98 | 35.16 | 1.24 |
| S-26 | 17.06 | 47.30 | 1.32 |
| S-12 | 12.01 | N.T. | 1.18 |
| S-67 | 11.08 | N.T. | 1.00 |
| S-44 | 9.40 | 27.97 | 1.08 |
| S-39 | 9.31 | 14.93 | 1.05 |
| S-71 | 9.26 | N.T. | 1.04 |
| S-43 | 6.06 | N.T. | 1.03 |
| S-85 | 4.92 | 31.56 | 1.11 |
| S-34 | 4.49 | N.T. | 0.94 |
| S-01 | 2.84 | 15.74 | 1.15 |
| S-24 | 0.35 | 35.88 | 0.78 |

Increased Progranulin Levels in Mouse Brains

Fourteen month old Tg2576 mice were infused (via implanted Alzet 1002 pumps) for two weeks with a total of 240 μg of goat (gt) anti-mouse Sortilin (R&D Systems, AF2934) or goat (gt) IgG polyclonal antibody or aCSF buffer alone (n=3/group), Mice were subsequently sacrificed and brains were dissected into left vs. right hippocampus, frontal cortex, and occipital cortex, for a total of 6 blocks per animal. Blocks were immediately extracted in N-Per (Thermo Scientific Pierce), or flash frozen and subsequently extracted at a later time. To isolate aggregated Abeta42 peptide, the insoluble protein fraction pellet was washed with TBSX, resuspended in 70% formic acid to 150 mg/ml based on pellet weight, and mixed by rotation at room temperature for 2 h with occasional vortexing. Samples were centrifuged (100,000×g, 1 h at 4° C.), and the formic acid-soluble fraction was neutralized with 20 volumes of 1 M Tris base, aliquoted, and frozen at 80° C. All extracts were measured for protein content using BCA (Thermo Scientific Pierce) or A280 spectrophotometry.

Levels of mouse Progranulin were measured using an R&D Systems Duoset ELISA Soluble and insoluble Abeta42 levels were measured using an ELISA kit from Life Technologies. Brain levels of the goat anti-Sortilin antibody were measured using a custom ELISA assay. Briefly, 2 μg/ml recombinant mouse Sortilin (R&D Systems) in PBS was plate-bound overnight at 4° C. on an Immulon ELISA plate. The next day, the plate was washed in PBS+0.05% TWEEN20 and blocked in PBS+1% BSA for 1 h at RT. 100 μl of diluted samples were added and incubated for 1 h at RT. Plates were washed and subsequently incubated with 100 μl of anti-goat HRP detection antibody (1:20,000, Jackson Immuno). Plates were washed again and incubated with 100 μl TMB substrate until color developed. The reaction was stopped by adding 50 μl of 2N sulfuric acid and color development was quantified using a Biotek plate reader.

Figure 11A:
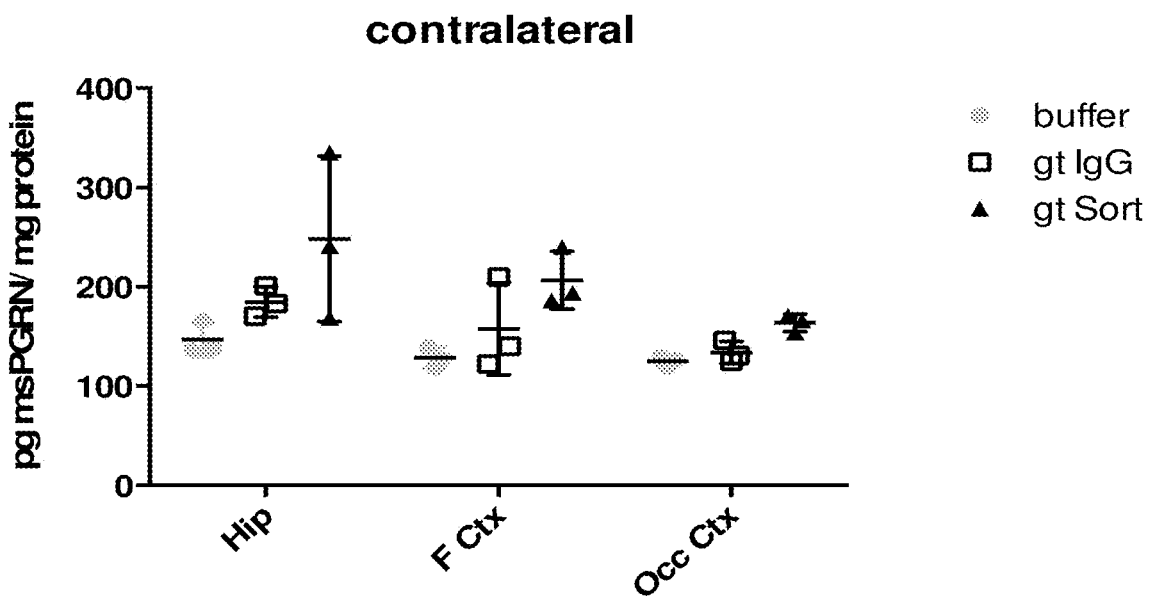
FIG. 11A-11F show results demonstrating that infusion of anti-Sortilin antibody elevates endogenous levels of brain Progranulin by several fold in the Tg2576 mouse model of Alzheimer's disease.
Figure 11B:
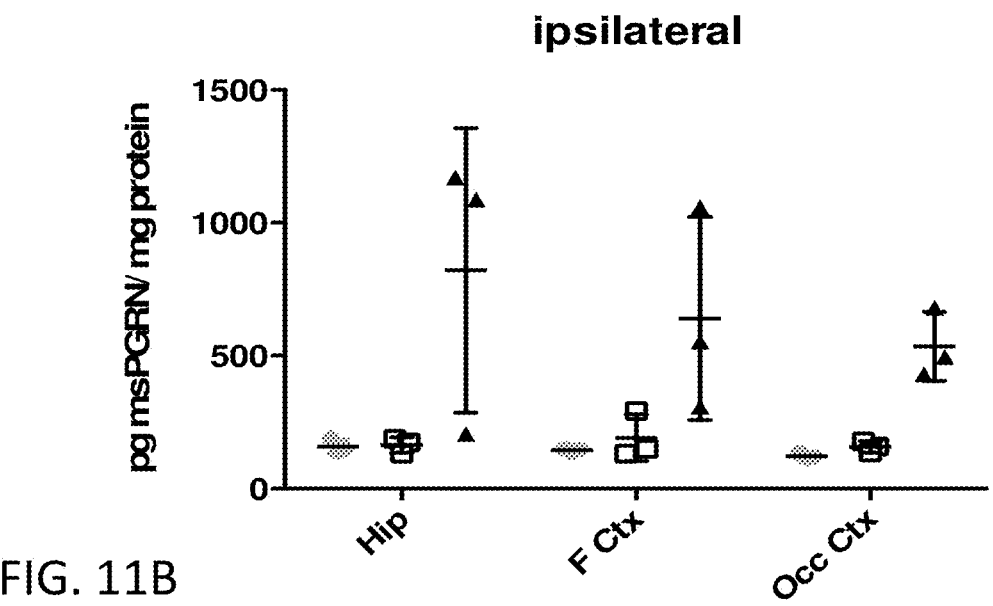
Figure 11C:
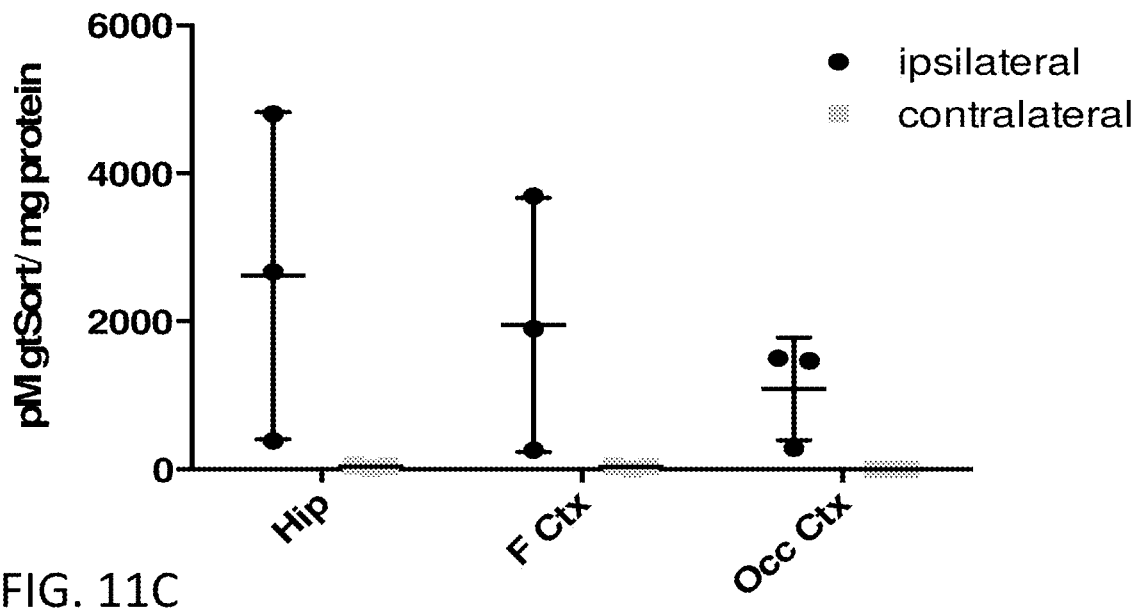
Figure 11D:
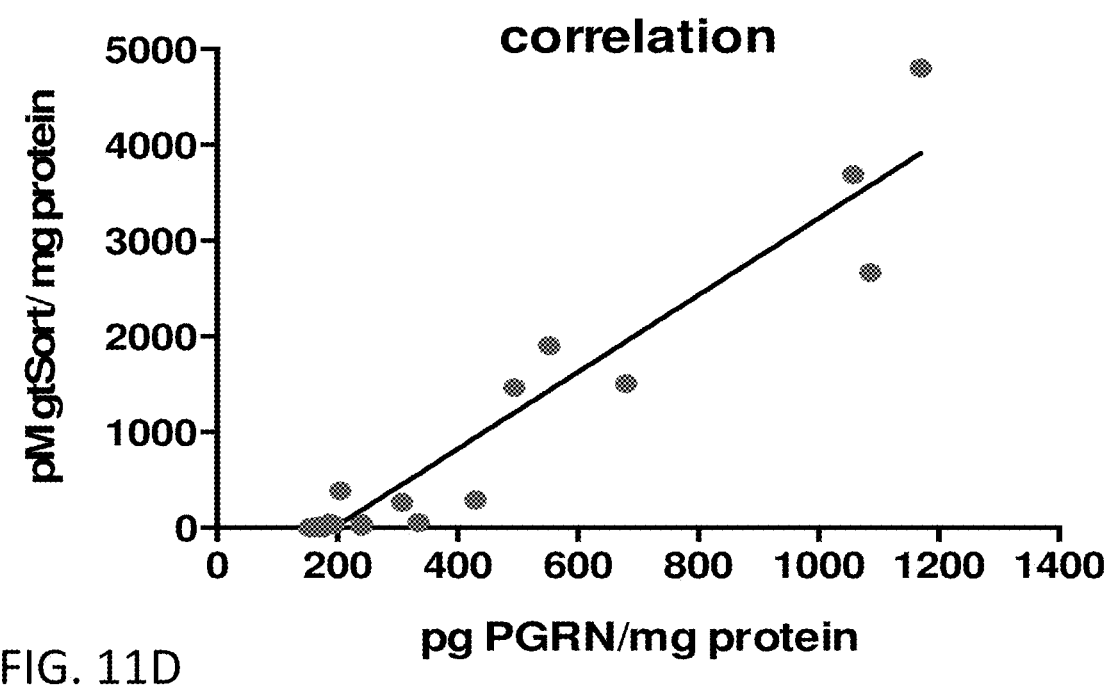

Compared to the control groups (gt IgG and aCSF buffer alone), infusion of mouse brains with a goat anti-Sortilin polyclonal antibody resulted in a strong increase in Progranulin levels in all three animals, across all three examined brain regions (FIGS. 11A and 11B). The increase in Progranulin levels was strongest on the right hemisphere that is ipsilateral to the infusion site (FIG. 11B). Consistent with these results, levels of the anti-Sortilin antibody were the highest in ipsilateral brain regions (hippocampus>frontal cortex>occipital cortex) (FIG. 11C). When antibody concentration was plotted against Progranulin levels, a strong positive correlation was observed with an R square value of 0.92 (FIG. 11D).

Figure 11E:
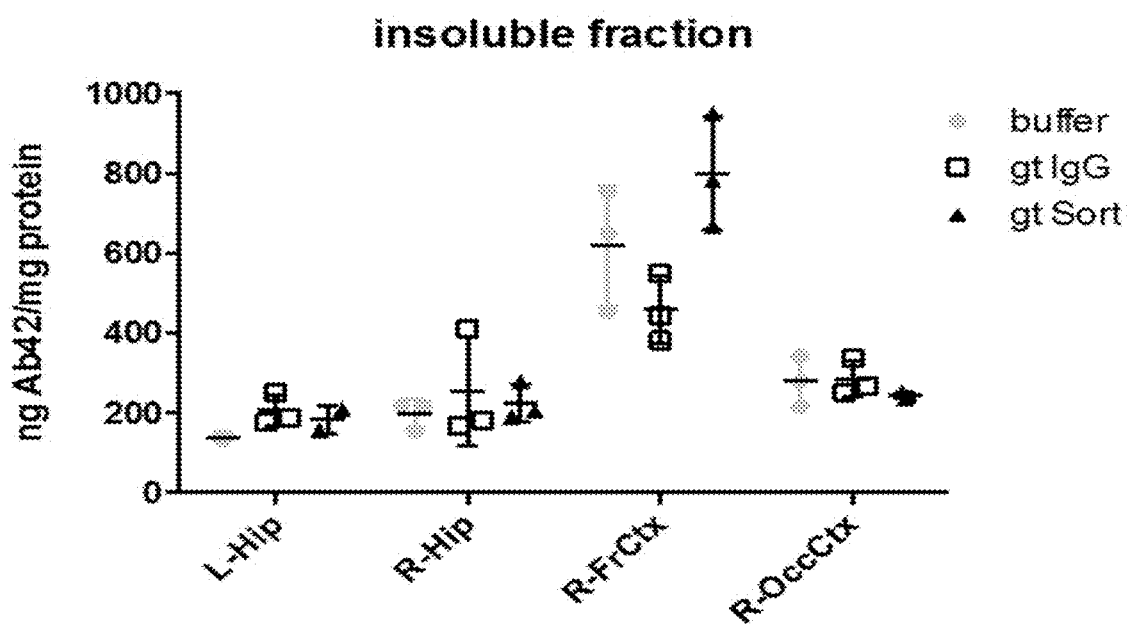
Figure 11F:
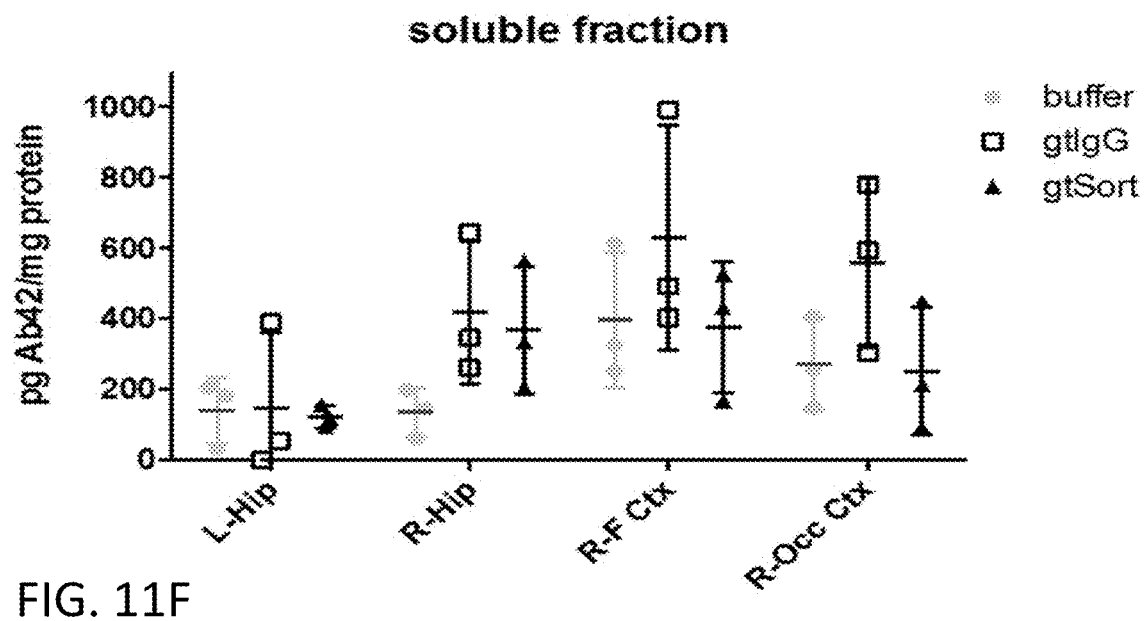

FIGS. 11E and 11F show levels of Abeta42 peptide measured in brain extracts using an ELISA from Life Technologies. FIG. 11E shows Abeta42 peptide levels in the insoluble, formic acid extracted, protein fraction and FIG. 11F shows Abeta42 peptide levels in the soluble protein fraction. The results indicate that the anti-Sortilin antibody appeared to have an effect on Abeta42 peptide levels in the insoluble, formic acid extracted, protein fraction.

Example 6: Blocking of Pro-NGF Binding to Sortilin

Biacore T200 SPR. analysis was used to examine blocking of pro-NGF binding to Sortilin by anti-Sortilin antibodies S-28, S-5, S-1, S-6, S-65, S-83, S-72, S-8, S-49, S-60, S-63, S-64, and S-76. SPR data was collected at 25° C. on a BiaCore T200 instrument and analyzed using BiaCore T200 Evaluation Software, version 2.0. HBS-EP+ (100 mM HEPES, 1.5 M NaCl, 30 mM EDTA, 0.5% v/v Surfactant P20, pH 7.4) was used as running buffer and for preparing reagents.

Human His-tagged Sortilin (200 nM, R&D Systems) was captured on a CM5 sensor chip immobilized with anti-His mouse IgG (60 s contact time, 30 μl/min flow rate, 0 s dissociation time). Human pro-NGF (400 nM) or HBS-EP+ buffer was flowed across the chip surface (60 s contact time, 30 μl/min flow rate, 0 s dissociation time). Anti-Sortilin antibody (200 nM) was flowed across the chip surface (60 s contact time, 30 μl/min flow rate, 30 s dissociation time). The chip surface was regenerated in between cycles using 10 mM glycine-HCl, pH 1.7 (75 s contact time, 30 μl/min flow rate, 60 s stabilization time). The resulting SPR signal was obtained as the difference in response from measurements performed on a blank flow cell.

Figure 12A:
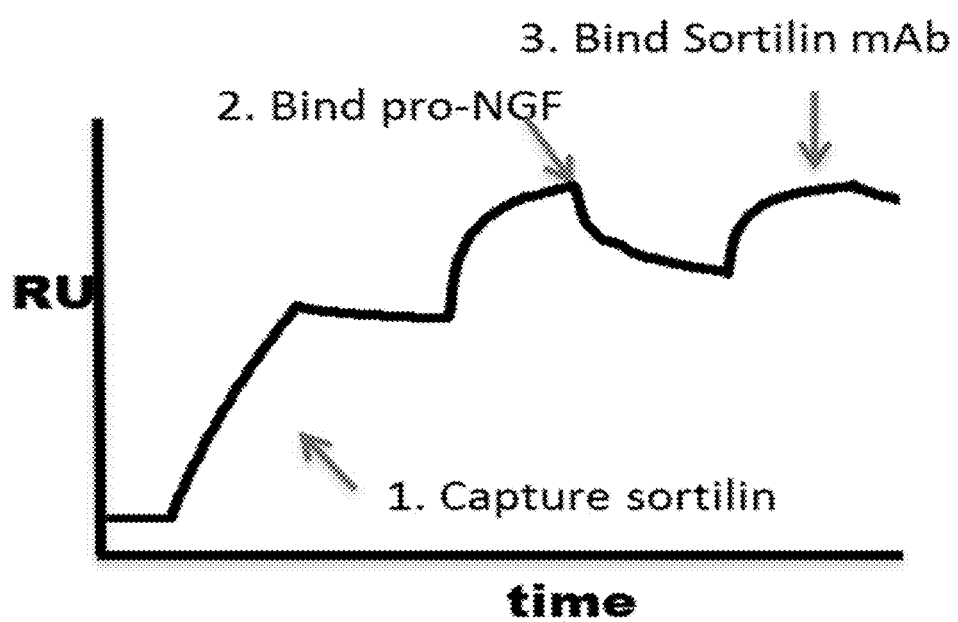
FIG. 12A depicts a surface plasmon resonance (SPR) biacore assay to monitor competition between pro-NGF and anti-Sortilin antibodies for binding to Sortilin. The assay shows human Sortilin captured to a Biacore chip followed by binding of pro-NGF to Sortilin, followed by binding of an anti-Sortilin antibody to Sortilin.
Figure 12B:
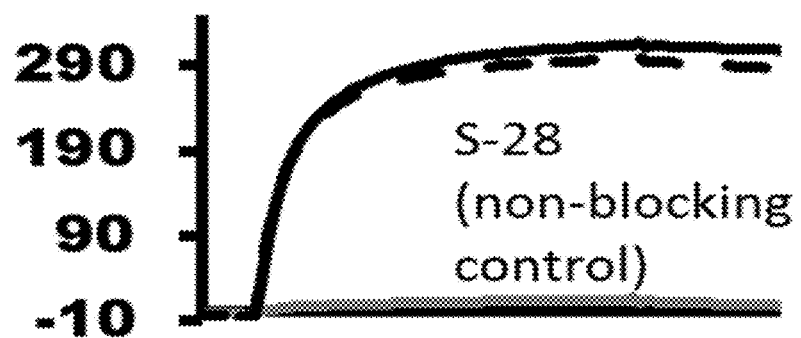
FIG. 12B depicts a non-blocking control. If pro-NGF and a given anti-Sortilin antibody bind the same region on Sortilin, the binding of pro-NGF will inhibit the subsequent binding of the anti-Sortilin antibody. Thus, if a given antibody binds Sortilin to the same degree in the presence (dashed lines) or absence (solid lines) of pro-NGF, as depicted in FIG. 12B, such antibody does not block pro-NGF binding to Sortilin.
Figure 12C:
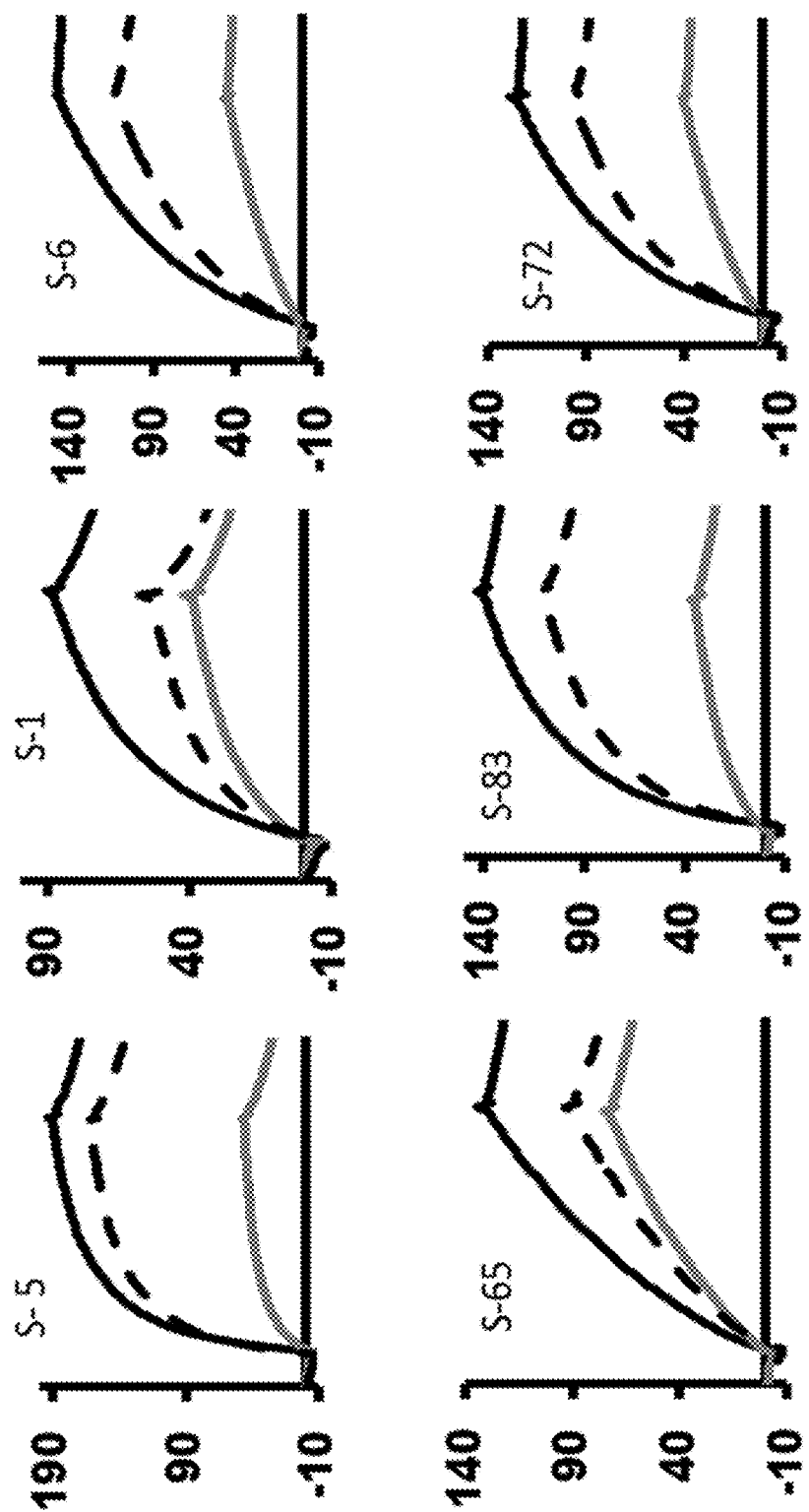
FIG. 12C depicts binding of anti-Sortilin antibodies to Sortilin in the presence (dashed lines) or absence (solid lines) of pro-NGF. The antibodies shown are partially blocked by the presence of pro-NGF bound to Sortilin. Antibodies S-1 and S-65 are strongly affected. Solid lines correspond to binding of antibodies to Sortilin in the absence of pro-NGF. Dashed lines correspond to binding of antibodies to Sortilin in the presence of pro-NGF. Grey lines correspond to binding of pro-NGF to Sortilin in the presences of pro-NGF (maximal competition)
Figure 12C:
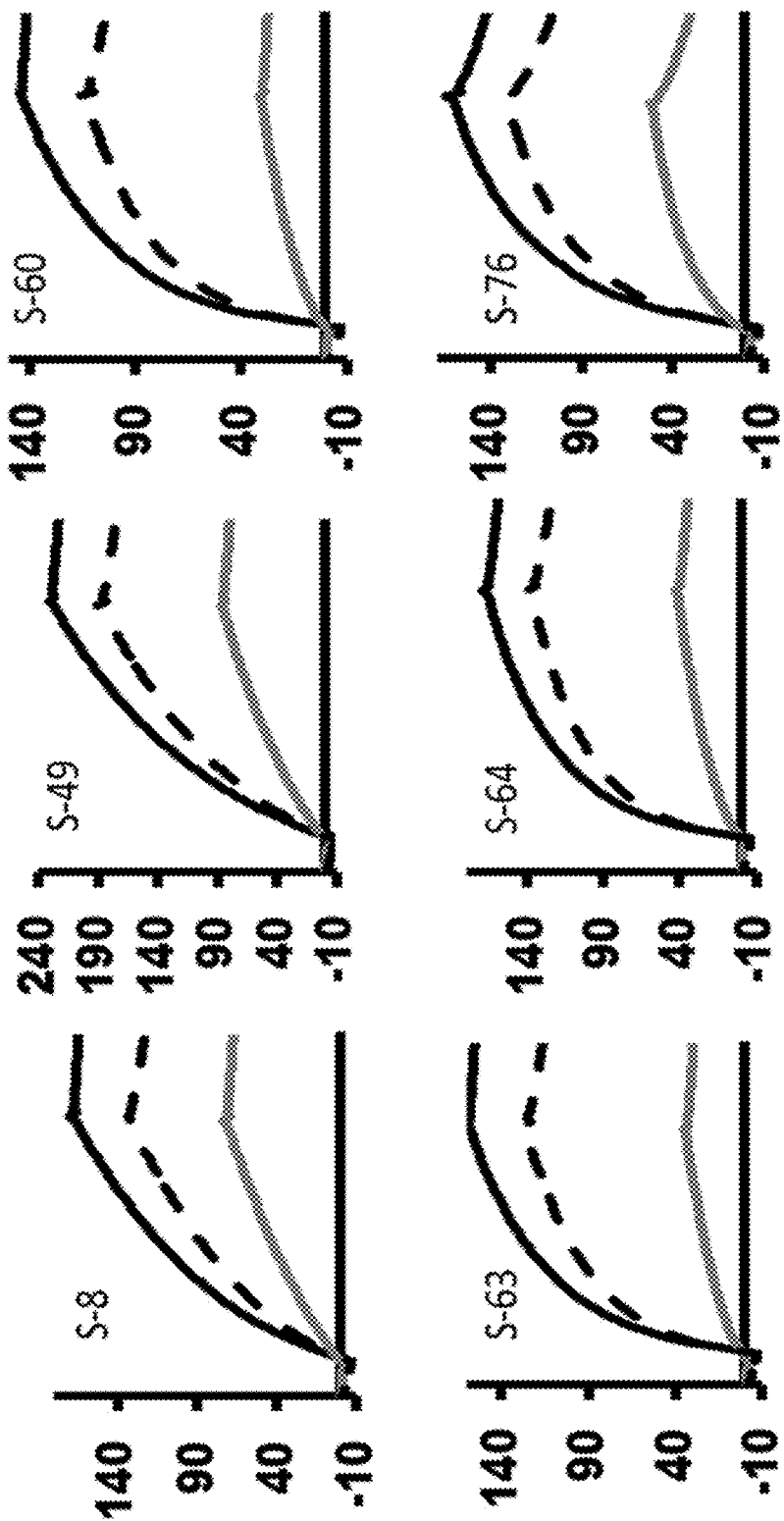
Figure 13A:
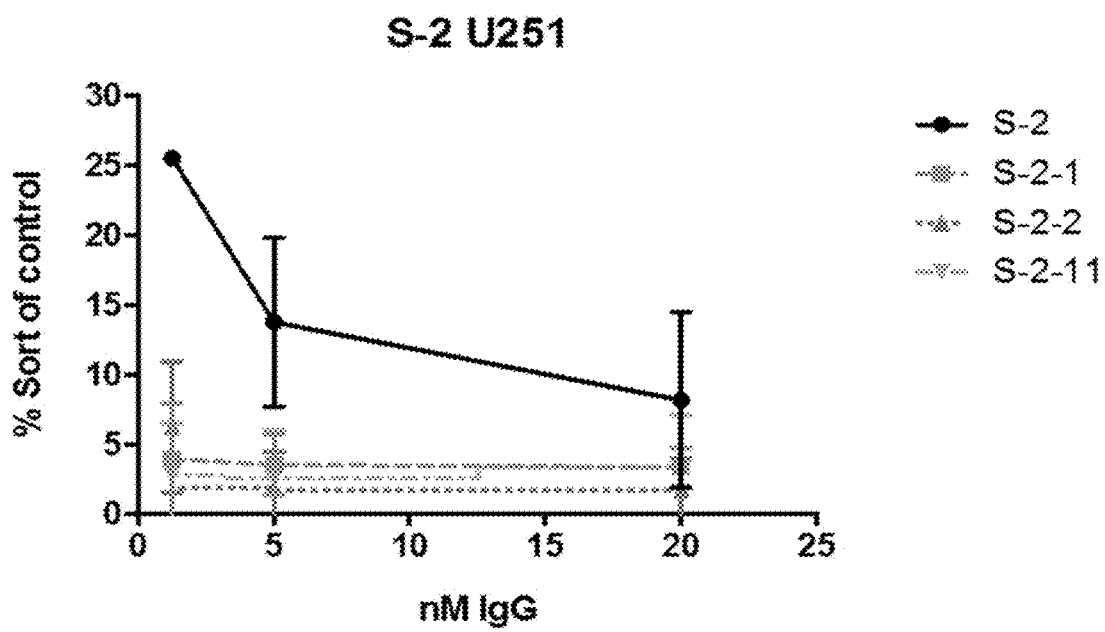
FIG. 13A-13G depicts levels of Sortilin cell surface expression after 72 hr incubation with anti-Sortilin antibodies at concentrations of 20 nM, 5 nM, or 1.25 nM.
Figure 13B:
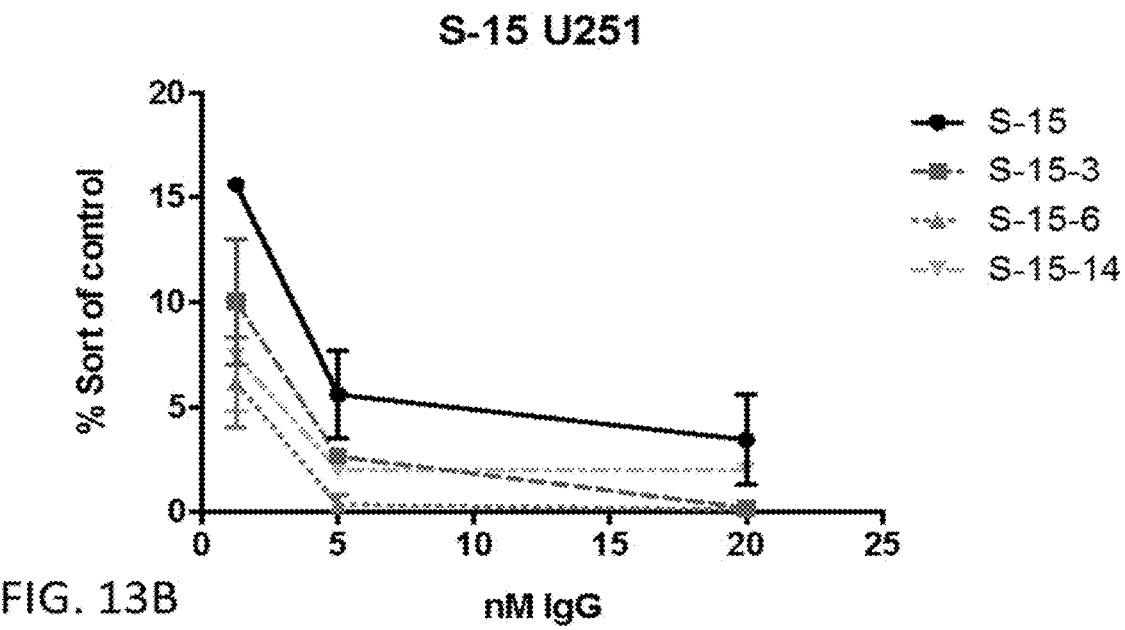
Figure 13C:
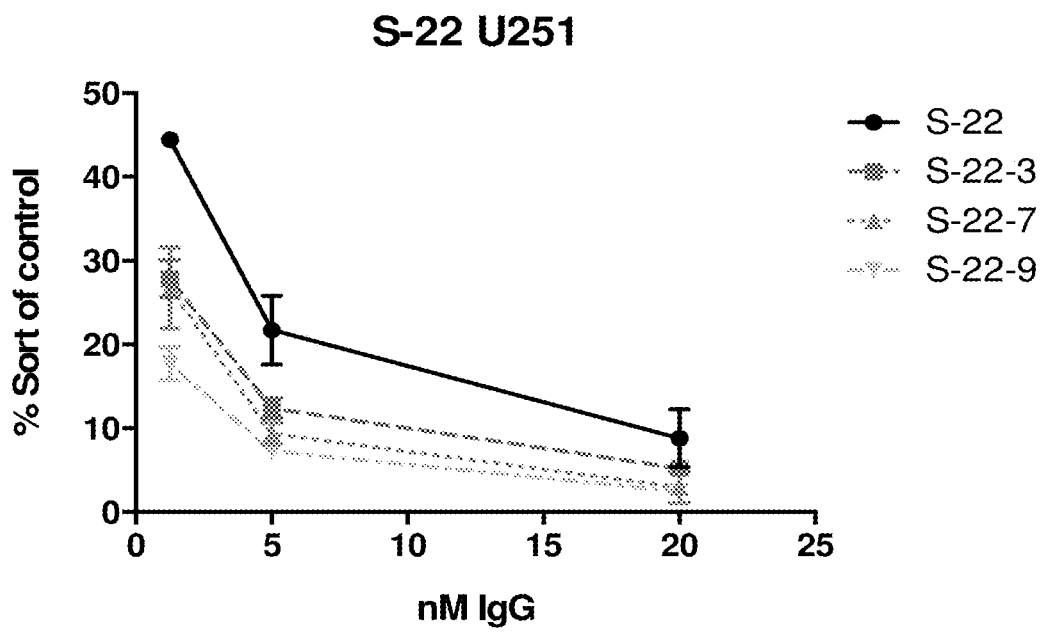
Figure 13D:
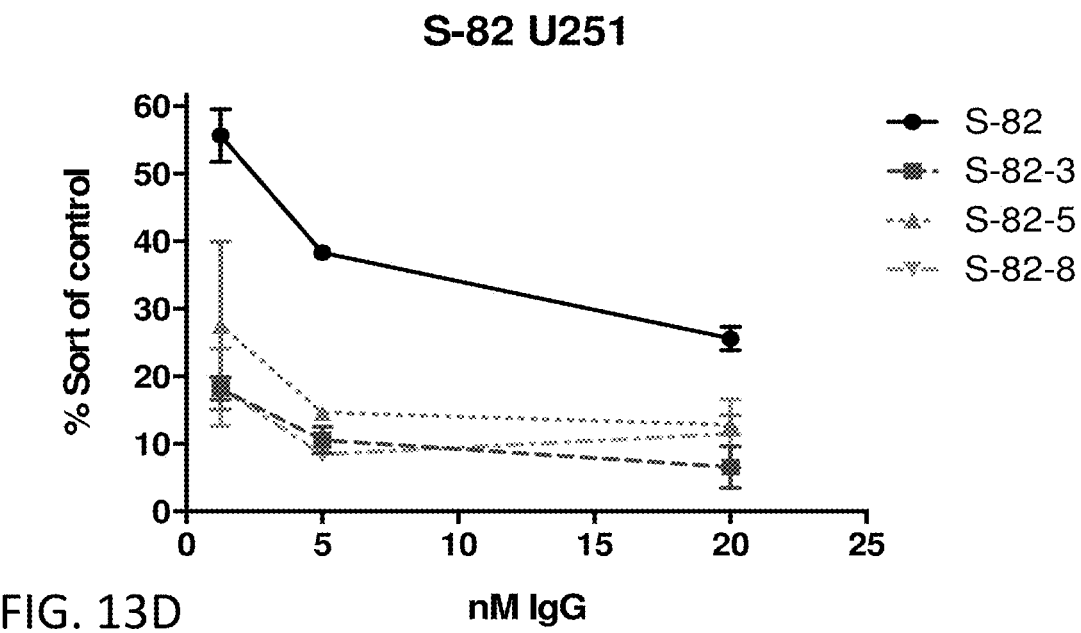
Figure 13E:
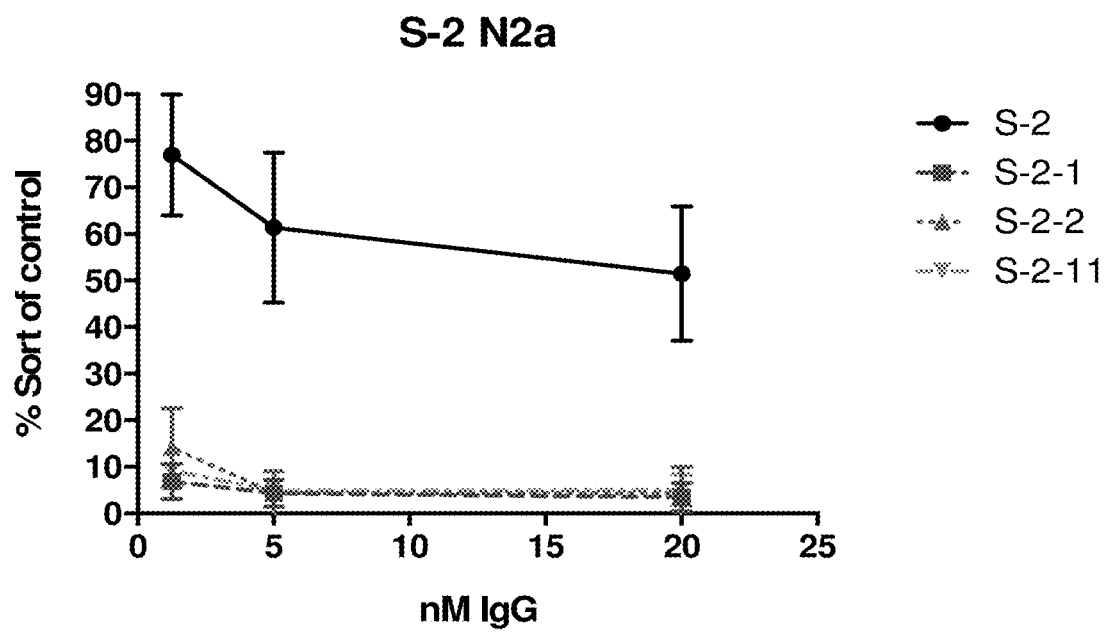
Figure 13F:
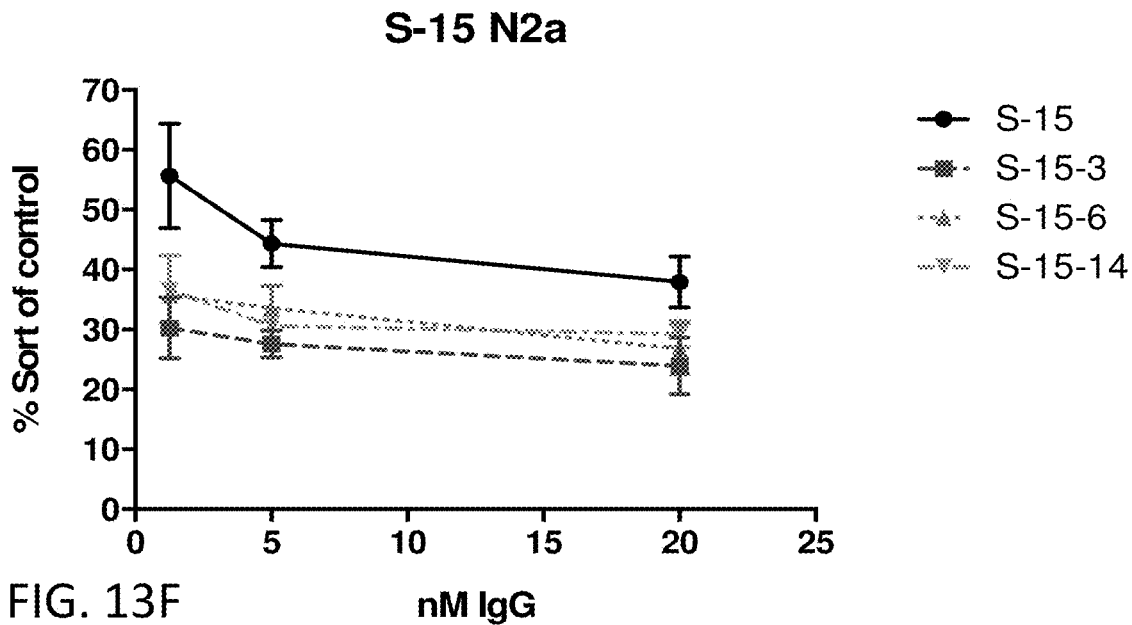
Figure 13G:
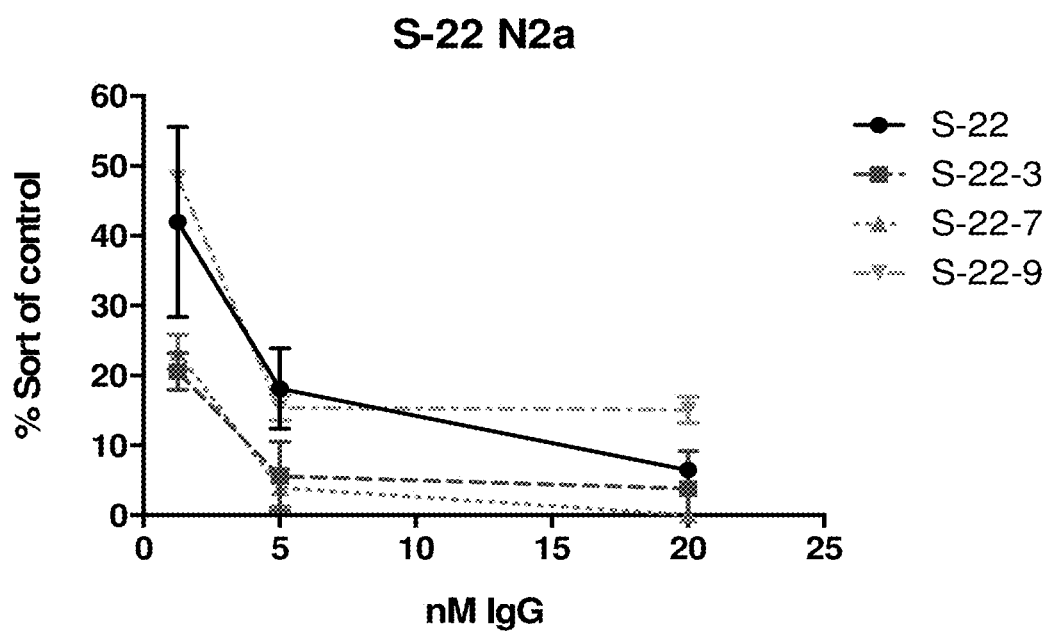

The results shown in FIG. 12A-12C demonstrate that binding of certain anti-Sortilin antibodies to Sortilin can be partially blocked by pro-NGF. FIG. 12A shows the experimental setup. FIG. 12B shows response traces for a control antibody (S-28) that does not block Progranulin. Binding of S-28 to Sortilin is not blocked by pre-incubation with pro-NGF. FIG. 12C shows that binding of anti-Sortilin antibodies S-1 and S-65 to Sortilin are most strongly blocked by pro-NGF binding to Sortilin (RU=response unit).

Example 7: Characterizing the Therapeutic Use of Sortilin Blocking Antibodies Utilizing Established Animal Models of Traumatic Brain Injury The therapeutic utility of Sortilin blocking antibodies can be tested in established animal models of traumatic brain injury (Tanaka, Y et al., (2013) Neuroscience 231 49-60).

For example a model of traumatic brain injury that induces the activation of microglia and astrocytes can be used. Eight- or nine week-old male C57BL/6J WT mice or Progranulin heterozygous mice can be used. Mice are purchased from Charles River Laboratories or the Jackson labs. Mice are anesthetized by intraperitoneal administration of xylazine hydrochloride (8 mg/kg) and chloral hydrate (300 mg/kg) dissolved in sterile saline, and subsequently placed in a stereotaxic apparatus (Narishige, Tokyo, Japan). An incision is made in the scalp and the cranium is exposed. The periosteum is cleaned from the skull, a hole is drilled over the right cerebral hemisphere with a dental drill, and the duramater is removed with a needle tip. A stainless steel cannula, with a 0.5-mm outer diameter, is used to make a longitudinal stab wound in the right hemisphere. The cannula is positioned at 1.3 mm lateral to the midline, and 1 mm posterior to bregma, and introduced into the brain until the tip reached a depth of 2 mm. The cannula is then shifted 2 mm caudally (bregma3 mm), and then shifts back 2 mm rostrally to its initial position. Finally, the cannula is removed from the brain, and the scalp wound is sutured. Mice are then treated with Sortilin blocking antibodies according to standard procedures and then analyzed by histology and immunofluorescent staining and behavioral tests Example 8: Characterizing the Therapeutic Use of Sortilin Blocking Antibodies Utilizing a Model of Parkinson's Neuro-Inflammation and Neuron Loss Following Toxin-Induced or Synuclein-Induced Injury The therapeutic utility of Sortilin blocking antibodies can also be tested in a model of neuro-inflammation and neuron loss following toxin-induced injury (Martens, L H et al., (2012) The Journal of Clinical Investigation, 122, 3955).

Three-month-old mice are treated with 4 i.p. injections of MPTP per day for 2 days (4 µg/g body weight) (Sigma-Aldrich) or PBS. MPTP, destroys the Dompainiergic neurons that degenerate in Parkinons's disease. Mice are treated with Sortilin blocking antibodies according to standard protocols and then analyzed using Stereological counting to quantify dopamine neurons and microglia in the SNpc. As described. Alternatively, Parkinson's models expressing genetic mutations in the gene for alpha-synuclein (A53T, A30P, and E46K) or, overexpressing of alpha-synuclein can be used (Maguire-Zeiss (2008) Pharmacol Res; 58(5-6): 271-280; Chesselet (2008) Exp Neurol 209: 22-27).

Example 9: Characterizing the Therapeutic use of Sortilin Blocking Antibodies Utilizing Animal Models for Aging, Seizures, Spinal Cord Injury, Retinal Dystrophy, Frontotemporal Dementia, and Alzheimer Disease The therapeutic utility of Sortilin blocking antibodies can also be tested in animal models for aging, seizures, spinal cord injury, retinal dystrophy, frontotemporal dementia, and Alzheimer disease, as previously described (e.g., Beattie, M S et al., (2002) Neuron 36, 375-386; Volosin, M et al., (2006) J. Neurosci. 26, 7756-7766; Nykjaer, A et al., (2005) Curr. Opin, Neurobiol. 15, 49-57; Jansen, P et al., (2007) Nat. Neurosci, 10, 1449-1457; Volosin, M et al., (2008) J. Neurosci. 28, 9870-9879; Fahnestock, M et al., (2001) Mol. Cell Neurosci. 18, 210-220; Nakamura, K et al., (2007) Cell Death, Differ, 14, 1552-1554; Yune, T et al., (2007) Brain Res. 1183, 32-42; Wei, Y et al., (2007) Neurosci. Lett. 429, 169-174; Provenzano, M J et al., (2008) Laryngoscope 118, 87-93; Nykjaer, A et al., (2004) Nature 427, 843-848; Harrington, A W et al., (2004) Proc. Natl. Acad. Sci. U.S.A. 101, 6226-6230; Teng, H K et al., (2005) J. Neurosci. 25, 5455-5463; Jansen, P et al., (2007) Nat, Neurosci. 10, 1449-1457; Volosin, M et al., (2008) J. Neurosci. 28, 9870-9879; Fan, Y J et al., (2008) Eur, J. Neurosci. 27, 2380-2390; Al-Shawi, R et al., (2008) Eur. J. Neurosci. 27, 2103-2114; and Yano, H et al., (2009) J. Neurosci. 29, 14790-14802).

Example 10: Characterizing the Therapeutic use of Sortilin Blocking Antibodies Utilizing Models of Atherosclerosis The therapeutic utility of Sortilin blocking antibodies can also be tested in models of Atherosclerosis, as previously described (e.g., Lance, A et al., (2011) Diabetes, 60, 2285; and Kjolby, M et al., (2012) Cell Metabolism 12, 213-223).

Example 11: Characterizing the Therapeutic use of Sortilin Blocking Antibodies Utilizing a Model of Infection The therapeutic utility of Sortilin blocking antibodies can also be tested in a model of infection. For example, Listeria monocytogenes or other infection in normal mice or Progranulin hets can be used, as previously described (e.g., Yin, F et al., (2009) J. Exp. Med, 207, 117-128).

Example 12: In Vivo Protection from EAE and Cuprizone in a Whole Animal

Adult 7-9 week-old female C57BL/6 mice (obtained from Charles River Laboratories) are injected in the tail base bilaterally with 200 µl of an innoculum containing 100 µg of myelin oligodendrocyte glycoprotein peptide 35-55 (amino acids MEVGWYRSPFSRVVHLYRNGK (SEQ ID NO:707); Seqlab) and 1 mg of Mycobacterium tuberculosis H37 Ra (Difco) in incomplete Freund's adjuvant (Difco). Pertussis toxin (200 ng; List Bio-logical Laboratories) is injected at day 0 and at day 2 after immunization. Clinical signs are scored as follows: 0, no clinical signs; 1, complete limp tail; 2, complete limp tail and abnormal gait; 3, one hind-limb paraparesis; 4, complete bind limb paraparesis; and 5, fore- and hind-limb paralysis or moribund. Only mice having disease onset (clinical score of 1 or more) at day 14 are used for experiments. Antagonistic anti-Sortilin, and/or Sortilin bispecific antibodies are injected intraperitoneally or intravenously in EAE-diseased mice at the day of the first clinical symptoms or at any other desired time (PLoS Med (2007) 4(4): e124).

Young or aged wild-type (WT) mice are fed a standard diet (Harlan) containing 0.2% cuprizone (CPZ) powdered oxalic bis(cyclohexylidenehydrazide) (Sigma-Aldrich) for 4, 6 or 12 weeks. For Histological and immunohistochemical analyses brains are removed after mouse perfusion with 4% paraformaldehyde (PFA), fixed in 4% PFA for 24 h, followed by immersion in 30% sucrose for 24-48 h. To evaluate myelin integrity and damage, as well as cell proliferation and inflammation sections or mouse brain are stained with anti-MBP (1:100; Abcam, ab7349), -dMBP (1:2000; Millipore, ab5864), -β APP (1:100; Invitrogen, 51-2700), -SMI-31 (1:1000; Covance, smi-31R), -Iba1 (1:600; Wako, 019-19741), -BrdU (1:250; Abcam, ab1893), -GFAP (1:200; invitrogen, 13-0300), -iNOS (1:100; BD Pharmingen, 610329), -LPL(1:400, from Dr. G. Olivecrona) and -MHC II (1:100; BD Pharmingen, 553549). For behavioral effects of the antibodies, mice are analyzed for locomotor activity using transparent polystyrene enclosures and computerized photobeam instrumentation. General activity variables (total ambulations, vertical rearings), along with indices of emotionality including time spent, distance traveled and entries, are analyzed. A battery of sensorimotor tests is performed to assess balance (ledge and platform), strength (inverted screen), coordination (pole and inclined screens) and initiation of movement (walking initiation). Motor coordination and balance are studied using a rotarod protocol (Cantoni et al., Acta Neuropathol (2015)129(3): 429-47).

Example 13: Characterization of the Therapeutic use of Sortilin Antagonistic or Bispecific Antibodies in Established Animal Models of Traumatic Brain Injury The therapeutic utility of Sortilin, and/or Sortilin bispecific antibodies is tested in established animal models of traumatic brain injury (Tanaka, Y et al. (2013) Neuroscience 231 49-60). For example, a model of traumatic brain injury that induces the activation of microglia and astrocytes is used. Eight or nine week-old male C5713L/6J WT mice or Progranulin heterozygous mice are used (purchased from Charles River Laboratories or Jackson Laboratories), Mice are anesthetized by intraperitoneal administration of xylazine hydrochloride (8 mg/kg) and chloral hydrate (300 mg/kg) dissolved in sterile saline, and subsequently placed in a stereotaxic apparatus (Narishige, Tokyo, japan). An incision is made in the scalp and the cranium is exposed. The periosteum is cleaned from the skull, a hole is drilled over the right cerebral hemisphere with a dental drill, and the duramater is removed with a needle tip. A stainless steel cannula, with a 0.5 mm outer diameter, is used to make a longitudinal stab wound in the right hemisphere. The cannula is positioned at 1.3 mm lateral to the midline, and 1 mm posterior to bregma, and introduced into the brain until the tip reaches a depth of 2 mm. The cannula is then shifted 2 mm caudally (bregma 3 mm), and then shifts back 2 mm rostrally to its initial position. Finally, the cannula is removed from the brain, and the scalp wound is sutured. Mice are then treated with antagonistic anti-Sortilin, and/or Sortilin bispecific antibodies according to standard procedures and then analyzed by histology and immunofluorescence staining and behavioral tests.

Example 14: Characterization of Therapeutic use of Sortilin Antibodies and/or Sortilin Bispecific Antibodies in a Model of Neuro-Inflammation and Neuron Loss Following Toxin-Induced Injury The therapeutic utility of Sortilin antibodies and/or Sortilin bispecific antibodies is tested in a model of neuro-inflammation and neuron loss following toxin-induced injury (Martens, L H et al., (2012) The journal of Clinical Investigation, 122, 3955). Three-month-old mice are treated with 4 intraperitoneal injections of MPTP (1-methyl-4-phenyl-1,2,3,6-tetrahydropyridine) per day for 2 days (4 µg/g body weight) (Sigma-Aldrich) or PBS. Mice are treated with antagonistic anti-Sortilin and/or Sortilin bispecific antibodies according to standard protocols and then analyzed using Stereological counting to quantify dopamine neurons and microglia in the substantia nigra pars compacta (SNpc), as described.

Example 15: Analysis of Ability of Anti-Sortilin Antibodies to Stimulate Viability of Innate Immune Cells and/or Neurons Wild-type (WT) mouse bone marrow derived macrophages are cultured in the presence of M-CSF, or Nerve cell cultures in standard conditions are exposed to Sortilin antibody and cell viability is measured. Macrophages isolated from the bone marrow of WT and KO mice are plated on non-tissue-culture-treated 96-well plates, pre-coated with either anti-Sortilin antibodies or control antibodies. Cells are cultured for 48 hours in the presence of 10 ng/ml M-CSF. Analysis of viability is performed using Cell Titer Glo kit (Promega). Plates are read with a BioTek Synergy Microplate Reader using GEN5 2.04 software.

Example 16: Analysis of Anti-Stroke Effect of Sortilin Antibodies

Transient occlusion of the middle cerebral artery (MCAO), a model that closely resembles human stroke, is used to induce cerebral infarction in mice. Monofilament (70SPRe, Doccol Corp, USA) is introduced into the internal carotid artery through an incision of the right common carotid artery. The middle cerebral artery is occluded for 30 minutes with a range of reperfusion times (6 h, 12 h, 24 h, 2 d, 7 d and 28 d). The effect of surgery is controlled using sham animals at 12 h and at 7 d. Sham animals undergo the same surgical procedure without occlusion of the middle cerebral artery. MCAO animals treated with antagonistic anti-Sortilin antibodies or control antibodies and tested for infarct volumetry, acute inflammatory response (12 h reperfusion), transcription of pro-inflammatory cytokines TNFa, IL-1a, and IL-1b, microglial activity (CD68, Iba1), transcription of chemokines CCL2 (MCP1), CCL3 (MIP1a), and the chemokine receptor CX3CR1, and invasion of CD3-positive T-cells (Sieber et al. (2013) PLoS ONE 8(0, e52982).

Example 17: Analysis of Anti-Alzheimer's Disease Effect of Anti-Sortilin Antibodies To evaluate the ability of anti-Sortilin antibodies to delay, prevent, or reverse the development of Alzheimer's disease (AD), 5×FAD mice are used. 5×FAD mice overexpress mutant human APP (695) with the Swedish (K670N, M671L), Florida (1716V), and London (V717I) familial Alzheimer's disease (FAD) mutations, along with human PSI harboring two FAD mutations, M146L and L286V. Both transgenes are regulated by the mouse Thy1 promoter to drive over expression on the brain and recapitulate major features of AD. Mice treated with the antagonistic anti-Sortilin antibodies or with control antibodies are tested for A beta plaque load with immunohistochemistry and by ELISA of tissue extracts. They are further tested for the number of microglia in the brain, and for reduction in cognitive deficit using Morris Water maze, a spatial learning and memory task, Radial Arm Water Maze, a spatial learning and memory task, Y Maze (quantifies spontaneous alternation as a measure of spatial cognition), novelty preference in in an open field, operant learning to assess learning and memory, and fear conditioning (mousebiology.org website:, Wang et al., (2015) Cell. pii: S0092-8674(15)00127-0).

Example 18: Analysis of the Protective Effect of Sortilin Antibodies in Wound Healing To evaluate the ability of anti-Sortilin antibodies to increase colonic wound repair following injury, a mouse model of biopsy injury in the colon is used. In this model, the endoscope with outer operating sheath is inserted to the mid-descending colon and the mucosa is surveyed to the ano-rectal junction. Then, a single full thickness area of the entire mucosa and submucosa is removed with flexible biopsy forceps with a diameter of 3 French, avoiding penetration of the muscularis propria. Each mouse is biopsy injured at 3-5 sites along the dorsal side of the colon (see, e.g., Seno H, 2008, *Proc Natl Acad. Sci USA.* 2009 Jan. 6; 106(1): 256-261). Cohorts of mice are treated with Sortilin antibodies 2 or 3 days after biopsy injury. Mice are monitored every day for 15 days, to check for weight loss and wound healing by measuring the surface area of lesions.

Example 19: Analysis of the Protective Effect of Sortilin Antibodies in Retinal Degeneration Antagonist anti-Sortilin antibodies decrease the accumulation and/or function of inflammatory macrophages, and as a result delay, prevent and/or treat age-related macular degeneration (AMD). AMD is a degenerative disease of the outer retina. It is thought that inflammation, particularly inflammatory cytokines and macrophages, contribute to AMD disease progression. The presence of macrophages in the proximity of AMD lesions is documented, in the drusen, Bruch's membrane, choroid and retina. Macrophages release tissue factor (TF) and vascular endothelial growth factor (VEGF), which triggers the expansion of new blood vessels formation in patients showing choroidal neovascularization.

The type of macrophage present in the macular choroid changes with age, displaying elevated levels of M2 macrophages in older eyes compared to younger eyes. However, advanced AMD maculae had higher M1 to M2 rations compared to normal autopsied eyes of similar age. (see, e.g., Cao X et al, (2011), *Pathol Int* 61(9): pp 528-35). This suggests a link between classical M1 macrophage activation in the eye in the late onset of AMD progression.

Retinal microglia cells are tissue-resident macrophages that are also normally present in the inner retina. In the event of damage, microglia can be activated and act as mediator of inflammation. Activated microglia has been detected in the AMD tissue samples and has been proposed as one potential contributor of inflammatory processed that lead to AMD pathogenesis (Gupta et al., (2003) *Exp Eye Res.,* 76(4):463-71.). The ability of antagonist Sortilin antibodies to prevent, delay, or reverse AMD is tested in one or more of AMD models (see, e.g., Pennesi et al., (2012) *Mol Aspects Med.;* 33(4): 487-509).

Overall inflammatory macrophages (either M1 and/or activated microglia) are documented to correlate with AMD disease progression and therefore represent a therapeutic target for antagonist Sortilin antibodies. Similar therapeutic benefit can be achieved in glaucoma and genetic forms or retinal degeneration such as retinitis pigmentosa.

The ability of anti-Sortilin antibodies to prevent, delay, or reverse retinal ganglion cell degeneration in glaucoma is tested in a glaucoma model (see, e.g., El-Danaf et al., (2015) *J Neurosci.* 11; 35(6):2329-43; Demetriades et al., (2013) *Invest Ophthalmol Vis Sci* 54: Abstract 4940). Likewise, the therapeutic benefit of anti-Sortilin antibodies in genetically induced retinal degeneration and retinitis pigmentosa is tested as described in Chang et al., (2002) Vision Res.; 42(4):517-25, and in Gargin et al, (2007) J Comp Neurol. 500(2): 222-238; and in "Retinal Degeneration Rat Model Resource Availability of P23H and S334 the Mutant Rhodopsin Transgenic Rats and RCS Inbred and RCS Congenic Strains of Rats," M M LaVail, Jun. 30, 2011. Likewise, the therapeutic benefit of anti-Sortilin antibodies in viral and toxin induced Choroidal and Retinal Neovascularization models can be tested as described in Hans et al., (2010) Prog Retin Eye Res.; 29(6): 500-519. Endponts for such studies include Electroretinography and fundus imaging, Optical coherence tomography, as well as histopathology.

Example 20: Characterization of the Therapeutic use of Sortilin Antibodies and/or Sortilin bispecific, Antibodies in a Model of Infection The therapeutic utility of agonistic anti-Sortilin and/or Sortilin bispecific antibodies is tested in a model of infection. For example, *Listeria monocytogenes* or other infection in normal mice or Progranulin heterozygous mice can be used, as previously described (e.g., Yin, F et al., (2009) J. Exp. Med, 207, 117-128).

Example 21: Characterization of the Therapeutic use of Sortilin Antibodies and/or Sortilin Bispecific Antibodies in a Model of Inflammatory Diseases and Bone Pathology The therapeutic utility of anti-Sortilin and/or Sortilin Bispecific antibodies is tested in a model of inflammatory diseases. For example rheumatoid arforitis or in an established model of another inflammatory disease (Mizoguchi (2012) Prog Mol Biol Transl Sci., 105:263-320; and Asquith et al., (2009) Eur 3 Immunol. 39:2040-4). Alternatively, anti-Sortilin and/or Sortilin Bispecific antibodies are tested in a model of intervertebral disc (IVD) degeneration (Zhao, P Y et al., (2015). SCIENTIFIC REPORTS. 5: 9102).

Example 22: Screening for Anti-Sortilin Antibodies and/or Sortilin Bispecific Antibodies that Promote Survival of Osteoclasts, Microglia, and/or Neurons Murine Bone Marrow precursor cells are obtained by flushing tibial and femoral marrow cells with cold PBS. After one wash with PBS, erythrocytes are lysed using ACK Lysing Buffer (Lonza), washed twice with PBS and suspended at $0.5 \times 10^6$ cells/ml in complete RPMI media (10% FCS, Pen/Strep, Gln, neAA) with the indicated amounts of 50 ng/ml M-CSF to make macrophages or 10 ng/ml GM-CSF. For M2-type macrophages, 10 ng/ml IL-4 is added to the cultured cells. For M1-type macrophages, 50 ng/ml IFN-γ is added. In some experiment LPS or zymosan is added to the cell culture at day 5, at a concentration of 1 µg/ml-0.01 ng/ml. Recombinant cytokines were purchased by Peprotech. To analyze viability of BM derived macrophages, cells of the indicated genotype are prepared as above and cultured in graded concentrations of MCSF. Cells are either plated at $10^5/200$ µl in a 96-well plate (for viability analysis using a luciferase based-assay) or at $0.5 \times 10^6/1$ ml in a 6-well plate (for Tripan Blue exclusion cell count) in non-tissue culture treated plates. Media containing fresh M-CSF is added at day 3. At the indicated time points cells are gently detached from the plates with 3 mM EDTA and counted using a Burker chamber. In some experiments cells are also stained for FACS analysis using CD11b antibody and DAPI. Alternatively, cells are directly incubated with ToxGlo reagent (Promega) and luciferase activity is determined. In some experiments MCSF is withdrawn or not from the culture media at day 5 and cell viability is analyzed 36 hours later by FACS.

Mature osteoclast cell cultures are differentiated in 24-well dishes with RANKL and M-CSF. After 4 days, complete medium is substituted with serum-free medium to induce apoptosis. Cells are treated with RANKL, PBS, and an anti-Sortilin and/or Sortilin Bispecific antibody, or an isotype-matched control antibody, during the overnight serum starvation. Cells are fixed in 1% paraformaldehyde and stained with a TUNEL-based kit (Millipore Corporation) according to manufacturer's instructions. Apoptotic nuclei are counted with a Nikon TE2000-E microscope with 20× magnification. Results are expressed as the percentage of apoptotic cells relative to the total number of cells in six randomly selected fields of the two wells, as described (e.g., Peng et al., (2010) Sci Signal, 3(122): ra38). Similar assays are performed with primary microglial Example 23: Production, Identification, and Characterization of Affinity-matured Anti-Sortilin Antibodies Materials and Methods
Sortilin Antibody Screen The anti-Sortilin antibodies S-2, S-15, S-22, S-60 and S-82 (termed "parent" antibodies) were affinity-matured. Briefly, diversified antibody libraries were created in yeast for each of the starting parent antibodies. The diversity was created by utilizing standard molecular cloning techniques to combine the parental heavy chain CDR-H3 and light chain (LC) with pre-existing genetic diversity in the CDR-H1 and CDR-H2 regions of the heavy chain (HC) (termed "H1/H2" optimization). This resulted in six libraries of roughly $10^8$ in size that were ready for selection to enrich for antibodies with improved affinity. Selection pressures used for screening the libraries included human and mouse Sortilin antigen equilibrium titration, parental antibody Fab competition kinetics, and the use of polyspecificity reagent deselection (as described, for example, in WO 2014/179363; Xu et al., Protein Eng Des Sel, Vol. 26(10), pp. 663-670). FACS flow cytometry was then employed to visualize and select antibodies, using standard techniques (see, e.g., Chao et al. Nature Protocols, 2006). The desired population was then carried forward into additional selection rounds. After 6 rounds of enrichment, yeast were plated out in order to obtain single antibody isolates, which were then produced and characterized as described in Example 1. Fifty affinity-improved antibodies from each of the six starting parental antibodies were thus obtained.

Three parental antibody clones were chosen for a second round of affinity maturation: 1) S-60, as the first round of affinity maturation did not yield any clones with significantly improved affinity; 2) affinity matured antibody clone S-15-6; and 3) affinity matured antibody clone S-15-10. The affinity matured cloned were chosen for a second round of affinity maturation, as the differences in affinity and function of these clones were not much improved in the first round of maturation. For the second round of affinity maturation, both heavy chain variable region (VH) and light chain variable region (VK) sequences were optimized, with a particular focus on CDR-H3.

Antibody IgG and Fab Production and Purification

Yeast clones were grown to saturation and then induced for 48 h at 30° C. with shaking. After induction, yeast cells were pelleted and the supernatants were harvested for purification. Immunoglobulins were purified using a Protein A column and eluted with acetic acid, pH 2.0. Fab fragments were generated by papain digestion and purified over CaptureSelect IgG-CH1 affinity matrix (LifeTechnologies).

Affinity Determination

The affinity of the anti-Sortilin antibodies was determined by measuring their $K_D$ by ForteBio and MSD. ForteBio affinity measurements were performed, at room temperature, generally as previously described (Estee et al., Mabs. 2013 March-April; 5(2):270-8). Briefly, ForteBio affinity measurements were performed by loading immunoglobulins (IgGs) on-line onto AHQ sensors. Sensors were equilibrated off-line in assay buffer for 30 min and then monitored on-line for 60 seconds for baseline establishment. For avid binding measurement, sensors with loaded IgGs were exposed to 100 nM antigen (human or mouse Sortilin Fc fusion) for 3 min, afterwards they were transferred to assay buffer for 3 min for off-rate measurement. Additional avid binding was determined by loading biotinylated Sortilin monomer on SA sensors and exposure to 100 nM IgG in solution. Monovalent binding measurements were obtained by loading human or mouse Sortilin Fc fusion antigens to AHQ sensor and followed by exposure to ~100 nM Sortilin antibody Fab. Additional monovalent measurements were made by loading biotinylated human or mouse Sortilin monomer to SA sensor followed by exposure to ~100 nM Fab in solution. Kinetics data were fit using a 1.1 binding model in the data analysis software provided by ForteBio.

For MSD-SET $K_D$ measurements, solution equilibrium titrations (SET) were performed in PBS+0.1% IgG-Free BSA (PBSF) with recombinant human or mouse Sortilin, held constant at 100 pM and incubated with 3- to 5-fold serial dilutions of antibody starting at around 50 nM. Antibodies (20 nM in PBS) were coated onto standard bind MSD-ECL plates overnight at 4° C. or at room temperature for 30 min. Plates were then blocked with 1% BSA for 30 min with shaking at 700 rpm, followed by three washes with wash buffer (PBSF+0.05% Tween 20). SET samples were applied and incubated on the plates for 150s with shaking at 700 rpm followed by one wash. Antigen captured on a plate was detected with 250 ng/ml sulfotag-labeled streptavidin in PBSF by incubation on the plate for 3 min. The plates were washed three times with wash buffer and then read on the MSD Sector Imager 2400 instrument using 1× Read Buffer T with surfactant. The percent free antigen was plotted as a function of titrated antibody in Prism and fit to a quadratic equation to extract the K. To improve throughput, liquid handling robots were used throughout MSD-SET experiments, including SET sample preparation.

Cell binding affinity measurements were performed at 4° using HEK293Tcells either transiently transfected with mouse Sortilin or stably expressing human Sortilin. Briefly, cells were harvested, washed in PBS and incubated with an amount of antibody close to the $K_D$ of the antibody ($K_D$ of parental for binding to human Sortilin: S2=1.1 nM, S15=3.3 M, S22=2.40 nM, S60=1.0 nM, S82=1.4 nM; Kd for binding to mouse Sortilin: S2=6.6 nM, S15=6.4 nM, S22=5.0 nM). Antibodies were diluted in FACS buffer (PBS+2% FBS+ 0.01% NaAzide). After incubation on ice for 1 h, cells were washed three times in FACS buffer and incubated with anti-human PE conjugated secondary antibody (BD Biosciences, 1:100 dilution) for 30 min on ice. Then cells were washed twice in 200 ul FACS buffer, and subsequently analyzed on a FACS Canto or iQE FACS screening instrument (Intellicyt Corp). The top three antibodies with increased binding to both human and mouse Sortilin (measured as median fluorescent intensity of PE) were selected for further analysis.

For determination of apparent affinity to cell-expressed Sortilin, antibodies were added to cells in a titration from 0.16-40 nM for human Sortilin and 0.39-50 nM for mouse Sortilin, and their binding $K_D$'s were determined by non-linear curve fitting (modified OneSiteTotal, Graph Pad Prism).

Sortilin downregulation in U-251 and N2A cells, Progranulin (PGRN) blocking on cells, and PGRN secretion by U-251 cells was performed as described in Example 5.

Results

Anti-Sortilin Antibody Selection

Affinity-matured anti-Sortilin antibody clones which showed improved affinity compared to the respective parental antibody were characterized further. After initial screening of all affinity-matured antibody clones, clones for each parental antibody were selected for further analysis.

Antibody Heavy Chain and Light Chain Variable Domain Sequences

Using standard techniques, the amino acid sequences encoding the heavy chain variable and the light chain variable domains of the selected affinity-matured antibody clones were determined. The EU or Kabat CDR sequences of the S-2 antibody variants are set forth in Table 11, the S-15 antibody variants are set forth in Table 12, the S-22 antibody variants are set forth in Table 13, the S-60 antibody variants are set forth in Table 14, and the S-S2 antibody variants are set forth in Table 15.

TABLE 11

Kabat CDR sequences of anti-Sortilin antibody S-2 variants

| Antibody | CDR L1 | CDR L2 | CDR L3 | CDR H1 | CDR H2 | CDR H3 |
|---|---|---|---|---|---|---|
| S-2 variants | RASQSISSYLN (SEQ ID NO: 7) | AASSLQS (SEQ ID NO: 27) | QQSDVSPIT (SEQ ID NO: 42) | YTFX$_1$ X$_2$ YX$_3$MX$_4$<br>X$_1$ is T, G, V, P, L, F, A or r<br>X$_2$ is G, A, or S<br>X$_3$ is Y, M, or L<br>X$_4$ is H or W<br>(SEQ ID NO: 480) | X$_1$X$_2$X$_3$PX$_4$X$_5$GX$_6$TX$_7$ YAQKFQG<br>X$_1$ is W, I, or G<br>X$_2$ is I, V, or T<br>X$_3$ is N, G, or L<br>X$_4$ is N, S, V, or M<br>X$_5$ is S, G, W, or Q<br>X$_6$ is G, F, A, Y, s, N, or R<br>X$_7$ is N, R, S, or M<br>(SEQ ID NO: 481) | ARGKRSSGWYEGYGMDV (SEQ ID NO: 180) |
| S-2-1 | RASQSISSYLN (SEQ ID NO: 7) | AASSLQS (SEQ ID NO: 27) | QQSDVSPIT (SEQ ID NO: 42) | YTFGAYYMH (SEQ ID NO: 482) | WINPNSGFTRYAQKFQG (SEQ ID NO: 493) | ARGKRSSGWYEGYGMDV (SEQ ID NO: 180) |
| S-2-2 | RASQSISSYLN (SEQ ID NO: 7) | AASSLQS (SEQ ID NO: 27) | QQSDVSPIT (SEQ ID NO: 42) | YTFVAYYMH (SEQ ID NO: 483) | WINPNSGATRYAQKFQG (SEQ ID NO: 494) | ARGKRSSGWYEGYGMDV (SEQ ID NO: 180) |
| S-2-3 | RASQSISSYLN (SEQ ID NO: 7) | AASSLQS (SEQ ID NO: 27) | QQSDVSPIT (SEQ ID NO: 42) | YTFGAYYMH (SEQ ID NO: 482) | WVNPNSGGTRYAQKFQG (SEQ ID NO: 495) | ARGKRSSGWYEGYGMDV (SEQ ID NO: 180) |
| S-2-4 | RASQSISSYLN (SEQ ID NO: 7) | AASSLQS (SEQ ID NO: 27) | QQSDVSPIT (SEQ ID NO: 42) | YTFTSYMMH (SEQ ID NO: 484) | IIGPSGGYTSYAQKFQG (SEQ ID NO: 496) | ARGKRSSGWYEGYGMDV (SEQ ID NO: 180) |
| S-2-5 | RASQSISSYLN (SEQ ID NO: 7) | AASSLQS (SEQ ID NO: 27) | QQSDVSPIT (SEQ ID NO: 42) | YTFPGYLMH (SEQ ID NO: 485) | WINFVSGSTNYAQKFQG (SEQ ID NO: 497) | ARGKRSSGWYEGYGMDV (SEQ ID NO: 180) |
| S-2-6 | RASQSISSYLN (SEQ ID NO: 7) | AASSLQS (SEQ ID NO: 27) | QQSDVSPIT (SEQ ID NO: 42) | YTFGAYYMH (SEQ ID NO: 482) | WVNPNSGGTNYAQKFQG (SEQ ID NO: 498) | ARGKRSSGWYEGYGMDV (SEQ ID NO: 180) |
| S-2-7 | RASQSISSYLN (SEQ ID NO: 7) | AASSLQS (SEQ ID NO: 27) | QQSDVSPIT (SEQ ID NO: 42) | YTFLAYYMH (SEQ ID NO: 486) | WINPSGGTRYAQKFQG (SEQ ID NO: 499) | ARGKRSSGWYEGYGMDV (SEQ ID NO: 180) |
| S-2-8 | RASQSISSYLN (SEQ ID NO: 7) | AASSLQS (SEQ ID NO: 27) | QQSDVSPIT (SEQ ID NO: 42) | YTFFSYYMH (SEQ ID NO: 486) | WINPSGGNTRYAQKFQG (SEQ ID NO: 500) | ARGKRSSGWYEGYGMDV (SEQ ID NO: 180) |
| S-2-9 | RASQSISSYLN (SEQ ID NO: 7) | AASSLQS (SEQ ID NO: 27) | QQSDVSPIT (SEQ ID NO: 42) | YFTFAYLMH (SEQ ID NO: 486) | WINPSGGSTSYAQKFQG (SEQ ID NO: 501) | ARGKRSSGWYEGYGMDV (SEQ ID NO: 180) |

TABLE 11-continued

Kabat CDR sequences of anti-Sortilin antibody S-2 variants

| Antibody | CDR L1 | CDR L2 | CDR L3 | CDR H1 | CDR H2 | CDR H3 |
| --- | --- | --- | --- | --- | --- | --- |
| S-2-10 | RASQSISSYLN (SEQ ID NO: 7) | AASSLQS (SEQ ID NO: 27) | QQSDVSPIT (SEQ ID NO: 42) | YRFASYYMH (SEQ ID NO: 489) | GILPSGGRTSYAQKFQG (SEQ ID NO: 502) | ARGKRSSGWYEGYGMDV (SEQ ID NO: 180) |
| S-2-11 | RASQSISSYLN (SEQ ID NO: 7) | AASSLQS (SEQ ID NO: 27) | QQSDVSPIT (SEQ ID NO: 42) | YTFLAYYMH (SEQ ID NO: 486) | WINPSWGSTSYAQKRQG (SEQ ID NO: 503) | ARGKRSSGWYEGYGMDV (SEQ ID NO: 180) |
| S-2-12 | RASQSISSYLN (SEQ ID NO: 7) | AASSLQS (SEQ ID NO: 27) | QQSDVSPIT (SEQ ID NO: 42) | YTFTAYYMH (SEQ ID NO: 490) | WTNPNSGGTMYAQKFQG (SEQ ID NO: 504) | ARGKRSSGWYEGYGMDV (SEQ ID NO: 180) |
| S-2-13 | RASQSISSYLN (SEQ ID NO: 7) | AASSLQS (SEQ ID NO: 27) | QQSDVSPIT (SEQ ID NO: 42) | YTFTFGYYMH (SEQ ID NO: 126) | WTNPNSGGTRYAQKFQG (SEQ ID NO: 505) | ARGKRSSGWYEGYGMDV (SEQ ID NO: 180) |
| S-2-14 | RASQSISSYLN (SEQ ID NO: 7) | AASSLQS (SEQ ID NO: 27) | QQSDVSPIT (SEQ ID NO: 42) | YTFGGYLMH (SEQ ID NO: 491) | WINPMSGGTRYAQKFQG (SEQ ID NO: 506) | ARGKRSSGWYEGYGMDV (SEQ ID NO: 180) |
| S-2-15 | RASQSISSYLN (SEQ ID NO: 7) | AASSLQS (SEQ ID NO: 27) | QQSDVSPIT (SEQ ID NO: 42) | YTFRAYYMH (SEQ ID NO: 492) | WINPSQSTSYAQKFQG (SEQ ID NO: 507) | ARGKRSSGWYEGYGMDV (SEQ ID NO: 180) |

TABLE 12

Kabat CDR sequences of anti-Sortilin antibody S-15 variants

| Antibody | CDR L1 | CDR L2 | CDR L3 | CDR H1 | CDR H1 | CDR H1 |
|---|---|---|---|---|---|---|
| S-15 variants | RASQSX$_1$X$_2$SNLA<br>X$_1$ is V or I<br>X$_2$ is S or G<br>(SEQ ID NO: 506) | GASTRAT<br>(SEQ ID NO: 29) | QQARLGPWT<br>(SEQ ID NO: 55) | YTX$_1$X$_2$X$_3$X$_4$X$_5$X$_6$S<br>X$_1$ is F or L<br>X$_2$ is T or A<br>X$_3$ is S or K<br>X$_4$ is Y, T, R, L, T, G, Q, or H<br>X$_5$ is Y, T, or L<br>X$_6$ is M or I<br>(SEQ ID NO: 509) | X$_1$INPX$_2$GGX$_3$X$_4$SYZX$_5$X$_6$FX$_7$G<br>X$_1$ is I or V<br>X$_2$ is S, W, Y, V, F, L, or I<br>X$_3$ is S or T<br>X$_4$ is T or A<br>X$_5$ is Q or R<br>X$_6$ is Y, T, or L<br>X$_7$ is Q or R<br>(SEQ ID NO: 510) | X$_1$RDPX$_2$GX$_3$X$_4$X$_5$X$_6$X$_7$PX$_8$X$_9$RX$_{10}$X$_{11}$X$_{12}$GX$_{13}$DV<br>X$_1$ is A, V, or T<br>X$_2$ is S, F, or G<br>X$_3$ is I or A<br>X$_4$ is A or G<br>X$_5$ is A, L, or V<br>X$_6$ is A, L, or P<br>X$_7$ is G, F, or Y<br>X$_8$ is A, G, or F<br>X$_9$ is S, G, or A<br>X$_{10}$ is Y, G, P, H or S<br>X$_{11}$ is Y or N<br>X$_{12}$ is Y, L, Q, or R<br>X$_{13}$ is M or L<br>(SEQ ID NO: 511) |
| S-15-1 | RASQSVSSNLA<br>(SEQ ID NO: 9) | GASTRAT<br>(SEQ ID NO: 29) | QQARLGPWT<br>(SEQ ID NO: 55) | YTFTSTYMS<br>(SEQ ID NO: 513) | IINPWGGTTSYAQKFQG<br>(SEQ ID NO: 525) | ARDPSGIAAAGPASRYYY GMDV<br>(SEQ ID NO: 190) |
| S-15-2 | RASQSVSSNLA<br>(SEQ ID NO: 9) | GASTRAT<br>(SEQ ID NO: 29) | QQARLGPWT<br>(SEQ ID NO: 55) | YTFTSYYMS<br>(SEQ ID NO: 514) | IINPYGGSTSYAQKFQG<br>(SEQ ID NO: 526) | ARDPSGIAAAGPASRYYY GMDV<br>(SEQ ID NO: 190) |
| S-15-3 | RASQSVSSNLA<br>(SEQ ID NO: 9) | GASTRAT<br>(SEQ ID NO: 29) | QQARLGPWT<br>(SEQ ID NO: 55) | YTFTSTYMS<br>(SEQ ID NO: 513) | IINPYGGSTSYAQKFQG<br>(SEQ ID NO: 526) | ARDPSGIAAAGPASRYYY GMDV<br>(SEQ ID NO: 190) |
| S-15-4 | RASQSVSSNLA<br>(SEQ ID NO: 9) | GASTRAT<br>(SEQ ID NO: 29) | QQARLGPWT<br>(SEQ ID NO: 55) | YTFTSYLMS<br>(SEQ ID NO: 515) | IINPYGGSTSYAQKFQG<br>(SEQ ID NO: 527) | ARDPSGIAAAGPASRYYY GMDV<br>(SEQ ID NO: 190) |
| S-15-5 | RASQSVSSNLA<br>(SEQ ID NO: 9) | GASTRAT<br>(SEQ ID NO: 29) | QQARLGPWT<br>(SEQ ID NO: 55) | YTFTSYLMS<br>(SEQ ID NO: 515) | VINPFGGSTSYAQKFQG<br>(SEQ ID NO: 528) | ARDPSGIAAAGPASRYYY GMDV<br>(SEQ ID NO: 190) |
| S-15-6 | RASQSVSSNLA<br>(SEQ ID NO: 9) | GASTRAT<br>(SEQ ID NO: 29) | QQARLGPWT<br>(SEQ ID NO: 55) | YTFTSRYMS<br>(SEQ ID NO: 516) | IINPVGGSTSYAQKFQG<br>(SEQ ID NO: 527) | ARDPSGIAAAGPASRYYY GMDV<br>(SEQ ID NO: 190) |
| S-15-6-1 | RASQSVSSNLA<br>(SEQ ID NO: 9) | GASTRAT<br>(SEQ ID NO: 29) | QQARLGPWT<br>(SEQ ID NO: 55) | YTFASRYMS<br>(SEQ ID NO: 517) | IINPVGGSTSYAQKFQG<br>(SEQ ID NO: 527) | ARDPSGIAAAGPAGRYYY GLDV<br>(SEQ ID NO: 540) |

TABLE 12-continued

Kabat CDR sequences of anti-Sortilin antibody S-15 variants

| Antibody | CDR L1 | CDR L2 | CDR L3 | CDR H1 | CDR H1 | CDR H1 |
|---|---|---|---|---|---|---|
| S-15-6-2 | RASQSVSSNLA (SEQ ID NO: 9) | GASTRAT (SEQ ID NO: 29) | QQARLGPWT (SEQ ID NO: 55) | YTFTSRYMS (SEQ ID NO: 516) | IINPVGGSTSYAQKFQG (SEQ ID NO: 527) | ARDPSGIAAAGPAGRYYY GMDV (SEQ ID NO: 541) |
| S-15-6-3 | RASQSVSSNLA (SEQ ID NO: 9) | GASTRAT (SEQ ID NO: 29) | QQARLGPWT (SEQ ID NO: 55) | YTFTSRYMS (SEQ ID NO: 516) | IINPVGGSTSYAQKFQG (SEQ ID NO: 527) | ARDPSGIAAASPASRHYY GMDV (SEQ ID NO: 542) |
| S-15-6-4 | RASQSVSSNLA (SEQ ID NO: 9) | GASTRAT (SEQ ID NO: 29) | QQARLGPWT (SEQ ID NO: 55) | YTLTSRYMS (SEQ ID NO: 518) | IINPVGGSTSYAQKFRG (SEQ ID NO: 529) | ARDPSGIAAAGPASRYYY GMDV (SEQ ID NO: 190) |
| S-15-6-5 | RASQSVSSNLA (SEQ ID NO: 9) | GASTRAT (SEQ ID NO: 29) | QQARLGPWT (SEQ ID NO: 55) | YTFTSRYMS (SEQ ID NO: 516) | IINPVGGSASYARKFQG (SEQ ID NO: 530) | ARDPSGIAAAGPASRYYY GMDV (SEQ ID NO: 190) |
| S-15-6-6 | RASQSVGSNLA (SEQ ID NO: 512) | GASTRAT (SEQ ID NO: 29) | QQARLGPWT (SEQ ID NO: 55) | YTFTSRYMS (SEQ ID NO: 516) | IINPVGGSTSYAQKFQG (SEQ ID NO: 527) | ARDPSGIAAAGPASRYYY GMDV (SEQ ID NO: 190) |
| S-15-6-7 | RASQSVSSNLA (SEQ ID NO: 9) | GASTRAT (SEQ ID NO: 29) | QQARLGPWT (SEQ ID NO: 55) | YTFTSRYMS (SEQ ID NO: 516) | IINPVGGSTSYAQKFQG (SEQ ID NO: 527) | ARDPSGIAAPGPAGRYYY GMDV (SEQ ID NO: 543) |
| S-15-6-8 | RASQSVSSNLA (SEQ ID NO: 9) | GASTRAT (SEQ ID NO: 29) | QQARLGPWT (SEQ ID NO: 55) | YTFTSRYMS (SEQ ID NO: 516) | IINPVGGSTSYAQKFQG (SEQ ID NO: 527) | ARDPSGIALAGPAGRYYY GMDV (SEQ ID NO: 544) |
| S-15-6-9 | RASQSVSSNLA (SEQ ID NO: 9) | GASTRAT (SEQ ID NO: 29) | QQARLGPWT (SEQ ID NO: 55) | YTFTSRYMS (SEQ ID NO: 516) | IINPVGGSTSYAQKFQG (SEQ ID NO: 527) | ARDPSGIALAGPASRGYY GMDV (SEQ ID NO: 545) |
| S-15-6-10 | RASQSVSSNLA (SEQ ID NO: 9) | GASTRAT (SEQ ID NO: 29) | QQARLGPWT (SEQ ID NO: 55) | YTFTSRYMS (SEQ ID NO: 516) | IINPVGGSTSYAQKFQG (SEQ ID NO: 527) | ARDPSGIALAGPASRPYY GMDV (SEQ ID NO: 546) |
| S-15-6-11 | RASQSVSSNLA (SEQ ID NO: 9) | GASTRAT (SEQ ID NO: 29) | QQARLGPWT (SEQ ID NO: 55) | YTFTSRYMS (SEQ ID NO: 516) | IINPVGGSTSYAQKFQG (SEQ ID NO: 527) | ARDPSGIALAGPASRYYL GMDV (SEQ ID NO: 547) |
| S-15-6-12 | RASQSVSSNLA (SEQ ID NO: 9) | GASTRAT (SEQ ID NO: 29) | QQARLGPWT (SEQ ID NO: 55) | YTFTSRYMS (SEQ ID NO: 516) | IINPVGGSTSYAQKFQG (SEQ ID NO: 527) | ARDPSGIALAGPGSRYYR GMDV (SEQ ID NO: 548) |
| S-15-6-13 | RASQSVSSNLA (SEQ ID NO: 9) | GASTRAT (SEQ ID NO: 29) | QQARLGPWT (SEQ ID NO: 55) | YTFTSRYMS (SEQ ID NO: 516) | IINPVGGSTSYAQKFQG (SEQ ID NO: 527) | ARDPSGIAVAGPASRYYY GMDV (SEQ ID NO: 549) |

TABLE 12-continued

Kabat CDR sequences of anti-Sortilin antibody S-15 variants

| Antibody | CDR L1 | CDR L2 | CDR L3 | CDR H1 | CDR H1 | CDR H1 |
|---|---|---|---|---|---|---|
| S-15-7 | RASQSVSSNLA (SEQ ID NO: 9) | GASTRAT (SEQ ID NO: 29) | QQARLGPWT (SEQ ID NO: 55) | YTFTSYLMS (SEQ ID NO: 515) | IINPLGGSTSYAQKFQG (SEQ ID NO: 531) | ARDPSGIAAAGPASRYYY GMDV (SEQ ID NO: 190) |
| S-15-8 | RASQSVSSNLA (SEQ ID NO: 9) | GASTRAT (SEQ ID NO: 29) | QQARLGPWT (SEQ ID NO: 55) | YTFTSLYIS (SEQ ID NO: 519) | VINPVGGSTSYAQKRQG (SEQ ID NO: 532) | ARDPSGIAAAGPASRYYY GMDV (SEQ ID NO: 190) |
| S-15-9 | RASQSVSSNLA (SEQ ID NO: 9) | GASTRAT (SEQ ID NO: 29) | QQARLGPWT (SEQ ID NO: 55) | YTFTSRYMS (SEQ ID NO: 516) | IINPLGGSTSYAQKRQG (SEQ ID NO: 531) | ARDPSGIAAAGPASRYYY GMDV (SEQ ID NO: 190) |
| S-15-10 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYAQKFQG (SEQ ID NO: 533) | ARDPSGIAAAGPASRYYY GMDV (SEQ ID NO: 190) |
| S-15-10-2 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYAQKFRG (SEQ ID NO: 534) | ARDPSGIAAAGPASRYYY GMDV (SEQ ID NO: 190) |
| S-15-10-3 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSASYAQKFRG (SEQ ID NO: 535) | ARDPSGIAAAGPAGRYYY GMDV (SEQ ID NO: 541) |
| S-15-10-4 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYAQKFRG (SEQ ID NO: 534) | TRDPSGIAAAGPASRYYY GMDV (SEQ ID NO: 551) |
| S-15-10-5 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYAQKFQG (SEQ ID NO: 533) | ARDPSGIAAAGPAGRYYY GMDV (SEQ ID NO: 541) |
| S-15-10-6 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYAQKFQG (SEQ ID NO: 533) | ARDPSGIALAGPASRYY GMDV (SEQ ID NO: 552) |
| S-15-10-7 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYAQKFQG (SEQ ID NO: 533) | ARDPSGIALAGPASRGYQ GMDV (SEQ ID NO: 553) |
| S-15-10-8 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYAQKFQG (SEQ ID NO: 533) | ARDPSGIALAFPASRYYY GMDV (SEQ ID NO: 554) |
| S-15-10-9 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYAQKFQG (SEQ ID NO: 533) | ARDPSGIALAGPASRGYY GMDV (SEQ ID NO: 545) |

TABLE 12-continued

Kabat CDR sequences of anti-Sortilin antibody S-15 variants

| Antibody | CDR L1 | CDR L2 | CDR L3 | CDR H1 | CDR H1 | CDR H1 |
|---|---|---|---|---|---|---|
| S-15-10-10 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYAQKFQG (SEQ ID NO: 533) | ARDPSGIAAAGPAARHYY GMDV (SEQ ID NO: 555) |
| S-15-10-11 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYAQKFQG (SEQ ID NO: 533) | ARDPFGIALAGPASRYYY GMDV (SEQ ID NO: 556) |
| S-15-10-12 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYAQKFQG (SEQ ID NO: 533) | ARDPSGIAAAFPAGRYYY GMDV (SEQ ID NO: 557) |
| S-15-10-13 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYARKFQG (SEQ ID NO: 536) | ARDPFGIALAGPASRYYY GMDV (SEQ ID NO: 556) |
| S-15-10-14 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINIGGSISYAQKRQG (SEQ ID NO: 537) | ARDPSGIAAAGPASRYYY GMDV (SEQ ID NO: 190) |
| S-15-10-15 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYAQKFQG (SEQ ID NO: 533) | ARDPGGAAAAGPASRYYY GMDV (SEQ ID NO: 559) |
| S-15-10-16 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYAQKFQG (SEQ ID NO: 533) | ARDPSGIAAAYPASRYYR GMDV (SEQ ID NO: 560) |
| S-15-10-17 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IVNPIGGSTSYAQRFQG (SEQ ID NO: 538) | ARDPSGIGLADPFSRYYY GMDV (SEQ ID NO: 561) |
| S-15-10-18 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYAQKFQG (SEQ ID NO: 533) | ARDPSGIALAGPASRSYY GMDV (SEQ ID NO: 562) |
| S-15-10-19 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYAQKFQG (SEQ ID NO: 533) | ARDPSGIAAAFPASRYYY GMDV (SEQ ID NO: 563) |
| S-15-10-20 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYAQKFQG (SEQ ID NO: 533) | ARDPSGIALLGPASRYYY GMDV (SEQ ID NO: 564) |
| S-15-10-21 | RASQSVSSNLA (SEQ ID NO: 9) | GASTRAT (SEQ ID NO: 29) | QQARLGPWT (SEQ ID NO: 55) | YTFTKYMS (SEQ ID NO: 520) | IINPIGGSTSYAQKFQG (SEQ ID NO: 533) | ARDPSGIAAAGPAGRYYY GMDV (SEQ ID NO: 541) |

TABLE 12-continued

Kabat CDR sequences of anti-Sortilin antibody S-15 variants

| Antibody | CDR L1 | CDR L2 | CDR L3 | CDR H1 | CDR H1 | CDR H1 |
|---|---|---|---|---|---|---|
| S-15-11 | RASQSVSSNLA (SEQ ID NO: 9) | GASTRAT (SEQ ID NO: 29) | QQARLGPWT (SEQ ID NO: 55) | YTFTSTYMS (SEQ ID NO: 513) | IINPVGGSTSYAQKFQG (SEQ ID NO: 527) | ARDPSGIAAAGPASRYYY GMDV (SEQ ID NO: 190) |
| S-15-12 | RASQSVSSNLA (SEQ ID NO: 9) | GASTRAT (SEQ ID NO: 29) | QQARLGPWT (SEQ ID NO: 55) | YTFTSLYMS (SEQ ID NO: 521) | IINPVGGSTSYAQKFQG (SEQ ID NO: 527) | ARDPSGIAAAGPASRYYY GMDV (SEQ ID NO: 190) |
| S-15-13 | RASQSVSSNLA (SEQ ID NO: 9) | GASTRAT (SEQ ID NO: 29) | QQARLGPWT (SEQ ID NO: 55) | YTFTSGYMS (SEQ ID NO: 522) | IINPYGGTTSYAQKFQG (SEQ ID NO: 539) | ARDPSGIAAAGPASRYYY GMDV (SEQ ID NO: 190) |
| S-15-14 | RASQSVSSNLA (SEQ ID NO: 9) | GASTRAT (SEQ ID NO: 29) | QQARLGPWT (SEQ ID NO: 55) | YTFTSQYMS (SEQ ID NO: 523) | IINPYGGSTSYAQKFQG (SEQ ID NO: 526) | ARDPSGIAAAGPASRYYY GMDV (SEQ ID NO: 190) |
| S-15-15 | RASQSVSSNLA (SEQ ID NO: 9) | GASTRAT (SEQ ID NO: 29) | QQARLGPWT (SEQ ID NO: 55) | YTFTSQYMS (SEQ ID NO: 523) | IINPVGGSTSYAQKFQG (SEQ ID NO: 527) | ARDPSGIAAAGPASRYYY GMDV (SEQ ID NO: 190) |
| S-15-16 | RASQSVSSNLA (SEQ ID NO: 9) | GASTRAT (SEQ ID NO: 29) | QQARLGPWT (SEQ ID NO: 55) | YTFTSHYMS (SEQ ID NO: 524) | IINPIGGSTSYAQKFQG (SEQ ID NO: 533) | ARDPSGIAAAGPASRYYY GMDV (SEQ ID NO: 190) |

TABLE 13

Kabat CDR sequences of anti-Sotilin antibody s-22 variants

| Antibody | CDR L1 | CDR L2 | CDR L3 | CDR H1 | CDR H2 | CDR H3 |
|---|---|---|---|---|---|---|
| S-22 variants | RASQSISSWLA (SEQ ID NO: 8) | KASSLES (SEQ ID NO: 28) | QQADGHIT (SEQ ID NO: 62) | $X_1TFX_2X_3YAX_4X_5$<br>$X_1$ if G or Y<br>$X_2$ is S, R, G, or T<br>$X_3$ is S, G, or N<br>$X_4$ is I or M<br>$X_5$ is S or A<br>(SEQ ID NO: 565) | $GIX_1PX_2X_3GX_4AX_5YAQKFQG$<br>$X_1$ is I or V<br>$X_2$ is I, R, G, A, S, T or Q<br>$X_3$ is F or G<br>$X_4$ is T, R, or W<br>$X_5$ is S, N, Q, or W<br>(SEQ ID NO: 566) | ARQGRKTGYYYYYGMDV (SEQ ID NO: 197) |
| S-22-2 | RASQSISSWLA (SEQ ID NO: 8) | KASSLES (SEQ ID NO: 28) | QQADGHIT (SEQ ID NO: 62) | GTFSSYAIS (SEQ ID NO: 130) | GIIPGFGTAQYAQKFQG (SEQ ID NO: 572) | ARQGRKTGYYYYYGMDV (SEQ ID NO: 197) |
| S-22-3 | RASQSISSWLA (SEQ ID NO: 8) | KASSLES (SEQ ID NO: 28) | QQADGHIT (SEQ ID NO: 62) | GTFRSYAIS (SEQ ID NO: 567) | GIIPGFGTAWYAQKFQG (SEQ ID NO: 573) | ARQGRKTGYYYYYGMDV (SEQ ID NO: 197) |
| S-22-4 | RASQSISSWLA (SEQ ID NO: 8) | KASSLES (SEQ ID NO: 28) | QQADGHIT (SEQ ID NO: 62) | GTFGSYAIS (SEQ ID NO: 568) | GIIPAFGTAWYAQKFQG (SEQ ID NO: 574) | ARQGRKTGYYYYYGMDV (SEQ ID NO: 197) |
| S-22-5 | RASQSISSWLA (SEQ ID NO: 8) | KASSLES (SEQ ID NO: 28) | QQADGHIT (SEQ ID NO: 62) | GTFSSYAIS (SEQ ID NO: 130) | GIIPSFGTASYAQKFQG (SEQ ID NO: 575) | ARQGRKTGYYYYYGMDV (SEQ ID NO: 197) |
| S-22-6 | RASQSISSWLA (SEQ ID NO: 8) | KASSLES (SEQ ID NO: 28) | QQADGHIT (SEQ ID NO: 62) | YFTFGYAMA (SEQ ID NO: 569) | GIIPTFGTAWYAQKFQG (SEQ ID NO: 576) | ARQGRKTGYYYYYGMDV (SEQ ID NO: 197) |
| S-22-7 | RASQSISSWLA (SEQ ID NO: 8) | KASSLES (SEQ ID NO: 28) | QQADGHIT (SEQ ID NO: 62) | GTFSSYAIS (SEQ ID NO: 130) | GIIPGFGRANYQAKFQG (SEQ ID NO: 577) | ARQGRKTGYYYYYGMDV (SEQ ID NO: 197) |
| S-22-8 | RASQSISSWLA (SEQ ID NO: 8) | KASSLES (SEQ ID NO: 28) | QQADGHIT (SEQ ID NO: 62) | GTFGSYAIS (SEQ ID NO: 568) | GIIPQFGTANYAQKFQG (SEQ ID NO: 578) | ARQGRKTGYYYYYGMDV (SEQ ID NO: 197) |
| S-22-9 | RASQSISSWLA (SEQ ID NO: 8) | KASSLES (SEQ ID NO: 28) | QQADGHIT (SEQ ID NO: 62) | GTFRNYAIS (SEQ ID NO: 570) | GIIPIGGWANYAQKRQG (SEQ ID NO: 579) | ARQGRKTGYYYYYGMDV (SEQ ID NO: 197) |
| S-22-9 | RASQSISSWLA (SEQ ID NO: 8) | KASSLES (SEQ ID NO: 28) | QQADGHIT (SEQ ID NO: 62) | GTFRNYAIS (SEQ ID NO: 570) | GIIPIGGWANYAQKRQG (SEQ ID NO: 579) | ARQGRKTGYYYYYGMDV (SEQ ID NO: 197) |

TABLE 14

Kabat CDR sequences of anti-Sortilin antibody s-60 variants

| Antibody | CDR L1 | CDR L2 | CDR L3 | CDR H1 | CDR H2 | CDR H3 |
|---|---|---|---|---|---|---|
| S-60 variants | RSSQX$_1$LLX$_2$SNGYNYLD<br>X$_1$ is S or G<br>X$_2$ is H or R<br>(SEQ ID NO: 560) | LGSNRX$_1$S<br>X$_1$ is A or V<br>(SEQ ID NO: 561) | MQQQETPLT (SEQ ID NO: 100) | YSISSX$_1$X$_2$YWG<br>X$_1$ is G or V<br>X$_2$ is Y or R<br>(SEQ ID NO: 582) | X$_1$IYX$_2$SGSTYYNPSLKS<br>X$_1$ is T, S or A<br>X$_2$ is H or P<br>(SEQ ID NO: 583) | ARQGSIKQGYYGMDV (SEQ ID NO: 233) |
| S-60-2 | RSSQSLLHSNGYNYLD (SEQ ID NO: 10) | LGSNRAS (SEQ ID NO: 30) | MQQQETPLT (SEQ ID NO: 100) | YSISSVRYWG (SEQ ID NO: 587) | AIYPSGSTYYNPSLKS (SEQ ID NO: 583) | ARQGSIKQGYYGMDV (SEQ ID NO: 233) |
| S-60-3 | RSSQSLLRSNGYNYLD (SEQ ID NO: 564) | LGSNRVS (SEQ ID NO: 586) | MQQQETPLT (SEQ ID NO: 100) | YSISSGYYWG (SEQ ID NO: 142) | TIYHSGSTYYNPSLKS (SEQ ID NO: 170) | ARQGSIKQGYYGMDV (SEQ ID NO: 233) |
| S-60-4 | RSSQGLLRSNGYNYLD (SEQ ID NO: 585) | LGSNRAS (SEQ ID NO: 30) | MQQQETPLT (SEQ ID NO: 100) | YSISSGYYWG (SEQ ID NO: 142) | TIYHSGSTYYNPSLKS (SEQ ID NO: 170) | ARQGSIKQGYYGMDV (SEQ ID NO: 233) |

TABLE 14-continued

Kabat CDR sequences of anti-Sortilin antibody s-60 variants

| Antibody | CDR L1 | CDR L2 | CDR L3 | CDR H1 | CDR H2 | CDR H3 |
|---|---|---|---|---|---|---|
| S-60-5 | RSSQSLLRSNGYNYLD (SEQ ID NO: 584) | LGSNRAS (SEQ ID NO: 30) | MQQQETPLT (SEQ ID NO: 100) | YSISSGYYWG (SEQ ID NO: 142) | TIYHSGSTYYNPSLKS (SEQ ID NO: 170) | ARQGSIKQGYYGMDV (SEQ ID NO: 233) |
| S-60-6 | RSSQSLLRSNGYNYLD (SEQ ID NO: 584) | LGSNRAS (SEQ ID NO: 30) | MQQQETPLT (SEQ ID NO: 100) | YSISSGYYWG (SEQ ID NO: 142) | TIYHSGSTYYNPSLKS (SEQ ID NO: 170) | ARQGSIKQGYYGMDV (SEQ ID NO: 233) |
| S-60-7 | RSSQSLLRSNGYNYLD (SEQ ID NO: 584) | LGSNRAS (SEQ ID NO: 30) | MQQQETPLT (SEQ ID NO: 100) | YSISSGYYWG (SEQ ID NO: 142) | TIYHSGSTYYNPSLKS (SEQ ID NO: 170) | ARQGSIKQGYYGMDV (SEQ ID NO: 233) |
| S-60-8 | RSSQSLLRSNGYNYLD (SEQ ID NO: 584) | LGSNRAS (SEQ ID NO: 30) | MQQQETPLT (SEQ ID NO: 100) | YSISSGYYWG (SEQ ID NO: 142) | TIYHSGSTYYNPSLKS (SEQ ID NO: 170) | ARQGSIKQGYYGMDV (SEQ ID NO: 233) |
| S-60-9 | RSSQSLLHSNGYNYLD (SEQ ID NO: 10) | LGSNRAS (SEQ ID NO: 30) | MQQQETPLT (SEQ ID NO: 100) | YSISSGYYWG (SEQ ID NO: 142) | TIYHSGSTYYNPSLKS (SEQ ID NO: 170) | ARQGSIKQGYYGMDV (SEQ ID NO: 233) |

TABLE 15

Kabat CDR sequences of anti-Sorilin antibody s-82 variants

| Antibody | CDR L1 | CDR L2 | CDR L3 | CDR H1 | CDR H2 | CDR H3 |
|---|---|---|---|---|---|---|
| S-82 variants | RASQSVSSSYLA (SEQ ID NO: 14) | GASSRAT (SEQ ID NO: 26) | QQSHVSPWT (SEQ ID NO: 122) | $X_1$SI$X_2$S$X_3X_4$YYWG $X_1$ is G or Y $X_2$ is S, V, Y, K, or P $X_3$ is S or R $X_4$ is D or E (SEQ ID NO: 589) | $X_1$IT$X_2X_3$GST$X_4$YNPSLKS $X_1$ is S, G, Q, or L $X_2$ is Y, W, or R $X_3$ is S, R, K, or A $X_4$ is Y or V (SEQ ID NO: 590) | ARGVGSGYSYGYRYFDY (SEQ ID NO: 253) |
| S-82-1 | RASQSVSSSYLA (SEQ ID NO: 14) | GASSRAT (SEQ ID NO: 26) | QQSHVSPWT (SEQ ID NO: 122) | GSIVSSDYYWG (SEQ ID NO: 591) | GIYYRGSTYYNPSLKS (SEQ ID NO: 597) | ARGVGSGYSYGYRYFDY (SEQ ID NO: 253) |
| S-82-2 | RASQSVSSSYLA (SEQ ID NO: 14) | GASSRAT (SEQ ID NO: 26) | QQSHVSPWT (SEQ ID NO: 122) | GSISSSDYYWG (SEQ ID NO: 147) | GIYYRGSTYYNPSLKS (SEQ ID NO: 597) | ARGVGSGYSYGYRYFDY (SEQ ID NO: 253) |
| S-82-3 | RASQSVSSSYLA (SEQ ID NO: 14) | GASSRAT (SEQ ID NO: 26) | QQSHVSPWT (SEQ ID NO: 122) | GSISSSDYYWG (SEQ ID NO: 147) | QIYYKGSTYYNPSLKS (SEQ ID NO: 598) | ARGVGSGYSYGYRYFDY (SEQ ID NO: 253) |
| S-82-4 | RASQSVSSSYLA (SEQ ID NO: 14) | GASSRAT (SEQ ID NO: 26) | QQSHVSPWT (SEQ ID NO: 122) | GSIYSSDYYWG (SEQ ID NO: 592) | SIYWRGSTYYNPSLKS (SEQ ID NO: 599) | ARGVGSGYSYGYRYFDY (SEQ ID NO: 253) |
| S-82-5 | RASQSVSSSYLA (SEQ ID NO: 14) | GASSRAT (SEQ ID NO: 26) | QQSHVSPWT (SEQ ID NO: 122) | GSIKSSEYYWG (SEQ ID NO: 593) | SIYRAGSTYYNPSLKS (SEQ ID NO: 600) | ARGVGSGYSYGYRYFDY (SEQ ID NO: 253) |
| S-82-6 | RASQSVSSSYLA (SEQ ID NO: 14) | GASSRAT (SEQ ID NO: 26) | QQSHVSPWT (SEQ ID NO: 122) | QSIPS-DYYWG (SEQ ID NO: 594) | SIYYRGSTVYNPSLKS (SEQ ID NO: 601) | ARGVGSGYSYGYRYFDY (SEQ ID NO: 253) |
| S-82-7 | RASQSVSSSYLA (SEQ ID NO: 14) | GASSRAT (SEQ ID NO: 26) | QQSHVSPWT (SEQ ID NO: 122) | GSISSSEYYWG (SEQ ID NO: 595) | LIYYRGSTYYNPSLKS (SEQ ID NO: 602) | ARGVGSGYSYGYRYFDY (SEQ ID NO: 253) |
| S-82-8 | RASQSVSSSYLA (SEQ ID NO: 14) | GASSRAT (SEQ ID NO: 26) | QQSHVSPWT (SEQ ID NO: 122) | GSISSREYYWG (SEQ ID NO: 596) | SIYRSGSTYYNPSLKS (SEQ ID NO: 603) | ARGVGSGYSYGYRYFDY (SEQ ID NO: 253) |

Characterization of Affinity-Matured Anti-Sortilin Antibody Binding

Cell binding affinities for the selected affinity-matured anti-Sortilin antibodies are shown in Table 16A and 16B. In the table, "N.B." indicates no binding, "P.F." indicated poor fit, "N.D." indicated not determined, "Bt-" indicates biotinylated, "hSort" indicates human Sortilin, "msSort" indicates mouse Sortilin, and "(M)" indicates monovalent.

TABLE 16A

Affinities of top affinity matured antibody clones

| Antibody | MSD Fab $K_D$ Bt-hSort (M) | MSD Fab $K_D$ Bt-msSort (M) | Fortebio Fab $K_D$ Bt-hSort (M) | ForteBio Fab $K_D$ Bt-msSort (M) |
|---|---|---|---|---|
| S-2-1 | 2.90E−11 | 7.30E−10 | 6.14E−10 | 1.92E−09 |
| S-2-2 | 2.70E−11 | 7.90E−10 | 3.08E−10 | 2.68E−09 |
| S-2-11 | 1.10E−11 | N.D. | 2.61E−10 | 7.59E−09 |
| S-15-3 | 2.60E−10 | 1.10E−10 | 9.43E−10 | 7.69E−10 |
| S-15-6 | 2.30E−10 | 7.00E−11 | 9.84E−10 | 6.78E−10 |
| S-15-6-12 | 2.30E−11 | N.D. | 9.57E−10 | 7.65E−10 |
| S-15-10-12 | 7.60E−11 | N.D. | 1.24E−09 | 1.21E−09 |
| S-15-10-13 | 3.20E−11 | N.D. | 1.18E−09 | 1.11E−09 |
| S-15-14 | 1.90E−10 | 1.00E−10 | 1.04E−09 | 7.58E−10 |
| S-22-3 | 9.70E−11 | 1.20E−09 | 6.98E−10 | 1.43E−09 |
| S-22-7 | 9.80E−11 | 5.70E−10 | 5.08E−10 | 7.51E−10 |
| S-22-9 | 4.80E−12 | N.D. | 5.75E−10 | 3.29E−09 |
| S-60-4 | 9.40E−11 | N.D. | 2.49E−09 | N.B. |
| S-60-5 | 6.50E−11 | N.D. | 2.00E−09 | N.B. |
| S-60-6 | 9.30E−11 | N.D. | 2.28E−09 | N.B. |
| S-82-3 | 5.60E−10 | N.B. | P.F. | N.B. |
| S-82-5 | N.D. | N.B. | 3.96E−09 | N.B. |
| S-82-8 | N.D. | N.B. | P.F. | N.B. |

TABLE 16B

Affinities of top affinity matured antibody clones

| Antibody | Binding to HEK293T+ hiSort ($K_D$ in M) | Binding to HEK293T+ msSort $K_D$ in M) |
|---|---|---|
| S-2-1 | 6.91E−10 | 2.65E−09 |
| S-2-2 | 1.21E−09 | 2.27E−09 |
| S-2-11 | 3.77E−10 | 1.54E−09 |
| S-15-3 | 5.25E−09 | 1.79E−08 |
| S-15-6 | 6.74E−09 | 1.89E−08 |
| S-15-6-12 | 3.84E−09 | 6.62E−09 |
| S-15-10-12 | 4.3E−09 | 8.89E−09 |
| S-15-10-13 | 2.88E−09 | 4.07E−09 |
| S-15-14 | 5.25E−09 | 1.94E−08 |
| S-22-3 | 1.08E−09 | 3.63E−09 |
| S-22-7 | 2.05E−09 | 4.78E−09 |
| S-22-9 | 8.10E−10 | 5.12E−09 |
| S-60-4 | 7.3E−10 | N.B. |
| S-60-5 | 5.6E−10 | N.B. |
| S-60-6 | 7.8E−10 | N.B. |
| S-82-3 | 5.90E−10 | N.B. |
| S-82-5 | 3.74E−10 | N.B. |
| S-82-8 | 3.99E−10 | N.B. |

Next, affinity-matured antibodies were compared to each other and their respective parental antibody in their ability to reduce native cell surface levels of Sortilin in human U-251 and mouse N2A cells. Antibodies were added to the cells for 72 hours at varying concentrations and Sortilin levels were measured by FACS using a DyLight conjugated antibody of a different bin than the test antibody (either S-29-DyLight650 or S-30-DyLight650). Affinity-matured antibodies overall showed enhanced ability to reduce native cell surface levels of Sortilin in both human and mouse cells (FIG. 13A-13G), especially at the lowest antibody (IgG) concentration of 1.25 nM.

Figure 14:
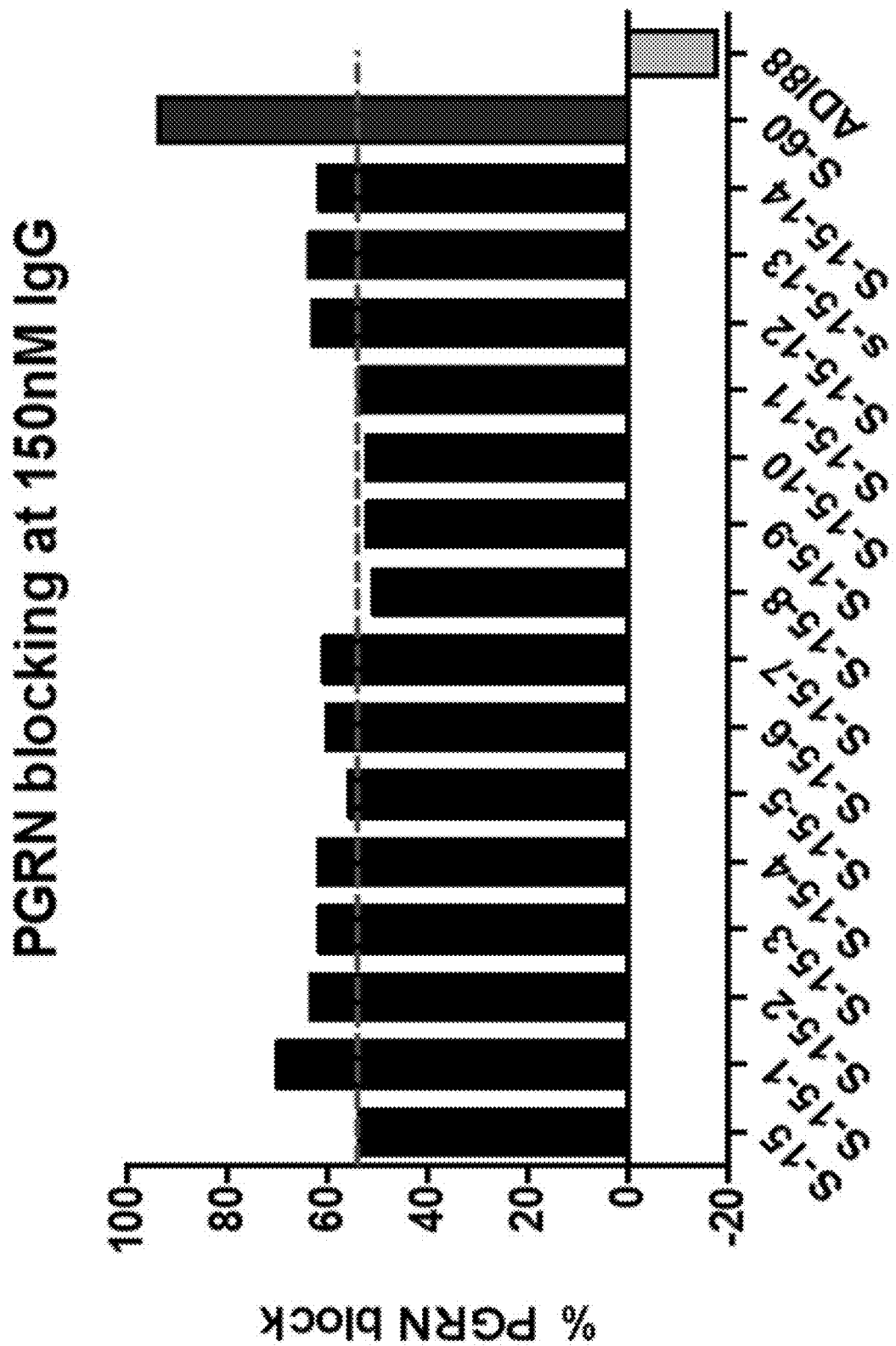
FIG. 14 depicts inhibition of binding of Progranulin (in percentage PGRN blocking) to HEK293T cells that express Sortilin by 150 nM of affinity-matured anti-Sortilin antibodies derived from antibody S-15. The affinity-matured antibody S-15-6 showed improvement in PGRN blocking.

The parental antibody S-15 and the affinity-matured antibodies derived therefrom were tested for their ability to block binding of 15 nM PGRN to Sortilin expressed on HEK293Tcells. As shown in FIG. 14, affinity-matured antibody clones of S-15 (e.g., S-15-1 to S-15-7, and S-15-12 to S-15-14) induced small increases in the ability to block binding of 15 nM PGRN to Sortilin as compared to the parental S-15 antibody.

In summary, we have identified at least three affinity matured clones with improved binding to both human and mouse Sortilin and with improved functionality in either downregulating Sortilin protein levels and/or blocking of PGRN binding.

The results indicated the identification of affinity-matured anti-Sortilin antibodies that have improved binding to both human Sortilin and mouse Sortilin and that have improved functionality in reducing native cell surface levels of Sortilin and/or blocking of PGRN binding to Sortilin, as compared to the respective parental antibody.

Example 24: Epitope Mapping of Anti-Sortilin Antibodies

Materials and Methods

Binding to Linear Epitopes

Antibody epitopes were mapped as described below. For the characterization of the antigen, the measurements were performed using an Ultraflex III MALDI ToF (Bruker) equipped with HM4 interaction module. This module contains a special detecting system designed to optimize detection up to 2MDa with nano-molar sensitivity.

Antigen and antibody samples were mixed to a final concentration of I1 µM to 0.5 µM, respectively, 1 µl of the mixture obtained was mixed with 1 µl of a matrix composed of a re-crystallized sinapinic acid matrix (10 mg/nil) in acetonitrile/water (1:1, v/v), TFA 0.1% (K200 MALDI Kit). After mixing, 1 µl of each sample was spotted on the MALDI plate (SCOUT 384), After crystallization at room temperature, the plate was introduced in the MALDI mass spectrometer and analyzed immediately, and analysis was repeated in triplicate.

The mixture prepared for the control experiment was cross-linked using K200 MALDI MS analysis kit. Nine microliters of the mixture is mixed with 1 µl of K200 Stabilizer reagent (2 mg/ml) and incubated at room temperature. After the incubation time (180 minutes) the samples were prepared for MALDI analysis as for the control experiments. The samples are analyzed by High-Mass MALDI immediately after crystallization.

In order to test whether the binding epitope is of linear nature, proteolysis of recombinant human Sortilin antigen with immobilized pepsin was performed. Fifty microliters of the antigen at a concentration of 4 µM were mixed with immobilized pepsin at 2.5 µM and incubated at room temperature for 30 minutes. After the incubation time the sample was centrifuged and the supernatant was pipetted. The completion of the proteolysis is controlled by High-Mass MALDI mass spectrometry in linear mode and reflectron mode. The pepsin proteolysis was optimized in order to obtain a large amount of peptide in the 1000-3500 Da range. Five microliters of the antigen peptides generated by proteolysis were mixed with 5 µl of S-2-11, S-15-6, S-60, S-22-9 or S-82-8 antibody at 2 µM and incubated at 37° C. for 2 hours. Afterwards, the mixture was mixed with 5 µl intact antigen at 2 µM. Interaction between the antibody and the antigen was performed as described above.

Peptide Mass Fingerprint of the Sortilin Antigen and Characterization of the Binding Interfaces For the peptide fingerprint, 10 μl of Sortilin (5 μM) was mixed with 10 μl of antibody (2.5 μM). 2 μl of DSS d0/d12 (2 mg/mL; DMF) was added followed by 3 hr incubation at room temperature. Reaction was stopped by adding 2 μl of Ammonium Bicarbonate at 400 mM (final=20 mM) followed by for incubation at room temperature. The solution was dried using a speedvac before suspension with 20 μl of H2O 8 M urea. After mixing 2 μl of DTT (500 mM) was added to the solution. The mixture was then incubated 1 hour at 37° C. After incubation, 2 μl of iodioacetamide (1M) was added before 1 hour incubation at room temperature in a dark room. After incubation, 80 μl of the proteolytic buffer was added. Subsequently 100 μl of the reduced/alkyled antigen was mixed with digestion enzymes from Roche Diagnostics (1.66 μl trypsin or 0.83 μl chymotrypsin or 0.83 μl ASP-N or 1.66 μl elastase or 3.32 μl thermolysin) and incubated overnight at 37° C. (trypsin, ASP-N, elastase), 2.5° C. (chymotrypsin), or 70° C. (thermolysin). After digestion 1% final of formic acid was added to the solution. The samples were then submitted to SPE washing on Atlantis dC18 3 μM 2.1*30 mm Column.

After proteolysis, 10 μl of the peptides generated were loaded onto a nano-liquid. chromatography system (Ultimate 3000, Dionex) and LTQ orbitrap mass spectrometry was performed.

In order to determine the epitope of antibodies S-2-11, S-15-6, S-22-9, S-60, and S-82-8 on Sortilin antigen with high resolution, the antibody/antigen complexes were incubated with deuterated cross-linkers and subjected to multi-enzymatic cleavage. After enrichment of the cross-linked peptides, the samples were analyzed by high resolution mass spectrometry (nLC-Orbitrap MS) and the data generated were analyzed using XQuest and Stavrox software. An nLC in combination with Orbitrap mass spectrometry was used. Five microliters of the antigen sample (concentration 4 μM) was mixed with 5 μl of the antibody sample (concentration 2 μM) in order to obtain an antibody/antigen mix with a final concentration 2 μM/1 μM. The mixture was incubated at 37° C. for 180 minutes. In a first step, 1 mg of d0 cross-linker was mixed with 1 mg of d12 cross-linker. The 2 mg prepared were mixed with 1 ml of DMF in order to obtain a 2 mg/nil solution of DSS do/d12. Ten microliters of the antibody/antigen mix prepared previously were mixed with 1 μl of the solution of cross-linker d0/d12 (2 mg/ml). The solution was incubated 180 minutes at room temperature in order to complete the cross-linking reaction. Ten microliters of the cross-linked solution was mixed with 40 μl of ammonium bicarbonate (25 mM, pH 8.3). After mixing 2 μl of DTT (500 mM) was added to the solution. The mixture was incubated 1 hour at 55° C. After incubation, 2 μl of iodioacetamide (1 M) was added and then incubated for 1 hour at room temperature in a dark room. After incubation, the solution was diluted 1/3 by adding 120 μl of the buffer used for the proteolysis. To 145 μl of the reduced/alkyled antigen was mixed with either 0.7 μl trypsin, 0.35 μl chymotrypsin, 0.35 μl ASP-N, 0.7 μl elastase, or 1.4 μl thermolysin. The proteolytic mixtures were incubated overnight at 37° C. (trypsin, ASP-N, elastase or 2.5° C. (chymotrypsin), or 70° C. (thermolysin). The cross-linker peptides were then analyzed using Xquest version 2.0 and the Stavrox 2.1 software.

Results

Binding to Linear Epitopes

Figures 15A, 15B:
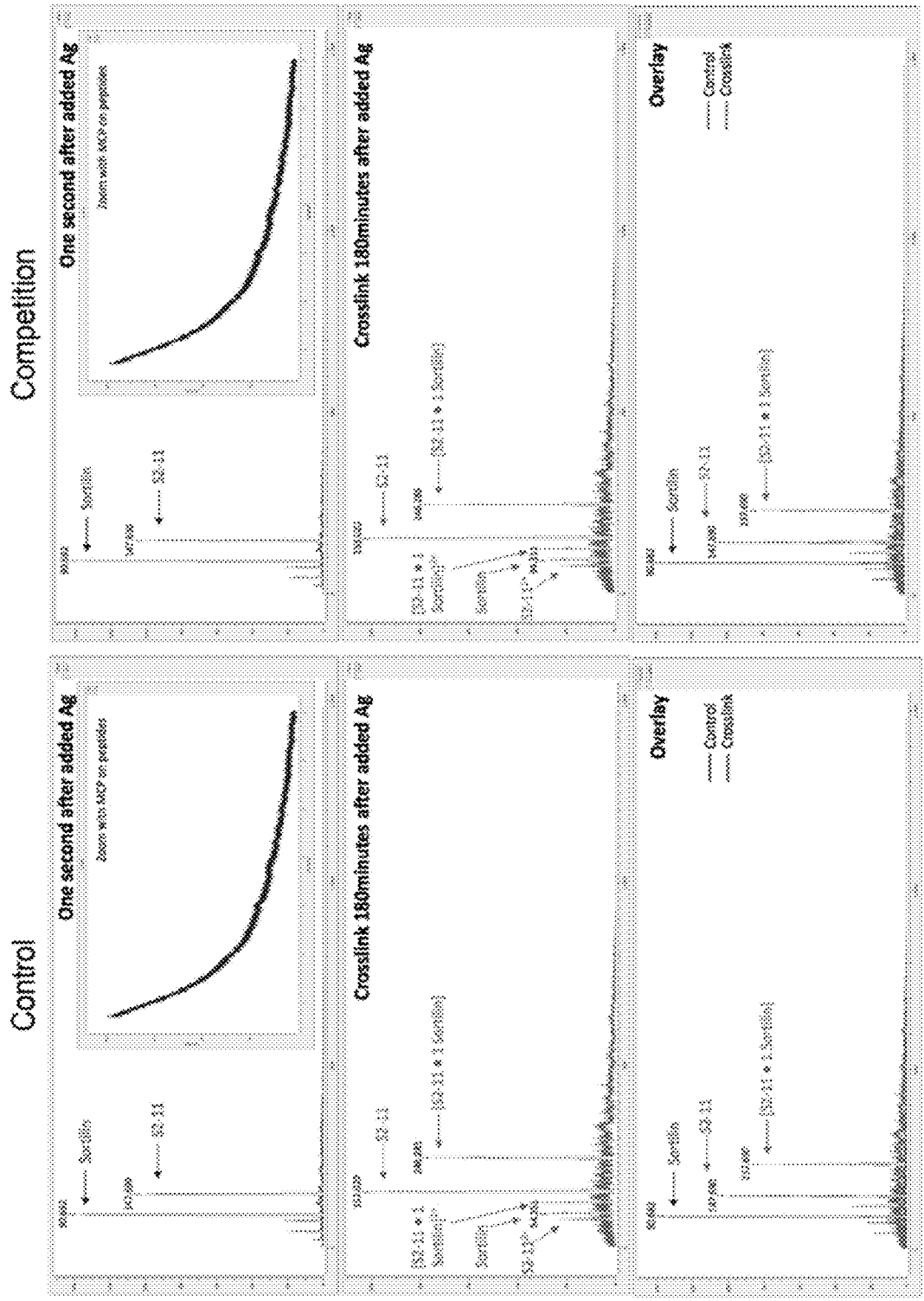
FIG. 15A and FIG. 15B depict mass spectroscopy profiles of antibody S-2-11 binding to Sortilin in the absence (FIG. 15A) or presence (FIG. 15B) of peptides derived from Sortilin digestion. Peptides did not compete with antibody binding to Sortilin. A similar lack of peptide competition was observed for other anti-Sortilin antibodies.

Affinity matured anti-Sortilin antibodies S-2-11, S-15-6, and S-60 each bind to Sortilin in a complex of 1:1 stochiometry. This binding was not inhibited by the presence of peptides (FIGS. 15A and 15B). The affinity-matured anti-Sortilin antibodies S-22-9 and S-82-8 each form both 1:1 and 1:2 (antibody:antigen) complexes with Sortilin. These complexes were not inhibited by the presence of peptides either. FIGS. 15A and 15B also indicate that Sortilin peptides did not compete with antibody S-2-11 binding to Sortilin. We observed A similar lack of Sortilin peptide competition was also observed for antibodies S-15-6, S-22-9, S-82-8, and S-60. The results indicate that the binding epitopes for antibodies S-2-11, S-15-6, S-22-9, S-82-8, and S-60 are conformational and/or discontinuous. This is consistent with an inability to map antibodies S-2-11, S-15-6, S-22-9, S-82-8, and S-60 onto Sortilin using a peptide library approach.

Figure 16A:
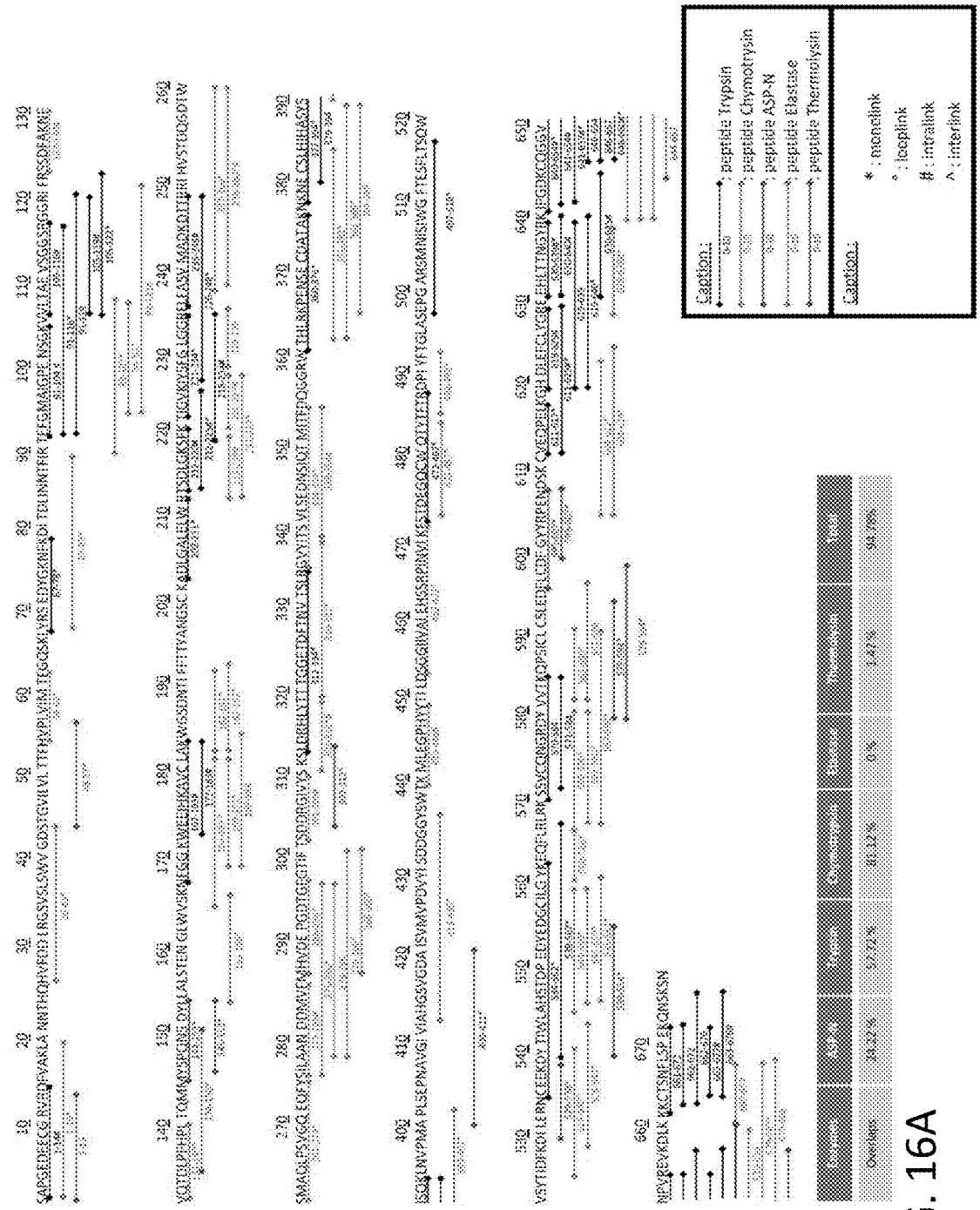
FIG. 16A is a schematic depiction of peptide coverage after enzymatic proteolysis of Sortilin. 94.78% of the Sortilin extracellular domain (ECD) (SEQ ID NO:714) was covered by peptides generated by proteolysis.

Peptide Mass Fingerprint of the Sortilin Antigen and Characterization of the Binding Interfaces After trypsin proteolysis, 52 peptides were identified in the sequence of Sortilin, covering 57.72% of the sequence. After chymotrypsin proteolysis 73 peptides were identified in the sequence of Sortilin, covering 81.12% of the sequence. After ASP-N proteolysis 12 peptides were identified in the sequence of Sortilin, covering 24.22% of the sequence. No peptides were identified in the sequence of Sortilin after Elastase proteolysis. After thermolysin proteolysis 2 peptides were identified in the sequence of Sortilin, covering 1.47% of the sequence. Combining the peptides from all proteolysis, 94.78% of the Sortilin sequence was covered (FIG. 16A). As 94.78% of the Sortilin extracellular domain was covered by peptides generated by proteolysis, it is believed that no epitopes were missed using this method.

Table 17 summarizes the results from the cross-linking experiments to determine epitopes. Thermolysine digestion did not result in any detectable peptides for any of the antibodies. For antibodies S-2-11, S-15-6, and S-22-9, two distinct epitopes were identified. For antibodies S-60 and S-82-8, a single epitope was identified. In the table, cross-linked amino acids are depicted in bold text.

TABLE 17A

| Antibody | Number of peptides | | |
|---|---|---|---|
| | Number of trypsin peptides | Number of chymo-trypsin peptides | Number of ASP-N peptides |
| S-2-11 | 7 | 5 | 0 |
| S-15-6 | 8 | 4 | 0 |
| S-22-9 | 2 | 8 | 3 |
| S-60 | 0 | 2 | 4 |
| S-82-8 | 1 | 2 | 0 |

TABLE 17B

Sortilin antibody binding regions

| Antibody | Sortilin binding region | Amino acid region of SEQ ID NO: 1 |
|---|---|---|
| S-2-11 | $^{237}$NGLWVSKNFGGKWEEIHKAVCLAK$^{260}$ (SEQ ID NO: 703) and $^{297}$KTIGVKIYSFGLGGRFLFASV$^{317}$ (SEQ ID NO: 699) | 237-260 and 297-317 |

TABLE 17B-continued

Sortilin antibody binding regions

| Antibody | Sortilin binding region | Amino acid region of SEQ ID NO: 1 |
|---|---|---|
| S-15-6 | $^{237}$NGLWVSKNFGG$^{247}$ (SEQ ID NO: 700) and $^{314}$FASVMADKDTTRRIHVSTDQGDTWS$^{338}$ (SEQ ID NO: 701) | 237-247 and 314-338 |
| S-22-9 | $^{207}$FVQTDLPFHPLTQMMYSPQNS$^{227}$ (SEQ ID NO: 702) and $^{237}$NGLWVSKNFGGKWEEIHKAVCLAK$^{260}$ (SEQ ID NO: 703) | 207-227 and 237-260 |
| S-60 | $^{207}$FVQTDLPFHPLTQMMYSPQNSDYLL$^{231}$ (SEQ ID NO: 704) | 207-231 |
| S-82-8 | $^{367}$EYGDTGFGTIFTSDDRGIVYSKSLD$^{391}$ (SEQ ID NO: 705) | 367-391 |

As indicated in Table 17B, the peptides recognized by antibody S-2-11 correspond to amino acid residues 237-260 and 297-317 of SEQ ID NO: 1 and have the amino acid sequences of: NGLWVSKNFGGKWEEIHKAVCLAK (SEQ ID NO:703) and KTIGVKIYSFGLGGRFLFA SV (SEQ ID NO:699). Further, the cross-linked residues within the peptides correspond to residues $K_{243}$ and $K_{248}$ within amino acid residues 237-260 of SEQ ID NO: 1; and residues $S_{305}$, $R_{311}$, and $S_{316}$ within amino acid residues 297-317 of SEQ ID NO: 1. The peptides recognized by antibody S-15-6 correspond to amino acid residues 237-247 and 314-338 of SEQ ID NO: 1 and have the amino acid sequences of: NGLWVSKNFGG (SEQ NO: 700) and FASVMAD KDTTRRIHVSTDQGDTWS (SEQ NO:701). Further, the cross-linked residues within the peptides correspond to residues $S_{242}$ and $K_{243}$ within amino acid residues 237-247 of SEQ ID NO: 1; and residues $S_{316}$ and $R_{325}$ within amino acid residues 314-338 of SEQ ID NO: 1. The peptides recognized by antibody S-22-9 correspond to amino acid residues 207-227 and 237-260 of SEQ ID NO: 1 and have the amino acid sequences of: FVQTDLPFHPLTQMMYSPQNS (SEQ ID NO:702) and NGLWVSKNFGGKWEEIHKAVCLAK (SEQ ID NO:703). Further, the cross-linked residues within the peptides correspond to residues $T_{210}$, $T_{218}$, and $S_{223}$ within amino acid residues 207-227 of SEQ ID NO: 1; and residues $K_{243}$, $K_{248}$, and $K_{254}$ within amino acid residues 237-260 of SEQ ID NO: 1. The peptide recognized by antibody S-60 corresponds to amino acid residues 207-231 of SEQ ID NO: 1 and has the amino acid sequence of: FVQTDLPFHPLTQMMYSPQNSDYLL (SEQ ID NO:704). Further, the cross-linked residues within the peptide corresponds to residues $T_{218}$, $Y_{222}$, $S_{223}$, and $S_{227}$ within amino acid residues 207-231 of SEQ ID NO: 1. The peptide recognized by antibody S-82-8 corresponds to amino acid residues 367-391 of SEQ ID NO: 1 and has the amino acid sequence of: EPGDTGFGTIFT SDDRGIVYSKSLD (SEQ ID NO:705). Further, the cross-linked residues within the peptide corresponds to residues $S_{379}$, $R_{382}$, and $Y_{386}$ within amino acid residues 367-391 of SEQ ID NO: 1.

Functional Mapping

Sortilin mutant variants HVPLVIMT131QVPLVIVS (in which residues 131-138 of SEQ ID NO: 1 are replaced with SEQ ID NO:706, in which underlined residues H, M, and T of the wild-type Sortilin amino acid sequence have been substituted with Q, V, and S, respectively) and S595R were generated using mutant primers and cloned into a plasmid vector pCMV-AC-IRES-GFP (from Origene). Anti-Sortilin antibodies S-30 and S-60 were conjugated with DyLight 650 antibody labeling kit (Thermo Scientific Pierce) according to manufacturer's instructions.

HEK293Tcells were transiently transfected with the plasmids using Fugene HD (Promega) according to the manufacturer's instructions. Transfected HEK293T cells were harvested after 24 hours, washed with PBS, and incubated with 5 μg/ml antibody for one hour on ice in FACS buffer (PBS+2% FBS). Cells were subsequently washed twice with 200 μl FACS buffer and analyzed on a FACS Canto and FlowJo software. GFP positive cells were selected and Sortilin expression was measured as median fluorescent intensity in the APC channel.

Figure 16B:
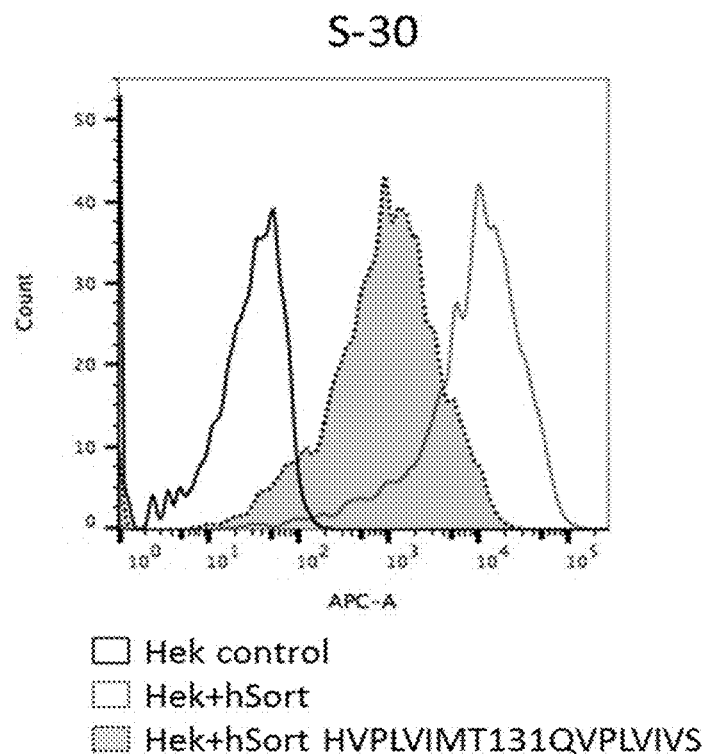
FIG. 16B shows reduced binding of the S-30 antibody to particular Sortilin mutants, where human amino acids were exchanged for mouse Sortilin amino acids. The results indicate that S-30 binding requires the amino acids HVPLVIMT (residues 131-138 of SEQ ID NO: 1) or a subset thereof. HVPLVIMT131QVPLVIVS refers to a Sortilin mutant in which HVPLVIMT (residues 131-138 of SEQ ID NO: 1) has been replaced with QVPLVIVS (SEQ ID NO: 706).
Figure 16C:
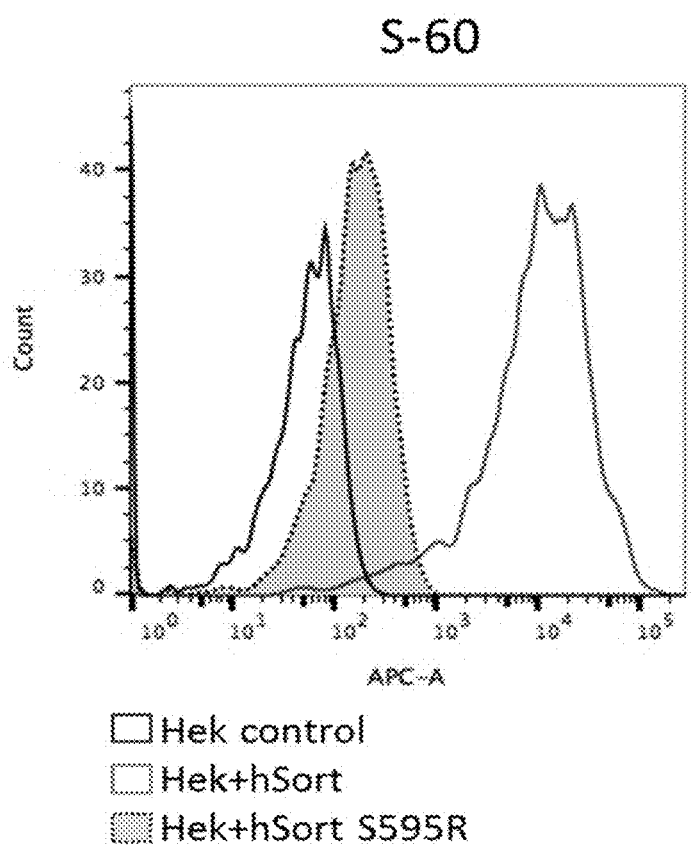
FIG. 16C shows reduced binding of the S-60 antibody to particular Sortilin mutants, where human amino acids were exchanged for mouse Sortilin amino acids. The results indicated that S-60 binding requires the 5595 amino acid.

The Sortilin mutant HVPLVIMT131QVPLVIVS (in which residues 131-138 of SEQ ID NO: 1 are replaced with SEQ ID NO: 706) strongly reduced binding of antibody S-30 (FIG. 16B), while binding of antibody S-60 was not reduced. In contrast, binding of antibody S-60 to the Sortilin mutant S595R was strongly reduced (FIG. 16C), while binding of antibody S-30 was not reduced. These results indicate that amino acids within the $^{131}$HVPLVIMT$^{138}$ peptide of Sortilin (residues 131-138 of SEQ ID NO: 1) are necessary for S-30 binding, and residue 5595 is critical for S-60 binding to Sortilin.

Shotgun Mutagenesis Epitope Mapping

Shotgun mutagenesis epitope mapping of anti-Sortilin antibodies was performed using an alanine-scanning library for the Sortilin protein. A Sortilin expression construct (NCBI Accession NP_002950) encoding a C-terminal VS epitope tag was subjected to high-throughput alanine scanning mutagenesis (outlined in Davidson and Doranz, 2014 Immunology 143, 13-20) to generate a comprehensive mutation library. Each of residues 78 to 755 was mutated, representing the Sortilin extracellular domain, most to alanine, while alanine codons were mutated to serine. In total, 678 Sortilin mutant expression constructs were generated, sequences confirmed, and arrayed into a 384-well plate, one mutant per well.

The Sortilin mutation library clones, arrayed in a 384-well microplate, were transfected individually into HEK-293T cells and allowed to express for 22 hours. Cells were then incubated with MAbs diluted in 10% normal goat serum (NGS) (Sigma-Aldrich, St. Louis, Mo.). Prior to library screening, primary MAb concentrations were determined using an independent immunofluorescence titration curve against cells expressing wild-type Sortilin to ensure that signals were within the linear range of detection. MAbs were detected using 3.75 μg/ml AlexaFluor488-conjugated secondary antibody (Jackson ImmunoResearch Laboratories, Westgrove, Pa.) in 10% NGS. Cells were washed twice with PBS and resuspended in Cellstripper (Cellgro, Manassas, Va.) with 0.1% BSA (Sigma-Aldrich. St. Louis, Mo.). Mean cellular fluorescence was detected using the Intellicyt high throughput flow cytometer (HTFC, Intellicyt, Albuquerque, N. Mex.). MAb reactivities against each mutant clone were calculated relative to wild-type Sortilin protein reactivity by subtracting the signal from mock-transfected controls, and normalizing to the signal from wild-type Sortilin-transfected controls.

Mutated residues within critical clones were identified as critical to the MAb epitope if they did not support reactivity of the test MAb but did support reactivity of control antibodies. This counter-screen strategy facilitated the exclusion of Sortilin mutants that were locally misfolded or that had an expression defect.

Figure 16E:
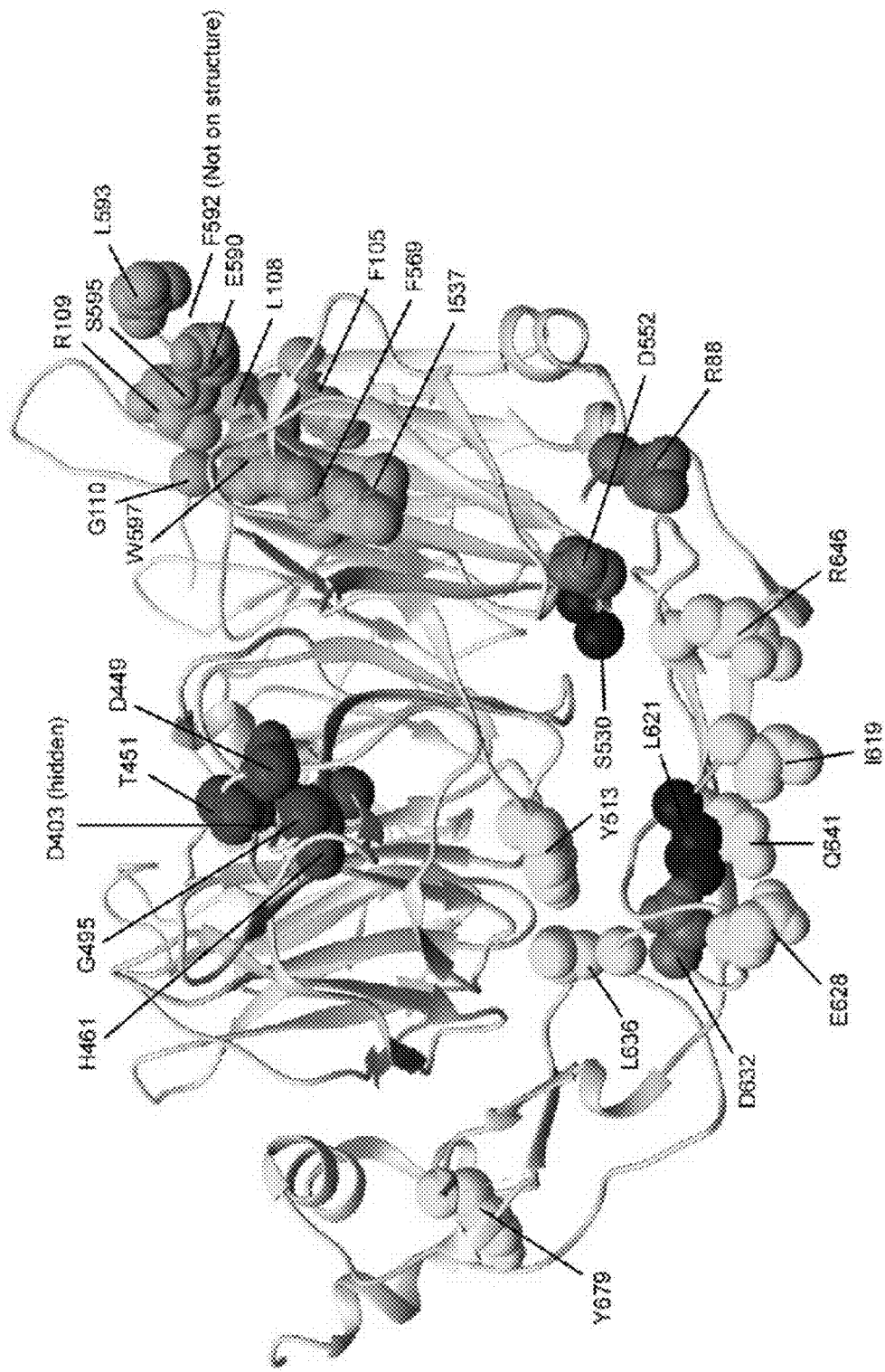
FIG. 16E depicts models of Sortilin indicating amino acid residues involved in antibody binding. Red spheres represent critical residues for antibody S-15-6, purple spheres represent critical residues for antibody S-2-2, blue spheres represent critical residues for antibody S-22-9, orange spheres represent critical residues for antibody S-60, yellow spheres represent critical residues for antibody S-82-8, and green spheres represent residue D632, which is critical for both antibody S-22-9 and antibody S-82-8.

FIG. 16D depicts the mean binding reactivities and ranges for all critical residues identified in the screens. The range was the difference between the duplicate experimental binding values. Primary critical residues were identified as residues where mutations were negative for test antibody binding (<30% of binding to WT) but positive for the control antibody (>80% WT). FIG. 16E depicts a crystal structure model of Sortilin (PDB ID 4PO7; Quistgaard et al., 2014) indicating the critical residues as spheres for each antibody tested. Red spheres represent critical residues for antibody S-15-6, purple spheres represent critical residues for antibody S-2-2, blue spheres represent critical residues for antibody S-22-9, orange spheres represent critical residues for antibody S-60, yellow spheres represent critical residues for antibody S-82-8, and green spheres represent residue D632, which is critical for both antibody S-22-9 and antibody S-82-8.

The amino acid residues critical for antibody binding are listed in Table 17C.

TABLE 17C

Residues involved in anti-Sortilin antibody binding

| Antibody | Critical Sortilin residues |
|---|---|
| S-2-2 | $R_{88}$ and $D_{552}$ |
| S-15-6 | $D_{403}$; $D_{449}$; $T_{451}$; $H_{461}$; and $G_{495}$ |
| S-22-9 | $S_{530}$; $L_{621}$; and $D_{632}$ |
| S-60 | $F_{105}$; $L_{108}$; $R_{109}$; $G_{110}$; $I_{537}$; $F_{569}$; $E_{590}$; $F_{592}$; $L_{593}$; $S_{595}$; and $W_{597}$ |
| S-82-8 | $Y_{513}$; $I_{619}$; $E_{628}$; $D_{632}$; $L_{636}$; $Q_{641}$; $R_{646}$; and $Y_{679}$ |

As indicated in Table 17C, the critical Sortilin residues involved in binding by antibody S-2-2 corresponded to amino acid residues $R_{88}$ and $D_{552}$ of SEQ ID NO: 1. The critical Sortilin residues involved in binding by antibody S-15-6corresponded to amino acid residues $D_{403}$, $D_{449}$, $T_{451}$, $H_{461}$, and $G_{495}$ of SEQ NO: 1. The critical Sortilin residues involved in binding by antibody S-22-9 corresponded to amino acid residues $S_{530}$, $L_{621}$, and $D_{632}$ of SEQ ID NO: 1. The critical Sortilin residues involved in binding by antibody S-60 corresponded to amino acid residues $F_{105}$, $L_{108}$, $R_{109}$, $G_{110}$, $I_{537}$, $F_{569}$, $E_{590}$, $F_{592}$, $L_{593}$, $S_{595}$, and $W_{597}$ of SEQ ID NO: 1. The critical Sortilin residues involved in binding by antibody S-82-8 corresponded to amino acid residues $Y_{513}$, $I_{619}$, $E_{628}$, $D_{632}$, $L_{636}$, $Q_{641}$, $R_{646}$, and $Y_{679}$ of SEQ ID NO: 1.

Example 25: Characterization of Interactions Between Sortilin and Neurotensin

Materials and Methods

Surface plasmon resonance (SPR) data were collected at a rate of 1 Hz at 25° C. on a BiaCore T200 instrument. Data analysis was performed using BiaCore T200 Evaluation Software, version 2.0. HBS-EP+ (100 mM HEPES, 1.5 M NaCl, 30 mM EDTA, 0.5% v/v Surfactant P20, pH 7.4) was used as running buffer and for preparing reagents.

Histidine-tagged human Sortilin (25 nM; R&D Biosystems) was captured (60 s contact time, 30 µl/min flow rate, 0 s stabilization time) on a CM5 sensor chip (GE Healthcare) immobilized with anti-histidine IgG. Human progranulin (PGRN; 50 nM; AdipoGen) containing 0 nM, 100 nM, or 500 nM Neurotensin (NTS; Sigma) was then flowed over the captured Sortilin surface (60 s contact time, 30 µl/min flow rate, 30 s dissociation time). The chip surface was regenerated in between cycles using 10 mM glycine-HCl, pH 1.7 (60 s contact time, 30 µl/min flow rate, 60 s stabilization time). The resulting SPR signal was obtained as the difference in response from measurements performed on a blank flow cell.

Anti-Sortilin antibodies S-15 (25 nM), S-22 (25 nM), S-49 (25 nM), and S-60 (25 nM) were captured (60 s contact time, 30 µl/min flow rate, 0 s dissociation time) on a CM5 sensor chip (GE Healthcare) immobilized with anti-human IgG (Jackson Labs). Human Sortilin (100 nM; R&D Biosystems) was pre-incubated with 0 nM, 100 nM, 500 nM, or 10,000 nM Neurotensin (NTS; Sigma) and then flowed over the captured anti-Sortilin surface (60 s contact time, 30 µl/min flow rate, 30 s dissociation time). The chip surface was regenerated in between cycles using 10 mM glycine-HCl, pH 1.7 (60 s contact time, 30 µl/min flow rate, 60 s stabilization time). The resulting SPR signal was obtained as the difference in response from measurements performed on a blank flow cell.

Results

Figure 17A:
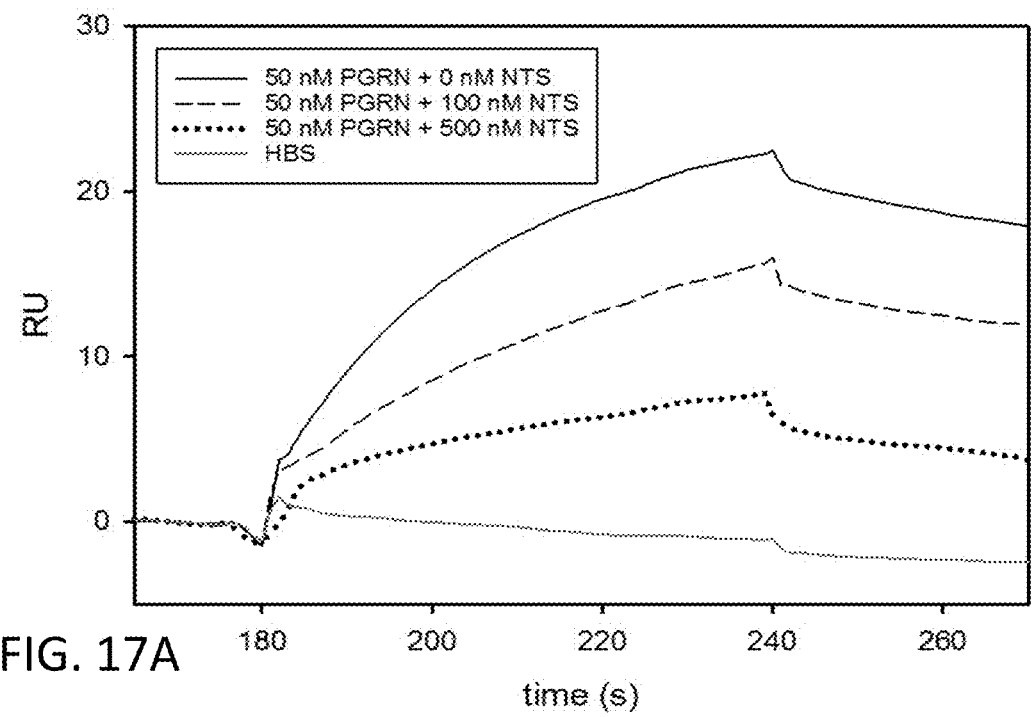
FIG. 17A-17E depict surface plasmon resonance traces.
Figure 17B:
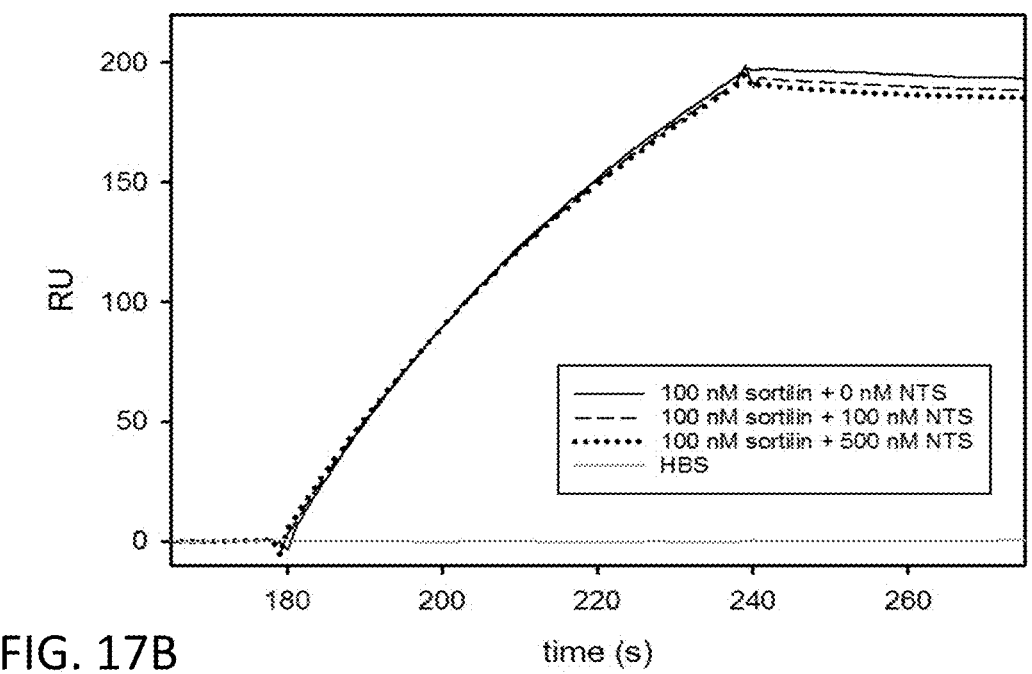
Figure 17C:
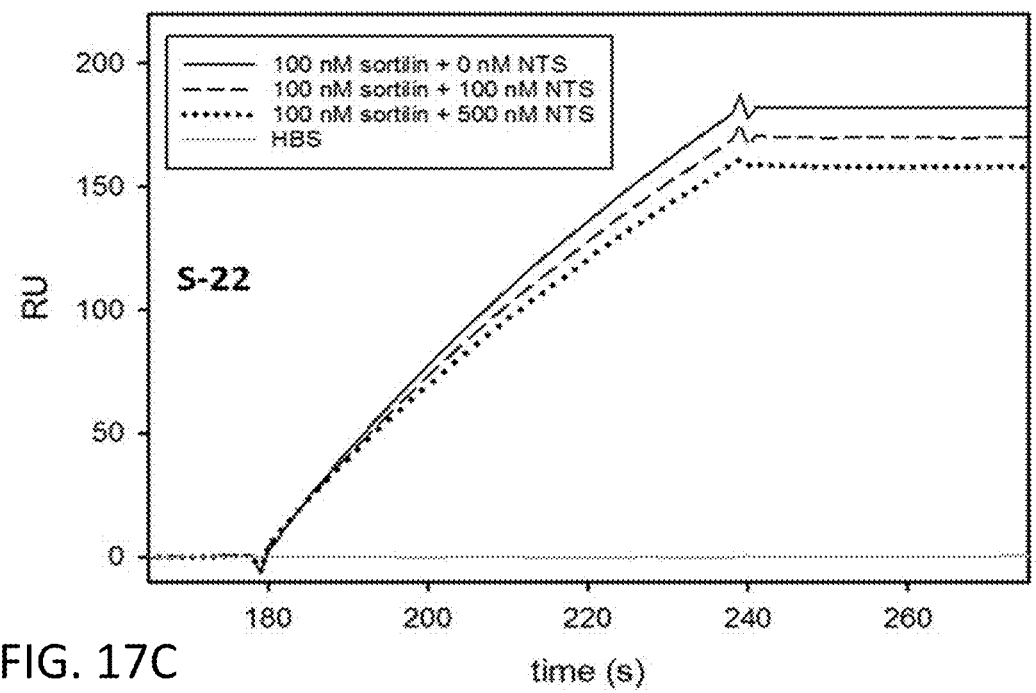
Figure 17D:
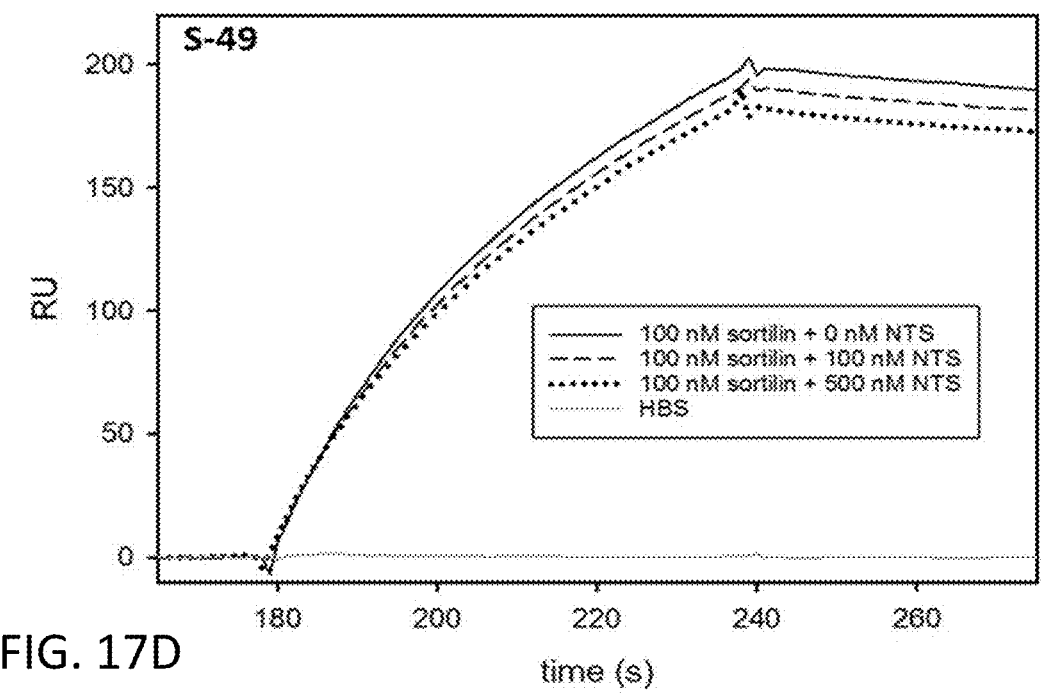
Figure 17E:
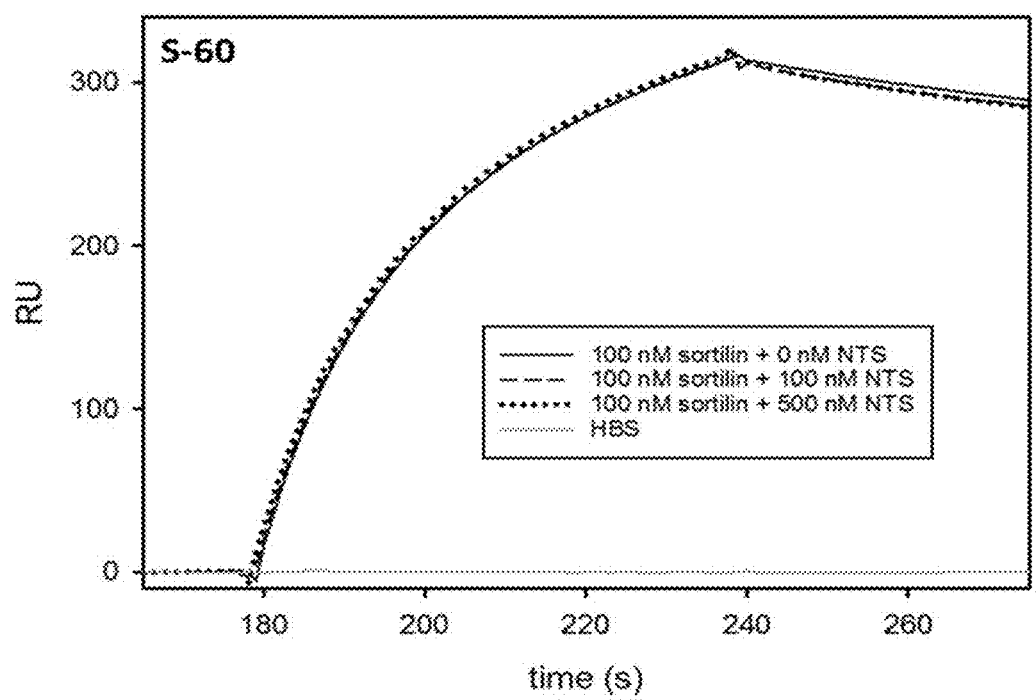

As shown in FIG. 17A, co-injection of Neurotensin blocked the binding of recombinant human Progranulin (PGRN) to human Sortilin, confirming that PGRN and Neurotensin bind to the same site on Sortilin. To test whether anti-Sortilin antibodies (S-15, S-22, S-49, and S-60) bind to the same site on Sortilin as does Neurotensin, the antibodies on the chip were captured and then co-injected with Sortilin pre-incubated with different doses of Neurotensin. Only a minor reduction in antibody binding to the Sortilin antigen was observed for antibodies S-15, S-22 and S-49 (FIGS. 17B, 17C, and 17D). However, no reduction in binding of S-60 to Sortilin was observed (FIG. 17E). As shown in Example 4, antibody S-60 is a PGRN-blocking antibody that blocks binding of PGRN to Sortilin. The results indicate that antibodies S-15, S-22, S-49, and S-60 do not bind Sortilin at the Neurotensin binding site. As Neurotensin can block binding of PGRN to Sortilin, but not of antibody S-60, it is believed that the ability of antibody S-60 to block PGRN binding to Sortilin is achieved by S-60 binding near the PGRN binding site on Sortilin, and perhaps occluding the PGRN binding site by steric hindrance, rather than by direct competition for the PGRN binding site on Sortilin. Furthermore, antibodies S-15, S-22, S-49, and S-60 represent bins 2, 3, 4 and 5 (n.d.), which suggests that the anti-Sortilin antibodies listed in Examples 1 and 23 that belong to bins 2, 3, and 4 bind also do not bind Sortilin at the Neurotensin binding site.

Example 26: Reduction of Levels of Sortilin in Cells

Materials and Methods

Human primary monocytes were isolated from heparinized human blood (Blood Centers of the Pacific) using Rosette Sep Human Monocyte Enrichment Cocktail (STEMCELL Technologies), according to the manufacturer's protocol. Monocytes were seeded in RPMI (Invitrogen)

containing 10% Fetal Calf Serum (Hyclone) and either 50 µg/ml M-CSF (Peprotech) to induce differentiation to macrophages or 100 µg/ml IL-4+100 µg/ml GM-CSF (Peprotech) to induce differentiation to dendritic cells. After 5 days, cells were harvested. For macrophages, only cells attached to the plate were harvested using a cell scraper. For dendritic cells, cells in suspension were collected. After washes in PBS, cells were plated at 0.4 Mi/well in 12-well plates.

Fifty nanomolar full length anti-Sortilin antibody (IgG) or anti-Sortilin antibody Fab was added to each well and incubated for 48 h. Cells were then lysed on ice using RIPA buffer (Thermo Fisher Scientific) with protease inhibitors (Life Technologies). Lysates were collected and centrifuged at 10,000×g for 10 min at 4° C. Supernatants were collected and protein concentration was measured using a BCA kit according to the manufacturer's instructions (Thermo Fisher Pierce). The following anti-Sortilin antibodies were used: S-2-11, S-5, S-15-6, S-22-9, S-60, and S-82-8.

Fifteen micrograms of protein was loaded per lane onto a 4-12% Bolt Bis-Tris protein gel (Life Technologies) and run at 150 V for 45 min. Protein was transferred onto a PVDF membrane using iBlot according to the manufacturer's instructions (Life Technologies). The membrane was then washed in TBS+0.05% Triton (TBST) and blocked for at least one hour at RT in TBST+5% BSA. Sortilin was labeled using anti-Neurotensin (BD Biosciences, 1:200) and Actin using anti-beta Actin (Santa Cruz, 1:500) diluted in TBST, with overnight incubation at 4° C. Membranes were then washed three times with TBST and incubated for one hour at RT in anti-mouse-HRP conjugated secondary antibody (Jackson Laboratories). Membranes were again washed three times in TBST and incubated for 1 min in ECL Western detection reagent (GE Life Sciences) and imaged on an Amersham Imager 600 (GE Life Sciences).

Results

Figure 18A:
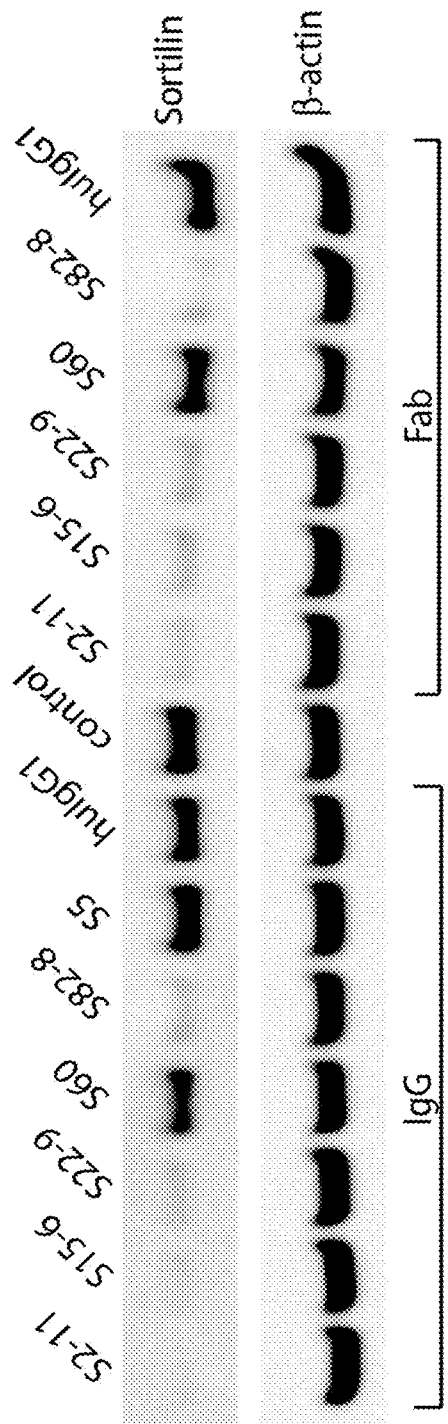
FIG. 18A depicts reduction in levels of Sortilin protein in human primary macrophages by both full-length antibodies (IgG) and antibody Fabs of anti-Sortilin antibodies.
Figure 18B:
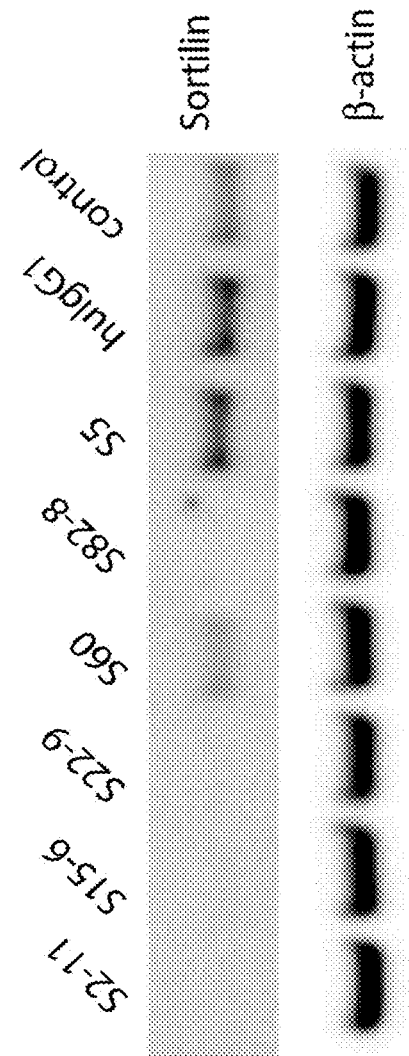
FIG. 18B depicts reduction in levels of Sortilin protein in human primary dendritic cells by full-length antibodies (IgG). 15 µg of protein was loaded onto gels, blotted, and stained with antibodies against Sortilin and beta-actin.

Compared to controls (control, control human IgG1, and human IgG1 Fab), treatment with 50 nM full-length antibodies or Fab fragments of anti-Sortilin S-2-11, S-15-6, S-22-9, and S-82-8 resulted in a strong reduction of Sortilin protein expression in human primary macrophages (FIG. 18A) and human primary dendritic cells (FIG. 18B) within 48 h. The anti-Sortilin antibody S-60 induced only a weak reduction of Sortilin protein expression in human primary monocytes, despite its ability to almost completely eliminate cell surface levels of Sortilin (FIGS. 18A and 18B). The anti-Sortilin antibody S-5 did not induce a reduction of Sortilin protein expression in human primary monocytes (FIGS. 18A and 18B). The results with antibody S-5 is consistent with the inability of antibody S-5 to reduce cell surface levels of Sortilin in U-251 cells (Example 5 and FIG. 10). These results indicate that anti-Sortilin antibody S-5 is a pure PGRN-binding blocker.

The results depicted in FIG. 18 indicate that human primary myeloid cells derived from patient blood samples can be used to measure the in vivo activity of anti-Sortilin antibodies that reduce levels of Sortilin protein. Similar results have also been demonstrated in vivo with mice.

Example 27: Characterization of Interactions Between Sortilin and Progranulin in Vivo Materials and Methods Recombinant anti-Sortilin antibodies were cloned into expression plasmids and produced in HEK293T cells by standard procedure as described in William J. Harris & John R. Adair, Eds. (Antibody Therapeutics, 1997). The expression plasmids into which the antibodies were cloned contain consensus human or murine IgG1 constant heavy and light chain regions, including a N297A mutation in the heavy chain Fc that prevents glycosylation of the antibody.

C57BL6 mice (Taconic), Sortilin knock-out mice, or Sortilin heterozygous mice were injected intraperitoneally with 40 mg/kg IgG on day 0. The following anti-Sortilin antibodies were used: S-2-11, S-15-6, S-20, and S-30.

Blood was collected after 4 h and on days 2, 5, 8, and 12 to isolate plasma and white blood cells. For plasma isolation, the blood was collected in heparinized tubes and centrifuged at 10,000×g for 10 min at 4° C. Plasma supernatant was collected at stored at −80° C. For subsequent white blood cell isolation, 1× volume of PBS+1 mM EDTA was added and cells were resuspended by vortexing. A 10× volume of 1×ACK lysis buffer (Lonza) was added and cells were incubated on ice for 10 min and subsequently centrifuged at 500×g for 10 min at 4° C. Supernatant was discarded and cells were resuspended in 10× volume of ACK lysis buffer and again incubated on ice for 5 min and subsequently centrifuged at 500×g for 10 min at 4° C. Cells were washed in 1 ml PBS+1 mM EDTA, spun again, and the supernatant was discarded and the cell pellet was stored at −80° C.

To isolate protein from white blood cells, cell pellets were resuspended in 50 µl N-Per (Thermo Scientific Pierce) containing a protease inhibitor cocktail. The solution was incubated on ice for 20 min and centrifuged at 10,000×g for 10 min at 4° C. Supernatant was collected, measured by BCA and loaded onto a protein gel as described in the previous section. Levels of human IgG1 antibodies in the plasma were determined using custom ELISA assay. Briefly, 96-well plates were coated overnight at 4° C. with 0.1 µg/well of goat anti-human Fab fragment specific for IgG (Jackson Immuno). Plates were washed three times in 200 µl wash buffer (PBS+0.05% Tween) and blocked in binding buffer (PBS+1% BSA) for 1 hr at RT. Plasma was diluted in binding buffer and added to the blocked plates and incubated for 1 h at 37° C. Plates were subsequently washed three times in 200 µl wash buffer and incubated with anti-human Fc specific HRP conjugated secondary antibody (Jackson Immuno Research) diluted at 1:10,000 in binding buffer for 1 hr at RT. Plates were washed three times in wash buffer and then 100 µl TMB substrate was added and incubated until sufficient color was developed. The reaction was stopped by adding 50 µl of 2 N sulfuric acid and the plate was read on a Synergy H1 plate reader (Biotek). The control IgG1 antibody was used as a standard concentration from 16-1000 pM. Levels of mouse IgG1 antibodies were tested using a similar ELISA setup. Plates were coated with 0.1 µg/well recombinant mouse Sortilin protein (R&D Systems) and anti-mouse Fc specific for goat IgG (Jackson Immuno Research) was used as a detection antibody at 1:10,000 dilution in binding buffer (PBS+3% BSA). The antibody that was injected was used as a standard from 37-3000 pM.

Levels of mouse Progranulin (PGRN) were measured using a Duoset ELISA kit from R&D Systems according to the manufacturer's protocol. Sortilin protein levels were measured in lysates of white blood cells using Western blotting and quantification thereof as described in Example 25.

For ICV infusion of antibodies into mouse brain, mice were implanted with subcutaneous Alzet osmotic minipumps (Model 1002, flow-rate=0.25 µl/h), that were coated and prefilled with the antibody (2 mg/ml) and connected to Alzet cannula (Brain Infusion Kit 3) for unilateral ICV administration. Prior to surgery, minipumps were primed following the directions provided by Alzet. In brief, all packages, bottles, syringes, and gloves were sprayed with 70% ethanol. The minipump was filled with the desired test article using a clean needle and syringe. It was then cleaned with an isopropanol-soaked tissue and put into a container of sterile 0.9% saline overnight at 37° C. to prime the pumps.

Mice were anesthetized using Isoflurane+oxygen using a vaporizer equipped with a mask. Afterward, each mouse was placed within a stereotaxic frame on an adjustable heating pad. While on the stereotaxic frame, the mice continued to receive Isoflurane anesthesia via a nose cone. Mice then received a local application of Marcaine (Bupivacaine+ epinephrine) at the incision site on the skull. The skin covering the skull was cleaned with surgical gauze and Betadine scrub, and then wiped with 75% ethanol on surgical gauze. A scalpel was used to make a 1-cm mid-sagittal incision through the skin covering the skull, exposing the bone. Sterile Q-tips with 0.9% normal saline or 3% $H_2O_2$ were used to clean any blood in the surgical field. Hemostats were used to grip the skin flaps and to retract laterally. Once the fascia and periostium were scraped away with a scalpel, it was possible to visualize the bregma. The minipump was first implanted subcutaneously along the scapula/back, to either the left, or right of the spine. Next, the location of the bur hole was marked with the tip of the scalpel or a fine tip marker, and a hole was drilled in the skull with a manual drill taking care not to damage the underlying dura or brain tissue. The Alzet cannula (Kit 3), attached to the minipump, was inserted into the lateral ventrical or hippocampus. Coordinates for the tips of the cannula for the lateral ventrical are: anterior-posterior (AP)=−0.3 mm to bregma, medial-lateral (ML)=−1.0 mm from midline and ventral (V)=−1.7 mm to dura, the toothbar set at 0 mm. After surgery, mice were housed individually in cages and provided food and water ad libitum. The condition of the mice was monitored daily after surgery. At the termination time point, all mice were euthanized. After euthanasia or spontaneous death, the minipump implantation site was opened and observations were recorded, including any signs of necrosis or fluid accumulation.

For peripheral injections into mice, antibodies in sterile PBS were administered either intraperitoneally (IP) or intravenously (IV) according to standard procedures. Blood samples of 50-200 µl werer drawn and collected into heparinized tubes. Subsequently the blood samples were centrifuged for 10 min at 2,000×g at 4° C. and plasma was collected.

The brain was dissected into left and right hippocampus, frontal cortex, and occipital cortex. To prepare brain lysates, 20 µl of N-Per/mg tissue was added along with protease and phosphatase inhibitors. Tissue and cells were disrupted by means of ultrasonification. After disruption, the tissue and N-per mixture were incubated on ice for 30 min and subsequently spun down with 20,000×g for 30 min. Supernatant was collected and stored at −80° C. until analysis. Anti-Sortilin antibody and mouse PGRN levels in brain lysate samples were measured using ELISA assays.

Results

Figure 19A:
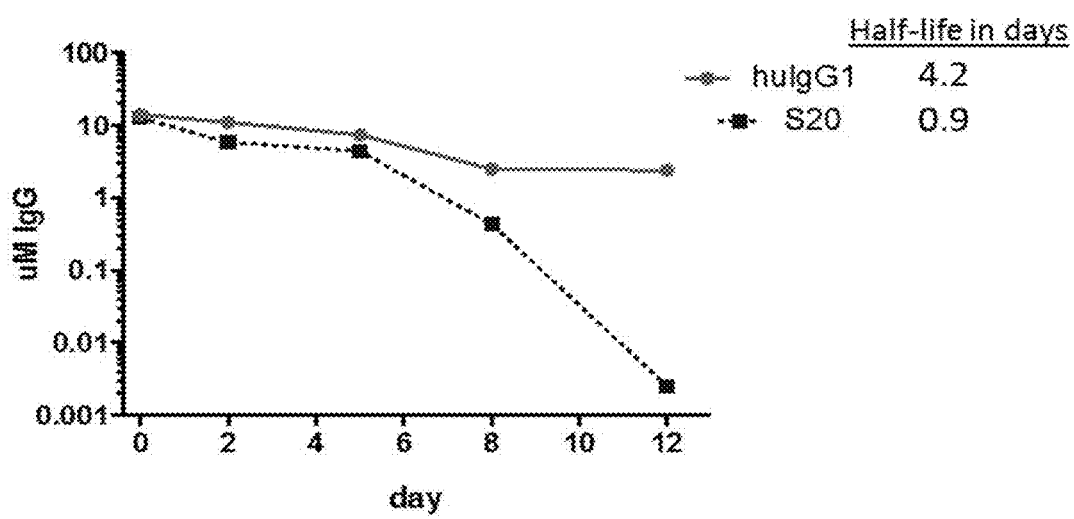
FIGS. 19A and 19B depict measurements of the half-lives of anti-Sortilin antibodies in vivo after intraperitoneal (IP) injection of 40 mg/kg on day 0.

Anti-Sortilin antibodies S-2-11, S-15-6, S-20, and S-30 were injected into mice intraperitoneally at 40 mg/kg on day 0. Antibody levels were measured on days 0 (4 hr after injection), 2, 5, 8, and 12 using custom ELISA assays Senim half-life was measured using a custom Excel add-in. As shown in FIG. 19A, antibody S-20 as huIgG1 N297A has a half-life of 0.9 days, while the isotype control antibody (huIgG1N297A) has a half-life of 4.2 days. Murine or human IgG1 N297A antibodies, which have a N297A mutation in their Fc region that prevents glycosylation and thus binding to Fc receptors, were used in these experiments.

Figure 19B:
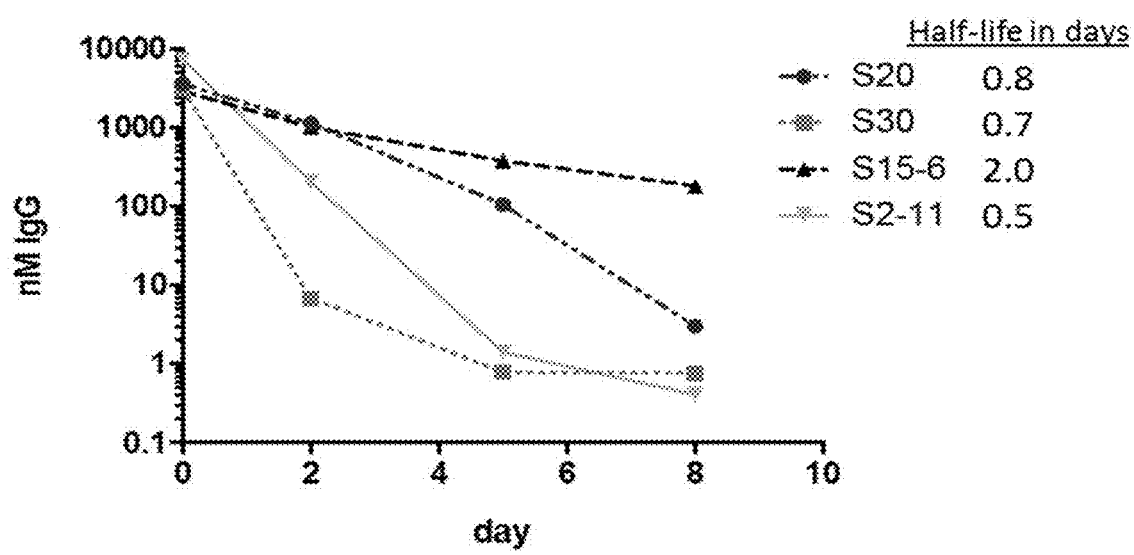

As shown in FIG. 19B, murine IgG1 N297A versions of anti-Sortilin antibodies S-2-11, S-15-6, S-20, and S-30 have half-lives ranging from 0.5 days to 2.0 days.

The anti-Sortilin antibodies have a shorter half-life than the control IgG, which is believed to be the result of target engagement. As shown in FIG. 19, antibodies S-15-6 and S-20 have the longest half-lives of the anti-Sortilin antibodies.

Figures 20A, 20B:
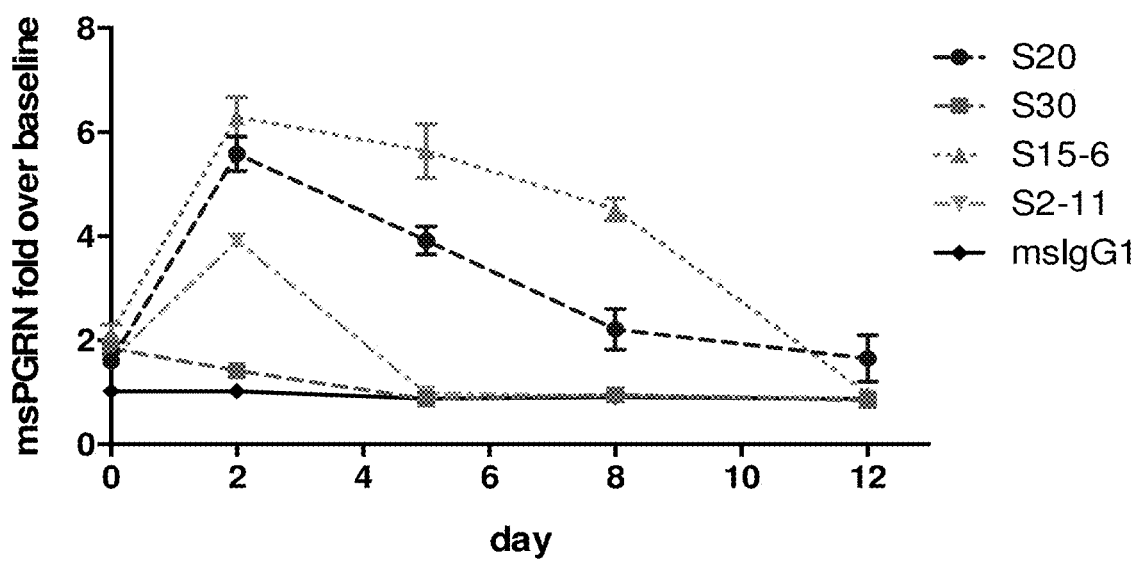
FIG. 20A-20D depict measurements of mouse Progranulin (PGRN) protein levels in mouse plasma samples at various times after injection of 40 mg/kg anti-Sortilin antibodies.
Figures 20C, 20D:
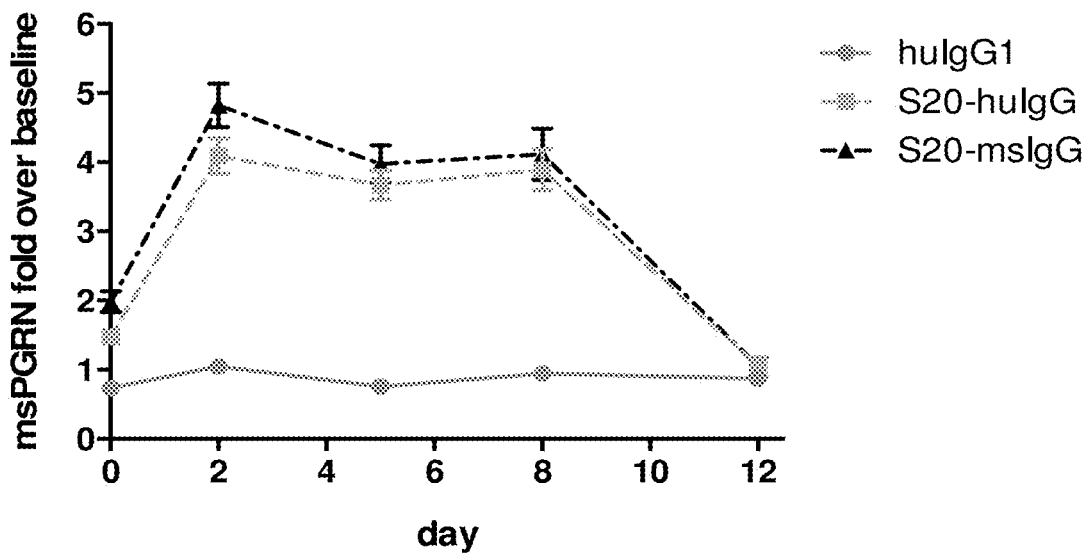

The anti-Sortilin antibodies were then tested to determine whether they can induce changes in protein levels of PGRN in the blood plasma of mice, using a mouse PGRN Duoset ELISA kit (R&D Systems). Anti-Sortilin antibodies S-2-11, S-15-6, and S-20, which induce a reduction in Sortilin levels in cells (FIGS. 10 and 18), were also able to induce an approximately 4-fold increase in PGRN protein levels in blood plasma of mice (FIG. 20A to 20D). While the increase in PGRN protein levels induced by antibody S-2-11 appears to be intermittent, antibodies S-20 and S-15-6 induce a significant increase in PGRN protein levels for up to 8 days (FIG. 20A to 20D). The pure PGRN-binding blocker antibody, S-30, is also able to significantly increase PGRN levels after 4 hours (FIGS. 20A and 20B). The results suggest that PGRN-blocking anti-Sortilin antibodies that do not induce a reduction in the cellular levels of Sortilin can also increase protein levels of PGRN. However, anti-Sortilin antibodies that induce a reduction in the cellular levels of Sortilin, such as antibodies S-15-6 and S-20, and that are also able to induce a prolonged effect on PGRN protein levels, as compared to anti-Sortilin antibodies that only block the interaction between Sortilin and PGRN, are believed to be more suitable for in vivo efficacy studies.

Figure 21A:
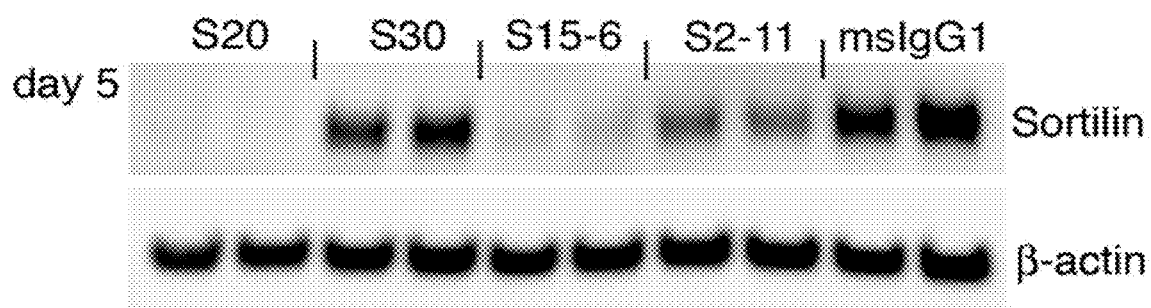
FIG. 21A-21F depict measurements of Sortilin protein levels using Western blot analysis of white blood cell lysates from mice. Anti-beta actin was used as a loading control and for normalization.
Figure 21B:
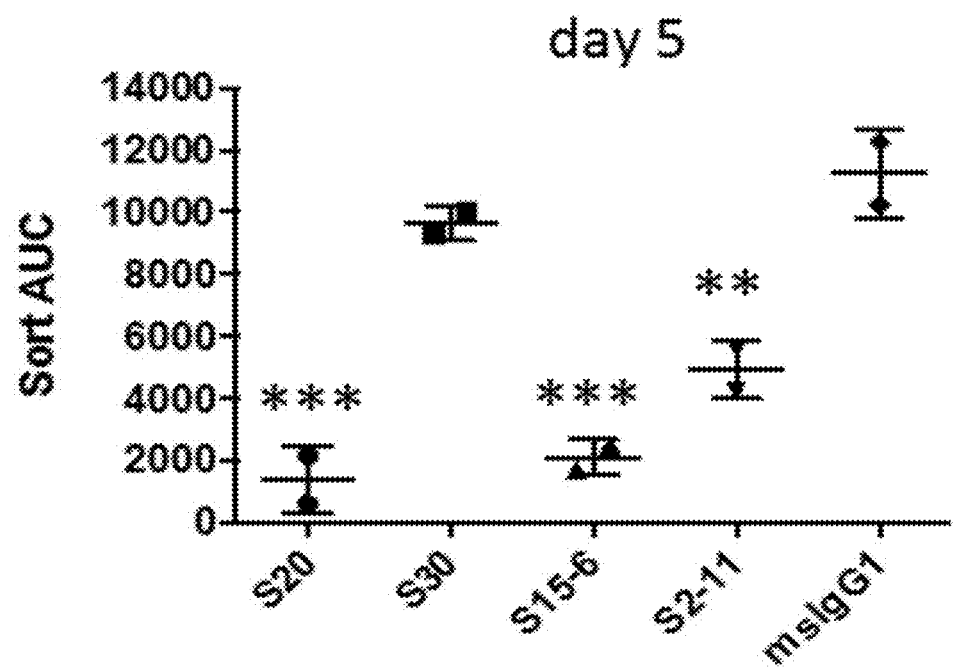
Figure 21C:
Figure 21D:
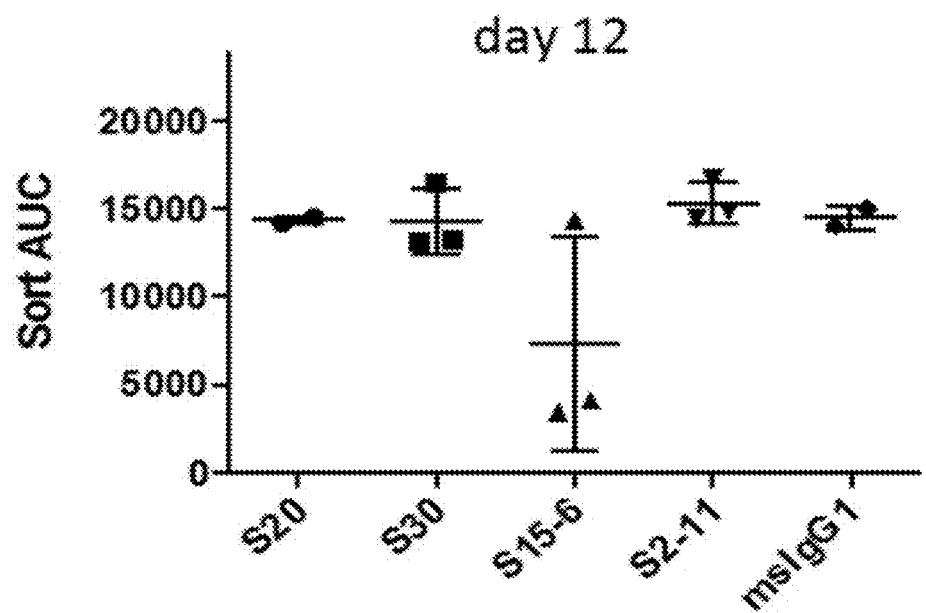

To confirm that the increase in PGRN protein levels induced by anti-Sortilin antibodies S-2-11, S-15-6, and S-20 was due to the induction of a reduction in the cellular levels of Sortilin, lysates from white blood cell samples obtained from treated mice were run on a protein gel and tested by Western blotting. Five days after injection, antibodies S-2-11, S-15-6, and S-20 induced a strong reduction in the levels of Sortilin protein in white blood cells (FIGS. 21A and 21B). White blood cells samples from mice twelve days after treatment with antibodies S-2-11, S-20, and S-30, showed levels of Sortilin protein that had returned to control levels (FIGS. 21C and 21D). However, white blood cell samples from mice twelve days after treatment with antibody S-15-6 still showed reduced levels of Sortilin protein (FIGS. 21C and 21D). Antibody S-30 does not appear to induce a reduction in the levels Sortilin protein (FIG. 21A to 21D), which is consistent with in vitro results (Table 10). Anti-Sortilin antibody S-30 is a specific PGRN blocker.

Figure 21E:
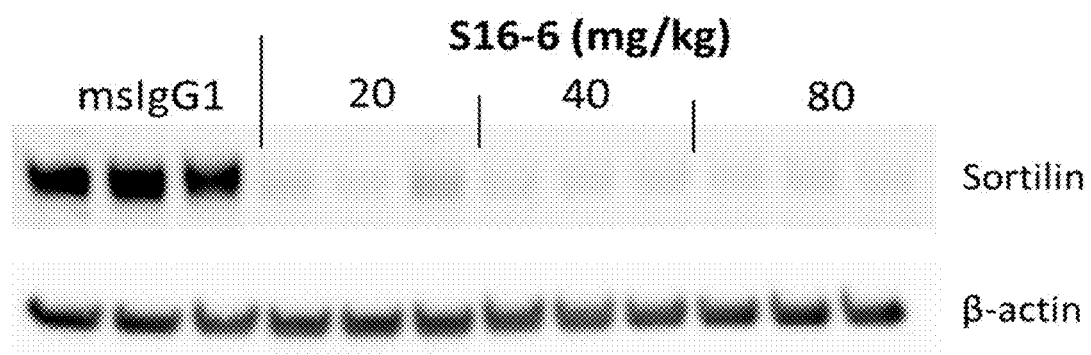
Figure 21F:
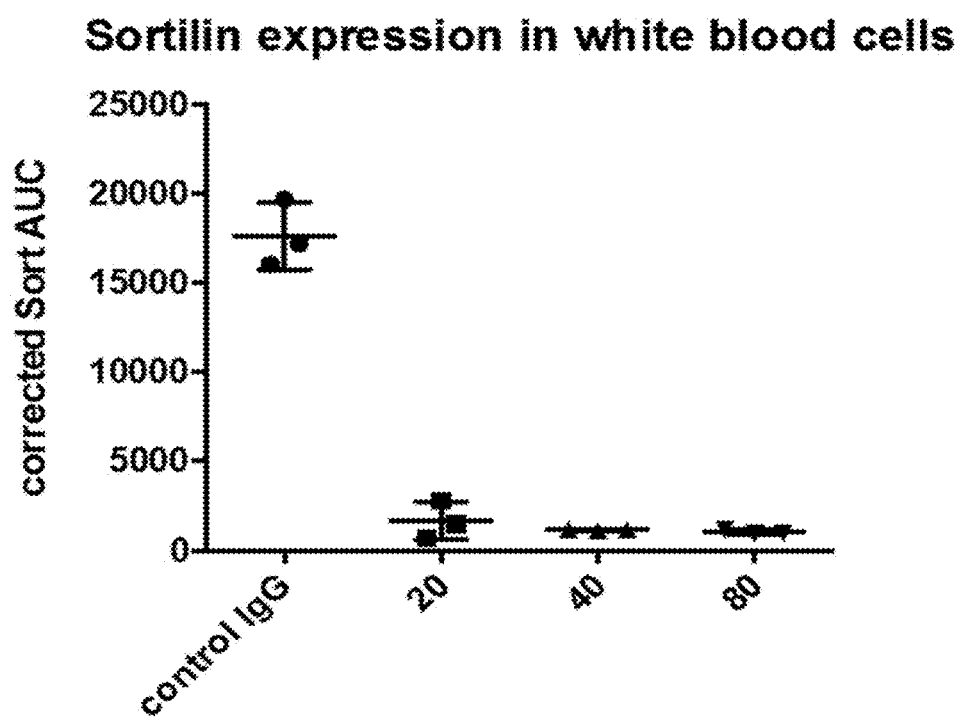

To measure target engagement after chronic injections, mice were injected once a week for six weeks with 20, 40, or 80 mg/kg of antibody S-15-6 or an msIgG1 control antibody. After 35 days, white blood cells were isolated from whole blood samples. A strong reduction in Sortilin protein levels was seen in samples obtained from mice at all injected doses (FIGS. 21E and 21F). These results indicate that lasting target engagement can be achieved.

Figure 22A:
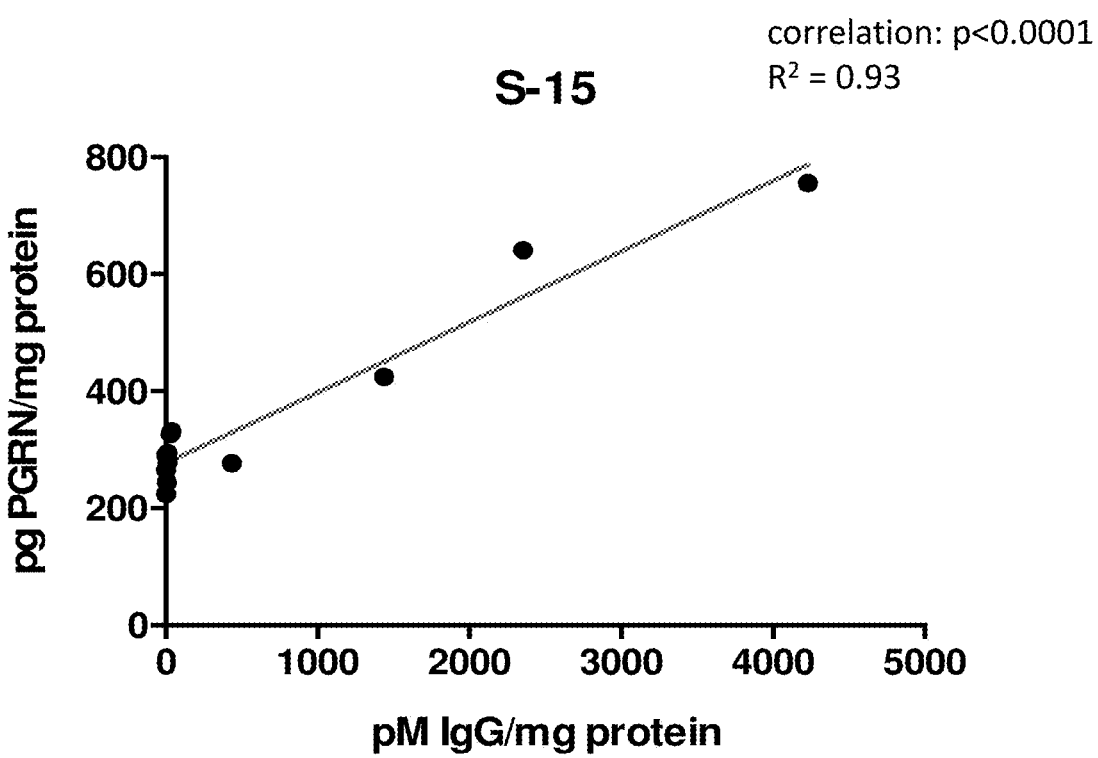
FIG. 22A-22D depict a positive correlation between IgG levels of anti-Sortilin antibodies and Progranulin (PGRN) protein levels in brain samples of wild-type (WT) mice after a 2 week ICV infusion. There was no significant correlation with the isotype control antibody.
Figure 22B:
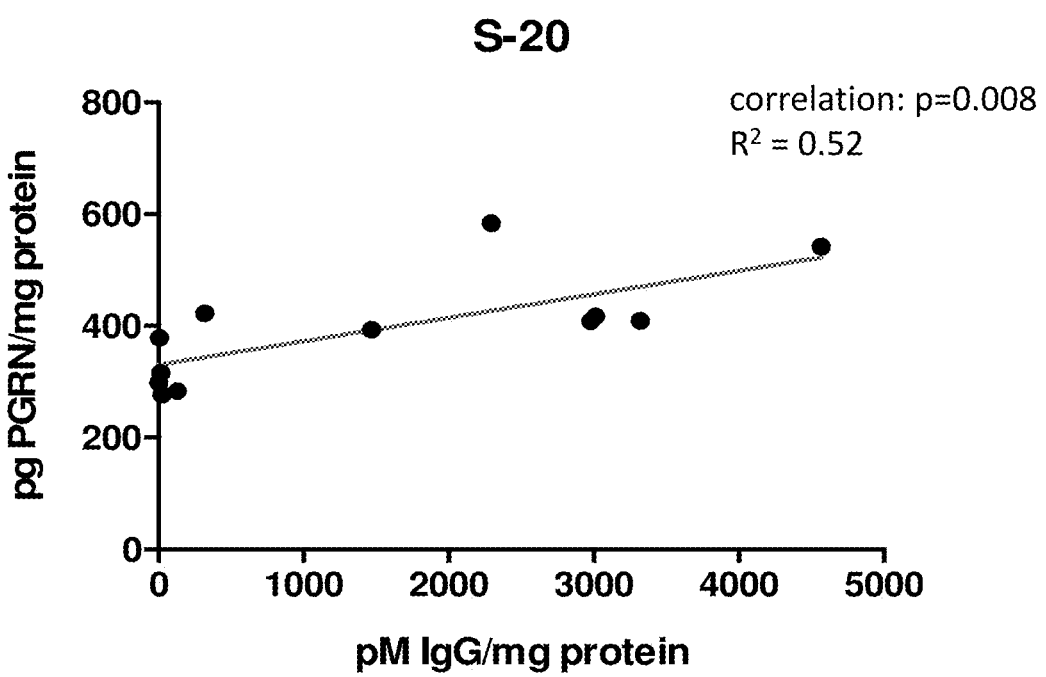
Figure 22C:
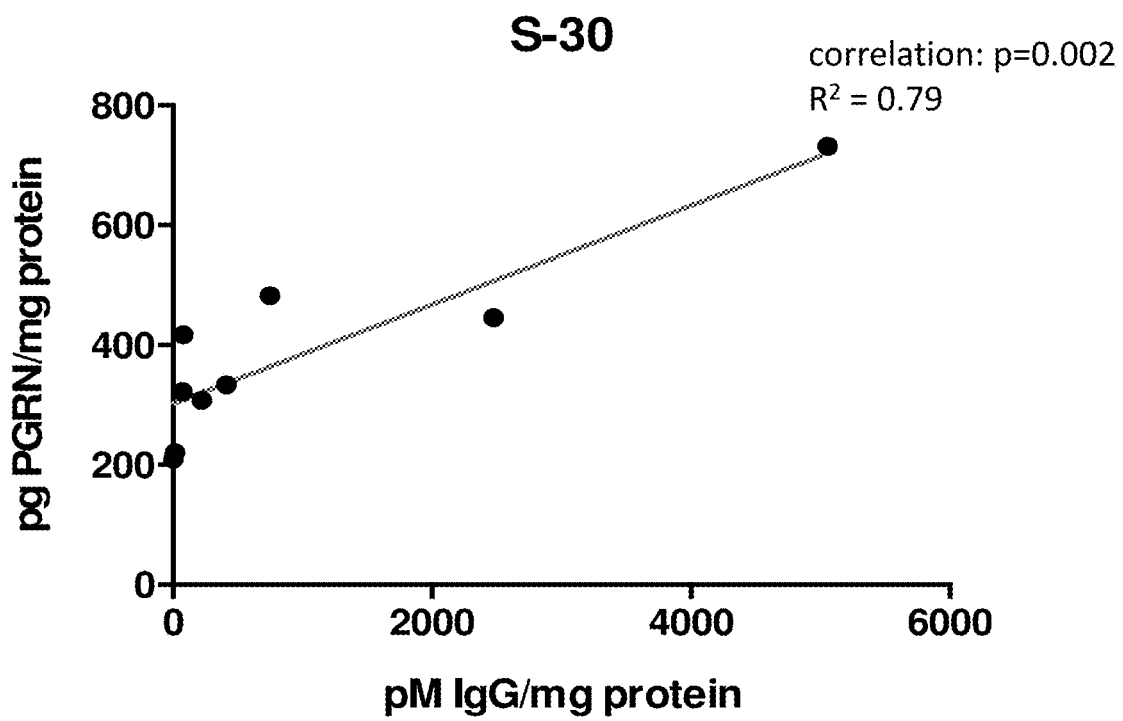
Figure 22D:
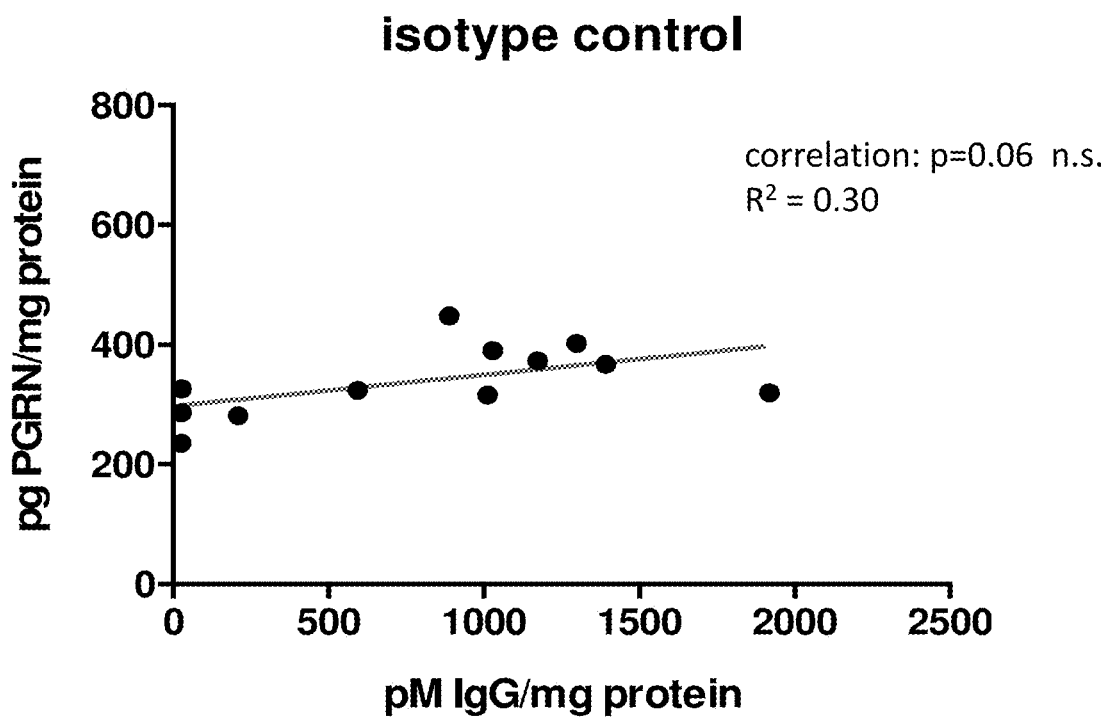

To measure target engagement of Sortilin antibodies in the brain, human IgG1 N297A versions of anti-Sortilin antibodies S-15, S-20, S-30, as well as a human isotype control antibody, were infused into the right lateral ventricle of the brain in mice using an Alzet osmotic minipump. After two weeks of infusion, brains were dissected into the left vs. right hippocampus, frontal cortex, and occipital cortex. Lysates were generated from these areas and human IgG levels were measured using ELISA assays. As shown in FIG. 22A to 22C, when antibody (IgG) levels were plotted against PGRN protein levels, a strong positive correlation was found between the two variables, indicating that increased doses of anti-Sortilin antibody can increase PGRN protein levels in the brain. There was no such correlation observed between levels of control IgG and PGRN protein levels (FIG. 22D).

Figure 23A:
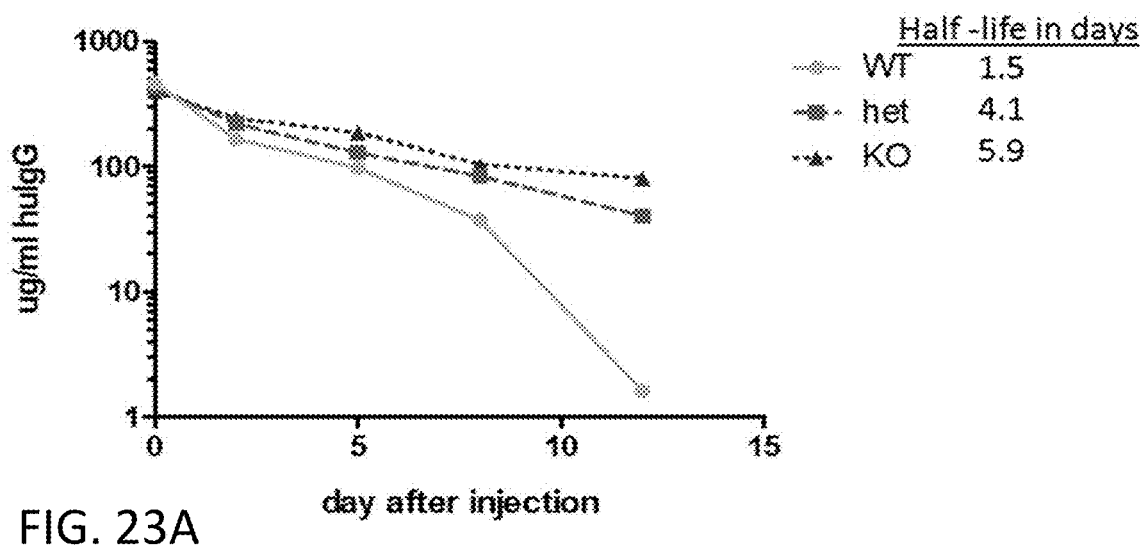
FIG. 23A depicts IgG levels measured after IV injection of 40 mg/kg of anti-Sortilin antibody S-15-6 huIgG1 N297A. The IgG half-life increases with reduced levels of Sortilin, demonstrating that the relatively short half-life of S-15-6 in wild-type (WT) mice is due to degradation after target engagement, rather than immunogenicity or other non-specific degradation.

To determine whether the effects on PGRN protein levels induce by anti-Sortilin antibodies are due to a reduction in Sortilin levels and not any off-target effects, a human IgG1 N297A version of antibody S-15-6 (huIgG) was tested in Sortilin knock-out (KO) mice, and in Sortilin heterozygous (Het) and wild-type (WT) littermates. Levels of antibody S-15-6 were measured in the plasma and it was observed that the half-life of the antibody increased dramatically as the levels of expressed Sortilin decreased (FIG. 23A). The results indicate that antibody S-15-6 specifically recognizes Sortilin and is likely recycled and degraded upon receptor engagement (i.e., binding to Sortilin).

Figure 23B:
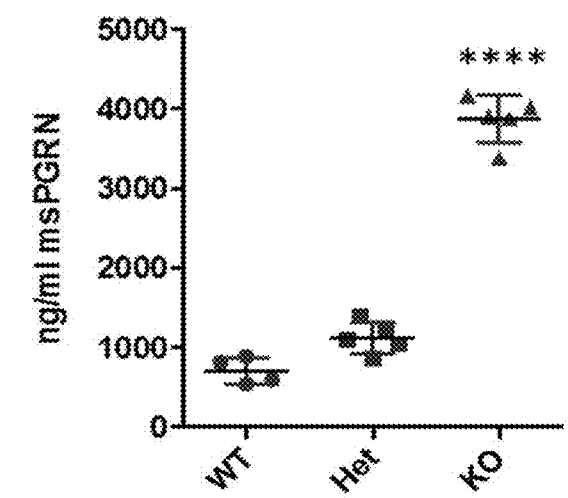
FIG. 23B depicts elevated baseline Progranulin (PGRN) protein levels in Sortilin knock-out (KO) mice, compared to Sortilin heterozygous (Het) and wild-type (WT) littermates. PGRN was measured in plasma samples using an ELISA assay.
Figure 23C:
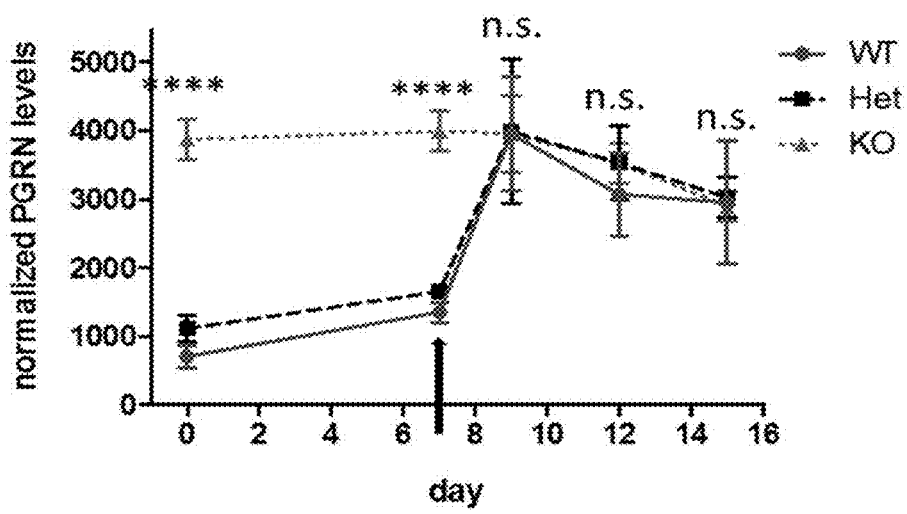
FIG. 23C depicts results showing that antibody S-15-6 induced an increase in Progranulin (PGRN) protein levels for up to eight days after injection into wild-type (WT) and Sortilin heterozygous (Het) mice, but not in Sortilin knock-out (KO) mice. The black arrow indicates injection of the S-15-6 antibody on day 7. ****$p<0.0001$, n.s.-not significant by one-way ANOVA, KO vs. Het and vs. WT.

Levels of PGRN in Sortilin knock-out mice were also determined. Baseline levels of PGRN protein were 4-fold higher in Sortilin knock-out mice (KO), as compared to wild-type (WT) littermates (FIG. 23B). Additionally, 40 mg/kg of antibody S-15-6 was injected at a single dose in Sortilin knock-out mice, as well as heterozygous (Het) and wild-type (WT) littermates, and PGRN protein levels were measured using ELISA assays. The results in FIG. 23C show that while injection of antibody S-15-6 into wild-type and Sortilin heterozygous mice strongly increased PGRN protein levels, no further increase in PGRN protein levels was observed in Sortilin knock-out mice, indicating that antibody S-15-6 increases PGRN protein levels specifically by reducing the levels of Sortilin protein, Example 28: Anti-Sortilin Antibodies Ameliorate Symptoms of Collagen-Induced Arforitis in Mice Materials and Methods On study days 0 and 21, mice were anesthetized with Isoflurane and given intradermal injections of a total of 100 µl of Type II collagen in Freund's complete adjuvant at the base of the tail. Collagen was prepared by making a 4 mg/ml solution in 0.01 N acetic acid. Equal volumes of collagen and 5 mg/ml Freund's adjuvant were emulsified by hand mixing. On study day 0, mice were randomized into treatment groups based on body weight. Following enrollment, treatment was initiated. Collagen was injected on day 0 and 21, 40 mg/kg of antibody S-15-6 as mouse IgG1 N297A, or control antibody MOPC-21 were injected intraperitoneally on study days 0, 3, 7, 10, 14, 17, 21, 24 and 28. Dexamethasone was dosed daily.

Body weights and clinical scoring of all four paws of the mice were recorded following enrollment. Paw scores were then measured daily from study day 18 to 35. Overall efficacy of test articles was based on daily paw scores, and an area under the curve (AUC) calculation of the paw scoring over time.

Figure 24:
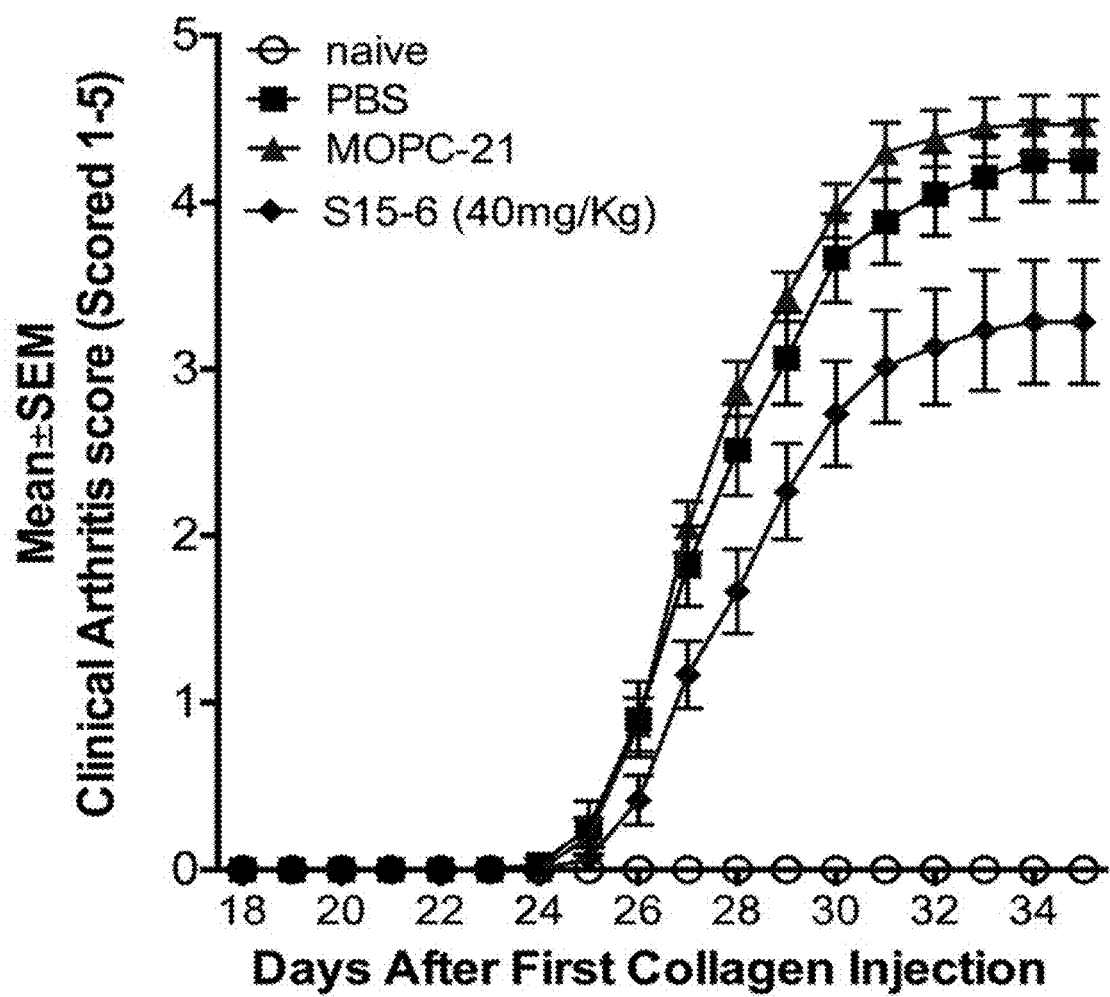
FIG. 24 depicts results from a collagen-induced arforitis study in mice. Bi-weekly injection of 40 mg/kg of anti-Sortilin antibody S-15-6 significantly lowered the clinical arforitis score compared to the control groups (PBS and MOPC-21/msIgG1).

Clinical paw scores were determined as follows:
0=Normal
1=1 bind or fore paw joint affected or minimal diffuse erythema and swelling
2=2 bind or fore paw joints affected or mild diffuse erythema and swelling
3=3 bind or fore paw joints affected or moderate diffuse erythema and swelling
4=Marked diffuse erythema and swelling, or 4 digit joints affected
5=Severe diffuse erythema and severe swelling entire paw, unable to flex digits Results Dosing animals with 4 0 mg/kg of anti-Sortilin antibody S-15-6 resulted in a modest, but statistically significant reduction in clinical paw scores, as well as a one-day delay in disease onset (FIG. 24). Table 18A and 18B show the p-values calculated using a t-test and two-way ANOVA indicating the statistical significance of the results depicted in FIG. 24.

TABLE 18A

| | T-Test | | |
|---|---|---|---|
| Days | S15-6 (40) Vs PBS | S15-6 (40) Vs MOPC-21 | MOPC-21 |
| 25 | 0.299 | 0.299 | 0.797 |
| 26 | 0.083 | 0.048 | 0.905 |
| 27 | 0.046 | 0.002 | 0.417 |
| 28 | 0.031 | 0.000 | 0.263 |
| 29 | 0.055 | 0.001 | 0.252 |
| 30 | 0.031 | 0.002 | 0.368 |
| 31 | 0.048 | 0.002 | 0.188 |
| 32 | 0.040 | 0.003 | 0.279 |
| 33 | 0.046 | 0.005 | 0.335 |
| 34 | 0.037 | 0.007 | 0.474 |
| 35 | 0.037 | 0.007 | 0.474 |

TABLE 18B

| Two-way ANOVA | |
|---|---|
| Individual Comparison | p-value |
| PBS vs. naive | <0.0001 |
| PBS vs. MOPC-21 | 0.8379 |
| PBS vs. DEX | <0.0001 |
| PBS vs. S15-6 (40 mg/kg) | 0.0003 |

These results indicate that anti-Sortilin antibody-induced increases in Prgranulin levels can reduce clinical symptoms of arforitis.

Example 29: Characterization of Sortilin Activity in Vivo

Materials and Methods

Lipopolysaccharide (LPS) from *E. coli* 0111:B4 was injected intraperitoneally at 0 mg/kg, 0.4 mg/kg, and 4 mg/kg into 9-10 week old C57Bl6 wild type mice and Sortilin −/− (Sortilin knock-out) mice. Serum samples were collected from the mice at 1.5 hours and at 6 hours following LPS administration. Cytokine and chemokine levels were then assessed using a BD Cytometric Bead Array mouse inflammation kit including IL-6, TNFalpha (TNF-α), IFN-gamma (IFN-γ), IL-10, IL12p70, and CCL2 and the flex set encompassing IL12/IL-23p40, IL-1beta (IL-1β), IL-1alpha (IL-1α), CXCL1, CCL3, CCL4, and CCL5. Peritoneal cavity lavage was performed at 6 hours following LPS administration to assess cell migration and infiltration. Analysis was performed using a BD FACSCanto II system.

Results

Figure 25A:
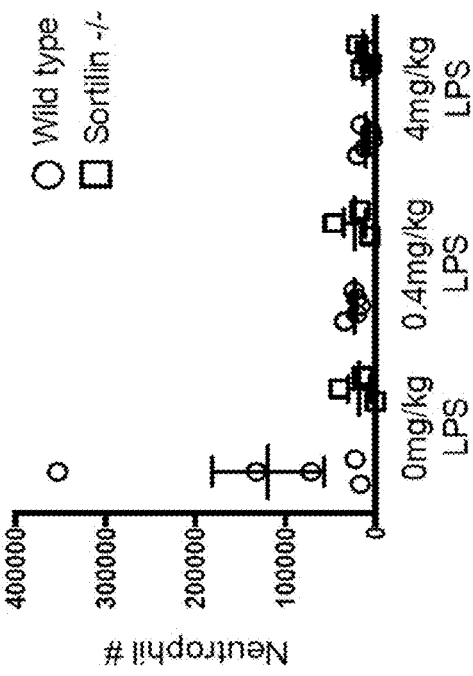
FIG. 25A depicts serum levels of progranulin after 6 hours of LPS treatment of wild type mice and Sortilin knock-out (Sortilin -/-) mice.
Figure 25B:
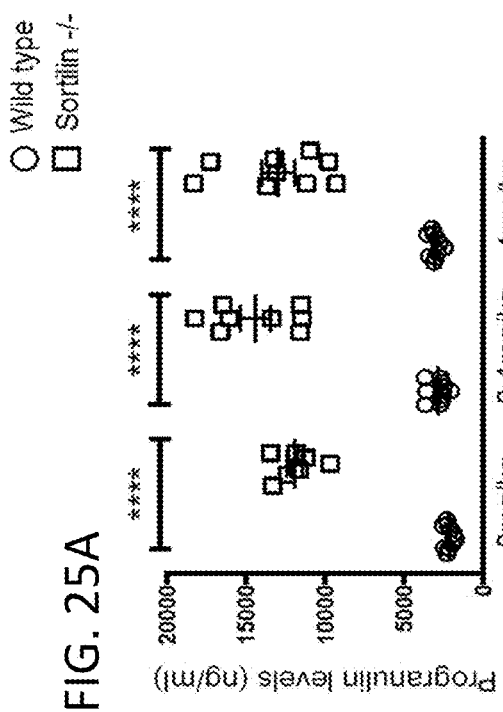
FIG. 25B depicts number of peritoneal neutrophils after 6 hours of LPS treatment of wild type mice and Sortilin knock-out (Sortilin -/-) mice.
Figure 25C:
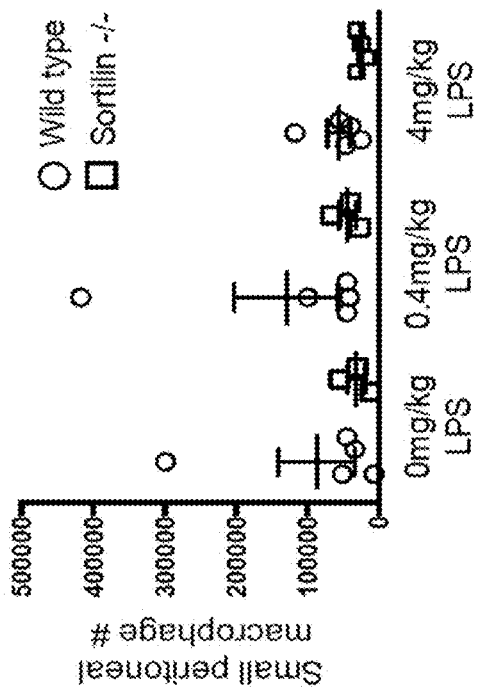
FIG. 25C depicts number of large peritoneal macrophages after 6 hours of LPS treatment of wild type mice and Sortilin knock-out (Sortilin -/-) mice.
Figure 25D:
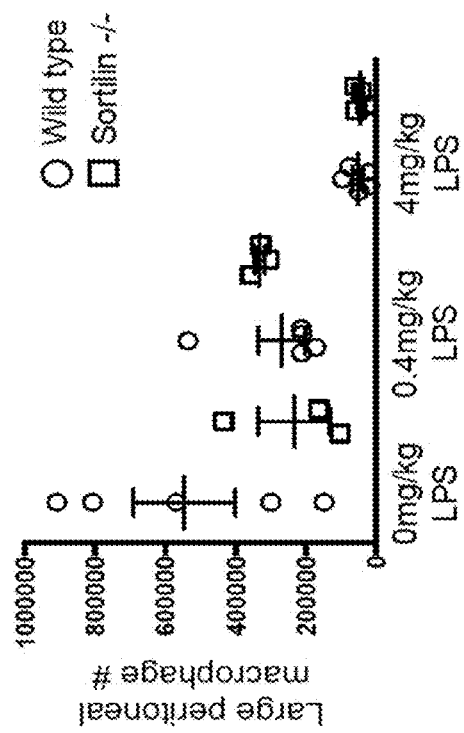
FIG. 25D depicts number of small peritoneal macrophages after 6 hours of LPS treatment of wild type mice and Sortilin knock-out (Sortilin -/-) mice. The results depict increased levels of progranulin; however, the number of peritoneal neutrophils, large peritoneal macrophages, and small peritoneal macrophages were not significantly different. Open circles represent wild type mice and open squares represent Sortilin knock-out mice. n=8-10 mice/group. *$p<0.01$, $p<0.001$, *$p<0.001$, and ****$p<0.0001$ by 1-way ANOVA with Tukey's multiple comparisons test.
Figure 26B:
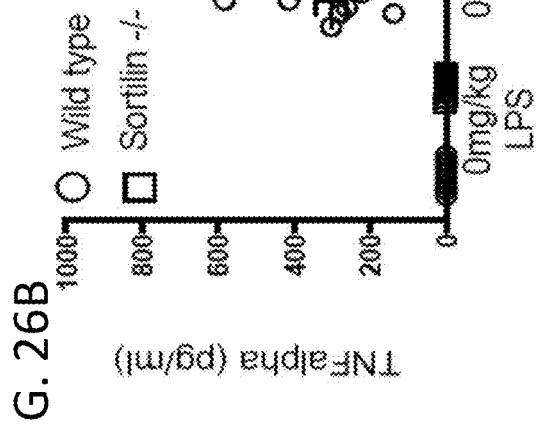
FIG. 26B depicts serum levels of TNFalpha after 1.5 hours of LPS treatment wild type mice and Sortilin knock-out (Sortilin -/-) mice.
Figure 26D:
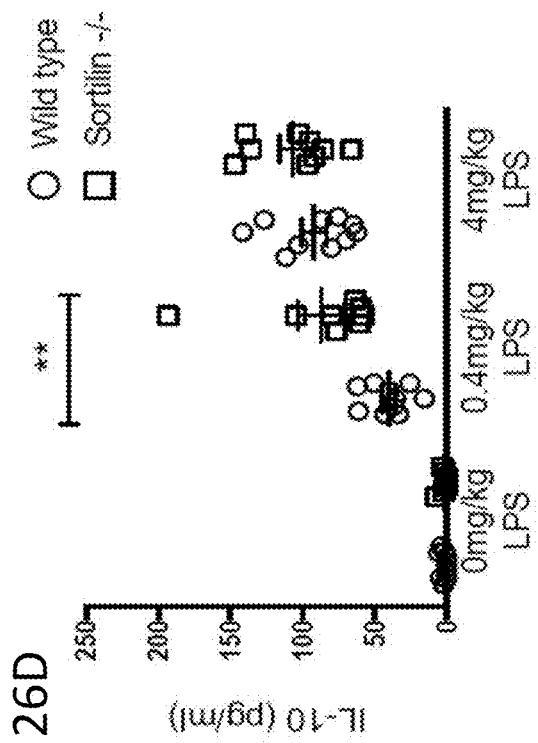
FIG. 26D depicts serum levels of IL-10 after 1.5 hours of LPS treatment wild type mice and Sortilin knock-out (Sortilin -/-) mice.
Figure 26A:
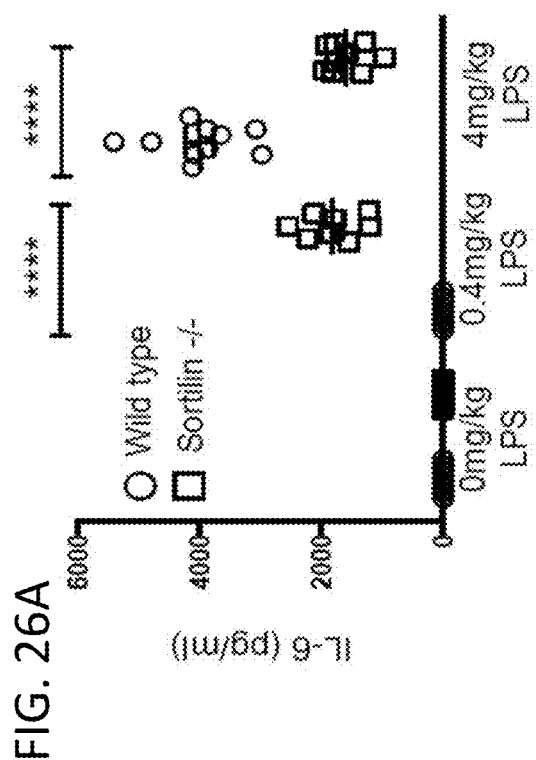
FIG. 26A depicts serum levels of IL-6 after 1.5 hours of LPS treatment wild type mice and Sortilin knock-out (Sortilin -/-) mice.
Figure 26C:
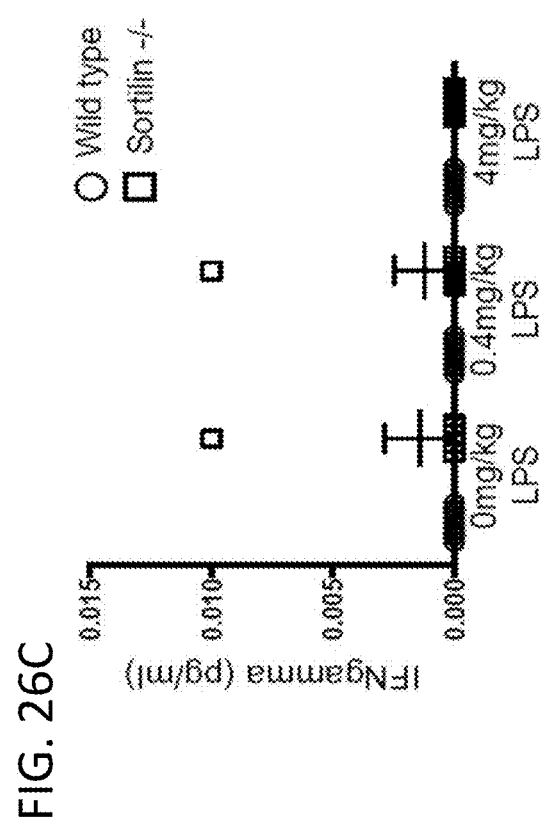
FIG. 26C depicts serum levels of IFNgamma after 1.5 hours of LPS treatment wild type mice and Sortilin knock-out (Sortilin -/-) mice.
Figure 26F:
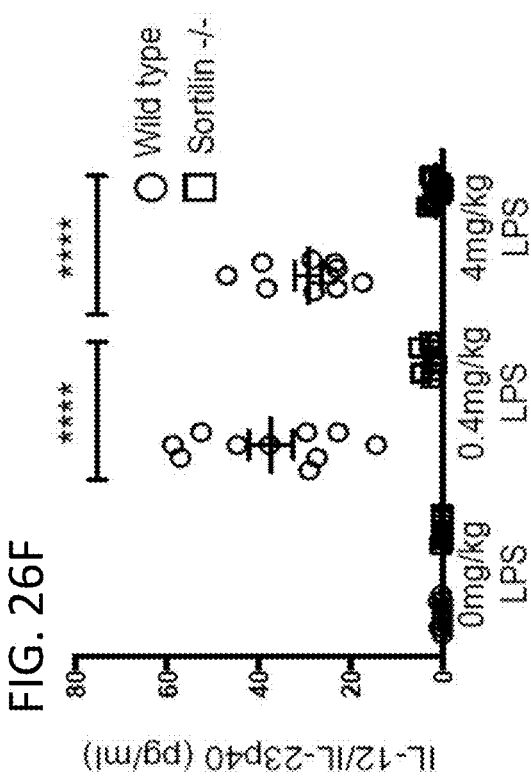
FIG. 26F depicts serum levels of IL-12/IL-23p40 after 1.5 hours of LPS treatment wild type mice and Sortilin knock-out (Sortilin -/-) mice.
Figure 26E:
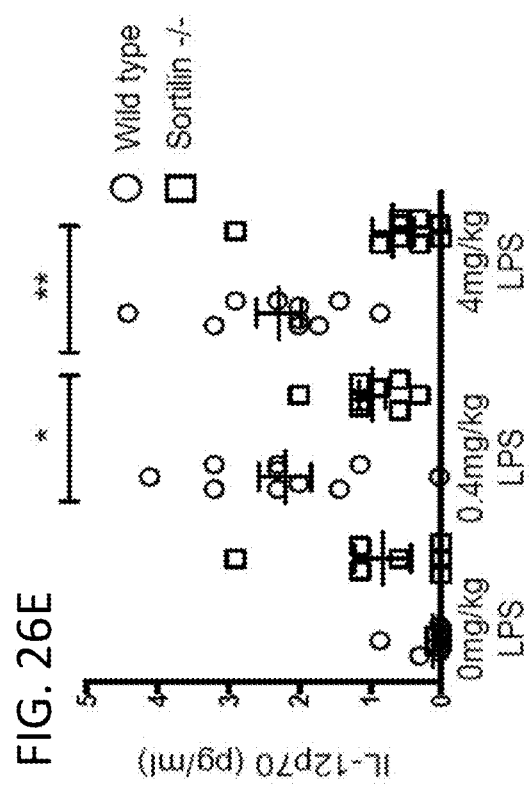
FIG. 26E depicts serum levels of IL-12p70 after 1.5 hours of LPS treatment wild type mice and Sortilin knock-out (Sortilin -/-) mice.
Figure 26H:
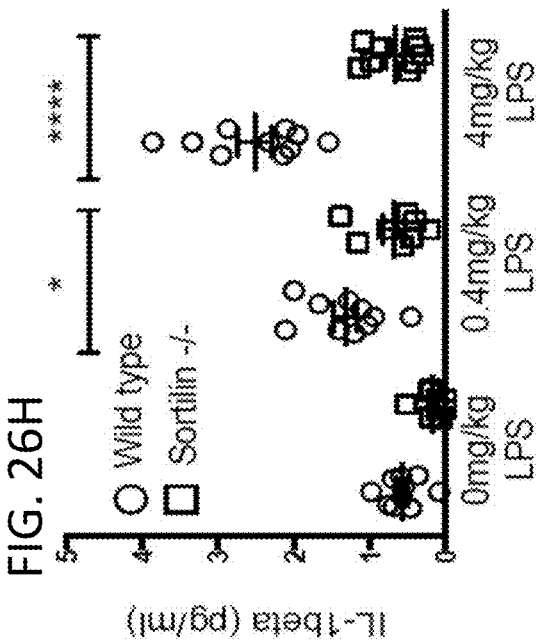
FIG. 26H depicts serum levels of IL-1beta after 1.5 hours of LPS treatment wild type mice and Sortilin knock-out (Sortilin -/-) mice. Open circles represent wild type mice and open squares represent Sortilin knock-out mice, n=8-10 mice/group. *$p<0.01$, $p<0.001$, *$p<0.001$, and ****$p<0.0001$. by 1-way ANOVA with Tukey's multiple comparisons test.
Figure 26G:
FIG. 26G depicts serum levels of IL-1alpha after 1.5 hours of LPS treatment wild type mice and Sortilin knock-out (Sortilin -/-) mice.
Figure 28A:
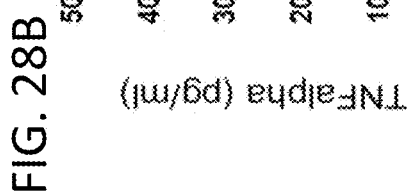
FIG. 28A depicts serum levels of IL-6 after 6 hours of LPS treatment wild type mice and Sortilin knock-out (Sortilin −/−) mice.
Figure 28B:
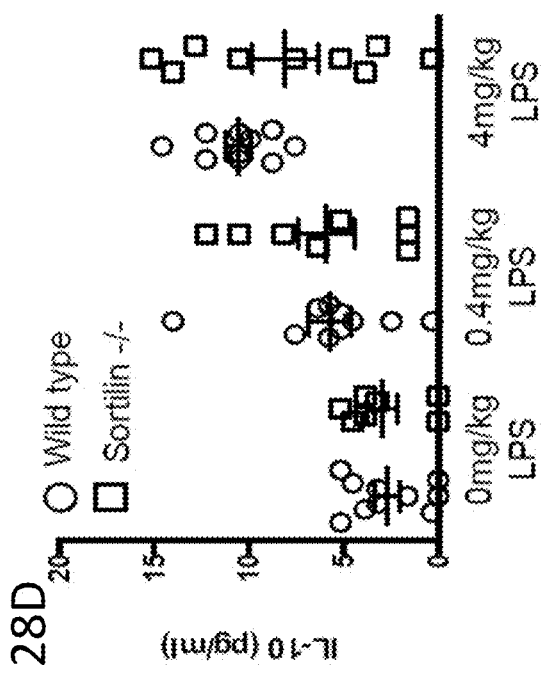
FIG. 28B depicts serum levels of TNFalpha after 6 hours of LPS treatment wild type mice and Sortilin knock-out (Sortilin −/−) mice.
Figure 28C:
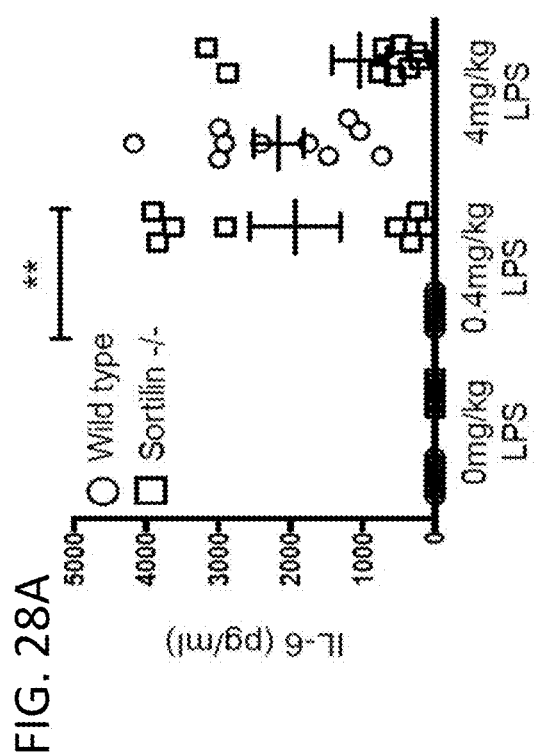
FIG. 28C depicts serum levels of IFNgamma after 6 hours of LPS treatment wild type mice and Sortilin knock-out (Sortilin −/−) mice.
Figure 28D:
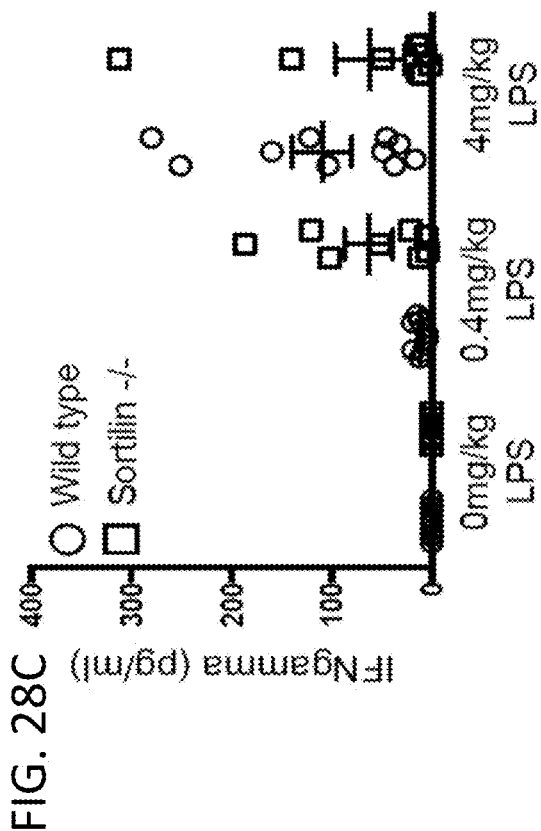
FIG. 28D depicts serum levels of IL-10 after 6 hours of LPS treatment wild type mice and Sortilin knock-out (Sortilin −/−) mice.
Figure 28F:
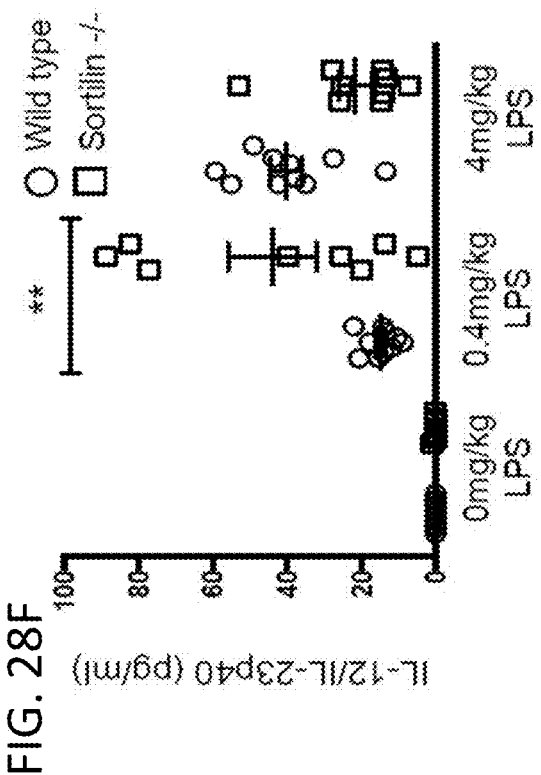
FIG. 28F depicts serum levels of IL-12/IL-23p40 after 6 hours of LPS treatment wild type mice and Sortilin knock-out (Sortilin −/−) mice.
Figure 28E:
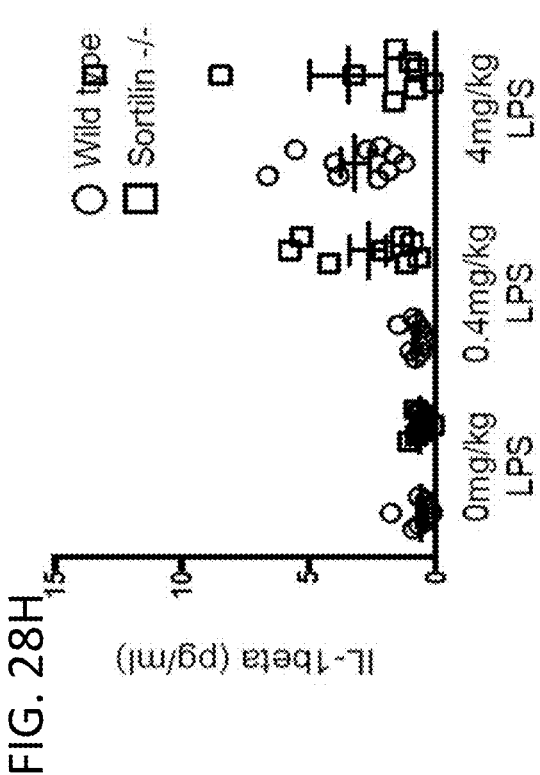
FIG. 28E depicts serum levels of IL-12p70 after 6 hours of LPS treatment wild type mice and Sortilin knock-out (Sortilin −/−) mice.
Figure 28H:
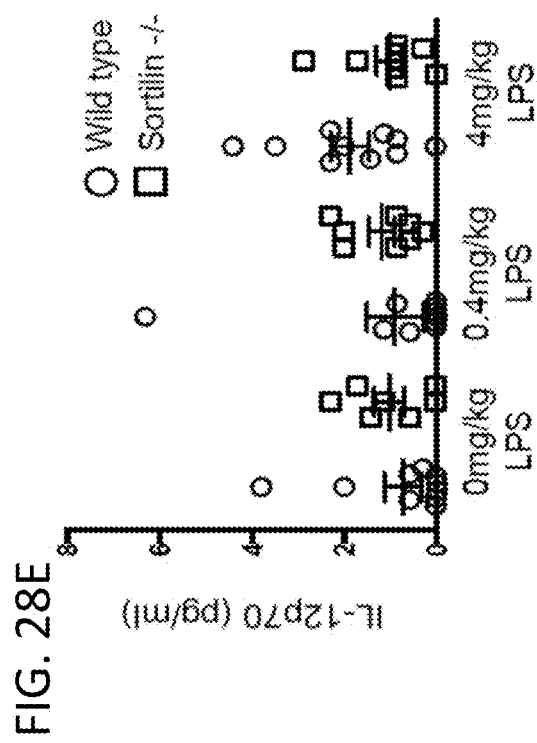
FIG. 28H depicts serum levels of IL-1beta after 6 hours of LPS treatment wild type mice and Sortilin knock-out (Sortilin −/−) mice. Open circles represent wild type mice and open squares represent Sortilin knock-out mice. n=8-10 mice/group. *$p<0.01$, $p<0.001$, *$p<0.001$, and ****$p<0.0001$ by 1-way ANOVA with Tukey's multiple comparisons test.
Figure 28G:
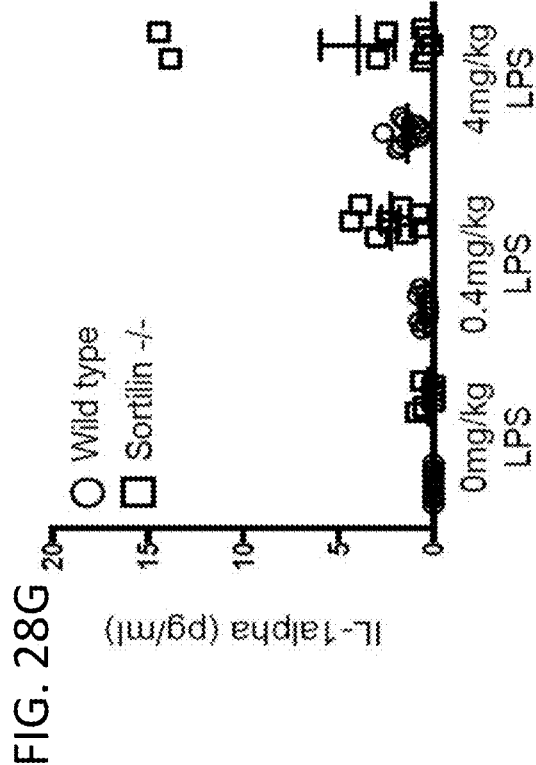
FIG. 28G depicts serum levels of IL-1 alpha after 6 hours of LPS treatment wild type mice and Sortilin knock-out (Sortilin −/−) mice.

The results in FIG. 25A indicate that serum levels of progranulin were elevated in Sortilin knock-out mice, as compared to wild type mice after 6 hours of LPS administration. Additionally, intraperitoneal injection of 0 mg/kg, 0.4 mg/kg, or 4 mg/kg LPS had no effect on the serum levels progranulin (FIG. 25A). As shown in FIG. 25b-25D, there was no change in the number of neutrophils, large peritoneal (CD11b+F4/80hi) macrophages, or small peritoneal (CD11b+F4/80lo) macrophages.

As shown in FIG. 26A-26H, serum levels of pro-inflammatory cytokines IL-6, IL12p70, IL12p40, and IL-1beta were decreased in Sortilin knock-out mice after 1.5 hours of treatment with 4 mg/kg LPS, as compared to wild type mice. An increase in serum levels of the anti-inflammatory cytokine IL-10 was seen in Sortilin knock-out mice treated with 0.4 mg/kg LPS (FIG. 26D'. As shown in FIG. 27A-27E, serum levels of chemokines, such as CXCL1, CCL2, CCL3, and CCL5, which are responsible for the recruitment of monocytes, dendritic cells, T cells, neutrophils, and other granulocytes, were decreased in Sortilin knock-out mice following treatment for 1.5 hours with LPS.

As shown in FIG. 28A-28H, Sortilin knock-out mice treated for 6 hours with 0.4 mg/kg LPS showed a modest increase in serum levels of IL-6, and Sortilin knock-out mice treated for 6 hours with 4 mg/kg LPS showed a decrease in serum levels of TNFalpha levels. As shown in FIG. 29A-29E, serum levels of CCL2, CCL3, and CCL4 were decreased in Sortilin knock-out mice treated for 6 hours with LPS.

The results indicate that the increased serum levels of progranulin in Sortilin knock-out mice may underlie the beneficial effect in the dampening of the inflammatory response to LPS. Anti-Sortilin antibodies that block Sortilin have the ability to raise progranulin levels, which also occurs in the Sortilin knock-out mice. Accordingly, it is thought that the anti-Sortilin antibodies of the present disclosure may have overlapping actions with Sortilin knock-out mice, including reduction of pro-inflammatory cytokines IL-6, TNFalpha, IL-12p40, and IL-1beta; as well and chemokines CXCL1, CCL2, CCL3, CCL4, and CCL5. It is further believed that the anti-Sortilin antibodies may also induce further activities induced by the reduction or inhibition of Sortilin, such as that of Sortilin knock-out mice.

Figure 30:
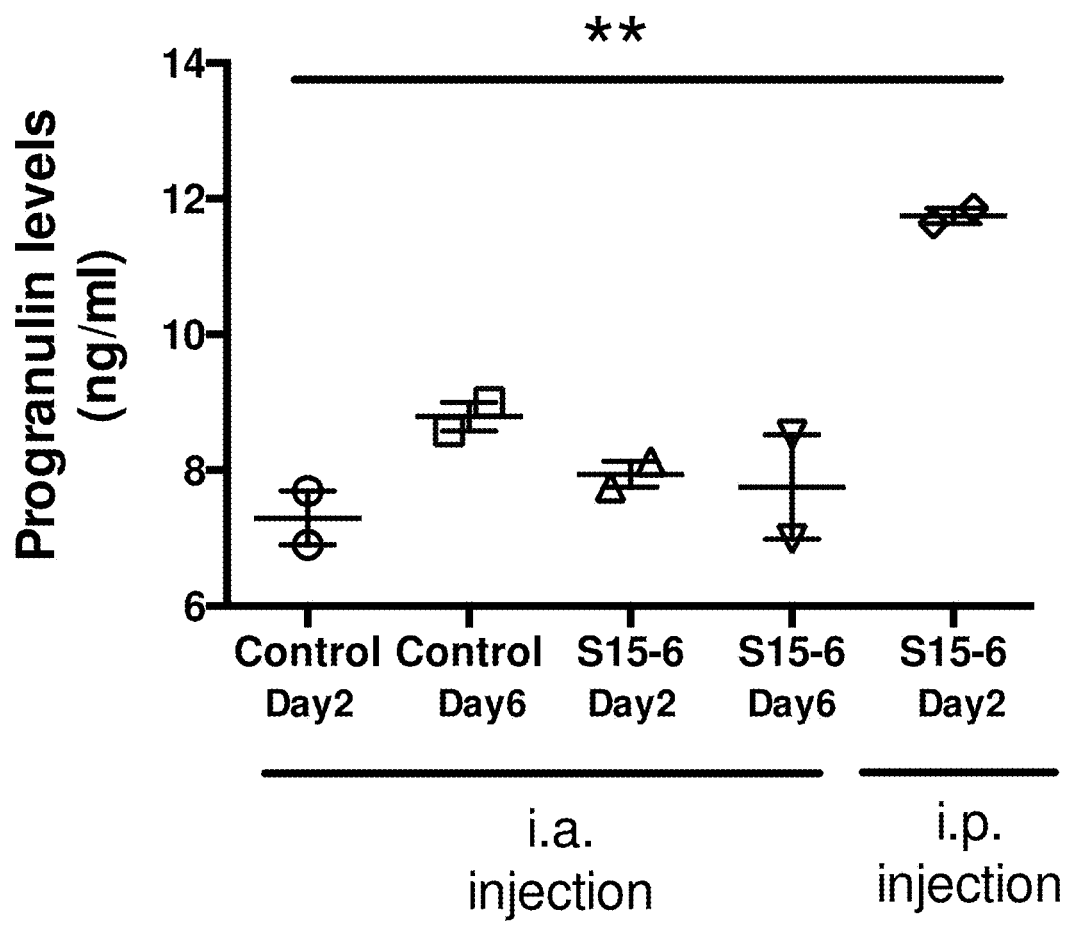
FIG. 30 depicts Progranulin (PGRN) protein levels in cerebrospinal fluid (CSF) samples obtained from rats two days or six days after intra-articular (i.a.) injection into the knee or intraperitoneal (i.p.) injection of anti-Sortilin antibody S-15-6 or control antibody. n=2 rats/group. **$p<0.001$ by 1-way ANOVA.

Example 30: Injection of Anti-Sortilin Antibodies into Periphery of Rats Increases Levels of Progranulin in Cerebrospinal Fluid of Rats Progranulin (PGRN) levels were measured from the cerebrospinal fluid (CSF) of rats injected with one dose of 1 mg/kg of anti-Sortilin antibody S-15-6 or control antibody delivered by intra-articular (i.a.) injection into the knee or by intraperitoneal (i.p.) injection. CSF samples were collected 2 or 6 days following injection. Progranluin levels were elevated following i.p. injection of S-15-6 as compared to rats treated with control antibody or treated by intra-articular injection of S-15-6 (FIG. 30). n=2 rats/group. *p<0.001 by 1-way ANOVA.

What is claimed is:

1. An isolated nucleic acid comprising a nucleic acid sequence encoding an anti-Sortilin antibody, wherein the anti-Sortilin antibody comprises an HVR-L1 comprising the amino acid sequence of SEQ ID NO: 9, an HVR-L2 comprising the amino acid sequence of SEQ ID NO: 29, an HVR-L3 comprising the amino acid sequence of SEQ ID NO: 55, an HVR-H1 comprising the amino acid sequence of SEQ ID NO: 520, an HVR-H2 comprising the amino acid sequence of SEQ ID NO: 533, and an HVR-H3 comprising the amino acid sequence of SEQ ID NO: 553.

2. A vector comprising the nucleic acid of claim 1.

3. An isolated host cell comprising the vector of claim 2.

4. A method of producing an anti-Sortilin antibody, comprising culturing the host cell of claim 3 under conditions suitable for production of the anti-Sortilin antibody by the host cell.

5. The method of claim 4, further comprising recovering the anti-Sortilin antibody produced by the host cell.

6. The isolated nucleic acid of claim 1, wherein the anti-Sortilin antibody increases extracellular levels of Progranulin and decreases cellular levels of Sortilin.

7. The isolated nucleic acid of claim 6, wherein the decrease in cellular levels of Sortilin is a decrease in cell surface levels of Sortilin, a decrease in intracellular levels of Sortilin, a decrease in total levels of Sortilin, or any combination thereof.

8. The isolated nucleic acid of claim 1, wherein the anti-Sortilin antibody induces Sortilin degradation, Sortilin cleavage, Sortilin internalization, or Sortilin down regulation.

9. The isolated nucleic acid of claim 1, wherein the anti-Sortilin antibody inhibits the interaction between Sortilin expressed on a cell and Progranulin.

10. The isolated nucleic acid of claim 1, wherein the anti-Sortilin antibody inhibits interaction between Sortilin and pro-nerve growth factor (pro-NGF).

11. The isolated nucleic acid of claim 1, wherein the anti-Sortilin antibody binds specifically to human Sortilin, mouse Sortilin, or both human Sortilin and mouse Sortilin.

12. The isolated nucleic acid of claim 11, wherein the anti-Sortilin antibody binds with a dissociation constant ($K_D$) for human Sortilin that ranges from about 0.005 nM to about 100 nM.

13. The isolated nucleic acid of claim 11, wherein the anti-Sortilin antibody binds with a dissociation constant ($K_D$) for mouse Sortilin that ranges from about 0.005 nM to about 100 nM.

14. The isolated nucleic acid of claim 1, wherein the anti-Sortilin antibody is a human antibody, a humanized antibody, a bispecific antibody, a monoclonal antibody, a multivalent antibody, a conjugated antibody, or a chimeric antibody.

15. The isolated nucleic acid of claim 14, wherein the anti-Sortilin antibody is a multivalent antibody recognizing a second antigen.

16. The isolated nucleic acid of claim 15, wherein the second antigen is an antigen facilitating transport across the blood-brain-barrier.

17. The isolated nucleic acid of claim 16, wherein the second antigen is selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, transmembrane domain protein 30A (TMEM 30(A)), a protein transduction domain, TAT, Syn-B, penetratin, a poly-arginine peptide, an angiopep peptide, and ANG1005.

18. The isolated nucleic acid of claim 1, wherein the anti-Sortilin antibody is an antibody fragment, and wherein the antibody fragment is an Fab, Fab', Fab'-SH, F(ab')$_2$, Fv, or scFv fragment.

19. The isolated nucleic acid of claim 1, wherein the anti-Sortilin antibody is an antibody fragment that binds to an epitope comprising amino acid residues on human Sortilin or a mammalian Sortilin protein.

20. The isolated nucleic acid of claim 1, wherein the anti-Sortilin antibody has an IgG1 or IgG4 isotype.

21. The isolated nucleic acid of claim 20, wherein:
(a) the anti-Sortilin antibody has a human IgG1 isotype and comprises one or more amino acid substitutions in the Fc region at a residue position selected from the group consisting of: N297A, N297Q, D265A, L234A, L235A, C226S, C229S, P238S, E233P, L234V, P238A, A327Q, A327G, P329A, K322A, L234F, L235E, P331S, T394D, A330L, M252Y, S254T, T256E, and any combination thereof, wherein the numbering of the residues is according to EU numbering; or
(b) the anti-Sortilin antibody has a human IgG4 isotype and comprises one or more amino acid substitutions in the Fc region at a residue position selected from the group consisting of: E233P, F234V, L234A/F234A, L235A, G237A, E318A, S228P, L236E, S241P, L248E, T394D, M252Y, S254T, T256E, N297A, N297Q, and any combination thereof, wherein the numbering of the residues is according to EU numbering.

22. The isolated nucleic acid of claim 20, wherein the anti-Sortilin antibody has a human IgG1 isotype and comprises an amino acid substitution in the Fc region at residue positions L234A, L235A, and P331S, wherein the numbering of the residues is according to EU numbering.

23. The isolated nucleic acid of claim 20, wherein the anti-Sortilin antibody has a human IgG4 isotype and comprises an amino acid substitution at residue positions S228P, F234A, and L235A, wherein the numbering of the residue position is according to EU numbering.

24. An isolated nucleic acid comprising a nucleic acid sequence encoding an anti-Sortilin antibody, wherein the anti-Sortilin antibody comprises a light chain variable domain comprising the amino acid sequence of SEQ ID NO: 343 and a heavy chain variable domain comprising the amino acid sequence of SEQ ID NO: 648.

25. A vector comprising the nucleic acid of claim 24.

26. An isolated host cell comprising the vector of claim 25.

27. A method of producing an anti-Sortilin antibody, comprising culturing the host cell of claim 26 under conditions suitable for production of the anti-Sortilin antibody by the host cell.

28. The method of claim 27, further comprising recovering the anti-Sortilin antibody produced by the host cell.

29. An isolated nucleic acid comprising a nucleic acid sequence encoding an anti-Sortilin antibody, wherein the anti-Sortilin antibody comprises a light chain variable domain comprising the amino acid sequence of SEQ ID NO: 343 and a heavy chain variable domain comprising the amino acid sequence of SEQ ID NO: 648, wherein the anti-Sortilin antibody has an IgG1 isotype and comprises an amino acid substitution in the Fc region at residue positions L234A, L235A and P331S, wherein the numbering of the residues is according to EU numbering.

30. A vector comprising the nucleic acid of claim 29.

31. An isolated host cell comprising the vector of claim 30.

32. A method of producing an anti-Sortilin antibody, comprising culturing the host cell of claim 31 under conditions suitable for production of the anti-Sortilin antibody by the host cell.

33. The method of claim 32, further comprising recovering the anti-Sortilin antibody produced by the host cell.

34. An isolated nucleic acid comprising a nucleic acid sequence encoding an anti-Sortilin antibody, wherein
(a) the anti-Sortilin antibody comprises an HVR-L1 comprising the amino acid sequence of SEQ ID NO: 9, an HVR-L2 comprising the amino acid sequence of SEQ ID NO: 29, and an HVR-L3 comprising the amino acid sequence of SEQ ID NO: 55; or
(b) the anti-Sortilin antibody comprises a light chain variable domain comprising the amino acid sequence of SEQ ID NO: 343.

35. A vector comprising the nucleic acid of claim 34.

36. An isolated host cell comprising the vector of claim 35.

37. A method of producing an anti-Sortilin antibody, comprising culturing the host cell of claim 36 under conditions suitable for production of the anti-Sortilin antibody by the host cell.

38. The method of claim 37, further comprising recovering the anti-Sortilin antibody produced by the host cell.

39. An isolated nucleic acid comprising a nucleic acid sequence encoding an anti-Sortilin antibody, wherein
(a) the anti-Sortilin antibody comprises an HVR-H1 comprising the amino acid sequence of SEQ ID NO: 520, an HVR-H2 comprising the amino acid sequence of SEQ ID NO: 533, and an HVR-H3 comprising the amino acid sequence of SEQ ID NO: 553; or
(b) the anti-Sortilin antibody comprises a heavy chain variable domain comprising the amino acid sequence of SEQ ID NO: 648.

40. A vector comprising the nucleic acid of claim 39.

41. An isolated host cell comprising the vector of claim 40.

42. A method of producing an anti-Sortilin antibody, comprising culturing the host cell of claim 41 under conditions suitable for production of the anti-Sortilin antibody by the host cell.

43. The method of claim 42, further comprising recovering the anti-Sortilin antibody produced by the host cell.

44. The isolated nucleic acid of claim 39, wherein the anti-Sortilin antibody has an IgG1 isotype and comprises an amino acid substitution in the Fc region at residue positions L234A, L235A and P331S, wherein the numbering of the residues is according to EU numbering.

45. An isolated host cell comprising nucleic acid encoding an anti-Sortilin antibody, wherein the host cell comprises:
 (a) a first nucleic acid encoding a polypeptide comprising a light chain variable domain, wherein the light chain variable domain comprises:
   i. an HVR-L1 comprising the amino acid sequence of SEQ ID NO: 9, an HVR-L2 comprising the amino acid sequence of SEQ ID NO: 29, and an HVR-L3 comprising the amino acid sequence of SEQ ID NO: 55; or
   ii. the amino acid sequence of SEQ ID NO: 343; and
 (b) a second nucleic acid encoding a polypeptide comprising a heavy chain variable domain, wherein the heavy chain variable domain comprises:
   i. an HVR-H1 comprising the amino acid sequence of SEQ ID NO: 520, an HVR-H2 comprising the amino acid sequence of SEQ ID NO: 533, and an HVR-H3 comprising the amino acid sequence of SEQ ID NO: 553; or
   ii. the amino acid sequence of SEQ ID NO: 648.

46. A method of producing an anti-Sortilin antibody, comprising culturing the host cell of claim 45 under conditions suitable for production of the anti-Sortilin antibody by the host cell.

47. The method of claim 46, further comprising recovering the anti-Sortilin antibody produced by the host cell.

48. The isolated host cell of claim 45, wherein the anti-Sortilin antibody has an IgG1 isotype and comprises an amino acid substitution in the Fc region at residue positions L234A, L235A and P331S, wherein the numbering of the residues is according to EU numbering.

* * * * *

UNITED STATES PATENT AND TRADEMARK OFFICE
CERTIFICATE OF CORRECTION

PATENT NO. : 11,186,645 B2
APPLICATION NO. : 16/741658
DATED : November 30, 2021
INVENTOR(S) : Rosenthal et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 33 days.

Signed and Sealed this
Seventh Day of February, 2023

Katherine Kelly Vidal
*Director of the United States Patent and Trademark Office*

SEQUENCE LISTING

```
<160> NUMBER OF SEQ ID NOS: 714

<210> SEQ ID NO 1
<211> LENGTH: 830
<212> TYPE: PRT
<213> ORGANISM: Artificial Sequence
<220> FEATURE:
<223> OTHER INFORMATION: Synthetic Construct

<400> SEQUENCE: 1

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
```

```
            180                 185                 190
Arg Gly Gly Arg Ile Phe Arg Ser Ser Asp Phe Ala Lys Asn Phe Val
            195                 200                 205
Gln Thr Asp Leu Pro Phe His Pro Leu Thr Gln Met Met Tyr Ser Pro
            210                 215                 220
Gln Asn Ser Asp Tyr Leu Leu Ala Leu Ser Thr Glu Asn Gly Leu Trp
225                 230                 235                 240
Val Ser Lys Asn Phe Gly Gly Lys Trp Glu Glu Ile His Lys Ala Val
            245                 250                 255
Cys Leu Ala Lys Trp Gly Ser Asp Asn Thr Ile Phe Phe Thr Thr Tyr
            260                 265                 270
Ala Asn Gly Ser Cys Lys Ala Asp Leu Gly Ala Leu Glu Leu Trp Arg
            275                 280                 285
Thr Ser Asp Leu Gly Lys Ser Phe Lys Thr Ile Gly Val Lys Ile Tyr
            290                 295                 300
Ser Phe Gly Leu Gly Gly Arg Phe Leu Phe Ala Ser Val Met Ala Asp
305                 310                 315                 320
Lys Asp Thr Thr Arg Arg Ile His Val Ser Thr Asp Gln Gly Asp Thr
            325                 330                 335
Trp Ser Met Ala Gln Leu Pro Ser Val Gly Gln Glu Gln Phe Tyr Ser
            340                 345                 350
Ile Leu Ala Ala Asn Asp Asp Met Val Phe Met His Val Asp Glu Pro
            355                 360                 365
Gly Asp Thr Gly Phe Gly Thr Ile Phe Thr Ser Asp Asp Arg Gly Ile
            370                 375                 380
Val Tyr Ser Lys Ser Leu Asp Arg His Leu Tyr Thr Thr Thr Gly Gly
385                 390                 395                 400
Glu Thr Asp Phe Thr Asn Val Thr Ser Leu Arg Gly Val Tyr Ile Thr
            405                 410                 415
Ser Val Leu Ser Glu Asp Asn Ser Ile Gln Thr Met Ile Thr Phe Asp
            420                 425                 430
Gln Gly Gly Arg Trp Thr His Leu Arg Lys Pro Glu Asn Ser Glu Cys
            435                 440                 445
Asp Ala Thr Ala Lys Asn Lys Asn Glu Cys Ser Leu His Ile His Ala
            450                 455                 460
Ser Tyr Ser Ile Ser Gln Lys Leu Asn Val Pro Met Ala Pro Leu Ser
465                 470                 475                 480
Glu Pro Asn Ala Val Gly Ile Val Ile Ala His Gly Ser Val Gly Asp
            485                 490                 495
Ala Ile Ser Val Met Val Pro Asp Val Tyr Ile Ser Asp Asp Gly Gly
            500                 505                 510
Tyr Ser Trp Thr Lys Met Leu Glu Gly Pro His Tyr Tyr Thr Ile Leu
            515                 520                 525
Asp Ser Gly Gly Ile Ile Val Ala Ile Glu His Ser Ser Arg Pro Ile
            530                 535                 540
Asn Val Ile Lys Phe Ser Thr Asp Glu Gly Gln Cys Trp Gln Thr Tyr
545                 550                 555                 560
Thr Phe Thr Arg Asp Pro Ile Tyr Phe Thr Gly Leu Ala Ser Glu Pro
            565                 570                 575
Gly Ala Arg Ser Met Asn Ile Ser Ile Trp Gly Phe Thr Glu Ser Phe
            580                 585                 590
Leu Thr Ser Gln Trp Val Ser Tyr Thr Ile Asp Phe Lys Asp Ile Leu
            595                 600                 605
```

```
Glu Arg Asn Cys Glu Glu Lys Asp Tyr Thr Ile Trp Leu Ala His Ser
    610                 615                 620
Thr Asp Pro Glu Asp Tyr Glu Asp Gly Cys Ile Leu Gly Tyr Lys Glu
625                 630                 635                 640
Gln Phe Leu Arg Leu Arg Lys Ser Ser Val Cys Gln Asn Gly Arg Asp
                645                 650                 655
Tyr Val Val Thr Lys Gln Pro Ser Ile Cys Leu Cys Ser Leu Glu Asp
                660                 665                 670
Phe Leu Cys Asp Phe Gly Tyr Tyr Arg Pro Glu Asn Asp Ser Lys Cys
                675                 680                 685
Val Glu Gln Pro Glu Leu Lys Gly His Asp Leu Glu Phe Cys Leu Tyr
    690                 695                 700
Gly Arg Glu Glu His Leu Thr Thr Asn Gly Tyr Arg Lys Ile Pro Gly
705                 710                 715                 720
Asp Lys Cys Gln Gly Gly Val Asn Pro Val Arg Glu Val Lys Asp Leu
                725                 730                 735
Lys Lys Lys Cys Thr Ser Asn Phe Leu Ser Pro Glu Lys Gln Asn Ser
                740                 745                 750
Lys Ser Asn Ser Val Pro Ile Ile Leu Ala Ile Val Gly Leu Met Leu
    755                 760                 765
Val Thr Val Val Ala Gly Val Leu Ile Val Lys Lys Tyr Val Cys Gly
770                 775                 780
Gly Arg Phe Leu Val His Arg Tyr Ser Val Leu Gln Gln His Ala Glu
785                 790                 795                 800
Ala Asn Gly Val Asp Gly Val Asp Ala Leu Asp Thr Ala Ser His Thr
                805                 810                 815
Asn Lys Ser Gly Tyr His Asp Asp Ser Asp Glu Asp Leu Leu
                820                 825                 830

<210> SEQ ID NO 2
<211> LENGTH: 825
<212> TYPE: PRT
<213> ORGANISM: Artificial Sequence
<220> FEATURE:
<223> OTHER INFORMATION: Synthetic Construct

<400> SEQUENCE: 2

Met Glu Arg Pro Arg Gly Ala Ala Asp Gly Leu Leu Arg Trp Pro Leu
1               5                   10                  15
Gly Leu Leu Leu Leu Leu Gln Leu Leu Pro Pro Ala Ala Val Gly Gln
                20                  25                  30
Asp Arg Leu Asp Ala Pro Pro Pro Ala Pro Pro Leu Leu Arg Trp
                35                  40                  45
Ala Gly Pro Val Gly Val Ser Trp Gly Leu Arg Ala Ala Pro Gly
    50                  55                  60
Gly Pro Val Pro Arg Ala Gly Arg Trp Arg Arg Gly Ala Pro Ala Glu
65                  70                  75                  80
Asp Gln Asp Cys Gly Arg Leu Pro Asp Phe Ile Ala Lys Leu Thr Asn
                85                  90                  95
Asn Thr His Gln His Val Phe Asp Leu Ser Gly Ser Val Ser Leu
                100                 105                 110
Ser Trp Val Gly Asp Ser Thr Gly Val Ile Leu Val Leu Thr Thr Phe
            115                 120                 125
Gln Val Pro Leu Val Ile Val Ser Phe Gly Gln Ser Lys Leu Tyr Arg
            130                 135                 140
```

```
Ser Glu Asp Tyr Gly Lys Asn Phe Lys Asp Ile Thr Asn Leu Ile Asn
145                 150                 155                 160

Asn Thr Phe Ile Arg Thr Glu Phe Gly Met Ala Ile Gly Pro Glu Asn
                165                 170                 175

Ser Gly Lys Val Ile Leu Thr Ala Glu Val Ser Gly Ser Arg Gly
            180                 185                 190

Gly Arg Val Phe Arg Ser Ser Asp Phe Ala Lys Asn Phe Val Gln Thr
        195                 200                 205

Asp Leu Pro Phe His Pro Leu Thr Gln Met Met Tyr Ser Pro Gln Asn
    210                 215                 220

Ser Asp Tyr Leu Leu Ala Leu Ser Thr Glu Asn Gly Leu Trp Val Ser
225                 230                 235                 240

Lys Asn Phe Gly Glu Lys Trp Glu Glu Ile His Lys Ala Val Cys Leu
                245                 250                 255

Ala Lys Trp Gly Pro Asn Asn Ile Ile Phe Phe Thr Thr His Val Asn
            260                 265                 270

Gly Ser Cys Lys Ala Asp Leu Gly Ala Leu Glu Leu Trp Arg Thr Ser
        275                 280                 285

Asp Leu Gly Lys Thr Phe Lys Thr Ile Gly Val Lys Ile Tyr Ser Phe
    290                 295                 300

Gly Leu Gly Gly Arg Phe Leu Phe Ala Ser Val Met Ala Asp Lys Asp
305                 310                 315                 320

Thr Thr Arg Arg Ile His Val Ser Thr Asp Gln Gly Asp Thr Trp Ser
                325                 330                 335

Met Ala Gln Leu Pro Ser Val Gly Gln Glu Gln Phe Tyr Ser Ile Leu
            340                 345                 350

Ala Ala Asn Glu Asp Met Val Phe Met His Val Asp Glu Pro Gly Asp
        355                 360                 365

Thr Gly Phe Gly Thr Ile Phe Thr Ser Asp Asp Arg Gly Ile Val Tyr
    370                 375                 380

Ser Lys Ser Leu Asp Arg His Leu Tyr Thr Thr Thr Gly Gly Glu Thr
385                 390                 395                 400

Asp Phe Thr Asn Val Thr Ser Leu Arg Gly Val Tyr Ile Thr Ser Thr
                405                 410                 415

Leu Ser Glu Asp Asn Ser Ile Gln Ser Met Ile Thr Phe Asp Gln Gly
            420                 425                 430

Gly Arg Trp Glu His Leu Arg Lys Pro Glu Asn Ser Lys Cys Asp Ala
        435                 440                 445

Thr Ala Lys Asn Lys Asn Glu Cys Ser Leu His Ile His Ala Ser Tyr
    450                 455                 460

Ser Ile Ser Gln Lys Leu Asn Val Pro Met Ala Pro Leu Ser Glu Pro
465                 470                 475                 480

Asn Ala Val Gly Ile Val Ile Ala His Gly Ser Val Gly Asp Ala Ile
                485                 490                 495

Ser Val Met Val Pro Asp Val Tyr Ile Ser Asp Asp Gly Gly Tyr Ser
            500                 505                 510

Trp Ala Lys Met Leu Glu Gly Pro His Tyr Tyr Thr Ile Leu Asp Ser
        515                 520                 525

Gly Gly Ile Ile Val Ala Ile Glu His Ser Asn Arg Pro Ile Asn Val
    530                 535                 540

Ile Lys Phe Ser Thr Asp Glu Gly Gln Cys Trp Gln Ser Tyr Val Phe
545                 550                 555                 560
```

```
Thr Gln Glu Pro Ile Tyr Phe Thr Gly Leu Ala Ser Glu Pro Gly Ala
                565                 570                 575

Arg Ser Met Asn Ile Ser Ile Trp Gly Phe Thr Glu Ser Phe Ile Thr
            580                 585                 590

Arg Gln Trp Val Ser Tyr Thr Val Asp Phe Lys Asp Ile Leu Glu Arg
        595                 600                 605

Asn Cys Glu Glu Asp Asp Tyr Thr Thr Trp Leu Ala His Ser Thr Asp
    610                 615                 620

Pro Gly Asp Tyr Lys Asp Gly Cys Ile Leu Gly Tyr Lys Glu Gln Phe
625                 630                 635                 640

Leu Arg Leu Arg Lys Ser Ser Val Cys Gln Asn Gly Arg Asp Tyr Val
                645                 650                 655

Val Ala Lys Gln Pro Ser Val Cys Pro Cys Ser Leu Glu Asp Phe Leu
            660                 665                 670

Cys Asp Phe Gly Tyr Phe Arg Pro Glu Asn Ala Ser Glu Cys Val Glu
        675                 680                 685

Gln Pro Glu Leu Lys Gly His Glu Leu Glu Phe Cys Leu Tyr Gly Lys
    690                 695                 700

Glu Glu His Leu Thr Thr Asn Gly Tyr Arg Lys Ile Pro Gly Asp Lys
705                 710                 715                 720

Cys Gln Gly Gly Met Asn Pro Ala Arg Glu Val Lys Asp Leu Lys Lys
                725                 730                 735

Lys Cys Thr Ser Asn Phe Leu Asn Pro Thr Lys Gln Asn Ser Lys Ser
            740                 745                 750

Asn Ser Val Pro Ile Ile Leu Ala Ile Val Gly Leu Met Leu Val Thr
        755                 760                 765

Val Val Ala Gly Val Leu Ile Val Lys Lys Tyr Val Cys Gly Gly Arg
    770                 775                 780

Phe Leu Val His Arg Tyr Ser Val Leu Gln Gln His Ala Glu Ala Asp
785                 790                 795                 800

Gly Val Glu Ala Leu Asp Ser Thr Ser His Ala Lys Ser Gly Tyr His
                805                 810                 815

Asp Asp Ser Asp Glu Asp Leu Leu Glu
            820                 825

<210> SEQ ID NO 3
<211> LENGTH: 825
<212> TYPE: PRT
<213> ORGANISM: Artificial Sequence
<220> FEATURE:
<223> OTHER INFORMATION: Synthetic Construct

<400> SEQUENCE: 3

Met Glu Arg Pro Arg Gly Ala Ala Asp Gly Leu Leu Arg Trp Pro Leu
1               5                   10                  15

Gly Leu Leu Leu Leu Leu Gln Leu Leu Pro Pro Ala Ala Val Gly Gln
                20                  25                  30

Asp Arg Leu Asp Ala Pro Pro Pro Ala Pro Pro Leu Leu Arg Trp
        35                  40                  45

Ala Gly Pro Val Gly Val Ser Trp Gly Leu Arg Ala Ala Ala Pro Gly
    50                  55                  60

Gly Pro Val Pro Arg Ala Gly Arg Trp Arg Arg Gly Ala Pro Ala Glu
65                  70                  75                  80

Asp Gln Asp Cys Gly Arg Leu Pro Asp Phe Ile Ala Lys Leu Thr Asn
                85                  90                  95
```

```
Asn Thr His Gln His Val Phe Asp Asp Leu Ser Gly Ser Val Ser Leu
                100                 105                 110

Ser Trp Val Gly Asp Ser Thr Gly Val Ile Leu Val Leu Thr Thr Phe
        115                 120                 125

Gln Val Pro Leu Val Ile Val Ser Phe Gly Gln Ser Lys Leu Tyr Arg
    130                 135                 140

Ser Glu Asp Tyr Gly Lys Asn Phe Lys Asp Ile Thr Asn Leu Ile Asn
145                 150                 155                 160

Asn Thr Phe Ile Arg Thr Glu Phe Gly Met Ala Ile Gly Pro Glu Asn
                165                 170                 175

Ser Gly Lys Val Ile Leu Thr Ala Glu Val Ser Gly Ser Arg Gly
            180                 185                 190

Gly Arg Val Phe Arg Ser Ser Asp Phe Ala Lys Asn Phe Val Gln Thr
        195                 200                 205

Asp Leu Pro Phe His Pro Leu Thr Gln Met Met Tyr Ser Pro Gln Asn
    210                 215                 220

Ser Asp Tyr Leu Leu Ala Leu Ser Thr Glu Asn Gly Leu Trp Val Ser
225                 230                 235                 240

Lys Asn Phe Gly Glu Lys Trp Glu Ile His Lys Ala Val Cys Leu
                245                 250                 255

Ala Lys Trp Gly Pro Asn Asn Ile Ile Phe Phe Thr Thr His Val Asn
            260                 265                 270

Gly Ser Cys Lys Ala Asp Leu Gly Ala Leu Glu Leu Trp Arg Thr Ser
        275                 280                 285

Asp Leu Gly Lys Thr Phe Lys Thr Ile Gly Val Lys Ile Tyr Ser Phe
    290                 295                 300

Gly Leu Gly Gly Arg Phe Leu Phe Ala Ser Val Met Ala Asp Lys Asp
305                 310                 315                 320

Thr Thr Arg Arg Ile His Val Ser Thr Asp Gln Gly Asp Thr Trp Ser
                325                 330                 335

Met Ala Gln Leu Pro Ser Val Gly Gln Glu Gln Phe Tyr Ser Ile Leu
            340                 345                 350

Ala Ala Asn Asp Asp Met Val Phe Met His Val Asp Glu Pro Gly Asp
        355                 360                 365

Thr Gly Phe Gly Thr Ile Phe Thr Ser Asp Asp Arg Gly Ile Val Tyr
    370                 375                 380

Ser Lys Ser Leu Asp Arg His Leu Tyr Thr Thr Thr Gly Gly Glu Thr
385                 390                 395                 400

Asp Phe Thr Asn Val Thr Ser Leu Arg Gly Val Tyr Ile Thr Ser Thr
                405                 410                 415

Leu Ser Glu Asp Asn Ser Ile Gln Ser Met Ile Thr Phe Asp Gln Gly
            420                 425                 430

Gly Arg Trp Glu His Leu Gln Lys Pro Glu Asn Ser Lys Cys Asp Ala
        435                 440                 445

Thr Ala Lys Asn Lys Asn Glu Cys Ser Leu His Ile His Ala Ser Tyr
    450                 455                 460

Ser Ile Ser Gln Lys Leu Asn Val Pro Met Ala Pro Leu Ser Glu Pro
465                 470                 475                 480

Asn Ala Val Gly Ile Val Ile Ala His Gly Ser Val Gly Asp Ala Ile
                485                 490                 495

Ser Val Met Val Pro Asp Val Tyr Ile Ser Asp Asp Gly Gly Tyr Ser
            500                 505                 510

Trp Ala Lys Met Leu Glu Gly Pro His Tyr Tyr Thr Ile Leu Asp Ser
```

515                 520                 525

Gly Gly Ile Ile Val Ala Ile Glu His Ser Asn Arg Pro Ile Asn Val
    530                 535                 540

Ile Lys Phe Ser Thr Asp Glu Gly Gln Cys Trp Gln Ser Tyr Val Phe
545                 550                 555                 560

Ser Gln Glu Pro Val Tyr Phe Thr Gly Leu Ala Ser Glu Pro Gly Ala
                565                 570                 575

Arg Ser Met Asn Ile Ser Ile Trp Gly Phe Thr Glu Ser Phe Leu Thr
            580                 585                 590

Arg Gln Trp Val Ser Tyr Thr Ile Asp Phe Lys Asp Ile Leu Glu Arg
        595                 600                 605

Asn Cys Glu Glu Asn Asp Tyr Thr Thr Trp Leu Ala His Ser Thr Asp
    610                 615                 620

Pro Gly Asp Tyr Lys Asp Gly Cys Ile Leu Gly Tyr Lys Glu Gln Phe
625                 630                 635                 640

Leu Arg Leu Arg Lys Ser Ser Val Cys Gln Asn Gly Arg Asp Tyr Val
                645                 650                 655

Val Ala Lys Gln Pro Ser Ile Cys Pro Cys Ser Leu Glu Asp Phe Leu
            660                 665                 670

Cys Asp Phe Gly Tyr Phe Arg Pro Glu Asn Ala Ser Glu Cys Val Glu
        675                 680                 685

Gln Pro Glu Leu Lys Gly His Glu Leu Glu Phe Cys Leu Tyr Gly Lys
    690                 695                 700

Glu Glu His Leu Thr Thr Asn Gly Tyr Arg Lys Ile Pro Gly Asp Arg
705                 710                 715                 720

Cys Gln Gly Gly Met Asn Pro Ala Arg Glu Val Lys Asp Leu Lys Lys
                725                 730                 735

Lys Cys Thr Ser Asn Phe Leu Asn Pro Lys Lys Gln Asn Ser Lys Ser
            740                 745                 750

Ser Ser Val Pro Ile Ile Leu Ala Ile Val Gly Leu Met Leu Val Thr
        755                 760                 765

Val Val Ala Gly Val Leu Ile Val Lys Lys Tyr Val Cys Gly Gly Arg
    770                 775                 780

Phe Leu Val His Arg Tyr Ser Val Leu Gln Gln His Ala Glu Ala Asp
785                 790                 795                 800

Gly Val Glu Ala Leu Asp Thr Ala Ser His Ala Lys Ser Gly Tyr His
                805                 810                 815

Asp Asp Ser Asp Glu Asp Leu Leu Glu
            820                 825

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = S or T
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 3
<223> OTHER INFORMATION: Xaa = D or N
<220> FEATURE:

```
<221> NAME/KEY: VARIANT
<222> LOCATION: 4, 5, 6, 7
<223> OTHER INFORMATION: Xaa = Any Amino Acid
<220> FEATURE:
<221> NAME/KEY: VARIANT
<222> LOCATION: 8
<223> OTHER INFORMATION: Xaa = W, F or Y

<400> SEQUENCE: 4

Xaa Xaa Xaa Xaa Xaa Xaa Xaa Xaa
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 4, 6, 8, 11
<223> OTHER INFORMATION: Xaa = Any Amino Acid
<220> FEATURE:
<221> NAME/KEY: VARIANT
<222> LOCATION: 3
<223> OTHER INFORMATION: Xaa = S or T
<220> FEATURE:
<221> NAME/KEY: VARIANT
<222> LOCATION: 5
<223> OTHER INFORMATION: Xaa = D or N
<220> FEATURE:
<221> NAME/KEY: VARIANT
<222> LOCATION: 9
<223> OTHER INFORMATION: Xaa = T or S
<220> FEATURE:
<221> NAME/KEY: VARIANT
<222> LOCATION: 10
<223> OTHER INFORMATION: Xaa = W, F or Y

<400> SEQUENCE: 5

Xaa Xaa Xaa Xaa Xaa Xaa Gly Xaa Xaa Xaa Xaa
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Construct

<400> SEQUENCE: 6

Arg Ala Ser Gln Ser Val Arg Ser Ser Tyr Leu Ala
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Construct

<400> SEQUENCE: 7

Arg Ala Ser Gln Ser Ile Ser Ser Tyr Leu Asn
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct
```

```
<400> SEQUENCE: 8

Arg Ala Ser Gln Ser Ile Ser Ser Trp Leu Ala
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic Construct

<400> SEQUENCE: 9

Arg Ala Ser Gln Ser Val Ser Ser Asn Leu Ala
1               5                   10

<210> SEQ ID NO 10
<211> LENGTH: 16
<212> TYPE: PRT
<213> ORGANISM: Artificial Sequence
<220> FEATURE:
<223> OTHER INFORMATION: Synthetic Construct

<400> SEQUENCE: 10

Arg Ser Ser Gln Ser Leu Leu His Ser Asn Gly Tyr Asn Tyr Leu Asp
1               5                   10                  15

<210> SEQ ID NO 11
<211> LENGTH: 12
<212> TYPE: PRT
<213> ORGANISM: Artificial Sequence
<220> FEATURE:
<223> OTHER INFORMATION: Synthetic Construct

<400> SEQUENCE: 11

Arg Ala Ser Gln Ser Val Ser Ser Ser Phe Leu Ala
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Construct

<400> SEQUENCE: 12

Arg Ala Ser Gln Gly Ile Ser Ser Trp Leu Ala
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic Construct

<400> SEQUENCE: 13

Arg Ala Ser Gln Ser Val Ser Ser Tyr Leu Ala
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic Construct
```

```
<400> SEQUENCE: 14

Arg Ala Ser Gln Ser Val Ser Ser Tyr Leu Ala
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic Construct

<400> SEQUENCE: 15

Arg Ala Ser Gln Ser Ile Asn Ser Tyr Leu Asn
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic Construct

<400> SEQUENCE: 16

Arg Ala Ser Gln Gly Ile Asp Ser Trp Leu Ala
1               5                   10

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Arg Ala Ser Gln Ser Val Ser Ser Ser Leu Ala
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic Construct

<400> SEQUENCE: 21

Arg Ala Ser Gln Gly Ile Ser Arg Trp Leu Ala
1               5                   10
```

```
<210> SEQ ID NO 22
<211> LENGTH: 11
<212> TYPE: PRT
<213> ORGANISM: Artificial Sequence
<220> FEATURE:
<223> OTHER INFORMATION: Synthetic Construct

<400> SEQUENCE: 22

Arg Ala Ser Gln Asp Ile Ser Ser Trp Leu Ala
1               5                   10

<210> SEQ ID NO 23

<400> SEQUENCE: 23

000

<210> SEQ ID NO 24
<211> LENGTH: 11
<212> TYPE: PRT
<213> ORGANISM: Artificial Sequence
<220> FEATURE:
<223> OTHER INFORMATION: Synthetic Construct

<400> SEQUENCE: 24

Arg Ala Ser Gln Ser Ile Ser Ser Phe Leu Asn
1               5                   10

<210> SEQ ID NO 25
<211> LENGTH: 17
<212> TYPE: PRT
<213> ORGANISM: Artificial Sequence
<220> FEATURE:
<223> OTHER INFORMATION: Synthetic Construct

<400> SEQUENCE: 25

Lys Ser Ser Gln Ser Val Leu Tyr Ser Ser Asn Asn Lys Asn Tyr Leu
1               5                   10                  15

Ala

<210> SEQ ID NO 26
<211> LENGTH: 7
<212> TYPE: PRT
<213> ORGANISM: Artificial Sequence
<220> FEATURE:
<223> OTHER INFORMATION: Synthetic Construct

<400> SEQUENCE: 26

Gly Ala Ser Ser Arg Ala Thr
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic Construct

<400> SEQUENCE: 27

Ala Ala Ser Ser Leu Gln Ser
1               5

<210> SEQ ID NO 28
<211> LENGTH: 7
<212> TYPE: PRT
<213> ORGANISM: Artificial Sequence
<220> FEATURE:
```

```
<223> OTHER INFORMATION: Synthetic Construct

<400> SEQUENCE: 28

Lys Ala Ser Ser Leu Glu Ser
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic Construct

<400> SEQUENCE: 29

Gly Ala Ser Thr Arg Ala Thr
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct

<400> SEQUENCE: 30

Leu Gly Ser Asn Arg Ala Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic Construct

<400> SEQUENCE: 31

Gly Ala Ser Ser Leu Gln Ser
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic Construct

<400> SEQUENCE: 32

Ala Ala Ser Asn Leu Gln Ser
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic Construct

<400> SEQUENCE: 33

Asp Ala Ser Lys Arg Ala Thr
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 34

Asp Ala Ser Asn Arg Ala Thr
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic Construct

<400> SEQUENCE: 35

Ser Ala Ser Ser Leu Gln Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic Construct

<400> SEQUENCE: 36

Trp Ala Ser Thr Arg Glu Ser
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic Construct

<400> SEQUENCE: 37

Ser Ala Ser Thr Arg Ala Thr
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic Construct

<400> SEQUENCE: 38

Leu Gly Ser His Arg Ala Ser
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic Construct

<400> SEQUENCE: 39

Asp Ser Ser Asn Arg Ala Thr
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 40

Leu Ala Ser Asn Arg Ala Ser
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic Construct

<400> SEQUENCE: 41

Gln Gln Ser Pro Trp Thr
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Construct

<400> SEQUENCE: 42

Gln Gln Ser Asp Val Ser Pro Ile Thr
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Construct

<400> SEQUENCE: 43

Gln Gln Tyr Lys Ser Tyr Pro Ile Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Construct

<400> SEQUENCE: 44

Gln Gln Phe Arg Val Leu Pro Pro Thr
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct

<400> SEQUENCE: 45

Met Gln Val Ser Thr Glu Pro Pro Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Construct

<400> SEQUENCE: 46
```

```
<210> SEQ ID NO 47
<211> LENGTH: 9
<212> TYPE: PRT
<213> ORGANISM: Artificial Sequence
<220> FEATURE:
<223> OTHER INFORMATION: Synthetic Construct

<400> SEQUENCE: 47

Asp Gln Leu Gly Ser Ser Pro Arg Thr
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Construct

<400> SEQUENCE: 48

Gln Gln Ala Lys Val Trp Pro Tyr Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Construct

<400> SEQUENCE: 49

Gln Gln Tyr Asn Ile Tyr Pro Leu Thr
1               5

<210> SEQ ID NO 50
<211> LENGTH: 10
<212> TYPE: PRT
<213> ORGANISM: Artificial Sequence
<220> FEATURE:
<223> OTHER INFORMATION: Synthetic Construct

<400> SEQUENCE: 50

Gln Gln Tyr Ala Asp Trp Pro Pro Ile Thr
1               5                   10

<210> SEQ ID NO 51

<400> SEQUENCE: 51

000

<210> SEQ ID NO 52
<211> LENGTH: 9
<212> TYPE: PRT
<213> ORGANISM: Artificial Sequence
<220> FEATURE:
<223> OTHER INFORMATION: Synthetic Construct

<400> SEQUENCE: 52

Gln Gln Tyr Asn Asn His Pro Pro Thr
1               5

<210> SEQ ID NO 53
```

```
<400> SEQUENCE: 53

000

<210> SEQ ID NO 54
<211> LENGTH: 9
<212> TYPE: PRT
<213> ORGANISM: Artificial Sequence
<220> FEATURE:
<223> OTHER INFORMATION: Synthetic Construct

<400> SEQUENCE: 54

Gln Gln His Tyr Val Gly Pro Phe Thr
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Construct

<400> SEQUENCE: 55

Gln Gln Ala Arg Leu Gly Pro Trp Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic Construct

<400> SEQUENCE: 56

Gln Gln Gly Asn Ser Tyr Pro Ile Thr
1               5

<210> SEQ ID NO 57

<400> SEQUENCE: 57

000

<210> SEQ ID NO 58
<211> LENGTH: 10
<212> TYPE: PRT
<213> ORGANISM: Artificial Sequence
<220> FEATURE:
<223> OTHER INFORMATION: Synthetic Construct

<400> SEQUENCE: 58

Gln Gln Gly Ala Asn Ala Pro Pro Arg Thr
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Synthetic Construct

<400> SEQUENCE: 59

Gln Gln Thr Asp Gly Lys Pro Pro Thr
1               5

<210> SEQ ID NO 60
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 60

Gln Gln Tyr Asp Gly Phe Pro Ile Thr
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic Construct

<400> SEQUENCE: 61

Gln Gln Lys Ala Ser Leu Pro Phe Thr
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic Construct

<400> SEQUENCE: 62

Gln Gln Ala Asp Gly His Ile Thr
1               5

<210> SEQ ID NO 63

<400> SEQUENCE: 63

000

<210> SEQ ID NO 64
<211> LENGTH: 9
<212> TYPE: PRT
<213> ORGANISM: Artificial Sequence
<220> FEATURE:
<223> OTHER INFORMATION: Synthetic Construct

<400> SEQUENCE: 64

Gln Gln Val Ala Val Ser Pro Ile Thr
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic Construct

<400> SEQUENCE: 65

Gln Gln Tyr Asp Ser Ala Pro Ile Thr
1               5

<210> SEQ ID NO 66
<211> LENGTH: 10
<212> TYPE: PRT
<213> ORGANISM: Artificial Sequence
<220> FEATURE:
<223> OTHER INFORMATION: Synthetic Construct

<400> SEQUENCE: 66
```

```
Gln Gln Gly Asn Ser Leu Pro Pro Ile Thr
1               5                   10

<210> SEQ ID NO 67

<400> SEQUENCE: 67

000

<210> SEQ ID NO 68
<211> LENGTH: 10
<212> TYPE: PRT
<213> ORGANISM: Artificial Sequence
<220> FEATURE:
<223> OTHER INFORMATION: Synthetic Construct

<400> SEQUENCE: 68

Met Gln Arg Leu Gln Ser Pro Leu Arg Thr
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic Construct

<400> SEQUENCE: 69

Met Gln Arg Ile Gln Gly Pro Pro Arg Thr
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Synthetic Construct

<400> SEQUENCE: 70

Met Gln Ala Leu Gly Pro Pro Ile Thr
1               5

<210> SEQ ID NO 71

<400> SEQUENCE: 71

000

<210> SEQ ID NO 72
<211> LENGTH: 9
<212> TYPE: PRT
<213> ORGANISM: Artificial Sequence
<220> FEATURE:
<223> OTHER INFORMATION: Synthetic Construct

<400> SEQUENCE: 72

Met Gln Gly Ile Glu Thr Pro Pro Thr
1               5

<210> SEQ ID NO 73

<400> SEQUENCE: 73

000

<210> SEQ ID NO 74
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 74

Gln Gln Tyr Gly Ser Pro Pro Leu Thr
1               5

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79
<211> LENGTH: 9
<212> TYPE: PRT
<213> ORGANISM: Artificial Sequence
<220> FEATURE:
<223> OTHER INFORMATION: Synthetic Construct

<400> SEQUENCE: 79

Met Gln Ala Ile Gln Gly Pro Ile Thr
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic Construct

<400> SEQUENCE: 80

Gln Gln Arg Ser Ala Leu Pro Phe Thr
1               5

<210> SEQ ID NO 81

<400> SEQUENCE: 81

000

<210> SEQ ID NO 82
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 82

Gln Gln Ala Leu Arg Ser Pro Leu Thr
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic Construct

<400> SEQUENCE: 83

Gln Gln Leu Gly Ser His Pro Pro Thr
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic Construct

<400> SEQUENCE: 84

Gln Gln Leu Asp Ser Ser Pro Ile Thr
1               5

<210> SEQ ID NO 85
<211> LENGTH: 10
<212> TYPE: PRT
<213> ORGANISM: Artificial Sequence
<220> FEATURE:
<223> OTHER INFORMATION: Synthetic Construct

<400> SEQUENCE: 85

Gln Gln Ser Gly Ser Val Pro Pro Ile Thr
1               5                   10

<210> SEQ ID NO 86

<400> SEQUENCE: 86

000

<210> SEQ ID NO 87

<400> SEQUENCE: 87

000

<210> SEQ ID NO 88
<211> LENGTH: 9
<212> TYPE: PRT
<213> ORGANISM: Artificial Sequence
<220> FEATURE:
<223> OTHER INFORMATION: Synthetic Construct

<400> SEQUENCE: 88

Gln Gln Tyr Asn Ser Trp Pro Ile Thr
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 89

Gln Gln Ala Gly Asp Tyr Pro Pro Thr
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic Construct

<400> SEQUENCE: 90

Met Gln Ala Leu Glu Arg Pro Pro Thr
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic Construct

<400> SEQUENCE: 91

Gln Gln Arg Ser Asn Tyr Pro Ile Thr
1               5

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95
<211> LENGTH: 8
<212> TYPE: PRT
<213> ORGANISM: Artificial Sequence
<220> FEATURE:
<223> OTHER INFORMATION: Synthetic Construct

<400> SEQUENCE: 95

Gln Gln Ala Asn Ala Leu Pro Thr
1               5

<210> SEQ ID NO 96

<400> SEQUENCE: 96

000

<210> SEQ ID NO 97
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 97

Glu Gln Tyr Gly Gly Ser Pro Ile Thr
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic Construct

<400> SEQUENCE: 98

Gln Gln Asp Arg Lys Gly Pro Leu Thr
1               5

<210> SEQ ID NO 99
<211> LENGTH: 10
<212> TYPE: PRT
<213> ORGANISM: Artificial Sequence
<220> FEATURE:
<223> OTHER INFORMATION: Synthetic Construct

<400> SEQUENCE: 99

Gln Gln His Gly Arg Leu Pro Pro Trp Thr
1               5                   10

<210> SEQ ID NO 100
<211> LENGTH: 9
<212> TYPE: PRT
<213> ORGANISM: Artificial Sequence
<220> FEATURE:
<223> OTHER INFORMATION: Synthetic Construct

<400> SEQUENCE: 100

Met Gln Gln Gln Glu Thr Pro Leu Thr
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic Construct

<400> SEQUENCE: 101

Gln Glu Tyr Leu Asn Tyr Pro Ile Thr
1               5

<210> SEQ ID NO 102

<400> SEQUENCE: 102

000

<210> SEQ ID NO 103
<211> LENGTH: 9
<212> TYPE: PRT
<213> ORGANISM: Artificial Sequence
<220> FEATURE:
<223> OTHER INFORMATION: Synthetic Construct

<400> SEQUENCE: 103

Gln Gln Leu Gly Ile Ala Pro Ile Thr
1               5
```

```
<210> SEQ ID NO 104
<211> LENGTH: 9
<212> TYPE: PRT
<213> ORGANISM: Artificial Sequence
<220> FEATURE:
<223> OTHER INFORMATION: Synthetic Construct

<400> SEQUENCE: 104

Gln Gln Leu Asp Ser Thr Pro Ile Thr
1               5

<210> SEQ ID NO 105
<211> LENGTH: 9
<212> TYPE: PRT
<213> ORGANISM: Artificial Sequence
<220> FEATURE:
<223> OTHER INFORMATION: Synthetic Construct

<400> SEQUENCE: 105

Met Gln Ala Arg Asp Gly Pro Ile Thr
1               5

<210> SEQ ID NO 106
<211> LENGTH: 10
<212> TYPE: PRT
<213> ORGANISM: Artificial Sequence
<220> FEATURE:
<223> OTHER INFORMATION: Synthetic Construct

<400> SEQUENCE: 106

Glu Gln Ala Asn Ser Leu Pro Pro Ile Thr
1               5                   10

<210> SEQ ID NO 107
<211> LENGTH: 9
<212> TYPE: PRT
<213> ORGANISM: Artificial Sequence
<220> FEATURE:
<223> OTHER INFORMATION: Synthetic Construct

<400> SEQUENCE: 107

Met Gln Arg Leu Glu Ala Pro Leu Thr
1               5

<210> SEQ ID NO 108

<400> SEQUENCE: 108

000

<210> SEQ ID NO 109
<211> LENGTH: 9
<212> TYPE: PRT
<213> ORGANISM: Artificial Sequence
<220> FEATURE:
<223> OTHER INFORMATION: Synthetic Construct

<400> SEQUENCE: 109

Gln Gln Ala Ala Asp Trp Pro Ile Thr
1               5

<210> SEQ ID NO 110

<400> SEQUENCE: 110

000
```

```
<210> SEQ ID NO 111
<211> LENGTH: 9
<212> TYPE: PRT
<213> ORGANISM: Artificial Sequence
<220> FEATURE:
<223> OTHER INFORMATION: Synthetic Construct

<400> SEQUENCE: 111

Gln Gln Ala Ala Ser Ser Pro Ile Thr
1               5

<210> SEQ ID NO 112
<211> LENGTH: 10
<212> TYPE: PRT
<213> ORGANISM: Artificial Sequence
<220> FEATURE:
<223> OTHER INFORMATION: Synthetic Construct

<400> SEQUENCE: 112

Gln Gln Ala Pro Ser Val Pro Pro Ile Thr
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Synthetic Construct

<400> SEQUENCE: 113

Gln Gln Ala Ser Val Tyr Pro Pro Ile Thr
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Synthetic Construct

<400> SEQUENCE: 114

Gln Gln Glu Thr Asn Met Pro Pro Ile Thr
1               5                   10

<210> SEQ ID NO 115
<211> LENGTH: 9
<212> TYPE: PRT
<213> ORGANISM: Artificial Sequence
<220> FEATURE:
<223> OTHER INFORMATION: Synthetic Construct

<400> SEQUENCE: 115

Gln Gln Tyr Asn Ala Leu Pro Arg Thr
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic Construct

<400> SEQUENCE: 116

Gln Gln Ser Tyr Arg Glu Pro Ile Thr
1               5

<210> SEQ ID NO 117
```

<400> SEQUENCE: 117

000

<210> SEQ ID NO 118
<211> LENGTH: 9
<212> TYPE: PRT
<213> ORGANISM: Artificial Sequence
<220> FEATURE:
<223> OTHER INFORMATION: Synthetic Construct

<400> SEQUENCE: 118

Gln Gln Tyr Ala Asn Ala Pro Ile Thr
1               5

<210> SEQ ID NO 119

<400> SEQUENCE: 119

000

<210> SEQ ID NO 120

<400> SEQUENCE: 120

000

<210> SEQ ID NO 121
<211> LENGTH: 9
<212> TYPE: PRT
<213> ORGANISM: Artificial Sequence
<220> FEATURE:
<223> OTHER INFORMATION: Synthetic Construct

<400> SEQUENCE: 121

Met Gln Ala Leu Asp Val Pro Leu Thr
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic Construct

<400> SEQUENCE: 122

Gln Gln Ser His Val Ser Pro Trp Thr
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic Construct

<400> SEQUENCE: 123

Gln Gln Tyr Asn Ala Phe Pro Pro Thr
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic Construct

```
<400> SEQUENCE: 124

Met Gln Ala Ile Asp Thr Pro Pro Thr
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic Construct

<400> SEQUENCE: 125

Glu Gln Tyr Ala Ser Ser Pro Tyr Thr
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic Construct

<400> SEQUENCE: 126

Tyr Thr Phe Thr Gly Tyr Tyr Met His
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic Construct

<400> SEQUENCE: 127

Tyr Thr Phe Thr Ser Tyr Gly Ile Ser
1               5

<210> SEQ ID NO 128

<400> SEQUENCE: 128

000

<210> SEQ ID NO 129
<211> LENGTH: 9
<212> TYPE: PRT
<213> ORGANISM: Artificial Sequence
<220> FEATURE:
<223> OTHER INFORMATION: Synthetic Construct

<400> SEQUENCE: 129

Tyr Thr Phe Thr Ser Tyr Tyr Met Ser
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic Construct

<400> SEQUENCE: 130

Gly Thr Phe Ser Ser Tyr Ala Ile Ser
1               5

<210> SEQ ID NO 131
```

<400> SEQUENCE: 131

000

<210> SEQ ID NO 132

<400> SEQUENCE: 132

000

<210> SEQ ID NO 133
<211> LENGTH: 9
<212> TYPE: PRT
<213> ORGANISM: Artificial Sequence
<220> FEATURE:
<223> OTHER INFORMATION: Synthetic Construct

<400> SEQUENCE: 133

Phe Thr Phe Gly Asp Tyr Ala Met His
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic Construct

<400> SEQUENCE: 134

Phe Thr Phe Asp Asp Tyr Ala Met His
1               5

<210> SEQ ID NO 135
<211> LENGTH: 9
<212> TYPE: PRT
<213> ORGANISM: Artificial Sequence
<220> FEATURE:
<223> OTHER INFORMATION: Synthetic Construct

<400> SEQUENCE: 135

Phe Thr Phe Ser Ser Tyr Ser Met Asn
1               5

<210> SEQ ID NO 136
<211> LENGTH: 9
<212> TYPE: PRT
<213> ORGANISM: Artificial Sequence
<220> FEATURE:
<223> OTHER INFORMATION: Synthetic Construct

<400> SEQUENCE: 136

Phe Thr Phe Ser Ser Tyr Ala Met Ser
1               5

<210> SEQ ID NO 137
<211> LENGTH: 9
<212> TYPE: PRT
<213> ORGANISM: Artificial Sequence
<220> FEATURE:
<223> OTHER INFORMATION: Synthetic Construct

<400> SEQUENCE: 137

Phe Thr Phe Ser Ser Ser Ala Met Ser
1               5

<210> SEQ ID NO 138

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 138

Phe Thr Phe Ser Asn Tyr Ala Met Ser
1               5

<210> SEQ ID NO 139
<211> LENGTH: 9
<212> TYPE: PRT
<213> ORGANISM: Artificial Sequence
<220> FEATURE:
<223> OTHER INFORMATION: Synthetic Construct

<400> SEQUENCE: 139

Phe Thr Phe Ser Thr Tyr Ala Met Ser
1               5

<210> SEQ ID NO 140
<211> LENGTH: 9
<212> TYPE: PRT
<213> ORGANISM: Artificial Sequence
<220> FEATURE:
<223> OTHER INFORMATION: Synthetic Construct

<400> SEQUENCE: 140

Phe Thr Phe Ser Ser Tyr Gly Met His
1               5

<210> SEQ ID NO 141

<400> SEQUENCE: 141

000

<210> SEQ ID NO 142
<211> LENGTH: 10
<212> TYPE: PRT
<213> ORGANISM: Artificial Sequence
<220> FEATURE:
<223> OTHER INFORMATION: Synthetic Construct

<400> SEQUENCE: 142

Tyr Ser Ile Ser Ser Gly Tyr Tyr Trp Gly
1               5                   10

<210> SEQ ID NO 143

<400> SEQUENCE: 143

000

<210> SEQ ID NO 144
<211> LENGTH: 11
<212> TYPE: PRT
<213> ORGANISM: Artificial Sequence
<220> FEATURE:
<223> OTHER INFORMATION: Synthetic Construct

<400> SEQUENCE: 144

Gly Ser Ile Ser Ser Gly Gly Tyr Tyr Trp Ser
1               5                   10

<210> SEQ ID NO 145
```

```
<211> LENGTH: 11
<212> TYPE: PRT
<213> ORGANISM: Artificial Sequence
<220> FEATURE:
<223> OTHER INFORMATION: Synthetic Construct

<400> SEQUENCE: 145

Gly Ser Ile Ser Ser Gly Thr Tyr Tyr Trp Ser
1               5                   10

<210> SEQ ID NO 146

<400> SEQUENCE: 146

000

<210> SEQ ID NO 147
<211> LENGTH: 11
<212> TYPE: PRT
<213> ORGANISM: Artificial Sequence
<220> FEATURE:
<223> OTHER INFORMATION: Synthetic Construct

<400> SEQUENCE: 147

Gly Ser Ile Ser Ser Ser Asp Tyr Tyr Trp Gly
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Synthetic Construct

<400> SEQUENCE: 148

Gly Ser Ile Ser Ser Ser Ser Tyr Tyr Trp Gly
1               5                   10

<210> SEQ ID NO 149
<211> LENGTH: 9
<212> TYPE: PRT
<213> ORGANISM: Artificial Sequence
<220> FEATURE:
<223> OTHER INFORMATION: Synthetic Construct

<400> SEQUENCE: 149

Tyr Ser Phe Thr Ser Tyr Trp Ile Gly
1               5

<210> SEQ ID NO 150
<211> LENGTH: 17
<212> TYPE: PRT
<213> ORGANISM: Artificial Sequence
<220> FEATURE:
<223> OTHER INFORMATION: Synthetic Construct

<400> SEQUENCE: 150

Trp Ile Asn Pro Asn Ser Gly Gly Thr Asn Tyr Ala Gln Lys Phe Gln
1               5                   10                  15

Gly

<210> SEQ ID NO 151
<211> LENGTH: 17
<212> TYPE: PRT
<213> ORGANISM: Artificial Sequence
<220> FEATURE:
<223> OTHER INFORMATION: Synthetic Construct
```

<400> SEQUENCE: 151

Ser Ile Asn Pro Asn Ser Gly Gly Thr Asn Tyr Ala Gln Lys Phe Gln
1               5                   10                  15

Gly

<210> SEQ ID NO 152
<211> LENGTH: 17
<212> TYPE: PRT
<213> ORGANISM: Artificial Sequence
<220> FEATURE:
<223> OTHER INFORMATION: Synthetic Construct

<400> SEQUENCE: 152

Ser Ile Ser Ala Tyr Asn Gly Asn Thr Asn Tyr Ala Gln Lys Leu Gln
1               5                   10                  15

Gly

<210> SEQ ID NO 153
<211> LENGTH: 17
<212> TYPE: PRT
<213> ORGANISM: Artificial Sequence
<220> FEATURE:
<223> OTHER INFORMATION: Synthetic Construct

<400> SEQUENCE: 153

Trp Ile Ser Ala Tyr Asn Gly Asn Thr Asn Tyr Ala Gln Lys Leu Gln
1               5                   10                  15

Gly

<210> SEQ ID NO 154

<400> SEQUENCE: 154

000

<210> SEQ ID NO 155
<211> LENGTH: 17
<212> TYPE: PRT
<213> ORGANISM: Artificial Sequence
<220> FEATURE:
<223> OTHER INFORMATION: Synthetic Construct

<400> SEQUENCE: 155

Ile Ile Asn Pro Ser Gly Gly Ser Thr Ser Tyr Ala Gln Lys Phe Gln
1               5                   10                  15

Gly

<210> SEQ ID NO 156
<211> LENGTH: 17
<212> TYPE: PRT
<213> ORGANISM: Artificial Sequence
<220> FEATURE:
<223> OTHER INFORMATION: Synthetic Construct

<400> SEQUENCE: 156

Gly Ile Ile Pro Ile Phe Gly Thr Ala Asn Tyr Ala Gln Lys Phe Gln
1               5                   10                  15

Gly

<210> SEQ ID NO 157
<211> LENGTH: 17
<212> TYPE: PRT

```
<213> ORGANISM: Artificial Sequence
<220> FEATURE:
<223> OTHER INFORMATION: Synthetic Construct

<400> SEQUENCE: 157

Ser Ile Ile Pro Ile Phe Gly Thr Ala Asn Tyr Ala Gln Lys Phe Gln
1               5                   10                  15

Gly

<210> SEQ ID NO 158
<211> LENGTH: 17
<212> TYPE: PRT
<213> ORGANISM: Artificial Sequence
<220> FEATURE:
<223> OTHER INFORMATION: Synthetic Construct

<400> SEQUENCE: 158

Gly Ile Ile Pro Ile Phe Gly Thr Ala Ser Tyr Ala Gln Lys Phe Gln
1               5                   10                  15

Gly

<210> SEQ ID NO 159

<400> SEQUENCE: 159

000

<210> SEQ ID NO 160
<211> LENGTH: 17
<212> TYPE: PRT
<213> ORGANISM: Artificial Sequence
<220> FEATURE:
<223> OTHER INFORMATION: Synthetic Construct

<400> SEQUENCE: 160

Gly Ile Ser Trp Asn Ser Gly Ser Ile Gly Tyr Ala Asp Ser Val Lys
1               5                   10                  15

Gly

<210> SEQ ID NO 161
<211> LENGTH: 17
<212> TYPE: PRT
<213> ORGANISM: Artificial Sequence
<220> FEATURE:
<223> OTHER INFORMATION: Synthetic Construct

<400> SEQUENCE: 161

Ser Ile Ser Ser Ser Ser Ser Tyr Ile Tyr Tyr Ala Asp Ser Val Lys
1               5                   10                  15

Gly

<210> SEQ ID NO 162
<211> LENGTH: 17
<212> TYPE: PRT
<213> ORGANISM: Artificial Sequence
<220> FEATURE:
<223> OTHER INFORMATION: Synthetic Construct

<400> SEQUENCE: 162

Ser Ile Ser Ser Ser Ser Asn Tyr Ile Tyr Tyr Ala Asp Ser Val Lys
1               5                   10                  15

Gly
```

```
<210> SEQ ID NO 163
<211> LENGTH: 17
<212> TYPE: PRT
<213> ORGANISM: Artificial Sequence
<220> FEATURE:
<223> OTHER INFORMATION: Synthetic Construct

<400> SEQUENCE: 163

Ala Ile Ser Gly Ser Gly Gly Ser Thr Tyr Tyr Ala Asp Ser Val Lys
1               5                   10                  15
Gly

<210> SEQ ID NO 164
<211> LENGTH: 17
<212> TYPE: PRT
<213> ORGANISM: Artificial Sequence
<220> FEATURE:
<223> OTHER INFORMATION: Synthetic Construct

<400> SEQUENCE: 164

Ala Ile Ser Ala Ser Gly Gly Ser Thr Tyr Tyr Ala Asp Ser Val Lys
1               5                   10                  15
Gly

<210> SEQ ID NO 165
<211> LENGTH: 17
<212> TYPE: PRT
<213> ORGANISM: Artificial Sequence
<220> FEATURE:
<223> OTHER INFORMATION: Synthetic Construct

<400> SEQUENCE: 165

Ser Ile Ser Gly Ser Gly Gly Ser Thr Tyr Tyr Ala Asp Ser Val Lys
1               5                   10                  15
Gly

<210> SEQ ID NO 166
<211> LENGTH: 17
<212> TYPE: PRT
<213> ORGANISM: Artificial Sequence
<220> FEATURE:
<223> OTHER INFORMATION: Synthetic Construct

<400> SEQUENCE: 166

Val Ile Ser Tyr Asp Gly Ser Asn Lys Tyr Tyr Ala Asp Ser Val Lys
1               5                   10                  15
Gly

<210> SEQ ID NO 167

<400> SEQUENCE: 167

000

<210> SEQ ID NO 168

<400> SEQUENCE: 168

000

<210> SEQ ID NO 169
<211> LENGTH: 16
<212> TYPE: PRT
<213> ORGANISM: Artificial Sequence
<220> FEATURE:
```

<223> OTHER INFORMATION: Synthetic Construct

<400> SEQUENCE: 169

Ser Ile Tyr His Ser Gly Ser Thr Tyr Tyr Asn Pro Ser Leu Lys Ser
1               5                   10                  15

<210> SEQ ID NO 170
<211> LENGTH: 16
<212> TYPE: PRT
<213> ORGANISM: Artificial Sequence
<220> FEATURE:
<223> OTHER INFORMATION: Synthetic Construct

<400> SEQUENCE: 170

Thr Ile Tyr His Ser Gly Ser Thr Tyr Tyr Asn Pro Ser Leu Lys Ser
1               5                   10                  15

<210> SEQ ID NO 171
<211> LENGTH: 16
<212> TYPE: PRT
<213> ORGANISM: Artificial Sequence
<220> FEATURE:
<223> OTHER INFORMATION: Synthetic Construct

<400> SEQUENCE: 171

Ser Ile Tyr His Ser Gly Asn Thr Tyr Tyr Asn Pro Ser Leu Lys Ser
1               5                   10                  15

<210> SEQ ID NO 172
<211> LENGTH: 16
<212> TYPE: PRT
<213> ORGANISM: Artificial Sequence
<220> FEATURE:
<223> OTHER INFORMATION: Synthetic Construct

<400> SEQUENCE: 172

Tyr Ile Tyr Tyr Ser Gly Ser Thr Val Tyr Asn Pro Ser Leu Lys Ser
1               5                   10                  15

<210> SEQ ID NO 173
<211> LENGTH: 16
<212> TYPE: PRT
<213> ORGANISM: Artificial Sequence
<220> FEATURE:
<223> OTHER INFORMATION: Synthetic Construct

<400> SEQUENCE: 173

Ser Ile Tyr Tyr Ser Gly Ser Thr Tyr Tyr Asn Pro Ser Leu Lys Ser
1               5                   10                  15

<210> SEQ ID NO 174
<211> LENGTH: 16
<212> TYPE: PRT
<213> ORGANISM: Artificial Sequence
<220> FEATURE:
<223> OTHER INFORMATION: Synthetic Construct

<400> SEQUENCE: 174

Asn Ile Tyr Tyr Ser Gly Ser Thr Tyr Tyr Asn Pro Ser Leu Lys Ser
1               5                   10                  15

<210> SEQ ID NO 175
<211> LENGTH: 16
<212> TYPE: PRT
<213> ORGANISM: Artificial Sequence
<220> FEATURE:
<223> OTHER INFORMATION: Synthetic Construct

<400> SEQUENCE: 175

Tyr Ile Tyr Tyr Ser Gly Ser Thr Tyr Tyr Asn Pro Ser Leu Lys Ser
1               5                   10                  15

<210> SEQ ID NO 176

<400> SEQUENCE: 176

000

<210> SEQ ID NO 177
<211> LENGTH: 16
<212> TYPE: PRT
<213> ORGANISM: Artificial Sequence
<220> FEATURE:
<223> OTHER INFORMATION: Synthetic Construct

<400> SEQUENCE: 177

Ser Ile Ser Tyr Ser Gly Ser Thr Tyr Tyr Asn Pro Ser Leu Lys Ser
1               5                   10                  15

<210> SEQ ID NO 178
<211> LENGTH: 17
<212> TYPE: PRT
<213> ORGANISM: Artificial Sequence
<220> FEATURE:
<223> OTHER INFORMATION: Synthetic Construct

<400> SEQUENCE: 178

Ile Ile Tyr Pro Gly Asp Ser Asp Thr Thr Tyr Ser Pro Ser Phe Gln
1               5                   10                  15

Gly

<210> SEQ ID NO 179
<211> LENGTH: 21
<212> TYPE: PRT
<213> ORGANISM: Artificial Sequence
<220> FEATURE:
<223> OTHER INFORMATION: Synthetic Construct

<400> SEQUENCE: 179

Ala Arg Ser Pro Gly Gly Ala Thr Asp Gly Leu Val Tyr Tyr Tyr Tyr
1               5                   10                  15

Tyr Gly Met Asp Val
            20

<210> SEQ ID NO 180
<211> LENGTH: 17
<212> TYPE: PRT
<213> ORGANISM: Artificial Sequence
<220> FEATURE:
<223> OTHER INFORMATION: Synthetic Construct

<400> SEQUENCE: 180

Ala Arg Gly Lys Arg Ser Ser Gly Trp Tyr Glu Gly Tyr Gly Met Asp
1               5                   10                  15

Val

<210> SEQ ID NO 181
<211> LENGTH: 15
<212> TYPE: PRT
<213> ORGANISM: Artificial Sequence
<220> FEATURE:
<223> OTHER INFORMATION: Synthetic Construct

<400> SEQUENCE: 181

Ala Arg Gly Gly Pro Gln Leu Arg Val Ala Glu Tyr Phe Gln His
1               5                   10                  15

<210> SEQ ID NO 182
<211> LENGTH: 13
<212> TYPE: PRT
<213> ORGANISM: Artificial Sequence
<220> FEATURE:
<223> OTHER INFORMATION: Synthetic Construct

<400> SEQUENCE: 182

Ala Arg Arg His Arg Ser Ser Thr Tyr Gly Met Asp Val
1               5                   10

<210> SEQ ID NO 183
<211> LENGTH: 19
<212> TYPE: PRT
<213> ORGANISM: Artificial Sequence
<220> FEATURE:
<223> OTHER INFORMATION: Synthetic Construct

<400> SEQUENCE: 183

Ala Arg Gly Val Gly Ser Thr Val Thr Leu Ala Tyr Tyr Tyr Tyr Gly
1               5                   10                  15

Met Asp Val

<210> SEQ ID NO 184
<211> LENGTH: 18
<212> TYPE: PRT
<213> ORGANISM: Artificial Sequence
<220> FEATURE:
<223> OTHER INFORMATION: Synthetic Construct

<400> SEQUENCE: 184

Ala Arg Asp Pro Ser Gly Gly Thr Thr Leu His Tyr Tyr Tyr Gly Met
1               5                   10                  15

Asp Val

<210> SEQ ID NO 185
<211> LENGTH: 20
<212> TYPE: PRT
<213> ORGANISM: Artificial Sequence
<220> FEATURE:
<223> OTHER INFORMATION: Synthetic Construct

<400> SEQUENCE: 185

Ala Arg Gln Gly Gly His Asp Ser Pro Thr Leu Tyr Tyr Tyr Tyr Tyr
1               5                   10                  15

Gly Met Asp Val
            20

<210> SEQ ID NO 186
<211> LENGTH: 19
<212> TYPE: PRT
<213> ORGANISM: Artificial Sequence
<220> FEATURE:
<223> OTHER INFORMATION: Synthetic Construct

<400> SEQUENCE: 186

Ala Arg Asp Pro Gly Gly Tyr Gly Pro Thr Leu Tyr Tyr Tyr Tyr Gly
1               5                   10                  15

Met Asp Val

<210> SEQ ID NO 187

<400> SEQUENCE: 187

000

<210> SEQ ID NO 188
<211> LENGTH: 14
<212> TYPE: PRT
<213> ORGANISM: Artificial Sequence
<220> FEATURE:
<223> OTHER INFORMATION: Synthetic Construct

<400> SEQUENCE: 188

Ala Arg Asp Leu Pro Lys Tyr Lys Trp Gly Trp Phe Asp Pro
1               5                   10

<210> SEQ ID NO 189

<400> SEQUENCE: 189

000

<210> SEQ ID NO 190
<211> LENGTH: 22
<212> TYPE: PRT
<213> ORGANISM: Artificial Sequence
<220> FEATURE:
<223> OTHER INFORMATION: Synthetic Construct

<400> SEQUENCE: 190

Ala Arg Asp Pro Ser Gly Ile Ala Ala Ala Gly Pro Ala Ser Arg Tyr
1               5                   10                  15

Tyr Tyr Gly Met Asp Val
            20

<210> SEQ ID NO 191
<211> LENGTH: 13
<212> TYPE: PRT
<213> ORGANISM: Artificial Sequence
<220> FEATURE:
<223> OTHER INFORMATION: Synthetic Construct

<400> SEQUENCE: 191

Ala Arg Ser Pro Tyr Ser Gly Thr Arg Asp Phe Asp Leu
1               5                   10

<210> SEQ ID NO 192

<400> SEQUENCE: 192

000

<210> SEQ ID NO 193
<211> LENGTH: 16
<212> TYPE: PRT
<213> ORGANISM: Artificial Sequence
<220> FEATURE:
<223> OTHER INFORMATION: Synthetic Construct

<400> SEQUENCE: 193

Ala Arg Asp Lys His Gly Arg Arg Gly Tyr Tyr Tyr Tyr Met Asp Val
1               5                   10                  15

<210> SEQ ID NO 194

```
<211> LENGTH: 19
<212> TYPE: PRT
<213> ORGANISM: Artificial Sequence
<220> FEATURE:
<223> OTHER INFORMATION: Synthetic Construct

<400> SEQUENCE: 194

Ala Arg Glu Ser Arg Ile Pro Gly Ser Gly Tyr Tyr Tyr Tyr Gly
1               5                   10                  15

Met Asp Val

<210> SEQ ID NO 195
<211> LENGTH: 17
<212> TYPE: PRT
<213> ORGANISM: Artificial Sequence
<220> FEATURE:
<223> OTHER INFORMATION: Synthetic Construct

<400> SEQUENCE: 195

Ala Arg Glu Gly Arg Met Ser Gly Trp Tyr Tyr Ala Tyr Gly Met Asp
1               5                   10                  15

Val

<210> SEQ ID NO 196
<211> LENGTH: 17
<212> TYPE: PRT
<213> ORGANISM: Artificial Sequence
<220> FEATURE:
<223> OTHER INFORMATION: Synthetic Construct

<400> SEQUENCE: 196

Ala Arg Glu Arg Arg Tyr Asp Gly Tyr Tyr Tyr Tyr Gly Met Asp
1               5                   10                  15

Val

<210> SEQ ID NO 197
<211> LENGTH: 17
<212> TYPE: PRT
<213> ORGANISM: Artificial Sequence
<220> FEATURE:
<223> OTHER INFORMATION: Synthetic Construct

<400> SEQUENCE: 197

Ala Arg Gln Gly Arg Lys Thr Gly Tyr Tyr Tyr Tyr Gly Met Asp
1               5                   10                  15

Val

<210> SEQ ID NO 198

<400> SEQUENCE: 198

000

<210> SEQ ID NO 199
<211> LENGTH: 12
<212> TYPE: PRT
<213> ORGANISM: Artificial Sequence
<220> FEATURE:
<223> OTHER INFORMATION: Synthetic Construct

<400> SEQUENCE: 199

Ala Lys Pro Leu Tyr Arg Gly Gly Pro Phe Asp Ile
1               5                   10
```

```
<210> SEQ ID NO 200
<211> LENGTH: 15
<212> TYPE: PRT
<213> ORGANISM: Artificial Sequence
<220> FEATURE:
<223> OTHER INFORMATION: Synthetic Construct

<400> SEQUENCE: 200

Ala Lys Gly Val Gly Gln Val Pro Ala Ser Val Ala Phe Asp Ile
1               5                   10                  15

<210> SEQ ID NO 201
<211> LENGTH: 16
<212> TYPE: PRT
<213> ORGANISM: Artificial Sequence
<220> FEATURE:
<223> OTHER INFORMATION: Synthetic Construct

<400> SEQUENCE: 201

Ala Arg Asp Arg Leu Gly Arg Gly Tyr Lys Trp Asn Trp Phe Asp Pro
1               5                   10                  15

<210> SEQ ID NO 202

<400> SEQUENCE: 202

000

<210> SEQ ID NO 203
<211> LENGTH: 13
<212> TYPE: PRT
<213> ORGANISM: Artificial Sequence
<220> FEATURE:
<223> OTHER INFORMATION: Synthetic Construct

<400> SEQUENCE: 203

Ala Arg Gly Gly Leu Asp Arg Trp Gly Ser Phe Asp Ile
1               5                   10

<210> SEQ ID NO 204
<211> LENGTH: 8
<212> TYPE: PRT
<213> ORGANISM: Artificial Sequence
<220> FEATURE:
<223> OTHER INFORMATION: Synthetic Construct

<400> SEQUENCE: 204

Ala Arg Gly Asp Gly Met Asp Val
1               5

<210> SEQ ID NO 205

<400> SEQUENCE: 205

000

<210> SEQ ID NO 206
<211> LENGTH: 13
<212> TYPE: PRT
<213> ORGANISM: Artificial Sequence
<220> FEATURE:
<223> OTHER INFORMATION: Synthetic Construct

<400> SEQUENCE: 206

Ala Lys Arg Gly Tyr Pro Gly Tyr Pro Ala Phe Asp Ile
1               5                   10
```

```
<210> SEQ ID NO 207

<400> SEQUENCE: 207

000

<210> SEQ ID NO 208
<211> LENGTH: 11
<212> TYPE: PRT
<213> ORGANISM: Artificial Sequence
<220> FEATURE:
<223> OTHER INFORMATION: Synthetic Construct

<400> SEQUENCE: 208

Ala Lys Thr Gly Gly Thr Tyr Gly Met Asp Val
1               5                   10

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213
<211> LENGTH: 12
<212> TYPE: PRT
<213> ORGANISM: Artificial Sequence
<220> FEATURE:
<223> OTHER INFORMATION: Synthetic Construct

<400> SEQUENCE: 213

Ala Lys Pro Leu Ser Ser Thr Gly Gly Gly Asn Ile
1               5                   10

<210> SEQ ID NO 214
<211> LENGTH: 15
<212> TYPE: PRT
<213> ORGANISM: Artificial Sequence
<220> FEATURE:
<223> OTHER INFORMATION: Synthetic Construct

<400> SEQUENCE: 214

Ala Arg Glu Val Met Ala Arg Ala Arg Thr Tyr Gly Met Asp Val
1               5                   10                  15

<210> SEQ ID NO 215

<400> SEQUENCE: 215

000
```

<210> SEQ ID NO 216
<211> LENGTH: 12
<212> TYPE: PRT
<213> ORGANISM: Artificial Sequence
<220> FEATURE:
<223> OTHER INFORMATION: Synthetic Construct

<400> SEQUENCE: 216

Ala Lys Leu Tyr Gln Gly Thr Pro Asp Phe Asp Leu
1               5                   10

<210> SEQ ID NO 217
<211> LENGTH: 18
<212> TYPE: PRT
<213> ORGANISM: Artificial Sequence
<220> FEATURE:
<223> OTHER INFORMATION: Synthetic Construct

<400> SEQUENCE: 217

Ala Lys Val Gly Gly Met Tyr Asp Gly Gly Val Tyr Tyr Tyr Gly Met
1               5                   10                  15

Asp Val

<210> SEQ ID NO 218
<211> LENGTH: 14
<212> TYPE: PRT
<213> ORGANISM: Artificial Sequence
<220> FEATURE:
<223> OTHER INFORMATION: Synthetic Construct

<400> SEQUENCE: 218

Ala Lys Thr Pro Ser Ser Ile Tyr Ala Ala Gly Met Asp Val
1               5                   10

<210> SEQ ID NO 219
<211> LENGTH: 14
<212> TYPE: PRT
<213> ORGANISM: Artificial Sequence
<220> FEATURE:
<223> OTHER INFORMATION: Synthetic Construct

<400> SEQUENCE: 219

Ala Arg Val Arg Gly Tyr Gly Gly Ser Asn Tyr Phe Asp Tyr
1               5                   10

<210> SEQ ID NO 220

<400> SEQUENCE: 220

000

<210> SEQ ID NO 221

<400> SEQUENCE: 221

000

<210> SEQ ID NO 222
<211> LENGTH: 20
<212> TYPE: PRT
<213> ORGANISM: Artificial Sequence
<220> FEATURE:
<223> OTHER INFORMATION: Synthetic Construct

<400> SEQUENCE: 222

Ala Arg Glu Ser Gly Asp Arg Ala Thr Leu Val Tyr Tyr Tyr Tyr
1               5                   10                  15

Gly Met Asp Val
            20

<210> SEQ ID NO 223
<211> LENGTH: 19
<212> TYPE: PRT
<213> ORGANISM: Artificial Sequence
<220> FEATURE:
<223> OTHER INFORMATION: Synthetic Construct

<400> SEQUENCE: 223

Ala Arg Asp Arg Gly Gly Tyr Ser Ser Leu Leu Pro Tyr Tyr Tyr
1               5                   10                  15

Met Asp Val

<210> SEQ ID NO 224
<211> LENGTH: 11
<212> TYPE: PRT
<213> ORGANISM: Artificial Sequence
<220> FEATURE:
<223> OTHER INFORMATION: Synthetic Construct

<400> SEQUENCE: 224

Ala Arg Asp Ala Tyr Glu Gly Arg Val Asp Val
1               5                   10

<210> SEQ ID NO 225
<211> LENGTH: 22
<212> TYPE: PRT
<213> ORGANISM: Artificial Sequence
<220> FEATURE:
<223> OTHER INFORMATION: Synthetic Construct

<400> SEQUENCE: 225

Ala Lys Gly Leu Glu Tyr Tyr Asp Ser Ser Arg Leu Tyr Tyr Pro Tyr
1               5                   10                  15

Tyr Tyr Tyr Met Asp Val
            20

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229
<211> LENGTH: 15
<212> TYPE: PRT
<213> ORGANISM: Artificial Sequence
<220> FEATURE:
<223> OTHER INFORMATION: Synthetic Construct

```
<400> SEQUENCE: 229

Ala Arg Gly Arg Pro Glu Leu Gly Trp Asp Lys Tyr Phe Gln His
1               5                   10                  15

<210> SEQ ID NO 230

<400> SEQUENCE: 230

000

<210> SEQ ID NO 231
<211> LENGTH: 19
<212> TYPE: PRT
<213> ORGANISM: Artificial Sequence
<220> FEATURE:
<223> OTHER INFORMATION: Synthetic Construct

<400> SEQUENCE: 231

Ala Arg Gly Pro Leu Lys Phe Tyr Tyr Gly Ser Gly Ser Tyr Gly Phe
1               5                   10                  15

Phe Asp Tyr

<210> SEQ ID NO 232
<211> LENGTH: 14
<212> TYPE: PRT
<213> ORGANISM: Artificial Sequence
<220> FEATURE:
<223> OTHER INFORMATION: Synthetic Construct

<400> SEQUENCE: 232

Ala Arg Gly Pro Pro Glu Leu Gly Lys Met Tyr Phe Gln His
1               5                   10

<210> SEQ ID NO 233
<211> LENGTH: 15
<212> TYPE: PRT
<213> ORGANISM: Artificial Sequence
<220> FEATURE:
<223> OTHER INFORMATION: Synthetic Construct

<400> SEQUENCE: 233

Ala Arg Gln Gly Ser Ile Lys Gln Gly Tyr Tyr Gly Met Asp Val
1               5                   10                  15

<210> SEQ ID NO 234
<211> LENGTH: 20
<212> TYPE: PRT
<213> ORGANISM: Artificial Sequence
<220> FEATURE:
<223> OTHER INFORMATION: Synthetic Construct

<400> SEQUENCE: 234

Ala Arg Gly Ser Pro Arg Phe Tyr Tyr Gly Ser Gly Ser Tyr Leu Asp
1               5                   10                  15

Leu Phe Asp Ile
            20

<210> SEQ ID NO 235

<400> SEQUENCE: 235

000

<210> SEQ ID NO 236
<211> LENGTH: 13
```

```
<212> TYPE: PRT
<213> ORGANISM: Artificial Sequence
<220> FEATURE:
<223> OTHER INFORMATION: Synthetic Construct

<400> SEQUENCE: 236

Ala Arg Ala Glu His Arg Gly Pro Arg Tyr Phe Asp Leu
1               5                   10

<210> SEQ ID NO 237
<211> LENGTH: 13
<212> TYPE: PRT
<213> ORGANISM: Artificial Sequence
<220> FEATURE:
<223> OTHER INFORMATION: Synthetic Construct

<400> SEQUENCE: 237

Ala Arg Glu Gly Gln Leu Pro Thr Gly Thr Phe Asp Tyr
1               5                   10

<210> SEQ ID NO 238
<211> LENGTH: 16
<212> TYPE: PRT
<213> ORGANISM: Artificial Sequence
<220> FEATURE:
<223> OTHER INFORMATION: Synthetic Construct

<400> SEQUENCE: 238

Ala Arg Asp Val Gly Arg Thr Gly Pro His Tyr Tyr Gly Met Asp Val
1               5                   10                  15

<210> SEQ ID NO 239
<211> LENGTH: 16
<212> TYPE: PRT
<213> ORGANISM: Artificial Sequence
<220> FEATURE:
<223> OTHER INFORMATION: Synthetic Construct

<400> SEQUENCE: 239

Ala Arg Leu His Ser Asp Tyr Ser Val Leu Tyr Tyr Gly Met Asp Val
1               5                   10                  15

<210> SEQ ID NO 240

<400> SEQUENCE: 240

000

<210> SEQ ID NO 241
<211> LENGTH: 20
<212> TYPE: PRT
<213> ORGANISM: Artificial Sequence
<220> FEATURE:
<223> OTHER INFORMATION: Synthetic Construct

<400> SEQUENCE: 241

Ala Arg Asp Arg Gly Gly Thr His Phe Gly Ala Asp His Tyr Tyr Tyr
1               5                   10                  15

Gly Met Asp Val
            20

<210> SEQ ID NO 242

<400> SEQUENCE: 242

000
```

```
<210> SEQ ID NO 243
<211> LENGTH: 13
<212> TYPE: PRT
<213> ORGANISM: Artificial Sequence
<220> FEATURE:
<223> OTHER INFORMATION: Synthetic Construct

<400> SEQUENCE: 243

Ala Arg Leu Pro Gly Tyr Pro Leu Gly Leu Phe Asp Ile
1               5                   10

<210> SEQ ID NO 244
<211> LENGTH: 16
<212> TYPE: PRT
<213> ORGANISM: Artificial Sequence
<220> FEATURE:
<223> OTHER INFORMATION: Synthetic Construct

<400> SEQUENCE: 244

Ala Arg Asp Arg Gly Arg Thr Glu Ser Tyr Tyr Tyr Gly Met Asp Val
1               5                   10                  15

<210> SEQ ID NO 245
<211> LENGTH: 12
<212> TYPE: PRT
<213> ORGANISM: Artificial Sequence
<220> FEATURE:
<223> OTHER INFORMATION: Synthetic Construct

<400> SEQUENCE: 245

Ala Arg Gly Val Gly Arg Tyr Arg Val Ala Asp Tyr
1               5                   10

<210> SEQ ID NO 246
<211> LENGTH: 18
<212> TYPE: PRT
<213> ORGANISM: Artificial Sequence
<220> FEATURE:
<223> OTHER INFORMATION: Synthetic Construct

<400> SEQUENCE: 246

Ala Arg Asp Arg Gly Met Gly Pro Lys Leu Tyr Tyr Tyr Gly Met
1               5                   10                  15

Asp Val

<210> SEQ ID NO 247
<211> LENGTH: 16
<212> TYPE: PRT
<213> ORGANISM: Artificial Sequence
<220> FEATURE:
<223> OTHER INFORMATION: Synthetic Construct

<400> SEQUENCE: 247

Ala Arg Gly Val Gly Ile Gln Gln Gln Leu Val Leu Gly Phe Asp Pro
1               5                   10                  15

<210> SEQ ID NO 248

<400> SEQUENCE: 248

000

<210> SEQ ID NO 249
<211> LENGTH: 13
<212> TYPE: PRT
<213> ORGANISM: Artificial Sequence
```

```
<220> FEATURE:
<223> OTHER INFORMATION: Synthetic Construct

<400> SEQUENCE: 249

Ala Arg Ser Leu Ala Met Ser Gly Ala Tyr Phe Asp Leu
1               5                   10

<210> SEQ ID NO 250

<400> SEQUENCE: 250

000

<210> SEQ ID NO 251

<400> SEQUENCE: 251

000

<210> SEQ ID NO 252
<211> LENGTH: 13
<212> TYPE: PRT
<213> ORGANISM: Artificial Sequence
<220> FEATURE:
<223> OTHER INFORMATION: Synthetic Construct

<400> SEQUENCE: 252

Ala Arg Glu Arg Trp Asp Leu Gly His Gly Met Asp Val
1               5                   10

<210> SEQ ID NO 253
<211> LENGTH: 17
<212> TYPE: PRT
<213> ORGANISM: Artificial Sequence
<220> FEATURE:
<223> OTHER INFORMATION: Synthetic Construct

<400> SEQUENCE: 253

Ala Arg Gly Val Gly Ser Gly Tyr Ser Tyr Gly Tyr Arg Tyr Phe Asp
1               5                   10                  15

Tyr

<210> SEQ ID NO 254
<211> LENGTH: 15
<212> TYPE: PRT
<213> ORGANISM: Artificial Sequence
<220> FEATURE:
<223> OTHER INFORMATION: Synthetic Construct

<400> SEQUENCE: 254

Ala Arg Gly Ser Pro Thr Trp Leu Arg Asp Tyr Tyr Met Asp Val
1               5                   10                  15

<210> SEQ ID NO 255
<211> LENGTH: 12
<212> TYPE: PRT
<213> ORGANISM: Artificial Sequence
<220> FEATURE:
<223> OTHER INFORMATION: Synthetic Construct

<400> SEQUENCE: 255

Ala Arg Gly Gly Thr Thr Trp Leu Val Ala Asp Val
1               5                   10

<210> SEQ ID NO 256
<211> LENGTH: 18
```

-continued

```
<212> TYPE: PRT
<213> ORGANISM: Artificial Sequence
<220> FEATURE:
<223> OTHER INFORMATION: Synthetic Construct

<400> SEQUENCE: 256

Ala Arg Gly Arg Gly Arg Tyr Ser Tyr Gly Tyr His Lys Ala Ala Phe
1               5                   10                  15

Asp Ile

<210> SEQ ID NO 257
<211> LENGTH: 23
<212> TYPE: PRT
<213> ORGANISM: Artificial Sequence
<220> FEATURE:
<223> OTHER INFORMATION: Synthetic Construct

<400> SEQUENCE: 257

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 258
<211> LENGTH: 23
<212> TYPE: PRT
<213> ORGANISM: Artificial Sequence
<220> FEATURE:
<223> OTHER INFORMATION: Synthetic Construct

<400> SEQUENCE: 258

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 259
<211> LENGTH: 23
<212> TYPE: PRT
<213> ORGANISM: Artificial Sequence
<220> FEATURE:
<223> OTHER INFORMATION: Synthetic Construct

<400> SEQUENCE: 259

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 260
<211> LENGTH: 23
<212> TYPE: PRT
<213> ORGANISM: Artificial Sequence
<220> FEATURE:
<223> OTHER INFORMATION: Synthetic Construct

<400> SEQUENCE: 260

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 261
<211> LENGTH: 23
```

```
<212> TYPE: PRT
<213> ORGANISM: Artificial Sequence
<220> FEATURE:
<223> OTHER INFORMATION: Synthetic Construct

<400> SEQUENCE: 261

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 262
<211> LENGTH: 23
<212> TYPE: PRT
<213> ORGANISM: Artificial Sequence
<220> FEATURE:
<223> OTHER INFORMATION: Synthetic Construct

<400> SEQUENCE: 262

Glu Ile Val Leu Thr Gln Ser Pro Ala Thr Leu Ser Val Ser Pro Gly
1               5                   10                  15

Glu Arg Ala Thr Leu Ser Cys
            20

<210> SEQ ID NO 263
<211> LENGTH: 23
<212> TYPE: PRT
<213> ORGANISM: Artificial Sequence
<220> FEATURE:
<223> OTHER INFORMATION: Synthetic Construct

<400> SEQUENCE: 263

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 264
<211> LENGTH: 23
<212> TYPE: PRT
<213> ORGANISM: Artificial Sequence
<220> FEATURE:
<223> OTHER INFORMATION: Synthetic Construct

<400> SEQUENCE: 264

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 265
<211> LENGTH: 23
<212> TYPE: PRT
<213> ORGANISM: Artificial Sequence
<220> FEATURE:
<223> OTHER INFORMATION: Synthetic Construct

<400> SEQUENCE: 265

Glu Ile Val Met Thr Gln Ser Pro Gly Thr Leu Ser Leu Ser Pro Gly
1               5                   10                  15

Glu Arg Ala Thr Leu Ser Cys
            20

<210> SEQ ID NO 266
```

```
<211> LENGTH: 23
<212> TYPE: PRT
<213> ORGANISM: Artificial Sequence
<220> FEATURE:
<223> OTHER INFORMATION: Synthetic Construct

<400> SEQUENCE: 266

Glu Ile Val Met Thr Gln Ser Pro Ala Thr Leu Ser Leu Ser Pro Gly
1               5                   10                  15

Glu Arg Ala Thr Leu Ser Cys
            20

<210> SEQ ID NO 267
<211> LENGTH: 23
<212> TYPE: PRT
<213> ORGANISM: Artificial Sequence
<220> FEATURE:
<223> OTHER INFORMATION: Synthetic Construct

<400> SEQUENCE: 267

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 268
<211> LENGTH: 23
<212> TYPE: PRT
<213> ORGANISM: Artificial Sequence
<220> FEATURE:
<223> OTHER INFORMATION: Synthetic Construct

<400> SEQUENCE: 268

Asp Ile Gln Leu Thr Gln Ser Pro Ser Ser Val Ser Ala Ser Val Gly
1               5                   10                  15

Asp Arg Val Thr Ile Thr Cys
            20

<210> SEQ ID NO 269
<211> LENGTH: 15
<212> TYPE: PRT
<213> ORGANISM: Artificial Sequence
<220> FEATURE:
<223> OTHER INFORMATION: Synthetic Construct

<400> SEQUENCE: 269

Trp Tyr Gln Gln Lys Pro Gly Gln Ala Pro Arg Leu Leu Ile Tyr
1               5                   10                  15

<210> SEQ ID NO 270
<211> LENGTH: 15
<212> TYPE: PRT
<213> ORGANISM: Artificial Sequence
<220> FEATURE:
<223> OTHER INFORMATION: Synthetic Construct

<400> SEQUENCE: 270

Trp Tyr Gln Gln Lys Pro Gly Lys Ala Pro Lys Leu Leu Ile Tyr
1               5                   10                  15

<210> SEQ ID NO 271
<211> LENGTH: 15
<212> TYPE: PRT
<213> ORGANISM: Artificial Sequence
<220> FEATURE:
<223> OTHER INFORMATION: Synthetic Construct
```

```
<400> SEQUENCE: 271

Trp Tyr Leu Gln Lys Pro Gly Gln Ser Pro Gln Leu Leu Ile Tyr
1               5                   10                  15

<210> SEQ ID NO 272
<211> LENGTH: 15
<212> TYPE: PRT
<213> ORGANISM: Artificial Sequence
<220> FEATURE:
<223> OTHER INFORMATION: Synthetic Construct

<400> SEQUENCE: 272

Trp Tyr Leu Gln Lys Pro Gly Gln Ser Pro Gln Leu Leu Ile Phe
1               5                   10                  15

<210> SEQ ID NO 273
<211> LENGTH: 15
<212> TYPE: PRT
<213> ORGANISM: Artificial Sequence
<220> FEATURE:
<223> OTHER INFORMATION: Synthetic Construct

<400> SEQUENCE: 273

Trp Tyr Gln Gln Lys Pro Gly Gln Pro Pro Lys Leu Leu Ile Tyr
1               5                   10                  15

<210> SEQ ID NO 274
<211> LENGTH: 15
<212> TYPE: PRT
<213> ORGANISM: Artificial Sequence
<220> FEATURE:
<223> OTHER INFORMATION: Synthetic Construct

<400> SEQUENCE: 274

Trp Tyr Gln Gln Lys Pro Gly Lys Ala Pro Lys Leu Leu Ile Ser
1               5                   10                  15

<210> SEQ ID NO 275
<211> LENGTH: 15
<212> TYPE: PRT
<213> ORGANISM: Artificial Sequence
<220> FEATURE:
<223> OTHER INFORMATION: Synthetic Construct

<400> SEQUENCE: 275

Trp Tyr Leu Gln Lys Pro Gly Gln Ser Pro Gln Val Leu Ile Tyr
1               5                   10                  15

<210> SEQ ID NO 276
<211> LENGTH: 32
<212> TYPE: PRT
<213> ORGANISM: Artificial Sequence
<220> FEATURE:
<223> OTHER INFORMATION: Synthetic Construct

<400> SEQUENCE: 276

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
                20                  25                  30

<210> SEQ ID NO 277
<211> LENGTH: 32
<212> TYPE: PRT
<213> ORGANISM: Artificial Sequence
```

<220> FEATURE:
<223> OTHER INFORMATION: Synthetic Construct

<400> SEQUENCE: 277

```
Gly Val Pro Ser Arg Phe Ser Gly Ser Gly Ser Gly Thr Asp Phe Thr
1               5                   10                  15
Leu Thr Ile Ser Ser Leu Gln Pro Glu Asp Phe Ala Thr Tyr Tyr Cys
            20                  25                  30
```

<210> SEQ ID NO 278
<211> LENGTH: 32
<212> TYPE: PRT
<213> ORGANISM: Artificial Sequence
<220> FEATURE:
<223> OTHER INFORMATION: Synthetic Construct

<400> SEQUENCE: 278

```
Gly Val Pro Ser Arg Phe Ser Gly Ser Gly Ser Gly Thr Glu Phe Thr
1               5                   10                  15
Leu Thr Ile Ser Ser Leu Gln Pro Asp Asp Phe Ala Thr Tyr Tyr Cys
            20                  25                  30
```

<210> SEQ ID NO 279
<211> LENGTH: 32
<212> TYPE: PRT
<213> ORGANISM: Artificial Sequence
<220> FEATURE:
<223> OTHER INFORMATION: Synthetic Construct

<400> SEQUENCE: 279

```
Gly Ile Pro Ala Arg Phe Ser Gly Ser Gly Ser Gly Thr Glu Phe Thr
1               5                   10                  15
Leu Thr Ile Ser Ser Leu Gln Ser Glu Asp Phe Ala Val Tyr Tyr Cys
            20                  25                  30
```

<210> SEQ ID NO 280
<211> LENGTH: 32
<212> TYPE: PRT
<213> ORGANISM: Artificial Sequence
<220> FEATURE:
<223> OTHER INFORMATION: Synthetic Construct

<400> SEQUENCE: 280

```
Gly Val Pro Asp Arg Phe Ser Gly Ser Gly Ser Gly Thr Asp Phe Thr
1               5                   10                  15
Leu Lys Ile Ser Arg Val Glu Ala Glu Asp Val Gly Val Tyr Tyr Cys
            20                  25                  30
```

<210> SEQ ID NO 281
<211> LENGTH: 32
<212> TYPE: PRT
<213> ORGANISM: Artificial Sequence
<220> FEATURE:
<223> OTHER INFORMATION: Synthetic Construct

<400> SEQUENCE: 281

```
Gly Ile Pro Ala Arg Phe Ser Gly Ser Gly Ser Gly Thr Asp Phe Thr
1               5                   10                  15
Leu Thr Ile Ser Ser Leu Glu Pro Glu Asp Phe Ala Val Tyr Tyr Cys
            20                  25                  30
```

<210> SEQ ID NO 282
<211> LENGTH: 32
<212> TYPE: PRT

```
<213> ORGANISM: Artificial Sequence
<220> FEATURE:
<223> OTHER INFORMATION: Synthetic Construct

<400> SEQUENCE: 282

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 283
<211> LENGTH: 10
<212> TYPE: PRT
<213> ORGANISM: Artificial Sequence
<220> FEATURE:
<223> OTHER INFORMATION: Synthetic Construct

<400> SEQUENCE: 283

Phe Gly Gly Gly Thr Lys Val Glu Ile Lys
1               5                   10

<210> SEQ ID NO 284
<211> LENGTH: 26
<212> TYPE: PRT
<213> ORGANISM: Artificial Sequence
<220> FEATURE:
<223> OTHER INFORMATION: Synthetic Construct

<400> SEQUENCE: 284

Gln Val Gln Leu Val Gln Ser Gly Ala Glu Val Lys Lys Pro Gly Ala
1               5                   10                  15

Ser Val Lys Val Ser Cys Lys Ala Ser Gly
            20                  25

<210> SEQ ID NO 285
<211> LENGTH: 26
<212> TYPE: PRT
<213> ORGANISM: Artificial Sequence
<220> FEATURE:
<223> OTHER INFORMATION: Synthetic Construct

<400> SEQUENCE: 285

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 286

<400> SEQUENCE: 286

000

<210> SEQ ID NO 287
<211> LENGTH: 26
<212> TYPE: PRT
<213> ORGANISM: Artificial Sequence
<220> FEATURE:
<223> OTHER INFORMATION: Synthetic Construct

<400> SEQUENCE: 287

Glu Val Gln Leu Val Glu Ser Gly Gly Gly Leu Val Gln Pro Gly Arg
1               5                   10                  15

Ser Leu Arg Leu Ser Cys Ala Ala Ser Gly
            20                  25
```

```
<210> SEQ ID NO 288
<211> LENGTH: 26
<212> TYPE: PRT
<213> ORGANISM: Artificial Sequence
<220> FEATURE:
<223> OTHER INFORMATION: Synthetic Construct

<400> SEQUENCE: 288

Glu Val Gln Leu Val Glu Ser Gly Gly Gly Leu Val Lys Pro Gly Gly
1               5                   10                  15

Ser Leu Arg Leu Ser Cys Ala Ala Ser Gly
            20                  25

<210> SEQ ID NO 289
<211> LENGTH: 26
<212> TYPE: PRT
<213> ORGANISM: Artificial Sequence
<220> FEATURE:
<223> OTHER INFORMATION: Synthetic Construct

<400> SEQUENCE: 289

Glu Val Gln Leu Leu Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 290
<211> LENGTH: 26
<212> TYPE: PRT
<213> ORGANISM: Artificial Sequence
<220> FEATURE:
<223> OTHER INFORMATION: Synthetic Construct

<400> SEQUENCE: 290

Gln Val Gln Leu Val Glu Ser Gly Gly Gly Val Val Gln Pro Gly Arg
1               5                   10                  15

Ser Leu Arg Leu Ser Cys Ala Ala Ser Gly
            20                  25

<210> SEQ ID NO 291
<211> LENGTH: 26
<212> TYPE: PRT
<213> ORGANISM: Artificial Sequence
<220> FEATURE:
<223> OTHER INFORMATION: Synthetic Construct

<400> SEQUENCE: 291

Gln Val Gln Leu Gln Glu Ser Gly Pro Gly Leu Val Lys Pro Ser Glu
1               5                   10                  15

Thr Leu Ser Leu Thr Cys Ala Val Ser Gly
            20                  25

<210> SEQ ID NO 292
<211> LENGTH: 26
<212> TYPE: PRT
<213> ORGANISM: Artificial Sequence
<220> FEATURE:
<223> OTHER INFORMATION: Synthetic Construct

<400> SEQUENCE: 292

Gln Val Gln Leu Gln Glu Ser Gly Pro Gly Leu Val Lys Pro Ser Gln
1               5                   10                  15

Thr Leu Ser Leu Thr Cys Thr Val Ser Gly
```

-continued

```
                    20                  25

<210> SEQ ID NO 293

<400> SEQUENCE: 293

000

<210> SEQ ID NO 294
<211> LENGTH: 26
<212> TYPE: PRT
<213> ORGANISM: Artificial Sequence
<220> FEATURE:
<223> OTHER INFORMATION: Synthetic Construct

<400> SEQUENCE: 294

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 295
<211> LENGTH: 26
<212> TYPE: PRT
<213> ORGANISM: Artificial Sequence
<220> FEATURE:
<223> OTHER INFORMATION: Synthetic Construct

<400> SEQUENCE: 295

Glu Val Gln Leu Val Gln Ser Gly Ala Glu Val Lys Lys Pro Gly Glu
1               5                   10                  15

Ser Leu Lys Ile Ser Cys Lys Gly Ser Gly
            20                  25

<210> SEQ ID NO 296
<211> LENGTH: 14
<212> TYPE: PRT
<213> ORGANISM: Artificial Sequence
<220> FEATURE:
<223> OTHER INFORMATION: Synthetic Construct

<400> SEQUENCE: 296

Trp Val Arg Gln Ala Pro Gly Gln Gly Leu Glu Trp Met Gly
1               5                   10

<210> SEQ ID NO 297
<211> LENGTH: 14
<212> TYPE: PRT
<213> ORGANISM: Artificial Sequence
<220> FEATURE:
<223> OTHER INFORMATION: Synthetic Construct

<400> SEQUENCE: 297

Trp Val Arg Gln Ala Pro Gly Lys Gly Leu Glu Trp Val Ala
1               5                   10

<210> SEQ ID NO 298
<211> LENGTH: 14
<212> TYPE: PRT
<213> ORGANISM: Artificial Sequence
<220> FEATURE:
<223> OTHER INFORMATION: Synthetic Construct

<400> SEQUENCE: 298

Trp Val Arg Gln Ala Pro Gly Lys Gly Leu Glu Trp Val Ser
1               5                   10
```

<210> SEQ ID NO 299
<211> LENGTH: 14
<212> TYPE: PRT
<213> ORGANISM: Artificial Sequence
<220> FEATURE:
<223> OTHER INFORMATION: Synthetic Construct

<400> SEQUENCE: 299

Trp Ile Arg Gln Pro Pro Gly Lys Gly Leu Glu Trp Ile Gly
1               5                   10

<210> SEQ ID NO 300
<211> LENGTH: 14
<212> TYPE: PRT
<213> ORGANISM: Artificial Sequence
<220> FEATURE:
<223> OTHER INFORMATION: Synthetic Construct

<400> SEQUENCE: 300

Trp Ile Arg Gln His Pro Gly Lys Gly Leu Glu Trp Ile Gly
1               5                   10

<210> SEQ ID NO 301
<211> LENGTH: 14
<212> TYPE: PRT
<213> ORGANISM: Artificial Sequence
<220> FEATURE:
<223> OTHER INFORMATION: Synthetic Construct

<400> SEQUENCE: 301

Trp Val Arg Gln Met Pro Gly Lys Gly Leu Glu Trp Met Gly
1               5                   10

<210> SEQ ID NO 302
<211> LENGTH: 30
<212> TYPE: PRT
<213> ORGANISM: Artificial Sequence
<220> FEATURE:
<223> OTHER INFORMATION: Synthetic Construct

<400> SEQUENCE: 302

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys
            20                  25                  30

<210> SEQ ID NO 303
<211> LENGTH: 30
<212> TYPE: PRT
<213> ORGANISM: Artificial Sequence
<220> FEATURE:
<223> OTHER INFORMATION: Synthetic Construct

<400> SEQUENCE: 303

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys
            20                  25                  30

<210> SEQ ID NO 304
<211> LENGTH: 30
<212> TYPE: PRT
<213> ORGANISM: Artificial Sequence
<220> FEATURE:
<223> OTHER INFORMATION: Synthetic Construct

```
<400> SEQUENCE: 304

Arg Val Thr Met Thr Arg Asp Thr Ser Thr Val Tyr Met Glu
1               5                  10                  15

Leu Ser Ser Leu Arg Ser Glu Asp Thr Ala Val Tyr Tyr Cys
            20                  25                  30

<210> SEQ ID NO 305
<211> LENGTH: 30
<212> TYPE: PRT
<213> ORGANISM: Artificial Sequence
<220> FEATURE:
<223> OTHER INFORMATION: Synthetic Construct

<400> SEQUENCE: 305

Arg Val Thr Ile Thr Ala Asp Glu Ser Thr Ser Thr Ala Tyr Met Glu
1               5                  10                  15

Leu Ser Ser Leu Arg Ser Glu Asp Thr Ala Val Tyr Tyr Cys
            20                  25                  30

<210> SEQ ID NO 306
<211> LENGTH: 30
<212> TYPE: PRT
<213> ORGANISM: Artificial Sequence
<220> FEATURE:
<223> OTHER INFORMATION: Synthetic Construct

<400> SEQUENCE: 306

Arg Phe Thr Ile Ser Arg Asp Asn Ala Lys Asn Ser Leu Tyr Leu Gln
1               5                  10                  15

Met Asn Ser Leu Arg Ala Glu Asp Thr Ala Val Tyr Tyr Cys
            20                  25                  30

<210> SEQ ID NO 307
<211> LENGTH: 30
<212> TYPE: PRT
<213> ORGANISM: Artificial Sequence
<220> FEATURE:
<223> OTHER INFORMATION: Synthetic Construct

<400> SEQUENCE: 307

Arg Phe Thr Ile Ser Arg Asp Asn Ala Lys Asn Ser Leu Tyr Leu Gln
1               5                  10                  15

Met Asn Ser Leu Arg Ala Glu Asp Thr Ala Leu Tyr Tyr Cys
            20                  25                  30

<210> SEQ ID NO 308
<211> LENGTH: 30
<212> TYPE: PRT
<213> ORGANISM: Artificial Sequence
<220> FEATURE:
<223> OTHER INFORMATION: Synthetic Construct

<400> SEQUENCE: 308

Arg Phe Thr Ile Ser Arg Asp Asn Ser Lys Asn Thr Leu Tyr Leu Gln
1               5                  10                  15

Met Asn Ser Leu Arg Ala Glu Asp Thr Ala Val Tyr Tyr Cys
            20                  25                  30

<210> SEQ ID NO 309
<211> LENGTH: 30
<212> TYPE: PRT
<213> ORGANISM: Artificial Sequence
<220> FEATURE:
```

<223> OTHER INFORMATION: Synthetic Construct

<400> SEQUENCE: 309

Arg Val Thr Ile Ser Val Asp Thr Ser Lys Asn Gln Phe Ser Leu Lys
1               5                   10                  15
Leu Ser Ser Val Thr Ala Ala Asp Thr Ala Val Tyr Tyr Cys
            20                  25                  30

<210> SEQ ID NO 310
<211> LENGTH: 30
<212> TYPE: PRT
<213> ORGANISM: Artificial Sequence
<220> FEATURE:
<223> OTHER INFORMATION: Synthetic Construct

<400> SEQUENCE: 310

Gln Val Thr Ile Ser Ala Asp Lys Ser Ile Ser Thr Ala Tyr Leu Gln
1               5                   10                  15
Trp Ser Ser Leu Lys Ala Ser Asp Thr Ala Met Tyr Tyr Cys
            20                  25                  30

<210> SEQ ID NO 311
<211> LENGTH: 11
<212> TYPE: PRT
<213> ORGANISM: Artificial Sequence
<220> FEATURE:
<223> OTHER INFORMATION: Synthetic Construct

<400> SEQUENCE: 311

Trp Gly Gln Gly Thr Thr Val Thr Val Ser Ser
1               5                   10

<210> SEQ ID NO 312
<211> LENGTH: 11
<212> TYPE: PRT
<213> ORGANISM: Artificial Sequence
<220> FEATURE:
<223> OTHER INFORMATION: Synthetic Construct

<400> SEQUENCE: 312

Trp Gly Gln Gly Thr Leu Val Thr Val Ser Ser
1               5                   10

<210> SEQ ID NO 313
<211> LENGTH: 11
<212> TYPE: PRT
<213> ORGANISM: Artificial Sequence
<220> FEATURE:
<223> OTHER INFORMATION: Synthetic Construct

<400> SEQUENCE: 313

Trp Gly Gln Gly Thr Met Val Thr Val Ser Ser
1               5                   10

<210> SEQ ID NO 314
<211> LENGTH: 11
<212> TYPE: PRT
<213> ORGANISM: Artificial Sequence
<220> FEATURE:
<223> OTHER INFORMATION: Synthetic Construct

<400> SEQUENCE: 314

Trp Gly Arg Gly Thr Leu Val Thr Val Ser Ser
1               5                   10

```
<210> SEQ ID NO 315
<211> LENGTH: 11
<212> TYPE: PRT
<213> ORGANISM: Artificial Sequence
<220> FEATURE:
<223> OTHER INFORMATION: Synthetic Construct

<400> SEQUENCE: 315

Trp Gly Lys Gly Thr Thr Val Thr Val Ser Ser
1               5                   10

<210> SEQ ID NO 316

<400> SEQUENCE: 316

000

<210> SEQ ID NO 317
<211> LENGTH: 105
<212> TYPE: PRT
<213> ORGANISM: Artificial Sequence
<220> FEATURE:
<223> OTHER INFORMATION: Synthetic Construct

<400> SEQUENCE: 317

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Pro Trp Thr Phe
                85                  90                  95

Gly Gly Gly Thr Lys Val Glu Ile Lys
            100                 105

<210> SEQ ID NO 318
<211> LENGTH: 128
<212> TYPE: PRT
<213> ORGANISM: Artificial Sequence
<220> FEATURE:
<223> OTHER INFORMATION: Synthetic Construct

<400> SEQUENCE: 318

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Gly Gly Ala Thr Asp Gly Leu Val Tyr Tyr Tyr Tyr
```

```
              100                 105                 110
Tyr Gly Met Asp Val Trp Gly Gln Gly Thr Thr Val Thr Val Ser Ser
            115                 120                 125
```

<210> SEQ ID NO 319
<211> LENGTH: 107
<212> TYPE: PRT
<213> ORGANISM: Artificial Sequence
<220> FEATURE:
<223> OTHER INFORMATION: Synthetic Construct

<400> SEQUENCE: 319

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Val Ser Pro Ile
                85                  90                  95

Thr Phe Gly Gly Gly Thr Lys Val Glu Ile Lys
            100                 105
```

<210> SEQ ID NO 320
<211> LENGTH: 124
<212> TYPE: PRT
<213> ORGANISM: Artificial Sequence
<220> FEATURE:
<223> OTHER INFORMATION: Synthetic Construct

<400> SEQUENCE: 320

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Arg Ser Ser Gly Trp Tyr Glu Gly Tyr Gly Met Asp
            100                 105                 110

Val Trp Gly Gln Gly Thr Thr Val Thr Val Ser Ser
        115                 120
```

<210> SEQ ID NO 321
<211> LENGTH: 107
<212> TYPE: PRT
<213> ORGANISM: Artificial Sequence
<220> FEATURE:
<223> OTHER INFORMATION: Synthetic Construct

<400> SEQUENCE: 321

-continued

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Lys Ser Tyr Pro Ile
                85                  90                  95

Thr Phe Gly Gly Gly Thr Lys Val Glu Ile Lys
            100                 105

<210> SEQ ID NO 322
<211> LENGTH: 122
<212> TYPE: PRT
<213> ORGANISM: Artificial Sequence
<220> FEATURE:
<223> OTHER INFORMATION: Synthetic Construct

<400> SEQUENCE: 322

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Pro Gln Leu Arg Val Ala Glu Tyr Phe Gln His Trp
            100                 105                 110

Gly Gln Gly Thr Leu Val Thr Val Ser Ser
        115                 120

<210> SEQ ID NO 323
<211> LENGTH: 107
<212> TYPE: PRT
<213> ORGANISM: Artificial Sequence
<220> FEATURE:
<223> OTHER INFORMATION: Synthetic Construct

<400> SEQUENCE: 323

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser

-continued

```
                65                  70                  75                  80
Glu Asp Phe Ala Val Tyr Tyr Cys Gln Gln Phe Arg Val Leu Pro Pro
                    85                  90                  95
Thr Phe Gly Gly Gly Thr Lys Val Glu Ile Lys
            100                 105

<210> SEQ ID NO 324
<211> LENGTH: 112
<212> TYPE: PRT
<213> ORGANISM: Artificial Sequence
<220> FEATURE:
<223> OTHER INFORMATION: Synthetic Construct

<400> SEQUENCE: 324

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Ser Thr Glu Pro Pro Thr Phe Gly Gly Gly Thr Lys Val Glu Ile Lys
            100                 105                 110

<210> SEQ ID NO 325
<211> LENGTH: 120
<212> TYPE: PRT
<213> ORGANISM: Artificial Sequence
<220> FEATURE:
<223> OTHER INFORMATION: Synthetic Construct

<400> SEQUENCE: 325

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Ser Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg His Arg Ser Ser Thr Tyr Gly Met Asp Val Trp Gly Gln
            100                 105                 110

Gly Thr Thr Val Thr Val Ser Ser
        115                 120

<210> SEQ ID NO 326
<211> LENGTH: 107
<212> TYPE: PRT
<213> ORGANISM: Artificial Sequence
<220> FEATURE:
```

-continued

<223> OTHER INFORMATION: Synthetic Construct

<400> SEQUENCE: 326

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Val Ala Asn Tyr Pro Arg
                85                  90                  95

Thr Phe Gly Gly Gly Thr Lys Val Glu Ile Lys
            100                 105

<210> SEQ ID NO 327
<211> LENGTH: 126
<212> TYPE: PRT
<213> ORGANISM: Artificial Sequence
<220> FEATURE:
<223> OTHER INFORMATION: Synthetic Construct

<400> SEQUENCE: 327

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Ser Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Val Gly Ser Thr Val Thr Leu Ala Tyr Tyr Tyr Tyr Gly
            100                 105                 110

Met Asp Val Trp Gly Gln Gly Thr Thr Val Thr Val Ser Ser
        115                 120                 125

<210> SEQ ID NO 328
<211> LENGTH: 108
<212> TYPE: PRT
<213> ORGANISM: Artificial Sequence
<220> FEATURE:
<223> OTHER INFORMATION: Synthetic Construct

<400> SEQUENCE: 328

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser

```
                     50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Asp Gln Leu Gly Ser Ser Pro
                 85                  90                  95

Arg Thr Phe Gly Gly Gly Thr Lys Val Glu Ile Lys
            100                 105

<210> SEQ ID NO 329
<211> LENGTH: 125
<212> TYPE: PRT
<213> ORGANISM: Artificial Sequence
<220> FEATURE:
<223> OTHER INFORMATION: Synthetic Construct

<400> SEQUENCE: 329

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Ala Pro Gly Gln Gly Leu Glu Trp Met
             35                  40                  45

Gly Ser Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Pro Ser Gly Gly Thr Thr Leu His Tyr Tyr Gly Met
                100                 105                 110

Asp Val Trp Gly Gln Gly Thr Thr Val Thr Val Ser Ser
            115                 120                 125

<210> SEQ ID NO 330
<211> LENGTH: 108
<212> TYPE: PRT
<213> ORGANISM: Artificial Sequence
<220> FEATURE:
<223> OTHER INFORMATION: Synthetic Construct

<400> SEQUENCE: 330

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Phe Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Ala Lys Val Trp Pro
                 85                  90                  95

Tyr Thr Phe Gly Gly Gly Thr Lys Val Glu Ile Lys
            100                 105

<210> SEQ ID NO 331
<211> LENGTH: 127
```

```
<212> TYPE: PRT
<213> ORGANISM: Artificial Sequence
<220> FEATURE:
<223> OTHER INFORMATION: Synthetic Construct

<400> SEQUENCE: 331

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Ser Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gln Gly Gly His Asp Ser Pro Thr Leu Tyr Tyr Tyr Tyr Tyr
            100                 105                 110

Gly Met Asp Val Trp Gly Gln Gly Thr Thr Val Thr Val Ser Ser
        115                 120                 125

<210> SEQ ID NO 332
<211> LENGTH: 107
<212> TYPE: PRT
<213> ORGANISM: Artificial Sequence
<220> FEATURE:
<223> OTHER INFORMATION: Synthetic Construct

<400> SEQUENCE: 332

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Ile Tyr Pro Leu
                85                  90                  95

Thr Phe Gly Gly Gly Thr Lys Val Glu Ile Lys
            100                 105

<210> SEQ ID NO 333
<211> LENGTH: 126
<212> TYPE: PRT
<213> ORGANISM: Artificial Sequence
<220> FEATURE:
<223> OTHER INFORMATION: Synthetic Construct

<400> SEQUENCE: 333

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
```

```
            35                  40                  45
Gly Trp Ile Ser Ala Tyr Asn Gly Asn Thr Asn Tyr Ala Gln Lys Leu
        50                  55                  60
Gln Gly Arg Val Thr Met Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                85                  90                  95
Ala Arg Asp Pro Gly Gly Tyr Gly Pro Thr Leu Tyr Tyr Tyr Tyr Gly
               100                 105                 110
Met Asp Val Trp Gly Gln Gly Thr Thr Val Thr Val Ser Ser
               115                 120                 125

<210> SEQ ID NO 334
<211> LENGTH: 108
<212> TYPE: PRT
<213> ORGANISM: Artificial Sequence
<220> FEATURE:
<223> OTHER INFORMATION: Synthetic Construct

<400> SEQUENCE: 334

Glu Ile Val Met Thr Gln Ser Pro Ala Thr Leu Ser Val Ser Pro Gly
 1               5                  10                  15
Glu Arg Ala Thr Leu Ser Cys Arg Ala Ser Gln Ser Val Ser Ser Asn
                20                  25                  30
Leu Ala Trp Tyr Gln Gln Lys Pro Gly Gln Ala Pro Arg Leu Leu Ile
            35                  40                  45
Tyr Gly Ala Ser Thr Arg Ala Thr Gly Ile Pro Ala Arg Phe Ser Gly
        50                  55                  60
Ser Gly Ser Gly Thr Glu Phe Thr Leu Thr Ile Ser Ser Leu Gln Ser
 65                  70                  75                  80
Glu Asp Phe Ala Val Tyr Tyr Cys Gln Gln Tyr Ala Asp Trp Pro Pro
                85                  90                  95
Ile Thr Phe Gly Gly Gly Thr Lys Val Glu Ile Lys
               100                 105

<210> SEQ ID NO 335

<400> SEQUENCE: 335

000

<210> SEQ ID NO 336

<400> SEQUENCE: 336

000

<210> SEQ ID NO 337
<211> LENGTH: 107
<212> TYPE: PRT
<213> ORGANISM: Artificial Sequence
<220> FEATURE:
<223> OTHER INFORMATION: Synthetic Construct

<400> SEQUENCE: 337

Glu Ile Val Leu Thr Gln Ser Pro Ala Thr Leu Ser Val Ser Pro Gly
 1               5                  10                  15
Glu Arg Ala Thr Leu Ser Cys Arg Ala Ser Gln Ser Val Ser Ser Asn
                20                  25                  30
Leu Ala Trp Tyr Gln Gln Lys Pro Gly Gln Ala Pro Arg Leu Leu Ile
```

```
                35                  40                  45
Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn His Pro Pro
                85                  90                  95

Thr Phe Gly Gly Gly Thr Lys Val Glu Ile Lys
            100                 105

<210> SEQ ID NO 338
<211> LENGTH: 121
<212> TYPE: PRT
<213> ORGANISM: Artificial Sequence
<220> FEATURE:
<223> OTHER INFORMATION: Synthetic Construct

<400> SEQUENCE: 338

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Pro Lys Tyr Lys Trp Gly Trp Phe Asp Pro Trp Gly
            100                 105                 110

Gln Gly Thr Leu Val Thr Val Ser Ser
        115                 120

<210> SEQ ID NO 339

<400> SEQUENCE: 339

000

<210> SEQ ID NO 340

<400> SEQUENCE: 340

000

<210> SEQ ID NO 341
<211> LENGTH: 107
<212> TYPE: PRT
<213> ORGANISM: Artificial Sequence
<220> FEATURE:
<223> OTHER INFORMATION: Synthetic Construct

<400> SEQUENCE: 341

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
```

```
                35                  40                  45
Tyr Gly Ala Ser Ser Leu Gln Ser Gly Val Pro Ser Arg Phe Ser Gly
                50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Val Gly Pro Phe
                85                  90                  95
Thr Phe Gly Gly Gly Thr Lys Val Glu Ile Lys
            100                 105
```

<210> SEQ ID NO 342
<211> LENGTH: 129
<212> TYPE: PRT
<213> ORGANISM: Artificial Sequence
<220> FEATURE:
<223> OTHER INFORMATION: Synthetic Construct

<400> SEQUENCE: 342

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Tyr Met Ser Trp Val Arg Gln Ala Pro Gly Gln Gly Leu Glu Trp Met
            35                  40                  45
Gly Ile Ile Asn Pro Ser Gly Gly Ser Thr Ser Tyr Ala Gln Lys Phe
        50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Asp Pro Ser Gly Ile Ala Ala Ala Gly Pro Ala Ser Arg Tyr
            100                 105                 110
Tyr Tyr Gly Met Asp Val Trp Gly Gln Gly Thr Thr Val Thr Val Ser
        115                 120                 125
Ser
```

<210> SEQ ID NO 343
<211> LENGTH: 107
<212> TYPE: PRT
<213> ORGANISM: Artificial Sequence
<220> FEATURE:
<223> OTHER INFORMATION: Synthetic Construct

<400> SEQUENCE: 343

```
Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
                20                  25                  30
Leu Ala Trp Tyr Gln Gln Lys Pro Gly Gln Ala Pro Arg Leu Leu Ile
            35                  40                  45
Tyr Gly Ala Ser Thr Arg Ala Thr Gly Ile Pro Ala Arg Phe Ser Gly
        50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Ala Arg Leu Gly Pro Trp
                85                  90                  95
Thr Phe Gly Gly Gly Thr Lys Val Glu Ile Lys
```

<210> SEQ ID NO 344
<211> LENGTH: 107
<212> TYPE: PRT
<213> ORGANISM: Artificial Sequence
<220> FEATURE:
<223> OTHER INFORMATION: Synthetic Construct

<400> SEQUENCE: 344

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Ser Tyr Pro Ile
                85                  90                  95

Thr Phe Gly Gly Gly Thr Lys Val Glu Ile Lys
            100                 105

<210> SEQ ID NO 345
<211> LENGTH: 120
<212> TYPE: PRT
<213> ORGANISM: Artificial Sequence
<220> FEATURE:
<223> OTHER INFORMATION: Synthetic Construct

<400> SEQUENCE: 345

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Pro Tyr Ser Gly Ser Arg Asp Phe Asp Leu Trp Gly Arg
            100                 105                 110

Gly Thr Leu Val Thr Val Ser Ser
        115                 120

<210> SEQ ID NO 346

<400> SEQUENCE: 346

000

<210> SEQ ID NO 347

<400> SEQUENCE: 347

<210> SEQ ID NO 348
<211> LENGTH: 108
<212> TYPE: PRT
<213> ORGANISM: Artificial Sequence
<220> FEATURE:
<223> OTHER INFORMATION: Synthetic Construct

<400> SEQUENCE: 348

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Ala Asn Ala Pro Pro
                85                  90                  95

Arg Thr Phe Gly Gly Gly Thr Lys Val Glu Ile Lys
            100                 105
```

<210> SEQ ID NO 349
<211> LENGTH: 123
<212> TYPE: PRT
<213> ORGANISM: Artificial Sequence
<220> FEATURE:
<223> OTHER INFORMATION: Synthetic Construct

<400> SEQUENCE: 349

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Lys His Gly Arg Arg Gly Tyr Tyr Tyr Tyr Met Asp Val
            100                 105                 110

Trp Gly Lys Gly Thr Thr Val Thr Val Ser Ser
        115                 120
```

<210> SEQ ID NO 350
<211> LENGTH: 107
<212> TYPE: PRT
<213> ORGANISM: Artificial Sequence
<220> FEATURE:
<223> OTHER INFORMATION: Synthetic Construct

<400> SEQUENCE: 350

```
Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asp Gly Lys Pro Pro
                85                  90                  95

Thr Phe Gly Gly Gly Thr Lys Val Glu Ile Lys
            100                 105

<210> SEQ ID NO 351
<211> LENGTH: 126
<212> TYPE: PRT
<213> ORGANISM: Artificial Sequence
<220> FEATURE:
<223> OTHER INFORMATION: Synthetic Construct

<400> SEQUENCE: 351

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Ser Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Arg Ile Pro Gly Ser Gly Tyr Tyr Tyr Tyr Tyr Gly
            100                 105                 110

Met Asp Val Trp Gly Gln Gly Thr Thr Val Thr Val Ser Ser
        115                 120                 125

<210> SEQ ID NO 352
<211> LENGTH: 108
<212> TYPE: PRT
<213> ORGANISM: Artificial Sequence
<220> FEATURE:
<223> OTHER INFORMATION: Synthetic Construct

<400> SEQUENCE: 352

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Gly Phe Pro 85                  90                  95

Ile Thr Phe Gly Gly Gly Thr Lys Val Glu Ile Lys
                100                 105

<210> SEQ ID NO 353
<211> LENGTH: 124
<212> TYPE: PRT
<213> ORGANISM: Artificial Sequence
<220> FEATURE:
<223> OTHER INFORMATION: Synthetic Construct

<400> SEQUENCE: 353

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Arg Met Ser Gly Trp Tyr Tyr Ala Tyr Gly Met Asp
                100                 105                 110

Val Trp Gly Gln Gly Thr Thr Val Thr Val Ser Ser
            115                 120

<210> SEQ ID NO 354
<211> LENGTH: 107
<212> TYPE: PRT
<213> ORGANISM: Artificial Sequence
<220> FEATURE:
<223> OTHER INFORMATION: Synthetic Construct

<400> SEQUENCE: 354

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Ala Ser Leu Pro Phe
                85                  90                  95

Thr Phe Gly Gly Gly Thr Lys Val Glu Ile Lys
                100                 105

<210> SEQ ID NO 355
<211> LENGTH: 124
<212> TYPE: PRT
<213> ORGANISM: Artificial Sequence
<220> FEATURE:
<223> OTHER INFORMATION: Synthetic Construct

<400> SEQUENCE: 355

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Arg Tyr Asp Gly Tyr Tyr Tyr Tyr Tyr Gly Met Asp
            100                 105                 110

Val Trp Gly Gln Gly Thr Thr Val Thr Val Ser Ser
            115                 120

<210> SEQ ID NO 356
<211> LENGTH: 106
<212> TYPE: PRT
<213> ORGANISM: Artificial Sequence
<220> FEATURE:
<223> OTHER INFORMATION: Synthetic Construct

<400> SEQUENCE: 356

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ala Asp Gly His Ile Thr
                85                  90                  95

Phe Gly Gly Gly Thr Lys Val Glu Ile Lys
            100                 105

<210> SEQ ID NO 357
<211> LENGTH: 124
<212> TYPE: PRT
<213> ORGANISM: Artificial Sequence
<220> FEATURE:
<223> OTHER INFORMATION: Synthetic Construct

<400> SEQUENCE: 357

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Ser Tyr Ala Gln Lys Phe
    50                  55                  60

Gln Gly Arg Val Thr Ile Thr Ala Asp Glu Ser Thr Ser Thr Ala Tyr

```
                65                  70                  75                  80
Met Glu Leu Ser Ser Leu Arg Ser Glu Asp Thr Ala Val Tyr Tyr Cys
                    85                  90                  95

Ala Arg Gln Gly Arg Lys Thr Gly Tyr Tyr Tyr Tyr Gly Met Asp
                100                 105                 110

Val Trp Gly Gln Gly Thr Thr Val Thr Val Ser Ser
            115                 120

<210> SEQ ID NO 358

<400> SEQUENCE: 358

000

<210> SEQ ID NO 359

<400> SEQUENCE: 359

000

<210> SEQ ID NO 360
<211> LENGTH: 108
<212> TYPE: PRT
<213> ORGANISM: Artificial Sequence
<220> FEATURE:
<223> OTHER INFORMATION: Synthetic Construct

<400> SEQUENCE: 360

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Val Ala Val Ser Pro
                85                  90                  95

Ile Thr Phe Gly Gly Gly Thr Lys Val Glu Ile Lys
            100                 105

<210> SEQ ID NO 361
<211> LENGTH: 119
<212> TYPE: PRT
<213> ORGANISM: Artificial Sequence
<220> FEATURE:
<223> OTHER INFORMATION: Synthetic Construct

<400> SEQUENCE: 361

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Gly Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
50                  55                  60

Lys Gly Arg Phe Thr Ile Ser Arg Asp Asn Ala Lys Asn Ser Leu Tyr
```

```
                65                  70                  75                  80
Leu Gln Met Asn Ser Leu Arg Ala Glu Asp Thr Ala Leu Tyr Tyr Cys
                    85                  90                  95

Ala Lys Pro Leu Tyr Arg Gly Gly Pro Phe Asp Ile Trp Gly Gln Gly
                100                 105                 110

Thr Met Val Thr Val Ser Ser
            115

<210> SEQ ID NO 362
<211> LENGTH: 108
<212> TYPE: PRT
<213> ORGANISM: Artificial Sequence
<220> FEATURE:
<223> OTHER INFORMATION: Synthetic Construct

<400> SEQUENCE: 362

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Ser Ala Pro
                85                  90                  95

Ile Thr Phe Gly Gly Gly Thr Lys Val Glu Ile Lys
                100                 105

<210> SEQ ID NO 363
<211> LENGTH: 122
<212> TYPE: PRT
<213> ORGANISM: Artificial Sequence
<220> FEATURE:
<223> OTHER INFORMATION: Synthetic Construct

<400> SEQUENCE: 363

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Val Gly Gln Val Pro Ala Ser Val Ala Phe Asp Ile Trp
                100                 105                 110

Gly Gln Gly Thr Met Val Thr Val Ser Ser
            115                 120

<210> SEQ ID NO 364
<211> LENGTH: 108
```

```
<212> TYPE: PRT
<213> ORGANISM: Artificial Sequence
<220> FEATURE:
<223> OTHER INFORMATION: Synthetic Construct

<400> SEQUENCE: 364

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                 55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Ser Leu Pro Pro
                85                  90                  95

Ile Thr Phe Gly Gly Gly Thr Lys Val Glu Ile Lys
            100                 105

<210> SEQ ID NO 365
<211> LENGTH: 123
<212> TYPE: PRT
<213> ORGANISM: Artificial Sequence
<220> FEATURE:
<223> OTHER INFORMATION: Synthetic Construct

<400> SEQUENCE: 365

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
 50                 55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Leu Gly Arg Gly Tyr Lys Trp Asn Trp Phe Asp Pro
            100                 105                 110

Trp Gly Gln Gly Thr Leu Val Thr Val Ser Ser
        115                 120

<210> SEQ ID NO 366

<400> SEQUENCE: 366

000

<210> SEQ ID NO 367

<400> SEQUENCE: 367

000

<210> SEQ ID NO 368
<211> LENGTH: 113
```

```
<212> TYPE: PRT
<213> ORGANISM: Artificial Sequence
<220> FEATURE:
<223> OTHER INFORMATION: Synthetic Construct

<400> SEQUENCE: 368

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Arg
                85                  90                  95

Leu Gln Ser Pro Leu Arg Thr Phe Gly Gly Gly Thr Lys Val Glu Ile
            100                 105                 110

Lys

<210> SEQ ID NO 369
<211> LENGTH: 120
<212> TYPE: PRT
<213> ORGANISM: Artificial Sequence
<220> FEATURE:
<223> OTHER INFORMATION: Synthetic Construct

<400> SEQUENCE: 369

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Asp Arg Trp Gly Ser Phe Asp Ile Trp Gly Gln
            100                 105                 110

Gly Thr Met Val Thr Val Ser Ser
        115                 120

<210> SEQ ID NO 370
<211> LENGTH: 113
<212> TYPE: PRT
<213> ORGANISM: Artificial Sequence
<220> FEATURE:
<223> OTHER INFORMATION: Synthetic Construct

<400> SEQUENCE: 370

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30
```

Asn Gly Tyr Asn Tyr Leu Asp Trp Tyr Leu Gln Lys Pro Gly Gln Ser
          35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Arg
                 85                  90                  95

Ile Gln Gly Pro Pro Arg Thr Phe Gly Gly Gly Thr Lys Val Glu Ile
                100                 105                 110

Lys

<210> SEQ ID NO 371
<211> LENGTH: 112
<212> TYPE: PRT
<213> ORGANISM: Artificial Sequence
<220> FEATURE:
<223> OTHER INFORMATION: Synthetic Construct

<400> SEQUENCE: 371

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
          35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gly Pro Pro Ile Thr Phe Gly Gly Gly Thr Lys Val Glu Ile Lys
                100                 105                 110

<210> SEQ ID NO 372
<211> LENGTH: 115
<212> TYPE: PRT
<213> ORGANISM: Artificial Sequence
<220> FEATURE:
<223> OTHER INFORMATION: Synthetic Construct

<400> SEQUENCE: 372

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
          35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Asp Gly Met Asp Val Trp Gly Gln Gly Thr Thr Val Thr
                100                 105                 110

<210> SEQ ID NO 373

<400> SEQUENCE: 373

000

<210> SEQ ID NO 374

<400> SEQUENCE: 374

000

<210> SEQ ID NO 375
<211> LENGTH: 112
<212> TYPE: PRT
<213> ORGANISM: Artificial Sequence
<220> FEATURE:
<223> OTHER INFORMATION: Synthetic Construct

<400> SEQUENCE: 375

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Phe Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile Glu Thr Pro Pro Thr Phe Gly Gly Gly Thr Lys Val Glu Ile Lys
            100                 105                 110
```

<210> SEQ ID NO 376
<211> LENGTH: 120
<212> TYPE: PRT
<213> ORGANISM: Artificial Sequence
<220> FEATURE:
<223> OTHER INFORMATION: Synthetic Construct

<400> SEQUENCE: 376

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Tyr Pro Gly Tyr Pro Ala Phe Asp Ile Trp Gly Gln
            100                 105                 110
```

```
Gly Thr Met Val Thr Val Ser Ser
        115                 120
```

<210> SEQ ID NO 377

<400> SEQUENCE: 377

000

<210> SEQ ID NO 378

<400> SEQUENCE: 378

000

<210> SEQ ID NO 379
<211> LENGTH: 108
<212> TYPE: PRT
<213> ORGANISM: Artificial Sequence
<220> FEATURE:
<223> OTHER INFORMATION: Synthetic Construct

<400> SEQUENCE: 379

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Pro Pro
                85                  90                  95

Leu Thr Phe Gly Gly Gly Thr Lys Val Glu Ile Lys
            100                 105
```

<210> SEQ ID NO 380
<211> LENGTH: 118
<212> TYPE: PRT
<213> ORGANISM: Artificial Sequence
<220> FEATURE:
<223> OTHER INFORMATION: Synthetic Construct

<400> SEQUENCE: 380

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Gly Gly Thr Tyr Gly Met Asp Val Trp Gly Gln Gly Thr
            100                 105                 110
```

Thr Val Thr Val Ser Ser
        115

<210> SEQ ID NO 381
<400> SEQUENCE: 381
000

<210> SEQ ID NO 382
<400> SEQUENCE: 382
000

<210> SEQ ID NO 383
<400> SEQUENCE: 383
000

<210> SEQ ID NO 384
<400> SEQUENCE: 384
000

<210> SEQ ID NO 385
<400> SEQUENCE: 385
000

<210> SEQ ID NO 386
<400> SEQUENCE: 386
000

<210> SEQ ID NO 387
<400> SEQUENCE: 387
000

<210> SEQ ID NO 388
<400> SEQUENCE: 388
000

<210> SEQ ID NO 389
<211> LENGTH: 112
<212> TYPE: PRT
<213> ORGANISM: Artificial Sequence
<220> FEATURE:
<223> OTHER INFORMATION: Synthetic Construct

<400> SEQUENCE: 389

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

```
Pro Gln Leu Leu Ile Phe Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ile Gln Gly Pro Ile Thr Phe Gly Gly Gly Thr Lys Val Glu Ile Lys
            100                 105                 110
```

<210> SEQ ID NO 390
<211> LENGTH: 119
<212> TYPE: PRT
<213> ORGANISM: Artificial Sequence
<220> FEATURE:
<223> OTHER INFORMATION: Synthetic Construct

<400> SEQUENCE: 390

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Leu Ser Ser Thr Gly Gly Gly Asn Ile Trp Gly Gln Gly
            100                 105                 110

Thr Met Val Thr Val Ser Ser
        115
```

<210> SEQ ID NO 391
<211> LENGTH: 107
<212> TYPE: PRT
<213> ORGANISM: Artificial Sequence
<220> FEATURE:
<223> OTHER INFORMATION: Synthetic Construct

<400> SEQUENCE: 391

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Ala Leu Pro Phe
                85                  90                  95

Thr Phe Gly Gly Gly Thr Lys Val Glu Ile Lys
            100                 105
```

<210> SEQ ID NO 392

<211> LENGTH: 122
<212> TYPE: PRT
<213> ORGANISM: Artificial Sequence
<220> FEATURE:
<223> OTHER INFORMATION: Synthetic Construct

<400> SEQUENCE: 392

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Val Met Ala Arg Ala Arg Thr Tyr Gly Met Asp Val Trp
            100                 105                 110
Gly Gln Gly Thr Thr Val Thr Val Ser Ser
        115                 120

<210> SEQ ID NO 393

<400> SEQUENCE: 393

000

<210> SEQ ID NO 394

<400> SEQUENCE: 394

000

<210> SEQ ID NO 395
<211> LENGTH: 108
<212> TYPE: PRT
<213> ORGANISM: Artificial Sequence
<220> FEATURE:
<223> OTHER INFORMATION: Synthetic Construct

<400> SEQUENCE: 395

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Ala Leu Arg Ser Pro
                85                  90                  95
Leu Thr Phe Gly Gly Gly Thr Lys Val Glu Ile Lys
            100                 105

<210> SEQ ID NO 396

```
<211> LENGTH: 119
<212> TYPE: PRT
<213> ORGANISM: Artificial Sequence
<220> FEATURE:
<223> OTHER INFORMATION: Synthetic Construct

<400> SEQUENCE: 396

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Tyr Gln Gly Thr Pro Asp Phe Asp Leu Trp Gly Arg Gly
            100                 105                 110

Thr Leu Val Thr Val Ser Ser
        115

<210> SEQ ID NO 397
<211> LENGTH: 108
<212> TYPE: PRT
<213> ORGANISM: Artificial Sequence
<220> FEATURE:
<223> OTHER INFORMATION: Synthetic Construct

<400> SEQUENCE: 397

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Gly Ser His Pro
                85                  90                  95

Pro Thr Phe Gly Gly Gly Thr Lys Val Glu Ile Lys
            100                 105

<210> SEQ ID NO 398
<211> LENGTH: 125
<212> TYPE: PRT
<213> ORGANISM: Artificial Sequence
<220> FEATURE:
<223> OTHER INFORMATION: Synthetic Construct

<400> SEQUENCE: 398

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Val Gly Gly Met Tyr Asp Gly Val Tyr Tyr Gly Met
            100                 105                 110

Asp Val Trp Gly Gln Gly Thr Thr Val Thr Val Ser Ser
         115                 120                 125

<210> SEQ ID NO 399
<211> LENGTH: 108
<212> TYPE: PRT
<213> ORGANISM: Artificial Sequence
<220> FEATURE:
<223> OTHER INFORMATION: Synthetic Construct

<400> SEQUENCE: 399

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Leu Asp Ser Ser Pro
                85                  90                  95

Ile Thr Phe Gly Gly Gly Thr Lys Val Glu Ile Lys
            100                 105

<210> SEQ ID NO 400
<211> LENGTH: 121
<212> TYPE: PRT
<213> ORGANISM: Artificial Sequence
<220> FEATURE:
<223> OTHER INFORMATION: Synthetic Construct

<400> SEQUENCE: 400

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Thr Pro Ser Ser Ile Tyr Ala Ala Gly Met Asp Val Trp Gly
            100                 105                 110
```

```
Gln Gly Thr Thr Val Thr Val Ser Ser
        115                 120

<210> SEQ ID NO 401
<211> LENGTH: 109
<212> TYPE: PRT
<213> ORGANISM: Artificial Sequence
<220> FEATURE:
<223> OTHER INFORMATION: Synthetic Construct

<400> SEQUENCE: 401

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Gly Ser Val Pro
                85                  90                  95

Pro Ile Thr Phe Gly Gly Gly Thr Lys Val Glu Ile Lys
            100                 105

<210> SEQ ID NO 402
<211> LENGTH: 121
<212> TYPE: PRT
<213> ORGANISM: Artificial Sequence
<220> FEATURE:
<223> OTHER INFORMATION: Synthetic Construct

<400> SEQUENCE: 402

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Gly Tyr Gly Ser Asn Tyr Phe Asp Tyr Trp Gly
            100                 105                 110

Gln Gly Thr Leu Val Thr Val Ser Ser
        115                 120

<210> SEQ ID NO 403

<400> SEQUENCE: 403

000

<210> SEQ ID NO 404
```

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407
<211> LENGTH: 107
<212> TYPE: PRT
<213> ORGANISM: Artificial Sequence
<220> FEATURE:
<223> OTHER INFORMATION: Synthetic Construct

<400> SEQUENCE: 407

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Ser Trp Pro Ile
                85                  90                  95

Thr Phe Gly Gly Gly Thr Lys Val Glu Ile Lys
            100                 105
```

<210> SEQ ID NO 408
<211> LENGTH: 127
<212> TYPE: PRT
<213> ORGANISM: Artificial Sequence
<220> FEATURE:
<223> OTHER INFORMATION: Synthetic Construct

<400> SEQUENCE: 408

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Gly Asp Arg Ala Thr Leu Val Tyr Tyr Tyr Tyr Tyr
            100                 105                 110
```

```
Gly Met Asp Val Trp Gly Gln Gly Thr Thr Val Thr Val Ser Ser
        115                 120                 125
```

<210> SEQ ID NO 409
<211> LENGTH: 108
<212> TYPE: PRT
<213> ORGANISM: Artificial Sequence
<220> FEATURE:
<223> OTHER INFORMATION: Synthetic Construct

<400> SEQUENCE: 409

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Gly Asp Tyr Pro
                85                  90                  95

Pro Thr Phe Gly Gly Gly Thr Lys Val Glu Ile Lys
            100                 105
```

<210> SEQ ID NO 410
<211> LENGTH: 126
<212> TYPE: PRT
<213> ORGANISM: Artificial Sequence
<220> FEATURE:
<223> OTHER INFORMATION: Synthetic Construct

<400> SEQUENCE: 410

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Gly Tyr Ser Ser Leu Leu Pro Tyr Tyr Tyr Tyr
            100                 105                 110

Met Asp Val Trp Gly Gln Gly Thr Thr Val Thr Val Ser Ser
        115                 120                 125
```

<210> SEQ ID NO 411
<211> LENGTH: 112
<212> TYPE: PRT
<213> ORGANISM: Artificial Sequence
<220> FEATURE:
<223> OTHER INFORMATION: Synthetic Construct

<400> SEQUENCE: 411

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Glu Arg Pro Pro Thr Phe Gly Gly Gly Thr Lys Val Glu Ile Lys
            100                 105                 110
```

<210> SEQ ID NO 412
<211> LENGTH: 118
<212> TYPE: PRT
<213> ORGANISM: Artificial Sequence
<220> FEATURE:
<223> OTHER INFORMATION: Synthetic Construct

<400> SEQUENCE: 412

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Tyr Glu Gly Arg Val Asp Val Trp Gly Gln Gly Thr
            100                 105                 110

Met Val Thr Val Ser Ser
        115
```

<210> SEQ ID NO 413
<211> LENGTH: 107
<212> TYPE: PRT
<213> ORGANISM: Artificial Sequence
<220> FEATURE:
<223> OTHER INFORMATION: Synthetic Construct

<400> SEQUENCE: 413

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

Glu Asp Phe Ala Val Tyr Tyr Cys Gln Gln Arg Ser Asn Tyr Pro Ile
                85                  90                  95

Thr Phe Gly Gly Gly Thr Lys Val Glu Ile Lys
            100                 105

<210> SEQ ID NO 414
<211> LENGTH: 129
<212> TYPE: PRT
<213> ORGANISM: Artificial Sequence
<220> FEATURE:
<223> OTHER INFORMATION: Synthetic Construct

<400> SEQUENCE: 414

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Glu Tyr Tyr Asp Ser Ser Arg Leu Tyr Tyr Pro Tyr
            100                 105                 110

Tyr Tyr Tyr Met Asp Val Trp Gly Lys Gly Thr Thr Val Thr Val Ser
        115                 120                 125

Ser

<210> SEQ ID NO 415

<400> SEQUENCE: 415

000

<210> SEQ ID NO 416

<400> SEQUENCE: 416

000

<210> SEQ ID NO 417

<400> SEQUENCE: 417

000

<210> SEQ ID NO 418

<400> SEQUENCE: 418

000

<210> SEQ ID NO 419

<400> SEQUENCE: 419

000

```
<210> SEQ ID NO 420

<400> SEQUENCE: 420

000

<210> SEQ ID NO 421
<211> LENGTH: 106
<212> TYPE: PRT
<213> ORGANISM: Artificial Sequence
<220> FEATURE:
<223> OTHER INFORMATION: Synthetic Construct

<400> SEQUENCE: 421

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ala Leu Pro Thr
                85                  90                  95

Phe Gly Gly Gly Thr Lys Val Glu Ile Lys
            100                 105

<210> SEQ ID NO 422
<211> LENGTH: 122
<212> TYPE: PRT
<213> ORGANISM: Artificial Sequence
<220> FEATURE:
<223> OTHER INFORMATION: Synthetic Construct

<400> SEQUENCE: 422

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Arg Pro Glu Leu Gly Trp Asp Lys Tyr Phe Gln His Trp
            100                 105                 110

Gly Gln Gly Thr Leu Val Thr Val Ser Ser
        115                 120

<210> SEQ ID NO 423

<400> SEQUENCE: 423

000
```

<210> SEQ ID NO 424

<400> SEQUENCE: 424

000

<210> SEQ ID NO 425
<211> LENGTH: 108
<212> TYPE: PRT
<213> ORGANISM: Artificial Sequence
<220> FEATURE:
<223> OTHER INFORMATION: Synthetic Construct

<400> SEQUENCE: 425

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Glu Gln Tyr Gly Gly Ser Pro
                85                  90                  95

Ile Thr Phe Gly Gly Gly Thr Lys Val Glu Ile Lys
            100                 105
```

<210> SEQ ID NO 426
<211> LENGTH: 126
<212> TYPE: PRT
<213> ORGANISM: Artificial Sequence
<220> FEATURE:
<223> OTHER INFORMATION: Synthetic Construct

<400> SEQUENCE: 426

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Pro Leu Lys Phe Tyr Tyr Gly Ser Gly Ser Tyr Gly Phe
            100                 105                 110

Phe Asp Tyr Trp Gly Gln Gly Thr Leu Val Thr Val Ser Ser
        115                 120                 125
```

<210> SEQ ID NO 427
<211> LENGTH: 107
<212> TYPE: PRT
<213> ORGANISM: Artificial Sequence
<220> FEATURE:
<223> OTHER INFORMATION: Synthetic Construct

<400> SEQUENCE: 427

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Arg Lys Gly Pro Leu
                85                  90                  95

Thr Phe Gly Gly Gly Thr Lys Val Glu Ile Lys
            100                 105

<210> SEQ ID NO 428
<211> LENGTH: 121
<212> TYPE: PRT
<213> ORGANISM: Artificial Sequence
<220> FEATURE:
<223> OTHER INFORMATION: Synthetic Construct

<400> SEQUENCE: 428

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Asn Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Pro Pro Glu Leu Gly Lys Met Tyr Phe Gln His Trp Gly
            100                 105                 110

Gln Gly Thr Leu Val Thr Val Ser Ser
        115                 120

<210> SEQ ID NO 429
<211> LENGTH: 109
<212> TYPE: PRT
<213> ORGANISM: Artificial Sequence
<220> FEATURE:
<223> OTHER INFORMATION: Synthetic Construct

<400> SEQUENCE: 429

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Gly Arg Leu Pro
                85                  90                  95

Pro Trp Thr Phe Gly Gly Gly Thr Lys Val Glu Ile Lys
            100                 105

<210> SEQ ID NO 430
<211> LENGTH: 112
<212> TYPE: PRT
<213> ORGANISM: Artificial Sequence
<220> FEATURE:
<223> OTHER INFORMATION: Synthetic Construct

<400> SEQUENCE: 430

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gln
                85                  90                  95

Gln Glu Thr Pro Leu Thr Phe Gly Gly Gly Thr Lys Val Glu Ile Lys
            100                 105                 110

<210> SEQ ID NO 431
<211> LENGTH: 122
<212> TYPE: PRT
<213> ORGANISM: Artificial Sequence
<220> FEATURE:
<223> OTHER INFORMATION: Synthetic Construct

<400> SEQUENCE: 431

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
                20                  25                  30

Tyr Tyr Trp Gly Trp Ile Arg Gln Pro Pro Gly Lys Gly Leu Glu Trp
            35                  40                  45

Ile Gly Thr Ile Tyr His Ser Gly Ser Thr Tyr Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Gly Ser Ile Lys Gln Gly Tyr Tyr Gly Met Asp Val Trp
            100                 105                 110

Gly Gln Gly Thr Thr Val Thr Val Ser Ser
        115                 120

<210> SEQ ID NO 432
<211> LENGTH: 107
<212> TYPE: PRT
<213> ORGANISM: Artificial Sequence
<220> FEATURE:
<223> OTHER INFORMATION: Synthetic Construct

<400> SEQUENCE: 432

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Glu Tyr Leu Asn Tyr Pro Ile
                85                  90                  95

Thr Phe Gly Gly Gly Thr Lys Val Glu Ile Lys
            100                 105

<210> SEQ ID NO 433
<211> LENGTH: 127
<212> TYPE: PRT
<213> ORGANISM: Artificial Sequence
<220> FEATURE:
<223> OTHER INFORMATION: Synthetic Construct

<400> SEQUENCE: 433

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Ser Pro Arg Phe Tyr Tyr Gly Ser Gly Ser Tyr Leu Asp
            100                 105                 110

Leu Phe Asp Ile Trp Gly Gln Gly Thr Met Val Thr Val Ser Ser
        115                 120                 125

<210> SEQ ID NO 434

<400> SEQUENCE: 434

000

<210> SEQ ID NO 435

<400> SEQUENCE: 435

000

<210> SEQ ID NO 436
<211> LENGTH: 108
<212> TYPE: PRT
<213> ORGANISM: Artificial Sequence

```
<220> FEATURE:
<223> OTHER INFORMATION: Synthetic Construct

<400> SEQUENCE: 436

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Gly Ile Ala Pro
                85                  90                  95

Ile Thr Phe Gly Gly Gly Thr Lys Val Glu Ile Lys
            100                 105

<210> SEQ ID NO 437
<211> LENGTH: 120
<212> TYPE: PRT
<213> ORGANISM: Artificial Sequence
<220> FEATURE:
<223> OTHER INFORMATION: Synthetic Construct

<400> SEQUENCE: 437

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ala Glu His Arg Gly Pro Arg Tyr Phe Asp Leu Trp Gly Arg
            100                 105                 110

Gly Thr Leu Val Thr Val Ser Ser
        115                 120

<210> SEQ ID NO 438
<211> LENGTH: 107
<212> TYPE: PRT
<213> ORGANISM: Artificial Sequence
<220> FEATURE:
<223> OTHER INFORMATION: Synthetic Construct

<400> SEQUENCE: 438

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asp Ser Thr Pro Ile
                85                  90                  95

Thr Phe Gly Gly Gly Thr Lys Val Glu Ile Lys
                100                 105

<210> SEQ ID NO 439
<211> LENGTH: 112
<212> TYPE: PRT
<213> ORGANISM: Artificial Sequence
<220> FEATURE:
<223> OTHER INFORMATION: Synthetic Construct

<400> SEQUENCE: 439

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Asp Gly Pro Ile Thr Phe Gly Gly Gly Thr Lys Val Glu Ile Lys
                100                 105                 110

<210> SEQ ID NO 440
<211> LENGTH: 120
<212> TYPE: PRT
<213> ORGANISM: Artificial Sequence
<220> FEATURE:
<223> OTHER INFORMATION: Synthetic Construct

<400> SEQUENCE: 440

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
                20                  25                  30

Tyr Tyr Trp Gly Trp Ile Arg Gln Pro Pro Gly Lys Gly Leu Glu Trp
            35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Gly Gln Leu Pro Gly Thr Phe Asp Tyr Trp Gly Gln
                100                 105                 110

Gly Thr Leu Val Thr Val Ser Ser
        115                 120

<210> SEQ ID NO 441
```

```
<211> LENGTH: 108
<212> TYPE: PRT
<213> ORGANISM: Artificial Sequence
<220> FEATURE:
<223> OTHER INFORMATION: Synthetic Construct

<400> SEQUENCE: 441

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Leu Pro Pro
                85                  90                  95

Ile Thr Phe Gly Gly Gly Thr Lys Val Glu Ile Lys
            100                 105

<210> SEQ ID NO 442
<211> LENGTH: 124
<212> TYPE: PRT
<213> ORGANISM: Artificial Sequence
<220> FEATURE:
<223> OTHER INFORMATION: Synthetic Construct

<400> SEQUENCE: 442

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Val Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Val Gly Arg Thr Gly Pro His Tyr Tyr Gly Met Asp
            100                 105                 110

Val Trp Gly Gln Gly Thr Thr Val Thr Val Ser Ser
        115                 120

<210> SEQ ID NO 443
<211> LENGTH: 112
<212> TYPE: PRT
<213> ORGANISM: Artificial Sequence
<220> FEATURE:
<223> OTHER INFORMATION: Synthetic Construct

<400> SEQUENCE: 443

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30
```

```
Asn Gly Tyr Asn Tyr Leu Asp Trp Tyr Leu Gln Lys Pro Gly Gln Ser
            35                  40                  45

Pro Gln Leu Leu Ile Tyr Leu Gly Ser His Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Arg
                 85                  90                  95

Leu Glu Ala Pro Leu Thr Phe Gly Gly Gly Thr Lys Val Glu Ile Lys
                100                 105                 110
```

<210> SEQ ID NO 444
<211> LENGTH: 124
<212> TYPE: PRT
<213> ORGANISM: Artificial Sequence
<220> FEATURE:
<223> OTHER INFORMATION: Synthetic Construct

<400> SEQUENCE: 444

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Gly Tyr Tyr Trp Ser Trp Ile Arg Gln His Pro Gly Lys Gly Leu Glu
         35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Leu His Ser Asp Tyr Ser Val Leu Tyr Tyr Gly Met Asp
                100                 105                 110

Val Trp Gly Gln Gly Thr Thr Val Thr Val Ser Ser
            115                 120
```

<210> SEQ ID NO 445

<400> SEQUENCE: 445

000

<210> SEQ ID NO 446

<400> SEQUENCE: 446

000

<210> SEQ ID NO 447
<211> LENGTH: 107
<212> TYPE: PRT
<213> ORGANISM: Artificial Sequence
<220> FEATURE:
<223> OTHER INFORMATION: Synthetic Construct

<400> SEQUENCE: 447

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Ser
             20                  25                  30
```

-continued

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Ala Ala Asp Trp Pro Ile
                85                  90                  95

Thr Phe Gly Gly Gly Thr Lys Val Glu Ile Lys
            100                 105

<210> SEQ ID NO 448
<211> LENGTH: 128
<212> TYPE: PRT
<213> ORGANISM: Artificial Sequence
<220> FEATURE:
<223> OTHER INFORMATION: Synthetic Construct

<400> SEQUENCE: 448

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Asp Arg Gly Gly Thr His Phe Gly Ala Asp His Tyr Tyr
            100                 105                 110

Tyr Gly Met Asp Val Trp Gly Gln Gly Thr Met Val Thr Val Ser Ser
        115                 120                 125

<210> SEQ ID NO 449

<400> SEQUENCE: 449

000

<210> SEQ ID NO 450

<400> SEQUENCE: 450

000

<210> SEQ ID NO 451
<211> LENGTH: 108
<212> TYPE: PRT
<213> ORGANISM: Artificial Sequence
<220> FEATURE:
<223> OTHER INFORMATION: Synthetic Construct

<400> SEQUENCE: 451

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Ala Ala Ser Ser Pro
                 85                  90                  95

Ile Thr Phe Gly Gly Gly Thr Lys Val Glu Ile Lys
            100                 105

<210> SEQ ID NO 452
<211> LENGTH: 121
<212> TYPE: PRT
<213> ORGANISM: Artificial Sequence
<220> FEATURE:
<223> OTHER INFORMATION: Synthetic Construct

<400> SEQUENCE: 452

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Val Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Leu Pro Gly Tyr Pro Leu Gly Leu Phe Asp Ile Trp Gly
            100                 105                 110

Gln Gly Thr Leu Val Thr Val Ser Ser
        115                 120

<210> SEQ ID NO 453
<211> LENGTH: 108
<212> TYPE: PRT
<213> ORGANISM: Artificial Sequence
<220> FEATURE:
<223> OTHER INFORMATION: Synthetic Construct

<400> SEQUENCE: 453

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Pro Ser Val Pro Pro
                 85                  90                  95

Ile Thr Phe Gly Gly Gly Thr Lys Val Glu Ile Lys
            100                 105

<210> SEQ ID NO 454
<211> LENGTH: 124
<212> TYPE: PRT
<213> ORGANISM: Artificial Sequence
<220> FEATURE:
<223> OTHER INFORMATION: Synthetic Construct

<400> SEQUENCE: 454

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Thr Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Gly Arg Thr Glu Ser Tyr Tyr Tyr Gly Met Asp
            100                 105                 110

Val Trp Gly Gln Gly Thr Thr Val Thr Val Ser Ser
        115                 120
```

<210> SEQ ID NO 455
<211> LENGTH: 108
<212> TYPE: PRT
<213> ORGANISM: Artificial Sequence
<220> FEATURE:
<223> OTHER INFORMATION: Synthetic Construct

<400> SEQUENCE: 455

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ala Ser Val Tyr Pro Pro
                85                  90                  95

Ile Thr Phe Gly Gly Gly Thr Lys Val Glu Ile Lys
            100                 105
```

<210> SEQ ID NO 456
<211> LENGTH: 120
<212> TYPE: PRT
<213> ORGANISM: Artificial Sequence
<220> FEATURE:
<223> OTHER INFORMATION: Synthetic Construct

<400> SEQUENCE: 456

```
Gln Val Gln Leu Gln Glu Ser Gly Pro Gly Leu Val Lys Pro Ser Gln
1               5                   10                  15
```

```
Thr Leu Ser Leu Thr Cys Thr Val Ser Gly Gly Ser Ile Ser Ser Gly
            20                  25                  30

Thr Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Gly Arg Tyr Arg Val Ala Asp Tyr Trp Gly Gln
            100                 105                 110

Gly Thr Leu Val Thr Val Ser Ser
            115                 120

<210> SEQ ID NO 457
<211> LENGTH: 108
<212> TYPE: PRT
<213> ORGANISM: Artificial Sequence
<220> FEATURE:
<223> OTHER INFORMATION: Synthetic Construct

<400> SEQUENCE: 457

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ser Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Glu Thr Asn Met Pro Pro
                85                  90                  95

Ile Thr Phe Gly Gly Gly Thr Lys Val Glu Ile Lys
            100                 105

<210> SEQ ID NO 458
<211> LENGTH: 107
<212> TYPE: PRT
<213> ORGANISM: Artificial Sequence
<220> FEATURE:
<223> OTHER INFORMATION: Synthetic Construct

<400> SEQUENCE: 458

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Ala Leu Pro Arg
                85                  90                  95
```

```
Thr Phe Gly Gly Gly Thr Lys Val Glu Ile Lys
            100                 105

<210> SEQ ID NO 459
<211> LENGTH: 126
<212> TYPE: PRT
<213> ORGANISM: Artificial Sequence
<220> FEATURE:
<223> OTHER INFORMATION: Synthetic Construct

<400> SEQUENCE: 459

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Gly Met Gly Pro Lys Tyr Tyr Tyr Tyr Tyr Gly
            100                 105                 110

Met Asp Val Trp Gly Gln Gly Thr Thr Val Thr Val Ser Ser
        115                 120                 125

<210> SEQ ID NO 460
<211> LENGTH: 107
<212> TYPE: PRT
<213> ORGANISM: Artificial Sequence
<220> FEATURE:
<223> OTHER INFORMATION: Synthetic Construct

<400> SEQUENCE: 460

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Phe
            20                  25                  30

Leu Asn Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Glu Pro Ile
                85                  90                  95

Thr Phe Gly Gly Gly Thr Lys Val Glu Ile Lys
            100                 105

<210> SEQ ID NO 461
<211> LENGTH: 124
<212> TYPE: PRT
<213> ORGANISM: Artificial Sequence
<220> FEATURE:
<223> OTHER INFORMATION: Synthetic Construct

<400> SEQUENCE: 461
```

-continued

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Gly Val Gly Ile Gln Gln Gln Leu Val Leu Gly Phe Asp
            100                 105                 110

Pro Trp Gly Gln Gly Thr Leu Val Thr Val Ser Ser
            115                 120
```

<210> SEQ ID NO 462

<400> SEQUENCE: 462

000

<210> SEQ ID NO 463

<400> SEQUENCE: 463

000

<210> SEQ ID NO 464
<211> LENGTH: 113
<212> TYPE: PRT
<213> ORGANISM: Artificial Sequence
<220> FEATURE:
<223> OTHER INFORMATION: Synthetic Construct

<400> SEQUENCE: 464

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Tyr Ala Asn Ala Pro Ile Thr Phe Gly Gly Gly Thr Lys Val Glu Ile
            100                 105                 110

Lys
```

<210> SEQ ID NO 465
<211> LENGTH: 121
<212> TYPE: PRT
<213> ORGANISM: Artificial Sequence
<220> FEATURE:
<223> OTHER INFORMATION: Synthetic Construct -continued

<400> SEQUENCE: 465

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Leu Ala Met Ser Gly Ala Tyr Phe Asp Leu Trp Gly
            100                 105                 110

Arg Gly Thr Leu Val Thr Val Ser Ser
            115                 120

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470
<211> LENGTH: 112
<212> TYPE: PRT
<213> ORGANISM: Artificial Sequence
<220> FEATURE:
<223> OTHER INFORMATION: Synthetic Construct

<400> SEQUENCE: 470

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Val Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Leu Asp Val Pro Leu Thr Phe Gly Gly Gly Thr Lys Val Glu Ile Lys
            100                 105                 110

<210> SEQ ID NO 471
<211> LENGTH: 121
<212> TYPE: PRT
<213> ORGANISM: Artificial Sequence
<220> FEATURE:
<223> OTHER INFORMATION: Synthetic Construct

<400> SEQUENCE: 471

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Glu Arg Trp Asp Leu Gly His Gly Met Asp Val Trp Gly
            100                 105                 110

Gln Gly Thr Thr Val Thr Val Ser Ser
        115                 120

<210> SEQ ID NO 472
<211> LENGTH: 108
<212> TYPE: PRT
<213> ORGANISM: Artificial Sequence
<220> FEATURE:
<223> OTHER INFORMATION: Synthetic Construct

<400> SEQUENCE: 472

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser His Val Ser Pro
            85                  90                  95

Trp Thr Phe Gly Gly Gly Thr Lys Val Glu Ile Lys
            100                 105

<210> SEQ ID NO 473
<211> LENGTH: 125
<212> TYPE: PRT
<213> ORGANISM: Artificial Sequence
<220> FEATURE:
<223> OTHER INFORMATION: Synthetic Construct -continued

<400> SEQUENCE: 473

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Gly Ser Gly Tyr Ser Tyr Gly Tyr Arg Tyr Phe
            100                 105                 110

Asp Tyr Trp Gly Gln Gly Thr Leu Val Thr Val Ser Ser
        115                 120                 125

<210> SEQ ID NO 474
<211> LENGTH: 107
<212> TYPE: PRT
<213> ORGANISM: Artificial Sequence
<220> FEATURE:
<223> OTHER INFORMATION: Synthetic Construct

<400> SEQUENCE: 474

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Ala Phe Pro Pro
                85                  90                  95

Thr Phe Gly Gly Gly Thr Lys Val Glu Ile Lys
            100                 105

<210> SEQ ID NO 475
<211> LENGTH: 123
<212> TYPE: PRT
<213> ORGANISM: Artificial Sequence
<220> FEATURE:
<223> OTHER INFORMATION: Synthetic Construct

<400> SEQUENCE: 475

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

```
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Ser Pro Thr Trp Leu Arg Asp Tyr Tyr Met Asp Val
            100                 105                 110

Trp Gly Lys Gly Thr Thr Val Thr Val Ser Ser
            115                 120

<210> SEQ ID NO 476
<211> LENGTH: 112
<212> TYPE: PRT
<213> ORGANISM: Artificial Sequence
<220> FEATURE:
<223> OTHER INFORMATION: Synthetic Construct

<400> SEQUENCE: 476

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Ala Ser Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Ile Asp Thr Pro Pro Thr Phe Gly Gly Gly Thr Lys Val Glu Ile Lys
            100                 105                 110

<210> SEQ ID NO 477
<211> LENGTH: 120
<212> TYPE: PRT
<213> ORGANISM: Artificial Sequence
<220> FEATURE:
<223> OTHER INFORMATION: Synthetic Construct

<400> SEQUENCE: 477

Gln Leu Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Ser
                 20                  25                  30

Ser Tyr Tyr Trp Gly Trp Ile Arg Gln Pro Pro Gly Lys Gly Leu Glu
             35                  40                  45

Trp Ile Gly Ser Ile Ser Tyr Ser Gly Ser Thr Tyr Tyr Asn Pro Ser
         50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Gly Thr Thr Trp Leu Val Ala Asp Val Trp Gly Gln
            100                 105                 110

Gly Thr Met Val Thr Val Ser Ser
            115                 120

<210> SEQ ID NO 478
```

```
<211> LENGTH: 108
<212> TYPE: PRT
<213> ORGANISM: Artificial Sequence
<220> FEATURE:
<223> OTHER INFORMATION: Synthetic Construct

<400> SEQUENCE: 478

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Glu Gln Tyr Ala Ser Ser Pro
                85                  90                  95

Tyr Thr Phe Gly Gly Gly Thr Lys Val Glu Ile Lys
            100                 105

<210> SEQ ID NO 479
<211> LENGTH: 125
<212> TYPE: PRT
<213> ORGANISM: Artificial Sequence
<220> FEATURE:
<223> OTHER INFORMATION: Synthetic Construct

<400> SEQUENCE: 479

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Thr Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Arg Gly Arg Tyr Ser Tyr Gly Tyr His Lys Ala Ala Phe
            100                 105                 110

Asp Ile Trp Gly Gln Gly Thr Met Val Thr Val Ser Ser
        115                 120                 125

<210> SEQ ID NO 480
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = T, G, V, P, L, F, A, or R
<220> FEATURE:
<221> NAME/KEY: VARIANT
<222> LOCATION: 5
<223> OTHER INFORMATION: Xaa = G, A, or S
<220> FEATURE:
```

```
<221> NAME/KEY: VARIANT
<222> LOCATION: 7
<223> OTHER INFORMATION: Xaa = Y, M, or L
<220> FEATURE:
<221> NAME/KEY: VARIANT
<222> LOCATION: 9
<223> OTHER INFORMATION: Xaa = H or W

<400> SEQUENCE: 480

Tyr Thr Phe Xaa Xaa Tyr Xaa Met Xaa
1               5

<210> SEQ ID NO 481
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = W, I, or G
<220> FEATURE:
<221> NAME/KEY: VARIANT
<222> LOCATION: 2
<223> OTHER INFORMATION: Xaa = I, V, or T
<220> FEATURE:
<221> NAME/KEY: VARIANT
<222> LOCATION: 3
<223> OTHER INFORMATION: Xaa = N, G, or L
<220> FEATURE:
<221> NAME/KEY: VARIANT
<222> LOCATION: 5
<223> OTHER INFORMATION: Xaa = N, S, V, or M
<220> FEATURE:
<221> NAME/KEY: VARIANT
<222> LOCATION: 6
<223> OTHER INFORMATION: Xaa = S, G, W, or Q
<220> FEATURE:
<221> NAME/KEY: VARIANT
<222> LOCATION: 8
<223> OTHER INFORMATION: Xaa = G, F, A, Y, S, N, or R
<220> FEATURE:
<221> NAME/KEY: VARIANT
<222> LOCATION: 10
<223> OTHER INFORMATION: Xaa = N, R, S, or M

<400> SEQUENCE: 481

Xaa Xaa Xaa Pro Xaa Xaa Gly Xaa Thr Xaa Tyr Ala Gln Lys Phe Gln
1               5                   10                  15

Gly

<210> SEQ ID NO 482
<211> LENGTH: 9
<212> TYPE: PRT
<213> ORGANISM: Artificial Sequence
<220> FEATURE:
<223> OTHER INFORMATION: Synthetic Construct

<400> SEQUENCE: 482

Tyr Thr Phe Gly Ala Tyr Tyr Met His
1               5

<210> SEQ ID NO 483
<211> LENGTH: 9
<212> TYPE: PRT
<213> ORGANISM: Artificial Sequence
<220> FEATURE:
<223> OTHER INFORMATION: Synthetic Construct

<400> SEQUENCE: 483
```

Tyr Thr Phe Val Ala Tyr Tyr Met His
1               5

<210> SEQ ID NO 484
<211> LENGTH: 9
<212> TYPE: PRT
<213> ORGANISM: Artificial Sequence
<220> FEATURE:
<223> OTHER INFORMATION: Synthetic Construct

<400> SEQUENCE: 484

Tyr Thr Phe Thr Ser Tyr Met Met His
1               5

<210> SEQ ID NO 485
<211> LENGTH: 9
<212> TYPE: PRT
<213> ORGANISM: Artificial Sequence
<220> FEATURE:
<223> OTHER INFORMATION: Synthetic Construct

<400> SEQUENCE: 485

Tyr Thr Phe Pro Gly Tyr Leu Met His
1               5

<210> SEQ ID NO 486
<211> LENGTH: 9
<212> TYPE: PRT
<213> ORGANISM: Artificial Sequence
<220> FEATURE:
<223> OTHER INFORMATION: Synthetic Construct

<400> SEQUENCE: 486

Tyr Thr Phe Leu Ala Tyr Tyr Met His
1               5

<210> SEQ ID NO 487
<211> LENGTH: 9
<212> TYPE: PRT
<213> ORGANISM: Artificial Sequence
<220> FEATURE:
<223> OTHER INFORMATION: Synthetic Construct

<400> SEQUENCE: 487

Tyr Thr Phe Phe Ser Tyr Tyr Met His
1               5

<210> SEQ ID NO 488
<211> LENGTH: 9
<212> TYPE: PRT
<213> ORGANISM: Artificial Sequence
<220> FEATURE:
<223> OTHER INFORMATION: Synthetic Construct

<400> SEQUENCE: 488

Tyr Thr Phe Thr Ala Tyr Leu Met His
1               5

<210> SEQ ID NO 489
<211> LENGTH: 9
<212> TYPE: PRT
<213> ORGANISM: Artificial Sequence
<220> FEATURE:
<223> OTHER INFORMATION: Synthetic Construct

<400> SEQUENCE: 489

Tyr Thr Phe Ala Ser Tyr Tyr Met Trp

```
1               5
```

<210> SEQ ID NO 490
<211> LENGTH: 9
<212> TYPE: PRT
<213> ORGANISM: Artificial Sequence
<220> FEATURE:
<223> OTHER INFORMATION: Synthetic Construct

<400> SEQUENCE: 490

```
Tyr Thr Phe Thr Ala Tyr Tyr Met His
1               5
```

<210> SEQ ID NO 491
<211> LENGTH: 9
<212> TYPE: PRT
<213> ORGANISM: Artificial Sequence
<220> FEATURE:
<223> OTHER INFORMATION: Synthetic Construct

<400> SEQUENCE: 491

```
Tyr Thr Phe Gly Gly Tyr Leu Met His
1               5
```

<210> SEQ ID NO 492
<211> LENGTH: 9
<212> TYPE: PRT
<213> ORGANISM: Artificial Sequence
<220> FEATURE:
<223> OTHER INFORMATION: Synthetic Construct

<400> SEQUENCE: 492

```
Tyr Thr Phe Arg Ala Tyr Tyr Met His
1               5
```

<210> SEQ ID NO 493
<211> LENGTH: 17
<212> TYPE: PRT
<213> ORGANISM: Artificial Sequence
<220> FEATURE:
<223> OTHER INFORMATION: Synthetic Construct

<400> SEQUENCE: 493

```
Trp Ile Asn Pro Asn Ser Gly Phe Thr Arg Tyr Ala Gln Lys Phe Gln
1               5                   10                  15

Gly
```

<210> SEQ ID NO 494
<211> LENGTH: 17
<212> TYPE: PRT
<213> ORGANISM: Artificial Sequence
<220> FEATURE:
<223> OTHER INFORMATION: Synthetic Construct

<400> SEQUENCE: 494

```
Trp Ile Asn Pro Asn Ser Gly Ala Thr Arg Tyr Ala Gln Lys Phe Gln
1               5                   10                  15

Gly
```

<210> SEQ ID NO 495
<211> LENGTH: 17
<212> TYPE: PRT
<213> ORGANISM: Artificial Sequence
<220> FEATURE:
<223> OTHER INFORMATION: Synthetic Construct

```
<400> SEQUENCE: 495

Trp Val Asn Pro Asn Ser Gly Gly Thr Arg Tyr Ala Gln Lys Phe Gln
1               5                   10                  15

Gly

<210> SEQ ID NO 496
<211> LENGTH: 17
<212> TYPE: PRT
<213> ORGANISM: Artificial Sequence
<220> FEATURE:
<223> OTHER INFORMATION: Synthetic Construct

<400> SEQUENCE: 496

Ile Ile Gly Pro Ser Gly Gly Tyr Thr Ser Tyr Ala Gln Lys Phe Gln
1               5                   10                  15

Gly

<210> SEQ ID NO 497
<211> LENGTH: 17
<212> TYPE: PRT
<213> ORGANISM: Artificial Sequence
<220> FEATURE:
<223> OTHER INFORMATION: Synthetic Construct

<400> SEQUENCE: 497

Trp Ile Asn Pro Val Ser Gly Ser Thr Asn Tyr Ala Gln Lys Phe Gln
1               5                   10                  15

Gly

<210> SEQ ID NO 498
<211> LENGTH: 17
<212> TYPE: PRT
<213> ORGANISM: Artificial Sequence
<220> FEATURE:
<223> OTHER INFORMATION: Synthetic Construct

<400> SEQUENCE: 498

Trp Val Asn Pro Asn Ser Gly Gly Thr Asn Tyr Ala Gln Lys Phe Gln
1               5                   10                  15

Gly

<210> SEQ ID NO 499
<211> LENGTH: 17
<212> TYPE: PRT
<213> ORGANISM: Artificial Sequence
<220> FEATURE:
<223> OTHER INFORMATION: Synthetic Construct

<400> SEQUENCE: 499

Trp Ile Asn Pro Asn Ser Gly Gly Thr Arg Tyr Ala Gln Lys Phe Gln
1               5                   10                  15

Gly

<210> SEQ ID NO 500
<211> LENGTH: 17
<212> TYPE: PRT
<213> ORGANISM: Artificial Sequence
<220> FEATURE:
<223> OTHER INFORMATION: Synthetic Construct

<400> SEQUENCE: 500

Trp Ile Asn Pro Ser Gly Gly Asn Thr Arg Tyr Ala Gln Lys Phe Gln
1               5                   10                  15
```

<210> SEQ ID NO 501
<211> LENGTH: 17
<212> TYPE: PRT
<213> ORGANISM: Artificial Sequence
<220> FEATURE:
<223> OTHER INFORMATION: Synthetic Construct

<400> SEQUENCE: 501

Trp Ile Asn Pro Ser Gly Gly Ser Thr Ser Tyr Ala Gln Lys Phe Gln
1               5                   10                  15

Gly

<210> SEQ ID NO 502
<211> LENGTH: 17
<212> TYPE: PRT
<213> ORGANISM: Artificial Sequence
<220> FEATURE:
<223> OTHER INFORMATION: Synthetic Construct

<400> SEQUENCE: 502

Gly Ile Leu Pro Ser Gly Gly Arg Thr Ser Tyr Ala Gln Lys Phe Gln
1               5                   10                  15

Gly

<210> SEQ ID NO 503
<211> LENGTH: 17
<212> TYPE: PRT
<213> ORGANISM: Artificial Sequence
<220> FEATURE:
<223> OTHER INFORMATION: Synthetic Construct

<400> SEQUENCE: 503

Trp Ile Asn Pro Ser Trp Gly Ser Thr Ser Tyr Ala Gln Lys Phe Gln
1               5                   10                  15

Gly

<210> SEQ ID NO 504
<211> LENGTH: 17
<212> TYPE: PRT
<213> ORGANISM: Artificial Sequence
<220> FEATURE:
<223> OTHER INFORMATION: Synthetic Construct

<400> SEQUENCE: 504

Trp Val Asn Pro Asn Ser Gly Gly Thr Met Tyr Ala Gln Lys Phe Gln
1               5                   10                  15

Gly

<210> SEQ ID NO 505
<211> LENGTH: 17
<212> TYPE: PRT
<213> ORGANISM: Artificial Sequence
<220> FEATURE:
<223> OTHER INFORMATION: Synthetic Construct

<400> SEQUENCE: 505

Trp Thr Asn Pro Asn Ser Gly Gly Thr Arg Tyr Ala Gln Lys Phe Gln
1               5                   10                  15

Gly

```
<210> SEQ ID NO 506
<211> LENGTH: 17
<212> TYPE: PRT
<213> ORGANISM: Artificial Sequence
<220> FEATURE:
<223> OTHER INFORMATION: Synthetic Construct

<400> SEQUENCE: 506

Trp Ile Asn Pro Met Ser Gly Gly Thr Arg Tyr Ala Gln Lys Phe Gln
1               5                   10                  15
Gly

<210> SEQ ID NO 507
<211> LENGTH: 17
<212> TYPE: PRT
<213> ORGANISM: Artificial Sequence
<220> FEATURE:
<223> OTHER INFORMATION: Synthetic Construct

<400> SEQUENCE: 507

Trp Ile Asn Pro Ser Gln Gly Ser Thr Ser Tyr Ala Gln Lys Phe Gln
1               5                   10                  15
Gly

<210> SEQ ID NO 508
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V or I
<220> FEATURE:
<221> NAME/KEY: VARIANT
<222> LOCATION: 7
<223> OTHER INFORMATION: Xaa = S or G

<400> SEQUENCE: 508

Arg Ala Ser Gln Ser Xaa Xaa Ser Asn Leu Ala
1               5                   10

<210> SEQ ID NO 509
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = F or L
<220> FEATURE:
<221> NAME/KEY: VARIANT
<222> LOCATION: 4
<223> OTHER INFORMATION: Xaa = T or A
<220> FEATURE:
<221> NAME/KEY: VARIANT
<222> LOCATION: 5
<223> OTHER INFORMATION: Xaa = S or K
<220> FEATURE:
<221> NAME/KEY: VARIANT
<222> LOCATION: 6
<223> OTHER INFORMATION: Xaa = Y, T, R, L, T, G, Q, or H
<220> FEATURE:
<221> NAME/KEY: VARIANT
<222> LOCATION: 7
<223> OTHER INFORMATION: Xaa = Y, T, or L
<220> FEATURE:
<221> NAME/KEY: VARIANT
```

```
<222> LOCATION: 8
<223> OTHER INFORMATION: Xaa = M or I

<400> SEQUENCE: 509

Tyr Thr Xaa Xaa Xaa Xaa Xaa Xaa Ser
1               5

<210> SEQ ID NO 510
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = I or V
<220> FEATURE:
<221> NAME/KEY: VARIANT
<222> LOCATION: 5
<223> OTHER INFORMATION: Xaa = S, W, Y, V, F, L, or I
<220> FEATURE:
<221> NAME/KEY: VARIANT
<222> LOCATION: 8
<223> OTHER INFORMATION: Xaa = S or T
<220> FEATURE:
<221> NAME/KEY: VARIANT
<222> LOCATION: 9
<223> OTHER INFORMATION: Xaa = T or A
<220> FEATURE:
<221> NAME/KEY: VARIANT
<222> LOCATION: 13
<223> OTHER INFORMATION: Xaa = Q or R
<220> FEATURE:
<221> NAME/KEY: VARIANT
<222> LOCATION: 14
<223> OTHER INFORMATION: Xaa = K or R
<220> FEATURE:
<221> NAME/KEY: VARIANT
<222> LOCATION: 16
<223> OTHER INFORMATION: Xaa = Q or R

<400> SEQUENCE: 510

Xaa Ile Asn Pro Xaa Gly Gly Xaa Xaa Ser Tyr Ala Xaa Xaa Phe Xaa
1               5                   10                  15

Gly

<210> SEQ ID NO 511
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = A, V, or T
<220> FEATURE:
<221> NAME/KEY: VARIANT
<222> LOCATION: 5
<223> OTHER INFORMATION: Xaa = S, F, or G
<220> FEATURE:
<221> NAME/KEY: VARIANT
<222> LOCATION: 7
<223> OTHER INFORMATION: Xaa = I or A
<220> FEATURE:
<221> NAME/KEY: VARIANT
<222> LOCATION: 8
<223> OTHER INFORMATION: Xaa = A or G
<220> FEATURE:
<221> NAME/KEY: VARIANT
<222> LOCATION: 9
<223> OTHER INFORMATION: Xaa = A, L, or V
<220> FEATURE:
```

```
<221> NAME/KEY: VARIANT
<222> LOCATION: 10
<223> OTHER INFORMATION: Xaa = A, L, or P
<220> FEATURE:
<221> NAME/KEY: VARIANT
<222> LOCATION: 11
<223> OTHER INFORMATION: Xaa = G, F, or Y
<220> FEATURE:
<221> NAME/KEY: VARIANT
<222> LOCATION: 13
<223> OTHER INFORMATION: Xaa = A, G, or F
<220> FEATURE:
<221> NAME/KEY: VARIANT
<222> LOCATION: 14
<223> OTHER INFORMATION: Xaa = S, G, A
<220> FEATURE:
<221> NAME/KEY: VARIANT
<222> LOCATION: 16
<223> OTHER INFORMATION: Xaa = Y, G, P, H, or S
<220> FEATURE:
<221> NAME/KEY: VARIANT
<222> LOCATION: 17
<223> OTHER INFORMATION: Xaa = Y or N
<220> FEATURE:
<221> NAME/KEY: VARIANT
<222> LOCATION: 18
<223> OTHER INFORMATION: Xaa = Y, L, Q, or R
<220> FEATURE:
<221> NAME/KEY: VARIANT
<222> LOCATION: 20
<223> OTHER INFORMATION: Xaa = M or L

<400> SEQUENCE: 511

Xaa Arg Asp Pro Xaa Gly Xaa Xaa Xaa Xaa Pro Xaa Xaa Arg Xaa
1               5                   10                  15

Xaa Xaa Gly Xaa Asp Val
            20

<210> SEQ ID NO 512
<211> LENGTH: 11
<212> TYPE: PRT
<213> ORGANISM: Artificial Sequence
<220> FEATURE:
<223> OTHER INFORMATION: Synthetic Construct

<400> SEQUENCE: 512

Arg Ala Ser Gln Ser Val Gly Ser Asn Leu Ala
1               5                   10

<210> SEQ ID NO 513
<211> LENGTH: 9
<212> TYPE: PRT
<213> ORGANISM: Artificial Sequence
<220> FEATURE:
<223> OTHER INFORMATION: Synthetic Construct

<400> SEQUENCE: 513

Tyr Thr Phe Thr Ser Thr Tyr Met Ser
1               5

<210> SEQ ID NO 514
<211> LENGTH: 9
<212> TYPE: PRT
<213> ORGANISM: Artificial Sequence
<220> FEATURE:
<223> OTHER INFORMATION: Synthetic Construct

<400> SEQUENCE: 514

Tyr Thr Phe Thr Ser Tyr Thr Met Ser
1               5
```

```
<210> SEQ ID NO 515
<211> LENGTH: 9
<212> TYPE: PRT
<213> ORGANISM: Artificial Sequence
<220> FEATURE:
<223> OTHER INFORMATION: Synthetic Construct

<400> SEQUENCE: 515

Tyr Thr Phe Thr Ser Tyr Leu Met Ser
1               5

<210> SEQ ID NO 516
<211> LENGTH: 9
<212> TYPE: PRT
<213> ORGANISM: Artificial Sequence
<220> FEATURE:
<223> OTHER INFORMATION: Synthetic Construct

<400> SEQUENCE: 516

Tyr Thr Phe Thr Ser Arg Tyr Met Ser
1               5

<210> SEQ ID NO 517
<211> LENGTH: 9
<212> TYPE: PRT
<213> ORGANISM: Artificial Sequence
<220> FEATURE:
<223> OTHER INFORMATION: Synthetic Construct

<400> SEQUENCE: 517

Tyr Thr Phe Ala Ser Arg Tyr Met Ser
1               5

<210> SEQ ID NO 518
<211> LENGTH: 9
<212> TYPE: PRT
<213> ORGANISM: Artificial Sequence
<220> FEATURE:
<223> OTHER INFORMATION: Synthetic Construct

<400> SEQUENCE: 518

Tyr Thr Leu Thr Ser Arg Tyr Met Ser
1               5

<210> SEQ ID NO 519
<211> LENGTH: 9
<212> TYPE: PRT
<213> ORGANISM: Artificial Sequence
<220> FEATURE:
<223> OTHER INFORMATION: Synthetic Construct

<400> SEQUENCE: 519

Tyr Thr Phe Thr Ser Leu Tyr Ile Ser
1               5

<210> SEQ ID NO 520
<211> LENGTH: 9
<212> TYPE: PRT
<213> ORGANISM: Artificial Sequence
<220> FEATURE:
<223> OTHER INFORMATION: Synthetic Construct

<400> SEQUENCE: 520

Tyr Thr Phe Thr Lys Tyr Tyr Met Ser
1               5
```

```
<210> SEQ ID NO 521
<211> LENGTH: 9
<212> TYPE: PRT
<213> ORGANISM: Artificial Sequence
<220> FEATURE:
<223> OTHER INFORMATION: Synthetic Construct

<400> SEQUENCE: 521

Tyr Thr Phe Thr Ser Leu Tyr Met Ser
1               5

<210> SEQ ID NO 522
<211> LENGTH: 9
<212> TYPE: PRT
<213> ORGANISM: Artificial Sequence
<220> FEATURE:
<223> OTHER INFORMATION: Synthetic Construct

<400> SEQUENCE: 522

Tyr Thr Phe Thr Ser Gly Tyr Met Ser
1               5

<210> SEQ ID NO 523
<211> LENGTH: 9
<212> TYPE: PRT
<213> ORGANISM: Artificial Sequence
<220> FEATURE:
<223> OTHER INFORMATION: Synthetic Construct

<400> SEQUENCE: 523

Tyr Thr Phe Thr Ser Gln Tyr Met Ser
1               5

<210> SEQ ID NO 524
<211> LENGTH: 9
<212> TYPE: PRT
<213> ORGANISM: Artificial Sequence
<220> FEATURE:
<223> OTHER INFORMATION: Synthetic Construct

<400> SEQUENCE: 524

Tyr Thr Phe Thr Ser His Tyr Met Ser
1               5

<210> SEQ ID NO 525
<211> LENGTH: 17
<212> TYPE: PRT
<213> ORGANISM: Artificial Sequence
<220> FEATURE:
<223> OTHER INFORMATION: Synthetic Construct

<400> SEQUENCE: 525

Ile Ile Asn Pro Trp Gly Gly Thr Thr Ser Tyr Ala Gln Lys Phe Gln
1               5                   10                  15

Gly

<210> SEQ ID NO 526
<211> LENGTH: 17
<212> TYPE: PRT
<213> ORGANISM: Artificial Sequence
<220> FEATURE:
<223> OTHER INFORMATION: Synthetic Construct

<400> SEQUENCE: 526

Ile Ile Asn Pro Tyr Gly Gly Ser Thr Ser Tyr Ala Gln Lys Phe Gln
1               5                   10                  15
```

Gly

<210> SEQ ID NO 527
<211> LENGTH: 17
<212> TYPE: PRT
<213> ORGANISM: Artificial Sequence
<220> FEATURE:
<223> OTHER INFORMATION: Synthetic Construct

<400> SEQUENCE: 527

Ile Ile Asn Pro Val Gly Gly Ser Thr Ser Tyr Ala Gln Lys Phe Gln
1               5                   10                  15

Gly

<210> SEQ ID NO 528
<211> LENGTH: 17
<212> TYPE: PRT
<213> ORGANISM: Artificial Sequence
<220> FEATURE:
<223> OTHER INFORMATION: Synthetic Construct

<400> SEQUENCE: 528

Val Ile Asn Pro Phe Gly Gly Ser Thr Ser Tyr Ala Gln Lys Phe Gln
1               5                   10                  15

Gly

<210> SEQ ID NO 529
<211> LENGTH: 17
<212> TYPE: PRT
<213> ORGANISM: Artificial Sequence
<220> FEATURE:
<223> OTHER INFORMATION: Synthetic Construct

<400> SEQUENCE: 529

Ile Ile Asn Pro Val Gly Gly Ser Thr Ser Tyr Ala Gln Lys Phe Arg
1               5                   10                  15

Gly

<210> SEQ ID NO 530
<211> LENGTH: 17
<212> TYPE: PRT
<213> ORGANISM: Artificial Sequence
<220> FEATURE:
<223> OTHER INFORMATION: Synthetic Construct

<400> SEQUENCE: 530

Ile Ile Asn Pro Val Gly Gly Ser Ala Ser Tyr Ala Arg Lys Phe Gln
1               5                   10                  15

Gly

<210> SEQ ID NO 531
<211> LENGTH: 17
<212> TYPE: PRT
<213> ORGANISM: Artificial Sequence
<220> FEATURE:
<223> OTHER INFORMATION: Synthetic Construct

<400> SEQUENCE: 531

Ile Ile Asn Pro Leu Gly Gly Ser Thr Ser Tyr Ala Gln Lys Phe Gln
1               5                   10                  15

Gly

<210> SEQ ID NO 532

```
<211> LENGTH: 17
<212> TYPE: PRT
<213> ORGANISM: Artificial Sequence
<220> FEATURE:
<223> OTHER INFORMATION: Synthetic Construct

<400> SEQUENCE: 532

Val Ile Asn Pro Val Gly Gly Ser Thr Ser Tyr Ala Gln Lys Phe Gln
1               5                   10                  15

Gly

<210> SEQ ID NO 533
<211> LENGTH: 17
<212> TYPE: PRT
<213> ORGANISM: Artificial Sequence
<220> FEATURE:
<223> OTHER INFORMATION: Synthetic Construct

<400> SEQUENCE: 533

Ile Ile Asn Pro Ile Gly Gly Ser Thr Ser Tyr Ala Gln Lys Phe Gln
1               5                   10                  15

Gly

<210> SEQ ID NO 534
<211> LENGTH: 17
<212> TYPE: PRT
<213> ORGANISM: Artificial Sequence
<220> FEATURE:
<223> OTHER INFORMATION: Synthetic Construct

<400> SEQUENCE: 534

Ile Ile Asn Pro Ile Gly Gly Ser Thr Ser Tyr Ala Gln Lys Phe Arg
1               5                   10                  15

Gly

<210> SEQ ID NO 535
<211> LENGTH: 17
<212> TYPE: PRT
<213> ORGANISM: Artificial Sequence
<220> FEATURE:
<223> OTHER INFORMATION: Synthetic Construct

<400> SEQUENCE: 535

Ile Ile Asn Pro Ile Gly Gly Ser Ala Ser Tyr Ala Gln Lys Phe Gln
1               5                   10                  15

Gly

<210> SEQ ID NO 536
<211> LENGTH: 17
<212> TYPE: PRT
<213> ORGANISM: Artificial Sequence
<220> FEATURE:
<223> OTHER INFORMATION: Synthetic Construct

<400> SEQUENCE: 536

Ile Ile Asn Pro Ile Gly Gly Ser Thr Ser Tyr Ala Arg Lys Phe Gln
1               5                   10                  15

Gly

<210> SEQ ID NO 537
<211> LENGTH: 17
<212> TYPE: PRT
<213> ORGANISM: Artificial Sequence
<220> FEATURE:
```

```
<223> OTHER INFORMATION: Synthetic Construct

<400> SEQUENCE: 537

Ile Ile Asn Pro Ile Gly Gly Ser Ile Ser Tyr Ala Gln Lys Phe Gln
1               5                   10                  15

Gly

<210> SEQ ID NO 538
<211> LENGTH: 17
<212> TYPE: PRT
<213> ORGANISM: Artificial Sequence
<220> FEATURE:
<223> OTHER INFORMATION: Synthetic Construct

<400> SEQUENCE: 538

Ile Val Asn Pro Ile Gly Gly Ser Thr Ser Tyr Ala Gln Arg Phe Gln
1               5                   10                  15

Gly

<210> SEQ ID NO 539
<211> LENGTH: 17
<212> TYPE: PRT
<213> ORGANISM: Artificial Sequence
<220> FEATURE:
<223> OTHER INFORMATION: Synthetic Construct

<400> SEQUENCE: 539

Ile Ile Asn Pro Tyr Gly Gly Thr Thr Ser Tyr Ala Gln Lys Phe Gln
1               5                   10                  15

Gly

<210> SEQ ID NO 540
<211> LENGTH: 22
<212> TYPE: PRT
<213> ORGANISM: Artificial Sequence
<220> FEATURE:
<223> OTHER INFORMATION: Synthetic Construct

<400> SEQUENCE: 540

Ala Arg Asp Pro Ser Gly Ile Ala Ala Ala Gly Pro Ala Gly Arg Tyr
1               5                   10                  15

Tyr Tyr Gly Leu Asp Val
            20

<210> SEQ ID NO 541
<211> LENGTH: 22
<212> TYPE: PRT
<213> ORGANISM: Artificial Sequence
<220> FEATURE:
<223> OTHER INFORMATION: Synthetic Construct

<400> SEQUENCE: 541

Ala Arg Asp Pro Ser Gly Ile Ala Ala Ala Gly Pro Ala Gly Arg Tyr
1               5                   10                  15

Tyr Tyr Gly Met Asp Val
            20

<210> SEQ ID NO 542
<211> LENGTH: 22
<212> TYPE: PRT
<213> ORGANISM: Artificial Sequence
<220> FEATURE:
<223> OTHER INFORMATION: Synthetic Construct
```

<400> SEQUENCE: 542

Ala Arg Asp Pro Ser Gly Ile Ala Ala Ala Gly Pro Ala Ser Arg His
1               5                   10                  15

Tyr Tyr Gly Met Asp Val
            20

<210> SEQ ID NO 543
<211> LENGTH: 22
<212> TYPE: PRT
<213> ORGANISM: Artificial Sequence
<220> FEATURE:
<223> OTHER INFORMATION: Synthetic Construct

<400> SEQUENCE: 543

Ala Arg Asp Pro Ser Gly Ile Ala Ala Pro Gly Pro Ala Ser Arg Gly
1               5                   10                  15

Tyr Tyr Gly Met Asp Val
            20

<210> SEQ ID NO 544
<211> LENGTH: 22
<212> TYPE: PRT
<213> ORGANISM: Artificial Sequence
<220> FEATURE:
<223> OTHER INFORMATION: Synthetic Construct

<400> SEQUENCE: 544

Ala Arg Asp Pro Ser Gly Ile Ala Leu Ala Gly Pro Ala Gly Arg Tyr
1               5                   10                  15

Tyr Tyr Gly Met Asp Val
            20

<210> SEQ ID NO 545
<211> LENGTH: 22
<212> TYPE: PRT
<213> ORGANISM: Artificial Sequence
<220> FEATURE:
<223> OTHER INFORMATION: Synthetic Construct

<400> SEQUENCE: 545

Ala Arg Asp Pro Ser Gly Ile Ala Leu Ala Gly Pro Ala Ser Arg Gly
1               5                   10                  15

Tyr Tyr Gly Met Asp Val
            20

<210> SEQ ID NO 546
<211> LENGTH: 22
<212> TYPE: PRT
<213> ORGANISM: Artificial Sequence
<220> FEATURE:
<223> OTHER INFORMATION: Synthetic Construct

<400> SEQUENCE: 546

Ala Arg Asp Pro Ser Gly Ile Ala Leu Ala Gly Pro Ala Ser Arg Pro
1               5                   10                  15

Tyr Tyr Gly Met Asp Val
            20

<210> SEQ ID NO 547
<211> LENGTH: 22
<212> TYPE: PRT
<213> ORGANISM: Artificial Sequence
<220> FEATURE:
<223> OTHER INFORMATION: Synthetic Construct

```
<400> SEQUENCE: 547

Ala Arg Asp Pro Ser Gly Ile Ala Leu Ala Gly Pro Ala Ser Arg Tyr
1               5                   10                  15

Tyr Leu Gly Met Asp Val
            20

<210> SEQ ID NO 548
<211> LENGTH: 22
<212> TYPE: PRT
<213> ORGANISM: Artificial Sequence
<220> FEATURE:
<223> OTHER INFORMATION: Synthetic Construct

<400> SEQUENCE: 548

Ala Arg Asp Pro Ser Gly Ile Ala Leu Ala Gly Pro Gly Ser Arg Tyr
1               5                   10                  15

Tyr Arg Gly Met Asp Val
            20

<210> SEQ ID NO 549
<211> LENGTH: 22
<212> TYPE: PRT
<213> ORGANISM: Artificial Sequence
<220> FEATURE:
<223> OTHER INFORMATION: Synthetic Construct

<400> SEQUENCE: 549

Ala Arg Asp Pro Ser Gly Ile Ala Val Ala Gly Pro Ala Ser Arg Tyr
1               5                   10                  15

Tyr Tyr Gly Met Asp Val
            20

<210> SEQ ID NO 550
<211> LENGTH: 22
<212> TYPE: PRT
<213> ORGANISM: Artificial Sequence
<220> FEATURE:
<223> OTHER INFORMATION: Synthetic Construct

<400> SEQUENCE: 550

Val Arg Asp Pro Ser Gly Ile Ala Ala Ala Gly Pro Ala Ser Arg Tyr
1               5                   10                  15

Tyr Tyr Gly Met Asp Val
            20

<210> SEQ ID NO 551
<211> LENGTH: 22
<212> TYPE: PRT
<213> ORGANISM: Artificial Sequence
<220> FEATURE:
<223> OTHER INFORMATION: Synthetic Construct

<400> SEQUENCE: 551

Thr Arg Asp Pro Ser Gly Ile Ala Ala Ala Gly Pro Ala Ser Arg Tyr
1               5                   10                  15

Tyr Tyr Gly Met Asp Val
            20

<210> SEQ ID NO 552
<211> LENGTH: 21
<212> TYPE: PRT
<213> ORGANISM: Artificial Sequence
<220> FEATURE:
```

-continued

```
<223> OTHER INFORMATION: Synthetic Construct

<400> SEQUENCE: 552

Ala Arg Asp Pro Ser Gly Ile Ala Leu Ala Gly Pro Ala Ser Arg Tyr
1               5                   10                  15

Tyr Gly Met Asp Val
            20

<210> SEQ ID NO 553
<211> LENGTH: 22
<212> TYPE: PRT
<213> ORGANISM: Artificial Sequence
<220> FEATURE:
<223> OTHER INFORMATION: Synthetic Construct

<400> SEQUENCE: 553

Ala Arg Asp Pro Ser Gly Ile Ala Leu Ala Gly Pro Ala Ser Arg Gly
1               5                   10                  15

Tyr Gln Gly Met Asp Val
            20

<210> SEQ ID NO 554
<211> LENGTH: 22
<212> TYPE: PRT
<213> ORGANISM: Artificial Sequence
<220> FEATURE:
<223> OTHER INFORMATION: Synthetic Construct

<400> SEQUENCE: 554

Ala Arg Asp Pro Ser Gly Ile Ala Leu Ala Phe Pro Ala Ser Arg Tyr
1               5                   10                  15

Tyr Tyr Gly Met Asp Val
            20

<210> SEQ ID NO 555
<211> LENGTH: 22
<212> TYPE: PRT
<213> ORGANISM: Artificial Sequence
<220> FEATURE:
<223> OTHER INFORMATION: Synthetic Construct

<400> SEQUENCE: 555

Ala Arg Asp Pro Ser Gly Ile Ala Ala Ala Gly Pro Ala Ala Arg His
1               5                   10                  15

Tyr Tyr Gly Met Asp Val
            20

<210> SEQ ID NO 556
<211> LENGTH: 22
<212> TYPE: PRT
<213> ORGANISM: Artificial Sequence
<220> FEATURE:
<223> OTHER INFORMATION: Synthetic Construct

<400> SEQUENCE: 556

Ala Arg Asp Pro Phe Gly Ile Ala Leu Ala Gly Pro Ala Ser Arg Tyr
1               5                   10                  15

Tyr Tyr Gly Met Asp Val
            20

<210> SEQ ID NO 557
<211> LENGTH: 22
<212> TYPE: PRT
<213> ORGANISM: Artificial Sequence
```

```
<220> FEATURE:
<223> OTHER INFORMATION: Synthetic Construct

<400> SEQUENCE: 557

Ala Arg Asp Pro Ser Gly Ile Ala Ala Ala Phe Pro Ala Gly Arg Tyr
1               5                   10                  15

Tyr Tyr Gly Met Asp Val
            20

<210> SEQ ID NO 558
<211> LENGTH: 22
<212> TYPE: PRT
<213> ORGANISM: Artificial Sequence
<220> FEATURE:
<223> OTHER INFORMATION: Synthetic Construct

<400> SEQUENCE: 558

Ala Arg Asp Pro Ser Gly Ile Ala Ala Ala Tyr Pro Ala Ser Arg Tyr
1               5                   10                  15

Asn Tyr Gly Met Asp Val
            20

<210> SEQ ID NO 559
<211> LENGTH: 22
<212> TYPE: PRT
<213> ORGANISM: Artificial Sequence
<220> FEATURE:
<223> OTHER INFORMATION: Synthetic Construct

<400> SEQUENCE: 559

Ala Arg Asp Pro Gly Gly Ala Ala Ala Ala Gly Pro Ala Ser Arg Tyr
1               5                   10                  15

Tyr Tyr Gly Met Asp Val
            20

<210> SEQ ID NO 560
<211> LENGTH: 22
<212> TYPE: PRT
<213> ORGANISM: Artificial Sequence
<220> FEATURE:
<223> OTHER INFORMATION: Synthetic Construct

<400> SEQUENCE: 560

Ala Arg Asp Pro Ser Gly Ile Ala Ala Ala Tyr Pro Ala Ser Arg Tyr
1               5                   10                  15

Tyr Arg Gly Met Asp Val
            20

<210> SEQ ID NO 561
<211> LENGTH: 22
<212> TYPE: PRT
<213> ORGANISM: Artificial Sequence
<220> FEATURE:
<223> OTHER INFORMATION: Synthetic Construct

<400> SEQUENCE: 561

Ala Arg Asp Pro Ser Gly Ile Gly Leu Ala Gly Pro Phe Ser Arg Tyr
1               5                   10                  15

Tyr Tyr Gly Met Asp Val
            20

<210> SEQ ID NO 562
<211> LENGTH: 22
<212> TYPE: PRT
```

```
<213> ORGANISM: Artificial Sequence
<220> FEATURE:
<223> OTHER INFORMATION: Synthetic Construct

<400> SEQUENCE: 562

Ala Arg Asp Pro Ser Gly Ile Ala Leu Ala Gly Pro Ala Ser Arg Ser
1               5                   10                  15

Tyr Tyr Gly Met Asp Val
            20

<210> SEQ ID NO 563
<211> LENGTH: 22
<212> TYPE: PRT
<213> ORGANISM: Artificial Sequence
<220> FEATURE:
<223> OTHER INFORMATION: Synthetic Construct

<400> SEQUENCE: 563

Ala Arg Asp Pro Ser Gly Ile Ala Ala Ala Phe Pro Ala Ser Arg Ser
1               5                   10                  15

Tyr Tyr Gly Met Asp Val
            20

<210> SEQ ID NO 564
<211> LENGTH: 22
<212> TYPE: PRT
<213> ORGANISM: Artificial Sequence
<220> FEATURE:
<223> OTHER INFORMATION: Synthetic Construct

<400> SEQUENCE: 564

Ala Arg Asp Pro Ser Gly Ile Ala Leu Leu Gly Pro Ala Ser Arg Tyr
1               5                   10                  15

Tyr Tyr Gly Met Asp Val
            20

<210> SEQ ID NO 565
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = G or Y
<220> FEATURE:
<221> NAME/KEY: VARIANT
<222> LOCATION: 4
<223> OTHER INFORMATION: Xaa = S, R, G, or T
<220> FEATURE:
<221> NAME/KEY: VARIANT
<222> LOCATION: 5
<223> OTHER INFORMATION: Xaa = S, G, or N
<220> FEATURE:
<221> NAME/KEY: VARIANT
<222> LOCATION: 8
<223> OTHER INFORMATION: Xaa = I or M
<220> FEATURE:
<221> NAME/KEY: VARIANT
<222> LOCATION: 9
<223> OTHER INFORMATION: Xaa = S or A

<400> SEQUENCE: 565

Xaa Thr Phe Xaa Xaa Tyr Ala Xaa Xaa
1               5

<210> SEQ ID NO 566
```

<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = I or V
<220> FEATURE:
<221> NAME/KEY: VARIANT
<222> LOCATION: 5
<223> OTHER INFORMATION: Xaa = I, R, G, A, S, T, or Q
<220> FEATURE:
<221> NAME/KEY: VARIANT
<222> LOCATION: 6
<223> OTHER INFORMATION: Xaa = F or G
<220> FEATURE:
<221> NAME/KEY: VARIANT
<222> LOCATION: 8
<223> OTHER INFORMATION: Xaa = T, R, or W
<220> FEATURE:
<221> NAME/KEY: VARIANT
<222> LOCATION: 10
<223> OTHER INFORMATION: Xaa = S, N, Q, or W

<400> SEQUENCE: 566

Gly Ile Xaa Pro Xaa Xaa Gly Xaa Ala Xaa Tyr Ala Gln Lys Phe Gln
1               5                   10                  15
Gly

<210> SEQ ID NO 567
<211> LENGTH: 9
<212> TYPE: PRT
<213> ORGANISM: Artificial Sequence
<220> FEATURE:
<223> OTHER INFORMATION: Synthetic Construct

<400> SEQUENCE: 567

Gly Thr Phe Arg Ser Tyr Ala Ile Ser
1               5

<210> SEQ ID NO 568
<211> LENGTH: 9
<212> TYPE: PRT
<213> ORGANISM: Artificial Sequence
<220> FEATURE:
<223> OTHER INFORMATION: Synthetic Construct

<400> SEQUENCE: 568

Gly Thr Phe Gly Ser Tyr Ala Ile Ser
1               5

<210> SEQ ID NO 569
<211> LENGTH: 9
<212> TYPE: PRT
<213> ORGANISM: Artificial Sequence
<220> FEATURE:
<223> OTHER INFORMATION: Synthetic Construct

<400> SEQUENCE: 569

Tyr Thr Phe Thr Gly Tyr Ala Met Ala
1               5

<210> SEQ ID NO 570
<211> LENGTH: 9
<212> TYPE: PRT
<213> ORGANISM: Artificial Sequence
<220> FEATURE:
<223> OTHER INFORMATION: Synthetic Construct

```
<400> SEQUENCE: 570

Gly Thr Phe Arg Asn Tyr Ala Ile Ser
1               5

<210> SEQ ID NO 571
<211> LENGTH: 17
<212> TYPE: PRT
<213> ORGANISM: Artificial Sequence
<220> FEATURE:
<223> OTHER INFORMATION: Synthetic Construct

<400> SEQUENCE: 571

Gly Ile Val Pro Arg Phe Gly Thr Ala Asn Tyr Ala Gln Lys Phe Gln
1               5                   10                  15

Gly

<210> SEQ ID NO 572
<211> LENGTH: 17
<212> TYPE: PRT
<213> ORGANISM: Artificial Sequence
<220> FEATURE:
<223> OTHER INFORMATION: Synthetic Construct

<400> SEQUENCE: 572

Gly Ile Ile Pro Gly Phe Gly Thr Ala Gln Tyr Ala Gln Lys Phe Gln
1               5                   10                  15

Gly

<210> SEQ ID NO 573
<211> LENGTH: 17
<212> TYPE: PRT
<213> ORGANISM: Artificial Sequence
<220> FEATURE:
<223> OTHER INFORMATION: Synthetic Construct

<400> SEQUENCE: 573

Gly Ile Ile Pro Gly Phe Gly Thr Ala Trp Tyr Ala Gln Lys Phe Gln
1               5                   10                  15

Gly

<210> SEQ ID NO 574
<211> LENGTH: 17
<212> TYPE: PRT
<213> ORGANISM: Artificial Sequence
<220> FEATURE:
<223> OTHER INFORMATION: Synthetic Construct

<400> SEQUENCE: 574

Gly Ile Ile Pro Ala Phe Gly Thr Ala Trp Tyr Ala Gln Lys Phe Gln
1               5                   10                  15

Gly

<210> SEQ ID NO 575
<211> LENGTH: 17
<212> TYPE: PRT
<213> ORGANISM: Artificial Sequence
<220> FEATURE:
<223> OTHER INFORMATION: Synthetic Construct

<400> SEQUENCE: 575

Gly Ile Ile Pro Ser Phe Gly Thr Ala Ser Tyr Ala Gln Lys Phe Gln
1               5                   10                  15
```

Gly

<210> SEQ ID NO 576
<211> LENGTH: 17
<212> TYPE: PRT
<213> ORGANISM: Artificial Sequence
<220> FEATURE:
<223> OTHER INFORMATION: Synthetic Construct

<400> SEQUENCE: 576

Gly Ile Ile Pro Thr Phe Gly Thr Ala Trp Tyr Ala Gln Lys Phe Gln
1               5                   10                  15

Gly

<210> SEQ ID NO 577
<211> LENGTH: 17
<212> TYPE: PRT
<213> ORGANISM: Artificial Sequence
<220> FEATURE:
<223> OTHER INFORMATION: Synthetic Construct

<400> SEQUENCE: 577

Gly Ile Ile Pro Gly Phe Gly Arg Ala Asn Tyr Ala Gln Lys Phe Gln
1               5                   10                  15

Gly

<210> SEQ ID NO 578
<211> LENGTH: 17
<212> TYPE: PRT
<213> ORGANISM: Artificial Sequence
<220> FEATURE:
<223> OTHER INFORMATION: Synthetic Construct

<400> SEQUENCE: 578

Gly Ile Ile Pro Gln Phe Gly Thr Ala Asn Tyr Ala Gln Lys Phe Gln
1               5                   10                  15

Gly

<210> SEQ ID NO 579
<211> LENGTH: 17
<212> TYPE: PRT
<213> ORGANISM: Artificial Sequence
<220> FEATURE:
<223> OTHER INFORMATION: Synthetic Construct

<400> SEQUENCE: 579

Gly Ile Ile Pro Ile Gly Gly Trp Ala Asn Tyr Ala Gln Lys Phe Gln
1               5                   10                  15

Gly

<210> SEQ ID NO 580
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = S or G
<220> FEATURE:
<221> NAME/KEY: VARIANT
<222> LOCATION: 8
<223> OTHER INFORMATION: Xaa = H or R

<400> SEQUENCE: 580

```
Arg Ser Ser Gln Xaa Leu Leu Xaa Ser Asn Gly Tyr Asn Tyr Leu Asp
1               5                   10                  15

<210> SEQ ID NO 581
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = A or V

<400> SEQUENCE: 581

Leu Gly Ser Asn Arg Xaa Ser
1               5

<210> SEQ ID NO 582
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = G or V
<220> FEATURE:
<221> NAME/KEY: VARIANT
<222> LOCATION: 7
<223> OTHER INFORMATION: Xaa = Y or R

<400> SEQUENCE: 582

Tyr Ser Ile Ser Ser Xaa Xaa Tyr Trp Gly
1               5                   10

<210> SEQ ID NO 583
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = T, S or A
<220> FEATURE:
<221> NAME/KEY: VARIANT
<222> LOCATION: 4
<223> OTHER INFORMATION: Xaa = H or P

<400> SEQUENCE: 583

Xaa Ile Tyr Xaa Ser Gly Ser Thr Tyr Tyr Asn Pro Ser Leu Lys Ser
1               5                   10                  15

<210> SEQ ID NO 584
<211> LENGTH: 16
<212> TYPE: PRT
<213> ORGANISM: Artificial Sequence
<220> FEATURE:
<223> OTHER INFORMATION: Synthetic Construct

<400> SEQUENCE: 584

Arg Ser Ser Gln Ser Leu Leu Arg Ser Asn Gly Tyr Asn Tyr Leu Asp
1               5                   10                  15

<210> SEQ ID NO 585
<211> LENGTH: 16
```

```
<212> TYPE: PRT
<213> ORGANISM: Artificial Sequence
<220> FEATURE:
<223> OTHER INFORMATION: Synthetic Construct

<400> SEQUENCE: 585

Arg Ser Ser Gln Gly Leu Leu Arg Ser Asn Gly Tyr Asn Tyr Leu Asp
1               5                   10                  15

<210> SEQ ID NO 586
<211> LENGTH: 7
<212> TYPE: PRT
<213> ORGANISM: Artificial Sequence
<220> FEATURE:
<223> OTHER INFORMATION: Synthetic Construct

<400> SEQUENCE: 586

Leu Gly Ser Asn Arg Val Ser
1               5

<210> SEQ ID NO 587
<211> LENGTH: 10
<212> TYPE: PRT
<213> ORGANISM: Artificial Sequence
<220> FEATURE:
<223> OTHER INFORMATION: Synthetic Construct

<400> SEQUENCE: 587

Tyr Ser Ile Ser Ser Val Arg Tyr Trp Gly
1               5                   10

<210> SEQ ID NO 588
<211> LENGTH: 16
<212> TYPE: PRT
<213> ORGANISM: Artificial Sequence
<220> FEATURE:
<223> OTHER INFORMATION: Synthetic Construct

<400> SEQUENCE: 588

Ala Ile Tyr Pro Ser Gly Ser Thr Tyr Tyr Asn Pro Ser Leu Lys Ser
1               5                   10                  15

<210> SEQ ID NO 589
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = G or Y
<220> FEATURE:
<221> NAME/KEY: VARIANT
<222> LOCATION: 4
<223> OTHER INFORMATION: Xaa = S, V, Y, K, or P
<220> FEATURE:
<221> NAME/KEY: VARIANT
<222> LOCATION: 6
<223> OTHER INFORMATION: Xaa = S or R
<220> FEATURE:
<221> NAME/KEY: VARIANT
<222> LOCATION: 7
<223> OTHER INFORMATION: Xaa = D or E

<400> SEQUENCE: 589

Xaa Ser Ile Xaa Ser Xaa Xaa Tyr Tyr Trp Gly
1               5                   10
```

```
<210> SEQ ID NO 590
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = S, G, Q, or L
<220> FEATURE:
<221> NAME/KEY: VARIANT
<222> LOCATION: 4
<223> OTHER INFORMATION: Xaa = Y, W, or R
<220> FEATURE:
<221> NAME/KEY: VARIANT
<222> LOCATION: 5
<223> OTHER INFORMATION: Xaa = S, R, K, or A
<220> FEATURE:
<221> NAME/KEY: VARIANT
<222> LOCATION: 9
<223> OTHER INFORMATION: Xaa = Y or V

<400> SEQUENCE: 590

Xaa Ile Tyr Xaa Xaa Gly Ser Thr Xaa Tyr Asn Pro Ser Leu Lys Ser
1               5                   10                  15

<210> SEQ ID NO 591
<211> LENGTH: 11
<212> TYPE: PRT
<213> ORGANISM: Artificial Sequence
<220> FEATURE:
<223> OTHER INFORMATION: Synthetic Construct

<400> SEQUENCE: 591

Gly Ser Ile Val Ser Ser Asp Tyr Tyr Trp Gly
1               5                   10

<210> SEQ ID NO 592
<211> LENGTH: 11
<212> TYPE: PRT
<213> ORGANISM: Artificial Sequence
<220> FEATURE:
<223> OTHER INFORMATION: Synthetic Construct

<400> SEQUENCE: 592

Gly Ser Ile Tyr Ser Ser Asp Tyr Tyr Trp Gly
1               5                   10

<210> SEQ ID NO 593
<211> LENGTH: 11
<212> TYPE: PRT
<213> ORGANISM: Artificial Sequence
<220> FEATURE:
<223> OTHER INFORMATION: Synthetic Construct

<400> SEQUENCE: 593

Gly Ser Ile Lys Ser Ser Glu Tyr Tyr Trp Gly
1               5                   10

<210> SEQ ID NO 594
<211> LENGTH: 10
<212> TYPE: PRT
<213> ORGANISM: Artificial Sequence
<220> FEATURE:
<223> OTHER INFORMATION: Synthetic Construct

<400> SEQUENCE: 594

Tyr Ser Ile Pro Ser Asp Tyr Tyr Trp Gly
1               5                   10
```

<210> SEQ ID NO 595
<211> LENGTH: 11
<212> TYPE: PRT
<213> ORGANISM: Artificial Sequence
<220> FEATURE:
<223> OTHER INFORMATION: Synthetic Construct

<400> SEQUENCE: 595

Gly Ser Ile Ser Ser Ser Glu Tyr Tyr Trp Gly
1               5                   10

<210> SEQ ID NO 596
<211> LENGTH: 11
<212> TYPE: PRT
<213> ORGANISM: Artificial Sequence
<220> FEATURE:
<223> OTHER INFORMATION: Synthetic Construct

<400> SEQUENCE: 596

Gly Ser Ile Ser Ser Arg Glu Tyr Tyr Trp Gly
1               5                   10

<210> SEQ ID NO 597
<211> LENGTH: 16
<212> TYPE: PRT
<213> ORGANISM: Artificial Sequence
<220> FEATURE:
<223> OTHER INFORMATION: Synthetic Construct

<400> SEQUENCE: 597

Gly Ile Tyr Tyr Arg Gly Ser Thr Tyr Tyr Asn Pro Ser Leu Lys Ser
1               5                   10                  15

<210> SEQ ID NO 598
<211> LENGTH: 16
<212> TYPE: PRT
<213> ORGANISM: Artificial Sequence
<220> FEATURE:
<223> OTHER INFORMATION: Synthetic Construct

<400> SEQUENCE: 598

Gln Ile Tyr Tyr Lys Gly Ser Thr Tyr Tyr Asn Pro Ser Leu Lys Ser
1               5                   10                  15

<210> SEQ ID NO 599
<211> LENGTH: 16
<212> TYPE: PRT
<213> ORGANISM: Artificial Sequence
<220> FEATURE:
<223> OTHER INFORMATION: Synthetic Construct

<400> SEQUENCE: 599

Ser Ile Tyr Trp Arg Gly Ser Thr Tyr Tyr Asn Pro Ser Leu Lys Ser
1               5                   10                  15

<210> SEQ ID NO 600
<211> LENGTH: 16
<212> TYPE: PRT
<213> ORGANISM: Artificial Sequence
<220> FEATURE:
<223> OTHER INFORMATION: Synthetic Construct

<400> SEQUENCE: 600

Ser Ile Tyr Arg Ala Gly Ser Thr Tyr Tyr Asn Pro Ser Leu Lys Ser
1               5                   10                  15

<210> SEQ ID NO 601
<211> LENGTH: 16
<212> TYPE: PRT
<213> ORGANISM: Artificial Sequence
<220> FEATURE:
<223> OTHER INFORMATION: Synthetic Construct

<400> SEQUENCE: 601

Ser Ile Tyr Tyr Arg Gly Ser Thr Val Tyr Asn Pro Ser Leu Lys Ser
1               5                   10                  15

<210> SEQ ID NO 602
<211> LENGTH: 16
<212> TYPE: PRT
<213> ORGANISM: Artificial Sequence
<220> FEATURE:
<223> OTHER INFORMATION: Synthetic Construct

<400> SEQUENCE: 602

Leu Ile Tyr Tyr Arg Gly Ser Thr Tyr Tyr Asn Pro Ser Leu Lys Ser
1               5                   10                  15

<210> SEQ ID NO 603
<211> LENGTH: 16
<212> TYPE: PRT
<213> ORGANISM: Artificial Sequence
<220> FEATURE:
<223> OTHER INFORMATION: Synthetic Construct

<400> SEQUENCE: 603

Ser Ile Tyr Arg Ser Gly Ser Thr Tyr Tyr Asn Pro Ser Leu Lys Ser
1               5                   10                  15

<210> SEQ ID NO 604
<211> LENGTH: 124
<212> TYPE: PRT
<213> ORGANISM: Artificial Sequence
<220> FEATURE:
<223> OTHER INFORMATION: Synthetic Construct

<400> SEQUENCE: 604

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Ala Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Phe Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Arg Ser Ser Gly Trp Tyr Glu Gly Tyr Gly Met Asp
            100                 105                 110

Val Trp Gly Gln Gly Thr Thr Val Thr Val Ser Ser
        115                 120

<210> SEQ ID NO 605
<211> LENGTH: 124
<212> TYPE: PRT
<213> ORGANISM: Artificial Sequence
<220> FEATURE:

-continued

<223> OTHER INFORMATION: Synthetic Construct

<400> SEQUENCE: 605

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Val Ala Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Ala Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Arg Ser Ser Gly Trp Tyr Glu Gly Tyr Gly Met Asp
            100                 105                 110

Val Trp Gly Gln Gly Thr Thr Val Thr Val Ser Ser
        115                 120

<210> SEQ ID NO 606
<211> LENGTH: 124
<212> TYPE: PRT
<213> ORGANISM: Artificial Sequence
<220> FEATURE:
<223> OTHER INFORMATION: Synthetic Construct

<400> SEQUENCE: 606

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Ala Tyr
            20                  25                  30

Tyr Met His Trp Val Arg Gln Ala Pro Gly Gln Gly Leu Glu Trp Met
        35                  40                  45

Gly Trp Val Asn Pro Asn Ser Gly Gly Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Arg Ser Ser Gly Trp Tyr Glu Gly Tyr Gly Met Asp
            100                 105                 110

Val Trp Gly Gln Gly Thr Thr Val Thr Val Ser Ser
        115                 120

<210> SEQ ID NO 607
<211> LENGTH: 124
<212> TYPE: PRT
<213> ORGANISM: Artificial Sequence
<220> FEATURE:
<223> OTHER INFORMATION: Synthetic Construct

<400> SEQUENCE: 607

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Met Met His Trp Val Arg Gln Ala Pro Gly Gln Gly Leu Glu Trp Met

```
                35                  40                  45
Gly Ile Ile Gly Pro Ser Gly Tyr Thr Tyr Ala Gln Lys Phe
        50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Gly Lys Arg Ser Ser Gly Trp Tyr Glu Gly Tyr Gly Met Asp
                100                 105                 110
Val Trp Gly Gln Gly Thr Thr Val Thr Val Ser Ser
        115                 120

<210> SEQ ID NO 608
<211> LENGTH: 124
<212> TYPE: PRT
<213> ORGANISM: Artificial Sequence
<220> FEATURE:
<223> OTHER INFORMATION: Synthetic Construct

<400> SEQUENCE: 608

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Pro Gly Tyr
                20                  25                  30
Leu Met His Trp Val Arg Gln Ala Pro Gly Gln Gly Leu Glu Trp Met
                35                  40                  45
Gly Trp Ile Asn Pro Val Ser Gly Ser Thr Asn Tyr Ala Gln Lys Phe
        50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Gly Lys Arg Ser Ser Gly Trp Tyr Glu Gly Tyr Gly Met Asp
                100                 105                 110
Val Trp Gly Gln Gly Thr Thr Val Thr Val Ser Ser
        115                 120

<210> SEQ ID NO 609
<211> LENGTH: 124
<212> TYPE: PRT
<213> ORGANISM: Artificial Sequence
<220> FEATURE:
<223> OTHER INFORMATION: Synthetic Construct

<400> SEQUENCE: 609

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Gly Ala Tyr
                20                  25                  30
Tyr Met His Trp Val Arg Gln Ala Pro Gly Gln Gly Leu Glu Trp Met
                35                  40                  45
Gly Trp Val Asn Pro Asn Ser Gly Gly Thr Asn Tyr Ala Gln Lys Phe
        50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
```

Ala Arg Gly Lys Arg Ser Ser Gly Trp Tyr Glu Gly Tyr Gly Met Asp
            100                 105                 110

Val Trp Gly Gln Gly Thr Thr Val Thr Val Ser Ser
            115                 120

<210> SEQ ID NO 610
<211> LENGTH: 124
<212> TYPE: PRT
<213> ORGANISM: Artificial Sequence
<220> FEATURE:
<223> OTHER INFORMATION: Synthetic Construct

<400> SEQUENCE: 610

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Leu Ala Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Arg Ser Ser Gly Trp Tyr Glu Gly Tyr Gly Met Asp
            100                 105                 110

Val Trp Gly Gln Gly Thr Thr Val Thr Val Ser Ser
            115                 120

<210> SEQ ID NO 611
<211> LENGTH: 124
<212> TYPE: PRT
<213> ORGANISM: Artificial Sequence
<220> FEATURE:
<223> OTHER INFORMATION: Synthetic Construct

<400> SEQUENCE: 611

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Phe Ser Tyr
            20                  25                  30

Tyr Met His Trp Val Arg Gln Ala Pro Gly Gln Gly Leu Glu Trp Met
        35                  40                  45

Gly Trp Ile Asn Pro Ser Gly Gly Asn Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Arg Ser Ser Gly Trp Tyr Glu Gly Tyr Gly Met Asp
            100                 105                 110

Val Trp Gly Gln Gly Thr Thr Val Thr Val Ser Ser
            115                 120

<210> SEQ ID NO 612
<211> LENGTH: 124
<212> TYPE: PRT
<213> ORGANISM: Artificial Sequence

```
<220> FEATURE:
<223> OTHER INFORMATION: Synthetic Construct

<400> SEQUENCE: 612

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
                20                  25                  30

Leu Met His Trp Val Arg Gln Ala Pro Gly Gln Gly Leu Glu Trp Met
            35                  40                  45

Gly Trp Ile Asn Pro Ser Gly Gly Ser Thr Ser Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Arg Ser Ser Gly Trp Tyr Glu Gly Tyr Gly Met Asp
            100                 105                 110

Val Trp Gly Gln Gly Thr Thr Val Thr Val Ser Ser
        115                 120

<210> SEQ ID NO 613
<211> LENGTH: 124
<212> TYPE: PRT
<213> ORGANISM: Artificial Sequence
<220> FEATURE:
<223> OTHER INFORMATION: Synthetic Construct

<400> SEQUENCE: 613

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Tyr
                20                  25                  30

Tyr Met Trp Trp Val Arg Gln Ala Pro Gly Gln Gly Leu Glu Trp Met
            35                  40                  45

Gly Gly Ile Leu Pro Ser Gly Gly Arg Thr Ser Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Arg Ser Ser Gly Trp Tyr Glu Gly Tyr Gly Met Asp
            100                 105                 110

Val Trp Gly Gln Gly Thr Thr Val Thr Val Ser Ser
        115                 120

<210> SEQ ID NO 614
<211> LENGTH: 124
<212> TYPE: PRT
<213> ORGANISM: Artificial Sequence
<220> FEATURE:
<223> OTHER INFORMATION: Synthetic Construct

<400> SEQUENCE: 614

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Leu Ala Tyr
                20                  25                  30
```

Tyr Met His Trp Val Arg Gln Ala Pro Gly Gln Gly Leu Glu Trp Met
            35                  40                  45

Gly Trp Ile Asn Pro Ser Trp Gly Ser Thr Ser Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Arg Ser Ser Gly Trp Tyr Glu Gly Tyr Gly Met Asp
            100                 105                 110

Val Trp Gly Gln Gly Thr Thr Val Thr Val Ser Ser
            115                 120

<210> SEQ ID NO 615
<211> LENGTH: 124
<212> TYPE: PRT
<213> ORGANISM: Artificial Sequence
<220> FEATURE:
<223> OTHER INFORMATION: Synthetic Construct

<400> SEQUENCE: 615

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Met His Trp Val Arg Gln Ala Pro Gly Gln Gly Leu Glu Trp Met
            35                  40                  45

Gly Trp Val Asn Pro Asn Ser Gly Gly Thr Met Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Arg Ser Ser Gly Trp Tyr Glu Gly Tyr Gly Met Asp
            100                 105                 110

Val Trp Gly Gln Gly Thr Thr Val Thr Val Ser Ser
            115                 120

<210> SEQ ID NO 616
<211> LENGTH: 124
<212> TYPE: PRT
<213> ORGANISM: Artificial Sequence
<220> FEATURE:
<223> OTHER INFORMATION: Synthetic Construct

<400> SEQUENCE: 616

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Thr Asn Pro Asn Ser Gly Gly Thr Arg Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Arg Ser Ser Gly Trp Tyr Glu Gly Tyr Gly Met Asp
            100                 105                 110

Val Trp Gly Gln Gly Thr Thr Val Thr Val Ser Ser
        115                 120

<210> SEQ ID NO 617
<211> LENGTH: 124
<212> TYPE: PRT
<213> ORGANISM: Artificial Sequence
<220> FEATURE:
<223> OTHER INFORMATION: Synthetic Construct

<400> SEQUENCE: 617

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Gly Tyr
            20                  25                  30

Leu Met His Trp Val Arg Gln Ala Pro Gly Gln Gly Leu Glu Trp Met
        35                  40                  45

Gly Trp Ile Asn Pro Met Ser Gly Gly Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Arg Ser Ser Gly Trp Tyr Glu Gly Tyr Gly Met Asp
            100                 105                 110

Val Trp Gly Gln Gly Thr Thr Val Thr Val Ser Ser
        115                 120

<210> SEQ ID NO 618
<211> LENGTH: 124
<212> TYPE: PRT
<213> ORGANISM: Artificial Sequence
<220> FEATURE:
<223> OTHER INFORMATION: Synthetic Construct

<400> SEQUENCE: 618

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ala Tyr
            20                  25                  30

Tyr Met His Trp Val Arg Gln Ala Pro Gly Gln Gly Leu Glu Trp Met
        35                  40                  45

Gly Trp Ile Asn Pro Ser Gln Gly Ser Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Arg Ser Ser Gly Trp Tyr Glu Gly Tyr Gly Met Asp
            100                 105                 110

Val Trp Gly Gln Gly Thr Thr Val Thr Val Ser Ser
        115                 120

<210> SEQ ID NO 619
<211> LENGTH: 129
<212> TYPE: PRT

<213> ORGANISM: Artificial Sequence
<220> FEATURE:
<223> OTHER INFORMATION: Synthetic Construct

<400> SEQUENCE: 619

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Thr
            20                  25                  30
Tyr Met Ser Trp Val Arg Gln Ala Pro Gly Gln Gly Leu Glu Trp Met
        35                  40                  45
Gly Ile Ile Asn Pro Trp Gly Gly Thr Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Asp Pro Ser Gly Ile Ala Ala Ala Gly Pro Ala Ser Arg Tyr
            100                 105                 110
Tyr Tyr Gly Met Asp Val Trp Gly Gln Gly Thr Thr Val Thr Val Ser
        115                 120                 125
Ser
```

<210> SEQ ID NO 620
<211> LENGTH: 129
<212> TYPE: PRT
<213> ORGANISM: Artificial Sequence
<220> FEATURE:
<223> OTHER INFORMATION: Synthetic Construct

<400> SEQUENCE: 620

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Thr Met Ser Trp Val Arg Gln Ala Pro Gly Gln Gly Leu Glu Trp Met
        35                  40                  45
Gly Ile Ile Asn Pro Tyr Gly Gly Ser Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Asp Pro Ser Gly Ile Ala Ala Ala Gly Pro Ala Ser Arg Tyr
            100                 105                 110
Tyr Tyr Gly Met Asp Val Trp Gly Gln Gly Thr Thr Val Thr Val Ser
        115                 120                 125
Ser
```

<210> SEQ ID NO 621
<211> LENGTH: 129
<212> TYPE: PRT
<213> ORGANISM: Artificial Sequence
<220> FEATURE:
<223> OTHER INFORMATION: Synthetic Construct

<400> SEQUENCE: 621

```
Gln Val Gln Leu Val Gln Ser Gly Ala Glu Val Lys Lys Pro Gly Ala
```

```
            1               5                   10                  15
Ser Val Lys Val Ser Cys Lys Ala Ser Gly Tyr Thr Phe Thr Ser Thr
                20                  25                  30

Tyr Met Ser Trp Val Arg Gln Ala Pro Gly Gln Gly Leu Glu Trp Met
        35                  40                  45

Gly Ile Ile Asn Pro Tyr Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Gly Pro Ala Ser Arg Tyr
                100                 105                 110

Tyr Tyr Gly Met Asp Val Trp Gly Gln Gly Thr Thr Val Thr Val Ser
            115                 120                 125

Ser
```

<210> SEQ ID NO 622
<211> LENGTH: 129
<212> TYPE: PRT
<213> ORGANISM: Artificial Sequence
<220> FEATURE:
<223> OTHER INFORMATION: Synthetic Construct

<400> SEQUENCE: 622

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Leu Met Ser Trp Val Arg Gln Ala Pro Gly Gln Gly Leu Glu Trp Met
        35                  40                  45

Gly Ile Ile Asn Pro Val Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Gly Pro Ala Ser Arg Tyr
                100                 105                 110

Tyr Tyr Gly Met Asp Val Trp Gly Gln Gly Thr Thr Val Thr Val Ser
            115                 120                 125

Ser
```

<210> SEQ ID NO 623
<211> LENGTH: 129
<212> TYPE: PRT
<213> ORGANISM: Artificial Sequence
<220> FEATURE:
<223> OTHER INFORMATION: Synthetic Construct

<400> SEQUENCE: 623

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Leu Met Ser Trp Val Arg Gln Ala Pro Gly Gln Gly Leu Glu Trp Met
        35                  40                  45
```

```
Gly Val Ile Asn Pro Phe Gly Gly Ser Thr Ser Tyr Ala Gln Lys Phe
            50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Pro Ser Gly Ile Ala Ala Ala Gly Pro Ala Ser Arg Tyr
                100                 105                 110

Tyr Tyr Gly Met Asp Val Trp Gly Gln Gly Thr Thr Val Thr Val Ser
            115                 120                 125

Ser

<210> SEQ ID NO 624
<211> LENGTH: 129
<212> TYPE: PRT
<213> ORGANISM: Artificial Sequence
<220> FEATURE:
<223> OTHER INFORMATION: Synthetic Construct

<400> SEQUENCE: 624

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Arg
                20                  25                  30

Tyr Met Ser Trp Val Arg Gln Ala Pro Gly Gln Gly Leu Glu Trp Met
            35                  40                  45

Gly Ile Ile Asn Pro Val Gly Gly Ser Thr Ser Tyr Ala Gln Lys Phe
        50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Pro Ser Gly Ile Ala Ala Ala Gly Pro Ala Ser Arg Tyr
                100                 105                 110

Tyr Tyr Gly Met Asp Val Trp Gly Gln Gly Thr Thr Val Thr Val Ser
            115                 120                 125

Ser

<210> SEQ ID NO 625
<211> LENGTH: 129
<212> TYPE: PRT
<213> ORGANISM: Artificial Sequence
<220> FEATURE:
<223> OTHER INFORMATION: Synthetic Construct

<400> SEQUENCE: 625

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ala Ser Arg
                20                  25                  30

Tyr Met Ser Trp Val Arg Gln Ala Pro Gly Gln Gly Leu Glu Trp Met
            35                  40                  45

Gly Ile Ile Asn Pro Val Gly Gly Ser Thr Ser Tyr Ala Gln Lys Phe
        50                  55                  60

Gln Gly Arg Val Thr Met Thr Arg Asp Thr Ser Thr Ser Thr Val Tyr
 65                  70                  75                  80
```

```
Met Glu Leu Ser Ser Leu Arg Ser Glu Asp Thr Ala Val Tyr Tyr Cys
                85                  90                  95

Ala Arg Asp Pro Ser Gly Ile Ala Ala Ala Gly Pro Ala Gly Arg Tyr
            100                 105                 110

Tyr Tyr Gly Leu Asp Val Trp Gly Gln Gly Thr Thr Val Thr Val Ser
        115                 120                 125

Ser

<210> SEQ ID NO 626
<211> LENGTH: 129
<212> TYPE: PRT
<213> ORGANISM: Artificial Sequence
<220> FEATURE:
<223> OTHER INFORMATION: Synthetic Construct

<400> SEQUENCE: 626

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Arg
            20                  25                  30

Tyr Met Ser Trp Val Arg Gln Ala Pro Gly Gln Gly Leu Glu Trp Met
        35                  40                  45

Gly Ile Ile Asn Pro Val Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Gly Pro Ala Gly Arg Tyr
            100                 105                 110

Tyr Tyr Gly Met Asp Val Trp Gly Gln Gly Thr Ala Val Thr Val Ser
        115                 120                 125

Ser

<210> SEQ ID NO 627
<211> LENGTH: 129
<212> TYPE: PRT
<213> ORGANISM: Artificial Sequence
<220> FEATURE:
<223> OTHER INFORMATION: Synthetic Construct

<400> SEQUENCE: 627

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Arg
            20                  25                  30

Tyr Met Ser Trp Val Arg Gln Ala Pro Gly Gln Gly Leu Glu Trp Met
        35                  40                  45

Gly Ile Ile Asn Pro Val Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Gly Pro Ala Ser Arg His
            100                 105                 110

Tyr Tyr Gly Met Asp Val Trp Gly Gln Gly Thr Thr Val Thr Val Ser
```

<210> SEQ ID NO 628
<211> LENGTH: 129
<212> TYPE: PRT
<213> ORGANISM: Artificial Sequence
<220> FEATURE:
<223> OTHER INFORMATION: Synthetic Construct

<400> SEQUENCE: 628

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Leu Thr Ser Arg
            20                  25                  30
Tyr Met Ser Trp Val Arg Gln Ala Pro Gly Gln Gly Leu Glu Trp Met
        35                  40                  45
Gly Ile Ile Asn Pro Val Gly Gly Ser Thr Ser Tyr Ala Gln Lys Phe
    50                  55                  60
Arg Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Asp Pro Ser Gly Ile Ala Ala Ala Gly Pro Ala Ser Arg Tyr
            100                 105                 110
Tyr Tyr Gly Met Asp Val Trp Gly Gln Gly Thr Thr Val Thr Val Ser
        115                 120                 125
Ser
```

<210> SEQ ID NO 629
<211> LENGTH: 129
<212> TYPE: PRT
<213> ORGANISM: Artificial Sequence
<220> FEATURE:
<223> OTHER INFORMATION: Synthetic Construct

<400> SEQUENCE: 629

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Arg
            20                  25                  30
Tyr Met Ser Trp Val Arg Gln Ala Pro Gly Gln Gly Leu Glu Trp Met
        35                  40                  45
Gly Ile Ile Asn Pro Val Gly Gly Ser Ala Ser Tyr Ala Arg Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Asp Pro Ser Gly Ile Ala Ala Ala Gly Pro Ala Ser Arg Tyr
            100                 105                 110
Tyr Tyr Gly Met Asp Val Trp Gly Gln Gly Thr Thr Val Thr Val Ser
        115                 120                 125
Ser
```

<210> SEQ ID NO 630
<211> LENGTH: 107

<212> TYPE: PRT
<213> ORGANISM: Artificial Sequence
<220> FEATURE:
<223> OTHER INFORMATION: Synthetic Construct

<400> SEQUENCE: 630

Glu Val Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ala Arg Leu Gly Pro Trp
                85                  90                  95

Thr Phe Gly Gly Gly Thr Lys Val Glu Ile Lys
            100                 105

<210> SEQ ID NO 631
<211> LENGTH: 129
<212> TYPE: PRT
<213> ORGANISM: Artificial Sequence
<220> FEATURE:
<223> OTHER INFORMATION: Synthetic Construct

<400> SEQUENCE: 631

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Arg
            20                  25                  30

Tyr Met Ser Trp Val Arg Gln Ala Pro Gly Gln Gly Leu Glu Trp Met
        35                  40                  45

Gly Ile Ile Asn Pro Val Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Pro Gly Pro Ala Ser Arg Gly
            100                 105                 110

Tyr Tyr Gly Met Asp Val Trp Gly Gln Gly Thr Thr Val Thr Val Ser
        115                 120                 125

Ser

<210> SEQ ID NO 632
<211> LENGTH: 129
<212> TYPE: PRT
<213> ORGANISM: Artificial Sequence
<220> FEATURE:
<223> OTHER INFORMATION: Synthetic Construct

<400> SEQUENCE: 632

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Arg
            20                  25                  30

Tyr Met Ser Trp Val Arg Gln Ala Pro Gly Gln Gly Leu Glu Trp Met
            35                  40                  45

Gly Ile Ile Asn Pro Val Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Leu Ala Gly Pro Ala Gly Arg Tyr
                100                 105                 110

Tyr Tyr Gly Met Asp Val Trp Gly Gln Gly Thr Thr Val Thr Val Ser
            115                 120                 125

Ser

<210> SEQ ID NO 633
<211> LENGTH: 129
<212> TYPE: PRT
<213> ORGANISM: Artificial Sequence
<220> FEATURE:
<223> OTHER INFORMATION: Synthetic Construct

<400> SEQUENCE: 633

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Arg
            20                  25                  30

Tyr Met Ser Trp Val Arg Gln Ala Pro Gly Gln Gly Leu Glu Trp Met
            35                  40                  45

Gly Ile Ile Asn Pro Val Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Leu Ala Gly Pro Ala Ser Arg Gly
                100                 105                 110

Tyr Tyr Gly Met Asp Val Trp Gly Gln Gly Thr Thr Val Thr Val Ser
            115                 120                 125

Ser

<210> SEQ ID NO 634
<211> LENGTH: 129
<212> TYPE: PRT
<213> ORGANISM: Artificial Sequence
<220> FEATURE:
<223> OTHER INFORMATION: Synthetic Construct

<400> SEQUENCE: 634

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Arg
            20                  25                  30

Tyr Met Ser Trp Val Arg Gln Ala Pro Gly Gln Gly Leu Glu Trp Met
            35                  40                  45

Gly Ile Ile Asn Pro Val Gly Gly Ser Thr Ser Tyr Ala Gln Lys Phe
        50                  55                  60

-continued

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Leu Ala Gly Pro Ala Ser Arg Pro
            100                 105                 110

Tyr Tyr Gly Met Asp Val Trp Gly Gln Gly Thr Thr Val Thr Val Ser
        115                 120                 125

Ser

<210> SEQ ID NO 635
<211> LENGTH: 129
<212> TYPE: PRT
<213> ORGANISM: Artificial Sequence
<220> FEATURE:
<223> OTHER INFORMATION: Synthetic Construct

<400> SEQUENCE: 635

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Arg
            20                  25                  30

Tyr Met Ser Trp Val Arg Gln Ala Pro Gly Gln Gly Leu Glu Trp Met
        35                  40                  45

Gly Ile Ile Asn Pro Val Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Leu Ala Gly Pro Ala Ser Arg Tyr
            100                 105                 110

Tyr Leu Gly Met Asp Val Trp Gly Gln Gly Thr Thr Val Thr Val Ser
        115                 120                 125

Ser

<210> SEQ ID NO 636
<211> LENGTH: 129
<212> TYPE: PRT
<213> ORGANISM: Artificial Sequence
<220> FEATURE:
<223> OTHER INFORMATION: Synthetic Construct

<400> SEQUENCE: 636

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Arg
            20                  25                  30

Tyr Met Ser Trp Val Arg Gln Ala Pro Gly Gln Gly Leu Glu Trp Met
        35                  40                  45

Gly Ile Ile Asn Pro Val Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Leu Ala Gly Pro Gly Ser Arg Tyr

```
                100                 105                 110
Tyr Arg Gly Met Asp Val Trp Gly Gln Gly Thr Thr Val Thr Val Ser
            115                 120                 125

Ser
```

<210> SEQ ID NO 637
<211> LENGTH: 129
<212> TYPE: PRT
<213> ORGANISM: Artificial Sequence
<220> FEATURE:
<223> OTHER INFORMATION: Synthetic Construct

<400> SEQUENCE: 637

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Arg
            20                  25                  30

Tyr Met Ser Trp Val Arg Gln Ala Pro Gly Gln Gly Leu Glu Trp Met
        35                  40                  45

Gly Ile Ile Asn Pro Val Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Val Ala Gly Pro Ala Ser Arg Tyr
            100                 105                 110

Tyr Tyr Gly Met Asp Val Trp Gly Gln Gly Thr Thr Val Thr Val Ser
        115                 120                 125

Ser
```

<210> SEQ ID NO 638
<211> LENGTH: 129
<212> TYPE: PRT
<213> ORGANISM: Artificial Sequence
<220> FEATURE:
<223> OTHER INFORMATION: Synthetic Construct

<400> SEQUENCE: 638

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Leu Met Ser Trp Val Arg Gln Ala Pro Gly Gln Gly Leu Glu Trp Met
        35                  40                  45

Gly Ile Ile Asn Pro Leu Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Gly Pro Ala Ser Arg Tyr
            100                 105                 110

Tyr Tyr Gly Met Asp Val Trp Gly Gln Gly Thr Thr Val Thr Val Ser
        115                 120                 125

Ser
```

```
<210> SEQ ID NO 639
<211> LENGTH: 129
<212> TYPE: PRT
<213> ORGANISM: Artificial Sequence
<220> FEATURE:
<223> OTHER INFORMATION: Synthetic Construct

<400> SEQUENCE: 639

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Leu
            20                  25                  30

Tyr Ile Ser Trp Val Arg Gln Ala Pro Gly Gln Gly Leu Glu Trp Met
        35                  40                  45

Gly Val Ile Asn Pro Val Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Gly Pro Ala Ser Arg Tyr
            100                 105                 110

Tyr Tyr Gly Met Asp Val Trp Gly Gln Gly Thr Thr Val Thr Val Ser
        115                 120                 125

Ser

<210> SEQ ID NO 640
<211> LENGTH: 129
<212> TYPE: PRT
<213> ORGANISM: Artificial Sequence
<220> FEATURE:
<223> OTHER INFORMATION: Synthetic Construct

<400> SEQUENCE: 640

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Arg
            20                  25                  30

Tyr Met Ser Trp Val Arg Gln Ala Pro Gly Gln Gly Leu Glu Trp Met
        35                  40                  45

Gly Ile Ile Asn Pro Leu Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Gly Pro Ala Ser Arg Tyr
            100                 105                 110

Tyr Tyr Gly Met Asp Val Trp Gly Gln Gly Thr Thr Val Thr Val Ser
        115                 120                 125

Ser

<210> SEQ ID NO 641
<211> LENGTH: 129
<212> TYPE: PRT
<213> ORGANISM: Artificial Sequence
<220> FEATURE:
<223> OTHER INFORMATION: Synthetic Construct
```

<400> SEQUENCE: 641

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Tyr Met Ser Trp Val Arg Gln Ala Pro Gly Gln Gly Leu Glu Trp Met
        35                  40                  45

Gly Ile Ile Asn Pro Ile Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Gly Pro Ala Ser Arg Tyr
            100                 105                 110

Tyr Tyr Gly Met Asp Val Trp Gly Gln Gly Thr Thr Val Thr Val Ser
        115                 120                 125

Ser

<210> SEQ ID NO 642
<211> LENGTH: 129
<212> TYPE: PRT
<213> ORGANISM: Artificial Sequence
<220> FEATURE:
<223> OTHER INFORMATION: Synthetic Construct

<400> SEQUENCE: 642

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Lys Tyr
            20                  25                  30

Tyr Met Ser Trp Val Arg Gln Ala Pro Gly Gln Gly Pro Glu Trp Met
        35                  40                  45

Gly Ile Ile Asn Pro Ile Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Arg Asp Pro Ser Gly Ile Ala Ala Ala Gly Pro Ala Ser Arg Tyr
            100                 105                 110

Tyr Tyr Gly Met Asp Val Trp Gly Gln Gly Thr Thr Val Thr Val Ser
        115                 120                 125

Ser

<210> SEQ ID NO 643
<211> LENGTH: 129
<212> TYPE: PRT
<213> ORGANISM: Artificial Sequence
<220> FEATURE:
<223> OTHER INFORMATION: Synthetic Construct

<400> SEQUENCE: 643

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr

-continued

```
                 20                  25                  30
Tyr Met Ser Trp Val Arg Gln Ala Pro Gly Gln Gly Leu Glu Trp Met
             35                  40                  45
Gly Ile Ile Asn Pro Ile Gly Gly Ser Thr Ser Tyr Ala Gln Lys Phe
         50                  55                  60
Arg Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Asp Pro Ser Gly Ile Ala Ala Ala Gly Pro Ala Ser Arg Tyr
                100                 105                 110
Tyr Tyr Gly Met Asp Val Trp Gly Gln Gly Thr Thr Val Thr Val Ser
            115                 120                 125
Ser

<210> SEQ ID NO 644
<211> LENGTH: 129
<212> TYPE: PRT
<213> ORGANISM: Artificial Sequence
<220> FEATURE:
<223> OTHER INFORMATION: Synthetic Construct

<400> SEQUENCE: 644

Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Lys Tyr
                 20                  25                  30
Tyr Met Ser Trp Val Arg Gln Ala Pro Gly Gln Gly Leu Glu Trp Met
             35                  40                  45
Gly Ile Ile Asn Pro Ile Gly Gly Ser Ala Ser Tyr Ala Gln Lys Phe
         50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Asp Pro Ser Gly Ile Ala Ala Ala Gly Pro Ala Gly Arg Tyr
                100                 105                 110
Tyr Tyr Gly Met Asp Val Trp Gly Gln Gly Thr Thr Val Thr Val Ser
            115                 120                 125
Ser

<210> SEQ ID NO 645
<211> LENGTH: 129
<212> TYPE: PRT
<213> ORGANISM: Artificial Sequence
<220> FEATURE:
<223> OTHER INFORMATION: Synthetic Construct

<400> SEQUENCE: 645

Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Lys Tyr
                 20                  25                  30
Tyr Met Ser Trp Val Arg Gln Ala Pro Gly Gln Gly Leu Glu Trp Met
             35                  40                  45
Gly Ile Ile Asn Pro Ile Gly Gly Ser Thr Ser Tyr Ala Gln Lys Phe
         50                  55                  60
```

```
Arg Gly Arg Val Thr Met Thr Arg Asp Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Asp Pro Ser Gly Ile Ala Ala Ala Gly Pro Ala Ser Arg Tyr
            100                 105                 110

Tyr Tyr Gly Met Asp Val Trp Gly Gln Gly Thr Val Thr Val Ser
        115                 120                 125

Ser

<210> SEQ ID NO 646
<211> LENGTH: 129
<212> TYPE: PRT
<213> ORGANISM: Artificial Sequence
<220> FEATURE:
<223> OTHER INFORMATION: Synthetic Construct

<400> SEQUENCE: 646

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Tyr Met Ser Trp Val Arg Gln Ala Pro Gly Gln Gly Leu Glu Trp Met
        35                  40                  45

Gly Ile Ile Asn Pro Ile Gly Gly Ser Thr Ser Tyr Ala Gln Lys Phe
    50                  55                  60

Gln Gly Arg Val Thr Met Thr Arg Asp Thr Ser Ala Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Gly Pro Ala Gly Arg Tyr
            100                 105                 110

Tyr Tyr Gly Met Asp Val Trp Gly Gln Gly Thr Val Thr Val Ser
        115                 120                 125

Ser

<210> SEQ ID NO 647
<211> LENGTH: 128
<212> TYPE: PRT
<213> ORGANISM: Artificial Sequence
<220> FEATURE:
<223> OTHER INFORMATION: Synthetic Construct

<400> SEQUENCE: 647

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Tyr Met Ser Trp Val Arg Gln Ala Pro Gly Gln Gly Leu Glu Trp Met
        35                  40                  45

Gly Ile Ile Asn Pro Ile Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

Ala Arg Asp Pro Ser Gly Ile Ala Leu Ala Gly Pro Ala Ser Arg Tyr
            100                 105                 110

Tyr Gly Met Asp Val Trp Gly Gln Gly Thr Thr Val Thr Val Ser Ser
        115                 120                 125

<210> SEQ ID NO 648
<211> LENGTH: 129
<212> TYPE: PRT
<213> ORGANISM: Artificial Sequence
<220> FEATURE:
<223> OTHER INFORMATION: Synthetic Construct

<400> SEQUENCE: 648

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Tyr Met Ser Trp Val Arg Gln Ala Pro Gly Gln Gly Leu Glu Trp Met
        35                  40                  45

Gly Ile Ile Asn Pro Ile Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Leu Ala Gly Pro Ala Ser Arg Gly
            100                 105                 110

Tyr Gln Gly Met Asp Val Trp Gly Gln Gly Thr Thr Val Thr Val Ser
        115                 120                 125

Ser

<210> SEQ ID NO 649
<211> LENGTH: 129
<212> TYPE: PRT
<213> ORGANISM: Artificial Sequence
<220> FEATURE:
<223> OTHER INFORMATION: Synthetic Construct

<400> SEQUENCE: 649

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Tyr Met Ser Trp Val Arg Gln Ala Pro Gly Gln Gly Leu Glu Trp Met
        35                  40                  45

Gly Ile Ile Asn Pro Ile Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Leu Ala Phe Pro Ala Ser Arg Tyr
            100                 105                 110

Tyr Tyr Gly Met Asp Val Trp Gly Gln Gly Thr Thr Val Thr Val Ser
        115                 120                 125

Ser

```
<210> SEQ ID NO 650
<211> LENGTH: 129
<212> TYPE: PRT
<213> ORGANISM: Artificial Sequence
<220> FEATURE:
<223> OTHER INFORMATION: Synthetic Construct

<400> SEQUENCE: 650
```

| Gln | Val | Gln | Leu | Val | Gln | Ser | Gly | Ala | Glu | Val | Lys | Lys | Pro | Gly | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ser Val Lys Val Ser Cys Lys Ala Ser Gly Tyr Thr Phe Thr Lys Tyr
         20                  25                  30

Tyr Met Ser Trp Val Arg Gln Ala Pro Gly Gln Gly Leu Glu Trp Met
         35                  40                  45

Gly Ile Ile Asn Pro Ile Gly Gly Ser Thr Ser Tyr Ala Gln Lys Phe
 50                  55                  60

Gln Gly Arg Val Thr Met Thr Arg Asp Thr Ser Ser Thr Val Tyr
 65                  70                  75                  80

Met Glu Leu Ser Ser Leu Arg Ser Glu Asp Thr Ala Val Tyr Tyr Cys
             85                  90                  95

Ala Arg Asp Pro Ser Gly Ile Ala Leu Ala Gly Pro Ala Ser Arg Gly
             100                 105                 110

Tyr Tyr Gly Met Asp Val Trp Gly Gln Gly Thr Thr Val Thr Val Ser
             115                 120                 125

Ser

```
<210> SEQ ID NO 651
<211> LENGTH: 129
<212> TYPE: PRT
<213> ORGANISM: Artificial Sequence
<220> FEATURE:
<223> OTHER INFORMATION: Synthetic Construct

<400> SEQUENCE: 651
```

Gln Val Gln Leu Val Gln Ser Gly Ala Glu Val Lys Lys Pro Gly Ala
 1               5                   10                  15

Ser Val Glu Val Ser Cys Lys Ala Ser Gly Tyr Thr Phe Thr Lys Tyr
             20                  25                  30

Tyr Met Ser Trp Val Arg Gln Ala Pro Gly Gln Gly Leu Glu Trp Met
         35                  40                  45

Gly Ile Ile Asn Pro Ile Gly Gly Ser Thr Ser Tyr Ala Gln Lys Phe
 50                  55                  60

Gln Gly Arg Val Thr Met Thr Arg Asp Thr Ser Ser Thr Val Tyr
 65                  70                  75                  80

Met Glu Leu Ser Ser Leu Arg Ser Glu Asp Thr Ala Val Tyr Tyr Cys
             85                  90                  95

Ala Arg Asp Pro Ser Gly Ile Ala Ala Ala Gly Pro Ala Ala Arg His
             100                 105                 110

Tyr Tyr Gly Met Asp Val Trp Gly Gln Gly Thr Thr Val Thr Val Ser
             115                 120                 125

Ser

```
<210> SEQ ID NO 652
<211> LENGTH: 129
<212> TYPE: PRT
<213> ORGANISM: Artificial Sequence
<220> FEATURE:
<223> OTHER INFORMATION: Synthetic Construct
```

-continued

<400> SEQUENCE: 652

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Tyr Met Ser Trp Val Arg Gln Ala Pro Gly Gln Gly Leu Glu Trp Met
        35                  40                  45

Gly Ile Ile Asn Pro Ile Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Phe Gly Ile Ala Leu Ala Gly Pro Ala Ser Arg Tyr
            100                 105                 110

Tyr Tyr Gly Met Asp Val Trp Gly Gln Gly Thr Thr Val Thr Val Ser
        115                 120                 125

Ser

<210> SEQ ID NO 653
<211> LENGTH: 129
<212> TYPE: PRT
<213> ORGANISM: Artificial Sequence
<220> FEATURE:
<223> OTHER INFORMATION: Synthetic Construct

<400> SEQUENCE: 653

Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Lys Tyr
            20                  25                  30

Tyr Met Ser Trp Val Arg Gln Ala Pro Gly Gln Gly Leu Glu Trp Met
        35                  40                  45

Gly Ile Ile Asn Pro Ile Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Phe Pro Ala Gly Arg Tyr
            100                 105                 110

Tyr Tyr Gly Met Asp Val Trp Gly Gln Gly Thr Thr Val Thr Val Ser
        115                 120                 125

Ser

<210> SEQ ID NO 654
<211> LENGTH: 129
<212> TYPE: PRT
<213> ORGANISM: Artificial Sequence
<220> FEATURE:
<223> OTHER INFORMATION: Synthetic Construct

<400> SEQUENCE: 654

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

-continued

Tyr Met Ser Trp Val Arg Gln Ala Pro Gly Gln Gly Leu Glu Trp Met
            35                  40                  45

Gly Ile Ile Asn Pro Ile Gly Gly Ser Thr Ser Tyr Ala Arg Lys Phe
 50                  55                  60

Gln Gly Arg Val Thr Met Thr Arg Asp Thr Ser Thr Gly Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Tyr Pro Ala Ser Arg Tyr
                100                 105                 110

Asn Tyr Gly Met Asp Val Trp Gly Gln Gly Thr Thr Val Thr Val Ser
            115                 120                 125

Ser

<210> SEQ ID NO 655
<211> LENGTH: 129
<212> TYPE: PRT
<213> ORGANISM: Artificial Sequence
<220> FEATURE:
<223> OTHER INFORMATION: Synthetic Construct

<400> SEQUENCE: 655

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Tyr Met Ser Trp Val Arg Gln Ala Pro Gly Gln Gly Leu Glu Trp Met
            35                  40                  45

Gly Ile Ile Asn Pro Ile Gly Gly Ser Ile Ser Tyr Ala Gln Lys Phe
 50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Gly Pro Ala Ser Arg Tyr
                100                 105                 110

Tyr Tyr Gly Met Asp Val Trp Gly Gln Gly Thr Thr Val Thr Val Ser
            115                 120                 125

Ser

<210> SEQ ID NO 656
<211> LENGTH: 129
<212> TYPE: PRT
<213> ORGANISM: Artificial Sequence
<220> FEATURE:
<223> OTHER INFORMATION: Synthetic Construct

<400> SEQUENCE: 656

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Tyr Met Ser Trp Val Arg Gln Ala Pro Gly Gln Gly Leu Glu Trp Met
            35                  40                  45

Gly Ile Ile Asn Pro Ile Gly Gly Ser Thr Ser Tyr Ala Gln Lys Phe
 50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Gly Ala Ala Ala Gly Pro Ala Ser Arg Tyr
            100                 105                 110

Tyr Tyr Gly Met Asp Val Trp Gly Gln Gly Thr Thr Val Thr Val Ser
            115                 120                 125

Ser

<210> SEQ ID NO 657
<211> LENGTH: 129
<212> TYPE: PRT
<213> ORGANISM: Artificial Sequence
<220> FEATURE:
<223> OTHER INFORMATION: Synthetic Construct

<400> SEQUENCE: 657

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
                20                  25                  30

Tyr Met Ser Trp Val Arg Gln Ala Pro Gly Gln Gly Leu Glu Trp Met
            35                  40                  45

Gly Ile Ile Asn Pro Ile Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Tyr Pro Ala Ser Arg Tyr
            100                 105                 110

Tyr Arg Gly Met Asp Val Trp Gly Gln Gly Thr Thr Val Thr Val Ser
            115                 120                 125

Ser

<210> SEQ ID NO 658
<211> LENGTH: 129
<212> TYPE: PRT
<213> ORGANISM: Artificial Sequence
<220> FEATURE:
<223> OTHER INFORMATION: Synthetic Construct

<400> SEQUENCE: 658

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
                20                  25                  30

Tyr Met Ser Trp Val Arg Gln Ala Pro Gly Gln Gly Leu Glu Trp Met
            35                  40                  45

Gly Ile Val Asn Pro Ile Gly Gly Ser Thr Ser Tyr Ala Gln Arg Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Gly Leu Ala Gly Pro Phe Ser Arg Tyr

```
                    100                 105                 110

Tyr Tyr Gly Met Asp Val Trp Gly Gln Gly Thr Thr Val Thr Val Ser
        115                 120                 125

Ser

<210> SEQ ID NO 659
<211> LENGTH: 129
<212> TYPE: PRT
<213> ORGANISM: Artificial Sequence
<220> FEATURE:
<223> OTHER INFORMATION: Synthetic Construct

<400> SEQUENCE: 659

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Tyr Met Ser Trp Val Arg Gln Ala Pro Gly Gln Gly Leu Glu Trp Met
        35                  40                  45

Gly Ile Ile Asn Pro Ile Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Leu Ala Gly Pro Ala Ser Arg Ser
            100                 105                 110

Tyr Tyr Gly Met Asp Val Trp Gly Gln Gly Thr Thr Val Thr Val Ser
        115                 120                 125

Ser

<210> SEQ ID NO 660
<211> LENGTH: 129
<212> TYPE: PRT
<213> ORGANISM: Artificial Sequence
<220> FEATURE:
<223> OTHER INFORMATION: Synthetic Construct

<400> SEQUENCE: 660

Gln Val Arg Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Lys Tyr
            20                  25                  30

Tyr Met Ser Trp Val Arg Gln Ala Pro Gly Gln Gly Leu Glu Trp Met
        35                  40                  45

Gly Ile Ile Asn Pro Ile Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Phe Pro Ala Ser Arg Ser
            100                 105                 110

Tyr Tyr Gly Met Asp Val Trp Gly Gln Gly Thr Thr Val Thr Val Ser
        115                 120                 125

Ser
```

```
<210> SEQ ID NO 661
<211> LENGTH: 129
<212> TYPE: PRT
<213> ORGANISM: Artificial Sequence
<220> FEATURE:
<223> OTHER INFORMATION: Synthetic Construct

<400> SEQUENCE: 661

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Tyr Met Ser Trp Val Arg Gln Ala Pro Gly Gln Gly Leu Glu Trp Met
        35                  40                  45

Gly Ile Ile Asn Pro Ile Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Leu Leu Gly Pro Ala Ser Arg Tyr
            100                 105                 110

Tyr Tyr Gly Met Asp Val Trp Gly Gln Gly Thr Thr Val Thr Val Ser
        115                 120                 125

Ser

<210> SEQ ID NO 662
<211> LENGTH: 129
<212> TYPE: PRT
<213> ORGANISM: Artificial Sequence
<220> FEATURE:
<223> OTHER INFORMATION: Synthetic Construct

<400> SEQUENCE: 662

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Tyr Met Ser Trp Val Arg Gln Ala Pro Gly Gln Gly Leu Glu Trp Met
        35                  40                  45

Gly Ile Ile Asn Pro Ile Gly Gly Ser Thr Ser Tyr Ala Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Gly Pro Ala Gly Arg Tyr
            100                 105                 110

Tyr Tyr Gly Met Asp Val Trp Gly Gln Gly Thr Thr Val Thr Val Ser
        115                 120                 125

Ser

<210> SEQ ID NO 663
<211> LENGTH: 129
<212> TYPE: PRT
<213> ORGANISM: Artificial Sequence
<220> FEATURE:
<223> OTHER INFORMATION: Synthetic Construct
```

<400> SEQUENCE: 663

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Thr
            20                  25                  30

Tyr Met Ser Trp Val Arg Gln Ala Pro Gly Gln Gly Leu Glu Trp Met
        35                  40                  45

Gly Ile Ile Asn Pro Val Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Gly Pro Ala Ser Arg Tyr
            100                 105                 110

Tyr Tyr Gly Met Asp Val Trp Gly Gln Gly Thr Thr Val Thr Val Ser
        115                 120                 125

Ser

<210> SEQ ID NO 664
<211> LENGTH: 129
<212> TYPE: PRT
<213> ORGANISM: Artificial Sequence
<220> FEATURE:
<223> OTHER INFORMATION: Synthetic Construct

<400> SEQUENCE: 664

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Leu
            20                  25                  30

Tyr Met Ser Trp Val Arg Gln Ala Pro Gly Gln Gly Leu Glu Trp Met
        35                  40                  45

Gly Ile Ile Asn Pro Val Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Gly Pro Ala Ser Arg Tyr
            100                 105                 110

Tyr Tyr Gly Met Asp Val Trp Gly Gln Gly Thr Thr Val Thr Val Ser
        115                 120                 125

Ser

<210> SEQ ID NO 665
<211> LENGTH: 129
<212> TYPE: PRT
<213> ORGANISM: Artificial Sequence
<220> FEATURE:
<223> OTHER INFORMATION: Synthetic Construct

<400> SEQUENCE: 665

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Gly

```
                  20                  25                  30

Tyr Met Ser Trp Val Arg Gln Ala Pro Gly Gln Gly Leu Glu Trp Met
            35                  40                  45

Gly Ile Ile Asn Pro Tyr Gly Gly Thr Thr Ser Tyr Ala Gln Lys Phe
        50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Gly Pro Ala Ser Arg Tyr
              100                 105                 110

Tyr Tyr Gly Met Asp Val Trp Gly Gln Gly Thr Thr Val Thr Val Ser
            115                 120                 125

Ser

<210> SEQ ID NO 666
<211> LENGTH: 129
<212> TYPE: PRT
<213> ORGANISM: Artificial Sequence
<220> FEATURE:
<223> OTHER INFORMATION: Synthetic Construct

<400> SEQUENCE: 666

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Gln
                20                  25                  30

Tyr Met Ser Trp Val Arg Gln Ala Pro Gly Gln Gly Leu Glu Trp Met
            35                  40                  45

Gly Ile Ile Asn Pro Tyr Gly Gly Ser Thr Ser Tyr Ala Gln Lys Phe
        50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Gly Pro Ala Ser Arg Tyr
              100                 105                 110

Tyr Tyr Gly Met Asp Val Trp Gly Gln Gly Thr Thr Val Thr Val Ser
            115                 120                 125

Ser

<210> SEQ ID NO 667
<211> LENGTH: 107
<212> TYPE: PRT
<213> ORGANISM: Artificial Sequence
<220> FEATURE:
<223> OTHER INFORMATION: Synthetic Construct

<400> SEQUENCE: 667

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Ile Ser Ser Trp
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60
```

```
Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ala Arg Leu Gly Pro Trp
                85                  90                  95

Thr Phe Gly Gly Gly Thr Lys Val Glu Ile Lys
            100                 105
```

<210> SEQ ID NO 668
<211> LENGTH: 129
<212> TYPE: PRT
<213> ORGANISM: Artificial Sequence
<220> FEATURE:
<223> OTHER INFORMATION: Synthetic Construct

<400> SEQUENCE: 668

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Gln
                20                  25                  30

Tyr Met Ser Trp Val Arg Gln Ala Pro Gly Gln Gly Leu Glu Trp Met
            35                  40                  45

Gly Ile Ile Asn Pro Val Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Gly Pro Ala Ser Arg Tyr
                100                 105                 110

Tyr Tyr Gly Met Asp Val Trp Gly Gln Gly Thr Thr Val Thr Val Ser
            115                 120                 125

Ser
```

<210> SEQ ID NO 669
<211> LENGTH: 129
<212> TYPE: PRT
<213> ORGANISM: Artificial Sequence
<220> FEATURE:
<223> OTHER INFORMATION: Synthetic Construct

<400> SEQUENCE: 669

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
                20                  25                  30

Tyr Met Ser Trp Val Arg Gln Ala Pro Gly Gln Gly Leu Glu Trp Met
            35                  40                  45

Gly Ile Ile Asn Pro Ile Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Gly Ile Ala Ala Ala Gly Pro Ala Ser Arg Tyr
                100                 105                 110

Tyr Tyr Gly Met Asp Val Trp Gly Gln Gly Thr Thr Val Thr Val Ser
            115                 120                 125
```

Ser

<210> SEQ ID NO 670
<211> LENGTH: 124
<212> TYPE: PRT
<213> ORGANISM: Artificial Sequence
<220> FEATURE:
<223> OTHER INFORMATION: Synthetic Construct

<400> SEQUENCE: 670

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Val Pro Arg Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gly Arg Lys Thr Gly Tyr Tyr Tyr Tyr Gly Met Asp
            100                 105                 110

Val Trp Gly Gln Gly Thr Thr Val Thr Val Ser Ser
        115                 120
```

<210> SEQ ID NO 671
<211> LENGTH: 124
<212> TYPE: PRT
<213> ORGANISM: Artificial Sequence
<220> FEATURE:
<223> OTHER INFORMATION: Synthetic Construct

<400> SEQUENCE: 671

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Phe Gly Thr Ala Gly Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gly Arg Lys Thr Gly Tyr Tyr Tyr Tyr Gly Met Asp
            100                 105                 110

Val Trp Gly Gln Gly Thr Thr Val Thr Val Ser Ser
        115                 120
```

<210> SEQ ID NO 672
<211> LENGTH: 124
<212> TYPE: PRT
<213> ORGANISM: Artificial Sequence
<220> FEATURE:
<223> OTHER INFORMATION: Synthetic Construct

```
<400> SEQUENCE: 672

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Phe Gly Thr Ala Trp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gly Arg Lys Thr Gly Tyr Tyr Tyr Tyr Tyr Gly Met Asp
            100                 105                 110

Val Trp Gly Gln Gly Thr Thr Val Thr Val Ser Ser
        115                 120

<210> SEQ ID NO 673
<211> LENGTH: 124
<212> TYPE: PRT
<213> ORGANISM: Artificial Sequence
<220> FEATURE:
<223> OTHER INFORMATION: Synthetic Construct

<400> SEQUENCE: 673

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Gly Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ala Phe Gly Thr Ala Trp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gly Arg Lys Thr Gly Tyr Tyr Tyr Tyr Tyr Gly Met Asp
            100                 105                 110

Val Trp Gly Gln Gly Thr Thr Val Thr Val Ser Ser
        115                 120

<210> SEQ ID NO 674
<211> LENGTH: 124
<212> TYPE: PRT
<213> ORGANISM: Artificial Sequence
<220> FEATURE:
<223> OTHER INFORMATION: Synthetic Construct

<400> SEQUENCE: 674

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

Gly Gly Ile Ile Pro Ser Phe Gly Thr Ala Ser Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gly Arg Lys Thr Gly Tyr Tyr Tyr Tyr Gly Met Asp
                100                 105                 110

Val Trp Gly Gln Gly Thr Thr Val Thr Val Ser Ser
            115                 120

<210> SEQ ID NO 675
<211> LENGTH: 124
<212> TYPE: PRT
<213> ORGANISM: Artificial Sequence
<220> FEATURE:
<223> OTHER INFORMATION: Synthetic Construct

<400> SEQUENCE: 675

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Ala Met Ala Trp Val Arg Gln Ala Pro Gly Gln Gly Leu Glu Trp Met
            35                  40                  45

Gly Gly Ile Ile Pro Thr Phe Gly Thr Ala Trp Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gly Arg Lys Thr Gly Tyr Tyr Tyr Tyr Gly Met Asp
                100                 105                 110

Val Trp Gly Gln Gly Thr Thr Val Thr Val Ser Ser
            115                 120

<210> SEQ ID NO 676
<211> LENGTH: 124
<212> TYPE: PRT
<213> ORGANISM: Artificial Sequence
<220> FEATURE:
<223> OTHER INFORMATION: Synthetic Construct

<400> SEQUENCE: 676

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Gly Phe Gly Arg Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gly Arg Lys Thr Gly Tyr Tyr Tyr Tyr Gly Met Asp
                100                 105                 110

Val Trp Gly Gln Gly Thr Thr Val Thr Val Ser Ser
        115                 120

<210> SEQ ID NO 677
<211> LENGTH: 124
<212> TYPE: PRT
<213> ORGANISM: Artificial Sequence
<220> FEATURE:
<223> OTHER INFORMATION: Synthetic Construct

<400> SEQUENCE: 677

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gln Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gly Arg Lys Thr Gly Tyr Tyr Tyr Tyr Gly Met Asp
            100                 105                 110

Val Trp Gly Gln Gly Thr Thr Val Thr Val Ser Ser
        115                 120

<210> SEQ ID NO 678
<211> LENGTH: 124
<212> TYPE: PRT
<213> ORGANISM: Artificial Sequence
<220> FEATURE:
<223> OTHER INFORMATION: Synthetic Construct

<400> SEQUENCE: 678

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Gly Gly Trp Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gly Arg Lys Thr Gly Tyr Tyr Tyr Tyr Gly Met Asp
            100                 105                 110

Val Trp Gly Gln Gly Thr Thr Val Thr Val Ser Ser
        115                 120

<210> SEQ ID NO 679
<211> LENGTH: 122
<212> TYPE: PRT
<213> ORGANISM: Artificial Sequence
<220> FEATURE:
<223> OTHER INFORMATION: Synthetic Construct -continued

<400> SEQUENCE: 679

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Val
            20                  25                  30

Arg Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Gly Ser Ile Lys Gln Gly Tyr Tyr Gly Met Asp Val Trp
            100                 105                 110

Gly Gln Gly Thr Thr Val Thr Val Ser Ser
        115                 120

<210> SEQ ID NO 680
<211> LENGTH: 122
<212> TYPE: PRT
<213> ORGANISM: Artificial Sequence
<220> FEATURE:
<223> OTHER INFORMATION: Synthetic Construct

<400> SEQUENCE: 680

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Val
            20                  25                  30

Arg Tyr Trp Gly Trp Ile Arg Gln Pro Pro Gly Lys Gly Leu Glu Trp
        35                  40                  45

Ile Gly Ala Ile Tyr Pro Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Gly Ser Ile Lys Gln Gly Tyr Tyr Gly Met Asp Val Trp
            100                 105                 110

Gly Gln Gly Thr Thr Val Thr Val Ser Ser
        115                 120

<210> SEQ ID NO 681
<211> LENGTH: 112
<212> TYPE: PRT
<213> ORGANISM: Artificial Sequence
<220> FEATURE:
<223> OTHER INFORMATION: Synthetic Construct

<400> SEQUENCE: 681

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Asn Gly Tyr Asn Tyr Leu Asp Trp Tyr Leu Gln Lys Pro Gly Gln Pro
        35                  40                  45

```
Pro Gln Leu Leu Ile Tyr Leu Gly Ser Asn Arg Val Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gln
                85                  90                  95

Gln Glu Thr Pro Leu Thr Phe Gly Gly Gly Thr Lys Val Glu Ile Lys
            100                 105                 110
```

<210> SEQ ID NO 682
<211> LENGTH: 112
<212> TYPE: PRT
<213> ORGANISM: Artificial Sequence
<220> FEATURE:
<223> OTHER INFORMATION: Synthetic Construct

<400> SEQUENCE: 682

```
Asp Ile Val Met Thr Gln Ser Pro Leu Ser Leu Pro Val Thr Pro Gly
1               5                   10                  15

Glu Ser Ala Ser Ile Ser Cys Arg Ser Ser Gln Gly Leu Leu Arg Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gln
                85                  90                  95

Gln Glu Thr Pro Leu Thr Phe Gly Gly Gly Thr Lys Val Glu Ile Lys
            100                 105                 110
```

<210> SEQ ID NO 683
<211> LENGTH: 112
<212> TYPE: PRT
<213> ORGANISM: Artificial Sequence
<220> FEATURE:
<223> OTHER INFORMATION: Synthetic Construct

<400> SEQUENCE: 683

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gln
                85                  90                  95

Gln Glu Thr Pro Leu Thr Phe Gly Gly Gly Thr Lys Val Glu Ile Lys
            100                 105                 110
```

<210> SEQ ID NO 684
<211> LENGTH: 112
<212> TYPE: PRT

-continued

<213> ORGANISM: Artificial Sequence
<220> FEATURE:
<223> OTHER INFORMATION: Synthetic Construct

<400> SEQUENCE: 684

Asp Ile Val Met Thr Gln Ser Pro Leu Ser Leu Pro Val Thr Pro Gly
1               5                   10                  15

Gly Pro Ala Ser Ile Ser Cys Arg Ser Ser Gln Ser Leu Leu Arg Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gln
                85                  90                  95

Gln Glu Thr Pro Leu Thr Phe Gly Gly Gly Thr Lys Val Glu Ile Lys
            100                 105                 110

<210> SEQ ID NO 685
<211> LENGTH: 125
<212> TYPE: PRT
<213> ORGANISM: Artificial Sequence
<220> FEATURE:
<223> OTHER INFORMATION: Synthetic Construct

<400> SEQUENCE: 685

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Val Ser Ser
            20                  25                  30

Asp Tyr Tyr Trp Gly Trp Ile Arg Gln Pro Pro Gly Lys Gly Leu Glu
        35                  40                  45

Trp Ile Gly Gly Ile Tyr Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Gly Ser Gly Tyr Ser Tyr Gly Tyr Arg Tyr Phe
            100                 105                 110

Asp Tyr Trp Gly Gln Gly Thr Leu Val Thr Val Ser Ser
        115                 120                 125

<210> SEQ ID NO 686
<211> LENGTH: 125
<212> TYPE: PRT
<213> ORGANISM: Artificial Sequence
<220> FEATURE:
<223> OTHER INFORMATION: Synthetic Construct

<400> SEQUENCE: 686

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Tyr Tyr Trp Gly Trp Ile Arg Gln Pro Pro Gly Lys Gly Leu Glu
        35                  40                  45

Trp Ile Gly Gly Ile Tyr Tyr Arg Gly Ser Thr Tyr Tyr Asn Pro Ser
            50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Gly Ser Gly Tyr Ser Tyr Gly Tyr Arg Tyr Phe
                100                 105                 110

Asp Tyr Trp Gly Gln Gly Thr Leu Val Thr Val Ser Ser
            115                 120                 125

<210> SEQ ID NO 687
<211> LENGTH: 125
<212> TYPE: PRT
<213> ORGANISM: Artificial Sequence
<220> FEATURE:
<223> OTHER INFORMATION: Synthetic Construct

<400> SEQUENCE: 687

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Asp Tyr Tyr Trp Gly Trp Ile Arg Gln Pro Pro Gly Lys Gly Leu Glu
            35                  40                  45

Trp Ile Gly Gln Ile Tyr Tyr Lys Gly Ser Thr Tyr Tyr Asn Pro Ser
            50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Gly Ser Gly Tyr Ser Tyr Gly Tyr Arg Tyr Phe
                100                 105                 110

Asp Tyr Trp Gly Gln Gly Thr Leu Val Thr Val Ser Ser
            115                 120                 125

<210> SEQ ID NO 688
<211> LENGTH: 125
<212> TYPE: PRT
<213> ORGANISM: Artificial Sequence
<220> FEATURE:
<223> OTHER INFORMATION: Synthetic Construct

<400> SEQUENCE: 688

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Tyr Ser Ser
                20                  25                  30

Asp Tyr Tyr Trp Gly Trp Ile Arg Gln Pro Pro Gly Lys Gly Leu Glu
            35                  40                  45

Trp Ile Gly Ser Ile Tyr Trp Arg Gly Ser Thr Tyr Tyr Asn Pro Ser
            50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Gly Ser Gly Tyr Ser Tyr Gly Tyr Arg Tyr Phe

```
                    100                 105                 110

Asp Tyr Trp Gly Gln Gly Thr Leu Val Thr Val Ser Ser
            115                 120                 125

<210> SEQ ID NO 689
<211> LENGTH: 125
<212> TYPE: PRT
<213> ORGANISM: Artificial Sequence
<220> FEATURE:
<223> OTHER INFORMATION: Synthetic Construct

<400> SEQUENCE: 689

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Lys Ser Ser
            20                  25                  30

Glu Tyr Tyr Trp Gly Trp Ile Arg Gln Pro Pro Gly Lys Gly Leu Glu
        35                  40                  45

Trp Ile Gly Ser Ile Tyr Arg Ala Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Gly Ser Gly Tyr Ser Tyr Gly Tyr Arg Tyr Phe
            100                 105                 110

Asp Tyr Trp Gly Gln Gly Thr Leu Val Thr Val Ser Ser
            115                 120                 125

<210> SEQ ID NO 690
<211> LENGTH: 124
<212> TYPE: PRT
<213> ORGANISM: Artificial Sequence
<220> FEATURE:
<223> OTHER INFORMATION: Synthetic Construct

<400> SEQUENCE: 690

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Pro Ser Asp
            20                  25                  30

Tyr Tyr Trp Gly Trp Ile Arg Gln Pro Pro Gly Lys Gly Leu Glu Trp
        35                  40                  45

Ile Gly Ser Ile Tyr Tyr Arg Gly Ser Thr Val Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Val Gly Ser Gly Tyr Ser Tyr Gly Tyr Arg Tyr Phe Asp
            100                 105                 110

Tyr Trp Gly Gln Gly Thr Leu Val Thr Val Ser Ser
            115                 120

<210> SEQ ID NO 691
<211> LENGTH: 125
<212> TYPE: PRT
<213> ORGANISM: Artificial Sequence
<220> FEATURE:
```

-continued

<223> OTHER INFORMATION: Synthetic Construct

<400> SEQUENCE: 691

```
Gln Leu Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Ser
            20                  25                  30
Glu Tyr Tyr Trp Gly Trp Ile Arg Gln Pro Pro Gly Lys Gly Leu Glu
        35                  40                  45
Trp Ile Gly Leu Ile Tyr Tyr Arg Gly Ser Thr Tyr Tyr Asn Pro Ser
    50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
            85                  90                  95
Cys Ala Arg Gly Val Gly Ser Gly Tyr Ser Tyr Gly Tyr Arg Tyr Phe
            100                 105                 110
Asp Tyr Trp Gly Gln Gly Thr Leu Val Thr Val Ser Ser
        115                 120                 125
```

<210> SEQ ID NO 692
<211> LENGTH: 125
<212> TYPE: PRT
<213> ORGANISM: Artificial Sequence
<220> FEATURE:
<223> OTHER INFORMATION: Synthetic Construct

<400> SEQUENCE: 692

```
Gln Leu Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Arg
            20                  25                  30
Glu Tyr Tyr Trp Gly Trp Ile Arg Gln Pro Pro Gly Lys Gly Leu Glu
        35                  40                  45
Trp Ile Gly Ser Ile Tyr Arg Ser Gly Ser Thr Tyr Tyr Asn Pro Ser
    50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
            85                  90                  95
Cys Ala Arg Gly Val Gly Ser Gly Tyr Ser Tyr Gly Tyr Arg Tyr Phe
            100                 105                 110
Asp Tyr Trp Gly Gln Gly Thr Leu Val Thr Val Ser Ser
        115                 120                 125
```

<210> SEQ ID NO 693
<211> LENGTH: 24
<212> TYPE: PRT
<213> ORGANISM: Artificial Sequence
<220> FEATURE:
<223> OTHER INFORMATION: Synthetic Construct

<400> SEQUENCE: 693

```
Thr Lys Cys Leu Arg Arg Glu Ala Pro Arg Trp Asp Ala Pro Leu Arg
1               5                   10                  15
Asp Pro Ala Leu Arg Gln Leu Leu
            20
```

```
<210> SEQ ID NO 694
<211> LENGTH: 8
<212> TYPE: PRT
<213> ORGANISM: Artificial Sequence
<220> FEATURE:
<223> OTHER INFORMATION: Synthetic Construct

<400> SEQUENCE: 694

Ser Ser Asp Phe Ala Lys Asn Phe
1               5

<210> SEQ ID NO 695
<211> LENGTH: 41
<212> TYPE: PRT
<213> ORGANISM: Artificial Sequence
<220> FEATURE:
<223> OTHER INFORMATION: Synthetic Construct

<400> SEQUENCE: 695

Gly Gly Thr Ala Thr Thr Gly Ala Gly Gly Thr Cys Gly Cys Gly
1               5                   10                  15

Ala Ala Cys Cys Ala Cys Ala Cys Thr Cys Ala Gly Ala Cys Ala Gly
            20                  25                  30

Cys Ala Ala Thr Gly Thr Cys Cys Cys
        35                  40

<210> SEQ ID NO 696
<211> LENGTH: 52
<212> TYPE: PRT
<213> ORGANISM: Artificial Sequence
<220> FEATURE:
<223> OTHER INFORMATION: Synthetic Construct

<400> SEQUENCE: 696

Gly Gly Gly Gly Gly Ala Ala Gly Thr Thr Gly Thr Cys Cys Thr Gly
1               5                   10                  15

Ala Gly Thr Gly Thr Cys Cys Thr Cys Gly Thr Thr Cys Gly Cys Cys
            20                  25                  30

Ala Cys Thr Cys Cys Gly Ala Gly Ala Thr Thr Gly Ala Gly Ala Gly
        35                  40                  45

Gly Ala Gly Ala
    50

<210> SEQ ID NO 697
<211> LENGTH: 44
<212> TYPE: PRT
<213> ORGANISM: Artificial Sequence
<220> FEATURE:
<223> OTHER INFORMATION: Synthetic Construct

<400> SEQUENCE: 697

Gly Gly Thr Ala Thr Thr Gly Ala Gly Gly Thr Cys Gly Cys Gly
1               5                   10                  15

Cys Cys Cys Cys Cys Ala Thr Gly Ala Ala Gly Ala Ala Gly Cys
            20                  25                  30

Ala Ala Ala Cys Ala Thr Cys Cys Gly Ala Gly Gly
        35                  40

<210> SEQ ID NO 698
<211> LENGTH: 49
<212> TYPE: PRT
<213> ORGANISM: Artificial Sequence
<220> FEATURE:
<223> OTHER INFORMATION: Synthetic Construct
```

<400> SEQUENCE: 698

Cys Ala Cys Gly Thr Thr Thr Gly Thr Ala Cys Ala Gly Gly Thr Ala
1               5                   10                  15
Cys Thr Cys Cys Cys Ala Gly Gly Cys Cys Gly Cys Gly Ala Cys Thr
                20                  25                  30
Cys Cys Gly Ala Gly Ala Thr Thr Gly Ala Gly Ala Gly Gly Ala Gly
            35                  40                  45
Ala

<210> SEQ ID NO 699
<211> LENGTH: 21
<212> TYPE: PRT
<213> ORGANISM: Artificial Sequence
<220> FEATURE:
<223> OTHER INFORMATION: Synthetic Construct

<400> SEQUENCE: 699

Lys Thr Ile Gly Val Lys Ile Tyr Ser Phe Gly Leu Gly Gly Arg Phe
1               5                   10                  15
Leu Phe Ala Ser Val
            20

<210> SEQ ID NO 700
<211> LENGTH: 11
<212> TYPE: PRT
<213> ORGANISM: Artificial Sequence
<220> FEATURE:
<223> OTHER INFORMATION: Synthetic Construct

<400> SEQUENCE: 700

Asn Gly Leu Trp Val Ser Lys Asn Phe Gly Gly
1               5                   10

<210> SEQ ID NO 701
<211> LENGTH: 25
<212> TYPE: PRT
<213> ORGANISM: Artificial Sequence
<220> FEATURE:
<223> OTHER INFORMATION: Synthetic Construct

<400> SEQUENCE: 701

Phe Ala Ser Val Met Ala Asp Lys Asp Thr Thr Arg Arg Ile His Val
1               5                   10                  15
Ser Thr Asp Gln Gly Asp Thr Trp Ser
            20                  25

<210> SEQ ID NO 702
<211> LENGTH: 21
<212> TYPE: PRT
<213> ORGANISM: Artificial Sequence
<220> FEATURE:
<223> OTHER INFORMATION: Synthetic Construct

<400> SEQUENCE: 702

Phe Val Gln Thr Asp Leu Pro Phe His Pro Leu Thr Gln Met Met Tyr
1               5                   10                  15
Ser Pro Gln Asn Ser
            20

<210> SEQ ID NO 703
<211> LENGTH: 24
<212> TYPE: PRT

<213> ORGANISM: Artificial Sequence
<220> FEATURE:
<223> OTHER INFORMATION: Synthetic Construct

<400> SEQUENCE: 703

Asn Gly Leu Trp Val Ser Lys Asn Phe Gly Gly Lys Trp Glu Glu Ile
1               5                   10                  15

His Lys Ala Val Cys Leu Ala Lys
            20

<210> SEQ ID NO 704
<211> LENGTH: 25
<212> TYPE: PRT
<213> ORGANISM: Artificial Sequence
<220> FEATURE:
<223> OTHER INFORMATION: Synthetic Construct

<400> SEQUENCE: 704

Phe Val Gln Thr Asp Leu Pro Phe His Pro Leu Thr Gln Met Met Tyr
1               5                   10                  15

Ser Pro Gln Asn Ser Asp Tyr Leu Leu
            20                  25

<210> SEQ ID NO 705
<211> LENGTH: 25
<212> TYPE: PRT
<213> ORGANISM: Artificial Sequence
<220> FEATURE:
<223> OTHER INFORMATION: Synthetic Construct

<400> SEQUENCE: 705

Glu Pro Gly Asp Thr Gly Phe Gly Thr Ile Phe Thr Ser Asp Asp Arg
1               5                   10                  15

Gly Ile Val Tyr Ser Lys Ser Leu Asp
            20                  25

<210> SEQ ID NO 706
<211> LENGTH: 8
<212> TYPE: PRT
<213> ORGANISM: Artificial Sequence
<220> FEATURE:
<223> OTHER INFORMATION: Synthetic Construct

<400> SEQUENCE: 706

Gln Val Pro Leu Val Ile Val Ser
1               5

<210> SEQ ID NO 707
<211> LENGTH: 21
<212> TYPE: PRT
<213> ORGANISM: Artificial Sequence
<220> FEATURE:
<223> OTHER INFORMATION: Synthetic Construct

<400> SEQUENCE: 707

Met Glu Val Gly Trp Tyr Arg Ser Pro Phe Ser Arg Val Val His Leu
1               5                   10                  15

Tyr Arg Asn Gly Lys
            20

<210> SEQ ID NO 708
<211> LENGTH: 10
<212> TYPE: PRT
<213> ORGANISM: Artificial Sequence
<220> FEATURE:

```
<223> OTHER INFORMATION: Synthetic Construct

<400> SEQUENCE: 708

His Ser Thr Asp Pro Glu Asp Tyr Glu Asp
1               5                   10

<210> SEQ ID NO 709
<211> LENGTH: 15
<212> TYPE: PRT
<213> ORGANISM: Artificial Sequence
<220> FEATURE:
<223> OTHER INFORMATION: Synthetic Construct

<400> SEQUENCE: 709

Ile Thr Phe Asp Gln Gly Gly Arg Trp Thr His Leu Arg Lys Pro
1               5                   10                  15

<210> SEQ ID NO 710
<211> LENGTH: 10
<212> TYPE: PRT
<213> ORGANISM: Artificial Sequence
<220> FEATURE:
<223> OTHER INFORMATION: Synthetic Construct

<400> SEQUENCE: 710

Cys Thr Ser Asn Phe Leu Ser Pro Glu Lys
1               5                   10

<210> SEQ ID NO 711
<211> LENGTH: 11
<212> TYPE: PRT
<213> ORGANISM: Artificial Sequence
<220> FEATURE:
<223> OTHER INFORMATION: Synthetic Construct

<400> SEQUENCE: 711

Leu Ser Thr Glu Asn Gly Leu Trp Val Ser Lys
1               5                   10

<210> SEQ ID NO 712
<211> LENGTH: 7
<212> TYPE: PRT
<213> ORGANISM: Artificial Sequence
<220> FEATURE:
<223> OTHER INFORMATION: Synthetic Construct

<400> SEQUENCE: 712

Gly Pro Glu Asn Ser Gly Lys
1               5

<210> SEQ ID NO 713
<211> LENGTH: 10
<212> TYPE: PRT
<213> ORGANISM: Artificial Sequence
<220> FEATURE:
<223> OTHER INFORMATION: Synthetic Construct

<400> SEQUENCE: 713

Leu Pro Phe His Pro Leu Thr Gln Met Met
1               5                   10

<210> SEQ ID NO 714
<211> LENGTH: 678
<212> TYPE: PRT
<213> ORGANISM: Homo sapiens

<400> SEQUENCE: 714
```

```
Ser Ala Pro Gly Glu Asp Glu Cys Gly Arg Val Arg Asp Phe Val
1               5                   10                  15

Ala Lys Leu Ala Asn Asn Thr His Gln His Val Phe Asp Asp Leu Arg
                20              25                  30

Gly Ser Val Ser Leu Ser Trp Val Gly Asp Ser Thr Gly Val Ile Leu
            35                  40                  45

Val Leu Thr Thr Phe His Val Pro Leu Val Ile Met Thr Phe Gly Gln
        50                  55                  60

Ser Lys Leu Tyr Arg Ser Glu Asp Tyr Gly Lys Asn Phe Lys Asp Ile
65                  70                  75                  80

Thr Asp Leu Ile Asn Asn Thr Phe Ile Arg Thr Glu Phe Gly Met Ala
                85                  90                  95

Ile Gly Pro Glu Asn Ser Gly Lys Val Val Leu Thr Ala Glu Val Ser
                100                 105                 110

Gly Gly Ser Arg Gly Gly Arg Ile Phe Arg Ser Ser Asp Phe Ala Lys
            115                 120                 125

Asn Phe Val Gln Thr Asp Leu Pro Phe His Pro Leu Thr Gln Met Met
            130                 135                 140

Tyr Ser Pro Gln Asn Ser Asp Tyr Leu Leu Ala Leu Ser Thr Glu Asn
145                 150                 155                 160

Gly Leu Trp Val Ser Lys Asn Phe Gly Gly Lys Trp Glu Glu Ile His
                165                 170                 175

Lys Ala Val Cys Leu Ala Lys Trp Gly Ser Asp Asn Thr Ile Phe Phe
                180                 185                 190

Thr Thr Tyr Ala Asn Gly Ser Cys Lys Ala Asp Leu Gly Ala Leu Glu
            195                 200                 205

Leu Trp Arg Thr Ser Asp Leu Gly Lys Ser Phe Lys Thr Ile Gly Val
210                 215                 220

Lys Ile Tyr Ser Phe Gly Leu Gly Gly Arg Phe Leu Phe Ala Ser Val
225                 230                 235                 240

Met Ala Asp Lys Asp Thr Thr Arg Arg Ile His Val Ser Thr Asp Gln
                245                 250                 255

Gly Asp Thr Trp Ser Met Ala Gln Leu Pro Ser Val Gly Gln Glu Gln
            260                 265                 270

Phe Tyr Ser Ile Leu Ala Ala Asn Asp Asp Met Val Phe Met His Val
            275                 280                 285

Asp Glu Pro Gly Asp Thr Gly Phe Gly Thr Ile Phe Thr Ser Asp Asp
            290                 295                 300

Arg Gly Ile Val Tyr Ser Lys Ser Leu Asp Arg His Leu Tyr Thr Thr
305                 310                 315                 320

Thr Gly Gly Glu Thr Asp Phe Thr Asn Val Thr Ser Leu Arg Gly Val
                325                 330                 335

Tyr Ile Thr Ser Val Leu Ser Glu Asp Asn Ser Ile Gln Thr Met Ile
            340                 345                 350

Thr Phe Asp Gln Gly Gly Arg Trp Thr His Leu Arg Lys Pro Glu Asn
            355                 360                 365

Ser Glu Cys Asp Ala Thr Ala Lys Asn Lys Asn Glu Cys Ser Leu His
            370                 375                 380

Ile His Ala Ser Tyr Ser Ile Ser Gln Lys Leu Asn Val Pro Met Ala
385                 390                 395                 400

Pro Leu Ser Glu Pro Asn Ala Val Gly Ile Val Ile Ala His Gly Ser
                405                 410                 415
```

-continued

```
Val Gly Asp Ala Ile Ser Val Met Val Pro Asp Val Tyr Ile Ser Asp
            420                 425                 430

Asp Gly Gly Tyr Ser Trp Thr Lys Met Leu Glu Gly Pro His Tyr Tyr
        435                 440                 445

Thr Ile Leu Asp Ser Gly Gly Ile Ile Val Ala Ile Glu His Ser Ser
    450                 455                 460

Arg Pro Ile Asn Val Ile Lys Phe Ser Thr Asp Glu Gly Gln Cys Trp
465                 470                 475                 480

Gln Thr Tyr Thr Phe Thr Arg Asp Pro Ile Tyr Phe Thr Gly Leu Ala
                485                 490                 495

Ser Glu Pro Gly Ala Arg Ser Met Asn Ile Ser Ile Trp Gly Phe Thr
            500                 505                 510

Glu Ser Phe Leu Thr Ser Gln Trp Val Ser Tyr Thr Ile Asp Phe Lys
        515                 520                 525

Asp Ile Leu Glu Arg Asn Cys Glu Glu Lys Asp Tyr Thr Ile Trp Leu
    530                 535                 540

Ala His Ser Thr Asp Pro Glu Asp Tyr Glu Asp Gly Cys Ile Leu Gly
545                 550                 555                 560

Tyr Lys Glu Gln Phe Leu Arg Leu Arg Lys Ser Ser Val Cys Gln Asn
                565                 570                 575

Gly Arg Asp Tyr Val Val Thr Lys Gln Pro Ser Ile Cys Leu Cys Ser
            580                 585                 590

Leu Glu Asp Phe Leu Cys Asp Phe Gly Tyr Tyr Arg Pro Glu Asn Asp
        595                 600                 605

Ser Lys Cys Val Glu Gln Pro Glu Leu Lys Gly His Asp Leu Glu Phe
    610                 615                 620

Cys Leu Tyr Gly Arg Glu Glu His Leu Thr Thr Asn Gly Tyr Arg Lys
625                 630                 635                 640

Ile Pro Gly Asp Lys Cys Gln Gly Gly Val Asn Pro Val Arg Glu Val
                645                 650                 655

Lys Asp Leu Lys Lys Lys Cys Thr Ser Asn Phe Leu Ser Pro Glu Lys
            660                 665                 670

Gln Asn Ser Lys Ser Asn
            675
```